US008394825B2

(12) United States Patent
Leese et al.

(10) Patent No.: US 8,394,825 B2
(45) Date of Patent: Mar. 12, 2013

(54) COMPOUND

(75) Inventors: Matthew Leese, Slough (GB); Fabrice Jourdan, Slough (GB); Meriel Kimberley, Slough (GB); Atul Purohit, Slough (GB); Michael John Reed, Slough (GB); Gillian Reed, legal representative, London (GB); Barry Victor Lloyd Potter, Slough (GB)

(73) Assignee: Sterix Limited, Berkshire (GB)

( * ) Notice: Subject to any disclaimer, the term of this patent is extended or adjusted under 35 U.S.C. 154(b) by 418 days.

(21) Appl. No.: 12/593,560

(22) PCT Filed: Mar. 27, 2008

(86) PCT No.: PCT/GB2008/001072
§ 371 (c)(1),
(2), (4) Date: Feb. 22, 2010

(87) PCT Pub. No.: WO2008/117061
PCT Pub. Date: Oct. 2, 2008

(65) Prior Publication Data
US 2010/0222299 A1 Sep. 2, 2010

(30) Foreign Application Priority Data

Mar. 28, 2007 (GB) .................................. 0706072.6

(51) Int. Cl.
*A61K 31/47* (2006.01)
*A61K 31/472* (2006.01)
*C07D 217/00* (2006.01)
(52) U.S. Cl. ........................................ 514/307; 546/139
(58) Field of Classification Search .................. 514/307; 546/139
See application file for complete search history.

(56) References Cited

U.S. PATENT DOCUMENTS

| 4,717,724 | A | 1/1988 | Schaper et al. | |
| 6,479,495 | B1 * | 11/2002 | Kosley et al. | 514/252.12 |
| 2004/0220179 | A1 | 11/2004 | Lu et al. | |
| 2007/0203118 | A1 | 8/2007 | Hofmeister et al. | |
| 2008/0033007 | A1 | 2/2008 | Miller et al. | |

FOREIGN PATENT DOCUMENTS

| CN | 1380288 | 11/2002 |
| CN | 101020689 | 8/2007 |
| DE | 102004031850 | 1/2006 |
| EP | 0 275 064 | 1/1987 |
| EP | 0 227 986 | 7/1987 |
| EP | 0 613 879 | 9/1994 |
| JP | 63301863 | 12/1988 |
| JP | 06135935 | 5/1994 |
| JP | 06135936 | 5/1994 |
| JP | 2003/313168 | 11/2003 |
| WO | WO 93/05064 | 3/1993 |
| WO | WO 96/15257 | 5/1996 |
| WO | WO 98/05635 | 2/1998 |
| WO | WO 98/07859 | 2/1998 |
| WO | WO 98/13348 | 2/1998 |
| WO | WO 98/08870 | 3/1998 |
| WO | WO 98/09985 | 3/1998 |
| WO | WO 98/17648 | 4/1998 |
| WO | WO 99/50453 | 10/1999 |
| WO | WO 99/52890 | 10/1999 |
| WO | WO 99/62882 | 12/1999 |
| WO | WO 03/045925 | 6/2003 |
| WO | WO 03/053939 | 7/2003 |
| WO | WO 03/095447 | 11/2003 |
| WO | WO 03/095625 | 11/2003 |
| WO | WO 2004/065379 | 8/2004 |
| WO | WO 2004/087153 | 10/2004 |
| WO | WO 2005/027882 | 3/2005 |
| WO | WO 2006/097323 | 9/2006 |
| WO | WO 2006/110638 | 10/2006 |
| WO | WO 2006/117669 | 11/2006 |
| WO | WO 2007/120638 | 10/2007 |

OTHER PUBLICATIONS

Hara, Hiroshi. Studies on tetrahydroisoquinolines. XXIV. A synthesis of dibenzo[c,f]-1-azabicyclo[3.3.1]nonanes and dibenzo[d,g]-1-azabicyclo[4.3.1]decanes. Chemical & Pharmaceutical Bulletin (1985), 33(7), 2705-11.*
CAplus registry No. RN 222620-81-7, Accessed Mar. 12, 2012.*
CAplus registry No. RN 172091-82-6 , Accessed Mar. 12, 2012.*
CAplus registry No. RN 172216-75-0 , Accessed Mar. 12, 2012.*
CAplus registry No. RN 156005-00-4, Accessed Mar. 12, 2012.*
Notification of Transmittal of the International Search Report and The Written Opinion of the International Searching Authority mailed Mar. 30, 2009.
Notification Concerning Transmittal of International Preliminary Report on Patentability mailed Oct. 8, 2009 (20 pages).
Boivin R.P. et al., Structure-Activity Relationships of 17α-Derivatives of Estrodiol as Inhibitors of Steroid Sulfatase, J. Med. Chem., 2000, vol. 43, p. 4465-4478.
Bradford M.M, A Rapid and Sensitive Method for the Quantitation of Microgram Quantities of Protein Utilizing the Principle of Protein-Dye Binding, Analytical Biochemistry, 1976, vol. 72, p. 248-254.
Bulman Page P.C. et al., Efficient Regioselective A-Ring Functionalization of Oestrogens, Tetrahedron, 1990, v46, No. 6, p. 2059-2068.
Database Registry accession No. RN:414892-55-0 Abstract. Retrieved from STN Database Registry May 13, 2002.
Fuks B.B. et al., Activation of the production of the tumor-necrosis factor by the combined action of lipopolysaccharide and muramyl dipeptide in vitro and in vivo, Biull Eksp. Biol. Med., 1987, vol. 104, No. 10, p. 497-499 (abstract).
Gennaro A.R. (ed.), in Remington's Pharmaceutical Sciences, 1985, Mack Publishing Co., p. 1292-1296.
Haldar S. et al., Bcl2 Is the Guardian of Microtubule Integrity, Cancer Research, 1997, vol. 57, p. 229-233.

(Continued)

*Primary Examiner* — Rebecca Anderson
*Assistant Examiner* — Samantha Shterengarts
(74) *Attorney, Agent, or Firm* — Hunton & Williams LLP

(57) ABSTRACT

The present invention involves tetrahydroisoquinoline compounds and their use in the inhibition and/or prevention of tumor growth.

48 Claims, 2 Drawing Sheets

OTHER PUBLICATIONS

Hara H. et al., "A novel synthesis of dibenzo[c,f]-1-azabicyclo[3.3.1]nonanes", Heterocycles, 1981, vol. 15, No. 2, p. 907-910. STN Chemical Abstracts accession No. 1981:407004. XP002508247.

Hara H. et al., "Studies on tetrahydroisoquinolines. XXIV. A synthesis of dibenzo[c,f]- 1-azabicyclo[3.3.1]nonanes and dibenzo[d,g]-1-azabicyclo[4.3.1]decanes", Chemical and Pharmaceutical Bulletin, 19985, vol. 33, No. 7, p. 2705-2711. XP009110016, 1985.

Haranaka K. et al., Antitumour effects of tumour necrosis factor: cytotoxic or necrotizing activity and its mechanism, Ciba Found. Symposium, 1987, vol. 131, p. 140-153.

IUBMB Enzyme Nomenclature entry for E.C. 3.1.6.2, downloaded Mar. 18, 2010.

Iwasa K. et al., "Simple isoquinoline and benzylisoquinoline alkaloids as potential antimicrobial alkaloids as potential antimicrobial, antimalarial, cytotoxic, and anti-HIV agents", Bioorganic and Medicinal Chemistry, 2001, vol. 9, No. 11, p. 2871-2884. XP002509523.

Labrie P. et al., "A Comparative Molecular Field Analysis (CoMFA) and Comparative Molecular Similarity Indices Analysis (CoMSIA) of Anthranilamide Derivatives that are multidrug resistance modulators", Journal of Medicinal Chemistry, 2006, vol. 49, No. 26, p. 7646-7660. XP002509522.

Le Roy I. et al., Genetic Correlation Between Steroid Sulfatase Concentration and Initiation of Attack Behavior in Mice, Behaviour Genetics, Mar. 1999, vol. 29, No. 9, p. 131-136.

Liu Z.-Z. et al., "Synthesis and antitumor activity of simplified ecteinascidin-saframycin analogs", Bioorganic & Medicinal Chemistry Letters, 2006, vol. 16, No. 5, p. 1282-1285. XP002508246.

Lodish H. et al. (ed.), "Molecular Cell Biology", 1995, 3rd edition, WH Freeman and Co., New York, p. 177-181.

Lodish H. et al. (ed.), "Molecular Cell Biology", 1995, 3rd edition, WH Freeman and Co., New York, p. 1051-1122.

Meyers R.A. (ed), Molecular Biology and Biotechnology, VCH, 1995, p. 202,203, 394, 396, 475, 790.

Notification Concerning Transmittal of the Informational Preliminary Report on Patentability mailed Oct. 8, 2009 (20 pages).

Paul W.E. et al., Lymphocyte Responses and Cytokines, Cell, 1994, vol. 76, p. 241-251.

Phillips H.J. Dye Exclusion Tests for Cell Viability, in Tissue culture and applications, editors Kruse D.F. and Patterson M.K., 1973, Academic Press, New York, chapter 5, p. 406-408.

Poole S, Cytokine Therapeutics, TibTech, 1995, vol. 13, No. 3, p. 81-82.

Sakura N. et al., Allergic disease as an association of steroid sulphatase deficiency, J. Inherit. Metab. Dis., Nov. 1997, vol. 20, No. 6, p. 807-810.

Stein C. et al., Cloning and Expression of Human Steroid-sulfase, J. Biol. Chem., 1989, vol. 264, p. 13865-13872.

Suau R. et al., "N-benzylisoquinoline alkaloids from Ceratocapnos heterocarpa", Phytochemistry, (Oxford), 1994, vol. 36, No. 1, p. 241-243. XP007906620.

Tomita M. et al., "Cleavage reaction of norcoraldyne by metallic alkali in liquid ammonia", Yakugaku Zasshi, 1961, vol. 81, p. 108-113. STN Chemical Abstracts accession No. 1961: 70772: XP002508248.

Yen P.H. et al., Cloning and Expression of Steroid Sulfatase cDNA and the Frequent Occurrence of Deletions in STS Deficiency: Implications for X-Y Interchange, Cell, 1987, vol. 49, p. 443-454.

* cited by examiner

COMPOUND

CROSS-REFERENCE TO RELATED APPLICATIONS

This application is a national stage of International Application No. PCT/GB2008/001072, filed Mar. 27, 2008, the disclosure of which is hereby incorporated by reference. This application also claims priority to U.K. Application No. 0706072.6 filed Mar. 28, 2007.

FIELD OF INVENTION

The present invention relates to a compound.
In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHA-S" denotes Dehydroepiandrosterone-Sulphate, "Adiol" denotes Androstenediol, "E1-STS" denotes Oestrone Sulphatase, "DHA-STS" denotes DHA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity.

Much of the oestrone so formed, however, is converted to oestrone sulphate (E1S) and there is now a considerable body of evidence showing that E1S in plasma and tissue acts as a reservoir for the formation of oestrone by the action of oestrone sulphatase.

In this regard, it is now believed that the oestrone sulphatase (E1-STS) pathway—i.e. the hydrolysis of oestrone sulphate to oestrone (E1S to E1) is a major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory.

Thus, oestrogen formation in malignant breast and endometrial tissues via the sulphatase pathway makes a major contribution to the high concentration of oestrogens which are present in these tumours.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

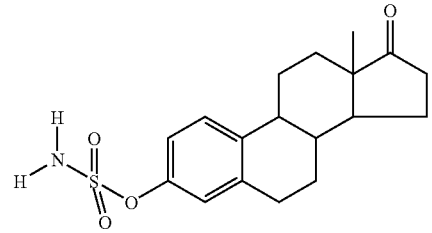 [SMILES: CC12CCC3c4ccc(OS(N)(=O)=O)cc4CCC3C1CCC2=O]

It is known that EMATE is a potent E1-STS inhibitor as it displays more than 99% inhibition of E1-STS activity in intact MCF-7 cells at 0.1 nM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat. Importantly, in post-menopausal women 90% of the androstenediol produced originates from the androgen dehydroepiandrosterone sulphate (DHA-S) which is secreted in large amounts by the adrenal cortex. DHA-S is converted to DHA by DHA sulphatase, which may be the same as, or different from, the enzyme, oestrone sulphatase, which is responsible for the hydrolysis of E1S.

During the last 10-15 years considerable research has also been carried out to develop potent aromatase inhibitors, some of which are now marketed. However, in three recent reports of postmenopausal women with breast cancer who received aromatase inhibitor therapy, plasma E1S concentrations remained between 400-1000 pg/ml.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

SUMMARY ASPECTS OF THE PRESENT INVENTION

The present invention is based on the surprising finding that the compounds of the present invention could be used as effective steroid sulphatase (STS) inhibitors; cell cycling modulators; apoptosis modulators; cell growth modulators; glucose uptake prevention and/or suppression agents; tumour angiogenesis prevention agents or inhibitors; microtubules disruptors; and/or apoptosis inducers.

The compounds of the present invention may comprise other substituents. These other substituents may, for example, further increase the activity of the compounds of the present invention and/or increase stability (ex vivo and/or in vivo).

DETAILED ASPECTS OF THE PRESENT INVENTION

According to one aspect of the present invention, there is provided use of a compound in the manufacture of a medicament to prevent and/or inhibit tumour growth, wherein the compound is of Formula I or Formula II

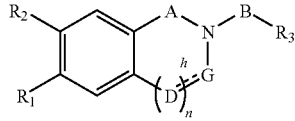

Formula I

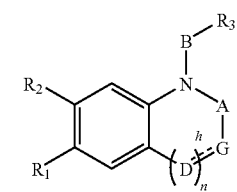

Formula II wherein

A is selected from $CR_{10}R_{11}$, $-S(=O)_2-$, $-NR_{12}-$, and $C=O$, wherein $R_{10}$ and $R_{11}$ independently selected from H, $-OH$, hydrocarbyl, $-CN$, $-NO_2$, and halogens, $R_{12}$ is selected from H and hydrocarbyl;

B is selected from $(CR_{13}R_{14})_{1-3}$, $C=O$, $CR_{15}R_{16}C=O$, $-S(=O)_2-$, $-NR_{17}-$ and $-NR_{18}-C(=O)-$, wherein each of $R_{13}$, $R_{14}$, $R_{15}$ and $R_{16}$ is independently selected from H, $-OH$, hydrocarbyl, $-CN$, $-NO_2$, and halogens, $R_{17}$ and $R_{18}$ are independently selected from H and hydrocarbyl;

$R_1$ is selected from OH, O-hydrocarbyl, O-heterohydrocarbyl, $-SO_2$-hydrocarbyl, $-CH=CH_2$, halogen, $-OSO_2NR_{19}R_{20}$, $-C(=O)-NR_{21}R_{22}$, $-NR_{23}-C(=O)H$ and $-NR_{35}R_{36}$ wherein each of $R_{19}$, $R_{20}$, $R_{21}$, $R_{22}$, $R_{23}$, $R_{35}$ and $R_{36}$ is independently is selected from H and hydrocarbyl;

$R_2$ is selected from H, $-O$-hydrocarbyl, $-S$-hydrocarbyl, hydrocarbyl, $-CN$, $-NO_2$, and halogens, $R_3$ is selected from

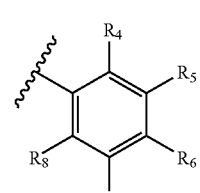

Formula A

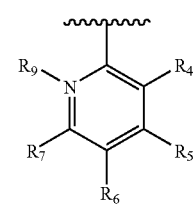

Formula B

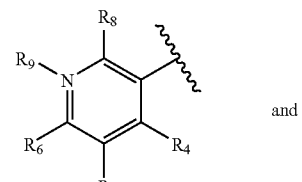

Formula C and

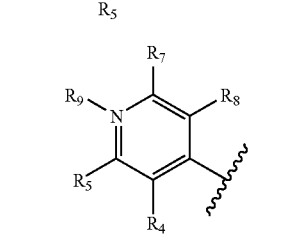

Formula D wherein each of $R_4$, $R_5$, $R_6$, $R_7$ and $R_8$ is independently selected from H, $-OH$, hydrocarbyl, $-O$-hydrocarbyl, $-COOH$ or an ester thereof, halocarbyl, $-O$-halocarbyl, acyl, $-O$-acyl, $-NR_{29}$-acyl, $-O-SO_2NR_{19}R_{20}$, $-NR_{30}R_{31}$, $-NR_{32}SO_2R_{33}$, $-CN$, $-NO_2$, and halogens, $R_9$ is selected from H and hydrocarbyl, and each $R_{29}$ to $R_{33}$ is independently selected from H and hydrocarbyl; and wherein two or more of $R_4$, $R_5$, $R_6$, $R_7$, $R_8$ and $R_9$ may together form a ring;

wherein h is an optional bond, wherein G is $CR_{24}R_{25}$, wherein $R_{24}$ and $R_{25}$ independently selected from H, $-OH$, hydrocarbyl, $-CN$, $-NO_2$, and halogens, or wherein when h is present G is $CR_{24}$, wherein $R_{24}$ is selected from H, $-OH$, hydrocarbyl, $-CN$, $-NO_2$, and halogens;

n is 0, 1 or 2, each D is independently selected from O, $NR_{26}$ and $CR_{27}R_{28}$, wherein each $R_{26}$ is independently selected from H and hydrocarbyl; and each $R_{27}$ and $R_{28}$ is independently selected from H, $-OH$, hydrocarbyl, $-CN$, $-NO_2$, and halogens.

According to one aspect of the present invention, there is provided a compound of Formula I or Formula II

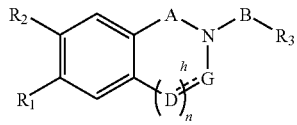

Formula I

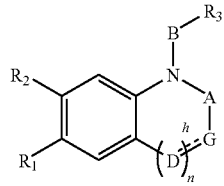

Formula II wherein

A is selected from $CR_{10}R_{11}$, —S(=O)$_2$—, —$NR_{12}$—, and C=O, wherein $R_{10}$ and $R_{11}$ independently selected from H, —OH, hydrocarbyl, —CN, —NO$_2$, and halogens, $R_{12}$ is selected from H and hydrocarbyl;

B is selected from $(CR_{13}R_{14})_{1-3}$, C=O, $CR_{15}R_{16}$C=O, —S(=O)$_2$—, —$NR_{17}$— and —$NR_{18}$—C(=O)—, wherein each of $R_{13}$, $R_{14}$, $R_{15}$ and $R_{16}$ is independently selected from H, —OH, hydrocarbyl, —CN, —NO$_2$, and halogens, $R_{17}$ and $R_{18}$ are independently selected from H and hydrocarbyl;

$R_1$ is selected from OH, O-hydrocarbyl, O-heterohydrocarbyl, —SO$_2$-hydrocarbyl, —CH=CH$_2$, halogen, —OSO$_2$NR$_{19}$R$_{20}$, —C(=O)—NR$_{21}$R$_{22}$, —NR$_{23}$—C(=O)H and —NR$_{35}$R$_{36}$ wherein each of $R_{19}$, $R_{20}$, $R_{21}$, $R_{22}$, $R_{23}$, $R_{35}$ and $R_{36}$ is independently is selected from H and hydrocarbyl;

$R_2$ is selected from H, —O-hydrocarbyl, —S-hydrocarbyl, hydrocarbyl, —CN, —NO$_2$, and halogens, $R_3$ is selected from

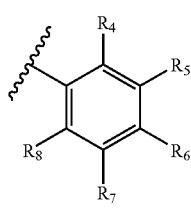

Formula A

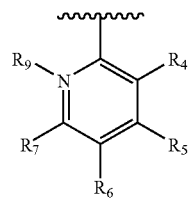

Formula B

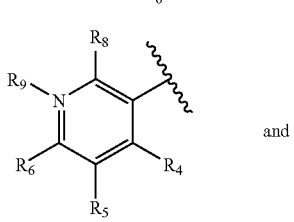

and

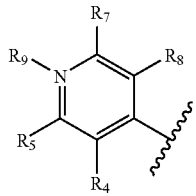

Formula D wherein each of $R_4$, $R_5$, $R_6$, $R_7$ and $R_8$ is independently selected from H, —OH, hydrocarbyl, —O-hydrocarbyl, —COOH or an ester thereof, halocarbyl, —O-halocarbyl, acyl, —O-acyl, —NR$_{29}$-acyl, —O—SO$_2$NR$_{19}$R$_{20}$, —NR$_{30}$R$_{31}$, —NR$_{32}$SO$_2$R$_{33}$, —CN, —NO$_2$, and halogens, $R_9$ is selected from H and hydrocarbyl, and each $R_{29}$ to $R_{33}$ is independently selected from H and hydrocarbyl; and wherein two or more of $R_4$, $R_5$, $R_6$, $R_7$, $R_8$ and $R_9$ may together form a ring;

wherein when $R_1$ is OH and $R_3$ is of Formula D, (i) at least one of $R_4$, $R_5$, $R_6$, $R_7$ and $R_8$ is independently selected from halocarbyl, —O-halocarbyl, —O-acyl, —NR$_{29}$-acyl, —O—SO$_2$NR$_{19}$R$_{20}$, —NR$_{30}$R$_{31}$, —NR$_{32}$SO$_2$R$_{33}$, —CN, and halogens, or (ii) two or more of $R_4$, $R_5$, $R_6$, $R_7$ and $R_8$ together form a ring, or (iii) at least three of $R_4$, $R_5$, $R_6$, $R_7$ and $R_8$ are independently selected from —OH, hydrocarbyl, —O-hydrocarbyl, halocarbyl, —O-halocarbyl, —O-acyl, —NR$_{29}$-acyl, —O—SO$_2$NR$_{19}$R$_{20}$, —NR$_{30}$R$_{31}$, —NR$_{32}$SO$_2$R$_{33}$, —CN, —NO$_2$, and halogens wherein h is an optional bond, wherein G is $CR_{24}R_{25}$, wherein $R_{24}$ and $R_{25}$ independently selected from H, —OH, hydrocarbyl, —CN, —NO$_2$, and halogens, or wherein when h is present G is $CR_{24}$, wherein $R_{24}$ is selected from H, —OH, hydrocarbyl, —CN, —NO$_2$, and halogens;

n is 0, 1 or 2, each D is independently selected from O, NR$_{26}$ and $CR_{27}R_{28}$, wherein each $R_{26}$ is independently selected from H and hydrocarbyl; and each $R_{27}$ and $R_{28}$ is independently selected from H, —OH, hydrocarbyl, —CN, —NO$_2$, and halogens.

According to one aspect of the present invention, there is provided a pharmaceutical composition comprising (a) a compound as defined herein and (b) a pharmaceutically acceptable carrier, diluent, excipient or adjuvant.

According to one aspect of the present invention, there is provided a (i) compound as defined herein, or (ii) composition as defined herein, for use in medicine.

According to one aspect of the present invention, there is provided use of (i) a compound as defined herein, or (ii) a composition as defined herein, in the manufacture of a medicament to prevent and/or inhibit tumour growth.

According to one aspect of the present invention, there is provided use of (i) a compound as defined herein, or (ii) a composition as defined herein, in the manufacture of a medicament for use in the therapy of a condition or disease associated with one or more of steroid sulphatase (STS) activity; carbonic anhydrase (CA) activity; cell cycling; apoptosis; cell growth; glucose uptake by a tumour; tumour angiogenesis; microtubules formation; and apoptosis.

According to one aspect of the present invention, there is provided use of (i) a compound as defined herein, or (ii) a composition as defined herein, in the manufacture of a medicament for use in the therapy of a condition or disease associated with one or more of adverse steroid sulphatase (STS) activity; adverse carbonic anhydrase (CA) activity; cell cycling; apoptosis; cell growth; glucose uptake by a tumour; tumour angiogenesis; microtubules formation; and apoptosis.

According to one aspect of the present invention, there is provided use of (i) a compound as defined herein, or (ii) a composition as defined herein, in the manufacture of a medicament for one or more of inhibiting steroid sulphatase (STS) activity; inhibiting carbonic anhydrase (CA) activity; modulating cell cycling; modulating apoptosis; modulating cell growth; preventing and/or suppressing glucose uptake by a tumour; preventing and/or inhibiting tumour angiogenesis; disrupting microtubules; and inducing apoptosis.

According to one aspect of the present invention, there is provided use of (i) a compound as defined herein, or (ii) a composition as defined herein, in the manufacture of a medicament for inhibiting steroid sulphatase (STS) activity.

According to one aspect of the present invention, there is provided use of (i) a compound as defined herein, or (ii) a composition as defined herein, in the manufacture of a medicament for inhibiting carbonic anhydrase (CA) activity.

According to one aspect of the present invention, there is provided use of (i) a compound as defined herein, or (ii) a composition as defined herein, in the manufacture of a medicament for inhibiting and/or preventing tumour angiogenesis.

According to one aspect of the present invention, there is provided use of (i) a compound as defined herein, or (ii) a composition as defined herein, in the manufacture of a medicament for modulating cell growth.

According to one aspect of the present invention, there is provided a method of treatment comprising administering to a subject in need of treatment (i) a compound as defined herein, or (ii) a composition as defined herein.

According to one aspect of the present invention, there is provided a method of treatment comprising administering to a subject in need of treatment (i) a compound as defined herein, or (ii) a composition as defined herein, in order to inhibit steroid sulphatase (STS) activity; to inhibit carbonic anhydrase (CA) activity, modulate cell cycling; modulate apoptosis; modulate cell growth; prevent and/or suppress glucose uptake by a tumour; prevent and/or inhibit tumour angiogenesis; disrupt microtubules; and/or induce apoptosis.

According to one aspect of the present invention, there is provided a method comprising (a) performing an assay for one or more of steroid sulphatase (STS) inhibition; carbonic anhydrase (CA) inhibition, cell cycling modulation; apoptosis modulation; cell growth modulation; prevention and/or suppression of glucose uptake by a tumour; tumour angiogenesis prevention and/or inhibition; microtubules disruption; and apoptosis induction, with one or more candidate compounds defined herein; (b) determining whether one or more of said candidate compounds is/are capable of one or more of steroid sulphatase (STS) inhibition; carbonic anhydrase (CA) inhibition, cell cycling modulation; apoptosis modulation; cell growth modulation; prevention and/or suppression of glucose uptake by a tumour; tumour angiogenesis prevention and/or inhibition; microtubules disruption; and apoptosis induction; and (c) selecting one or more of said candidate compounds that is/are capable of one or more of steroid sulphatase (STS) inhibition; carbonic anhydrase (CA) inhibition, cell cycling modulation; apoptosis modulation; cell growth modulation; prevention and/or suppression of glucose uptake by a tumour; tumour angiogenesis prevention and/or inhibition; microtubules disruption; and apoptosis induction.

In any one of the methods of the present invention, one or more additional steps may be present. For example, the method may also include the step of modifying the identified candidate compound (such as by chemical and/or enzymatic techniques) and the optional additional step of testing that modified compound for one or more of steroid sulphatase (STS) inhibition; carbonic anhydrase (CA) inhibition, cell cycling modulation; apoptosis modulation; cell growth modulation; prevention and/or suppression of glucose uptake by a tumour; tumour angiogenesis prevention and/or inhibition; microtubules disruption; and apoptosis induction. By way of further example, the method may also include the step of determining the structure (such as by use of crystallographic techniques) of the identified candidate compound and then performing computer modeling studies—such as to further increase its action. Thus, the present invention also encompasses a computer having a dataset (such as the crystallographic co-ordinates) for said identified candidate compound. The present invention also encompasses that identified candidate compound when presented on a computer screen for the analysis thereof—such as enzyme and/or protein binding studies.

According to one aspect of the present invention, there is provided a compound identified by the method of the present invention.

The present invention also encompasses the novel compounds of the present invention (such as those presented herein), as well as processes for making same (such as the processes presented herein) as well as novel intermediates (such as those presented herein) for use in those processes.

For ease of reference, these and further aspects of the present invention are now discussed under appropriate section headings. However, the teachings under each section are not necessarily limited to each particular section.

Some Advantages

One key advantage of the present invention is that the compounds of the present invention can prevent and/or inhibit tumour angiogenesis.

One key advantage of the present invention is that the compounds of the present invention can modulate cell cycling.

One key advantage of the present invention is that the compounds of the present invention can modulate apoptosis.

One key advantage of the present invention is that the compounds of the present invention can modulate cell growth.

One key advantage of the present invention is that the compounds of the present invention can prevent and/or suppress glucose uptake by a tumour.

One key advantage of the present invention is that the compounds of the present invention can inhibit steroid sulphatase (STS) activity.

One key advantage of the present invention is that the compounds of the present invention can disrupt microtubules.

In this respect, microtubules, together with microfilaments and intermediate filaments form part of the cytoskeletal system of a cell. Microtubules are responsible for many of cell movements-examples include the beating of cilia and flagella and the transport of membrane vesicles in the cytoplasm. All these movements result from the polymerisation and depolymerisation of microtubules or the actions of the microtubule motor proteins dynein and kinesins. Some other cell movements, such as the alignment and separation of chromosomes during meiosis and mitosis result from both mechanisms. Microtubules also direct cell movement but in some cases, microtubules serve purely structural functions.

A microtubule is composed of subunits that are heterodimers of α-tubulin and β-tubulin monomers. There are two populations of microtubules: stable, long-lived microtubules and dynamic, short lived microtubules. Dynamic microtubules are found when the microtubule structures need to assemble and dissemble quickly. For example, during mitosis, the cytosolic microtubule network characteristic of interphase cells disappears and the tubulin from it is used to form the spindle apparatus which partitions chromosomes equally to the daughter cells. When mitosis is complete, the spindle disassembles and the interphase microtubule network reforms.

Drugs that inhibit mitosis provide a useful means to manipulate the microtubules in a cell. Three drugs: colchicine, vinblastine and taxol—all purified from plants—have proved to be very powerful probes of microtubule function partly because they bind only to tubulin or microtubules and not to other proteins and also because their concentrations in cells can be easily controlled.

Because of their effects on mitosis, microtubule inhibitors have been widely used to treat illness and more recently as anticancer agents, since blockage of spindle formation will preferentially inhibit rapidly dividing cells like cancer cells. A highly effective anti-ovarian cancer agent is taxol. In ovarian cancer cells, which undergo rapid cell divisions, mitosis is blocked by taxol treatment while other functions carried out by intact microtubules are not affected. A comprehensive review of microtubules can be found in "Molecular Cell Biology" (Ed: Lodish et at 1995 WH Freeman and Co. New York pp 1051-1122).

One key advantage of the present invention is that the compounds of the present invention can induce apoptosis.

Apoptosis is induced by MT-targeting drugs, a process which may involve the phosphorylation (and inactivation) of the apoptosis regulator, the bcl-2 protein (Halder, Cancer Res. 57: 229, 1997).

The present invention is based on the surprising finding that the compound provides an effective treatment of cancer.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity. Here, by the term "non-oestrogenic" means exhibiting no or substantially no systemic oestrogenic activity, such as that determined by Protocol 4.

For some applications, the compounds have an oestrogenic effect.

Another advantage is that some of the compounds may not be capable of being metabolised to compounds which display or induce hormonal activity.

For some applications, preferably the compounds have a reversible action.

For some applications, preferably the compounds have an irreversible action.

Some of the compounds of the present invention are also advantageous in that they may be orally active.

Some of the compounds of the present invention may useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. acne, psoriasis and contact dermatitis; graft versus host disease; eczema; asthma and organ rejection following transplantation. The compounds of the present invention are useful particularly when pharmaceuticals may need to be administered from an early age.

In one embodiment, the compounds of the present invention are useful for the treatment of breast cancer.

Thus, some of the compounds of the present invention are also believed to have therapeutic uses other than for the treatment of endocrine-dependent cancers, such as the treatment of autoimmune diseases.

For ease of reference, these and further aspects of the present invention are now discussed under appropriate section headings. However, the teachings under each section are not necessarily limited to each particular section.

Preferable Aspects

Use

As described above the present invention provides use of a compound in the manufacture of a medicament to prevent and/or inhibit tumour growth, wherein the compound is of Formula I or Formula II

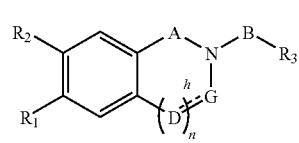

Formula I

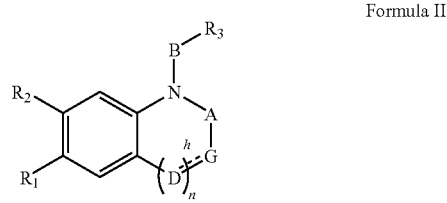

Formula II wherein

A is selected from $CR_{10}R_{11}$, —$S(=O)_2$—, —$NR_{12}$—, and $C=O$, wherein $R_{10}$ and $R_{11}$ independently selected from H, —OH, hydrocarbyl, —CN, —$NO_2$, and halogens, $R_{12}$ is selected from H and hydrocarbyl;

B is selected from $(CR_{13}R_{14})_{1-3}$, $C=O$, $CR_{15}R_{16}C=O$, —$S(=O)_2$—, —$NR_{17}$— and —$NR_{18}$—$C(=O)$—, wherein each of $R_{13}$, $R_{14}$, $R_{15}$ and $R_{16}$ is independently selected from H, —OH, hydrocarbyl, —CN, —$NO_2$, and halogens, $R_{17}$ and $R_{18}$ are independently selected from H and hydrocarbyl;

$R_1$ is selected from OH, O-hydrocarbyl, O-heterohydrocarbyl, —$SO_2$-hydrocarbyl, —$CH=CH_2$, halogen, —$OSO_2NR_{19}R_{20}$, —$C(=O)$—$NR_{21}R_{22}$, —$NR_{23}$—$C(=O)H$ and —$NR_{35}R_{36}$ wherein each of $R_{19}$, $R_{20}$, $R_{21}$, $R_{22}$, $R_{23}$, $R_{35}$ and $R_{36}$ is independently is selected from H and hydrocarbyl;

$R_2$ is selected from H, —O-hydrocarbyl, —S-hydrocarbyl, hydrocarbyl, —CN, —$NO_2$, and halogens, $R_3$ is selected from

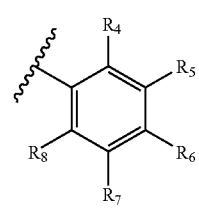

Formula A

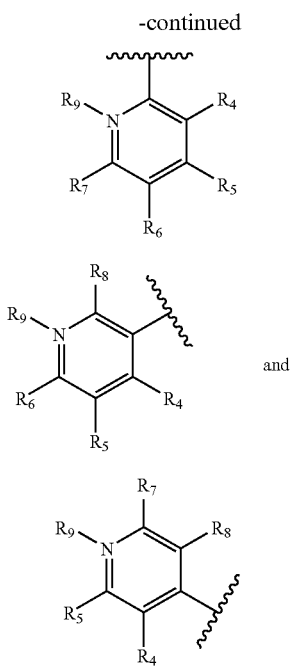

Formula B and

Formula C

Formula D wherein each of $R_4$, $R_5$, $R_6$, $R_7$ and $R_8$ is independently selected from H, —OH, hydrocarbyl, —O-hydrocarbyl, —COOH or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens, $R_9$ is selected from H and hydrocarbyl, and each $R_{29}$ to $R_{33}$ is independently selected from H and hydrocarbyl; and wherein two or more of $R_4$, $R_5$, $R_6$, $R_7$, $R_8$ and $R_9$ may together form a ring;

wherein h is an optional bond, wherein G is $CR_{24}R_{25}$, wherein $R_{24}$ and $R_{25}$ independently selected from H, —OH, hydrocarbyl, —CN, —$NO_2$, and halogens, or wherein when h is present G is $CR_{24}$, wherein $R_{24}$ is selected from H, —OH, hydrocarbyl, —CN, —$NO_2$, and halogens;

n is 0, 1 or 2, each D is independently selected from O, $NR_{26}$ and $CR_{27}R_{28}$, wherein each $R_{26}$ is independently selected from H and hydrocarbyl; and each $R_{27}$ and $R_{28}$ is independently selected from H, —OH, hydrocarbyl, —CN, —$NO_2$, and halogens.

In this aspect preferably $R_1$ is selected from OH, O-hydrocarbyl, O-heterohydrocarbyl, —CH═$CH_2$, halogen, —$OSO_2NR_{19}R_{20}$, —C(═O)—$NR_{21}R_{22}$, —$NR_{23}$—C(═O)H and —$NR_{35}R_{36}$ Preferably when $R_1$ is OH and $R_3$ is of Formula D, (i) at least one of $R_4$, $R_5$, $R_6$, $R_7$ and $R_8$ is independently selected from halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, and halogens, or (ii) two or more of $R_4$, $R_5$, $R_6$, $R_7$ and $R_8$ together form a ring, or (iii) at least three of $R_4$, $R_5$, $R_6$, $R_7$ and $R_8$ are independently selected from —OH, hydrocarbyl, —O-hydrocarbyl, halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens.

The term "halocarbyl" as used herein means a group comprising at least C and halogen and may optionally comprise H and/or one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the halocarbyl group comprises more than one C then those carbons need not necessarily be linked to each other. For example, at least two of the carbons may be linked via a suitable element or group. Thus, the halocarbyl group may contain hetero atoms. Suitable hetero atoms will be apparent to those skilled in the art and include, for instance, sulphur, nitrogen and oxygen. In one preferred aspect the "halocarbyl" is a halohydrocarbyl group, that is a group comprising at least C, halogen and H and may comprises one or more other suitable substituents, such as those listed herein.

The term "heterohydrocarbyl" as used herein means a group comprising at least C, H and one of sulphur, nitrogen and oxygen and may optionally comprises one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the halocarbyl group comprises more than one C then those carbons need not necessarily be linked to each other. For example, at least two of the carbons may be linked via a suitable element or group.

The term "hydrocarbyl group" as used herein means a group comprising at least C and H and may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

Compound

As described above the present invention provides a compound of Formula I or Formula II

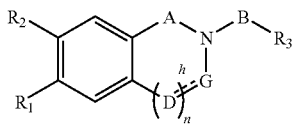

Formula I

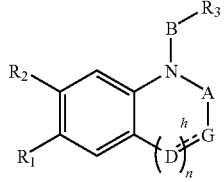

Formula II wherein

A is selected from $CR_{10}R_{11}$, —S(═O)$_2$—, —$NR_{12}$—, and C═O, wherein $R_{10}$ and $R_{11}$ independently selected from H, —OH, hydrocarbyl, —CN, —$NO_2$, and halogens, $R_{12}$ is selected from H and hydrocarbyl;

B is selected from $(CR_{13}R_{14})_{1-3}$, C═O, $CR_{15}R_{16}$C═O, —S(═O)$_2$—, —$NR_{17}$— and —$NR_{18}$—C(═O)—, wherein each of $R_{13}$, $R_{14}$, $R_{15}$ and $R_{16}$ is independently selected from H, —OH, hydrocarbyl, —CN, —$NO_2$, and halogens, $R_{17}$ and $R_{18}$ are independently selected from H and hydrocarbyl;

$R_1$ is selected from OH, O-hydrocarbyl, O-heterohydrocarbyl, —$SO_2$-hydrocarbyl, —CH=$CH_2$, halogen, —$OSO_2NR_{19}R_{20}$, —C(=O)—$NR_{21}R_{22}$, —$NR_{23}$—C(=O)H and —$NR_{35}R_{36}$ wherein each of $R_{19}$, $R_{20}$, $R_{21}$, $R_{22}$, $R_{23}$, $R_{35}$ and $R_{36}$ is independently is selected from H and hydrocarbyl;

$R_2$ is selected from H, —O-hydrocarbyl, —S-hydrocarbyl, hydrocarbyl, —CN, —$NO_2$, and halogens, $R_3$ is selected from

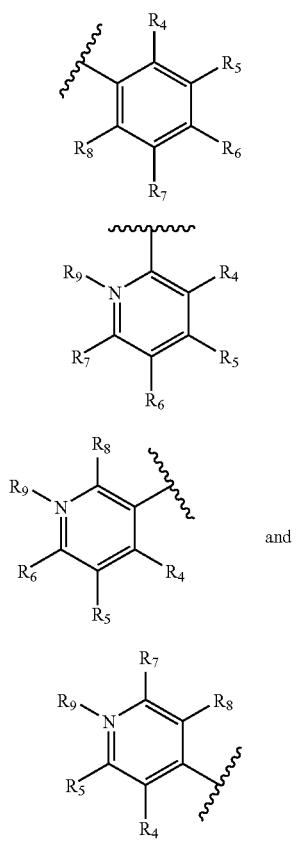

Formula A

Formula B

Formula C and

Formula D wherein each of $R_4$, $R_5$, $R_6$, $R_7$ and $R_8$ is independently selected from H, —OH, hydrocarbyl, —O-hydrocarbyl, —COON or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens, $R_9$ is selected from H and hydrocarbyl, and each $R_{29}$ to $R_{33}$ is independently selected from H and hydrocarbyl; and wherein two or more of $R_4$, $R_5$, $R_6$, $R_7$, $R_8$ and $R_9$ may together form a ring;

wherein when $R_1$ is OH and $R_3$ is of Formula D, (i) at least one of $R_4$, $R_5$, $R_6$, $R_7$ and $R_8$ is independently selected from halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, and halogens, or (ii) two or more of $R_4$, $R_5$, $R_6$, $R_7$ and $R_8$ together form a ring, or (iii) at least three of $R_4$, $R_5$, $R_6$, $R_7$ and $R_8$ are independently selected from —OH, hydrocarbyl, —O-hydrocarbyl, halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens wherein h is an optional bond, wherein G is $CR_{24}R_{25}$, wherein $R_{24}$ and $R_{25}$ independently selected from H, —OH, hydrocarbyl, —CN, —$NO_2$, and halogens, or wherein when h is present G is $CR_{24}$, wherein $R_{24}$ is selected from H, —OH, hydrocarbyl, —CN, —$NO_2$, and halogens;

n is 0, 1 or 2, each D is independently selected from O, $NR_{26}$ and $CR_{27}R_{28}$, wherein each $R_{26}$ is independently selected from H and hydrocarbyl; and each $R_{27}$ and $R_{28}$ is independently selected from H, —OH, hydrocarbyl, —CN, —$NO_2$, and halogens In one preferred aspect the compound is capable of one or more of inhibiting steroid sulphatase (STS) activity; modulating cell cycling; modulating apoptosis; modulating cell growth; preventing and/or suppressing glucose uptake by a tumour; preventing and/or inhibiting tumour angiogenesis; disrupting microtubules; and inducing apoptosis.

In one preferred embodiment of the present invention, one or more of the hydrocarbyl groups is a hydrocarbon group. In one preferred embodiment of the present invention, each hydrocarbyl group is a hydrocarbon group.

Here the term "hydrocarbon" means any one of an alkyl group, an alkenyl group, an alkynyl group, an acyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

The alkyl group may be selected from one of $C_1$-$C_{20}$ alkyl, $C_1$-$C_{10}$ alkyl, $C_1$-$C_5$ alkyl, and $C_1$-$C_3$ alkyl. In one aspect the alkyl group is $C_{1-10}$ alkyl. In one aspect the alkyl group is $C_{1-5}$ alkyl. In one aspect the alkyl group is $C_{1-3}$ alkyl. Preferred alkyl groups are —$CH_3$ and —$CH_2CH_3$.

In one preferred embodiment of the present invention, one or more of the hydrocarbyl groups is an oxyhydrocarbyl group. In one preferred embodiment of the present invention, each hydrocarbyl group is an oxyhydrocarbyl group.

The term "oxyhydrocarbyl group" as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one preferred embodiment of the present invention, the or each or one or more of the oxyhydrocarbyl groups is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Preferably the oxyhydrocarbyl group is an alkoxy group. Preferably the oxyhydrocarbyl group is of the formula $C_{1-6}O$ (such as a $C_{1-3}O$).

In one aspect the compounds is of Formula II

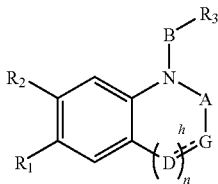

Formula II

Preferably the compound is of Formula I

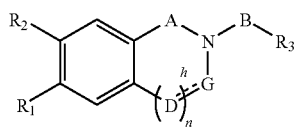

Formula I

A

As discussed herein A is selected from $CR_{10}R_{11}$, —S(=O)$_2$—, —$NR_{12}$—, and C=O, wherein $R_{10}$ and $R_{11}$ independently selected from H, —OH, hydrocarbyl, —CN, —$NO_2$, and halogens, $R_{12}$ is selected from H and hydrocarbyl.

In a preferred aspect A is selected from $CR_{10}R_{11}$ and C=O, wherein $R_{10}$ and $R_{11}$ independently selected from H, —OH, hydrocarbyl, —CN, —$NO_2$, and halogens. More preferably A is selected from $CR_{10}R_{11}$ and C=O, wherein $R_{10}$ and $R_{11}$ independently selected from H, —OH, hydrocarbyl and halogens, for example A may be is selected from $CH_2$ and C=O.

B

As discussed herein B is selected from $(CR_{13}R_{14})_{1-3}$, C=O, $CR_{15}R_{16}$C=O, —S(=O)$_2$—, —$NR_{17}$— and —$NR_{18}$—C(=O)—, wherein each of $R_{13}$, $R_{14}$, $R_{15}$ and $R_{16}$ is independently selected from H, —OH, hydrocarbyl, —CN, —$NO_2$, and halogens, $R_{17}$ and $R_{18}$ are independently selected from H and hydrocarbyl;

In one preferred aspect B is selected from $(CR_{13}R_{14})_{1-3}$, C=O, and —S(=O)$_2$—, wherein each of $R_{13}$ and $R_{14}$, is independently selected from H, —OH, hydrocarbyl, —CN, —$NO_2$, and halogens. Preferably B is selected from $CR_{13}R_{14}$, C=O, and —S(=O)$_2$—, wherein each of $R_{13}$ and $R_{14}$, is independently selected from H, —OH, hydrocarbyl, —CN, —$NO_2$, and halogens. More preferably B is selected from $(CH_2)_{1-3}$, C=O, and —S(=O)$_2$—, such as $CH_2$, C=O, and —S(=O)$_2$—.

Preferably each of $R_{13}$ and $R_{14}$ is independently selected from H and hydrocarbyl. In one aspect each of $R_{13}$ and $R_{14}$ is independently selected hydrocarbyl. In one preferred embodiment of the present invention each of $R_{13}$ and $R_{14}$ is independently selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect each of $R_{13}$ and $R_{14}$ is independently selected from H and $C_{1-10}$ alkyl. In one aspect each of $R_{13}$ and $R_{14}$ is independently selected from $C_{1-10}$ alkyl. In one aspect each of $R_{13}$ and $R_{14}$ is independently selected from H and $C_{1-5}$ alkyl. In one aspect each of $R_{13}$ and $R_{14}$ is independently selected from $C_{1-5}$ alkyl. In one aspect each of $R_{13}$ and $R_{14}$ is independently selected from H and $C_{1-3}$ alkyl. In one aspect $R^5$ is $C_{1-3}$ alkyl. Preferably each of $R_{13}$ and $R_{14}$ is —$CH_3$.

R1

As discussed herein, $R_1$ is selected from OH, O-hydrocarbyl, O-heterohydrocarbyl, —$SO_2$-hydrocarbyl, —CH=$CH_2$, halogen, —$OSO_2NR_{19}R_{20}$, —C(=O)—$NR_{21}R_{22}$, —$NR_{23}$—C(=O)H and —$NR_{35}R_{36}$ wherein each of $R_{19}$, $R_{20}$, $R_{21}$, $R_{22}$, $R_{23}$, R35 and $R_{36}$ is independently is selected from H and hydrocarbyl.

In one aspect, $R_1$ is selected from OH, O-heterohydrocarbyl, —$SO_2$-hydrocarbyl, —CH=$CH_2$, halogen, —$OSO_2NR_{19}R_{20}$, —C(=O)—$NR_{21}R_{22}$, —$NR_{23}$—C(=O)H and —$NR_{35}R_{36}$ wherein each of $R_{19}$, $R_{20}$, $R_{21}$, $R_{22}$, $R_{23}$, $R_{35}$ and $R_{36}$ is independently is selected from H and hydrocarbyl.

In one preferred aspect $R_1$ is selected from OH, O-heterohydrocarbyl, and —$OSO_2NR_{19}R_{20}$, wherein each of $R_{19}$ and $R_{20}$ is independently is selected from H and hydrocarbyl.

In one aspect $R^1$ is a —$OSO_2NR_{19}R_{20}$ group, namely a sulphamate group.

The term "sulphamate" includes an ester of sulphamic acid, or an ester of an N-substituted derivative of sulphamic acid, or a salt thereof.

In one aspect $R^1$ is a sulphamate group. In this aspect the compound of the present invention may be referred to as a sulphamate compound.

Preferably the sulphamate group of $R^1$, is a sulphamate group of the formula

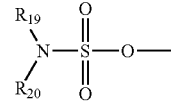

wherein $R_{19}$ and $R_{20}$ are independently selected from H or a hydrocarbyl group.

Preferably $R_{19}$ and $R_{20}$ are independently selected from H, alkyl, cycloalkyl, alkenyl, acyl and aryl, or combinations thereof, or together represent alkylene, wherein the or each alkyl or cycloalkyl or alkenyl or aryl optionally contains one or more hetero atoms or groups.

When substituted, the N-substituted compounds of this invention may contain one or two N-alkyl, N-alkenyl, N-cycloalkyl, N-acyl, or N-aryl substituents, preferably containing or each containing a maximum of 10 carbon atoms. When $R_{19}$ and/or $R_{20}$ is alkyl, the preferred values are those where $R_{19}$ and $R_{20}$ are each independently selected from lower alkyl groups containing from 1 to 5 carbon atoms, that is to say methyl, ethyl, propyl etc. Preferably $R_{19}$ and $R_{20}$ are both methyl. When $R_{19}$ and/or $R_{20}$ is aryl, typical values are phenyl and tolyl (-$PhCH_3$; o-, m- or p-). Where $R_{19}$ and $R_{20}$ represent cycloalkyl, typical values are cyclopropyl, cyclopentyl, cyclohexyl etc. When joined together $R_{19}$ and $R_{20}$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino.

Within the values alkyl, cycloalkyl, alkenyl, acyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl. A non-limiting example of a hydrocarbyl group is an acyl group.

In some embodiments, the sulphamate group may form a ring structure by being fused to (or associated with) one or more atoms in or on the steroidal ring system.

In some embodiments, there may be more than one sulphamate group. By way of example, there may be two sulphamates (i.e. bis-sulphamate compounds).

In some preferred embodiments, at least one of $R_{19}$ and $R_{20}$ is H.

In some preferred embodiments, each of $R_{19}$ and $R_{20}$ is H.

In some preferred embodiments $R^1$ is a sulphamate group and the compound is suitable for use as an inhibitor of oestrone sulphatase (E.C. 3.1.6.2).

In some preferred embodiments if the sulphamate group on the sulphamate compound were to be replaced with a sulphate group to form a sulphate compound then the sulphate compound would be hydrolysable by a steroid sulphatase enzyme (E.C.3.1.6.2).

In some preferred embodiments if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 mM.

In some preferred embodiments if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 μM.

O-hydrocarbyl

In one preferred aspect $R_1$ is O-hydrocarbyl.

Preferably $R_1$ is selected from or the O-hydrocarbyl group is selected from O-aryl groups such as an O-phenyl and O-benzyl groups, and O-alkyl groups.

Preferably $R_1$ is selected from or the O-hydrocarbyl group is selected from an alkyl group and a benzyl.

The hydrocarbyl of the O-hydrocarbyl group may be selected from one of $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

O-heterohydrocarbyl

In one preferred aspect $R_1$ is O-heterohydrocarbyl.

Preferably $R_1$ is selected from or the O-heterohydrocarbyl group is selected from O-acyl groups such as an O-acetyl group.

Preferably $R_1$ is selected from or the O-heterohydrocarbyl group is selected from an alkoxy benzyl group. Preferably the alkoxy benzyl group is a C1-6 alkoxy benzyl group. More preferably the alkoxy benzyl group is a methoxy benzyl group, such as a 2-methoxy benzyl group or a 3-methoxy benzyl group.

In one preferred aspect $R_1$ is selected from OH, O-acetyl group —$OSO_2NH_2$, and methoxy benzyl groups.

—$OC(=O)NR_{21}R_{22}$

In one preferred aspect $R_1$ is —$OC(=O)NR_{21}R_{22}$, wherein $R_{21}$ and $R_{22}$ are independently selected from H and hydrocarbyl Preferably $R_{21}$ and $R_{22}$ are independently selected from H and hydrocarbyl. In one aspect $R_{21}$ and $R_{22}$ are independently selected from hydrocarbyl. In one preferred embodiment of the present invention $R_{21}$ and $R_{22}$ are independently selected from one of H, $C_1$-$C_{20}$ hydrocarbyl, $C_1$-$C_{10}$ hydrocarbyl, $C_1$-$C_5$ hydrocarbyl, $C_1$-$C_3$ hydrocarbyl, hydrocarbon groups, $C_1$-$C_{20}$ hydrocarbon, $C_1$-$C_{10}$ hydrocarbon, $C_1$-$C_5$ hydrocarbon, $C_1$-$C_3$ hydrocarbon, alkyl groups, $C_1$-$C_{20}$ alkyl, $C_1$-$C_{10}$ alkyl, $C_1$-$C_5$ alkyl, and $C_1$-$C_3$ alkyl.

In one aspect $R_{21}$ and $R_{22}$ are independently selected from H and $C_{1-10}$ alkyl. In one aspect $R_{21}$ and $R_{22}$ are independently selected from $C_{1-10}$ alkyl. In one aspect $R_{21}$ and $R_{22}$ are independently selected from H and $C_{1-5}$ alkyl. In one aspect $R_{21}$ and $R_{22}$ are independently selected from $C_{1-5}$ alkyl. In one aspect $R_{21}$ and $R_{22}$ are independently selected from H and $C_{1-3}$ alkyl. In one aspect $R_{21}$ and $R_{22}$ are independently selected from $C_{1-3}$ alkyl. Preferably $R_{21}$ and $R_{22}$ are both H.

$R_2$

As discussed herein $R_2$ is selected from H, —O-hydrocarbyl, —S-hydrocarbyl, hydrocarbyl, —CN, —$NO_2$, and halogens, In one preferred aspect $R_2$ is selected from —O-hydrocarbyl groups. Preferably the —O-hydrocarbyl group is an alkoxy group. Preferably $R_2$ is of the formula $CO_{1-6}$ (such as a $C_{1-3}O$). Preferably $R_2$ is of the formula —$O(CH_2)_{1-10}CH_3$, —$O(CH_2)_{1-5}CH_3$, —$O(CH_2)_{1-2}CH_3$. In a highly preferred aspect $R_2$ is methoxy.

In one preferred embodiment of the present invention, $R_2$ is a hydrocarbon group. Preferably $R_2$ is an alkyl group. Preferably the alkyl group is a $C_{1-6}$ alkyl group (such as a $C_{1-3}$ alkyl group). Preferably the hydrocarbyl group $R_2$ is of the formula —$(CH_2)_{1-10}CH_3$, —$(CH_2)_{1-5}CH_3$, —$(CH_2)_{1-2}CH_3$. In a highly preferred aspect $R_2$ is ethyl.

In one preferred embodiment of the present invention $R_2$ is selected from one of $C_1$-$C_{10}$ hydrocarbyl, $C_1$-$C_5$ hydrocarbyl, $C_1$-$C_3$ hydrocarbyl, hydrocarbon groups, $C_1$-$C_{10}$ hydrocarbon, $C_1$-$C_5$ hydrocarbon, $C_1$-$C_3$ hydrocarbon, alkyl groups, $C_1$-$C_{10}$ alkyl, $C_1$-$C_5$ alkyl, and $C_1$-$C_3$ alkyl.

In one preferred embodiment of the present invention, the $R_2$ is a hydrocarbylsulphanyl group such as a —S-hydrocarbyl group.

The term "hydrocarbylsulphanyl" means a group that comprises at least hydrocarbyl group (as herein defined) and sulphur. That sulphur group may be optionally oxidised. Preferably the hydrocarbylsulphanyl is of the formula —S-hydrocarbyl wherein the hydrocarbyl is as described herein.

The term "hydrocarbylsulphanyl group" as used herein with respect to $R_2$ means a group comprising at least C, H and S and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbylsulphanyl group comprises more than one C then those carbons need not necessarily be linked to each other. For example, at least two of the carbons may be linked via a suitable element or group. Thus, the hydrocarbylsulphanyl group may contain further hetero atoms. Suitable hetero atoms will be apparent to those skilled in the art and include, for instance, nitrogen.

In one preferred embodiment of the present invention, the $R_2$ is a hydrocarbonsulphanyl group. The term "hydrocarbonsulphanyl group" as used herein with respect to $R_2$ means a group consisting of C, H and S. Preferably the hydrocarbonsulphanyl is of the formula —S-hydrocarbon wherein the hydrocarbon is as described herein.

Preferably the hydrocarbonsulphanyl group $R_2$ is of the formula $C_{1-6}S$ (such as a $C_{1-3}S$). Preferably the oxyhydrocarbyl group $R_2$ is of the formula —$S(CH_2)_{1-10}CH_3$, —$S(CH_2)_{1-5}CH_3$, —$S(CH_2)_{1-2}CH_3$. In a highly preferred aspect $R_2$ is —S-Me.

R3

In one aspect $R_3$ is a group of Formula A

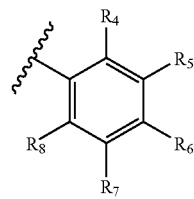

Formula A wherein each of $R_4$, $R_5$, $R_6$, $R_7$ and $R_8$ is independently selected from H, —OH, hydrocarbyl, —O-hydrocarbyl, —COOH or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens, wherein each $R_{29}$ to $R_{33}$ is independently selected from H and hydrocarbyl; and wherein two or more of $R_4$, $R_5$, $R_6$, $R_7$, $R_8$ and $R_9$ may together form a ring.

In one aspect $R_3$ is a group of Formula B

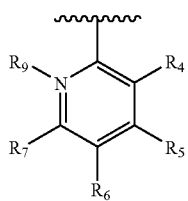

Formula B wherein each of $R_4$, $R_5$, $R_6$, and $R_7$ is independently selected from H, —OH, hydrocarbyl, —O-hydrocarbyl, —COOH or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens, $R_9$ is selected from H and hydrocarbyl, and each $R_{29}$ to $R_{33}$ is independently selected from H and hydrocarbyl; and wherein two or more of $R_4$, $R_5$, $R_6$, $R_7$, and $R_9$ may together form a ring.

In one aspect $R_3$ is a group of Formula C

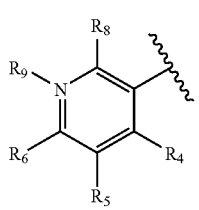

Formula C wherein each of $R_4$, $R_5$, $R_6$, and $R_8$ is independently selected from H, —OH, hydrocarbyl, —O-hydrocarbyl, —COOH or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens, $R_9$ is selected from H and hydrocarbyl, and each $R_{29}$ to $R_{33}$ is independently selected from H and hydrocarbyl; and wherein two or more of $R_4$, $R_5$, $R_6$, $R_8$, and $R_9$ may together form a ring.

In one aspect $R_3$ is a group of Formula D

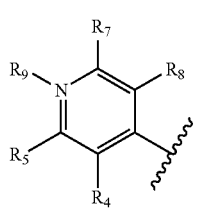

Formula D wherein each of $R_4$, $R_5$, $R_7$, and $R_8$ is independently selected from H, —OH, hydrocarbyl, —O-hydrocarbyl, —COOH or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens, $R_9$ is selected from H and hydrocarbyl, and each $R_{29}$ to $R_{33}$ is independently selected from H and hydrocarbyl; and wherein two or more of $R_4$, $R_5$, $R_7$, $R_8$, and $R_9$ may together form a ring.

$R_4$, $R_5$, $R_6$, $R_7$ and $R_8$

As discussed herein, each of $R_4$, $R_5$, $R_7$, $R_8$, and $R_9$ is independently selected from H, —OH, hydrocarbyl, —O-hydrocarbyl, —COOH or an ester thereof, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens.

In one aspect each of $R_4$, $R_5$, $R_6$, $R_7$ and $R_8$ is independently selected from H, —OH, C1-6 alkyl, C1-6 aryl, —O—C1-6 alkyl, —O—C1-6 aryl, —COOH or a C1-6 alkyl ester thereof, C1-6 halocarbyl, —O—C1-6 halocarbyl, —O-acetyl, —$NR_{29}$-acetyl, —O—$SO_2NR_{19}R_{20}$, —$NR_{30}R_{31}$, —$NR_{32}SO_2R_{33}$, —CN, —$NO_2$, and halogens, wherein each $R_{29}$ to $R_{33}$ is independently selected from H and C1-6 alkyl In one aspect each of $R_4$, $R_5$, $R_6$, $R_7$ and $R_8$ is independently selected from H, —OH, C1-6 alkyl, C1-6 aryl, —O—C1-6 alkyl, —O—C1-6 aryl, —COOH or a C1-6 alkyl ester thereof, C1-6 halocarbyl, —O—C1-6 halocarbyl, —O-acetyl, —NH-acetyl, —O—$SO_2NH_2$, —$NH_2$, —NH—$SO_2$—$NH_2$, —CN, —$NO_2$, and halogens.

In one aspect each of $R_4$, $R_5$, $R_6$, $R_7$ and $R_8$ is independently selected from H, —OH, Me, Et, —OMe, —OEt, —OPh, —O-iPr, —COOMe, —$CF_3$, —$OCF_3$, F, Cl, —O-acetyl, —NH-acetyl, —O—$SO_2NH_2$, —$NH_2$, —NH—$SO_2$—$NH_2$, —CN, and —$NO_2$.

In one aspect each of $R_4$, $R_5$, $R_6$, $R_7$ and $R_8$ is independently selected from H, —OH, Me, —OMe, —OEt, —OPh, —O-iPr, —COOMe, —$CF_3$, —$OCF_3$, F, Cl, —O-acetyl, —NH-acetyl, —O—$SO_2NH_2$, —$NH_2$, —NH—$SO_2$—$NH_2$, —CN, and —$NO_2$.

In one aspect $R_4$ is selected from H, —OH, —O-hydrocarbyl, —COOH or a salt thereof, and —CN.

In one aspect $R_4$ is selected from H, —OH, —OMe, —COOH and —CN.

In one aspect $R_5$ is selected from H, —OH, hydrocarbyl, —O-hydrocarbyl, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens.

In one aspect $R_5$ is selected from H, —OH, Me, Et, —OMe, —OEt, —OPh, —O-iPr, —$CF_3$, —$OCF_3$, F, Cl, —O-acetyl, —NH-acetyl, —O—$SO_2NH_2$, —$NH_2$, —NH—$SO_2$—$NH_2$, —CN, and —$NO_2$.

In one aspect $R_5$ is selected from H, —OH, Me, —OMe, —OEt, —OPh, —O-iPr, —$CF_3$, —$OCF_3$, F, Cl, —O-acetyl, —NH-acetyl, —O—$SO_2NH_2$, —$NH_2$, —NH—$SO_2$—$NH_2$, —CN, and —$NO_2$.

In one aspect $R_6$ is selected from H, —O-hydrocarbyl and —CN.

In one aspect $R_6$ is selected from H, —OMe, and —CN.

In one aspect $R_7$ is selected from H, and —O-hydrocarbyl.

In one aspect $R_7$ is selected from H and —OMe.

In one aspect $R_9$ is H.

In one aspect $R_9$ is selected from H and C1-6 alkyl.

In one preferred aspect at least one of $R_4$, $R_5$, $R_6$, $R_7$ and $R_8$ is independently selected from halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, and halogens, $R_{29}$ to $R_{33}$ Preferably each $R_{29}$ to $R_{33}$ is independently selected from H and C1-6 alkyl.

h

In one preferred aspect optional bond h is not present.

G

As discussed herein G is $CR_{24}R_{25}$, wherein $R_{24}$ and $R_{25}$ independently selected from H, —OH, hydrocarbyl, —CN, —$NO_2$, and halogens, or wherein when h is present G is $CR_{24}$, wherein $R_{24}$ is selected from H, —OH, hydrocarbyl, —CN, —$NO_2$, and halogens.

In one preferred aspect G is $CR_{24}R_{25}$, wherein $R_{24}$ and $R_{25}$ independently selected from H and hydrocarbyl, or wherein when h is present G is $CR_{24}$, wherein $R_{24}$ is selected from H and hydrocarbyl. Preferably G is $CR_{24}R_{25}$, wherein $R_{24}$ and $R_{25}$ independently selected from H and C1-6 alkyl, or wherein when h is present G is $CR_{24}$, wherein $R_{24}$ is selected from H and C1-6 alkyl. More preferably $CR_{24}R_{25}$, wherein $R_{24}$ and $R_{25}$ independently selected from H, Et and Me, or wherein when h is present G is $CR_{24}$, wherein $R_{24}$ is selected from H and Me. More preferably G is $CR_{24}R_{25}$, wherein $R_{24}$ and $R_{25}$ independently selected from H and Me, or wherein when h is present G is $CR_{24}$, wherein $R_{24}$ is selected from H and Me.

In one preferred aspect G is selected from —$CH_2$—, —CHEt-, —CHMe- and —$CMe_2$—, or wherein when h is present G is selected from —CH— and —CMe-.

In one preferred aspect G is selected from —$CH_2$—, —CHMe- and —$CMe_2$—, or wherein when h is present G is selected from —CH— and —CMe-.

n

As discussed herein n is 0, 1 or 2. Preferably n is 1. In one alternative preferred aspect, n is 0.

D

As discussed herein each D is independently selected from O, $NR_{26}$ and $CR_{27}R_{28}$, wherein each $R_{26}$ is independently selected from H and hydrocarbyl; and each $R_{27}$ and $R_{28}$ is independently selected from H, —OH, hydrocarbyl, —CN, —$NO_2$, and halogens.

Preferably each D is independently selected $CR_{27}R_{28}$, wherein each $R_{27}$ and $R_{28}$ is independently selected from H, —OH, hydrocarbyl, —CN, —$NO_2$, and halogens.

In one preferred aspect, each D is independently selected $CR_{27}R_{28}$, wherein each $R_{27}$ and $R_{28}$ is independently selected from H, OH, C1-6 alkoxy and C1-6 alkyl. In one preferred aspect, each D is independently selected $CR_{27}R_{28}$, wherein each $R_{27}$ and $R_{28}$ is independently selected from H and C1-6 alkyl.

In one highly preferred aspect, the or each D is independently selected from CHOH, CHOMe, CHOEt, and $CH_2$. In one highly preferred aspect the or each D is $CH_2$.

Halogens

A number of groups defined herein may be selected from halogens. It will be appreciated that each of these groups may each be independently selected from chlorine, fluorine, bromine or iodine. Preferably the halogen is fluorine.

Preferred Aspects

The present invention provides the following preferred aspects:

when $R_1$ is OH and $R_3$ is of Formula D, (i) at least one of $R_4$, $R_5$, $R_6$, $R_7$ and $R_8$ is independently selected from halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, and halogens, when $R_1$ is OH and $R_3$ is of Formula D, (ii) two or more of $R_4$, $R_5$, $R_6$, $R_7$ and $R_8$ together form a ring two or more of $R_4$, $R_5$, $R_6$, $R_7$ and $R_8$ together form a ring when $R_1$ is OH and $R_3$ is of Formula D, (iii) at least three of $R_4$, $R_5$, $R_6$, $R_7$ and $R_8$ are independently selected from —OH, hydrocarbyl, —O-hydrocarbyl, halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens at least three of $R_4$, $R_5$, $R_6$, $R_7$ and $R_8$ are independently selected from —OH, hydrocarbyl, —O-hydrocarbyl, halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, and halogens.

—$SO_2$-hydrocarbyl is a —$SO_2$—C1-6 alkyl group

—$SO_2$-hydrocarbyl is —$SO_2$-Me

Other Substituents

The compound of the present invention or for use in the invention may have substituents other than those of formula I. By way of example, these other substituents may be one or more of: one or more sulphamate group(s), one or more halo groups, one or more O groups, one or more hydroxy groups, one or more amino groups, one or more sulphur containing group(s), one or more hydrocarbyl group(s)—such as an oxy-hydrocarbyl group.

Composition

As described above according to one aspect of the present invention, there is provided a pharmaceutical composition comprising (a) (i) a compound as defined herein, or (ii) a composition as defined herein, and (b) a pharmaceutically acceptable carrier, diluent, excipient or adjuvant.

In accordance with the present invention the composition of the present invention may comprise more than one biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc.

BRMs may play a role in modulating the immune and inflammatory response in disorders. Examples of BRMs include: Tumour Necrosis Factor (TNF), granulocyte colony stimulating factor, erythropoietin, insulin-like growth factor (IGF), epidermal growth factor (EGF), transforming growth factor (TGF), platelet-derived growth factor (PDGF), interferons (IFNs), interleukins, tissue plasminogen activators, P-, E- or L-Selectins, ICAM-1, VCAM, Selectins, addressins etc.

Preferably, the biological response modifier is a cytokine.

A cytokine is a molecule—often a soluble protein—that allows immune cells to communicate with each other. These molecules exert their biological functions through specific receptors expressed on the surface of target cells. Binding of the receptors triggers the release of a cascade of biochemical signals which profoundly affect the behaviour of the cell bearing the receptor (Poole, S 1995 TibTech 13: 81-82). Many cytokines and their receptors have been identified at the molecular level (Paul and Sedar 1994, Cell 76: 241-251) and make suitable molecules of therapeutic value as well as therapeutic targets in their own right.

More details on cytokines can be found in Molecular Biology and Biotechnology (Pub. VCH, Ed. Meyers, 1995, pages 202, 203, 394, 390, 475, 790).

Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β.

For the present invention, preferably the cytokine is tumour necrosis factor (TNF).

More preferably the cytokine is TNF-α.

TNF is a cytokine produced by macrophages and lymphocytes which mediates inflammatory and immunopathological responses. TNF has been implicated in the progression of diseases which include but are not limited to immunomodulation disorder, infection, cell proliferation, angiogenesis (neovascularisation), tumour metastasis, apoptosis, sepsis, and endotoxaemia.

The necrotising action of TNF in vivo mainly relates to capillary injury. TNF causes necrosis not only in tumour tissue but also in granulation tissue. It causes morphological changes in growth inhibition of and cytoxicity against cultured vascular endothelial cells (Haranka et al 1987 Ciba Found Symp 131: 140-153).

For the preferred aspect of the present invention, the TNF may be any type of TNF—such as TNF-α, TNF-β, including derivatives or mixtures thereof.

Teachings on TNF may be found in the art—such as WO-A-98/08870 and WO-A-98/13348.

The TNF can be prepared chemically or it can be extracted from sources. Preferably, the TNF is prepared by use of recombinant DNA techniques.

With this aspect of the present invention the compositions of the present invention are more potent in vivo than the compounds alone or TNF alone. Moreover, in some aspects the combination of compounds and TNF is more potent than one would expect from the potency of the compound alone i.e. this is a synergistic relationship between them.

In addition, the present invention contemplates the composition of the present invention further comprising an inducer of the biological response modifier—such as in vivo inducer of the biological response modifier.

In accordance with the present invention, the components of the composition can be added in admixture, simultaneously or sequentially. Furthermore, in accordance with the present invention it may be possible to form at least a part of the composition in situ (such as in vivo) by inducing the expression of—or increasing the expression of—one of the components. For example, it may be possible to induce the expression of—or increase the expression of—the biological response modifier, such as TNF. By way of example, it may be possible to induce the expression of—or increase the expression of—TNF by adding bacterial lipopolysaccharide (LPS) and muramyl dipeptide (MDP). In this regard, bacterial LPS and MDP in combination can stimulate TNF production from murine spleen cells in vitro and tumour regression in vivo (Fuks et al Biull Eksp Biol Med 1987 104: 497-499).

In the method of treatment, the subject is preferably a mammal, more preferably a human. For some applications, preferably the human is a woman.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS activity.

Assay for Determining STS Activity Using Cancer Cells (Protocol 1)

Inhibition of Steroid Sulphatase Activity in JEG3 Cells

Steroid sulphatase activity is measured in vitro using intact JEG3 choriocarcinoma cells. This cell line may be used to study the control of human breast cancer cell growth. It possesses significant steroid sulphatase activity (Boivin et al., J. Med. Chem., 2000, 43: 4465-4478) and is available in from the American Type Culture Collection (ATCC).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of JEG3 cells in triplicate 25 cm$^2$ tissue culture flasks are washed with Earle's Balanced Salt Solution (EBSS from ICN Flow, High Wycombe, U.K.) and incubated for 3-4 hours at 37° C. with 5 pmol ($7 \times 10^5$ dpm) [6,7-3H] oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (3-4 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes (Protocol 2)

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C]oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity (Protocol 3)

Inhibition of Oestrone Sulphatase Activity in Vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for determining Oestrogenic Activity (Protocol 4)

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight ×100.

Compounds having no significant effect on uterine growth are not oestrogenic.

Biotechnological Assays for Determining STS Activity (Protocol 5)

The ability of compounds to inhibit oestrone sulphatase activity can also be assessed using amino acid sequences or nucleotide sequences encoding STS, or active fragments, derivatives, homologues or variants thereof in, for example, high-through put screens. Such assays and methods for their practice are taught in WO 03/045925 which is incorporated herein by reference.

In one preferred aspect, the present invention relates to a method of identifying agents that selectively modulate STS, which compounds have the formula (I).

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4-hydroxyandrostenedione (4-OHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-$\alpha$; Interferon alpha, beta and gamma; TGF-$\beta$. For some applications, preferably the cytokine is tumour necrosis factor (TNF). For some applications, the TNF may be any type of TNF—such as TNF-$\alpha$, TNF-$\beta$, including derivatives or mixtures thereof. More preferably the cytokine is TNF-$\alpha$. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration.

Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgment of the physician.

Cell Cycling

The compounds of the present invention may be useful in the method of treatment of a cell cycling disorder.

As discussed in "Molecular Cell Biology" 3rd Ed. Lodish at al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay (Protocol 7)

Procedure
Stage 1
MCF-7 breast cancer cells are seeded into multi-well culture plates at a density of 105 cells/well. Cells were allowed to attach and grown until about 30% confluent when they are treated as follows:
Control—no treatment
Compound of Interest (COI) 20 μM
Cells are grown for 6 days in growth medium containing the COI with changes of medium/COI every 3 days. At the end of this period cell numbers were counted using a Coulter cell counter.
Stage 2
After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.
Cancer
As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2—OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of Neurodegenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflammatory Conditions

We believe that some of the compounds of the present invention may be useful in treating inflammatory conditions—such as conditions associated with any one or more of:
s autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; antiimmune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynecological diseases, posterior uveitis, intermediate uveitis, anterior uveitis; conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

In addition, or in the alternative, the compound or composition of the present invention may be useful in the treatment of the disorders listed selected from endometriosis, uterus fibromyoma, induction of mono-ovulation (in polycystic ovarian disease [PCOD] patients). induction of multiple follicullar development in (ART patients), preterm labor/cervical incompetency and recurrent abortion.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^4R^5NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

Preferred preparations are also presented in the following text.

Summary

In summation, the present invention provides novel compounds for use as steroid sulphatase inhibitors and/or aromatase inhibitors and/or modulators of apoptosis and/or modulators of cell cycling and/or cell growth, and pharmaceutical compositions containing them.

EXAMPLES

The present invention will now be described in further detail by way of example only with reference to the accompanying figures in which.

Figure 1:
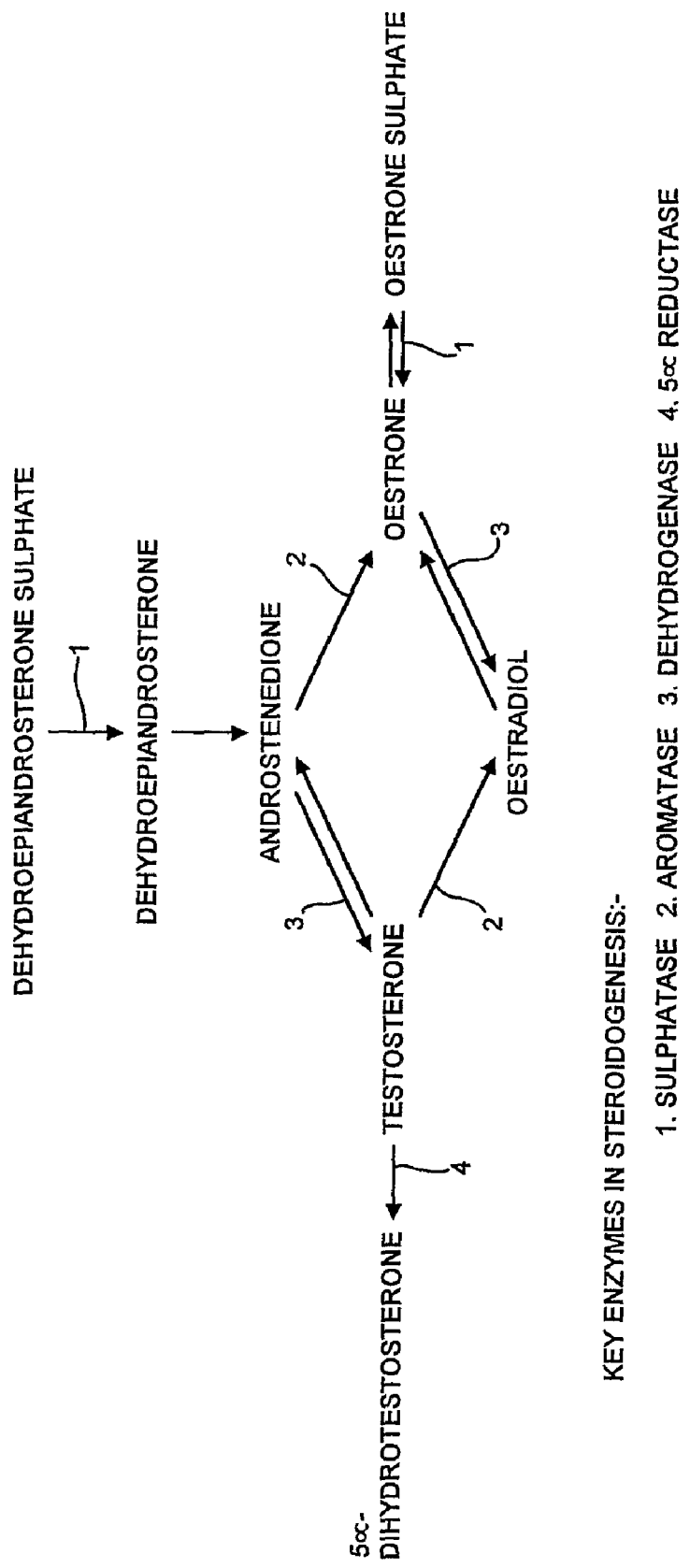
FIG. 1 shows a scheme.
Figure 2:
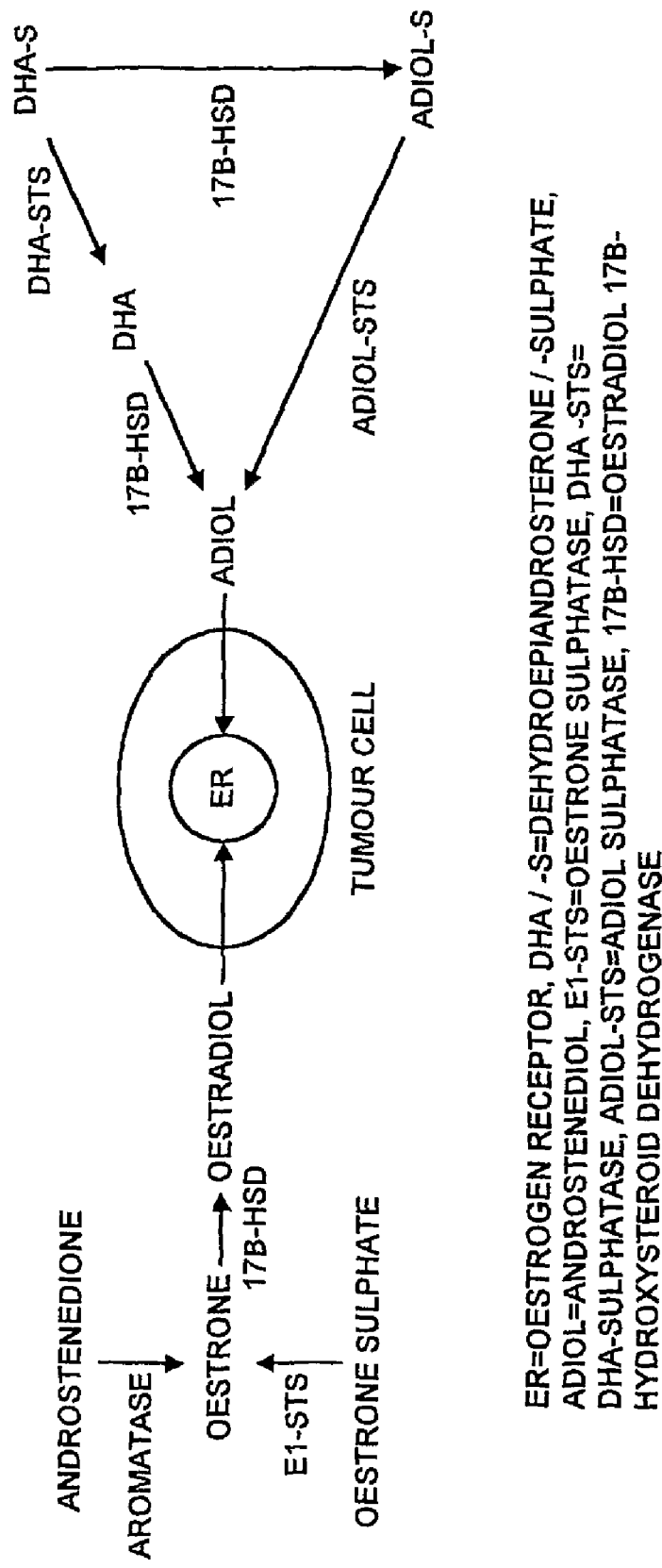
FIG. 2 shows a scheme

The present invention will now be described only by way of example. However, it is to be understood that the examples also present preferred compounds of the present invention, as well as preferred routes for making same and useful intermediates in the preparation of same.

Synthesis

Synthetic Routes

Compounds in accordance with the present invention were synthesised in accordance with the synthetic routes and schemes.

The present invention will now be described only by way of example. However, it is to be understood that the examples also present preferred compounds of the present invention, as well as preferred routes for making same and useful intermediates in the preparation of same.

Synthesis of 6-(benzyloxy)-2-benzyl-1,2,3,4-tetrahydroisoquinolines

Method 1:

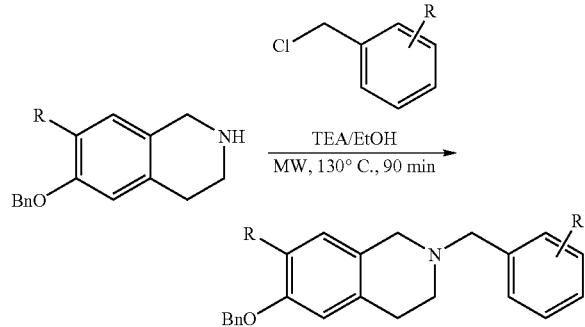

A solution of 6-(benzyloxy)-1,2,3,4-tetrahydroisoquinoline (1.5 mmol) and the appropriate benzyl bromide (1.8 mmol) in TEA (0.5 mL, 3.6 mmol) and ethanol (2.5 mL) was heated at 130° C. for 90 minutes under microwave energy. After addition of water (20 mL) and ethyl acetate (80 mL), the organic layer was separated and washed with water, brine, dried (MgSO$_4$) and concentrated under reduced pressure. The resulting yellow solid was purified by flash chromatography (hexane/ethyl acetate or DCM/ethyl acetate) to give the desired compound.

6-Benzyloxy-2-(3-methoxybenzyl)-1,2,3,4-tetrahydroisoquinoline 1

350 mg (65%), colorless oil, R$_f$: 0.45 (Hexane/EtOAc 2:1), $^1$H NMR (270 MHz, CDCl$_3$) δ 2.75 (2H, t, J 5.9 Hz, H3), 2.90 (2H, t, J 5.9 Hz, CH$_2$), 3.62 (2H, s, CH$_2$), 3.69 (2H, s, CH$_2$), 3.83 (3H, s, CH$_3$O), 5.06 (2H, s, OCH$_2$), 6.77 (1H, s, ArH), 6.80 (1H, dd, J 8.4 and 2.6 Hz, ArH), 6.85 (1H, ddd, J 8.2, 3.4 and 1.2 Hz, ArH), 6.94 (1H, d, J 8.4 Hz, ArH), 7.01 (1H, d, J 3.4 Hz, ArH), 7.01-7.05 (1H, m, ArH), 7.28 (1H, t, J 8.2 Hz, ArH), 7.30-7.47 (5H, m, ArH), $^{13}$C NMR (67.5 MHz, CDCl$_3$) δ 29.4 (CH$_2$), 50.4 (CH$_2$), 55.1 (CH$_3$O), 55.6 (CH$_2$), 62.7 (CH$_2$), 69.9 (OCH$_2$), 112.6 (CH(Ar)), 112.8 (CH(Ar)), 114.2 (CH(Ar)), 114.3 (CH(Ar)), 121.3 (CH(Ar)), 127.3 (2×CH(Ar)), 127.4 (C(Ar)), 127.5 (CH(Ar)), 127.8 (CH(Ar)), 128.4 (2×CH(Ar)), 129.2 (CH(Ar)), 135.5 (C(Ar)), 137.1 (C(Ar)) 140.1 (C(Ar)), 157.0 (C(Ar)) and 159.6 (C(Ar)). LC/MS (APCI+) t$_r$=2.10 min m/z 360.58 (M$^+$+H); MeOH/H$_2$O 95/5; HPLC t$_r$=5.70 min (97.9%). (CH3CN/H2O 90/10)

2-Benzyl-6-benzyloxy-7-methoxy-1,2,3,4-tetrahydroisoquinoline 2

0.32 g (59%), white solid: m.p. 97-98° C., R$_f$: 0.43 (EtOAc/Hexane 1:1), $^1$H NMR (270 MHz, CDCl$_3$) δ 2.71 (4H, m, 2×CH$_2$), 3.53 (2H, s, CH$_2$), 3.66 (2H, s, CH$_2$), 3.80 (3H, s, CH$_3$O), 5.10 (2H, s, OCH$_2$), 6.50 (1H, s, ArH), 6.61 (1H, s, ArH), 7.25-7.45 (5H, m, ArH). $^{13}$C NMR (67.5 MHz, CDCl$_3$) δ 28.7 (CH$_2$), 50.9 (CH$_2$), 55.9 (CH$_2$), 56.1 (CH$_3$O), 62.9 (CH$_2$), 71.1 (CH$_2$), 110.1 (CH(Ar)), 114.3 (CH(Ar)), 126.3 (C(Ar)), 127.2 (CH(Ar)), 127.4 (CH(Ar)), 127.5 (C(Ar)), 127.8 (CH(Ar)), 128.4 (CH(Ar)), 128.6 (CH(Ar)), 129.2 (CH(Ar)), 137.4 (C(Ar)), 138.5 (C(Ar)), 146.7 (C(Ar)), 147.9 (C(Ar)). LC/MS (APCI+) t$_r$=1.73 min m/z 360.52 (M$^+$+H); MeOH/H$_2$O 95/5; HPLC t$_r$=5.04 min (100%). (CH$_3$CN/H$_2$O 90/10); HRMS (Electrospray) calcd. for C$_{24}$H$_{25}$NO$_2$ (MH$^+$), 360.1958 found. 360.1955.

6-Benzyloxy-7-methoxy-2-(4-methoxybenzyl)-1,2,3,4-tetrahydroisoquinoline 3

0.33 g (57%), white solid: mp=96-97° C., R$_f$: 0.43 (EtOAc/Hexane 1:1), $^1$H NMR (270 MHz, CDCl$_3$) δ 2.72 (4H, m, 2×CH$_2$), 3.53 (2H, s, CH$_2$), 3.61 (2H, s, CH$_2$), 3.81 (3H, s, CH$_3$O), 3.81 (3H, s, CH$_3$O), 5.11 (2H, s, OCH$_2$), 6.51 (1H, s, ArH), 6.63 (1H, s, ArH), 6.88 (2H, dd, J 7.4 and 2.0 Hz, ArH), 7.26-7.45 (7H, m, ArH). $^{13}$C NMR (67.5 MHz, CDCl$_3$) δ 28.7 (CH$_2$), 50.8 (CH$_2$), 55.3 (CH$_2$), 55.7 (CH$_3$O), 56.1 (CH$_3$O), 62.3 (CH$_2$), 71.2 (OCH$_2$), 110.1 (CH(Ar)), 113.7 (CH(Ar)), 114.3 (CH(Ar)), 126.3 (C(Ar)), 127.3 (CH(Ar)), 127.5 (C(Ar)), 127.8 (CH(Ar)), 127.8 (CH(Ar)), 128.6 (CH(Ar)), 130.5 (C(Ar)), 137.1 (C(Ar)), 146.6 (C(Ar)), 147.7 (C(Ar)), 158.6 (C(Ar)). LC/MS (APCI+) t$_r$=1.67 min m/z 390.49 (M$^+$+H); MeOH/H$_2$O 95/5; HPLC t$_r$=4.13 min (95.5%). (CH$_3$CN/H$_2$O 90/10); HRMS (Electrospray) calcd. for C$_{24}$H$_{25}$NO$_2$ (MH$^+$), 390.2064 found. 390.2065

6-Benzyloxy-7-methoxy-2-(3-methoxybenzyl)-1,2,3,4-tetrahydroisoquinoline 4

0.39 g (67%), White solid: mp=71-72° C., R$_f$: 0.44 (EtOAc/Hexane 1:1) $^1$H NMR (270 MHz, CDCl$_3$) δ 2.64-2.76 (4H, m, 2×CH$_2$), 3.54 (2H, s, CH$_2$), 3.64 (2H, s, CH$_2$), 3.80 (3H, s, CH$_3$O), 3.81 (3H, s, CH$_3$O), 5.10 (2H, s, OCH$_2$), 6.51 (1H, s, ArH), 6.63 (1H, s, ArH), 6.83 (1H, ddd, J 8.2, 2.8 and 0.9 Hz, ArH), 6.97 (3H, m, ArH), 7.25-7.45 (5H, m, ArH). $^{13}$C NMR (67.5 MHz, CDCl$_3$) δ 28.7 (CH$_2$), 50.8 (CH$_2$), 55.3 (CH$_3$O), 55.9 (CH$_2$), 56.1 (CH$_3$O), 62.8 (CH$_2$), 71.2 (OCH$_2$), 110.1 (CH(Ar)), 112.8 (CH(Ar)), 114.3 (CH(Ar)), 114.4 (CH(Ar)), 121.5 (CH(Ar)), 126.3 (C(Ar)), 127.3 (CH(Ar)), 127.5 (C(Ar)), 127.8 (CH(Ar)), 128.5 (CH(Ar)), 129.3 (CH(Ar)), 137.3 (C(Ar)), 140.2 (C(Ar)), 146.7 (C(Ar)), 148.0 (C(Ar)) and 159.8 (C(Ar)). LC/MS (APCI+) t$_r$=1.73 min m/z 390.55 (M$^+$+H); (MeOH/H$_2$O 99/1); HPLC t$_r$=3.77 min (99%). (CH$_3$CN/H$_2$O 90/10); HRMS (Electrospray) calcd. for C$_{25}$H$_{27}$NO$_3$ (MH$^+$), 390.2064 found. 390.2063

6-Benzyloxy-7-methoxy-2-(2-methoxybenzyl)-1,2,3,4-tetrahydroisoquinoline 5

0.37 g (63%), white powder, mp=85-86° C., R$_f$: 0.37 (EtOAc/Hexane 1:1) $^1$H NMR (270 MHz, CDCl$_3$) δ 2.75 (4H, m, 2×CH$_2$), 3.59 (2H, s, CH$_2$), 3.70 (2H, s, CH$_2$), 3.81 (3H, s, CH$_3$O), 3.83 (3H, s, CH$_3$O), 5.10 (2H, s, OCH$_2$), 6.51 (1H, s, ArH), 6.61 (1H, s, ArH), 6.87 (1H, dd, J 8.4 Hz and 1.0 Hz, ArH), 6.94 (1h, dt, J 7.4 and 1.0 Hz, ArH), 7.21-7.44 (7H, m, ArH). $^{13}$C NMR (67.5 MHz, CDCl$_3$) δ 28.8 (C4), 50.9 (C3), 55.5 (CH$_3$O), 55.8 (C1), 56.1 (CH$_3$O), 60.5 (NCH$_2$Ph), 71.1 (OCH$_2$Ph), 110.2 (C8), 110.5 (Ar), 114.3 (C5), 120.4 (Ar), 126.4 (C8a), 126.6, 127.3 and 127.7 (Ph), 127.9 (C4a), 128.1, 128.5 and 137.4 (Ph), 146.5 (C7), 147.9 (C6) and 157.9 (Ar). LC/MS (APCI+) t$_r$=1.72 min m/z 390.49 (M$^+$+H); MeOH/H$_2$O 95/5; HPLC t$_r$=5.12 min (98.5%). (CH$_3$CN/H$_2$O 90/10)

6-Benzyloxy-2-(3,5-dimethoxybenzyl)-7-methoxy-1,2,3,4-tetrahydroisoquinoline 6

0.36 g (62%), white solid: mp=95-96° C., R$_f$: 0.44 (EtOAc/Hexane 1:1) $^1$H NMR (270 MHz, CDCl$_3$) δ 2.65-2.77 (4H, m, 2×CH$_2$), 3.54 (2H, s, CH$_2$), 3.60 (2H, s, CH$_2$), 3.78 (6H, s, 2×CH$_3$O), 3.81 (3H, s, CH$_3$O), 5.10 (2H, s, OCH$_2$), 6.37 (1H, t, J 2.5 Hz, ArH), 6.51 (1H, s, ArH), 6.56 (2H, d, J 2.5 Hz, ArH), 6.62 (1H, s, ArH), 7.27-7.44 (5H, m, ArH). $^{13}$C NMR (67.5 MHz, CDCl$_3$) δ 28.7 (CH$_2$), 50.7 (CH$_2$), 55.4 (2×CH$_3$O), 55.8 (CH$_2$), 56.1 (CH$_3$O), 63.0 (CH$_2$), 71.1 (OCH$_2$), 99.2 (CH(Ar)), 106.8 (2×CH(Ar)), 110.1 (CH(Ar)), 114.2 (CH(Ar)), 126.2 (C(Ar)), 127.4 (CH(Ar)), 127.4 (C(Ar)), 127.8 (CH(Ar)), 128.6 (CH(Ar)), 137.4 (C(Ar)), 141.0 (C(Ar)), 146.6 (C(Ar)), 147.9 (C(Ar)) and 160.8 (C(Ar)). LC/MS (APCI+) t$_r$=5.54 min m/z 420.39 (M$^+$+H); MeOH/H$_2$O 95/5; HPLC t$_r$=3.27 min (99.4%). (CH$_3$CN/H$_2$O 90/10); HRMS (Electrospray) calcd. for C$_{26}$H$_{30}$NO$_4$ (MH$^+$), 420.2169 found. 420.6167

6-Benzyloxy-7-methoxy-2-(3-methylbenzyl)-1,2,3,4-tetrahydroisoquinoline 7

0.46 g (82%), a white powder, mp=81-82° C., R$_f$: 0.69 (EtOAc/Hexane 1:1), $^1$H NMR (270 MHz, CDCl$_3$) δ 2.35 (3H, s, CH$_3$Ph), 2.69-2.76 (4H, m, 2×CH$_2$), 3.52 (2H, s, CH$_2$), 3.63 (2H, s, CH$_2$), 3.81 (3H, s, CH$_3$O), 5.10 (2H, s, OCH$_2$), 6.51 (1H, s, ArH), 6.62 (1H, s, ArH), 7.07-7.44 (9H, m, ArH). $^{13}$C NMR (67.5 MHz, CDCl$_3$) δ 21.5 (CH$_3$), 28.8 (CH$_2$), 50.9 (CH$_2$), 55.8 (CH$_2$), 56.2 (CH$_3$O), 62.9 (CH$_2$), 71.1 (OCH$_2$), 110.1 (CH(Ar)), 126.3 (C(Ar)), 126.4 (CH(Ar)) and 127.3 (CH(Ar)), 127.5 (C(Ar)), 127.8 (CH(Ar)), 128.0 (CH(Ar)), 128.2 (CH(Ar)), 128.6 (CH(Ar)), 130.0 (CH(Ar)), 137.4 (C(Ar)), 138.0 (C(Ar)) and 138.4 (C(Ar)), 146.7 (CH(Ar)) and 147.9 (CH(Ar)). LC/MS (APCI+) t$_r$=1.89 min m/z 374.62 (M$^+$+H); MeOH/H$_2$O 95/5; HPLC t$_r$=11.26 min (98.7%). (MeOH/H$_2$O 96/4)

6-Benzyloxy-7-methoxy-2-(3-phenoxybenzyl)-1,2,3,4-tetrahydroisoquinoline 8

0.53 g (78%), white powder, mp=111-112° C., R$_f$: 0.70 (EtOAc/Hexane 1:1), $^1$H NMR (270 MHz, CDCl$_3$) δ 2.65-2.75 (4H, m, 2×CH$_2$), 3.54 (2H, s, CH$_2$), 3.64 (2H, s, CH$_2$), 3.82 (3H, s, CH$_3$O), 5.10 (2H, s, OCH$_2$), 6.51 (1H, s, ArH), 6.62 (1H, s, ArH), 6.91 (1H, ddd, J 8.2, 2.5 and 1.0 Hz, ArH), 6.98-7.15 (5H, m, Ar), 7.25-7.45 (8H, m, Ar), $^{13}$C NMR (67.5 MHz, CDCl$_3$) δ 28.7 (CH$_2$), 50.8 (CH$_2$), 55.8 (CH$_2$), 56.2 (CH$_3$O), 62.5 (CH$_2$), 71.1 (OCH$_2$), 110.1 (CH(Ar)), 114.3 (CH(Ar)), 117.7 (CH(Ar)), 118.3 (CH(Ar)), 119.7 (CH(Ar)), 123.2 (CH(Ar)), 124.0 (CH(Ar)), 126.3 (C(Ar)), 127.3 (CH(Ar)), 127.4 (C(Ar)), 127.8 (CH(Ar)), 128.6 (CH(Ar)), 129.6 (CH(Ar)), 129.8(CH(Ar)), 137.4 (C(Ar)) and 140.7 (C(Ar)), 146.7 (C(Ar)), 147.9 (C(Ar)), 157.3 (C(Ar)) and 157.4 (C(Ar)). LC/MS (APCI+) t$_r$=2.09 min m/z 452.56 (M$^+$+H); MeOH/H$_2$O 95/5; HPLC t$_r$=11.68 min (99.8%). (MeOH/H$_2$O 96/4)

6-Benzyloxy-7-methoxy-2-(3-(triisopropylsilyloxy)benzyl)-1,2,3,4-tetrahydroisoquinoline 9

0.64 g (82%), white powder, mp=78-79° C., R$_f$: 0.62 (Hexane/EtOAc 3:1), $^1$H NMR (270 MHz, CDCl$_3$) δ 1.08 (18H, d, J 6.7 Hz, (CH$_3$)$_2$CHSi), 1.15-1.30 (3H, m, (CH$_3$)$_2$CHSi), 2.64-2.75 (4H, m, 2×CH$_2$), 3.52 (2H, s, CH$_2$), 3.60 (2H, s, CH$_2$), 3.81 (3H, s, CH$_3$O), 5.10 (2H, s, OCH$_2$), 6.49 (1H, s, ArH), 6.61 (1H, s, ArH), 6.75-6.80 (1H, m, ArH), 6.91-6.96 (2H, m, ArH), 7.16 (1H, t, J 7.7 Hz, ArH), 7.27-7.44 (5H, m, ArH), $^{13}$C NMR (67.5 MHz, CDCl$_3$) δ 12.7((CH$_3$)$_2$CHSi), 18.0((CH$_3$)$_2$CHSi), 28.8 (CH$_2$), 50.7 (CH$_2$), 55.9 (CH$_2$), 56.1 (CH$_3$O), 62.7 (CH$_2$), 71.2 (OCH$_2$), 110.1 (CH(Ar)), 114.3 (CH(Ar)), 118.6 (CH(Ar)), 120.8 (CH(Ar)), 126.4 (C4a), 127.4 (CH(Ar)), 127.6 (C(Ar)), 127.8 CH(Ar)), 128.6 (CH(Ar)), 129.2 (CH(Ar)), 137.4 (C(Ar)), 140.0 (C(Ar)), 146.6 (C(Ar)), 147.9 (C(Ar)) and 156.1 (C(Ar)). LC/MS (APCI+) t$_r$=5.96 min m/z 532.71 (M$^+$+H); MeOH/H$_2$O 95/5; HPLC t$_r$=14.56 min (99.25%). (MeOH)

6-Benzyloxy-7-methoxy-2-(3-nitrobenzyl)-1,2,3,4-tetrahydroisoquinoline 10

0.50 g (83%), cream color powder, mp=109-110° C., R$_f$: 0.32 (Hexane/EtOAc 2:1), $^1$H NMR (270 MHz, CDCl$_3$) δ 2.70-2.74 (2H, m, CH$_2$) 2.76-2.78 (2H, m, CH$_2$), 3.55 (2H, s, CH$_2$), 3.75 (2H, s, CH$_2$), 3.81 (3H, s, CH$_3$O), 5.09 (2H, s, OCH$_2$), 6.50 (1H, s, ArH), 6.63 (1H, s, ArH), 7.24-7.44 (5H, m, ArH), 7.49 (1H, t, J 7.8 Hz, ArH), 7.74 (1H, d, J 7.8 Hz, ArH), 8.12 (1H, d, J 7.8 Hz, ArH), 8.25(1H, s, ArH), $^{13}$C NMR (67.5 MHz, CDCl$_3$) δ 28.5 (CH$_2$), 50.8 (CH$_2$), 55.6 (CH$_2$), 56.0 (CH$_3$O), 61.7 (CH$_2$), 71.1 (OCH$_2$), 109.9 (CH (Ar)), 114.2 (CH(Ar)), 122.3 (CH(Ar)), 123.7 (CH(Ar)), 125.9 (C(Ar)), 126.8 (C(Ar)), 127.2 (2×CH(Ar)), 127.7 (CH (Ar)), 128.5 (CH(Ar)), 129.2 (CH(Ar)), 135.0 (CH(Ar)), 137.2 (C(Ar)), 140.9 (C(Ar)), 146.7 (C(Ar)), 147.9 (C(Ar)) and 148.3 (C(Ar)). LC/MS (APCI+) t$_r$=1.57 min m/z 405.60 (M$^+$+H); MeOH/H$_2$O 95/5; HPLC t$_r$=4.12 min (99.83%). (CH$_3$CN/H$_2$O 95/5)

6-Benzyloxy-7-methoxy-2-(pyridin-3-ylmethyl)-1,2,3,4-tetrahydroisoquinoline 11

0.33 g (83%), yellow powder, mp=78-79° C., R$_f$: 0.26 (EtOAc/MeOH 20:1), $^1$H NMR (270 MHz, CDCl$_3$) δ 2.64-2.76 (4H, m, 2×CH$_2$), 3.52 (2H, s, CH$_2$), 3.64 (2H, s, CH$_2$), 3.79 (3H, s, CH$_3$O), 5.08 (2H, s, OCH$_2$), 6.48 (1H, s, ArH), 6.61 (1H, s, ArH), 7.22-7.45 (6H, m, 5×ArH and 1×PyrH), 7.77 (1H, ddd, J 7.8, 1.7 and 1.4 Hz, ArH), 8.50 (1H, dd, J 4.8 and 1.7 Hz, ArH), 8.57 (1H, d, J 1.4 Hz, ArH), 8.25(1H, s, ArH), $^{13}$C NMR (67.5 MHz, CDCl$_3$) δ 28.7 (CH$_2$), 50.9 (CH$_2$), 55.7 (CH$_2$), 56.2 (CH$_3$O), 60.0 (CH$_2$), 71.2 (OCH$_2$), 110.0 (CH(Ar)), 114.3 (CH(Ar)), 123.5 (CHpyr), 126.1 (C(Ar)), 127.0 (C(Ar)), 127.3 (2×CH(Ar)), 127.8 (CH(Ar)), 128.6 (CH(Ar)), 134.0 (Cpyr), 136.9 (CHpyr), 137.3 (C(Ar)), 146.8 (C(Ar)), 148.0 (C(Ar)), 148.8 (CHpyr) and 150.5 (CHpyr). LC/MS (APCI+) t$_r$=4.73 min m/z 361.46 (M$^+$+H); MeOH/H$_2$O 95/5 to 50/50 in 5 min; HPLC t$_r$=5.24 min (85.4%). (CH$_3$CN/H$_2$O 90:10)

6-Benzyloxy-7-methoxy-2-(pyridin-2-ylmethyl)-1,2,3,4-tetrahydroisoquinoline 12

0.45 g (83%), white powder, mp=73-74° C., R$_f$: 0.48 (EtOAc/MeOH 10:1), $^1$H NMR (270 MHz, CDCl$_3$) δ 2.76 (4H, s, 2×CH$_2$), 3.60 (2H, s, CH$_2$), 3.79 (3H, s, CH$_3$O), 3.81 (2H, s, CH$_2$), 5.09 (2H, s, OCH$_2$), 6.49 (1H, s, ArH), 6.61 (1H, s, ArH), 7.15 (1H, ddd, =7.4, 4.9 and 1.2 Hz, PyrH), 7.22-7.50 (6H, m, 5×ArH and 1×PyrH), 7.64 (11-1, dt, J 7.7 and 1.7 Hz, PyrH), 8.55 (1H, ddd, J 4.9 1.7 and 0.9 Hz, PyrH), $^{13}$C NMR (67.5 MHz, CDCl$_3$) δ 28.8 (CH$_2$), 51.2 (CH$_2$), 55.9 (CH$_2$), 56.1 (CH$_3$O), 64.5 (CH$_2$), 71.2 (OCH$_2$), 110.1 (CH(Ar)), 114.4 (CH(Ar)), 122.2 (CHpyr), 123.2 (CHpyr), 126.2 (C(Ar)), 127.3 (2×CH(Ar)), 127.4 (C(Ar)), 127.8 (CH(Ar)), 128.6 (CH(Ar)), 136.6 (CHpyr), 137.4 (C(Ar)), 146.7 (C(Ar)), 148.0 (C(Ar)), 149.2 (CHpyr) and 158.9 (Cpyr). LC/MS (APCI+) t$_r$=4.88 min m/z 361.59 (M$^+$+H); MeOH/H$_2$O 95/5 to 50/50 in 5 min HPLC t$_r$=5.17 min (98.34%). (CH$_3$CN/H$_2$O 90:10).

6-Benzyloxy-7-methoxy-2-(pyridin-4-ylmethyl)-1,2,3,4-tetrahydroisoquinoline 13

0.33 g (61%), white powder, mp=125-126° C., $R_f$: 0.32 (EtOAc), $^1$H NMR (270 MHz, CDCl$_3$) δ 2.65-2.78 (4H, m, 2×CH$_2$), 3.54 (2H, s, CH$_2$), 3.65 (2H, s, CH$_2$), 3.81 (3H, s, CH$_3$O), 5.10 (2H, s, OCH$_2$), 6.49 (1H, s, ArH), 6.63 (1H, s, ArH), 7.26-7.45 (7H, m, 5×ArH and 2×PyrH), 8.54 (2H, dd, J 4.5 and 1.5 Hz, PyrH), $^{13}$C NMR (67.5 MHz, CDCl$_3$) δ 28.7 (CH$_2$), 51.0 (CH$_2$), 55.9 (CH$_2$), 56.2 (CH$_3$O), 61.6 (CH$_2$), 71.2 (OCH$_2$), 110.0 (CH(Ar)), 114.3 (CH(Ar)), 123.9 (2×CHpyr), 126.0 (C(Ar)), 127.0 (C(Ar)), 127.3 (2×CH(Ar)), 127.8 (CH(Ar)), 128.6 (2×CH(Ar)), 137.3 (CH(Ar)), 146.9 (C(Ar)), 147.9 (Cpyr), 148.0 (C(Ar)), and 150.0 (2×CHpyr). LC/MS (ES−) $t_r$=1.37 min m/z 359.40 (M$^+$+H); MeOH/H$_2$O 95/5. HPLC $t_r$=5.50 min (99.38%). (CH$_3$CN/H$_2$O 90:10)

6-Benzyloxy-7-methoxy-2-(4-methoxyphenethyl)-1,2,3,4-tetrahydroisoquinoline 14

250 mg (41%), light yellow powder, mp=88-89° C., $R_f$: 0.15 (Hexane/EtOAc 1:1), $^1$H NMR (270 MHz, CDCl$_3$) δ2.67-2.89 (8H, m, 4×CH$_2$), 3.62 (2H, s, CH$_2$), 3.78 (3H, s, OCH$_3$), 3.84 (3H, s, OCH$_3$), 5.10 (2H, s, OCH$_2$) 6.55 (1H, s, ArH), 6.62 (1H, s, ArH), 6.81-6.86 (m, 2H, ArH), 7.13-7.16 (2H, m, ArH), 7.25-7.44 (5H, m, ArH), $^{13}$C NMR (67.5 MHz, CDCl$_3$) δ 28.7 (CH$_2$), 33.2 (CH$_2$), 51.1 (CH$_2$), 55.4 (CH$_3$O), 55.9 (Cl), 56.2 (CH3O), 60.6 (CH$_2$), 71.2 (CH$_2$O), 110.1 (CH(Ar)), 113.9 (2×CH(Ar)), 114.3 (CH(Ar)), 126.2 (C(Ar)), 127.4 (2×CH(Ar)), 127.8 (CH(Ar)), 128.6 (2×CH(Ar)), 129.7 (2×CH(Ar)), 132.5 (C(Ar)), 137.4 (C(Ar)), 146.7 (C(Ar)), 148.0 (C(Ar)) and 158.0 (C(Ar)). LC/MS (APCI+) $t_r$=5.58 min m/z 404.56 (M$^+$+H); MeOH/H$_2$O 95/5 to 50/50 in 5 min. HPLC $t_r$=8.18 min (99.9%). (CH$_3$CN/H$_2$O 90/10)

6-Benzyloxy-2-(2-(3,4-dimethoxyphenyl)-2-oxoethyl)-7-methoxy-1,2,3,4-tetrahydroisoquinoline 15

370 mg (75%), white powder, mp=126-127° C., $R_f$: 0.13 (Hexane/EtOAc 1:1), $^1$H NMR (270 MHz, CDCl$_3$) δ 2.75-2.86 (4H, m, 2×CH$_2$), 3.72 (2H, s, CH$_2$), 3.81 (3H, s, CH$_3$O), 3.92 (3H, s CH$_3$O), 3.93 (5H, s, CH$_2$ and CH$_3$O), 5.10 (2H, s, OCH$_2$), 6.51 (1H, s, ArH), 6.61 (1H, s, ArH), 6.85 (1H, d, J 8.4 Hz, ArH), 7.27-7.44 (5H, m, ArH), 7.60 (1H, d, J 2.0 Hz, ArH), 7.74 (1H, dd, J 8.4 and 2.0 Hz, ArH), $^{13}$C NMR (67.5 MHz, CDCl$_3$) δ 28.1 (CH$_2$), 51.0 (CH$_2$), 55.3 (CH$_2$), 55.9 (CH$_3$O), 56.0 (CH$_3$O), 56.1 (CH$_3$O), 63.6 (CH$_2$), 71.0 (OCH$_2$), 109.8 (CH(Ar)), 109.9 (CH(Ar)), 110.3 (CH(Ar)), 114.1 (CH(Ar)), 123.1 (CH(Ar)), 125.7 (C(Ar)), 126.6 (C(Ar)), 127.2 (2×CH(Ar)), 127.7 (CH(Ar)), 128.5 (2×CH(Ar)), 129.1 (C(Ar)), 137.2 (C(Ar)), 146.7 (C(Ar)), 147.9 (C(Ar)), 148.9 (C(Ar)), 153.4 (C(Ar)) and 195.1 (CO). LC/MS (ES+) $t_r$=1.28 min m/z 448.42 (M$^+$+H); MeOH/H$_2$O 50/50; HPLC $t_r$=5.25 min (99.25%). (CH$_3$CN/H$_2$O 90/10)

6-Benzyloxy-7-methoxy-2-(2,3,4-trimethoxybenzyl)-1,2,3,4-tetrahydroisoquinoline 16

0.29 g (43%), yellow oil $R_f$: 0.35 (Hexane/EtOAc 1:2), $^1$H NMR (270 MHz, CDCl$_3$) δ 2.66-2.75 (4H, m, 2×CH$_2$), 3.56 (2H, s, CH$_2$), 3.63 (2H, s, CH$_2$), 3.81 (3H, s, CH$_3$O), 3.85 (3H, s, CH$_3$O), 3.88 (3H, s, CH$_3$O), 5.09 (2H, s, OCH$_2$), 6.52 (1H, s, ArH), 6.62 (1H, s, ArH), 6.65 (1H, d, J 8.6 Hz, ArH), 7.08 (1H, d, J 8.6 Hz, ArH), 7.27-7.43 (5H, m, ArH), $^{13}$C NMR (67.5 MHz, CDCl$_3$) δ 28.9 (CH$_2$), 50.7 (CH$_2$), 55.7 (CH$_2$), 56.1 (CH$_3$O), 56.2 (CH$_3$O), 56.4 (CH$_2$), 60.9 (CH$_3$O), 61.3 (OCH$_3$), 71.2 (OCH$_2$Ph), 107.2 (CH(Ar)), 110.3 (CH(Ar)), 114.4 (CH(Ar)), 124.4 (C(Ar)), 125.0 (CH(Ar)), 126.5 (C(Ar)), 127.4 (2×CH(Ar)), 127.8 (CH(Ar)), 128.0 (C(Ar)), 128.5 (2×CH(Ar)), 137.5 (C(Ar)), 142.4 (C(Ar)), 146.7 (C(Ar)), 148.0 (C(Ar)), 152.7 (C(Ar)) and 152.9 (C(Ar)).

6-Benzyloxy-7-methoxy-2-(2,4,5-trimethoxybenzyl)-1,2,3,4-tetrahydroisoquinoline 17

240 mg (36%), white powder, mp=110-111° C., $R_f$: 0.20 (Hexane/EtOAc 1:2), $^1$H NMR (270 MHz, CDCl$_3$) δ 2.65-2.76 (4H, m, 2×CH$_2$), 3.58 (2H, s, CH$_2$), 3.63 (2H, s, CH$_2$), 3.80 (3H, s, CH$_3$O), 3.81 (3H, s, CH$_3$O), 3.82 (3H, s, CH$_3$O), 3.88 (3H, s, CH$_3$O), 5.09 (2H, s, OCH$_2$), 6.52 (1H, s, ArH), 6.53 (1H, s, ArH), 6.61 (1H, s, ArH), 7.00 (1H, s, ArH), 7.27-7.43 (5H, m, ArH), $^{13}$C NMR (67.5 MHz, CDCl$_3$) δ 28.8 (CH$_2$), 50.6 (CH$_2$), 55.3 (CH$_2$), 55.9 (CH$_2$), 56.2 (CH$_3$O), 56.3 (CH$_3$O), 56.7 (CH$_3$O), 56.8 (CH$_3$O), 61.7 (CH$_2$), 71.2 (OCH$_2$), 97.9 (CH(Ar)), 110.3 (CH(Ar)), 114.3 (CH(Ar)), 114.5 (CH(Ar)), 118.3 (C(Ar)), 126.5 (C(Ar)), 127.4 (2×CH(Ar)), 127.8 (CH(Ar)), 127.9 (C(Ar)), 128.5 (2×CH(Ar)), 137.5 (C(Ar)), 143.2 (C(Ar)), 146.7 (C(Ar)), 148.0 (C(Ar)), 148.6 (C(Ar)) and 152.2 (C(Ar)). LC/MS (ES+) $t_r$=1.82 min m/z 450.61 (M$^+$+H); MeOH/H$_2$O 95/5; HPLC $t_r$=3.02 min (98.5%). (CH$_3$CN/H$_2$O 90:10)

6-Benzyloxy-7-methoxy-2-(3,4-dimethoxybenzyl)-1,2,3,4-tetrahydroisoquinoline 18

430 mg, (68%), white powder: mp=98-99° C., $R_f$: 0.30 (Hexane/EtOAc 1:2), $^1$1-1 NMR (270 MHz, CDCl$_3$) δ 2.99-3.16 (4H, br, 2×CH$_2$), 3.81 (3H, s, CH$_3$O), 3.87 (5H, s, CH$_2$ and CH$_3$O), 3.94 (3H, s, CH$_3$O), 4.01 (2H, s, CH$_2$), 5.10 (2H, s, OCH$_2$), 6.47 (1H, s, ArH), 6.64 (1H, s, ArH), 6.81 (1H, d, J 8.2 Hz, ArH), 6.91 (1H, dd, J 8.2 and 1.7 Hz, ArH), 7.26-7.50 (6H, m, ArH). LC/MS (ES+) $t_r$=1.48 min m/z 420.61 (M$^+$+H); MeOH/H$_2$O 95/5; HPLC $t_r$=6.45 min (97.9%). (CH$_3$CN/H$_2$O 70:30)

6-Benzyloxy-7-methoxy-2-(3,4,5-trimethoxybenzyl)-1,2,3,4-tetrahydroisoquinoline 19

520 mg (77%), white powder: mp=144-145° C., $R_f$: 0.38 (Hexane/EtOAc 1:2), $^1$H NMR (270 MHz, CDCl$_3$) δ 2.65-2.78 (4H, m, 2×CH$_2$), 3.55 (2H, s, CH$_2$), 3.58 (2H, s, CH$_2$), 3.82 (3H, s, CH$_3$O), 3.84 (3H, s, CH$_3$O), 3.85 (6H, s, CH$_3$O), 5.10 (2H, s, OCH$_2$), 6.53 (1H, s, ArH), 6.61 (2H, s, ArH), 6.63 (1H, s, ArH), 7.27-7.44 (5H, m, ArH), $^{13}$C NMR (67.5 MHz, CDCl$_3$) δ 28.8 (CH$_2$), 50.7 (CH$_2$), 56.0 (CH$_2$), 56.2 (3×CH$_3$O), 61.0 (CH$_3$O), 63.1 (CH$_2$), 71.2 (OCH$_2$), 105.7 (2×CH(Ar)), 110.2 (CH(Ar)), 114.3 (CH(Ar)), 126.3 (C(Ar)), 127.3 (2×CH(Ar)), 127.5 (C(Ar)), 127.8 (CH(Ar)), 128.6 (2×CH(Ar)), 134.5 (C(Ar)), 136.9 (C(Ar)), 137.4 (C(Ar)), 146.8 (C(Ar)), 148.0 (C(Ar)) and 153.2 (2×C(Ar)). LC/MS (ES+) $t_r$=1.36 min m/z 450.61 (M$^+$+H); MeOH/H$_2$O 95/5; HPLC $t_r$=6.39 min (99.7%). (CH$_3$CN/H$_2$O 90:10)

6-Benzyloxy-7-methoxy-2-(2,3-dimethoxybenzyl)-1,2,3,4-tetrahydroisoquinoline 20

430 mg (68%), light yellow powder, mp=106-107° C., $R_f$: 0.46 (Hexane/EtOAc 1:2), $^1$H NMR (270 MHz, CDCl$_3$) δ 2.73 (4H, s, 2×CH$_2$), 3.57 (2H, s, CH$_2$), 3.71 (2H, s, CH$_2$), 3.80 (3H, s, CH$_3$O), 3.83 (3H, s, CH$_3$O), 3.87 (3H, s, CH$_3$O), 5.09 (2H, s, OCH$_2$), 6.51 (1H, s, ArH), 6.61 (1H, s, ArH), 6.84 (1H, dd, J 7.2 and 1.7 Hz, ArH), 7.00-7.08 (2H, m, ArH), 7.27-7.44 (5H, m, ArH), $^{13}$C NMR (67.5 MHz, CDCl$_3$) δ 29.0 (CH$_2$), 51.0 (CH$_2$), 55.7 (CH$_2$), 55.8 (CH$_3$O), 56.1 (CH$_3$O), 56.2 (CH$_2$), 61.0 (OCH$_3$), 71.2 (OCH$_2$), 110.1 (CH(Ar)), 111.1 (CH(Ar)), 114.3 (CH(Ar)), 122.6 (CH(Ar)), 123.9 (CH(Ar)), 126.4 (C(Ar)), 127.4 (2×CH(Ar)), 127.8 (C(Ar)), 128.6 (2×CH(Ar)), 132.4 (C(Ar)), 137.4 (C(Ar)), 146.6 (C(Ar)), 147.8 (C(Ar)), 147.9 (C(Ar)) and 152.8 (C(Ar)). LC/MS (APCI−) t$_r$=1.58 min m/z 418.11(M−H)$^−$; MeOH/H$_2$O 95/5; HPLC t$_r$=3.13 min (94.3%). (CH$_3$CN/H$_2$O 90:10)

6-Benzyloxy-7-methoxy-2-(2,5-dimethoxybenzyl)-1,2,3,4-tetrahydroisoquinoline 21

440 mg (70%), yellow powder, mg=103-104° C., R$_f$: 0.41 (Hexane/EtOAc 1:2), $^1$H NMR (270 MHz, CDCl$_3$) δ 2.73-2.75 (4H, m, 2×CH$_2$), 3.61 (2H, s, CH$_2$), 3.69 (2H, s, CH$_2$), 3.76 (3H, s, CH$_3$O), 3.79 (3H, s, CH$_3$O), 3.82 (3H, s, CH$_3$O), 5.10 (2H, s, OCH$_2$Ph), 6.53 (1H, s, ArH), 6.62 (1H, s, ArH), 6.76 (1H, dd, J 8.6 and 2.9 Hz, ArH), 6.81 (1H, d, J 8.6 Hz, ArH), 7.06 (1H, d, J 2.9 Hz, ArH), 7.28-7.46 (5H, m, ArH). $^{13}$C NMR (67.5 MHz, CDCl$_3$) δ 28.8 (C4), 50.9 (C3), 55.9 (C1), 56.2 (CH$_3$O), 56.3 (CH$_3$O), 71.2 (OCH$_2$Ph), 110.2 (CH(Ar)), 111.7 (CH(Ar)), 112.5 (CH(Ar)), 114.3 (CH(Ar)), 116.1 (CH(Ar)), 126.4 (C(Ar)), 127.4 (2×CH(Ar)), 127.8 (C(Ar)), 127.9 (C(Ar)), 128.0 (C(Ar)), 128.6 (2×CH(Ar)), 137.4 (C(Ar)), 146.7 (C(Ar)), 147.9 (C(Ar)), 152.1 (C(Ar)) and 153.7 (C(Ar)). LC/MS (ES+) t$_r$=1.77 min m/z 418.11 (M−H)$^−$; MeOH/H$_2$O 95/5; HPLC t$_r$=3.33 min (95.7%). (CH$_3$CN/H$_2$O 90:10).

6-Benzyloxy-2-(3-fluorobenzyl)-7-methoxy-1,2,3,4-tetrahydroisoquinoline 22

336 mg, 80%, colourless solid; mp 77-79.5° C. $^1$H NMR (270 MHz; CDCl$_3$) 2.67-2.75 (4H, m, 2×CH$_2$), 3.53 (2H, s, CH$_2$), 3.64 (2H, s, CH$_2$), 3.81 (3H, s, OCH$_3$), 5.10 (2H, s, CH$_2$Ph), 6.50 (1H, s, CH), 6.61 (1H, s, CH), 6.91-6.98 (1H, m, CH), 7.10-7.15 (2H, m, 2×CH), 7.23-7.44 (6H, m, CH and 5×CH, phenyl). $^{13}$C NMR (67.5 MHz; CDCl$_3$) 28.72 (CH$_2$), 50.91 (CH$_2$), 55.78 (CH$_2$), 56.16 (OCH$_3$), 62.32 (CH$_2$), 71.17 (CH$_2$), 110.08 (CH), 114.08 (d, J=21.2 Hz, CH), 114.31 (CH), 115.82 (d, J=21.2 Hz, CH), 124.59 (d, J=2.5 Hz, CH), 126.18 (C), 127.27 (C), 127.36 (2×CH), 127.84 (CH), 128.59 (2×CH), 129.79 (d, J=8.1 Hz, CH), 137.37 (C), 141.37 (d, J=7.5 Hz, C), 146.76 (C), 147.97 (C), 163.07 (d, J=245.6 Hz, C—F). LC/MS (APCI+) t$_r$=5.66 min, m/z 378.52 (M$^+$+H). HRMS (ES+) calcd. for C$_{24}$H$_{25}$FNO$_2$ (M$^+$+H) 378.1864, found 378.1866. HPLC t$_r$=8.63 min (>98%).

Method 2:

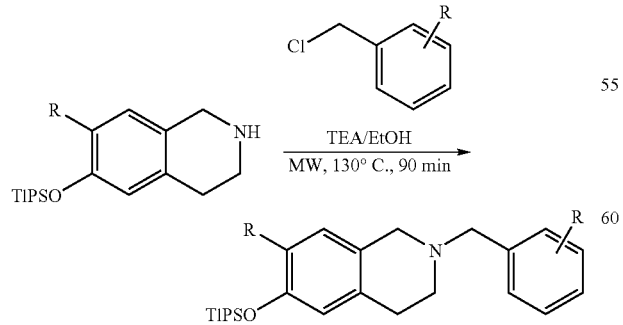

A solution of 7-methoxy-6-(triisopropylsilyloxy)-1,2,3,4-tetrahydroisoquinoline (0.5 g, 1.5 mmol) and the appropriate benzyl bromide (1.8 mmol) in TEA (0.5 mL, 3.6 mmol) and ethanol (2.5 mL) was heated at 130C. for 90 minutes under microwave energy. After addition of water (20 mL) and ethyl acetate (80 mL), the organic layer was separated and washed with water, brine, dried (MgSO$_4$) and concentrated under reduced pressure. The resulting yellow solid was purified by flash chromatography (hexane/ethyl acetate or DCM/ethyl acetate) to give the desired compound.

2-(3-Acetoxybenzyl)-7-methoxy-6-triisopropylsilyloxy-1,2,3,4-tetrahydroisoquinoline 23

290 mg (65%), yellow oil, R$_f$: 0.20 (Hexane/EtOAc 3:1), 0.66 (Hexane/EtOAc 1:1), $^1$H NMR (270 MHz, CDCl$_3$) δ 1.05 (18H, d, J 6.7 Hz, (CH$_3$)$_2$CHSi), 1.12-1.30 (3H, m, (CH$_3$)$_2$CHSi), 2.60 (3H, s, CH$_3$CO), 2.65-2.76 (4H, m, 2×CH$_2$), 3.54 (2H, s, CH$_2$), 3.70 (5H, s, OCH$_3$ and CH$_2$), 6.42 (1H, s, ArH), 6.58 (1H, s, ArH), 7.42 (1H, t, J 7.7 Hz, ArH), 7.62 (1H, dt, J 7.7 and 1.5 Hz, ArH), 7.86 (1H, dt, J 7.7 and 1.5 Hz, ArH), 7.95 (1H, t, J 1.5 Hz, ArH), $^{13}$C NMR (67.5 MHz, CDCl$_3$) δ 13.0 ((CH$_3$)$_2$CHSi), 18.0 ((CH$_3$)$_2$CHSi), 26.9 (CH$_3$CO), 28.4 (CH$_2$), 50.9 (CH$_2$), 55.7 (CH$_3$O), 55.9 (CH$_2$), 62.5 (CH$_2$), 110.2 (CH(Ar)), 120.2 (CH(Ar)), 126.2 (C(Ar)), 126.9 (C(Ar)), 127.3 (CH(Ar)), 128.7 (CH(Ar)), 129.0 (CH(Ar)), 134.1 (CH(Ar)), 137.3 (C(Ar)), 139.1 (C(Ar)), 144.0 (C(Ar)), 149.1 (C(Ar)) and 198.5 (CO). LC/MS (APCI+) t$_r$=3.80 min m/z 468.57 (M$^+$+H); MeOH/H$_2$O 95/5 to 50/50 in 5 min. HPLC t$_r$=30.53 min (80.9%). (CH$_3$CN/H$_2$O 90/10)

2-(3-Cyanobenzyl)-7-methoxy-6-triisopropylsilyloxy-1,2,3,4-tetrahydroisoquinoline 24

329 mg, 82%, yellow oil, $^1$H NMR (270 MHz; CDCl$_3$) 1.07 (18H, d, J =6.7 Hz, 6×CH$_3$CH), 1.13-1.28 (3H, m, 3×CH), 2.66-2.75 (4H, m, 2×CH$_2$), 3.51 (2H, s, CH$_2$), 3.67 (2H, s, CH$_2$), 3.71 (3H, s, OCH$_3$), 6.42 (1H, s, CH), 6.59 (1H, s, CH), 7.42 (1H, t, J=7.7 Hz, CH), 7.56 (1H, dt, J=7.7, 1.5 Hz, CH), 7.64 (1H, app d, J=7.7 Hz, CH), 7.70 (1H, brs, CH). $^{13}$C NMR (100 MHz; CDCl$_3$) 12.87 (3×CH), 17.98 (6×CH$_3$), 28.27 (CH$_2$), 50.84 (CH$_2$), 55.58 (OCH$_3$), 55.67 (CH$_2$), 61.83 (CH$_2$), 110.14 (CH), 112.39 (C), 118.93 (C), 120.12 (CH), 125.84 (C), 126.50 (C), 129.13 (CH), 130.91 (CH), 132.46 (CH), 133.45 (CH), 140.12 (C), 144.02 (C), 149.08 (C). LC/MS (APCI+) t$_r$=3.85 min, m/z 451.43 (M$^+$+H).

2-(4-Cyanobenzyl)-7-methoxy-6-triisopropylsilyloxy-1,2,3,4-tetrahydroisoquinoline 25

123 mg, 92%, yellow oil, $^1$H NMR (270 MHz; CDCl$_3$) 1.07 (18H, d, J=6.7 Hz, 6×CH$_3$), 1.13-1.31 (3H, m, 3×CHSi), 2.66-2.75 (4H, m, 2×CH$_2$), 3.52 (2H, s, CH$_2$), 3.70 (2H, s, CH$_2$), 3.71 (3H, s, OCH$_3$), 6.41 (1H, s, CH), 6.58 (1H, s, CH), 7.51 (2H, ~d, J=8.2 Hz, 2×CH), 7.61 (2H, ~d, J=8.4 Hz, 2×CH). $^{13}$C NMR (67.5 MHz; CDCl$_3$) 12.98 (3×CH), 18.05 (6×CH$_3$), 28.40 (CH$_2$), 50.97 (CH$_2$), 55.64 (OCH$_3$), 55.87 (CH$_2$), 62.27 (CH$_2$), 110.20 (CH), 111.00 (C), 119.06 (C), 120.21 (CH), 125.95 (C), 126.68 (C), 129.83 (2×CH), 132.25 (2×CH), 144.10 (C), 144.38 (C), 149.16 (C). LC/MS (APCI+) t$_r$=3.70 min, m/z 451.43 (M$^+$+H).

7-Methoxy-2-(3-nitrobenzyl)-6-triisopropylsilyloxy-1,2,3,4-tetrahydroisoquinoline 26

452 mg, 83%, yellow solid; mp 57.3-58.6° C. $^1$H NMR. (270 MHz; CDCl$_3$) 1.07 (18H, d, J=6.7 Hz, 6×CH$_3$), 1.13-1.28 (3H, m, 3×CHSi), 2.69-2.76 (4H, m, 2×CH$_2$), 3.54 (2H, s, CH$_2$), 3.71 (3H, s, OCH$_3$), 3.74 (2H, s, CH$_2$), 6.42 (1H, s, CH), 6.59 (1H, s, CH), 7.49 (1H, t, J=7.9 Hz, CH), 7.75 (1H, d, J=7.7 Hz, CH), 8.12 (1H, ddd, J=8.2, 2.5, 1.1 Hz, CH), 8.25 (1H, t, J =1.7 Hz, CH). $^{13}$C NMR (67.5 MHz; CDCl$_3$) 12.97 (3×CH), 18.06 (6×CH$_3$), 28.47 (CH$_2$), 50.97 (CH$_2$), 55.67 (OCH$_3$), 55.87 (CH$_2$), 62.02 (CH$_2$), 110.18 (CH), 120.20 (CH), 122.37 (CH), 123.88 (CH), 125.99 (C), 126.72 (C), 129.34 (CH), 135.22 (CH), 141.04 (C), 144.05 (C), 148.43 (C), 149.14 (C). LC/MS (APCI+) t$_r$=4.76 min, m/z 471.58 (M$^+$+H). HRMS calcd. for C$_{26}$H$_{39}$N$_2$O$_4$Si (M$^+$+H) 471.2674, found 471.2667.

2-(3-Cyanobenzyl)-7-methoxy-6-triisopropylsilyloxy-1,2,3,4-tetrahydroisoquinoline 27

322 mg, 78%, yellow oil, $^1$H NMR (270 MHz; CDCl$_3$) 1.08 (18H, d, J=6.7 Hz, 6×CH$_3$), 1.13-1.29 (3H, m, 3×CHSi), 2.66-2.75 (4H, m, 2×CH$_2$), 3.52 (2H, s, CH$_2$), 3.62 (2H, s, CH$_2$), 3.72 (3H, s, OCH$_3$), 6.43 (1H, s, CH), 6.59 (1H, s, CH), 7.23-7.28 (3H, m, 3×CH), 7.40 (1H, s, CH). $^{13}$C NMR (67.5 MHz; CDCl$_3$) 12.99 (3×CH), 18.06 (6×CH$_3$), 28.51 (CH$_2$), 50.92 (CH$_2$), 55.67 (CH$_3$), 55.89 (CH$_2$), 62.37 (CH$_2$), 110.31 (CH), 120.20 (CH), 126.15 (C), 127.04 (C), 127.28 (C), 127.35 (CH), 129.16 (CH), 129.69 (CH), 134.29 (C), 140.79 (C), 143.99 (C), 149.09 (C). LC/MS (APCI+) t$_r$=6.75 min, m/z 460.43 (M$^+$+H).

7-Methoxy-2-(3-(trifluoromethoxy)benzyl)-6-triisopropylsilyloxy-1,2,3,4-tetrahydroisoquinoline 28

238 mg, 52%, pale blue oil. $^1$H NMR (270 MHz; CDCl$_3$) 1.07 (18H, d, J=6.7 Hz, 6×CH$_3$), 1.14-1.28 (3H, m, 3×CH), 2.65-2.74 (4H, m, 2×CH), 3.53 (2H, s, CH$_2$), 3.66 (2H, s, CH$_2$), 3.71 (3H, s, OCH$_3$), 6.43 (1H, s, CH), 6.58 (1H, s, CH), 7.09-7.12 (1H, m, CH), 7.20-7.38 (3H, m, 3×CH). LC/MS (ES+) t$_r$=5.93 min, m/z 510.49 (M$^+$+H).

2-(2-Hydroxybenzyl)-7-methoxy-6-triisopropylsilyloxy-1,2,3,4-tetrahydroisoquinoline 29

171 mg, 70%, pale yellow oil, $^1$H NMR (270 MHz; CDCl$_3$) 1.07 (18H, d, J=6.7 Hz, 6×CH$_3$), 1.15-1.29 (3H, m, 3×CH), 2.79 (4H, brs, 2×CH$_2$), 3.65 (2H, brs, CH$_2$), 3.72 (3H, s, OCH$_3$), 3.85 (2H, s, CH$_2$), 6.43 (1H, s, CH), 6.59 (1H, s, CH), 6.76-6.86 (2H, m, 2×CH), 7.01 (1H, dd, J=7.4, 1.5 Hz, CH), 7.15-7.21 (1H, m, CH). LC/MS (ES+) t$_r$=4.66 min, m/z 442.57 (M$^+$+H).

6-Benzyloxy-2-(4-cyanobenzyl)-7-methoxy-1,2,3,4-tetrahydroisoquinoline 29A

White powder (0.36 g, 62%), mp=161-162° C., R$_f$: 0.41 (EtOAc/Hexane 1:1), $^1$H NMR (270 MHz, CDCl$_3$) δ 2.65-2.76 (4H, m, 2×CH$_2$), 3.53 (2H, s, CH$_2$), 3.70 (2H, s, CH$_2$), 3.81 (3H, s, CH$_3$O), 5.10 (2H, s, CH$_2$), 6.49 (1H, s, ArH), 6.63 (1H, s, ArH), 7.21-7.44 (7H, m, ArH), 7.50 (2H, m, ArH), 7.60 (2H, m, ArH); $^{13}$C NMR (67.5 MHz, CDCl$_3$) δ 28.7 (CH$_2$), 51.0 (CH$_2$), 55.8 (CH$_2$), 56.1 (CH$_3$O), 62.3 (CH$_2$), 71.1 (CH$_2$), 110.0 (CH(Ar)), 111.0 (C(Ar)), 114.3 (CH(Ar)), 119.1 (CN), 126.0 (C(Ar)), 127.0 (C(Ar)), 127.3(2×CH(Ar)), 127.9 (CH(Ar)), 128.6 (2×CH(Ar)), 129.5 (2×CH(Ar)), 132.3 (2CH(Ar)), 137.3 (C(Ar)) and 144.6 (C(Ar)), 146.9 (C(Ar)), 148.1 (C(Ar)). LC/MS (APCI+) t$_r$=1.39 min m/z 385.51 (M$^+$+H); (MeOH/H$_2$O 95/5). HRMS calcd. for C$_{25}$H$_{25}$N$_2$O$_2$ (MH$^+$), 385.1911 found. 385.1912; HPLC t$_r$=2.71 min (97.7%). (CH$_3$CN/H$_2$O 90/10).

6-Benzyloxy-2-(3-hydroxybenzyl)-7-methoxy-1,2,3,4-tetrahydroisoquinoline 30

A solution of 6-(benzyloxy)-7-methoxy-2-(3-(triisopropylsilyloxy)benzyl)-1,2,3,4-tetrahydroisoquinoline (2.7 g, 5 mmol) in THF (50 mL) was cooled to 0° C. and 1M TBAF/THF (5.5 mL, 5.5 mmol) added drop wise. The solution was stirred at 0 C. for 1 h 30 min and water (20 mL) added as well as EtOAc (80 mL). The organic layer was washed with water, brine, dried with MgSO$_4$, filtered and concentrated under reduced pressure. The resulting solid was washed with hexane, filtered and dried. 1.7 g (90%), white powder, mp=78-79° C.; R$_f$: 0.12 (Hexane/EtOAc 3:1), $^1$H NMR (270 MHz, CDCl$_3$) δ 2.63-2.78 (4H, m, 2×CH$_2$), 3.52 (2H, s, CH$_2$), 3.58 (2H, s, CH$_2$), 3.79 (3H, s, CH$_3$O), 5.08 (2H, s, OCH$_2$), 6.48 (1H, s, ArH), 6.60 (1H, s, ArH), 6.68 (1H, dd, J 8.2 and 2.5 Hz, ArH), 6.82 (1H, d, J 2.5 Hz, ArH), 6.88 (1H, d, J 7.7 Hz, ArH), 7.15 (1H, dd, J 8.2 and 7.7 Hz, 1H, ArH), 7.26-7.47 (5H, m, ArH). $^{13}$C NMR (67.5 MHz, CDCl$_3$) δ 12.7((CH$_3$)$_2$CHSi), 18.0((CH$_3$)$_2$CHSi), 28.8 (CH$_2$), 50.7 (CH$_2$), 55.9 (CH$_2$), 56.1 (CH$_3$O), 62.7 (CH$_2$), 71.2 (OCH$_2$), 110.1 (CH(Ar)), 114.3 (CH(Ar)), 118.6 (CH(Ar)), 120.8 (CH(Ar)), 126.4 (C(Ar)), 127.4 (CH(Ar)), 127.6 (C(Ar)), 127.8 CH(Ar)), 128.6 (CH(Ar)), 129.2 (CH(Ar)), 137.4 (C(Ar)), 140.0 (C(Ar)), 146.6 (C(Ar)), 147.9 (C(Ar)) and 156.1 (C(Ar)). LC/MS (APCI+) t$_r$=5.12 min m/z 376.59 (M$^+$+H); MeOH/H$_2$O 50/50 to 95/5 (5 min); HPLC t$_r$=3.26 min (100%). (CH$_3$CN/H$_2$O 90/10)

6-(Benzyloxy)-2-(3-ethoxybenzyl)-7-methoxy-1,2,3,4-tetrahydroisoquinoline 31

A mixture of 30 (450 mg, 1.2 mmol), EtI (0.19 mL, 2.4 mmol) and K$_2$CO$_3$ (207 mg, 1.5 mmol) in EtOH was stirred at rt for 18 hours. After addition of water, the organics were extracted with ethyl acetate, the organic layer washed with water, brine, dried (MgSO$_4$), filtered and the solvents evaporated under reduced pressure. The crude solid was purified by flash chromatography (hexane/ethyl acetate 4:1) to give 200 mg (41%) of yellow oil, R$_f$: 0.68 (Hexane/EtOAc 1:1), $^1$H NMR (270 MHz, CDCl$_3$) δ 1.39 (3H, t, J 6.9 Hz, CH$_3$), 2.65-2.79 (4H, m, 2×CH$_2$), 3.54 (2H, s, CH$_2$), 3.63 (2H, s, CH$_2$), 3.80 (3H, s, CH$_3$O), 4.01 (2H, q, J 6.9 Hz, CH$_2$), 5.09 (2H, s, CH$_2$), 6.50 (1H, s, ArH), 6.61 (1H, s, ArH), 6.79 (1H, ddd, J 7.9, 2.2 and 1.0 Hz, ArH), 6.93-6.96 (2H, m, ArH), 7.20 (1H, t, J 7.9 Hz, 1H, ArH), 7.26-7.44 (5H, m, ArH), $^{13}$C NMR (67.5 MHz, CDCl$_3$) δ 15.0 (CH$_3$), 28.7 (CH$_2$), 50.8 (CH$_2$), 55.8 (CH$_2$), 56.1 (CH$_3$O), 62.8 (CH$_2$), 63.4 (CH$_2$O), 71.2 (CH$_2$O), 110.1 (CH(Ar)), 113.3 (CH(Ar)), 114.3 (CH(Ar)), 115.1 (CH(Ar)), 121.4 (CH(Ar)), 126.3 (C(Ar)), 127.3 (2×CH(Ar)), 127.5 (C(Ar)), 127.8 (CH(Ar)), 128.6 (2×CH (Ar)), 129.3 (CH(Ar)), 137.4 (C(Ar)), 140.1 (C(Ar)), 146.6 (C(Ar)), 147.9 (C(Ar)) and 159.1 (C(Ar)). LC/MS (APCI+) t$_r$=5.68 min m/z 404.59 (M$^+$+H); MeOH/H2O 50/50 to 95/5 (5 min); HPLC t$_r$=8.80 min (84.7%). (CH$_3$CN/H$_2$O 90/10)

6-(Benzyloxy)-2-(3-isopropoxybenzyl)-7-methoxy-1,2,3,4-tetrahydroisoquinoline 32

Sodium hydride (48 mg, 1.2 mmol) was added to a solution of 30 (300 mg, 0.8 mmol) in THF (10 ml) and the reaction mixture was stirred at rt for 20 min. 2-Iodopropane (0.12 ml, 1.2 mmol) was added and the reaction mixture was stirred at rt for 26 h. Further 2-iodopropane (0.36 ml, 3.6 mmol) was added and the reaction mixture was heated at 60° C. 24 h. The solution was concentrated in vacuo, water was added and the aqueous layer was extracted with ethyl acetate (3×). The combined organic phases were washed with brine, dried (MgSO$_4$) and concentrated in vacuo. Purification (flashmaster: 50 g, 100% hex-100% EtOAc over 35 min) afforded the title compound (259 mg, 77%) as a colourless oil; $^1$H NMR (270 MHz; CDCl$_3$) 1.31 (6H, d, J=6.2 Hz, 2×CH$_3$), 2.66-2.75 (4H, m, 2×CH$_2$), 3.54 (2H, s, CH$_2$), 3.62 (2H, s, CH$_2$), 3.80 (3H, s, OCH$_3$), 4.54 (1H, septet, J=6.2 Hz, CH), 5.09 (2H, s, CH$_2$Ph), 6.50 (1H, s, CH), 6.61 (1H, s, CH), 6.77-6.81 (1H, m, CH), 6.91-6.94 (2H, m, 2×CH), 7.16-7.47 (6H, m, 5×CH, phenyl). $^{13}$C NMR (67.5 MHz; CDCl$_3$) 22.18 (CH$_3$), 28.77 (CH$_2$), 50.80 (CH$_2$), 55.85 (CH$_2$), 56.16 (OCH$_3$), 62.85 (CH$_2$), 69.75 (CH), 71.18 (CH$_2$), 110.13 (CH), 114.30 (CH), 114.59 (CH), 116.47 (CH), 126.31 (C), 127.35 (CH), 127.55 (C), 127.82 (CH), 128.58 (CH), 129.32 (CH), 137.40 (C), 140.16 (C), 146.69 (C), 147.91 (C), 158.02 (C). LC/MS (APCI−) t$_r$=7.47 min, m/z 416.35 (M−H)$^-$.

3-((6-(Benzyloxy)-7-methoxy-3,4-dihydroisoquinolin-2(1H)-yl)methyl)phenyl acetate 33

A solution of 30 (450 mg, 1.2 mmol), acetic anhydride (0.13 mL, 1.4 mmol), TEA (0.2 mL, 1.4 mmol) in CHCl$_3$ (10 mL) was stirred at rt o/n. After addition of CHCl$_3$ (50 mL), the organic layer was washed with water, brine, dried (MgSO$_4$), filtered and concentrated. The crude product was purified by flash chromatography (hexane/EtOAc 4:1 to 3:1) to give 450 mg (90%) of white powder. mp=94-95° C., R$_f$: 0.51 (Hexane/EtOAc 1:1), $^1$H NMR (270 MHz, CDCl$_3$) δ 2.28 (3H, s, CH3CO), 2.65-2.77 (4H, m, 2×CH$_2$), 3.52 (2H, s, CH$_2$), 3.65 (2H, s, CH$_2$), 3.80 (3H, s, CH$_3$O), 5.10 (2H, s, OCH$_2$), 6.50 (1H, s, ArH), 6.61 (1H, s, ArH), 6.98 (1H, ddd, J 7.9 and 2.2 and 1.2 Hz, ArH), 7.13-7.19 (1H, m, ArH), 7.21-7.44 (7H, m, ArH). $^{13}$C NMR (67.5 MHz, CDCl$_3$) δ 21.3 (CH$_3$CO), 28.7 (CH$_2$), 50.9 (CH$_2$), 55.8 (CH$_2$), 56.1 (CH$_3$O), 62.4 (CH$_2$), 71.2 (OCH$_2$), 110.1 (CH(Ar)), 114.3 (CH(Ar)), 120.4 (CH(Ar)), 122.0 (CH(Ar)), 126.2 (C(Ar)), 126.5 (CH(Ar)), 127.3 (CH(Ar)), 127.4 (C(Ar)), 127.8 (CH(Ar)), 128.6 (CH(Ar)), 129.3 (CH(Ar)), 137.4 (C(Ar)), 140.6 (C(Ar)), 146.7 (C(Ar)), 147.9 (C(Ar)), 150.8 (C(Ar)) and 169.7 (CO). LC/MS (ES+) t$_r$=5.06 min m/z 418.48 (M$^+$+H); MeOH/H$_2$O 50/50 to 95/5 (5 min) HPLC t$_r$=4.74 min (100%). (CH$_3$CN/H$_2$O 90/10)

2-(3-Aminobenzyl)-6-(benzyloxy)-7-methoxy-1,2,3,4-tetrahydroisoquinoline 34

6-(Benzyloxy)-7-methoxy-2-(3-nitrobenzyl)-1,2,3,4-tetrahydroisoquinoline (1.61 g, 4 mmol) was added to a suspension of Raney Nickel (1.5 g of 50% slurry in water, washed 3×5 mL of methanol) in methanol (50 mL). After drop wise addition of hydrazine hydrate (1 mL), the mixture was refluxed for 30 minute, cooled to RT and filtered through celite. The solvent was removed under reduced pressure and the resulting yellow solid was stirred in diethyl ether, filtered and dried, yielding 1.4 g (93%) of a yellow powder, mp=114-115° C., R$_f$: 0.38 (EtOAc/MeOH 10:1), $^1$H NMR (270 MHz, CDCl$_3$) δ 2.68-2.77 (4H, m, 2×CH$_2$), 3.53 (2H, s, CH$_2$), 3.58 (2H, s, CH$_2$), 3.81 (3H, s, CH$_3$O), 5.11 (2H, s, OCH$_2$), 6.52 (1H, s, ArH), 6.59 (1H, dd, J 8.2 and 1.5 Hz, ArH), 6.63 (1H, s, ArH), 6.75-6.78 (2H, m, ArH), 7.12 (1H, t, J 8.0 Hz, 1H, ArH), 7.29-7.45 (5H, m, ArH), $^{13}$C NMR (67.5 MHz, CDCl$_3$) δ 28.7 (CH$_2$), 51.0 (CH$_2$), 55.9 (CH$_2$), 56.1, (CH$_3$O), 63.0 (CH$_2$), 71.2 (CH$_2$O), 110.2 (CH(Ar)), 114.0 (CH(Ar)), 114.4 (CH(Ar)), 115.7 (CH(Ar)), 119.5 (CH(Ar)), 126.3 (C(Ar)), 127.4 (2×CH(Ar)), 127.6 (C8a), 127.9 (CH(Ar)), 128.6 (2×CH(Ar)), 129.2 (CH(Ar)), 137.4 (C(Ar)), 139.8 (C(Ar)), 146.6 (C(Ar)), 146.7 (C(Ar)) and 147.9 (C(Ar)). LC/MS (APCI+) t$_r$=1.32 min m/z 375.63 (M$^+$+H); MeOH/H2O 50/50 to 95/5 (5 min); HPLC t$_r$=6.86 min (98.33%). (CH$_3$CN/H$_2$O 90/10)

2-(3-Acetamidobenzyl)-6-(benzyloxy)-7-methoxy-1,2,3,4-tetrahydroisoquinoline 35

A solution of 3-((6-(benzyloxy)-7-methoxy-3,4-dihydroisoquinolin-2(1H)-yl)methyl)aniline (300 mg, 0.8 mmol), acetic anhydride (0.26 mL, 2.7 mmol), TEA (0.39 mL, 2.7 mmol) in CHCl$_3$ (30 mL) was stirred at RT for 3 h. After addition of water, the organic layer was separated, washed water, brine, dried (MgSO4), filtered and concentrated under reduced pressure. 280 mg of yellow oil was obtained which was flash columned (EtOAc/Hexane 10/1) then re-columned with DCM/EtOAc (2:1 to 1:5) to give 180 mg (54%) of a white powder. Mp=63-66° C. R$_f$: 0.26 (EtOAc/MeOH 20:1), $^1$H NMR (270 MHz, CDCl$_3$) δ 2.14 (3H, s, CH$_3$CO), 2.68-2.75 (4H, m, 2×CH$_2$), 2.84 (br, 1H, NH), 3.52 (2H, s, CH$_2$), 3.64 (2H, s, CH$_2$), 3.79 (3H, s, CH$_3$O), 5.09 (2H, s, OCH$_2$), 6.48 (1H, s, ArH), 6.60 (1H, s, ArH), 7.11 (1H, d, J 7.7 Hz, 1H, ArH), 7.24-7.43 (7H, m, ArH), 7.53 (1H, d, J 8.2, ArH). $^{13}$C NMR (67.5 MHz, CDCl$_3$) δ 24.7 (CH$_3$CO), 28.6 (CH$_2$), 50.9 (CH$_2$), 55.6 (CH$_2$), 56.1 (CH$_3$O), 62.5 (CH$_2$), 71.2 (CH$_2$O), 110.1 (CH(Ar)), 114.2 (CH(Ar)), 118.9 (CH(Ar)), 120.3 (CH(Ar)), 125.1 (CH(Ar)), 126.1 (C(Ar)), 127.1 (C(Ar)), 127.3 (2×CH(Ar)), 127.8 (CH(Ar)), 128.6 (2×CH(Ar)), 129.1 (CH(Ar)), 137.3 (C(Ar)), 138.0 (C(Ar)), 139.3 (C(Ar)), 146.7 (C(Ar)), 147.9 (C(Ar)) and 168.6 (CO). LC/MS (APCI+) t$_r$=4.93 min m/z 417.44 (M$^+$+H); MeOH/H$_2$O 95/5 to 50/50 in 5 min; HPLC t$_r$=5.03 min (93.4%). (CH$_3$CN/H$_2$O 90:10)

6-(Benzyloxy)-2-(3-methanesulfonylaminobenzyl)-7-methoxy-1,2,3,4-tetrahydroisoquinoline 36

Mesyl chloride (0.09 mL, 1.2 mmol) was added drop wise to a solution of 6-benzyloxy-2-(3-(aminobenzyl)-7-methoxy-1,2,3,4-tetrahydroisoquinoline (374 mg, 1 mmol) in pyridine (2 mL). The mixture was stirred for an 18 hours at room temperature. After addition of water, the organics were extracted with ethyl acetate, the organic layer was washed with water, brine, dried (MgSO4), filtered and concentrated. The crude white solid was purified by flash chromatography (hexane/EtOAc 1:4) to give 260 mg (58%) of white powder. mp=132-133° C., R$_f$: 0.44 (EtOAc), $^1$H NMR (270 MHz, CDCl$_3$) δ 2.64-2.76 (4H, m, 2×CH$_2$), 2.97 (3H, s, CH3SO$_2$), 3.52 (2H, s, CH$_2$), 3.63 (2H, s, CH$_2$), 3.80 (3H, s, CH$_3$O), 5.09 (2H, s, OCH$_2$), 6.49 (1H, s, ArH), 6.61 (1H, s, ArH), 7.12-7.44 (10H, m, ArH, NH). $^{13}$C NMR (67.5 MHz, CDCl$_3$) δ 28.7 (CH$_2$), 39.5 (CH$_3$SO$_2$), 50.9 (CH$_2$), 55.8 (CH$_2$), 56.2 (CH$_3$O), 62.3 (CH$_2$), 71.1 (OCH$_2$), 110.1 (C8), 114.3 (C5), 119.5 (CH(Ar)), 121.3 (CH(Ar)), 126.1 (CH(Ar)), 126.2 (C4a), 127.2 (C8a), 127.3 (2×CH(Ar)), 127.8 (CH(Ar)), 128.6 (2×CH(Ar)), 129.6 (CH(Ar)), 136.9 (C(Ar)), 137.3 (C(Ar)), 140.6 (C(Ar)), 146.8 (C(Ar)), 148.0 (C(Ar)). LC/MS (ES+) t$_r$=4.62 min m/z 453.40 (M$^+$+H); MeOH/H$_2$O 50/50 to 95/5 (5 min); HPLC t$_r$=5.97 min (100%). (CH$_3$CN/H$_2$O 90/10)

2-(3-(Methoxycarbonyl)benzyl)-6-triisopropylsilyloxy-7-methoxy-1,2,3,4-tetrahydroisoquinoline 36A Purification (flashmaster: 20 g, gradient elution hex/EtOAc) afforded the title compound (318 mg, 73%) as a colourless oil. $^1$H NMR (270 MHz; CDCl$_3$) 1.06 (18H, d, J=6.7 Hz, 6×C H$_3$CH), 1.14-1.28 (3H, m, 3×CH), 2.68-2.74 (4H, m, 4×CH$_2$), 3.52 (2H, s, 2×CH), 3.69 (2H, s, 2×CH), 3.70

(3H, s, OCH$_3$), 3.90 (3H, s, OCH$_3$), 6.41 (1H, s, CH), 6.57 (1H, brd, J=7.7 Hz, CH), 7.94 (1H, dt, J 7.7, 1.3 Hz, CH), 8.03 (1H, brs, CH). $^{13}$C NMR (67.5 MHz; CDCl$_3$) 12.96 (3×CH), 18.05 (6×CH$_3$), 28.51 (CH$_2$), 50.89 (CH$_2$), 52.21 (CH$_3$), 55.66 (CH$_3$), 55.90 (CH$_2$), 62.59 (CH$_2$), 110.27 (CH), 120.18 (CH), 126.16 (C), 127.07 (C), 128.52 (CH), 130.24 (C), 130.34 (C), 133.88 (CH), 139.01 (C), 143.94 (C), 149.06 (C), 167.31 (C). LC/MS (APCI−) t$_r$=3.76 min, m/z 326.15 (M-Si(iPr)$_3$-H)$^−$.

6-Benzyloxy-2-(3-acetoxybenzyl)-7-methoxy-1,2,3,4-tetrahydroisoquinoline 36B

A solution of 6-benzyloxy-2-(3-hydroxybenzyl)-7-methoxy-1,2,3,4-tetrahydroisoquinoline 30 (450 mg, 1.2 mmol), acetic anhydride (0.13 mL, 1.4 mmol), TEA (0.2 mL, 1.4 mmol) in CHCl$_3$ (10 mL) was stirred at rt for 18 hours. After addition of CHCl$_3$ (50 mL), the organic layer was washed with water, brine, dried (MgSO$_4$), filtered and concentrated. The crude product was purified by flash chromatography (hexane/EtOAc 4:1 to 3:1) to give a white powder (450 mg, 90%), mp=94-95° C., R$_f$: 0.51 (Hexane/EtOAc 1:1), $^1$H NMR (270 MHz, CDCl$_3$) δ 2.28 (3H, s, CH$_3$), 2.65-2.77 (4H, m, 2×CH$_2$), 3.52 (2H, s, CH$_2$), 3.65 (2H, s, CH$_2$), 3.80 (3H, s, CH$_3$O), 5.10 (2H, s, CH$_2$), 6.50 (1H, s, ArH), 6.61 (1H, s, ArH), 6.98 (1H, ddd, J=7.9 and 2.2 and 1.2 Hz, ArH), 7.13-7.19 (1H, m, ArH), 7.21-7.44 (7H, m, ArH); $^{13}$C NMR (67.5 MHz, CDCl$_3$) δ 21.3 (CH$_3$), 28.7 (CH$_2$), 50.9 (CH$_2$), 55.8 (CH$_2$), 56.1 (CH$_3$O), 62.4 (CH$_2$), 71.2 (CH$_2$), 110.1 (CH(Ar)), 114.3 (CH(Ar)), 120.4 (CH(Ar)), 122.0 (CH(Ar)), 126.2 (C(Ar)), 126.5 (CH(Ar)), 127.3 (2×CH(Ar)), 127.4 (C(Ar)), 127.8 (CH(Ar)), 128.6 (2×CH(Ar)), 129.3 (CH(Ar)), 137.4 (C(Ar)), 140.6 (C(Ar)), 146.7 (C(Ar)), 147.9 (C(Ar)), 150.8 (C(Ar)) and 169.7 (CO). LC/MS (ES+) t$_r$=4.06 min m/z 418.48 (M$^+$+H); gradient MeOH/H$_2$O 50/50 to 95/5 (5 min); HPLC t$_r$=4.74 min (100%). (CH$_3$CN/H$_2$O 90/10)

Synthesis of
6-hydroxy-2-benzyl-1,2,3,4-tetrahydroisoquinolines

Method 1:

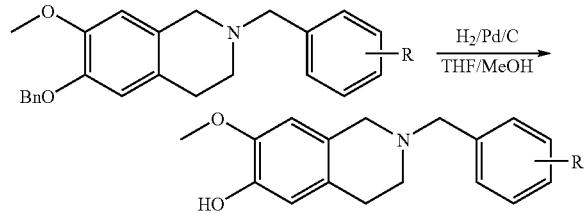

A solution of 6-(benzyloxy)-2-benzyl-1,2,3,4-tetrahydroisoquinoline (1 mmol) in THF (20 mL) and methanol (20 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The crude mixture was purified by flash chromatography (hexane/ethyl acetate) or (DCM/ethyl acetate).

6-Hydroxy-2-(3-methoxybenzyl)-1,2,3,4-tetrahydroisoquinoline 37

White powder, 205 mg (76%), mp=223-224° C., R$_f$: 0.29 (Hexane/EtOAc 1:1), $^1$H NMR (270 MHz, CDCl$_3$) δ 2.67-2.78 (4H, m, 2×CH$_2$), 3.55 (2H, s, CH$_2$), 3.65 (2H, s, CH$_2$), 3.76 (3H, s, CH$_3$O), 6.40 (1H, d, J 2.5 Hz, ArH), 6.51 (1H, dd, J 8.4, 2.5 Hz, ArH), 6.79 (1H, d, J 8.4 Hz, ArH), 6.81 (1H, dd, J 8.4 and 2.0 Hz, ArH), 6.93-6.97 (2H, m, ArH), 7.22 (1H, t, J 8.4 Hz, ArH), $^{13}$C NMR (67.5 MHz, CDCl$_3$) δ 29.0 (CH$_2$), 50.6 (CH$_2$), 55.3 (CH$_3$O), 55.6 (CH$_2$), 62.8 (CH$_2$), 113.1 (CH(Ar)), 113.4 (CH(Ar)), 114.6 (CH(Ar)), 115.1 (CH(Ar)), 121.8 (CH(Ar)), 126.6 (C(Ar)), 127.8 (CH(Ar)), 129.3 (CH(Ar)), 135.6 (C(Ar)), 139.5 (C(Ar)), 154.2 (C(Ar)) and 159.7 (C(Ar)). LC/MS (APCI+) t$_r$=4.43 min m/z 270.46 (M$^+$+H); MeOH/H2) 95/5; HPLC t$_r$=4.80 min (97.1%). (CH3CN/H2O 90/10)

2-Benzyl-6-hydroxy-7-methoxy-1,2,3,4-tetrahydroisoquinoline 38

Light yellow powder, 105 mg (39%), mp 134-135° C., R$_f$: 0.47 (ethyl acetate/hexane 3:1), $^1$H NMR (270 MHz, CDCl$_3$) δ 2.68-2.80 (4H, m, 2×CH$_2$), 3.52 (2H, s, CH$_2$), 3.66 (2H, s, CH$_2$), 3.79 (3H, s, CH$_3$O), 5.49 (1H, br, OH), 6.44 (1H, s, ArH), 6.64 (1H, s, ArH), 7.22-7.40 (5H, m, ArH), $^{13}$C NMR (67.5 MHz, CDCl$_3$) δ 28.5 (CH$_2$), 50.9 (CH$_2$), 55.8 (CH$_2$), 56.0 (CH$_3$O), 62.8 (CH$_2$), 108.8 (CH(Ar)), 114.3 (CH(Ar)), 126.1 (C(Ar)), 127.0 (C(Ar)), 127.2 (CH(Ar)), 128.4 (2×CH(Ar)), 129.3 (2×CH(Ar)), 138.4 (C(Ar)), 144.0 (C(Ar)) and 144.9 (C(Ar)). LC/MS (APCI+) t$_r$=1.33 min m/z 270.46 (M$^+$+H); HPLC t$_r$=3.06 min (97.42%). (CH$_3$CN/H$_2$O 90/10); HRMS (Electrospray) calcd. for C$_{17}$H$_{19}$NO$_2$ (MH$^+$), 270.1489 found. 270.1488

6-Hydroxy-7-methoxy-2-(4-methoxybenzyl)-1,2,3,4-tetrahydroisoquinoline 39

Light yellow powder, 180 mg (60%), mp 162-163° C., R$_f$: 0.12 (ethyl acetate/hexane 1:1), $^1$H NMR (270 MHz, CDCl$_3$) δ 2.69-2.78 (4H, m, 2×CH$_2$), 3.49 (2H, s, CH$_2$), 3.60 (2H, s, CH$_2$), 3.79 (3H, s, CH$_3$O), 3.80 (3H, s, CH$_3$O), 5.41 (1H, br, OH), 6.44 (1H, s, ArH), 6.62 (1H, s, ArH), 6.86 (2H, m, ArH), 7.29 (2H, m, ArH). $^{13}$C NMR (67.5 MHz, CDCl$_3$) δ 27.5 (CH$_2$), 50.3 (CH$_2$), 55.1 (CH$_2$), 55.3 (CH$_3$O), 55.9 (CH$_3$O), 61.6 (CH$_2$), 109.1 (CH(Ar)) 113.7 (2×CH(Ar)), 114.6 (CH(Ar)), 124.6 (C(Ar)), 126.2 (C(Ar)), 128.5 (C(Ar)), 130.9 (2×CH(Ar)), 144.4 (C(Ar)), 145.5 (C(Ar)) and 159.1 (C(Ar)). LC/MS (APCI+) t$_r$=1.67 min m/z 300.50 (M$^{30}$ +) HPLC t$_r$=6.99 min (97.6%). (MeOH/H$_2$O 99/1); HRMS (Electrospray) calcd. for C$_{18}$H$_{21}$NO$_3$ (MH$^+$), 300.1594 found. 300.1593.

6-Hydroxy-7-methoxy-2-(3-methoxybenzyl)-1,2,3,4-tetrahydroisoquinoline 40

Light yellow powder, 180 mg (60%), mp 161-162° C., R$_f$: 0.21 (ethyl acetate/hexane 1:1), $^1$H NMR (270 MHz, CDCl$_3$) δ 2.67-2.80 (4H, m, 2×CH$_2$), 3.53 (2H, s, CH$_2$), 3.64 (2H, s, CH$_2$), 3.79 (6H, s, 2×CH$_3$O), 5.55 (1H, br, OH), 6.45 (1H, s, ArH), 6.64 (1H, s, ArH), 6.81 (1H, ddd, J 8.1, 2.4 and 1.0 Hz, ArH), 6.96 (2H, m, ArH), 7.23 (1H, t, J 8.1 Hz, ArH), $^{13}$C NMR (67.5 MHz, CDCl$_3$) δ 28.6 (CH$_2$), 50.9 (CH$_2$), 55.3 (CH$_3$O), 55.9 (CH$_2$), 56.1 (CH$_3$O), 62.9 (CH$_2$), 108.9 (CH(Ar)) 112.8 (CH(Ar)), 114.2 (CH(Ar)), 114.5 (CH(Ar)), 121.4 (CH(Ar)), 126.2 (C(Ar)), 127.0 (C(Ar)), 129.3 (CH(Ar)), 140.2 (C(Ar)), 144.0 (C(Ar)), 145.0 (C(Ar)) and 159.7 (C(Ar)). LC/MS (APCI+) t$_r$=1.31 min m/z 300.44 (M$^+$+H) (MeOH/H$_2$O 95/5); HPLC t$_r$=2.76 min (97.4%). (CH$_3$CN/H$_2$O 90/10); HRMS (Electrospray) calcd. for C$_{18}$H$_{22}$NO$_3$ (MH$^+$), 300.1594 found. 300.1591

6-Hydroxy-7-methoxy-2-(2-methoxybenzyl)-1,2,3,4-tetrahydroisoquinoline 41

Yellow powder, 190 mg (63%), mp=128-129° C., $R_f$: 0.27 (EtOAc/Hexane 2:1), $^1$H NMR (270 MHz, CDCl$_3$) δ 2.73-2.82 (4H, m, 2×CH$_2$), 3.60 (2H, s, CH$_2$), 3.71 (2H, s, CH$_2$), 3.80 (3H, s, CH$_3$O), 3.83 (3H, s, CH$_3$O), 5.47 (1H, br, OH), 6.46 (1H, s, ArH), 6.63 (1H, s, ArH), 6.87 (1H, d, J 7.9 Hz, ArH), 6.94 (1H, dt, J 7.4 and 1.0 Hz, ArH), 7.24 (1H, dt, J 7.4 and 1.7 Hz, ArH), 7.43 (1H, dd, J 7.4 and 1.7 Hz, ArH). $^{13}$C NMR (67.5 MHz, CDCl$_3$) δ 28.5 (CH$_2$), 51.0 (CH$_2$), 55.6 (CH$_3$O), 55.8 (CH$_2$), 55.9 (CH$_2$), 56.1 (CH$_3$O), 108.9 (CH(Ar)), 110.5 (CH(Ar)), 114.3 (CH(Ar)), 114.6 (Ar), 120.4 (CH(Ar)), 126.4 (C(Ar)), 127.1 (C(Ar)), 128.1 (CH(Ar)), 130.4 (CH(Ar)), 144.0 (C(Ar)), 144.8 (C(Ar)), 157.9 (C(Ar)). LC/MS (APCI+) $t_r$=5.65 min m/z 300.44 (M$^+$+H); HPLC $t_r$=4.12 min (94%). (CH$_3$CN/H$_2$O 90/10)

6-Hydroxy-2-(3,5-dimethoxybenzyl)-7-methoxy-1,2,3,4-tetrahydroisoquinoline 42

Yellow powder, 285 mg (86%), mp=127-128° C., $R_f$: 0.28 (EtOAc/Hexane 2:1), $^1$H NMR (270 MHz, CDCl$_3$) δ 2.68-2.78 (4H, m, 2×CH$_2$), 3.53 (2H, s, CH$_2$), 3.60 (2H, s, CH$_2$), 3.78 (6H, s, 2×CH$_3$O), 3.80 (3H, s, CH$_3$O), 6.37 (1H, t, J 2.4 Hz, ArH), 6.46 (1H, s, ArH), 6.57 (2H, d, J 2.4 Hz, ArH), 6.64 (1H, s, ArH), $^{13}$C NMR (67.5 MHz, CDCl$_3$) δ 28.5 (CH$_2$), 50.9 (CH$_2$), 55.5 (2×CH$_3$O), 55.8 (CH$_2$), 56.1 (CH$_3$O), 62.9 (CH$_2$), 56.1 (CH$_3$O), 99.30 (CH(Ar)), 106.9 (2×CH(Ar)), 109.0 (CH(Ar)), 114.3 (CH(Ar)), 126.0 (C(Ar)), 127.0 (C(Ar)), 144.0 (C(Ar)), 144.8 (C(Ar)) and 160.8 (2×Ar). LC/MS (APCI+) $t_r$=4.48 min m/z 330.42 (M$^+$+H); HPLC $t_r$=3.58 min (98.2%). (CH$_3$CN/H$_2$O 70/30)

6-Hydroxy-7-methoxy-2-(3-phenoxybenzyl)-1,2,3,4-tetrahydroisoquinoline 43

Yellow powder, 255 mg (71%), mp=139-140° C., $R_f$: 0.52 (EtOAc/Hexane 1:1), $^1$H NMR (270 MHz, CDCl$_3$) δ 2.67-2.76 (4H, m, 2×CH$_2$), 3.53 (2H, s, CH$_2$), 3.64 (2H, s, CH$_2$), 3.80 (3H, s, CH$_3$O), 6.45 (1H, s, ArH), 6.64 (1H, s, ArH), 6.90 (1H, ddd, J 8.2, and 1.6 Hz, ArH), 6.99-7.15 (5H, m, Ar), 7.28-7.35 (3H, m, Ar), $^{13}$C NMR (67.5 MHz, CDCl$_3$) δ 28.5 (CH$_2$), 50.8 (CH$_2$), 55.7 (CH$_2$), 56.0 (CH$_3$O), 62.5 (CH$_2$), 108.8 (CH(Ar)), 114.2 (CH(Ar)), 117.6 (CH(Ar)), 118.8 (CH(Ar)), 119.7 (CH(Ar)), 123.2 (CH(Ar)), 124.1 (CH(Ar)), 126.1 (C(Ar)), 127.0 (C(Ar)), 129.6 (CH(Ar)), 129.8 (CH(Ar)), 140.7 (C(Ar)), 144.0 (C(Ar)), 144.9 (C(Ar)), 157.3 (C(Ar)) and 157.4 (C(Ar)). LC/MS (APCI+) $t_r$=5.40 min m/z 362.47 (M$^+$+H); HPLC $t_r$=5.14 min (99.8%). (MeOH/H$_2$O 90/10)

6-Hydroxy-7-methoxy-2-(3-methylbenzyl)-1,2,3,4-tetrahydroisoquinoline 44

Yellow powder, 170 mg (60%), mp=128-129° C., $R_f$: 0.53 (EtOAc/Hexane 1:1), $^1$H NMR (270 MHz, CDCl$_3$) δ 2.34 (3H, s, CH$_3$), 2.68-2.78 (4H, m, 2×CH$_2$), 3.52 (2H, s, CH$_2$), 3.63 (2H, s, CH$_2$), 3.80 (3H, s, CH$_3$O), 6.45 (1H, s, ArH), 6.64 (1H, s, ArH), 7.06-7.10 (1H, m, ArH), 7.14-7.25 (3H, m, ArH). $^{13}$C NMR (67.5 MHz, CDCl$_3$) δ 21.5 (CH$_3$), 28.5 (CH$_2$), 51.0 (CH$_2$), 55.9 (CH$_2$), 56.0 (CH$_3$O), 62.9 (CH$_2$), 108.9 (CH(Ar)), 114.2 (CH(Ar)), 126.2 (C(Ar)), 126.3 (CH(Ar)), 127.0 (C(Ar)), 127.9 (CH(Ar)), 128.2 (CH(Ar)), 130.0 (CH(Ar)), 138.0 (C(Ar)), 138.3 (C(Ar)), 144.0 (C(Ar)), 144.9 (C(Ar)). LC/MS (APCI+) $t_r$=5.40 min m/z 362.47 (M$^+$+H); HPLC $t_r$=5.14 min (99.8%). (MeOH/H$_2$O 90/10)

6-Hydroxy-7-methoxy-2-(3-(triisopropylsilyloxy)benzyl)-1,2,3,4-tetrahydroisoquinoline 45

A solution of 6-(benzyloxy)-7-methoxy-2-(3-(triisopropylsilyloxy)benzyl)-1,2,3,4-tetrahydroisoquinoline (425 mg, 0.8 mmol) in THF (10 mL) and methanol (30 mL) was stirred with 10% Pd/C (40 mg) under hydrogen for 30 minutes. After filtration through celite and evaporation of the solvents under reduced pressure, the residual oil was purified by flash chromatography (hexane/ethyl acetate 5/1 to 4/1) to give 250 mg (71%) of a yellow oil. $R_f$: 0.30 (Hexane/EtOAc 3:1), $^1$H NMR (270 MHz, CDCl$_3$) δ 1.09 (18H, d, J 6.7 Hz, (CH$_3$)$_2$CHSi), 1.16-1.31 (3H, m, (CH$_3$)$_2$CHSi), 2.66-2.77 (4H, m, 2×CH$_2$), 3.52 (2H, s, CH$_2$), 3.61 (2H, s, CH$_2$), 3.79 (3H, s, CH$_3$O), 6.44 (1H, s, ArH), 6.62 (1H, s, ArH), 6.74-6.81 (1H, m, ArH), 6.93-6.96 (2H, m, ArH), 7.16 (1H, t, J 7.8 Hz, ArH), $^{13}$C NMR (67.5 MHz, CDCl$_3$) δ 12.8((CH$_3$)$_2$CHSi), 18.0 ((CH$_3$)$_2$CHSi), 28.5 (CH$_2$), 50.8 (CH$_2$), 55.8 (CH$_2$), 56.0 (CH$_3$O), 62.7 (CH$_2$), 108.9 (CH(Ar)), 114.4 (CH(Ar)), 118.6 (CH(Ar)), 120.8 (CH(Ar)), 122.0 (CH(Ar)), 126.2 (C(Ar)), 127.1 (C(Ar)), 129.2 (CH(Ar)), 139.9 (C(Ar)), 144.0 (C(Ar)), 145.0 (C(Ar)) and 156.1 (C(Ar)). LC/MS (APCI+) $t_r$=5.96 min m/z 532.71 (M$^+$+H); MeOH/H$_2$O) 95/5; HPLC $t_r$=16.49 min (100%). (CH$_3$CN/H$_2$O 90/10)

6-Hydroxy-7-methoxy-2-(4-methoxyphenethyl)-1,2,3,4-tetrahydroisoquinoline 46

Yellow powder, 280 mg (90%), mp=170-171° C., $R_f$: 0.18 (Hexane/EtOAc 1:2), $^1$H NMR (270 MHz, CDCl$_3$) δ 2.67-2.88 (8H, m, 4×CH$_2$), 3.62 (2H, s, CH$_2$), 3.78 (3H, s, OCH$_3$), 3.82 (3H, s, OCH$_3$), 6.50 (1H, s, ArH), 6.63 (1H, s, ArH), 6.80-6.85 (m, 2H, ArH), 7.12-7.18 (2H, m, ArH), $^{13}$C NMR (67.5 MHz, CDCl$_3$) δ 28.5 (CH$_2$), 33.1 (CH$_2$), 51.2 (CH$_2$), 55.4 (CH$_3$O), 55.9 (CH$_2$), 56.0 (CH$_3$O), 60.6 (CH$_2$), 108.9 (CH(Ar)), 113.9 (2×CH(Ar)), 114.4 (CH(Ar)), 125.9 (C(Ar)), 126.9 (C(Ar)), 129.7 (2×CH(Ar)), 132.5 (C(Ar)), 144.1 (C(Ar)), 145.1 (C(Ar)) and 158.0 (C(Ar)). LC/MS (APCI+) $t_r$=4.57 min m/z 314.49 (M$^+$+H); MeOH/H$_2$O 95/5 to 50/50 in 5 min. HPLC $t_r$=6.99 min (99.03%). (CH$_3$CN/H$_2$O 90/10)

6-Hydroxy-7-methoxy-2-(pyridin-3-ylmethyl)-1,2,3,4-tetrahydroisoquinoline 47

Yellow powder, 145 mg (53%), mp=165-166° C., $R_f$: 0.26 (EtOAc/MeOH 20:1), $^1$H NMR (270 MHz, CDCl$_3$/CD$_3$COCDl$_3$ 3:1) δ 2.47-2.58 (4H, m, 2×CH$_2$), 3.23 (2H, s, CH$_2$), 3.47 (2H, s, CH$_2$), 3.58 (3H, s, CH$_3$O), 6.26 (1H, s, ArH), 6.41 (1H, s, ArH), 7.08 (1H, dd, J 7.8 and 4.9 Hz, PyrH), 7.56 (1H, dt, J 7.8, 1.7 Hz, PyrH), 8.31 (1H, dd, J 4.9 and 1.7 Hz, PyrH), 8.38 (1H, d, J 1.7 Hz, PyrH), $^{13}$C NMR (67.5 MHz, CDCl$_3$/CD$_3$COCDl$_3$ 3:1) δ 28.3 (CH$_2$), 50.7 (CH$_2$), 55.6 (CH$_2$), 55.8 (CH$_3$O), 59.8 (CH$_2$), 108.9 (CH(Ar)), 114.4 (CH(Ar)), 123.4 (CHpyr), 125.3 (C(Ar)), 126.4 (C(Ar)), 134.0 (Cpyr), 136.7 (CHpyr), 144.3 (C(Ar)), 145.3 (C(Ar)), 148.4 (CHpyr) and 150.1 (CHpyr). LC/MS (APCI+) $t_r$=1.04 min m/z 271.30 (M$^+$+H); MeOH/H$_2$O 95/5. HPLC $t_r$=4.26 min (97.33%). (CH$_3$CN/H$_2$O 90:10)

6-Hydroxy-7-methoxy-2-(pyridin-2-ylmethyl)-1,2,3,4-tetrahydroisoquinoline 48

Yellow powder, 185 mg (69%), mp=137-138° C., $R_f$: 0.39 (EtOAc/MeOH 10:1), $^1$H NMR (270 MHz, CDCl$_3$) δ 2.72-

2.826 (4H, m, 2×CH$_2$), 3.59 (2H, s, CH$_2$), 3.79 (3H, s, CH$_3$O), 3.82 (2H, s, CH$_2$), 5.78 (1H, br, OH), 6.45 (1H, s, ArH), 6.64 (1H, s, ArH), 7.17 (1H, ddd, =7.4, 4.9 and 1.0 Hz, PyrH), 7.50 (1H, d, J 7.7 Hz, PyrH), 7.66 (1H, dt, J 7.7 and 2.0 Hz, PyrH), 8.56 (1H, ddd, J 4.9 2.0 and 1.0 Hz, PyrH), $^{13}$C NMR (67.5 MHz, CDCl$_3$) δ 28.6 (CH$_2$), 51.2 (CH$_2$), 55.9 (CH$_2$), 56.0 (CH$_3$O), 64.4 (CH$_2$), 108.8 (CH(Ar)), 114.3 (CH(Ar)), 122.2 (CHpyr), 123.2 (CHpyr), 126.0 (C(Ar)), 127.0 (C(Ar)), 136.6 (CHpyr), 144.1 (C(Ar)), 145.0 (C(Ar)), 149.2 (CHpyr) and 159.0 (Cpyr). LC/MS (APCI+) t$_r$=3.34 min m/z 271.44 (M$^+$+H); MeOH/H$_2$O 95/5 to 50/50 in 5 min; HPLC t$_r$=4.32 min (99.5%). (CH$_3$CN/H$_2$O 90:10)

6-Hydroxy-7-methoxy-2-(pyridin-4-ylmethyl)-1,2,3,4-tetrahydroisoquinoline 49

Yellow powder, 73 mg (54%), R$_f$: 0.30 (EtOAc/MeOH 10:1), $^1$H NMR (270 MHz, CDCl$_3$) δ 2.67-2.82 (4H, m, 2×CH$_2$), 3.52 (2H, s, CH$_2$), 3.66 (2H, s, CH$_2$), 3.80 (3H, s, CH$_3$O), 5.77 (1H, br, OH), 6.44 (1H, s, ArH), 6.66 (1H, s, ArH), 7.33 (2H, dd, J 4.6 and 1.5 Hz, 2×PyrH), 8.54 (2H, dd, J 4.6 and 1.5 Hz, PyrH), $^{13}$C NMR (67.5 MHz, CDCl$_3$) δ 28.5 (CH$_2$), 51.1 (CH$_2$), 55.9 (CH$_2$), 56.0 (CH$_3$O), 61.6 (CH$_2$), 108.8 (CH(Ar)), 114.4 (CH(Ar)), 123.9 (2×CHpyr), 125.7 (C(Ar)), 126.8 (C(Ar)), 144.3 (C(Ar)), 145.1 (Cpyr), 148.0 (C(Ar)), and 149.9 (2×CHpyr). LC/MS (ES−) t$_r$=1.04 min m/z 269.34 (M$^+$+H); MeOH/H$_2$O 95/5. HPLC t$_r$=4.31 min (98.64%). (CH$_3$CN/H$_2$O 90:10)

6-Hydroxy-7-methoxy-2-(3-acetamidobenzyl)-1,2,3,4-tetrahydroisoquinoline 50

Light yellow solid, 165 mg (51, R$_f$: 0.42 (EtOAc/MeOH 10:1), $^1$H NMR (270 MHz, CD$_3$COCD$_3$) δ 2.06 (3H, s, CH$_3$CO), 2.64-2.73 (4H, m, 2×CH$_2$), 3.43 (2H, s, CH$_2$), 3.59 (2H, s, CH$_2$), 3.75 (3H, s, CH$_3$O), 6.55 (2H, s, ArH), 7.03 (1H, d, J 7.4 Hz, 1H, ArH), 7.23 (1H, dd, J 8.2 and 7.4 Hz, ArH), 7.60 (1H, s, ArH), 7.63 (1H, d, J 8.2 Hz, ArH), 9.13 (1H, br, NH), $^{13}$C NMR (67.5 MHz, CD$_3$COCD$_3$) δ 23.5 (CH$_3$CO), 28.7 (CH$_2$), 51.1 (CH$_2$), 55.4 (CH$_3$O), 55.6 (CH$_2$), 62.6 (CH$_2$), 109.6 (CH(Ar)), 114.7 (CH(Ar)), 117.8 (CH(Ar)), 119.2 (CH(Ar)), 123.5 (CH(Ar)), 125.9 (C(Ar)), 126.6 (C(Ar)), 128.5 (CH(Ar)), 139.8 (2×C(Ar)), 145.0 (C(Ar)), 145.9 (C(Ar)) and 168.1 (CO). LC/MS (APCI+) t$_r$=3.78 min m/z 327.54 (M$^+$+H); MeOH/H$_2$O 50/50 to 95/5 (5 min); LC/MS (ES−) t$_r$=3.78 min m/z 325.33 (M−H)$^−$; MeOH/H$_2$O 50/50 to 95/5 (5 min); HPLC t$_r$=4.32 min (96.9%) (CH$_3$CN/H$_2$O 90/10)

6-Hydroxy-7-methoxy-2-(3-acetoxybenzyl)-1,2,3,4-tetrahydroisoquinoline 51

Light yellow powder, 165 mg (50%), mp=120-122° C., R$_f$: 0.37 (Hexane/EtOAc 1:1), $^1$H NMR (270 MHz, CDCl$_3$) δ 2.28 (3H, s, CH$_3$), 2.67-2.80 (4H, m, 2×CH$_2$), 3.51 (2H, s, CH$_2$), 3.66 (2H, s, CH$_2$), 3.80 (3H, s, CH$_3$O), 5.46 (1H, s, OH), 6.45 (1H, s, ArH), 6.64 (1H, s, ArH), 6.98 (1H, ddd, J 7.9 and 2.2 and 1.2 Hz, ArH), 7.14 (1H, t, J 1.7 Hz, ArH), 7.21-7.26 (1H, m, ArH), 7.32 (1H, t, J 7.7 Hz, ArH), $^{13}$C NMR (67.5 MHz, CDCl$_3$) δ 21.3 (CH$_3$), 28.6 (CH$_2$), 51.0 (CH$_2$), 55.8 (CH$_2$), 56.1 (CH$_3$O), 62.4 (CH$_2$), 108.9 (CH(Ar)), 114.3 (CH(Ar)), 120.4 (CH(Ar)), 122.0 (CH(Ar)), 126.1 (C(Ar)), 126.5 (CH(Ar)), 127.0 (C(Ar)), 129.3 (CH(Ar)), 140.6 (C(Ar)), 144.0 (C7), 144.9 (C(Ar)), 150.8 (C(Ar)) and 169.7 (CO). LC/MS (ES+) t$_r$=3.88 min m/z 328.36 (M$^+$+H); MeOH/H$_2$O 50/50 to 95/5 (5 min); HPLC t$_r$=4.41 min (93.1%). (CH$_3$CN/H$_2$O 90/10).

6-Hydroxy-7-methoxy-2-(3-methanesulfonylaminobenzyl)-1,2,3,4-tetrahydroisoquinoline 52

Yellow powder, 340 mg (94%), mp=99-101° C., R$_f$: 0.27 (EtOAc), $^1$H NMR (270 MHz, CDCl$_3$) δ 2.66-2.78 (4H, m, 2×CH$_2$), 2.98 (3H, s, CH$_3$), 3.51 (2H, s, CH$_2$), 3.64 (2H, s, CH$_2$), 3.79 (3H, s, CH$_3$O), 6.44 (1H, s, ArH), 6.62 (1H, s, ArH), 7.14-7.33 (5H, m, ArH, NH), $^{13}$C NMR (67.5 MHz, CDCl$_3$) δ 28.5 (CH$_2$), 39.5 (CH$_3$), 50.9 (CH$_2$), 55.8 (CH$_2$), 56.1 (CH$_3$O), 62.3 (CH$_2$), 108.9 (CH(Ar)), 114.4 (CH(Ar)), 119.5 (CH(Ar)), 121.4 (CH(Ar)), 125.9 (C(Ar)), 126.1 (CH(Ar)), 126.9 (C(Ar)), 129.7 (CH(Ar)), 136.9 (C(Ar)), 140.5 (C(Ar)), 144.1 (C(Ar)), 145.0 (C(Ar)). LC/MS (ES−) t$_r$=1.09 min m/z 361.54 (M$^−$-H); MeOH/H$_2$O 95/5; HPLC t$_r$=3.91 min (99.57%). (CH$_3$CN/H$_2$O 90/10)

2-(2-(3,4-Dimethoxyphenyl)-2-oxoethyl)-6-hydroxy-7-methoxy-1,2,3,4-tetrahydroisoquinoline 53

Yellow powder, 140 mg (39%), mp=149-150° C., R$_f$: 0.21 (Hexane/EtOAc 1:5), $^1$H NMR (270 MHz, CDCl$_3$) δ 2.80-2.88 (4H, m, 2×CH$_2$), 3.71 (2g s, CH$_2$), 3.80 (3H, s, CH$_3$O), 3.91 (3H, s CH$_3$O), 3.93 (5H, s, CH$_3$O and CH$_2$), 4.98 (11-1, br, OH), 6.46 (1H, s, 6.64 (1H, s, ArH), 6.85 (1H, d, J 8.4 Hz, ArH), 7.61(1H, d, J 2.0 Hz, ArH), 7.74 (1H, dd, J 8.4 and 2.0 Hz, ArH), $^{13}$C NMR (67.5 MHz, CDCl$_3$) δ 28.2 (CH$_2$), 51.3 (CH$_2$), 55.7 (CH$_2$), 56.0 (CH$_3$O), 56.1 (CH$_3$O), 56.2 (CH$_3$O), 64.1 (CH$_2$), 108.7 (CH(Ar)), 110.0 (CH(Ar)), 110.5 (CH(Ar)), 114.3 (CH(Ar)), 123.2 (CH(Ar)), 125.6 (C(Ar)), 126.7 (C(Ar)), 129.3 (C(Ar)), 144.1 (C(Ar)), 145.0 (C(Ar)), 149.0 (C(Ar)), 153.5 (C(Ar)) and 195.5 (CO).

6-Hydroxy-7-methoxy-2-(3,4,5-trimethoxybenzyl)-1,2,3,4-tetrahydroisoquinoline 54

Yellow powder, 215 mg (60%), mp=170-171° C., R$_f$: 0.27 (EtOAc), $^1$H NMR (270 MHz, CDCl$_3$) δ 2.66-2.81 (4H, m, 2×CH$_2$), 3.53 (2H, s, CH$_2$), 3.59 (2H, s, CH$_2$), 3.81 (3H, s, CH$_3$O), 3.84 (3H, s, CH$_3$O), 3.85 (6H, s, CH$_3$O), 5.49 (1H, br, OH), 6.48 (1H, s, ArH), 6.62 (2H, s, ArH), 6.66 (1H, s, ArH), $^{13}$C NMR (67.5 MHz, CDCl$_3$) δ 28.6 (CH$_2$), 50.8 (CH$_2$), 56.0 (CH$_2$), 56.1 (CH$_3$O), 56.2 (2×CH$_3$O), 61.0 (CH$_3$O), 63.0 (CH$_2$), 105.7 (2×CH(Ar)), 108.9 (CH(Ar)), 114.3 (CH(Ar)), 126.1 (C(Ar)), 127.1 (C(Ar)), 127.8 (CH(Ar)), 134.4 (C(Ar)), 136.9 (C(Ar)), 144.1 (C(Ar)), 145.0 (C(Ar)) and 153.2 (2×C(Ar)). LC/MS (APCI−) t$_r$=1.15 min m/z 358.15 (M−H)$^−$; MeOH/H$_2$O 95/5; HPLC t$_r$=1.66 min (98.3%). (CH$_3$CN/H$_2$O 90:10)

6-Hydroxy-7-methoxy-2-(2,5-dimethoxybenzyl)-1,2,3,4-tetrahydroisoquinoline 55

Yellow powder, 158 mg (48%), mp=104-105° C., R$_f$: 0.30 (EtOAc), $^1$H NMR (270 MHz, CDCl$_3$) δ 2.71-2.80 (4H, m, 2×CH$_2$), 3.60 (2H, s, CH$_2$), 3.68 (2H, s, CH$_2$), 3.75 (3H, s, CH$_3$O), 3.79 (3H, s, CH$_3$O), 3.80 (3H, s, CH$_3$O), 5.60 (1H, br, OH), 6.47 (1H, s, ArH), 6.63 (1H, s, ArH), 6.73-6.82 (2H, m, ArH), 7.06 (1H, d, J 2.9 Hz, ArH), $^{13}$C NMR (67.5 MHz, CDCl$_3$) δ 28.6 (CH$_2$), 50.9 (CH$_2$), 55.7 (CH$_2$), 55.8 (CH$_3$O), 55.9 (CH$_2$), 56.1 (CH$_3$O), 56.3 (CH$_3$O), 108.9 (CH(Ar)), 111.7 (CH(Ar)), 112.5 CH(Ar)), 114.3 (CH(Ar)), 116.1 (CH(Ar)), 126.5 (C(Ar)), 127.2 (C(Ar)), 127.9 (C(Ar)), 144.0 (C(Ar)), 144.9 (C(Ar)), 152.1 (C(Ar)) and 153.7 (C(Ar)).

LC/MS (APCI−) $t_r$=2.30 min m/z 327.98 (M−H)⁻; MeOH/H₂O 95/5; HPLC $t_r$=2.60 min (>99.9%). (MeOH)

6-Hydroxy-7-methoxy-2-(2,3-dimethoxybenzyl)-1,2,3,4-tetrahydroisoquinoline 56

Yellow powder, 160 mg (49%), mp=101-102° C., $R_f$: 0.38 (EtOAc), ¹H NMR (270 MHz, CDCl₃) δ 2.69-2.78 (4H, m, 2×CH₂), 3.56 (2H, s, CH₂), 3.72 (2H, s, CH₂), 3.78 (3H, s, CH₃O), 3.83 (3H, s, CH₃O), 3.86 (3H, s, CH₃O), 5.41 (1H, br, OH), 6.46 (1H, s, ArH), 6.61 (1H, s, ArH), 6.84 (1H, dd, J 7.4 and 2.2 Hz, ArH), 6.99-7.08 (2H, m, ArH), ¹³C NMR (67.5 MHz, CDCl₃) δ 28.8 (CH₂), 51.0 (CH₂), 55.7 (CH₂), 55.8 (CH₃O), 56.0 (CH₃O), 56.2 (CH₂), 61.0 (CH₃O), 108.9 (CH(Ar)), 111.1 (CH(Ar)), 114.2 CH(Ar), 122.6 (CH(Ar)), 123.9(CH(Ar)), 126.5 (C(Ar)), 127.1 (C(Ar)), 132.3 (C(Ar)), 143.9 (C(Ar)), 144.8 (C(Ar)), 147.8 (C(Ar)) and 152.8 (C(Ar)). LC/MS (APCI−) $t_r$=1.93 min m/z 327.98 (M−H)⁻; MeOH/H₂O 80/20; HPLC $t_r$=2.32 min (100%). (MeOH)

6-Hydroxy-7-methoxy-2-(3,4-dimethoxybenzyl)-1,2,3,4-tetrahydroisoquinoline 57

Yellow powder, 170 mg (51%), mp=146-147° C., $R_f$: 0.27 (EtOAc), ¹H NMR (270 MHz, CDCl₃) δ 2.66-2.79 (4H, m, 2×CH₂), 3.51 (2H, s, CH₂), 3.59 (2H, s, CH₂), 3.80 (3H, s, CH₃O), 3.86 (3H, s, CH₃O), 3.87 (3H, s, CH₃O), 5.56 (1H, br, OH), 6.45 (1H, s, ArH), 6.64 (1H, s, ArH), 6.81 (1H, d, J 8.2 Hz, ArH), 6.88 (1H, dd, J 8.2 and 1.7 Hz, ArH), 6.96 (1H, d, J 1.7 Hz, ArH), ¹³C NMR (67.5 MHz, CDCl₃) δ 28.5 (CH₂), 50.7 (CH₂), 55.9 (CH₂), 56.0 (2×CH₃O), 56.1 (CH₃O), 62.6 (CH₂), 108.9 (CH(Ar)), 110.7 (CH(Ar)), 112.1 CH(Ar), 114.3 (CH(Ar)), 121.3 (CH(Ar)), 126.2 (C(Ar)), 127.1 (C(Ar)), 131.1 (C(Ar)), 144.1 (C(Ar)), 144.9 (C(Ar)), 148.2 (C(Ar)) and 149.0 (C(Ar)). LC/MS (APCI−) $t_r$=1.93 min m/z 327.98 (M−H)⁻; MeOH/H₂O 80/20; HPLC $t_r$=2.32 min (97.2%). (MeOH)

6-Hydroxy-7-methoxy-2-(2,3,4-trimethoxybenzyl)-1,2,3,4-tetrahydroisoquinoline 58

Yellow powder, 265 mg (74%), mp=65-66° C., $R_f$: 0.52 (EtOAc), ¹H NMR (270 MHz, CDCl₃) δ 2.66-2.759 (4H, m, 2×CH₂), 3.55 (2H, s, CH₂), 3.63 (2H, s, CH₂), 3.80 (3H, s, CH₃O), 3.85 (3H, s, CH₃O), 3.88 (6H, s, 2×CH₃O), 5.49 (1H, br, OH), 6.46 (1H, s, ArH), 6.63 (1H, s, ArH), 6.65 (1H, d, J 8.7 Hz, ArH), 7.09 (1H, d, J 8.7 Hz, ArH), ¹³C NMR (67.5 MHz, CDCl₃) δ 28.6 (CH₂), 50.7 (CH₂), 55.6 (CH₂), 56.1 (2×CH₃O), 56.2 (CH₂), 60.9 (CH₃O), 61.4 (OCH₃), 107.1 (CH(Ar)), 108.9 (CH(Ar)), 114.2 (CH(Ar)), 125.2 (CH(Ar)), 126.1 (C(Ar)), 127.0 (C(Ar)), 142.0 (C(Ar)), 142.8 (C(Ar)), 144.0 (C(Ar)), 144.9 (C(Ar)), 152.7 (C(Ar)) and 153.0 (C(Ar)). LC/MS (APCI−) $t_r$=1.03 min m/z 358.21 (M−H)⁻; MeOH/H₂O 95/5; HPLC $t_r$=2.50 min (98.8%). (CH₃CN/H₂O)

6-Hydroxy-7-methoxy-2-(2,4,5-trimethoxybenzyl)-1,2,3,4-tetrahydroisoquinoline 59

Yellow powder, 170 mg (48%), mp=152-153° C., $R_f$: 0.48 (EtOAc), ¹H NMR (270 MHz, CDCl₃) δ 2.67-2.79 (4H, m, 2×CH₂), 3.57 (2H, s, CH₂), 3.64 (2H, s, CH₂), 3.80 (3H, s, CH₃O), 3.81 (3H, s, CH₃O), 3.82 (3H, s, CH₃O), 3.89 (3H, s, CH₃O), 5.61 (1H, br, OH), 6.46 (1H, s, ArH), 6.62 (1H, s, ArH), 7.01 (1H, s, ArH), ¹³C NMR (67.5 MHz, CDCl₃) δ 28.6 (CH₂), 50.6 (CH₂), 55.3 (CH₂), 55.8 (CH₂), 56.0 (CH₃O), 56.2 (CH₃O), 56.6 (CH₃O), 56.8 (OCH₃), 97.6 (CH(Ar)), 108.9 (CH(Ar)), 114.2 (CH(Ar)), 114.3 (CH(Ar)), 118.0 (C(Ar)), 126.4 (C(Ar)), 127.1 (C(Ar)), 143.1 (C(Ar)), 144.0 (C(Ar)), 144.9 (C(Ar)), 148.5 (C(Ar)) and 152.1 (C(Ar)). LC/MS (APCI−) $t_r$=0.60 min m/z 358.21 (M−H)⁻; MeOH/H₂O 95/5; HPLC $t_r$=2.41 min (98.2%). (CH₃CN/H₂O 90/10)

2-(3-Fluorobenzyl)-6-hydroxy-7-methoxy-1,2,3,4-tetrahydroisoquinoline 60

150 mg, 57%, yellow solid, mp 125-127° C. ¹H NMR (270 MHz; DMSO-d₆) 2.60-2.63 (4H, m, 2×CH₂), 3.40 (2H, s, CH₂), 3.62 (2H, s, CH₂), 3.67 (3H, s, OCH₃), 6.49 (1H, s, CH), 6.54 (1H, s, CH), 7.04-7.21 (3H, m, 3×CH), 7.34-7.40 (1H, m, CH), 8.70 (1H, brs, OH). ¹³C NMR (100 MHz; DMSO-d₆) 28.06 (CH₂), 50.62 (CH₂), 55.12 (CH₂), 55.59 (OCH₃), 61.28 (CH₂), 110.14 (CH), 113.77 (d, J=21.3 Hz, CH), 115.17 (d, J=19.9 Hz, CH), 115.27 (CH), 124.71 (d, J=2.4 Hz, C), 124.93 (CH), 125.88 (C), 130.12 (d, J=8.4 Hz, CH), 141.83 (d, J=6.9 Hz, C), 144.72 (C), 145.87 (C), 161.32 (d, J=241.9 Hz, C—F). LC/MS (APCI+) $t_r$=5.03 min, m/z 288.35 (M⁺+H). HRMS (ES+) calcd. for C₁₇H₁₉FNO₂ (M⁺+H) 288.1394, found 288.1393. HPLC $t_r$=3.68 min (>98%).

2-(3-Isopropoxybenzyl)-6-hydroxy-7-methoxy-1,2,3,4-tetrahydroisoquinoline 61

134 mg, 70%, pale yellow solid. mp 143-146° C. ¹H NMR (270 MHz; CDCl₃) 1.31 (6H, d, J=5.9 Hz, 2×CH₃), 2.68-2.77 (4H, m, 2×CH₂), 3.52 (2H, s, CH₂), 3.62 (2H, s, CH₂), 3.81 (3H, s, OCH₃), 4.55 (1H, Septet, J=5.9 Hz, CH), 6.45 (1H, s, CH), 6.63 (1H, s, CH), 6.76-6.80 (1H, m, CH), 6.92-6.94 (2H, m, 2×CH), 7.21 (1H, t, J=7.7 Hz, CH). ¹³C NMR (67.5 MHz; CDCl₃) 22.18 (CH₃), 28.59 (CH₃), 50.89 (CH₂), 55.87 (CH₃), 56.05 (OCH₃), 62.82 (CH₂), 69.76 (CH), 108.90 (CH), 114.31 (CH), 114.63 (CH), 116.47 (CH), 121.34 (CH), 126.24 (C), 127.10 (C), 129.30 (CH), 140.16 (C), 144.03 (C), 144.91 (C), 158.03 (C). LC/MS (APCI−) $t_r$=1.1 min, m/z 326.09 (M−H)⁻. HPLC $t_r$=2.60 min (>99%). Anal. Calcd. for C₂₀H₂₅NO₃: C, 73.37; H, 7.70; N, 4.28. Found C, 73.5; H, 7.90; N, 4.13%.

Method 2:

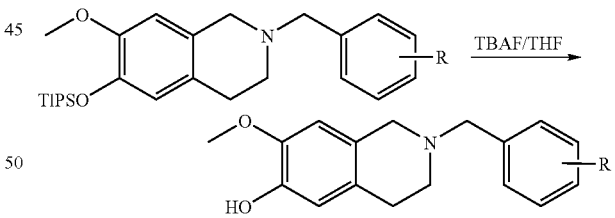

A solution of 2-benzyl-7-methoxy-6-triisopropylsilyloxy-1,2,3,4-tetrahydroisoquinoline (1 mmol) in THF (20 mL) was stirred with a 1M solution of TBAF/THF (1.1 mmol) for 60 minutes at RT. After addition of water, the organics were extracted with ethyl acetate (80 mL) and the organic layer washed with water, brine, dried (MgSO₄), filtered and concentrated under reduced pressure. The residual oil/solid was purified by flash chromatography (hexane/ethyl acetate).

6-Hydroxy-7-methoxy-2-(3-acetylbenzyl)-1,2,3,4-tetrahydroisoquinoline 62

Yellow solid, 220 mg (71%), mp=132-134° C., $R_f$: 0.22 (Hexane/EtOAc 1:2), ¹H NMR (270 MHz, CDCl₃) δ 2.60 (s, 3H, CH$_3$CO), 2.67-2.80 (4H, m, 2×CH$_2$), 3.52 (2H, s, CH$_2$), 3.71 (2H, s, CH$_2$), 3.79 (3H, s, OCH$_3$), 5.55 (1H, br, OH), 6.44 (1H, s, ArH), 6.64 (1H, s, ArH), 7.42 (1H, t, J 7.7 Hz, ArH), 7.62 (1H, dt, J 7.7 and 1.6 Hz, ArH), 7.85 (1H, dt, J 7.7 & 1.2 Hz, ArH), 7.95 (1H, m, ArH), $^{13}$C NMR (67.5 MHz, CDCl$_3$) δ 26.9 (CH$_3$CO), 28.6 (CH$_2$), 51.0 (CH$_2$), 55.8 (CH$_2$), 56.0 (CH$_3$O), 62.5 (CH$_2$), 108.8 (CH(Ar)), 114.3 (CH(Ar)), 126.0 (C(Ar)), 127.0 (C(Ar)), 127.3 (CH(Ar)), 128.7 (CH(Ar)), 129.0 (CH(Ar)), 134.0 (CH(Ar)), 137.3 (C(Ar)), 139.3 (C(Ar)), 144.1 (C(Ar)), 144.9 (C(Ar)) and 198.5 (CO). LC/MS (APCI+) t$_r$=4.06 min m/z 312.47 (M$^+$+H); MeOH/H2O 95/5 to 50/50 in 5 min. HPLC t$_r$=4.68 min (92%). (CH$_3$CN/H$_2$O 90/10)

2-(3-Ethoxybenzyl)-6-hydroxy-7-methoxy-1,2,3,4-tetrahydroisoquinoline 63

Yellow powder, 155 mg (50%), mp=105-106° C., R$_f$: 0.31 (Hexane/EtOAc 1:1), $^1$H NMR (270 MHz, CDCl$_3$) δ 1.39 (3H, t, J 7.2 Hz, CH$_3$), 2.66-2.80 (4H, m, 2×CH$_2$), 3.53 (2H, s, CH$_2$), 3.64 (2H, s, CH$_2$), 3.79 (3H, s, CH$_3$O), 4.02 (2H, q, J 7.2 Hz, CH$_2$), 6.45 (1H, s, ArH), 6.63 (1H, s, ArH), 6.80 (1H, ddd, J 8.0, 2.2 and 1.0 Hz, ArH), 6.93-6.96 (2H, m, ArH), 7.22 (1H, t, J 8.0 Hz, 1H, ArH), $^{13}$C NMR (67.5 MHz, CDCl$_3$) δ 15.0 (CH$_3$), 28.5 (CH$_2$), 50.8 (CH$_2$), 55.8 (CH$_2$), 56.0 (CH$_3$O), 62.8 (CH$_2$), 63.4 (CH$_2$O), 108.9 (CH(Ar)), 113.3 (CH(Ar)), 114.3 (CH(Ar)), 115.1 (CH(Ar)), 121.4 (CH(Ar)), 126.1 (C(Ar)), 127.0 (C(Ar)), 129.3 (CH(Ar)), 140.0 (C(Ar)), 144.0 (C(Ar)), 144.9 (C(Ar)) and 159.1 (C(Ar)). LC/MS (APCI+) t$_r$=4.82 min m/z 314.55 (M$^+$+H); MeOH/H$_2$O 50/50 to 95/5 (5 min); HPLC t$_r$=5.68 min (94.6%). (CH$_3$CN/H$_2$O 90/10).

2-(3-Cyanobenzyl)-6-hydroxy-7-methoxy-1,2,3,4-tetrahydroisoquinoline 64

157 mg, 73%, pale yellow oil. Crystallisation from diethyl ether and hexane afford a pure sample. mp 113-155° C. $^1$H NMR (400 MHz; CDCl$_3$) 2.71 (2H, t, J 5.6 Hz, CH$_2$), 2.79 (2H, t, J 6.0 Hz, CH$_2$), 3.51 (2H, s, CH$_2$), 3.68 (2H, s, CH$_2$), 3.80 (3H, s, OCH$_3$), 6.45 (1H, s, CH), 6.65 (1H, s, CH), 7.43 (1H, t, J 8.0 Hz, CH), 7.64 (1H, d, J 8.0 Hz, CH) & 7.69 (1H, s, CH). $^{13}$C NMR (100 MHz; CDCl$_3$) 28.33 (CH$_2$), 50.89 (CH$_2$), 55.60 (CH$_3$), 55.93 (CH$_2$), 61.75 (CH$_2$), 108.69 (CH), 112.34 (C), 114.23 (CH), 118.91 (C), 125.48 (C), 126.65 (C), 129.12 (CH), 130.88 (CH), 132.37 (CH), 133.38 (CH), 140.17 (C), 144.09 (C) & 144.91 (C). LC/MS (APCI−) t$_r$=3.96 min, m/z 293.45 (M$^+$−H). HPLC t$_r$=2.94 min (>95%)

2-(4-Cyanobenzyl)-6-hydroxy-7-methoxy-1,2,3,4-tetrahydroisoquinoline 65

160 mg, 76%, yellow powder. mp 165-166.5° C. $^1$H NMR 270 MHz; CDCl$_3$) 2.68-2.72 (2H, m, CH$_2$), 2.76-2.80 (2H, m, CH$_2$), 3.51 (2H, s, CH$_2$), 3.70 (2H, s, CH$_2$), 3.80 (3H, s, OCH$_3$), 5.54 (1H, brs, OH), 6.44 (1H, s, CH), 6.65 (1H, s, CH), 7.51 (2H, ~d, J 8.7 Hz, 2×CH), 7.61 (2H, ~d, J 8.4 Hz, 2×CH). $^{13}$C NMR (67.5 MHz; CDCl$_3$) 28.52 (CH$_2$), 51.11 (CH$_2$), 55.86 (OCH$_3$), 56.06 (CH$_2$), 62.28 (CH$_2$), 108.76 (CH), 110.97 (C), 114.34 (CH), 119.11 (C), 126.68 (C), 126.79 (C), 129.56 (2×CH), 132.28 (2×CH), 144.18 (C), 144.52 (C), 144.99 (C). LC/MS (APCI+) t$_r$=3.95 min, m/z 295.93 (M$^+$+H). HRMS (ES+) calcd. for C$_{18}$H$_{19}$N$_2$O$_2$ (M$^+$+H) 295.1441, found 295.1539. HPLC t$_r$=3.40 min (>95%).

6-Hydroxy-7-methoxy-2-(3-nitrobenzyl)-1,2,3,4-tetrahydroisoquinoline 66

213 mg, 78%, yellow solid. mp 127-128° C. $^1$H NMR (270 MHz; CDCl$_3$) 2.71-2.79 (4H, m, 2×CH$_2$), 3.54 (2H, s, CH$_2$), 3.74 (2H, s, CH$_2$), 3.80 (3H, s, OCH$_3$), 5.51 (1H, s, OH), 6.44 (1H, s, CH), 6.65 (1H, s, CH), 7.49 (1H, t, J 7.9 Hz, CH), 7.75 (1H, d, J 7.9 Hz, CH), 8.12 (1H, ddd, J 8.2, 2.5, 1.0 Hz, CH), 8.24 (1H, t, J 1.7 Hz, CH). $^{13}$C NMR (67.5 MHz; CDCl$_3$) 28.49 (CH$_2$), 51.03 (CH$_2$), 55.76 (CH$_2$), 56.06 (OCH$_3$), 61.89 (CH$_2$), 108.79 (CH), 114.35 (CH), 122.39 (CH), 123.84 (CH), 125.639 (C), 126.79 (C), 126.36 (CH), 135.20 (CH), 140.99 (C), 144.19 (C), 145.02 (C), 148.43 (C). LC/MS (APCI+) t$_r$=4.32 min, m/z 315.49 (M$^+$+H). HRMS (ES+) calcd. for C$_{17}$H$_{19}$N$_2$O$_4$ (M$^+$+H) 315.1339, found 315.1338. HPLC t$_r$=3.04 min (>95%).

2-(3-Chlorobenzyl)-6-hydroxy-7-methoxy-1,2,3,4-tetrahydroisoquinoline 67

195 mg, 92%, yellow solid. mp 118-119.5° C. $^1$H NMR (270 MHz; CDCl$_3$) 2.68-2.72 (2H, m, CH$_2$), 2.76-2.80 (2H, m, CH$_2$), 3.51 (2H, s, CH$_2$), 3.62 (2H, s, CH$_2$), 3.80 (3H, s, OCH$_3$), 6.45 (1H, s, CH), 6.65 (1H, s, CH), 7.22-7.27 (3H, m, 3×CH), 7.40 (1H, d, J 1.2 Hz, CH).
$^{13}$C NMR (67.5 MHz; CDCl$_3$) 28.53 (CH$_2$), 51.0 (CH$_2$), 55.78 (OCH$_3$), 56.06 (CH$_2$), 62.26 (CH$_2$), 108.85 (CH), 114.34 (CH), 125.89 (C), 126.91 (C), 127.25 (CH), 127.38 (CH), 129.13 (CH), 129.65 (CH), 134.29 (C), 140.76 (C), 144.13 (C), 144.97 (C). LC/MS (APCI+) t$_r$=4.92 min, m/z 304.53 (M$^+$+H). HPLC t$_r$=4.18 min (>99%). Anal. Calc. for C$_{17}$H$_{18}$ClNO$_2$: C, 67.21; H, 5.97; N, 4.61. Found: C, 67.1; H, 6.05; N, 4.46%.

6-Hydroxy-7-methoxy-2-(3-trifluoromethoxybenzyl)-1,2,3,4-tetrahydroisoquinoline 68

95 mg, 60%, yellow solid. mp 122-124° C. $^1$H NMR (270 MHz; CDCl$_3$) 2.67-2.72 (2H, m, CH$_2$), 2.76-2.81 (2H, m, CH$_2$), 3.53 (2H, s, CH$_2$), 3.67 (2H, s, CH$_2$), 3.81 (3H, s, OCH$_3$), 5.47 (1H, s, OH), 6.45 (1H, s, CH), 6.65 (1H, s, CH), 7.09-7.12 (1H, m, CH), 7.26-7.37 (3H, m, 3×CH). $^{13}$C NMR (67.5 MHz; CDCl$_3$) 28.50 (CH$_2$), 50.89 (CH$_2$), 55.79 (CH$_2$), 56.05 (OCH$_3$), 62.07 (CH$_2$), 108.87 (CH), 114.37 (CH), 119.56 (CH), 121.43 (CH), 125.93 (C), 126.97 (C), 127.30 (CH), 129.64 (CH), 141.19 (C), 144.16 (C), 145.0 (C), 149.47 (C). LC/MS (ES+) t$_r$=1.41 min, m/z 354.57 (M$^+$+H). HPLC t$_r$=4.9 min (>97%).

2-(2-Hydroxybenzyl)-6-hydroxy-7-methoxy-1,2,3,4-tetrahydroisoquinoline 69

78 mg, 71%, colourless solid. mp 151.9-152.6° C. $^1$H NMR (270 MHz; CDCl$_3$) 2.83 (4H, brs, 2×CH$_2$), 3.65 (2H, s, CH$_2$), 3.80 (3H, s, OCH$_3$), 3.86 (2H, s, CH$_2$), 6.46 (1H, s, CH), 6.66 (1H, s, CH), 6.77-6.84 (2H, m, 2 ×CH), 7.02 (1H, brd, J 7.4 Hz, CH), 7.19 (1H, td, J 7.7, 1.6 Hz, CH). $^{13}$C NMR (67.5 MHz; CDCl$_3$) 28.07 (CH$_2$), 50.26 (CH$_2$), 55.04 (CH$_2$), 56.04 (OCH$_3$), 61.16 (CH$_2$), 108.76 (CH), 114.21 (CH), 116.30 (CH), 119.17 (CH), 121.39 (C), 124.63 (C), 126.28 (C), 128.72 (CH), 128.93 (CH), 144.39 (C), 145.14 (C), 158.08 (C). LC/MS (APCI−) t$_r$=1.27 min, m/z 283.95 (M−H)$^-$. HPLC t$_r$=1.63 min (>98%).

2-(3-Hydroxybenzyl)-7-methoxy-1,2,3,4-tetrahydroisoquinolin-6-ol 70

A solution of 6-benzyloxy-2-(3-(hydroxybenzyl)-7-methoxy-1,2,3,4-tetrahydroisoquinoline (340 mg, 0.91 mmol) in THF (20 mL) and methanol (10 mL) was stirred with 10% Pd/C (40 mg) under hydrogen for 0.5 h. After filtration through celite and evaporation of the solvents under reduced pressure, the residual oil was purified by flash chromatography (ethyl acetate) giving 200 mg (78%) of a yellow powder, mp=177-178° C.; $R_f$: 0.29 (EtOAc), $^1$H NMR (270 MHz, CDCl$_3$/CD$_3$COCD$_3$ 5:1) δ 2.41-2.51 (4H, m, 2×CH$_2$), 3.24 (2H, s, CH$_2$), 3.34 (2H, s, CH$_2$), 3.53 (3H, s, CH$_3$O), 6.21 (1H, s, ArH), 6.35 (1H, s, ArH), 6.49 (1H, ddd, J 7.2, 3.0 & 1.2 Hz, ArH), 6.61 (1H, d, J 7.2 Hz, ArH), 6.64 (1H, d, J 3.0 Hz, ArH), 6.88 (1H, t J 7.2 Hz, 1H, ArH). $^{13}$C NMR (67.5 MHz, CDCl$_3$/CD$_3$COCD$_3$ 5:1) δ 28.3 (CH$_2$), 50.7 (CH$_2$), 55.4 (CH$_2$), 55.7 (CH$_3$O), 62.3 (CH$_2$), 109.0 (CH(Ar)), 114.0 (CH(Ar)), 114.3 (CH(Ar)), 115.8 (CH(Ar)), 120.2 (CH(Ar)), 125.6 (C(Ar)), 126.5 (C(Ar)), 129.1 (CH(Ar)), 144.1 (C(Ar)), 144.3 (C(Ar)), 145.1 (C(Ar)) and 156.9 (C(Ar)). LC/MS (APCI+) $t_r$=1.48 min m/z 286.52 (M$^+$+H); MeOH/H$_2$O 50/50 to 95/5 (5 min); HPLC $t_r$=4.43 min (99.16%). (CH$_3$CN/H$_2$O 90/10)

2-(3-(Methoxycarbonyl)benzyl)-6-hydroxy-7-methoxy-1,2,3,4-tetrahydroisoquinoline 70A From 36A. Purification (flashmaster: 20 g, gradient elution hex/EtOAc) afforded the title compound (159 mg, 77%) as a yellow solid. mp 156-158° C. $^1$H NMR (270 MHz; CDCl$_3$) 2.68-2.78 (4H, m, 4×CH), 3.51 (2H, s, 2×CH), 3.69 (2H, s, 2×CH), 3.79 (3H, s, OCH$_3$), 3.90 (3H, s, OCH$_3$) 5.51 (1H, brs, OH), 6.44 (1H, s, CH), 6.64 (1H, s, CH), 7.40 (1H, t, J=7.7 Hz, CH), 7.61 (1H, d, J=7.6 Hz, CH), 7.92 (1H, dt, J 7.7, 1.3 Hz, CH), 8.03 (1H, brs, CH). $^{13}$C NMR (67.5 MHz; CDCl$_3$) 28.54 (CH$_2$), 50.97 (CH$_2$), 52.22 (CH$_3$), 55.79 (CH$_2$), 56.05 (CH$_3$), 62.46 (CH$_2$), 108.86 (CH), 114.32 (CH), 125.95 (C), 126.95 (C), 128.54 (CH), 130.27 (CH), 133.83 (CH), 139.01 (C), 144.11 (C), 144.96 (C), 167.31 (C). LC/MS (APCI−) $t_r$=0.92 min, m/z 326.15 (M−H)$^-$. HPLC $t_r$=1.55 min (>99%). Anal. Calcd. for C$_{19}$H$_{21}$NO$_4$: C, 69.71; H, 6.47; N, 4.28. Found: C, 4.22; H, 69.6; N, 6.41%.

6,7-Dimethoxy-2-(3,4,5-trimethoxybenzyl)-1,2,3,4-tetrahydroisoquinoline 70B

A mixture of 6,7-dimethoxytetrahydroisoquinoline hydrochloride (0.23 g, 1 mmol), 3,4,5-trimethoxybenzyl chloride (0.26 g, 1.2 mmol) in TEA (0.5 mL) and ethanol (2.5 mL) was subjected to microwave heating to 130° C. for 1 h. The mixture was poured into water, the organics extracted with ethyl acetate and the organic layer washed with water, brine, dried (MgSO$_4$), filtered and concentrated under reduced pressure. The resultant crude solid was purified by flash chromatography (hexane/ethyl acetate 6:1 to 1:1) to give a white solid which was stirred in diethyl ether, filtered and dried under vacuum to afford a white powder (230 mg, 62%), mp=118-119° C., $R_f$: 0.43 (EtOAc), $^1$H NMR (270 MHz, CDCl$_3$) δ 2.70 (2H, t, J=5.6 Hz, CH$_2$), 2.81 (2H, t, J=5.6 Hz, CH$_2$), 3.55 (2H, s, CH$_2$), 3.59 (2H, s, CH$_2$), 3.81 (3H, s, CH$_3$O), 3.83 (3H, s, CH$_3$O), 3.84 (3H, s, CH$_3$O), 3.85 (6H, s, CH$_3$O), 6.50 (1H, s, ArH), 6.60 (1H, s, ArH), 6.62 (2H, s, ArH); $^{13}$C NMR (67.5 MHz, CDCl$_3$) δ 28.8 (CH$_2$), 50.7 (CH$_2$), 55.9 (CH$_2$), 56.0 (2×CH$_3$O), 56.2 (2×CH$_3$O), 61.0 (CH$_3$O), 63.1 (CH$_2$), 105.6 (2×CH(Ar)), 109.5 (CH(Ar)), 111.4 (CH(Ar)), 126.3 (C(Ar)), 126.8 (C(Ar)), 134.5 (C(Ar)), 136.7 (C(Ar)), 147.3 (C(Ar)), 147.6 (C(Ar)), 153.2 (2×CH(Ar)). LC/MS (ES+) $t_r$=0.93 min m/z 374.27 (M+H)$^+$; MeOH/H$_2$O 95/5; HPLC $t_r$=3.62 min (99.2%). (CH$_3$CN/H$_2$O 70:30)

7-Methoxy-6-O-acetyl-2-(3,4,5-trimethoxybenzyl)-1,2,3,4-tetrahydroisoquinoline 70C A solution of 6-hydroxy-7-methoxy-2-(3,4,5-trimethoxybenzyl)-1,2,3,4-tetrahydroisoquinoline 54 (108 mg, 0.3 mmol), triethylamine (0.21 mL, 1.6 mmol) and acetic anhydride (0.16 mL, 1.6 mmol) in CHCl$_3$ (10 mL) was stirred at rt for 24 hours. After addition CHCl$_3$ (30 mL), the organic layer was washed with water (4×30 mL), brine, dried (MgSO$_4$), filtered and the solvent evaporated under reduced pressure. The resultant yellow solid was stirred in diethyl ether, filtered, dried under vacuum to yield a white powder (95 mg, 79%), mp=143-144° C., $R_f$: 0.47 (EtOAc), $^1$H NMR (270 MHz, CDCl$_3$) δ 2.28 (3H, s, CH$_3$), 2.69-2.83 (4H, m, 2×CH$_2$), 3.60 (4H, s, 2×CH$_2$), 3.75 (3H, s, CH$_3$O), 3.84 (3H, s, CH$_3$O), 3.85 (6H, s, CH$_3$O), 6.58 (1H, s, ArH), 6.62 (2H, s, ArH), 6.77 (1H, s, ArH); $^{13}$C NMR (67.5 MHz, CDCl$_3$) δ 20.7(CH$_3$), 28.3 (CH$_2$), 50.5 (CH$_2$), 55.9 (CH$_2$), 56.0 (CH$_3$O), 56.2 (2×CH$_3$O), 60.9 (CH$_3$O), 62.8 (CH$_2$), 105.7 (2×CH(Ar)), 110.5 (CH(Ar)), 122.7 (CH(Ar)), 124.1 (C(Ar)), 126.5 (C(Ar)), 133.3 (C(Ar)), 136.9 (C(Ar)), 138.1 (C(Ar)), 149.1 (C(Ar)), 153.3 (2×CH(Ar)) and 169.4 (CO). LC/MS (ES+) $t_r$=0.96 min m/z 402.24(M+H)$^+$; MeOH/H$_2$O 95/5; HPLC $t_r$=1.99 min (99%). (CH$_3$CN/H$_2$O 90:10).

7-Methoxy-6-O-methanesulfonyl-2-(3,4,5-trimethoxybenzyl)-1,2,3,4-tetrahydroisoquinoline 70D A solution of 6-hydroxy-7-methoxy-2-(3,4,5-trimethoxybenzyl)-1,2,3,4-tetrahydroisoquinoline 54 (80 mg, 0.22 mmol) in pyridine (1 mL) was cooled to 0° C. and methanesulfonyl chloride (20 μL, 0.26 mmol) added. The solution was stirred for 2 hours at 0° C. then 4 hours at rt. After addition of water (5 mL), the organic were extracted with ethyl acetate, the organic layer was washed with water, brine, dried (MgSO$_4$), filtered and concentrated under reduced pressure. The resultant solid was purified by flash chromatography (hexane/ethyl acetate 1:1) to give 80 mg of white solid which was stirred in diethyl ether, filtered and dried. White powder (70 mg, 73%), m.p. 134-135° C., $R_f$=0.58 (ethyl acetate), $^1$H NMR (270 MHz, CDCl$_3$) δ 2.68-2.84 (4H, m, 2×CH$_2$), 3.15 (3H, m, CH$_3$), 3.57 (2H, s, CH$_2$), 3.59 (2H, s, CH$_2$), 3.81 (3H, s, CH$_3$O), 3.83 (3H, s, CH$_3$O), 3.85 (6H, s, CH$_3$O), 6.61 (2H, s, ArH), 7.04 (1H, s, ArH); $^{13}$C NMR (67.5 MHz, CDCl$_3$) δ 28.3 (CH$_2$), 38.2 (CH$_3$), 50.4 (CH$_2$), 55.9 (CH$_2$), 56.1 (CH$_3$O), 56.2 (2×CH$_3$O), 61.0 (CH$_3$O), 62.9 (CH$_2$), 70.8 (CH$_2$), 105.6 (2×CH(Ar)), 110.9 (CH(Ar)), 124.5 (CH(Ar)), 127.4 (C(Ar)), 134.2 (C(Ar)), 135.0 (C(Ar)), 136.7 (C(Ar)), 137 (C(Ar)), 149.3 (2×C(Ar)), 153.3 (C(Ar)). LC/MS (ES+) $t_r$=0.66 min m/z 438.14 (M+1)$^+$; MeOH/H$_2$O 95/5. HPLC $t_r$=1.87 min (97.4%). (acetonitrile/water 90/10).

Synthesis of 6-O-sulfamoyl-2-benzyl-1,2,3,4-tetrahydroisoquinolines

A solution of 6-hydroxy-2-benzyl-1,2,3,4-tetrahydroisoquinoline (0.5 mmol) and sulfamoyl chloride (1 mmol) in DMA (1 mL) was stirred at rt under nitrogen for 24 hours. After addition of water (5 mL) and KHCO$_3$ (150 mg, 1.5 mmol) the reaction mixture was extracted into ethyl acetate (2×50 mL), the organic layers washed with water and brine, then dried (MgSO$_4$) and evaporated. The crude product was purified by flash chromatography (hexane/ethyl acetate or DMC/ethyl acetate)

2-(3-Methoxybenzyl)-6-O-sulfamoyl-1,2,3,4-tetrahydroisoquinoline 71

White solid, 140 mg (69%), mp 139-140° C., $R_f$: 0.25 (Hexane/EtOAc 1:1), $^1$H NMR (270 MHz, CDCl$_3$) δ 2.72 (2H, t, J 5.4 Hz, CH$_2$), 2.88 (2H, t, J 5.4 Hz, CH$_2$), 3.59 (2H, s, CH$_2$), 3.65 (2H, s, CH$_2$), 3.79 (3H, s, CH$_3$O), 4.30 (2H, br, NH$_2$), 6.82 (1H, ddd, J 8.2, 2.5 and 1.0 Hz, ArH), 6.92-6.96 (2H, m, ArH), 6.99-7.03 (3H, m, ArH), 7.23 (1H, t, J 8.2 Hz, ArH), $^{13}$C NMR (67.5 MHz, CDCl$_3$) δ 29.1 (CH$_2$), 50.1 (CH$_2$), 55.3 (CH$_3$O), 55.5 (CH$_2$), 62.6 (CH$_2$), 112.9 (CH (Ar)), 114.7 (CH(Ar)), 119.4 (CH(Ar)), 121.6 (CH(Ar)), 122.0 (CH(Ar)), 128.1 (CH(Ar)), 129.4 (CH(Ar)), 134.1 (C(Ar)), 136.5 (C(Ar)), 139.5 (C(Ar)), 148.3 (C(Ar)) and 159.8 (C(Ar)). LC/MS (APCI+) t$_r$=4.23 min m/z 349.56 (M$^+$+H); MeOH/H$_2$O 50/50 to 95/5 in 5 min; HPLC t$_r$=3.95 min (96.3%). (CH$_3$CN/H$_2$O 90/10)

7-Methoxy-2-(3-methoxybenzyl)-6-O-sulfamoyl-1,2,3,4-tetrahydroisoquinoline 72

Light yellow powder, 150 mg (80%), mp 144-145° C., R$_f$: 0.21 (ethyl acetate/hexane 1:1), $^1$H NMR (270 MHz, CDCl$_3$/CD$_3$OD 5/1) δ 2.66-2.77 (4H, m, 2×CH$_2$), 3.10 (2H, br, NH$_2$), 3.51 (2H, s, CH$_2$), 3.60 (2H, s, CH$_2$), 3.74 (3H, s, CH$_3$O), 3.75 (3H, s, CH$_3$O), 6.55 (1H, s, ArH), 6.79 (1H, d, J 7.9 Hz, ArH), 6.82 (2H, s, ArH), 7.04 (1H, s, ArH), 7.21 (1H, t, J 7.9 Hz, ArH), $^{13}$C NMR (67.5 MHz, CDCl$_3$/CD$_3$OD 5/1) δ 27.8 (CH$_2$), 50.4 (CH$_2$), 55.3, (CH$_3$O), 55.6 (CH$_2$), 56.2 (CH$_3$O), 62.7 (CH$_2$), 110.9 (CH(Ar)) 112.9 (CH(Ar)), 114.8 (CH(Ar)), 121.7 (CH(Ar)), 123.8 (CH(Ar)), 126.9 (C(Ar)), 129.4 (C(Ar)), 133.9 (C(Ar)), 137.7 (C(Ar)) 138.9 (C(Ar)), 149.6 (C(Ar)) and 159.7 (C(Ar)). LC/MS (APCI+) t$_r$=4.21 min m/z 379.34 (M$^+$+H); HPLC t$_r$=3.01 min (99.6%). (CH$_3$CN/H$_2$O 70/30)

7-Methoxy-2-(4-methoxybenzyl)-6-O-sulfamoyl-1,2,3,4-tetrahydroisoquinoline 73

Light yellow powder, 140 mg (75%), mp 104-105° C., R$_f$: 0.42 (ethyl acetate), $^1$H NMR (270 MHz, CDCl$_3$) δ 2.69-2.82 (4H, m, 2×CH$_2$), 3.54 (2H, s, CH$_2$), 3.61 (2H, s, CH$_2$), 3.78 (3H, s, CH$_3$O), 3.79 (3H, s, CH$_3$O), 6.59 (1H, s, ArH), 6.88 (2H, m, ArH), 7.07 (1H, s, ArH), 7.26 (2H, m, ArH), $^{13}$C NMR (67.5 MHz, CDCl$_3$) δ 28.2 (CH$_2$), 50.4 (CH$_2$), 55.4, (CH$_3$O), 55.6 (CH$_2$), 56.3 (CH$_3$O), 62.1 (CH$_2$), 111.1 (CH (Ar)), 113.7 (2×CH(Ar)), 124.2 (CH(Ar)), 127.7 (C(Ar)), 129.9 (C(Ar)), 130.4 (2×CH(Ar)), 134.4 (C(Ar)), 138.2 (C(Ar)), 150.4 (C(Ar)) and 159.6 (C(Ar)). LC/MS (APCI+) t$_r$=4.12 min m/z 379.34 (M$^+$+H); HPLC t$_r$=2.15 min (98.9%). (CH$_3$CN/H$_2$O 90/10); HRMS (Electrospray) calcd. for C$_{18}$H$_{22}$N$_2$O$_5$S (MH$^+$), 379.1322 found. 379.1322

2-Benzyl-7-methoxy-6-O-sulfamoyl-1,2,3,4-tetrahydroisoquinoline 74

Light yellow powder, 55 mg (79%), mp 113-114° C., R$_f$: 0.61 (ethyl acetate), $^1$H NMR (270 MHz, CDCl$_3$) δ 2.71-2.84 (4H, m, 2×CH$_2$), 3.56 (2H, s, CH$_2$), 3.68 (2H, s, CH$_2$), 3.80 (3H, s, CH$_3$O), 4.97 (1H, br, OH), 6.60 (1H, s, ArH), 7.07 (1H, s, ArH), 7.26-7.40 (5H, m, ArH), $^{13}$C NMR (67.5 MHz, CDCl$_3$) δ 28.2 (CH$_2$), 50.5 (CH$_2$), 55.7 (CH$_2$), 56.4 (CH$_3$O), 62.6 (CH$_2$), 111.2 (CH(Ar)), 124.2 (CH(Ar)), 127.4 (CH (Ar)), 127.7 (C(Ar)), 128.5 (2×CH(Ar)) and 129.2 (2×CH (Ar)), 134.9 (C(Ar)), 137.3 (C(Ar)), 138.0 (C(Ar)) and 149.3 (C(Ar)). LC/MS (APCI+) t$_r$=4.18 min m/z 349.37 (M$^+$+H); HPLC t$_r$=2.11 min (97.7%). (CH$_3$CN/H$_2$O 90/10)

7-Methoxy-2-(2-methoxybenzyl)-6-O-sulfamoyl-1,2,3,4-tetrahydroisoquinoline 75

Light yellow powder, 105 mg (55%), mp 126-127° C., R$_f$: 0.43 (ethyl acetate), $^1$H NMR (270 MHz, CDCl$_3$/CD$_3$OD 5/1) δ 2.78 (4H, m, 2×CH$_2$), 3.48 (2H, br, NH$_2$), 3.62 (2H, s, CH$_2$), 3.73 (2H, s, CH$_2$), 3.79 (3H, s, CH$_3$O), 3.83 (3H, s, CH$_3$O), 6.61 (1H, s, ArH), 6.90 (1H, d, J 7.9 Hz, ArH), 6.95 (1H, dt, J 7.4 and 1.0 Hz, ArH), 7.09 (1H, s, ArH), 7.25-7.36 (2H, m, ArH), $^{13}$C NMR (67.5 MHz, CDCl$_3$/CD$_3$OD 5/1) δ 27.6 (CH$_2$), 50.3 (CH$_2$), 55.6 (2×CH$_3$O), 55.6 (CH$_2$), 60.7 (CH$_2$), 110.6 (CH(Ar)) 111.0 (CH(Ar)), 120.5 (CH(Ar)), 123.8 (CH (Ar)), 124.8 (C(Ar)), 126.8 (C(Ar)), 128.9 (CH(Ar)), 131.2 (CH(Ar)), 133.8 (C(Ar)), 137.5 (C(Ar)), 149.7 (C(Ar)) and 158.1 (C(Ar)). LC/MS (APCI+) t$_r$=3.96 min m/z 379.34 (M$^+$+H); HPLC t$_r$=2.45 min (99.6%). (CH$_3$CN/H$_2$O 90/10).

2-(3,5-Dimethoxybenzyl)-7-methoxy-6-O-sulfamoyl-1,2,3,4-tetrahydroisoquinoline 76

Light yellow powder, 145 mg (71%), mp 147-148° C., R$_f$: 0.55 (ethyl acetate), $^1$H NMR (270 MHz, CDCl$_3$/CD$_3$OD 5/1) δ 2.63-2.77 (4H, m, 2×CH$_2$), 3.48 (2H, s, CH$_2$), 3.54 (2H, s, CH$_2$), 3.61 (2H, br, NH$_2$), 3.71 (6H, s, 2×CH$_3$O), 3.72 (3H, s, CH$_3$O), 6.30 (1H, t, J 2.2 Hz, ArH), 6.46 (1H, d, J 2.2 Hz, ArH), 6.53 (1H, s, ArH),7.02 (1H, s, ArH), $^{13}$C NMR (67.5 MHz, CDCl$_3$/CD$_3$OD 5/1) δ 27.7 (CH$_2$), 50.4 (CH$_2$), 55.3 (2×CH$_3$O), 55.6 (CH$_2$), 56.0 (CH$_3$O), 62.7 (CH$_2$), 99.3 (CH (Ar)), 106.1 (CH(Ar))), 110.8 (CH(Ar)), 123.6 (CH(Ar)), 126.6 (C(Ar)), 133.8 (C(Ar)), 137.4 (C(Ar)), 139.6 (C(Ar)), 149.6 (C(Ar)) and 160.7 (C(Ar)). LC/MS (APCI+) t$_r$=4.20 min m/z 409.25 (M$^+$+H); HPLC t$_r$=2.05 min (99.6%). (CH$_3$CN/H$_2$O 90/10).

7-Methoxy-2-(3-methylbenzyl)-6-O-sulfamoyl-1,2,3,4-tetrahydroisoquinoline 77

Yellow powder, 120 mg (67%), mp=142-143° C., R$_f$: 0.41 (EtOAc/Hexane 1:1), $^1$H NMR (270 MHz, CDCl$_3$) δ 2.34 (3H, s, CH$_3$), 2.71-2.84 (4H, m, 2×CH$_2$), 3.56 (2H, s, CH$_2$), 3.64 (2H, s, CH$_2$), 3.80 (3H, s, CH$_3$O), 5.02 (2H, br, NH$_2$), 6.60 (1H, s, ArH), 7.07 (1H, s, ArH), 7.10-7.22 (4H, m, ArH), $^{13}$C NMR (67.5 MHz, CDCl$_3$) δ 21.5 (CH$_3$), 28.2 (CH$_2$), 50.5 (CH$_2$), 55.7 (CH$_2$), 56.4 (CH$_3$O), 62.7 (CH$_2$), 111.2 (CH (Ar)), 124.2 (CH(Ar)), 126.3 (CH(Ar)), 127.6 (C(Ar)), 128.1 (CH(Ar)), 128.3 (CH(Ar)), 130.0 (CH(Ar)), 134.8 (C(Ar)), 137.3 (C(Ar)), 137.8 (C(Ar)), 138.2 (C(Ar)), 149.3 (C(Ar)). LC/MS (APCI−) t$_r$=4.59 min m/z 361.40 (M$^+$+H); HPLC t$_r$=3.90 min (96.3%). (MeOH/H$_2$O 70/30).

7-Methoxy-2-(3-phenoxybenzyl)-6-O-sulfamoyl-1,2,3,4-tetrahydroisoquinoline 78

Yellow powder, 180 mg (82%), mp=68-69° C., R$_f$: 0.36 (EtOAc/Hexane 1:1), $^1$H NMR (270 MHz, CDCl$_3$) δ 2.68-2.79 (4H, m, 2×CH$_2$), 3.56 (2H, s, CH$_2$), 3.64 (2H, s, CH$_2$), 3.80 (3H, s, CH$_3$O), 4.80 (2H, br, NH$_2$), 6.59 (1H, s, ArH), 6.90 (1H, dd, J 7.9, 1.7 Hz, ArH), 6.98-7.02 (2H, m, ArH), 7.05-7.12 (4H, m, ArH), 7.25-7.35 (3H, m, ArH), $^{13}$C NMR (67.5 MHz, CDCl$_3$) δ 28.2 (CH$_2$), 50.4 (CH$_2$), 55.7 (CH$_2$), 56.4 (CH$_3$O), 62.3 (CH$_2$), 111.2 (CH(Ar)), 117.8 (CH(Ar)), 118.9 (2×CH(Ar)), 119.6 (CH(Ar)), 123.3 (CH(Ar)), 124.0 (CH(Ar)), 124.1 (CH(Ar)), 127.6 (C(Ar)), 129.7 (CH(Ar)), 129.9 (2×CH(Ar)), 134.7 (C(Ar)), 137.3 (C(Ar)), 140.2 (C(Ar)), 149.3 (C(Ar)), 157.2 (C(Ar)) and 157.4 (C(Ar)). LC/MS (APCI−) t$_r$=5.05 min m/z 439.66 (M$^+$−H); HPLC t$_r$=2.20 min (99.7%). (MeOH/H$_2$O 90/10).

7-Methoxy-2-(3-(O-sulfamoyl)benzyl)-6-O-sulfamoyl-1,2,3,4-tetrahydroisoquinoline 79

Light yellow powder, 170 mg (76%), R$_f$: 0.68 (EtOAc), $^1$H NMR (270 MHz, CDCl$_3$/CD$_3$COCD$_3$ 5:1) δ 2.44-2.55 (4H, m, 2×CH$_2$), 3.31 (2H, s, CH$_2$), 3.43 (2H, s, CH$_2$), 3.55 (3H, s, CH$_3$O), 6.05 (2H, br, NH$_2$), 6.30 (2H, br, NH$_2$), 6.36 (1H, s, ArH), 6.80 (1H, s, ArH), 6.96 (1H, dt, J 7.7, 1.0 Hz, ArH), 7.03-7.11 (3H, m, ArH), $^{13}$C NMR (67.5 MHz, CDCl$_3$/CD$_3$COCD$_3$ 5:1) δ 28.1 (CH$_2$), 50.4 (CH$_2$), 55.5 (CH$_2$), 55.8 (CH$_3$O), 61.7 (CH$_2$), 110.7 (CH(Ar)), 120.8 (CH(Ar)), 122.4 (CH(Ar)), 123.7 (CH(Ar)), 126.6 (C(Ar)), 127.0 (CH(Ar)), 129.3 (CH(Ar)), 134.0 (C(Ar)), 137.3 (C(Ar)), 140.5 (C(Ar)), 149.7 (C(Ar)) and 150.4 (C(Ar)). LC/MS (APCI+) t$_r$=3.26 min m/z 444.32 (M$^+$+H); MeOH/H2O 50/50 to 95/5 (5 min); HPLC t$_r$=3.20 min (100%). (CH3CN/H2O 90/10).

2-(3-Ethoxybenzyl)-7-methoxy-6-O-sulfamoyl-1,2,3,4-tetrahydroisoquinoline 80

Light yellow powder, 140 mg (71%), mp=64-65° C., R$_f$: 0.18 (Hexane/EtOAc 1:1), $^1$H NMR (270 MHz, CDCl$_3$) δ 1.39 (3H, t, J 6.9, CH$_3$), 2.69-2.84 (4H, m, 2×CH$_2$), 3.56 (2H, s, CH$_2$), 3.64 (2H, s, CH$_2$), 3.80 (3H, s, CH$_3$O), 4.02 (2H, q, J 6.9, CH$_2$), 5.00 (2H, br, NH$_2$), 6.59(1H, s, ArH), 6.80 (1H, dd, J 7.9, 2.0, ArH), 6.91-6.94 (2H, m, ArH), 7.06 (1H, s, ArH), 7.22 (1H, t, J 7.9, ArH), $^{13}$C NMR (67.5 MHz, CDCl$_3$) δ 15.0 (CH$_3$), 28.2 (CH$_2$), 50.5 (CH$_2$), 55.7 (CH$_2$), 56.4 (CH$_3$O), 62.6 (CH$_2$), 63.5 (CH$_2$O), 111.2 (CH(Ar)), 113.4 (CH(Ar)), 115.1 (CH(Ar)), 121.4 (CH(Ar)), 124.1 (CH(Ar)), 127.7 (C(Ar)), 129.4 (CH(Ar)), 134.8 (C(Ar)), 137.30 (C(Ar)), 139.60 (C(Ar)), 149.3 (C(Ar)) and 159.2 (C(Ar)). LC/MS (APCI+) t$_r$=4.53 min m/z 393.43 (M$^+$+H); MeOH/H$_2$O 50/50 to 95/5 (5 min); HPLC t$_r$=4.35 min (95.2%). (CH$_3$CN/H$_2$O 90/10)

7-Methoxy-2-(pyridin-3-ylmethyl)-6-O-sulfamoyl-1,2,3,4-tetrahydroisoquinoline 81

Yellow powder, 110 mg (63%); mp=139-140° C., R$_f$: 0.24 (EtOAc/MeOH 10:1), $^1$H NMR (270 MHz, CDCl$_3$/CD$_3$COCDl$_3$ 5:1) δ 2.47-2.58 (4H, m, 2×CH$_2$), 3.33 (2H, s, CH$_2$), 3.40 (2H, br, NH$_2$), 3.46 (2H, s, CH$_2$), 3.54 (3H, s, CH$_3$O), 6.37 (1H, s, ArH), 6.83 (1H, s, ArH), 7.09 (1H, dd, J 7.7, 4.9 Hz, PyrH), 7.55 (1H, d, J 7.7 Hz, 1H, PyrH), 8.22 (1H, d, J 4.9 Hz, 1H, PyrH), 8.29 (s, 1H, PyrH), $^{13}$C NMR (67.5 MHz, CDCl$_3$/CD$_3$COCDl$_3$ 5:1) δ 27.8 (CH$_2$), 50.3 (CH$_2$), 55.4 (CH$_2$), 55.7 (CH$_3$O), 59.4 (CH$_2$), 63.5 (CH$_2$O), 110.6 (CH(Ar)), 122.3 (C(Ar)), 123.6 (CHpyr), 123.7 (CH(Ar)), 126.3 (C(Ar)), 133.4 (C(Ar)), 133.7 (Cpyr), 137.2 (CHpyr), 137.5 (C(Ar)), 148.1 (CHpyr) and 149.7 (CHpyr). LC/MS (APCI+) t$_r$=2.97 min m/z 350.52 (M$^+$+H); MeOH/H$_2$O 50/50 to 95/5 (5 min); HPLC t$_r$=3.38 min (96.2%). (CH$_3$CN/H$_2$O 90/10)

2-(3-Acetylbenzyl)-7-methoxy-6-O-sulfamoyl-1,2,3,4-tetrahydroisoquinoline 82

Yellow powder, 130 mg (66%), mp=144-145° C., R$_f$: 0.36 (EtOAc), $^1$H NMR (270 MHz, CDCl$_3$/CD$_3$COCD$_3$ 4:1) δ 2.15 (s, 3H, CH$_3$), 2.27-2.38 (4H, m, 2×CH$_2$), 3.12 (2H, s, CH$_2$), 3.29 (2H, s, CH$_2$), 3.33 (3H, s, OCH$_3$), 6.19 (3H, br, NH$_2$ and ArH), 6.60 (1H, s, ArH), 7.00 (1H, t, J 7.7 Hz, ArH), 7.17 (1H, dt, J 7.7 and 1 Hz, ArH), 7.44 (1H, dt, J 7.7 and 1.2 Hz, ArH), 7.53 (1H, m, ArH), $^{13}$C NMR (67.5 MHz, CDCl$_3$/CD$_3$COCD$_3$ 4:1) δ 26.1 (CH$_3$), 27.9 (CH$_2$), 50.3 (CH$_2$), 55.3 (CH$_2$), 55.7 (CH$_3$O), 61.8 (CH$_2$), 110.4 (CH(Ar)), 123.5 (CH(Ar)), 126.1 (C(Ar)), 126.9 (CH(Ar)), 128.2 (CH(Ar)), 128.3 (CH(Ar)), 133.2 (CH(Ar)), 133.7 (C(Ar)), 136.9 (C(Ar)), 137.1 (C(Ar)), 138.9 (C(Ar)), 149.6 (C(Ar)), and 197.3 (CO). LC/MS (ES−) t$_r$=1.01 min m/z 389.56 (M$^-$−H); MeOH/H$_2$O 95/5; HPLC t$_r$=4.02 min (96.3%). (CH$_3$CN/H$_2$O 90/10)

7-Methoxy-2-(4-methoxyphenethyl)-6-O-sulfamoyl-1,2,3,4-tetrahydroisoquinoline 83

Light yellow powder, 145 mg (75%), mp=140-141° C., R$_f$: 0.42 (EtOAc), $^1$H NMR (270 MHz, CDCl$_3$) δ 2.70-2.88 (8H, m, 4×CH$_2$), 3.68 (2H, s, CH$_2$), 3.78 (3H, s, OCH$_3$), 3.84 (3H, s, OCH$_3$), 5.10 (2H, br, NH$_2$), 6.65 (1H, s, ArH), 6.81-6.86 (m, 2H, ArH), 7.08 (1H, s, ArH), 7.11-7.16 (2H, m, ArH), $^{13}$C NMR (67.5 MHz, CDCl$_3$) δ 28.1 (CH$_2$), 33.0 (CH$_2$), 50.6 (CH$_2$), 55.4 (CH$_3$O), 55.9 (CH$_2$), 56.4 (CH$_3$O), 60.2 (CH$_2$), 111.1 (CH(Ar)), 113.9 (2×CH(Ar)), 124.2 (CH(Ar)), 125.9 (C(Ar)), 127.5 (C(Ar)), 129.7 (2×CH(Ar)), 132.1 (C(Ar)), 134.5 (C(Ar)), 137.4 (C(Ar)), 149.4 (C(Ar)) and 158.1 C(Ar)). LC/MS (ES−) t$_r$=1.13 min m/z 391.57 (M$^-$−H); MeOH/H$_2$O 95/5. HPLC t$_r$=4.42 min (97.4%). (CH$_3$CN/H$_2$O 90/10).

7-Methoxy-2-(pyridin-2-ylmethyl)-6-O-sulfamoyl-1,2,3,4-tetrahydroisoquinoline 84

White powder, 105 mg (61%), mp=162-163° C., R$_f$: 0.21 (EtOAc/MeOH 10:1), $^1$H NMR (270 MHz, CDCl$_3$/CD$_3$OD10:1) δ 2.63-2.72 (4H, m, 2×CH$_2$), 3.52 (2H, s, CH$_2$), 3.67 (3H, s, CH$_3$ O), 3.70 (2H, s, CH$_2$), 6.49 (1H, s, ArH), 6.96 (1H, s, ArH), 7.14 (1H, ddd, =7.4, 4.9 and 1.0 Hz, PyrH), 7.40 (1H, d, J 7.9 Hz, PyrH), 7.62 (1H, dt, J 7.7 and 1.7 Hz, PyrH), 8.37 (1H, ddd, J 4.9, 1.7 and 1.0 Hz, PyrH), $^{13}$C NMR (67.5 MHz, CDCl$_3$/CD$_3$OD10:1) δ 27.8 (CH$_2$), 50.5 (CH$_2$), 55.6 (CH$_2$), 55.9 (CH$_3$O), 63.4 (CH$_2$), 110.8 (CH(Ar)), 122.7 (CHpyr), 123.6 (CHpyr), 123.7 (CH(Ar)), 126.5 (C(Ar)), 133.5 (C(Ar)), 137.4 (CHpyr), 137.5 (C(Ar)), 148.5 (CHpyr) 149.7 (C(Ar)), and 157.5 (Cpyr). LC/MS (ES−) t$_r$=1.09 min m/z 348.51 (M$^{+-}$H); MeOH/H$_2$O 95/5; HPLC t$_r$=3.57 min (100%). (CH$_3$CN/H$_2$O 90/10)

2-(3-Acetamidobenzyl)-7-methoxy-6-O-sulfamoyl-1,2,3,4-tetrahydroisoquinoline 85

Light yellow powder, 150 mg (75%), R$_f$: 0.18 (EtOAc/MeOH 10:1), mp=124-126° C., $^1$H NMR (270 MHz, CDCl$_3$/CD$_3$COCDl$_3$ 5:1) δ 2.06 (3H, s, CH$_3$), 2.66-2.77 (4H, m, 2×CH$_2$), 3.52 (2H, s, CH$_2$), 3.60 (2H, s, CH$_2$), 3.73 (3H, s, CH$_3$O), 5.89 (2H, br, NH$_2$), 6.53 (1H, s, ArH), 6.97 (1H, d, J 7.7, 1H, ArH), 7.03 (1H, s, ArH), 7.21 (1H, dd, J 8.2 and 7.7, ArH), 7.26-7.30 (1H, m, PyrH), 7.61 (1H, ddd, J 8.2, 2.0, 1.0, ArH). $^{13}$C NMR (67.5 MHz, CDCl$_3$/CD$_3$COCDl$_3$ 5:1) δ 23.9 (CH$_3$), 27.3 (CH$_2$), 50.3 (CH$_2$), 55.4 (CH$_2$), 56.1 (CH$_3$O), 62.3 (CH$_2$), 110.8 (CH(Ar)), 119.5 (CH(Ar)), 120.4 (CH(Ar)), 123.8 (CH(Ar)), 125.3 (CH(Ar)), 126.2 (C(Ar)), 129.0 (CH(Ar)), 133.0 (C(Ar)), 136.9 (C(Ar)), 137.7 (C(Ar)), 138.7 (C(Ar)), 149.8 (C(Ar)) and 169.9 (CO). LC/MS (ES+) t$_r$=3.29 min m/z 406.43 (M$^+$+H); MeOH/H$_2$O 50/50 to 95/5 (5 min); HPLC t$_r$=3.67 min (96.3%). (CH$_3$CN/H$_2$O 90/10)

7-Methoxy-2-(pyridin-4-ylmethyl)-6-O-sulfamoyl-1,2,3,4-tetrahydroisoquinoline 86

Light white powder, 135 mg (77%), R$_f$: 0.24 (EtOAc/MeOH 10:1), $^1$H NMR (270 MHz, CDCl$_3$/CD$_3$COCDl$_3$ 3:1) δ 2.45-2.57 (4H, m, 2×CH$_2$), 3.32 (2H, s, CH$_2$), 3.44 (2H, s, CH$_2$), 3.54 (3H, s, CH$_3$O), 6.14 (2H, br, NH$_2$), 6.36 (1H, s, ArH), 6.82 (1H, s, ArH), 7.09 (2H, d, J 4.7, 2×PyrH), 8.27 (2H, d, J 4.7, 1.5, PyrH), $^{13}$C NMR (67.5 MHz, CDCl$_3$/CD$_3$COCDl$_3$ 3:1) δ 28.1 (CH$_2$), 50.6 (CH$_2$), 55.6 (CH$_2$), 55.7

(CH$_3$O), 61.2 (CH$_2$), 110.6 (CH(Ar)), 123.6 (2×CHpyr), 123.8 (CH(Ar)), 126.3 (C(Ar)), 133.6 (C(Ar)), 137.2 (C(Ar)), 147.6 (Cpyr), 149.6 (2×CHpyr) and 149.7 (C(Ar)). LC/MS (ES−) t$_r$=1.04 min m/z 349.38 (M$^+$+H); MeOH/H$_2$O 95/5. HPLC t$_r$=3.46 min (97.1%). (CH$_3$CN/H$_2$O 90:10)

2-(3-Acetoxybenzyl)-7-methoxy-6-O-sulfamoyl-1,2,3,4-tetrahydroisoquinoline 87

Yellow powder, 170 mg (85%), mp=64-65° C., R$_f$: 0.16 (Hexane/EtOAc 1:1), $^1$H NMR (270 MHz, CDCl$_3$) δ 2.28 (3H, s, CH$_3$), 2.70-2.86 (4H, m, 2×CH$_2$), 3.55 (2H, s, CH$_2$), 3.67 (2H, s, CH$_2$), 3.81 (3H, s, CH$_3$O), 4.98 (2H, s, NH$_2$), 6.60 (1H, s, ArH), 6.99 (1H, ddd, J 7.9, 2.2, 1.2, ArH), 7.07 (1H, s, ArH), 7.12 (1H, dd, J 2.2, 1.2, ArH), 7.20-7.26 (1H, m, ArH), 7.34 (1H, t, J 7.9, ArH), $^{13}$C NMR (67.5 MHz, CDCl$_3$) δ 21.3 (CH$_3$), 28.3 (CH$_2$), 50.7 (CH$_2$), 55.7 (CH$_2$), 56.4 (CH$_3$O), 62.2 (CH$_2$), 111.1 (CH(Ar)), 120.5 (CH(Ar)), 122.0 (CH(Ar)), 124.2 (CH(Ar)), 126.4 (CH(Ar)), 127.7 (C(Ar)), 129.4 (CH(Ar)), 134.8 (C(Ar)), 137.3 (C(Ar)), 140.2 (C(Ar)), 149.3 (C(Ar)), 150.8 (C(Ar)) and 169.8 (CO). LC/MS (ES−) t$_r$=1.02 min m/z 405.17 (M$^+$−H); MeOH/H$_2$O 95/5; HPLC t$_r$=3.96 min (98.57%). (CH$_3$CN/H$_2$O 90/10)

7-Methoxy-2-(3-(methylsulfonamido)benzyl)-1,2,3,4-tetrahydroisoquinolin-6-yl sulfamate 88

Light yellow powder, 140 mg (63%), mp=151-152° C., R$_f$: 0.17 (EtOAc), $^1$H NMR (270 MHz, CDCl$_3$/CD$_3$COCD$_3$ 3:1) δ 2.28-2.39 (4H, m, 2×CH$_2$), 2.56 (3H, s, CH$_3$), 3.15 (2H, s, CH$_2$), 3.26 (2H, s, CH$_2$), 3.38 (3H, s, CH$_3$O), 6.17 (2R, br, NH$_2$), 6.23 (1H, s, ArH), 6.64 (1H, s, ArH), 6.74-6.96 (4H, m, ArH), $^{13}$C NMR (67.5 MHz, CDCl$_3$/CD$_3$COCD$_3$ 3:1) δ 28.0 (CH$_2$), 38.5 (CH$_3$), 50.2 (CH$_2$), 55.4 (CH$_2$ and CH$_3$O), 61.9 (CH$_2$), 110.5 (CH(Ar)), 118.8 (CH(Ar)), 120.4 (CH(Ar)), 123.5 (CH(Ar)), 124.7 (CH(Ar)), 126.3 (C(Ar)), 129.0 (CH(Ar)), 133.9 (C(Ar)), 137.1 (C(Ar)), 137.9 (C(Ar)), 139.9 (C(Ar)), 149.6 (C(Ar)). LC/MS (ES−) t$_r$=0.97 min m/z 440.43 (M$^−$−H); MeOH/H$_2$O 95/5; HPLC t$_r$=3.32 min (99.0%). (CH$_3$CN/H$_2$O 90/10)

2-(2-(3,4-Dimethoxyphenyl)-2-oxoethyl)-6-O-sulfamoyl-7-methoxy-1,2,3,4-tetrahydroisoquinoline 89

Yellow powder, 165 mg (75%), mp=152-153° C., R$_f$: 0.15 (Hexane/EtOAc 1:5), $^1$H NMR (270 MHz, CD$_3$COCD$_3$) δ 2.76-2.88 (4H, m, 2×CH$_2$), 3.70 (2H, s, CH$_2$), 3.75 (3H, s, CH$_3$O), 3.86 (3H, s CH$_3$O), 3.88 (3H, s, CH$_3$O), 3.93 (2H, s, CH$_2$), 6.66 (1H, s, ArH), 6.69 (2H, br, NH$_2$), 6.94 (1H, d, J 8.4 Hz, ArH), 7.01 (1H, s, ArH), 7.57 (1H, d, J 2.0 Hz, ArH), 7.74 (1H, dd, J 8.4 and 2.0 Hz, ArH), $^{13}$C NMR (67.5 MHz, CD$_3$COCD$_3$) δ 28.2 (CH$_2$), 51.0 (CH$_2$), 55.5 (CH$_2$), 55.6 (CH$_3$O), 55.8 (2×CH$_3$O), 64.1 (CH$_2$), 110.4 (CH(Ar)), 110.7 (CH(Ar)), 110.8 (CH(Ar)), 123.3 (CH(Ar)), 123.9 (CH(Ar)), 126.2 (C(Ar)), 129.2 (C(Ar)), 133.8 (C(Ar)), 137.1 (C(Ar)), 149.0 (C(Ar)), 150.1 (C(Ar)), 153.6 (C(Ar)) and 195.1 (CO). LC/MS (ES−) t$_r$=1.02 min m/z 435.44 (M−H)$^−$; MeOH/H$_2$O 95/5; HPLC t$_r$=1.22 min (97.3%). (CH$_3$CN/H$_2$O 90/10)

7-Methoxy-2-(3,4,5-trimethoxybenzyl)-6-O-sulfamoyl-1,2,3,4-tetrahydroisoquinoline 90

Yellow powder, 125 mg (57%), mp=143-144° C., R$_f$: 0.32 (EtOAc), $^1$H NMR (270 MHz, CDCl$_3$) δ 2.70-2.84 (4H, m, 2×CH$_2$), 3.58 (2H, s, CH$_2$), 3.61 (2H, s, CH$_2$), 3.81 (3H, s, CH$_3$O), 3.83 (3H, s, CH$_3$O), 3.84 (6H, s, CH$_3$O), 5.10 (2H, br, NH$_2$), 6.61 (3H, s, ArH), 7.07 (1H, s, ArH), $^{13}$C NMR (67.5 MHz, CDCl$_3$) δ 28.1 (CH$_2$), 50.4 (CH$_2$), 55.7 (CH$_2$), 56.2 (2×CH$_3$O), 56.4 (CH$_3$O), 61.0 (CH$_3$O), 62.8 (CH$_2$), 105.7 (2×CH(Ar)), 111.2 (CH(Ar)), 124.2 (CH(Ar)), 127.6 (C(Ar)), 133.7 (C(Ar)), 134.6 (C(Ar)), 137.0 (C(Ar)), 137.4 (C(Ar)), 149.4 (C(Ar)) and 153.3 (2×C(Ar)). LC/MS (APCI−) t$_r$=0.94 min m/z 437.19 (M−H)$^−$; MeOH/H$_2$O 95/5; HPLC t$_r$=1.63 min (99.5%). (CH$_3$CN/H$_2$O 90:10).

7-Methoxy-2-(2,3-dimethoxybenzyl)-6-O-sulfamoyl-1,2,3,4-tetrahydroisoquinoline 91

Yellow powder, 135 mg (66%), mp=145-146° C., R$_f$: 0.41 (EtOAc), $^1$H NMR (270 MHz, CDCl$_3$) δ 2.79-2.85 (4H, m, 2×CH$_2$), 3.66 (2H, s, CH$_2$), 3.79 (2H, s, CH$_2$), 3.80 (3H, s, CH$_3$O), 3.83 (3H, s, CH$_3$O), 3.87 (3H, s, CH$_3$O), 4.95 (2H, br, NH$_2$), 6.61 (1H, s, ArH), 6.85-6.89 (1H, m, ArH), 7.03-7.07 (3H, m, ArH), $^{13}$C NMR (67.5 MHz, CDCl$_3$) δ 28.1 (CH$_2$), 50.4 (CH$_2$), 55.2 (CH$_2$), 55.7 (CH$_2$), 55.8 (CH$_3$O), 56.4 (CH$_3$O), 61.1 (CH$_3$O), 111.1 (2×CH(Ar)), 111.6 (CH(Ar)), 122.8 (CH(Ar)), 124.1 (CH(Ar)), 127.4 (C(Ar)), 132.8 (C(Ar)), 137.4 (C(Ar)), 141.3 (C(Ar)), 147.9 (C(Ar)), 149.3 and 152.8 (C(Ar)). LC/MS (APCI−) t$_r$=0.92 min m/z 407.15 (M−H)$^−$; MeOH/H2O 95/5; HPLC t$_r$=1.77 min (97.0%). (CH$_3$CN/H$_2$O 90:10).

7-Methoxy-2-(3,4-dimethoxybenzyl)-6-O-sulfamoyl-1,2,3,4-tetrahydroisoquinoline 92

Yellow powder, 140 mg (70%), mp=155-156° C., R$_f$: 0.28 (EtOAc), $^1$H NMR (270 MHz, CDCl$_3$) δ 2.65-2.82 (4H, m, 2×CH$_2$), 3.52 (2H, s, CH$_2$), 3.59 (2H, s, CH$_2$), 3.77 (3H, s, CH$_3$O), 3.78 (3H, s, CH$_3$O), 3.79 (3H, s, CH$_3$O), 6.77 (1H, s, ArH), 6.89 (2H, s, NH$_2$), 6.91-6.93 (2H, m, ArH), 7.00 (1H, s, ArH), 7.04 (1H, s, ArH), $^{13}$C NMR (67.5 MHz, CDCl$_3$) δ 28.4 (CH$_2$), 50.6 (CH$_2$), 55.2 (CH$_3$O), 55.3 (CH$_3$O), 55.4 (CH$_3$O), 55.6 (CH$_2$), 62.2 (CH$_2$), 111.0 (CH(Ar)), 111.6 (CH(Ar)), 112.5 CH(Ar)), 121.0 (CH(Ar)), 123.7 (CH(Ar)), 126.6 (C(Ar)), 131.3 (C(Ar)), 134.5 (C(Ar)), 137.5 (C(Ar)), 148.7 (C(Ar)), 149.5 (C(Ar)) and 150.2 (C(Ar)). LC/MS (APCI−) t$_r$=0.93 min m/z 407.21 (M−H)$^−$; MeOH/H$_2$O 95/5; HPLC t$_r$=1.65 min (99.7%). (CH$_3$CN/H$_2$O)

7-Methoxy-2-(2,3,4-trimethoxybenzyl)-6-O-sulfamoyl-1,2,3,4-tetrahydroisoquinoline 93

Yellow powder, 175 mg (79%): mp=79-80° C., R$_f$: 0.35 (EtOAc), $^1$H NMR (270 MHz, CDCl$_3$) δ 2.71-2.82 (4H, m, 2×CH$_2$), 3.61 (2H, s, CH$_2$), 3.65 (2H, s, CH$_2$), 3.80 (3H, s, CH$_3$O), 3.85 (3H, s, CH$_3$O), 3.88 (6H, s, 2×CH$_3$O), 6.61 (1H, s, ArH), 6.65 (1H, d, J 8.6 Hz, ArH), 7.05 (1H, s, ArH), 7.06 (1H, d, J 8.6 Hz, ArH), $^{13}$C NMR (67.5 MHz, CDCl$_3$) δ 28.3 (CH$_2$), 50.3 (CH$_2$), 55.6 (CH$_2$), 56.0 (CH$_3$O), 56.1 (CH$_2$), 56.4 (CH$_3$O), 60.9 (CH$_3$O), 61.4 (CH$_3$O), 107.2 (CH(Ar)), 111.2 (CH(Ar)), 123.5 (C(Ar)), 124.1 CH(Ar)), 125.2 (CH(Ar)), 127.7 (C(Ar)), 134.8 (C(Ar)), 137.3 (C(Ar)), 142.3 (C(Ar)), 149.3 (C(Ar)), 152.7 (C(Ar)) and 153.1 (C(Ar)). LC/MS (APCI−) t$_r$=0.84 min m/z 437.07 (M−H)$^−$; MeOH/H$_2$O 95/5; HPLC t$_r$=1.87 min (99.8%). (CH$_3$CN/H$_2$O 90:10).

7-Methoxy-2-(2,5-dimethoxybenzyl)-6-O-sulfamoyl-1,2,3,4-tetrahydroisoquinoline 94

Yellow powder, 150 mg (74%): mp=138-139° C., R$_f$: 0.41 (EtOAc), $^1$H NMR (270 MHz, CDCl$_3$) δ 2.73-2.82 (4H, m, 2×CH$_2$), 3.63 (2H, s, CH$_2$), 3.68 (2H, s, CH$_2$), 3.76 (3H, s, CH$_3$O), 3.79 (3H, s, CH$_3$O), 3.81 (H, s, CH$_3$O), 4.90 (2H, br, NH$_2$), 6.61 (1H, s, ArH), 6.76 (1H, dd, J 8.8 and 2.9 Hz, ArH), 6.82 (1H, d, J 8.8 Hz, ArH), 7.02 (1H, d, J 2.9 Hz, ArH), 7.06 (1H, s, ArH), $^{13}$C NMR (67.5 MHz, CDCl$_3$) δ 28.2 (CH$_2$), 50.5 (CH$_2$), 55.7 (CH$_2$), 55.8 (CH$_2$), 55.9 (CH$_3$O), 56.3 (CH$_3$O), 56.4 (CH$_3$O), 111.2 (CH(Ar)), 111.7 (CH(Ar)), 112.6 (CH(Ar)), 116.3 (CH(Ar)), 124.1 (CH(Ar)), 127.3 (C(Ar)), 127.8 (C(Ar)), 135.1 (C(Ar)), 137.2 (C(Ar)), 149.2 (C(Ar)), 152.1 (C(Ar)) and 153.6 (C(Ar)). LC/MS (APCI–) t$_r$=0.89 min m/z 407.02 (M–H)$^-$; MeOH/H$_2$O 95/5; HPLC t$_r$=1.91 min (98.0%). (CH$_3$CN/H$_2$O 90/10)

7-Methoxy-2-(2,4,5-trimethoxybenzyl)-6-O-sulfamoyl-1,2,3,4-tetrahydroisoquinoline 95

Yellow powder, 140 mg (64%): mp=166-167° C., R$_f$: 0.16 (EtOAc), $^1$H NMR (270 MHz, CDCl$_3$/CD$_3$COCD$_3$ 5/1) δ 2.63-2.74 (4H, m, 2×CH$_2$), 3.54 (2H, s, CH$_2$), 3.58 (2H, s, CH$_2$), 3.74 (6H, s, 2×CH$_3$O), 3.75 (3H, s, CH$_3$O), 3.82 (H, s, CH$_3$O), 5.60 (2H, br, NH$_2$), 6.47 (1H, s, ArH), 6.54 (1H, s, ArH), 6.91 (1H, s, ArH), 6.99 (1H, s, ArH), $^{13}$C NMR (67.5 MHz, CDCl$_3$/CD$_3$COCD$_3$ 5/1) δ 29.8 (CH$_2$), 49.7 (CH$_2$), 55.3 (CH$_2$), 55.8 (CH$_2$), 56.0 (CH$_3$O), 56.1 (CH$_3$O), 56.5 (CH$_3$O), 56.6 (OCH$_3$), 97.1 (CH(Ar)), 110.0 (CH(Ar)), 110.9 (CH(Ar)), 114.2 (C(Ar)), 123.8 (CH(Ar)), 126.4 (C(Ar)), 127.1 (C(Ar)), 143.0 (C(Ar)), 145.4 (C(Ar)), 148.6 (C(Ar)), 149.8 (C(Ar)) and 152.2 (C(Ar)). LC/MS (APCI–) t$_r$=0.85 min m/z 437.20 (M–H)$^-$; MeOH/H$_2$O 95/5; HPLC t$_r$=1.81 min (98.2%). (CH$_3$CN/H$_2$O 90/10)

7-Methoxy-2-(3-(triisopropylsilyloxy)benzyl)-6-O-sulfamoyl-1,2,3,4-tetrahydroisoquinoline 96

A solution of 6-hydroxy-7-methoxy-2-(3-(triisopropylsilyloxy)benzyl)-1,2,3,4-tetrahydroisoquinoline (200 mg, 0.45 mmol), 2,6-t-butyl-4methylpyridine (205 mg, 1 mmol) and sulfamoyl chloride (1.80 mmol) in DCM (5 mL) was stirred at RT for 60 h. Water (5 mL) and NaHCO$_3$ (pH8) were added and the organics were extracted with ethyl acetate. The organic layer was washed with water, brine, dried (MgSO$_4$), filtered and the solvent evaporated under vacuum. The residual oil was purified by flash chromatography (hexane/ethyl acetate 4:1 to 3:2) to give a yellow oil that slowly crystallized. Yellow powder, 100 mg (63%); mp=110-112° C., R$_f$: 0.15 (Hexane/EtOAc 3:1), $^1$H NMR (270 MHz, CDCl$_3$) δ 1.08 (18H, d, J 6.9 Hz, (CH$_3$)$_2$CHSi), 1.16-1.30 (3H, m, (CH$_3$)$_2$CHSi), 2.66-2.81 (4H, m, 2×CH$_2$), 3.54 (2H, s, CH$_2$), 3.61 (2H, s, CH$_2$), 3.79 (3H, s, CH$_3$O), 5.02 (2H, br, NH$_2$), 6.58 (1H, s, ArH), 6.78 (1H, ddd, J 7.9, 2.2 and 1.0 Hz, ArH), 6.89-6.94 (2H, m, ArH), 7.05 (1H, s, ArH), 7.16 (1H, t, J 7.9 Hz, ArH), $^{13}$C NMR (67.5 MHz, CDCl$_3$) δ 12.7((CH$_3$)$_2$CHSi), 18.0 ((CH$_3$)$_2$CHSi), 28.2 (CH$_2$), 50.3 (CH$_2$), 55.7 (CH$_2$), 56.3 (CH$_3$O), 62.5 (CH$_2$), 111.1 (CH(Ar)), 118.8 (CH(Ar)), 120.8 (CH(Ar)), 121.9 (CH(Ar)), 124.0 (CH(Ar)), 127.7 (C(Ar)), 129.3 (CH(Ar)), 134.9 (C(Ar)), 137.3 (C(Ar)), 139.5 (C(Ar)), 149.3 (C(Ar)) and 156.2 (C(Ar)). LC/MS (ES–) t$_r$=2.50 min m/z 519.56 (M$^-$–H); MeOH/H$_2$O) 95/5; HPLC t$_r$=16.55 min (94.55%). (CH$_3$CN/H$_2$O 90/10).

2-(3-Hydroxybenzyl)-7-methoxy-6-O-sulfamoyl-1,2,3,4-tetrahydroisoquinoline 97

A solution of 7-methoxy-2-(3-(triisopropylsilyloxy)benzyl)-6-O-sulfamoyl-1,2,3,4-tetrahydroisoquinoline (85 mg, 0.16 mmol) in THF (10 mL) was cooled to 0° C. and a 1M solution TBAF/THF (0.18 mL, 0.18 mmol) was added drop wise. The reaction mixture was allowed to warm to rt and stirred 1 hour. After addition of water (10 mL), the organics were extracted with ethyl acetate and the organic layer was washed with water, brine, dried (MgSO$_4$), filtered and concentrated under reduced pressure. The resulting oil was purified by flash chromatography (hexane/ethyl actetate 3/2 to 1/5) to give 45 mg of yellow solid that was stirred in diethyl ether/hexane 1:2, filtered and dried. Yellow powder, 38 mg (66%), mp=134-135° C., R$_f$: 0.42 (EtOAc), $^1$H NMR (270 MHz, CD$_3$COCD$_3$) δ 2.67-2.81 (4H, m, 2×CH$_2$), 3.51 (2H, s, CH$_2$), 3.59 (2H, s, CH$_2$), 3.78 (3H, s, CH$_3$O), 6.73 (1H, dd, J 7.9, 2.5, ArH), 6.77 (1H, s, ArH), 6.84 (1H, d, J 7.4 Hz, ArH), 6.88-6.93 (2H, m, ArH, OH), 7.04 (1H, s, ArH), 7.14 (1H, dd, J 7.9 and 7.4 Hz, ArH), $^{13}$C NMR (67.5 MHz, CD$_3$COCD$_3$) δ 28.4 (CH$_2$), 50.8 (CH$_2$), 55.4 (CH$_3$O), 55.6 (CH$_2$), 62.4 (CH$_2$), 110.9 (CH(Ar)), 114.0 (CH(Ar)), 115.6 (CH(Ar)), 119.9 (CH(Ar)), 123.7 (CH(Ar)), 126.5 (C(Ar)), 129.3 (CH(Ar)), 134.5 (C(Ar)), 137.5 (C(Ar)), 140.5 (C(Ar)), 150.2 (C(Ar)) and 157.6 (C(Ar)). LC/MS (ES–) t$_r$=1.01 min m/z 363.37 (M$^-$–H); MeOH/H$_2$O 95/5 HPLC t$_r$=3.72 min (98.5%). (CH$_3$CN/H$_2$O 90/10).

2-(3-Cyanobenzyl)-7-methoxy-6-O-sulfamoyl-1,2,3,4-tetrahydroisoquinoline 98

134 mg, 83%,yellow oil. Crystallisation from ethyl acetate/hexane to afforded yellow powder (68 mg, 42%). mp 136-138.5° C. $^1$H NMR (270 MHz; DMSO-d$_6$) 2.69-2.76 (4H, m, 2×CH$_2$), 3.50 (2H, s, CH$_2$), 3.71 (5H, s, CH$_2$ and OCH$_3$), 6.82 (1H, s, CH$_2$), 7.04 (1H, s, CH), 7.57 (1H, t, J=7.7 Hz, CH), 7.71-7.84 (5H, m, 3×CH and NH$_2$). $^{13}$C NMR (67.5 MHz; DMSO-d$_6$) 28.37 (CH$_2$), 50.80 (CH$_2$), 55.48 (CH$_2$), 56.34 (OCH$_3$), 61.16 (CH$_2$), 111.67 (CH), 111.82 (C), 119.47 (C), 123.32 (CH), 126.34 (C), 130.16 (CH), 131.52 (CH), 132.64 (CH), 134.02 (C), 134.20 (C), 137.62 (C), 140.85 (C), 150.19 (C). LC/MS (APCI–) t$_r$=3.69 min, m/z 372.54 (M$^+$–H). LRMS (CI+) 374.2 (M$^+$+H, 10%) and 295.2 (M$^+$+H—SO$_2$NH$_2$, 80%). HRMS (ES+) calcd. for C$_{18}$H$_{20}$N$_3$O$_4$S (M$^+$+H) 374.1169, found 374.1167. HPLC t$_r$=8.94 min (>97%).

2-(4-Cyanobenzyl)-7-methoxy-6-O-sulfamoyl-1,2,3,4-tetrahydroisoquinoline 99

111 mg, 67%, yellow powder. mp 154-156° C. $^1$H NMR (270 MHz; DMSO-d$_6$) 2.68-2.70 (2H, m, CH$_2$), 2.74-2.78 (2H, m, CH$_2$), 3.50 (2H, s, CH$_2$), 3.71 (3H, s, OCH$_3$), 3.80 (3H, s, CH$_2$), 6.81 (1H, s, CH), 7.04 (1H, s, CH), 7.57 (2H, ~d, J 8.4 Hz, 2×CH), 7.82 (2H, ~d, J 8.4 Hz, 2×CH), 7.84 (2H, brs, NH$_2$). $^{13}$C NMR (67.5 MHz; DMSO-d$_6$) 28.38 (CH$_2$), 50.88 (CH$_2$), 55.60 (CH$_2$), 56.35 (OCH$_3$), 61.61 (CH$_2$), 110.33 (C), 111.65 (CH), 119.51 (C), 123.33 (CH), 126.32 (C), 130.03 (2×CH), 132.84 (2×CH), 133.99 (C), 137.63 (C), 145.23 (C), 150.19 (C). LC/MS (APCI+) t$_r$=3.74 min, m/z 373.86 (M$^+$+H). HRMS (ES+) calcd. for C$_{18}$H$_{20}$N$_3$O$_4$S (M$^+$+H) 374.1169, found 374.1171. HPLC t$_r$=8.37 min (>98%).

7-Methoxy-2-(3-nitrobenzyl)-6-O-sulfamoyl-1,2,3,4-tetrahydroisoquinoline 100

121 mg, 85%, yellow powder. mp 160.9-164° C. $^1$H NMR (270 MHz; DMSO-d$_6$) 2.72-2.77 (4H, m, 2×CH$_2$), 3.54 (2H, s, CH$_2$), 3.71 (3H, s, OCH$_3$), 3.84 (2H, s, CH$_2$), 6.81 (1H,s , CH), 7.05 (1H, s, CH), 7.66 (1H, t, J 7.9 Hz, CH), 7.82-7.85 (3H, m, CH and NH$_2$), 8.13-8.17 (1H, m, CH), 8.22 (1H, brs, CH). $^{13}$C NMR (100 MHz; DMSO-d$_6$) 27.84 (CH), 50.28 (CH), 54.93 (CH), 55.82 (OCH$_3$), 60.50 (CH), 111.15 (CH), 122.14 (CH), 122.83 (CH), 123.03 (CH), 125.79 (C), 129.89 (CH), 133.45 (C), 135.41 (CH), 137.12 (C), 141.09 (C), 147.93 (C), 149.67 (C). LC/MS (APCI+) t$_r$=4.01 min, m/z 394.45 (M⁺+H). HRMS (ES+) calcd. for $C_{17}H_{19}N_3O_6SNa$ (M⁺+Na) 416.0887, found 416.0888. HPLC $t_r$=2.75 min (>99%).

2-(3-Chlorobenzyl)-7-methoxy-6-O-sulfamoyl-1,2,3,4-tetrahydroisoquinoline 101

95 mg, 45%, yellow powder. mp 124.8-127.8° C. $^1$H NMR (270 MHz; DMSO-$d_6$) 2.69 (2H, d, J 4.6 Hz, $CH_2$), 2.74 (2H, ~d, J 4.6 Hz, $CH_2$), 3.49 (2H, s, $CH_2$), 3.66 (2H, s, $CH_2$), 3.71 (3H, s, $OCH_3$), 6.82 (1H, s, CH), 7.04 (1H, s, CH), 7.32-7.42 (4H, m, 4×CH), 7.84 (2H, brs, $NH_2$). $^{13}$C NMR (67.5 MHz; DMSO-$d_6$) 28.42 ($CH_2$), 50.86 ($CH_2$), 55.54 ($CH_2$), 56.35 ($OCH_3$), 61.49 ($CH_2$), 111.67 (CH), 123.33 (CH), 126.37 (C), 127.58 (CH), 127.88 (C), 128.87 (CH), 130.76 (CH), 133.57 (C), 134.10 (C), 137.59 (C), 141.77 (C), 150.19 (C). LC/MS (APCI+) $t_r$=4.60 min, m/z 382.93 (M⁺+H). HRMS (ES+) calcd. for $C_{17}H_{20}ClN_2O_4S$ (M⁺+H) 303.0827, found 383.0829. HPLC $t_r$=4.60 min (>98%).

7-Methoxy-2-(3-trifluoromethoxybenzyl)-6-O-sulfamoyl-1,2,3,4-tetrahydroisoquinoline 102

60 mg, 71%, yellow powder. mp 109.5-110.1° C. $^1$H NMR (400 MHz; DMSO-$d_6$) 2.66-2.69 (2H, m, $CH_2$), 2.74-2.76 (2H, m, $CH_2$), 3.35 (2H, s, $CH_2$), 3.53 (2H, s, $CH_2$), 3.71 (3H, s, $OCH_3$), 6.82(1H, s, CH), 7.04 (1H, s, CH), 7.26-7.28 (1H, m, CH), 7.34 (1H, s, CH), 7.40 (1H, d, J 7.6 Hz, CH), 7.49 (1H, t, J 8.0 Hz, CH), 7.84 (2H, brs, $NH_2$). $^{13}$C NMR (67.5 MHz; DMSO-$d_6$) 27.83 ($CH_2$), 50.18 ($CH_2$), 55.03 ($CH_2$), 55.83 ($OCH_3$), 60.75 ($CH_2$), 111.15 (CH), 119.56 (CH), 120.14 (q, J=254.6 Hz, $CF_3$), 120.71 (CH), 122.82 (CH), 125.83 (C), 127.66 (CH), 130.28 (CH), 133.53 (C), 137.11 (C), 141.55 (C), 148.57 (C), 149.70 (C). LC/MS (APCI−) $t_r$=1.07 min, m/z 431.02 (M−H)⁻. HPLC $t_r$=1.70 min (>99%).

2-(3-Fluorobenzyl)-7-methoxy-6-O-sulfamoyl-1,2,3,4-tetrahydroisoquinoline 103

103 mg, 78%, yellow powder. mp 120-124° C. $^1$H NMR (270 MHz; DMSO-$d_6$) 2.69 (2H, d, J 5.0 Hz, $CH_2$), 2.74 (2H, d, J 4.7 Hz, $CH_2$), 3.50 (2H, s, $CH_2$), 3.67 (2H, s, $CH_2$), 3.71 (3H, s, $OCH_3$), 6.82 (1H, s, CH), 7.04 (1H, s, CH), 7.04-7.22 (3H, m, 3×CH), 7.35-7.43 (1H, m, CH), 7.85 (2H, s, $NH_2$). $^{13}$C NMR (100 MHz; DMSO-$d_6$) 27.8 ($CH_2$), 50.28 ($CH_2$), 54.99 ($CH_2$), 55.85 ($OCH_3$), 60.99 ($CH_2$), 111.17 (CH), 113.95 (d, J 20.6 Hz, CH), 115.24 (d, J 21.4 Hz, CH), 122.83 (CH), 124.77 (CH), 125.83 (C), 130.28 (d, J 8.4 Hz, CH), 133.45 (C), 137.15 (C), 141.41 (d, J 6.9 Hz, C), 149.72 (C), 162.36 (d, J 241.6 Hz, CF). LC/MS (APCI+) $t_r$=4.26 min, m/z 367.44 (M⁺+H). HPLC $t_r$=4.0 min (>99%). Anal. calc. for $C_{17}H_{19}FN_2O_4S$: C, 55.73; H, 5.23; N, 7.65. Found: C, 55.5; H, 5.22; N. 7.55%.

2-(3-Isopropoxybenzyl)-7-methoxy-6-O-sulfamoyl-1,2,3,4-tetrahydroisoquinoline 104

78 mg, 72%, yellow solid. mp 80° C. dec. $^1$H NMR (270 MHz; DMSO-$d_6$) 1.25 (6H, d, J 5.9 Hz, 2×$CH_3$), 2.66 (2H, d, J 4.9 Hz, $CH_2$), 2.73 (2H, d, J 4.9 Hz, $CH_2$), 3.49 (2H, s, $CH_2$), 3.60 (2H, s, $CH_2$), 3.71 (3H, s, $OCH_3$), 4.58 (1H, septet, J 5.9 Hz, CH), 6.79-6.81 (2H, m, 2×CH), 6.88-6.89 (2H, m, 2×CH), 7.03 (1H, s, CH), 7.22 (1H, t, J 8.0 Hz, CH), 7.82 (2H, brs, NH). $^{13}$C NMR (67.5 MHz; DMSO-$d_6$) 22.41 ($CH_3$), 28.47 ($CH_2$), 50.79 ($CH_2$), 55.71 ($CH_2$), 56.36 ($CH_3$), 62.25 ($CH_2$), 69.43 (CH), 111.64 (CH), 114.60 (CH), 116.22 (CH), 121.16 (CH), 123.33 (CH), 126.47 (C), 129.90 (CH), 134.28 (C), 137.58 (C), 140.61 (C), 150.19 (C), 158.02 (C). LC/MS (APCI−) $t_r$=0.86 min, m/z 405.07 (M−H)⁻. HPLC $t_r$=0.86 min (>95%).

2-(3-(Methoxycarbonyl)benzyl)-6-O-sulfamoyl-7-methoxy-1,2,3,4-tetrahydroisoquinoline 104A (89 mg, 78%) as a yellow solid. mp 145-146° C. dec. $^1$H NMR (270 MHz; DMSO-$d_6$) 2.70-2.76 (4H, m, 2×$CH_2$), 3.50 (2H, s, $CH_2$), 3.70 (3H, s, $OCH_3$), 3.72 (2H, s, $CH_2$), 3.85 (3H, s, $OCH_3$), 6.80 (1H, s, CH), 7.04 (1H, s, CH), 7.51 (1H, t, J=7.6 Hz, CH), 7.64 (1H, d, J=7.6 Hz, CH), 7.83 (2H, brs, $NH_2$), 7.88 (1H, dt, J=7.6, 1.5 Hz, CH), 7.97 (1H, s, CH). $^{13}$C NMR (67.5 MHz; DMSO-$d_6$) 28.41 ($CH_2$), 50.90 ($CH_2$), 52.73 ($OCH_3$), 55.55 ($CH_2$), 56.35 ($OCH_3$), 61.75 ($CH_2$), 111.68 (CH), 123.34 (CH), 126.36 (C), 128.49 (CH), 129.38 (CH), 129.80 (CH), 130.24 (C), 134.08 (C), 134.21 (CH), 137.59 (C), 139.85 (C), 150.20 (C), 166.83 (C). LC/MS (APCI−) $t_r$=0.83 min, m/z 405.07 (M−H)⁻. HPLC $t_r$=1.72 min (>97%).

Synthesis of 2-benzoyl-6-benzyloxy-1,2,3,4-tetrahydroisoquinolines

General Method

The appropriate benzoylchloride or bromide (1.8 mmol) was added in a portionwise manner to a solution of 6-(benzyloxy)-1,2,3,4-tetrahydroisoquinoline (1.5 mmol) and TEA (0.42 mL, 3 mmol) in $CHCl_3$ (30 mL) and the mixture was stirred for 18 hours at room temperature. After addition of water (10 mL) the organics were extracted with ethyl acetate (80 mL), the organic layer was washed with water, brine, dried ($MgSO_4$), filtered and evaporated under reduced pressure. The resulting oil/solid was purified by flash chromatography (hexane/ethyl acetate 10:1 to 1:1).

6-Benzyloxy-2-(3,5-dimethoxybenzoyl)-1,2,3,4-tetrahydroisoquinoline 105

White powder 400 mg (66%), mp=116°117C, $R_f$: 0.35 (Hexane/EtOAc 1:1), $^1$H NMR (270 MHz, $CDCl_3$) δ 2.81 and 2.91 (2H, br, $CH_2$), 3.60-3.93 (2H, br, $CH_2$), 3.79 (6H, s, 2×$OCH_3$), 4.50 & 4.79 (2H, br, $CH_2$), 5.04 (2H, s, $OCH_2$), 6.50 (1H, t, J 2.2 Hz, ArH), 6.54 (2H, br, ArH), 6.76-7.09 (3H, br, ArH), 7.28-7.43 (5H, m, ArH). LC/MS (ES+) $t_r$=1.37 min m/z 404.59 (M+H)⁺; MeOH/$H_2O$ 95/5; LC/MS (ES+) $t_r$=1.37 min m/z 426.55 (M⁺+23); MeOH/$H_2O$ 95/5; HPLC $t_r$=1.81 min (98.6%). ($CH_3CN/H_2O$ 90/10)

6-Benzyloxy-7-methoxy-2-(2-methoxybenzoyl)-1,2,3,4-tetrahydroisoquinoline 106

White powder, 0.46 g (79%), nip 92-93° C., $R_f$: 0.22 (ethyl acetate/hexane 1:1), $^1$H NMR (270 MHz, $CDCl_3$) δ 2.63 & 2.79 (2H, m, $CH_2$), 3.44 & 3.85 (2H, m, $CH_2$), 3.72, 3.76, 3.81 & 3.88 (6H, s, 2×$CH_3O$), 4.34 & 4.84 (2H, br, $CH_2$), 5.11 (2H, s, $OCH_2$), 6.38-7.46 (11H, m, ArH). LC/MS (APCI+) $t_r$=4.35 min m/z 402.51 (M⁺−H) and $t_r$=4.90 min m/z 404.46 (M⁺+H), MeOH/$H_2O$ 50/50 to 95/5, 5 min; HPLC $t_r$=1.98 min (34.6%) and $t_r$=2.18 min (65.4%). ($CH_3OH/H_2O$ 90/10).

6-Benzyloxy-7-methoxy-2-(3-methoxybenzoyl)-1,2,3,4-tetrahydroisoquinoline 107

Thick colorless oil, 0.50 g (83%), $R_f$: 0.26 (ethyl acetate/hexane 1:1). $^1$H NMR (270 MHz, $CDCl_3$) δ 2.70 & 2.81 (2H, m, $CH_2$), 3.58 & 3.86 (2H, m, $CH_2$), 3.80 (6H, s, 2×$CH_3O$), 4.49 & 4.79 (2H, br, CH$_2$), 5.11 (2H, s, OCH$_2$), 6.64 & 6.68 (2H, br, ArH), 6.97 (3H, m, ArH), 7.26-7.46 (6H, m, ArH). LC/MS (APCI+) t$_r$=4.69 min m/z 402.45 (M$^+$–H) and t$_r$=5.05 min m/z 404.46 (M$^+$+H); HPLC t$_r$=2.02 min (13.2%) and t$_r$=2.22 min (83.7%). (CH$_3$OH/H$_2$O 90/10)

7-Methoxy-2-(4-methoxybenzoyl)-6-benzyloxy-1,2,3,4-tetrahydroisoquinoline 108

White powder, 0.52 g (85%), mp 126-127° C., R$_f$: 0.31 (ethyl acetate/hexane 1:1), $^1$H NMR (270 MHz, CDCl$_3$) δ 2.77 (2H, br, CH$_2$), 3.67 (2H, br, CH$_2$), 3.83 (6H, s, 2×CH$_3$O), 4.73 (2H, br, CH$_2$), 5.11 (2H, s, OCH$_2$), 6.65 (1H, s, ArH), 6.91 (2H, m, ArH), 7.26 -7.45 (8H, s, ArH). LC/MS (APCI+) t$_r$=1.29 min m/z 404.53 (M$^+$+H); MeOH/H$_2$O 50/50 to 95/5, 5 min; HPLC t$_r$=2.78 min (96.0%). (CH$_3$CN/H$_2$O 90/10); HRMS (ES) calcd. for C$_{25}$H$_{25}$NO$_4$ (MH$^+$), 404.1856 found. 404.1858.

6-Benzyloxy-2-(3,4-Dimethoxybenzoyl)-1,2,3,4-tetrahydroisoquinoline 109

White powder, 0.58 g (89%), mp 126-127° C., R$_f$: 0.28 (ethyl acetate/hexane 1:1), $^1$H NMR (270 MHz, CDCl$_3$) δ 2.77 (2H, br, CH$_2$), 3.83 (2H, br, CH$_2$), 3.88 (3H, s, CH$_3$O), 3.89 (3H, s, CH$_3$O), 3.90 (3H, s, CH$_3$O), 4.61 & 4.74 (2H, br, CH$_2$), 5.11 (2H, s, OCH$_2$), 6.65 (1H, s, ArH), 6.86 (1H, d, J 8.9 Hz, ArH), 7.01 (1H, s, ArH), 7.03 (1H, dd, J 8.9 & 2.0 Hz, ArH), 7.23 -7.46 (6H, m, ArH). LC/MS (APCI+) t$_r$=4.28 min m/z 432.48 (M$^+$–H) and t$_r$=4.64 min m/z 434.50 (M$^+$+H), MeOH/H$_2$O 50/50 to 95/5, 5 min; HPLC t$_r$=2.84 min (11.3%). (CH$_3$CN/H$_2$O 70/30) and t$_r$=3.29 min (88.7%). (CH$_3$CN/H$_2$0 70/30); HRMS (ES) calcd. for C$_{26}$H$_{28}$NO$_5$ (MH$^+$), 434.1962 found. 434.1966.

6-Benzyloxy-2-(3,5-dimethoxybenzoyl)-7-methoxy-1,2,3,4-tetrahydroisoquinoline 110

White powder, 0.52 g (85%), mp 130-131° C., R$_f$: 0.31 (ethyl acetate/hexane 1:1), $^1$H NMR (270 MHz, CDCl$_3$) δ 2.70 & 2.81 (2H, br, CH$_2$), 3.58 & 3.92 (2H, br, CH$_2$), 3.83 (6H, s, 2×CH$_3$O), 4.49 & 4.78 (2H, br, CH$_2$), 5.11 (2H, s, OCH$_2$), 6.42, 6.63-6.68 (2H, br, ArH), 6.50 (1H, t, J 2.2 Hz, ArH), 6.55 (2H, d, J 2.2 Hz, ArH), 7.26 -7.45 (5H, m, ArH). LC/MS (APCI+) t$_r$=5.02 min m/z 434.43 (M$^+$+H); MeOH/H$_2$O 50/50 to 95/5, 5 min; HPLC t$_r$=2.35 min (100%). (CH$_3$CN/H$_2$O 90/10); HRMS (ES) calcd. for C$_{26}$H$_{27}$NO$_5$ (MH$^+$), 434.1962 found. 434.1962

6-Benzyloxy-7-methoxy-2-(3,4,5-trimethoxybenzoyl)-1,2,3,4-tetrahydroisoquinoline 111

White powder, 0.55 g (79%), mp 63-64° C., R$_f$: 0.19 (hexane/ethyl acetate 1/1), $^1$H NMR (270 MHz, CDCl$_3$) δ 2.80 (2H, br, CH$_2$), 3.60 & 3.80 (2H, br, CH$_2$), 3.85 (6H, s, CH$_3$O), 3.86 (6H, s, CH$_3$O), 4.50 & 4.77 (2H, br, CH$_2$), 5.12 (2H, s, CH$_2$), 6.44 & 6.65 (4H, br, ArH), 7.25-7.44 (5H, m, Ph). LC/MS (ES+) t$_r$=1.16 min m/z 496.26 ((M+Na)$^+$, 100%), 464.28 (M+1)$^+$; MeOH/H$_2$O 95/5; HPLC t$_r$=1.92 min (96.7%). (CH$_3$CN/H$_2$O 90/10)

2-(3-Cyanobenzoyl)-6-benzyloxy-7-methoxy-1,2,3,4-tetrahydroisoquinoline 112

White powder, 310 mg (52%), mp=156°157° C., R$_f$: 0.18 (Hexane/EtOAc 1:1), $^1$H NMR (270 MHz, CDCl$_3$) δ 2.70-2.87 (2H, br, CH$_2$), 3.52-3.57 & 3.91-3.95 (2H, br, CH$_2$), 3.79 & 3.97 (3H, s, OCH$_3$), 4.46 & 4.80 (2H, br, CH$_2$), 5.12 (2H, s, OCH2), 6.40-6.68 (2H, br, ArH), 7.27-7.45 (5H, m, ArH), 7.52-7.58 (1H, m, ArH), 7.66-7.75 (3H, m, ArH). LC/MS (ES+) t$_r$=1.16 min m/z 421.54 (M$^+$+23); MeOH/H$_2$O 95/5; HPLC t$_r$=4.36 min (94.3%). (CH$_3$CN/H$_2$O 90/10).

2-(4-Cyanobenzoyl)-6-benzyloxy-7-methoxy-1,2,3,4-tetrahydroisoquinoline 113

White powder to give 300 mg (50%), mp=187°189 C., R$_f$: 0.31 (Hexane/EtOAc 1:1), $^1$H NMR (270 MHz, CDCl$_3$) δ 2.68-2.83 (2H, br, CH$_2$), 3.50-3.54 & 3.90-3.95 (2H, br, CH$_2$), 3.78 & 3.87 (3H, s, OCH$_3$), 4.42 & 4.80 (2H, br, CH$_2$), 5.12 (2H, s, OCH$_2$), 6.38-6.68 (2H, br, ArH), 7.26-7.44 (5H, m, ArH), 7.53 (2H, dd, J 6.7 & 1.7 Hz, ArH), 7.72 (2H, dd, J 6.7 & 1.7 Hz, ArH). LC/MS (ES+) t$_r$=1.12 min m/z 421.6 (M$^+$+23); MeOH/H$_2$O 95/5; HPLC t$_r$=1.50 min (98.6%). (CH$_3$CN/H$_2$O 90/10).

Synthesis of 2-benzoyl-6-hydroxy-1,2,3,4-tetrahydroisoquinolines

General Method:

A solution of 2-benzoyl-6-(benzyloxy)-1,2,3,4-tetrahydroisoquinoline (1 mmol) in THF (20 mL) and methanol (20 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The crude mixture was purified by flash chromatography (hexane/ethyl acetate3:1 to 1:1) and the resulting solid stirred in diethyl ether, filtered and dried under vacuum.

2-(3,5-Dimethoxybenzoyl)-6-hydroxy-1,2,3,4-tetrahydroisoquinoline 114

White powder, 260 mg (82%), mp=170-171° C., R$_f$: 0.32 (Hexane/EtOAc 1:2), $^1$H NMR (270 MHz, CDCl$_3$) δ 2.69-2.91 (2H, br, CH$_2$), 3.59 & 3.92 (2H, br, CH$_2$), 3.78 (6H, s, 2×OCH$_3$), 4.48 & 4.78 (2H, br, CH$_2$), 5.79 (1H, br, ArH), 6.45-7.03 (5H, m, ArH). LC/MS (ES+) t$_r$=1.37 min m/z 426.55 (M$^+$+23); MeOH/H$_2$O 95/5; HPLC t$_r$=1.24 min (99.5%). (CH$_3$CN/H$_2$O 90/10).

6-Hydroxy-7-methoxy-2-(2-methoxybenzoyl)-1,2,3,4-tetrahydroisoquinoline 115

White solid: 280 mg (94%), mp=176-177° C., R$_f$: 0.27 (EtOAc/Hexane 1:1), $^1$H NMR (270 MHz, CDCl$_3$) δ 2.68 & 2.82 (2H, br, CH$_2$), 3.42 & 4.18 (2H, br, CH$_2$), 3.74, 3.76, 3.81 & 3.87 (6H, s, 2×CH$_3$O), 4.34 & 4.83 (2H, br, CH$_2$), 5.55 & 5.57 (1H, s, OH), 6.34-6.71 (2H, br, ArH), 6.92 (1H, d, J 8.4 Hz, ArH), 6.98 (1, m, ArH), 7.26 (1H, m, ArH), 7.35 (1H, m, ArH). LC/MS (APCI+) t$_r$=1.14 min m/z 314.42 (M$^+$+H). (MeOH/H$_2$O 95/5); HPLC t$_r$=1.97 min (100%). (MeOH/H$_2$O 90/10).

6-Hydroxy-7-methoxy-2-(3-methoxybenzoyl)-1,2,3,4-tetrahydroisoquinoline 116

White powder: 215 mg (68%), mp=141-142° C., R$_f$: 0.31 (EtOAc/Hexane 1:1), $^1$H NMR (270 MHz, CDCl$_3$) δ 2.73 & 2.85 (2H, br, CH$_2$), 3.59 & 3.94 (2H, br, CH$_2$), 3.78 & 3.87 (6H, s, 2×CH$_3$O), 4.48 & 4.79 (2H, br, CH$_2$), 5.57 (1H, s, OH), 6.36-6.69 (2H, br, ArH), 6.94-7.01 (3H, m, ArH), 7.32

(1H, dd, J 8.8 and 7.4 Hz, ArH). LC/MS (APCI+) t$_r$=1.16 min m/z 314.42 (M$^+$+H). (MeOH/H$_2$O 95/5); HPLC t$_r$=1.98 min (100%). (MeOH/H$_2$O 90/10).

6-Hydroxy-7-methoxy-2-(4-methoxybenzoyl)-1,2,3,4-tetrahydroisoquinoline 117

White powder, 280 mg (89%), mp=173-174° C., R$_f$: 0.29 (EtOAc/Hexane 2:1), $^1$H NMR (400 MHz, DMSO-d6) δ 2.68 (2H, t, J 6.9 Hz, CH$_2$), 3.70 (2H, br, CH$_2$), 3.80 (6H, s, 2×CH$_3$O), 4.57 (2H, s, CH$_2$), 6.55 (1H, s, ArH), 6.78 (1H, br, ArH), 7.00 (2H, m, ArH), 7.41 (2H, m, ArH), 8.84 (1H, s, OH). LC/MS (APCI+) t$_r$=0.99 min m/z 314.42 (M$^+$+H); MeOH/H$_2$O 95/5 HPLC t$_r$=4.65 min (100%). (MeOH/H$_2$O 99/1); HRMS (ES) calcd. for C$_{18}$H$_{20}$NO$_4$ (MH$^+$), 314.1387 found. 314.1386

2-(3,4-Dimethoxybenzoyl)-6-hydroxy-7-methoxy-1,2,3,4-tetrahydroisoquinoline 118

White powder, 320 mg (94%), mp=132-133° C., R$_f$: 0.14 (EtOAc/Hexane 2:1), $^1$H NMR (400 MHz, CDCl$_3$) δ 2.80 (2H, br, CH$_2$), 3.83 (2H, br, CH$_2$), 3.88 (3H, s, CH$_3$O), 3.90 (6H, s, 2×CH$_3$O), 4.61 and 4.72 (2H, br, CH$_2$), 5.62 (1H, s, OH), 6.60 (1H, br, ArH), 6.69 (1H, br, ArH), 6.86 (1H, d, J 8.9 Hz, ArH), 7.02 (1H, s, ArH), 7.03 (1H, d, J 8.9 Hz, ArH), 8.84 (1H, s, OH). LC/MS (APCI+) t$_r$=0.95 min m/z 344.27 (M$^+$+H); MeOH/H$_2$O 95/5; HPLC t$_r$=1.87 min (100%). (CH$_3$CN/H$_2$O 90/10); HRMS (ES) calcd. for C$_{19}$H$_{22}$NO$_5$ (MH$^+$), 344.1492 found. 344.1493

2-(3,5-Dimethoxybenzoyl)-6-hydroxy-7-methoxy-1,2,3,4-tetrahydroisoquinoline 119

White powder, 320 mg (94%), mp=139-137° C., R$_f$: 0.26 (EtOAc/Hexane 2:1), $^1$H NMR (400 MHz, CDCl$_3$) δ 2.73 & 2.84 (2H, br, CH$_2$), 3.59 & 3.93 (2H, br, CH$_2$), 3.79 (9H, s, 3×CH$_3$O), 4.48 & 4.77 (2H, br, CH$_2$), 5.58 (1H, s, OH), 6.38 & 6.64 (1H, br, ArH), 6.50 (1H, t, J 2.2 Hz, ArH), 6.55 (2H, d, J 2.2 Hz, ArH), 6.68 (1H, br, ArH). LC/MS (APCI+) t$_r$=0.99 min m/z 344.33 (M$^+$+H); MeOH/H$_2$O 95/5; HPLC t$_r$=1.93 min (100%). (CH$_3$CN/H$_2$O 90/10).

6-Hydroxy-7-methoxy-2-(3,4,5-trimethoxybenzoyl)-1,2,3,4-tetrahydroisoquinoline 120

White powder, 335 mg (90%), mp 172-173° C., R$_f$: 0.71 (ethyl acetate), $^1$H NMR (270 MHz, CDCl$_3$) δ 2.79 (2H, br, CH$_2$), 3.62 & 3.83 (2H, br, CH$_2$), 3.85 (12H, s, CH$_3$O), 4.50 & 4.76 (2H, br, CH$_2$), 5.54 (1H, s, OH), 6.41 & 6.66 (3H, br, ArH), 6.70 (1H, s, ArH). LC/MS (ES−) t$_r$=0.89 min m/z 372.07 (M−1)$^-$, 100%); MeOH/H$_2$O 95/5; HPLC t$_r$=2.10 min (100%). (acetonitrile/water 70/30).

Synthesis of 2-benzoyl-6-O-sulfamoyl-1,2,3,4-tetrahydroisoquinolines

General Method:
A solution of 2-benzoyl-6-hydroxy-1,2,3,4-tetrahydroisoquinoline (0.5 mmol) and sulfamoyl chloride (1 mmol) in DMA (1 mL) was stirred at rt under nitrogen for 24 hours. After addition of water (5 mL) the organics were extracted into ethyl acetate (2×50 mL), the organic layers washed with water and brine, then dried (MgSO$_4$) and evaporated. The crude product was purified by flash chromatography (hexane/ethyl acetate).

2-(3,5-Dimethoxybenzoyl)-6-O-sulfamoyl-1,2,3,4-tetrahydroisoquinoline 121

White powder (120 mg, 60%), mp=169-170° C., R$_f$: 0.27 (Hexane/EtOAc 1:2), $^1$H NMR (270 MHz, CD3COCD$_3$) δ 2.91 (2H, t, J 5.1 Hz, CH$_2$), 3.66 (2H, br, CH$_2$), 3.81 (6H, s, 2×OCH$_3$), 4.76 (2H, br, CH$_2$), 6.56-6.58 (3H, m, ArH), 7.12-7.14 (3H, m, ArH), 7.28 (2H, br, NH$_2$). LC/MS (ES−) t$_r$=0.95 min m/z 391.44 (M−H)$^-$; MeOH/H$_2$O 95/5; HPLC t$_r$=1.19 min (99.7%). (CH$_3$CN/H$_2$O 90/10)

7-Methoxy-2-(2-methoxybenzoyl)-6-O-sulfamoyl-1,2,3,4-tetrahydroisoquinoline 122

White solid: 140 mg (72%), mp=193-194° C., R$_f$: 0.58 (EtOAc), $^1$H NMR (270 MHz, CDCl$_3$/CD$_3$OD 5:1) δ 2.80 & 2.87 (2H, br, CH$_2$), 3.38-3.45 (2H, br, CH$_2$), 3.68, 3.71, 3.76 & 3.82 (6H, s, 2×CH$_3$O), 3.74 & 4.05 (2H, br, CH$_2$), 4.81 (2H, s, NH$_2$), 6.44 & 6.78 (1H, s, ArH), 6.88-6.98 (2H, m, ArH), 7.06-7.11 (1H, s, ArH), 7.15-7.19 (1H, m, ArH), 7.31-7.38 (1H, m, ArH). LC/MS (APCI−) t$_r$=3.31 min m/z 391.49 (M$^+$+H). (gradient MeOH/H$_2$O from 50/50 to 95/5 in 5 min); HPLC t$_r$=2.25 min (100%). (MeOH/H$_2$O 90/10)

7-Methoxy-2-(3-methoxybenzoyl)-6-O-sulfamoyl-1,2,3,4-tetrahydroisoquinoline 123

White solid: 130 mg (66%), mp=186-187° C., R$_f$: 0.67 (EtOAc), $^1$H NMR (270 MHz, CDCl$_3$/CD$_3$OD 5:1) δ 2.77-2.87 (2H, br, CH$_2$), 3.60-3.76 (2H, br, CH$_2$), 3.80 & 3.86 (6H, s, 2×CH$_3$O), 4.53 & 4.81 (2H, br, CH$_2$), 6.50 & 6.80 (1H, br, ArH), 6.92-6.98 (3H, m, ArH), 7.12 (1H, br, ArH), 7.32 (1H, t, J 8.2 Hz, ArH). LC/MS (APCI−) t$_r$=3.39 min m/z 391.49 (M$^+$+H). (gradient MeOH/H$_2$O from 50/50 to 95/5 in 5 min); HPLC t$_r$=2.20 min (100%). (MeOH/H$_2$O 90/10)

7-Methoxy-2-(4-methoxybenzoyl)-6-O-sulfamoyl-1,2,3,4-tetrahydroisoquinoline 124

White powder, 165 mg (85%), mp 171-172° C., R$_f$: 0.65 (EtOAc), $^1$H NMR (270 MHz, CDCl$_3$) δ 2.70 (2H, br, CH$_2$), 3.53 (2H, br, CH$_2$), 3.96 (6H, s, 2×CH$_3$O), 4.50 & 4.64 (2H, br, CH$_2$), 6.61 & 6.69 (1H, br, ArH), 6.81 (2H, m, ArH), 7.01 (1H, s, ArH), 7.27 (2H, m, ArH). LC/MS (APCI+) t$_r$=3.38 min m/z 393.38 (M$^+$+H); MeOH/H$_2$O 95/5; HPLC t$_r$=1.86 min (100%). (CH$_3$CN/H$_2$O 90/10); HRMS (ES) calcd. for C$_{18}$H$_{20}$N$_2$O$_6$S (MH$^+$), 393.1115 found. 393.1112

2-(3,4-Dimethoxybenzoyl)-7-methoxy-6-O-sulfamate-1,2,3,4-tetrahydroisoquinoline 125

White powder, 160 mg (76%), mp 155-156° C., R$_f$: 0.58 (EtOAc), $^1$H NMR (270 MHz, CDCl$_3$/CD$_3$OD 5:1) δ 2.73 (2H, br, CH$_2$), 3.59 & 3.72 (2H, br, CH$_2$), 3.77 (3H, s, CH$_3$O), 3.79 (6H, s, 2×CH$_3$O), 4.52 & 4.65 (2H, br, CH$_2$), 6.61 & 6.70 (1H, br, ArH), 6.80 (1H, d, J 8.2 Hz, ArH), 6.87 (1H, d, J 2.0 Hz, ArH), 6.90 (1H, dd, J 8.2 and 2.0 Hz, ArH), 7.03 (1H, s, ArH). LC/MS (APCI+) t$_r$=3.00 min m/z 423.42 (M$^+$+H); MeOH/H$_2$O 95/5; HPLC t$_r$=1.76 min (100%). (CH$_3$CN/H$_2$O 90/10)

2-(3,5-Dimethoxybenzoyl)-7-methoxy-6-O-sulfamoyl-1,2,3,4-tetrahydroisoquinoline 126

White powder, 180 mg (85%), mp 170-171° C., R$_f$: 0.55 (EtOAc), $^1$H NMR (270 MHz, CDCl$_3$/CD$_3$OD 5:1) δ 2.70 & 2.80 (2H, t, J 5.3 Hz, CH$_2$), 3.55 & 3.82 (2H, t, J 5.3 Hz, CH$_2$), 3.63 (s, 2H, NH$_2$), 3.71 (9H, s, 3×CH$_3$O), 4.46 & 4.72 (2H, br, CH$_2$), 6.44 (2H, s, ArH), 6.46 & 6.74 (1H, br, ArH), 7.05 (1H, br, ArH). LC/MS (APCI+) t$_r$=3.54 min ink 423.35 (M$^+$+H); MeOH/H$_2$O 95/5; HPLC t$_r$=2.47 min (100%). (CH$_3$CN/H$_2$O 70/30)

7-methoxy-6-O-sulfamoyl-2-(3,4,5-trimethoxybenzoyl)-1,2,3,4-tetrahydroisoquinoline 127

White solid, 170 mg (74%), mp 174-175° C., R$_f$ 0.47 (ethyl acetate), $^1$H NMR (400 MHz, CDCl$_3$/CD$_3$COCD$_3$) δ 2.55 (2H, br, CH$_2$), 3.41 (2H, br, CH$_2$), 3.54 (6H, s, 2×CH$_3$O), 3.57 (6H, s, 2×CH$_3$O), 4.50 (2H, br, NH$_2$), 6.16 (2H, br, ArH), 6.40-6.50 (3H, s+br, CH and NH$_2$) and 6.84 (1H, s, ArH). LC/MS (ES−) t$_r$=0.90 min m/z 451.05 ((M−1)$^-$, 100%); MeOH/H$_2$O 95/5 ; HPLC t$_r$=1.46 min (99.7%). (acetonitrile/water 70/30)

6-Benzyloxy-2-(benzoyl)-3,4-dihydro-2H-isoquinolin-1-ones

Method 1:
A solution of 6-benzyloxy-7-methoxy-3,4-dihydro-2H-isoquinolin-1-one (280 mg, 1 mmol) in 5 mL DMF was cooled to 0-5° C. and 60% NaH (60 mg, 1.5 mmol) was added portion wise. The suspension was stirred for 1 hour at room temperature and, after addition of benzoyl chloride (1.1 mmol) 4 hours at 80° C. The mixture was cooled to RT, water (20 mL) was added and the organics were extracted with ethyl acetate (2×50 mL). The organic layer was washed with water, brine, dried (MgSO$_4$) and filtered. Ethyl acetate was removed under reduced pressure and the residual oil purified by flash chromatography (ethyl acetate/hexane 1/8 to 1/2) affording 330 mg (89%) of white powder.

6-Benzyloxy-7-methoxy-2-(4-methoxybenzoyl)-3,4-dihydro-2H-isoquinolin-1-one 128

White powder, 260 mg (63%), mp 151-152° C., R$_f$: 0.72 (ethyl acetate/hexane 1:3), $^1$H NMR (270 MHz, CDCl$_3$) δ 3.02 (2H, t, J 6.1 Hz, CH$_2$), 3.83 (3H, s, CH$_3$O), 3.86 (3H, s, CH$_3$O), 4.04 (2H, t, J 6.1 Hz, CH$_2$), 5.23 (2H, s, OCH$_2$), 6.73 (1H, s, ArH), 6.88 (2H, d, J 8.7 Hz, ArH), 7.30-7.46 (5H, m, ArH). 7.58 (1H, s, ArH), 7.62 (2H, d, J 8.7 Hz, ArH), $^{13}$C NMR (67.5 MHz, CDCl$_3$) δ 29.7 (CH$_2$), 44.9 (CH$_2$), 55.5 (CH$_3$O), 56.2 (CH$_3$O), 70.9 (OCH$_2$), 111.3 (CH(Ar)), 111.5 (CH(Ar)), 113.4 (2×CH(Ar)), 121.1 (C(Ar)), 127.3 (2×CH(Ar)), 128.3 (CH(Ar)), 128.5 (C(Ar)), 128.9 (2×CH(Ar)), 130.9 (2×CH(Ar)), 134.4 (C(Ar)), 136.1 (C(Ar)), 148.7 C(Ar)), 152.6 (C(Ar)), 158.3 (C(Ar)), 162.6 (CO) and 174.1 (CO). LC/MS (APCI+) t$_r$=4.73 min m/z 418.57 (M$^+$+H). (gradient MeOH/H$_2$O from 50/50 to 95/5 in 5 min); HPLC t$_r$=2.14 min (100%). (CH$_3$CN/H$_2$O 90/10); HRMS (ES) calcd. C$_{25}$H$_{23}$NO$_5$ for (MH$^+$), 418.1649 found. 418.1651

6-(Benzyloxy)-2-(3,5-dimethoxybenzoyl)-7-methoxy-3,4-dihydro-2H-isoquinolin-1-one 129

White powder, 135 mg (30%), mp 180-181° C., R$_f$: 0.72 (ethyl acetate/hexane 1:3), $^1$H NMR (270 MHz, CDCl$_3$) δ 3.02 (2H, t, J 6.2 Hz, CH$_2$), 3.78 (6H, s, CH$_3$O), 3.85 (3H, s, CH$_3$O), 4.06 (2H, t, J 6.2 Hz, CH$_2$), 5.23 (2H, s, OCH$_2$Ph), 6.56 (1H, t, J 2.2 Hz, ArH), 6.70 (2H, d, J 2.2 Hz, ArH), 6.73 (1H, s, ArH), 7.29-7.46 (5H, m, ArH), 7.56 (1H, s, ArH), $^{13}$C NMR (67.5 MHz, CDCl$_3$) δ 28.2 (CH$_2$), 44.6 (CH$_2$), 55.6 (CH$_3$O), 56.1 (2×CH$_3$O), 71.0 (OCH$_2$), 103.4 (CH(Ar)), 105.8 (2×CH(Ar)), 111.4 (CH(Ar)) and 111.5 (CH(Ar)), 120.7 (C(Ar)), 127.2 (2×CH(Ar)), 128.2 (CH(Ar)), 128.8 (2×CH(Ar)), 134.5 (C(Ar)), 136.0 and 138.7 (C(Ar)), 148.8 (C(Ar)), 152.7 (C(Ar)), 160.4 (2×C(Ar)), 165.5 (CO) and 174.5 (CO); LC/MS (APCI+) t$_r$=1.29 min m/z 448.54 (M$^+$+H); (gradient MeOH/H$_2$O from 50/50 to 95/5 in 5 min; HPLC t$_r$=2.77 min (100%). (CH$_3$CN/H$_2$O 90/10); HRMS (Electrospray) calcd. for C$_{26}$H$_{25}$NO$_6$ (MH$^+$), 448.1755 found. 448.1756.

Method 2:
A mixture of 2-benzoyl-6-(benzyloxy)-1,2,3,4-tetrahydroisoquinoline (1 mmol), KMnO$_4$ (790 mg, 5 mmol) and 18-crown-6 (50 mg, 0.19 mmol) in DCM (20 mL) was stirred at room temperature. The reaction was monitored by TLC. Upon completion, sodium metabisulfite (95 mg, 5 mmol) and 1 mL 2M aqueous HCl were added and the solution stirred for 30 minutes. The suspension was filtered through celite and the organics were extracted with CHCl$_3$ (2×50 mL). The organic layer was washed with water, brine, dried with MgSO$_4$, filtered and the solvents were evaporated under reduced pressure. The crude product was purified by flash chromatography (hexane/EtOAc).

6-Benzyloxy-7-methoxy-2-(2-methoxybenzoyl)-3,4-dihydro-2H-isoquinoline-1-one 130

White powder, 170 mg (40%), mp=163-164° C., R$_f$: 0.64 (Hexane/EtOAc 1:1), $^1$H NMR (270 MHz, CDCl$_3$) δ 2.98 (2H, t, J 6.2 Hz, CH$_2$), 3.63 (3H, s, CH$_3$O), 3.83 (3H, s, CH$_3$O), 4.19 (2H, t, J 6.2 Hz, CH$_2$), 5.22 (2H, s, OCH$_2$), 6.72 (1H, s, ArH), 6.86 (1H, d, J 8.4 Hz, ArH), 7.01 (1H, dt, J 8.4 and 0.8 Hz, ArH), 7.28-7.46 (7H, m, ArH), 7.56 (1H, s, ArH), $^{13}$C NMR (100 MHz, CDCl$_3$) δ 28.3 (CH$_2$), 43.4 (CH$_2$), 55.7 (CH$_3$O), 56.2 (CH$_3$O), 70.9 (OCH$_2$), 110.8 (CH(Ar)), 111.2 (CH(Ar)), 111.4 (CH(Ar)), 120.8 (CH(Ar)), 121.1 (C(Ar)), 127.3 (2×CH(Ar)), 127.5 (C(Ar)), 128.3 (CH(Ar)), 128.5 (CH(Ar)), 128.9 (2×CH(Ar)), 131.5 (CH(Ar)), 134.8 (C(Ar)), 136.1 (C(Ar)), 148.7 (C(Ar)), 152.6 (C(Ar)), 155.6 (C(Ar)), 165.0 (CO) and 170.8 (CO); LC/MS (ES+) t$_r$=1.22 min m/z 440.49 (M$^+$+23); MeOH/H$_2$O 95/5; LC/MS (ES−) t$_r$=1.22 min m/z 416.44 (M−H)−; MeOH/H$_2$O 95/5; HPLC t$_r$=1.63 min (97.7%). (CH$_3$CN/H$_2$O 90/10).

6-Benzyloxy-7-methoxy-2-(3-methoxybenzoyl)-3,4-dihydro-2H-isoquinoline-1-one 131

White powder, 175 mg (42%), mp=141-143° C., R$_f$: 0.47 (Hexane/EtOAc 1:1), $^1$H NMR (270 MHz, CDCl$_3$) δ 3.03 (2H, t, J 6.2 Hz, CH$_2$), 3.81 (3H, s, CH$_3$O), 3.85 (3H, s, CH$_3$O), 4.08 (2H, t, J 6.2 Hz, CH$_2$), 5.23 (2H, s, OCH$_2$), 6.73 (1H, s, ArH), 7.01 (1H, ddd, J 8.2, 2.7 and 1.2 Hz, ArH), 7.11-7.15 (2H, m, ArH), 7.26-7.45 (6H, m, ArH), 7.56 (1H, s, ArH), $^{13}$C NMR (100 MHz, CDCl$_3$) δ 28.2 (CH$_2$), 44.6 (CH$_2$), 55.5 (CH$_3$O), 56.2 (CH$_3$O), 71.0 (OCH$_2$), 111.4 (CH(Ar)), 111.5 (CH(Ar)), 113.2 (CH(Ar)), 117.4 (CH(Ar)), 120.4 (CH(Ar)), 120.7 (C(Ar)), 127.3 (2×CH(Ar)), 128.3 (CH(Ar)), 128.9 (2×CH(Ar)), 129.2 (CH(Ar)), 134.5 (C(Ar)), 136.1 (C(Ar)), 138.0 (C(Ar)), 148.9 (C(Ar)), 152.8 (C(Ar)), 159.4 (C(Ar)), 165.6 (CO) and 174.5 (CO). LC/MS (ES+) t$_r$=1.27 min m/z 440.43 (M+23)$^+$; MeOH/H$_2$O 95/5; LC/MS (ES−) t$_r$=1.22 min m/z 416.38 (M−H)$^-$; MeOH/H$_2$O 95/5; HPLC t$_r$=1.68 min (90.3%). (CH$_3$CN/H$_2$O 90/10).

6-Benzyloxy-2-(3,5-dimethoxybenzoyl)-3,4-dihydro-2H-isoquinoline-1-one 132

White powder. 125 mg (30%), mp=158-159° C., R$_f$: 0.70 (Hexane/EtOAc 1:1), $^1$H NMR (270 MHz, CDCl$_3$) δ 3.13

(2H, t, J 6.2 Hz, $CH_2$), 3.77 (6H, s, $CH_3O$), 4.08 (2H, t, J 6.2 Hz, $CH_2$), 5.13 (2H, s, $OCH_2$), 6.56 (1H, t, J 2.4 Hz, ArH), 6.72 (2H, d, J 2.4 Hz, ArH), 6.83 (1H, d, J 2.4 Hz, ArH), 6.93 (1H, dd, J 8.9 & 2.4 Hz, ArH), 7.30-7.44 (5H, m, ArH), 8.02 (1H, d, J 8.9 Hz, ArH), $^{13}C$ NMR (67.5 MHz, $CDCl_3$) δ 29.0 ($CH_2$), 44.4 ($CH_2$), 55.6 (2×$CH_3O$), 70.3 ($OCH_2$), 103.5 (CH(Ar)), 106.0 (2×CH(Ar)), 113.2 (CH(Ar)), 114.2 (CH(Ar)), 121.1 (C(Ar)), 127.5 (2×CH(Ar)), 128.4 (CH(Ar)), 128.8 (2×CH(Ar)), 132.2 (CH(Ar)), 136.1 (C(Ar)), 138.6 (C(Ar)), 142.6 (C(Ar)), 160.5 (2×C(Ar)), 163.0 (C(Ar)), 165.8 (C(Ar)), and 174.4 (CO); LC/MS (ES+) $t_r$=1.31 min m/z 418.72 ($M^+$+1); MeOH/H2O 95/5; HPLC $t_r$=1.79 min (99.1%). ($CH_3CN/H_2O$ 90/10).

6-(Benzyloxy)-7-methoxy-2-(3,4-dimethoxybenzoyl)-3,4-dihydro-2H-isoquinoline-1-one 133

White powder, 180 mg (40%), mp=200-201° C., $R_f$: 0.23 (Hexane/EtOAc 1:1), $^1H$ NMR (270 MHz, $CDCl_3$) δ 3.04 (2H, t, J 6.2 Hz, $CH_2$), 3.87 (3H, s, $CH_3O$), 3.90 (6H, s, 2×$OCH_3$), 4.04 (2H, t, J 6.2 Hz, $CH_2$), 5.23 (2H, s, $OCH_2$), 6.74 (1H, s, ArH), 6.81 (1H, d, J 8.4 Hz, ArH), 7.20 (1H, dd, J 8.4 and 2.0 Hz, ArH), 7.26 (1H, d, J 2.0 Hz, ArH), 7.28-7.46 (5H, m, ArH), 7.58 (1H, s, ArH), $^{13}C$ NMR (100 MHz, $CDCl_3$) δ 27.5 ($CH_2$), 44.3 ($CH_2$), 55.2 ($CH_3O$), 55.3 ($CH_3O$), 55.4 ($CH_3O$), 70.2 ($OCH_2$), 109.2 (CH(Ar)), 110.6 (CH(Ar)), 110.7 (CH(Ar)) 110.8 (CH(Ar)), 120.8 (C(Ar)), 122.5 (CH(Ar)), 127.2 (2×CH(Ar)) 128.2 (CH(Ar)), 128.5 (C(Ar)), 128.7 2×CH(Ar)), 134.3 (C(Ar)), 136.0 (C(Ar)), 148.6 (C(Ar)), 148.8 (C(Ar)), 152.1 (C(Ar)), 152.6 (C(Ar)), 165.7 (CO) and 174.2 (CO). LC/MS (ES+) $t_r$=1.19 min m/z 470.52 (M+Na)$^+$; MeOH/H2O 95/5 ; HPLC $t_r$=4.49 min (100%). ($CH_3CN/H_2O$ 90/10)

6-Benzyloxy-7-methoxy-2-(3,4,5-trimethoxybenzoyl)-3,4-dihydro-2H-isoquinolin-1-one 134

White powder, 120 mg (25%), mp 195-196° C., $R_f$: 0.56 (Hexane/EtOAc 1:1), $^1H$ NMR (270 MHz, $CDCl_3$) δ 3.05 (2H, t, J 6.2 Hz, $CH_2$), 3.83 (6H, s, $CH_3O$), 3.87 (3H, s), 3.87 (3H, s), 4.05 (2H, t, J 6.2 Hz, $CH_2$), 5.23 (2H, s, $CH_2$), 6.75 (1H, s, ArH), 6.84 (2H, s, ArH), 7.29-7.46 (5H, m, Ph), 7.56 (1H, s, ArH), $^{13}C$ NMR (100 MHz, $CDCl_3$) δ 28.2 ($CH_2$), 45.0 ($CH_2$), 56.2 ($CH_3O$), 56.3 (2×$CH_3O$), 61.0 ($CH_3O$), 71.0 ($OCH_2Ph$), 105.7 (2×CH(Ar)), 111.4 (CH(Ar)), 111.5 (CH(Ar)) 120.7 (C(Ar)), 127.3 (2×CH(Ar)), 128.4 (CH(Ar)), 128.9 (2×CH(Ar)) 131.8 (C(Ar)), 134.4 (C(Ar)), 136.1 (C(Ar)), 141.1 (C(Ar)), 148.9 (C(Ar)), 152.8 (C(Ar)), 152.9 (2×C(Ar)), 165.6 (CO) and 174.4 (CO); LC/MS (ES+) $t_r$=0.97 min m/z 500.18 ($M^+$+Na, 100%), 478.20 (M+1); MeOH/H2O 95/5 ; HPLC $t_r$=1.98 and 2.43 min (98.2%). ($CH_3CN/H_2O$ 90/10)

6-Benzyloxy-2-(3-cyanobenzoyl)-7-methoxy-3,4-dihydro-2H-isoquinoline-1-one 135

White powder, 130 mg (32%), mp=195-196° C., $R_f$: 0.68 (Hexane/EtOAc 1:1), $^1H$ NMR (270 MHz, $CDCl_3$) δ 3.05 (2H, t, J 6.2 Hz, $CH_2$), 3.82 (3H, s, $CH_3O$), 3.86 (2H, t, J 6.2 Hz, $CH_2$), 5.24 (2H, s, $OCH_2$), 6.74 (1H, s, ArH), 7.30-7.45 (5H, m, ArH), 7.49-7.55 (2H, m, ArH), 7.74 (1H, ddd, J 7.9, 1.7 and 1.5 Hz, ArH), 7.79 (1H, ddd, J 7.9, 1.7 and 1.2 Hz, ArH), 7.82 (1H, d, J 1.5 and 1.2 Hz, ArH), $^{13}C$ NMR (100 MHz, $CDCl_3$) δ 28.1 ($CH_2$), 44.4 ($CH_2$), 56.1 ($CH_3O$), 71.0 ($OCH_2$), 111.3 (CH(Ar)), 111.4 (CH(Ar)) 112.4 (CN), 118.1 (C(Ar)), 120.0 (C(Ar)), 127.1 (2×CH(Ar)), 128.2 (CH(Ar)), 127.8 (2×CH(Ar)) 129.0 (CH(Ar)), 131.5 (CH(Ar)), 131.9 (CH(Ar)), 134.3 (CH(Ar)), 134.5 (C(Ar)), 135.8 (C(Ar)), 138.0 (C(Ar)), 149.0 (C(Ar)), 153.1 (C(Ar)), 165.4 (CO) and 172.1 (CO); LC/MS (ES+) $t_r$=1.21 min m/z 435.58 ($M^+$+Na); MeOH/H2O 95/5; HPLC $t_r$=4.70 min (99.31%). ($CH_3CN/H_2O$ 90/10).

6-(Benzyloxy)-2-(4-cyanobenzoyl)-7-methoxy-3,4-dihydro-2H-isoquinoline-1-one 136

White powder, 135 mg (33%), mp=158-159° C., $R_f$: 0.62 (Hexane/EtOAc 1:1), $^1H$ NMR (270 MHz, $CDCl_3$) δ 3.05 (2H, t, J 6.4 Hz, $CH_2$), 3.85 (3H, s, $CH_3O$), 4.11 (2H, t, J 6.4 Hz, $CH_2$), 5.23 (2H, s, $OCH_2$), 6.74 (1H, s, ArH), 7.30-7.45 (5H, m, ArH), 7.50 (1H, s, ArH), 7.61 (2H, d, J 6.6 Hz, ArH), 7.68 (2H, d, J 6.6 Hz, ArH). $^{13}C$ NMR (100 MHz, $CDCl_3$) δ 28.1 ($CH_2$), 44.3 ($CH_2$), 56.2 ($CH_3O$), 71.0 ($OCH_2$), 111.4 (CH(Ar)), 111.5 (CH(Ar)) 114.5 (CN), 118.3 (C(Ar)), 120.1 (C(Ar)), 127.3 (2×CH(Ar)), 128.2 (2×CH(Ar)), 128.4 (CH(Ar)), 128.9 (2×CH(Ar)) 132.0 (2×CH(Ar)), 134.7 (2×C(Ar)), 136.0 (C(Ar)), 141.1 (C(Ar)), 149.1 (C(Ar)), 153.3 (C(Ar)), 165.4 (CO) and 172.6 (CO) LC/MS (ES+) $t_r$=1.31 min m/z 418.72 ($M^+$+1); MeOH/H2O 95/5 ; HPLC $t_r$=1.79 min (99.1%). ($CH_3CN/H_2O$ 90/10).

2-(Benzoyl)-6-hydroxy-3,4-dihydro-2H-isoquinolin-1-ones

General Method:

A solution of 2-benzoyl-6-(benzyloxy)-3,4-dihydro-2H-isoquinolin-1-one (0.5 mmol) in THF (10 mL) and methanol (10 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The crude mixture was purified by flash chromatography (hexane/ethyl acetate3:1 to 1:1) and the resulting solid was recrystalized in ethyl acetate/hexane 5/1.

2-(3,5-Dimethoxybenzoyl)-6-hydroxy-3,4-dihydro-2H-isoquinoline-1-one 137

White powder (165 mg, 100%), mp=178-179° C., $R_f$: 0.78 (Hexane/EtOAc 1:2), $^1H$ NMR (270 MHz, $CD_3COCD_3$) δ 3.14 (2H, t, J 6.2 Hz, $CH_2$), 3.77 (6H, s, $CH_3O$), 4.02 (2H, t, J 6.2 Hz, $CH_2$), 6.59 (1H, t, J 2.2 Hz, ArH), 6.72 (2H, d, J 2.2 Hz, ArH), 6.81 (1H, d, J 2.2 Hz. ArH), 6.83 (1H, dd, J 8.4 & 2.2 Hz, ArH), 7.83 (1H, dd, J 8.9 & 2.4 Hz, ArH), $^{13}C$ NMR (67.5 MHz, $CD_3COCD_3$) δ 28.4 ($CH_2$), 44.3 ($CH_2$), 55.0 (2×$CH_3O$), 102.4 (CH(Ar)), 106.2 (2×CH(Ar)), 114.0 (CH(Ar)), 114.8 (CH(Ar)), 119.7 (C(Ar)), 131.6 (CH(Ar)), 139.4 (C(Ar)), 143.6 (C(Ar)), 160.6 (2×C(Ar)), 162.7 (C(Ar)), 165.0 (C(Ar)), and 173.9 (CO). LC/MS (ES−) $t_r$=1.05 min m/z 326.51 (M−H)−; MeOH/H2O 95/5; HPLC $t_r$=1.24 min (94.7%). ($CH_3CN/H_2O$ 90/10).

6-Hydroxy-7-methoxy-2-(2-methoxybenzoyl)-3,4-dihydro-2H-isoquinoline-1-one 138

White powder, (150 mg, 92%), mp=199-200° C., $R_f$: 0.47 (Hexane/EtOAc 1:1), $^1H$ NMR (270 MHz, DMSO-$d_6$) δ 2.94 (2H, t, J 6.2 Hz, $CH_2$), 3.57 (3H, s, $CH_3O$), 3.74 (3H, s, $CH_3O$), 4.05 (2H, t, J 6.2 Hz, $CH_2$), 6.76 (1H, s, ArH), 6.93-7.00 (2H, m, ArH), 7.27 (1H, dd, J 7.4 and 1.7 Hz, ArH), 7.32 (1H, s, ArH), 7.34-7.41 (1H, m, ArH), 10.21 (1H, s, OH), $^{13}C$ NMR (67.5 MHz, DMSO-$d_6$) δ 27.8 ($CH_2$), 43.5 ($CH_2$), 56.1 (2×$CH_3O$), 111.7 (CH(Ar)), 111.9 (CH(Ar)), 114.5 (CH (Ar)), 119.2 (C(Ar)), 120.8 (CH(Ar)), 128.2 (C(Ar)), 128.5 (CH(Ar)), 131.4 (CH(Ar)), 136.1 (C(Ar)), 147.5 (C(Ar)), 152.6 (C(Ar)), 155.8 (C(Ar)), 164.7 (CO) and 170.3 (CO). LC/MS (ES−) $t_r$=1.07 min m/z 326.51 (M−H)−; MeOH/H$_2$O 95/5; HPLC t'=1.28 min (99.7%). (CH$_3$CN/H$_2$O 90/10.

6-Hydroxy-7-methoxy-2-(3-methoxybenzoyl)-3,4-dihydro-2H-isoquinoline-1-one 139

White powder, 125 mg (80%), mp=198-199° C., $R_f$: 0.21 (Hexane/EtOAc 1:1), $^1$H NMR (270 MHz, DMSO-d$_6$) δ 3.03 (2H, t, J 5.9 Hz, CH$_2$), 3.75 (3H, s, CH$_3$O), 3.76 (3H, s, CH$_3$O), 3.95 (2H, t, J 5.9 Hz, CH$_2$), 6.77 (1H, s, ArH), 7.05-7.10 (3H, m, ArH), 7.32 (1H, dt, =6.7 and 1.0 Hz, ArH), 7.34 (1H, s, ArH), 10.21 (1H, s, OH), $^{13}$C NMR (100 MHz, DMSO-d$_6$) δ 27.7 (CH$_2$), 45.0 (CH$_2$), 55.8 (CH$_3$O), 56.1 (CH$_3$O), 111.7 (CH(Ar)), 113.8 (CH(Ar)), 114.6. (CH(Ar)), 116.9 (CH(Ar)), 118.9 (C(Ar)), 120.7 (CH(Ar)), 129.7 (CH(Ar)), 136.2 (C(Ar)), 138.8 (C(Ar)), 147.5 (C(Ar)), 152.7 (C(Ar)), 159.4 (C(Ar)), 165.4 (CO) and 174.2 (CO). LC/MS (ES−) $t_r$=1.08 min m/z 326.58 (M−H)−; MeOH/H$_2$O 95/5; HPLC $t_r$=1.30 min (99.3%). (CH$_3$CN/H$_2$O 90/10)

6-Hydroxy-7-methoxy-2-(4-methoxybenzoyl)-3,4-dihydro-2H-isoquinolin-1-one 140

White powder, 155 mg (96%), mp=224-225° C., $R_f$: 0.43 (ethyl acetate), $^1$H NMR (270 MHz, DMSO-d6) δ 3.01 (2H, t, J 5.7 Hz, CH$_2$), 3.77 (3H, s, CH$_3$O), 3.82 (3H, s, CH$_3$O), 3.90 (2H, t, J 5.7 Hz, CH$_2$), 6.77 (1H, s, ArH), 6.95 (2H, d, J 8.6 Hz, ArH), 7.36 (1H, s, ArH), 7.55 (2H, d, J 8.6 Hz, ArH), 10.19 (1H, br, OH), $^{13}$C NMR (67.5 MHz, DMSO-d6) δ 27.2 (CH$_2$), 44.8 (CH$_2$), 55.4 (CH$_3$O), 55.6 (CH$_3$O), 111.2 (CH), 113.3 (2×CH(Ar)), 114.1 (CH(Ar)), 118.6 (C(Ar)), 128.4 (C(Ar)), 130.7 (2×CH(Ar)), 135.5 (C(Ar)), 146.9 (C(Ar)), 152.0 (Ar), 162 (C(Ar)), 165.1 (C(Ar)), 173.6 (CO). LC/MS (APCI+) $t_r$=3.27 min m/z 328.46 (M$^+$+H). (gradient MeOH/H$_2$O from 50/50 to 95/5 in 5 min); HPLC $t_r$=1.90 min (100%). (CH$_3$CN/H$_2$O 90/10); HRMS (ES) calcd. for C$_{24}$H$_{25}$NO$_2$ (MH$^+$), 328.1179 found. 328.1181

2-(3,5-Dimethoxybenzoyl)-6-hydroxy-7-methoxy-3,4-dihydro-2H-isoquinolin-1-one 141

White powder, 145 mg (81%), mp 198-199° C., $R_f$: 0.33 (ethyl acetate/hexane 1:1), $^1$H NMR (270 MHz, CDCl$_3$) δ 3.05 (2H, t, J 6.2 Hz, CH$_2$), 3.78 (6H, s, CH$_3$O), 3.86 (3H, s, CH$_3$O), 4.07 (2H, t, J 6.2 Hz, CH$_2$), 6.16 (1H, s, OH), 6.56 (1H, t, J 2.2 Hz, ArH), 6.71 (2H, d, J 2.2 Hz, ArH), 6.79 (1H, s, ArH), 7.54 (1H, s, ArH), $^{13}$C NMR (67.5 MHz, CDCl$_3$) δ 28.1 (CH$_2$), 44.7 (CH$_2$), 55.6 (2×CH$_3$O), 56.2 (CH$_3$O), 103.3 (CH(Ar)) and 105.8 (2×CH(Ar)), 111.0 (CH(Ar)) 113.1 (CH(Ar)), 120.1 (C(Ar)), 135.4 (C(Ar)), 138.8 (C(Ar)), 146.0 (C(Ar)), 150.8 (C(Ar)), 160.2 (2×C(Ar)), 165.5 (C(Ar)) and 174.4 (CO). LC/MS (APCI+) $t_r$=4.12 min m/z 358.25 (M$^+$+H); MeOH/H$_2$O 95/5; HPLC $t_r$=2.08 min (100%). (CH$_3$CN/H$_2$O 90/10)

2-(3,4-Dimethoxybenzoyl)-6-hydroxy-7-methoxy-3,4-dihydro-2H-isoquinoline-1-one 142

White powder, 155 mg (87%), mp=199-200° C., $R_f$: 0.21 (Hexane/EtOAc 1:1), $^1$H NMR (400 MHz, DMSO-d$_6$) δ 3.02 (2H, t, J 5.9 Hz, CH$_2$), 3.75 (3H, s, CH$_3$O), 3.76 (3H, s, CH$_3$O), 3.81 (3H, s, CH$_3$O), 3.90 (2H, t, J 5.9 Hz, CH$_2$), 6.77 (1H, s, ArH), 6.96 (1H, d, J 9.2 Hz, ArH), 7.15-7.18 (2H, m, ArH), 7.36 (1H, s, ArH), 10.20 (1H, br, OH); $^{13}$C NMR (67.5 MHz, DMSO-d$_6$) δ 27.2 (CH$_2$), 44.9 (CH$_2$), 55.5 (CH$_3$O), 55.6 (CH$_3$O), 55.7 (CH$_3$O), 110.6 (CH(Ar)), 111.2 (CH(Ar)), 111.6 (CH(Ar)), 114.1 (CH(Ar)), 118.6 (C(Ar)), 122.6 (CH(Ar)), 128.5 (C(Ar)), 135.5 (C(Ar)), 147.0 (C(Ar)), 148.1 (C(Ar)), 151.8 (C(Ar)), 152.1 (C(Ar)), 165.1 (CO) and 173.7 (CO). LC/MS (ES−) $t_r$=1.05 min m/z 356.60 (M−H)−; MeOH/H$_2$O 95/5; HPLC $t_r$=1.22 min (100%). (CH$_3$CN/H$_2$O 90/10)

6-Hydroxy-7-methoxy-2-(3,4,5-trimethoxybenzoyl)-3,4-dihydro-2H-isoquinolin-1-one 143

White powder, 185 mg (96%), mp 175-176° C., $R_f$: 0.30 (ethyl acetate/hexane 1:1), $^1$H NMR (270 MHz, CDCl$_3$) δ 3.07 (2H, t, J 6.4 Hz, CH$_2$), 3.83 (6H, s, 2×CH$_3$O), 3.88 (3H, s, CH$_3$O), 3.89 (3H, s, CH$_3$O), 4.06 (2H, t, J 6.4 Hz, CH$_2$), 6.18 (1H, s, ArH), 6.80 (1H, s, ArH), 6.85 (2H, s, ArH), 7.55 (1H, s, OH), $^{13}$C NMR (100 MHz, CDCl$_3$) δ 28.0 (CH$_2$), 45.0 (CH$_2$), 56.2 (CH$_3$O), 56.3 (2×CH$_3$O), 61.0 (CH$_3$O), 105.7 (2×CH(Ar)), 111.0 (CH(Ar)), 113.2 (CH(Ar)) 120.2 (C(Ar)), 131.9 (C(Ar)), 135.4 (C(Ar)), 141.1 (C(Ar)), 146.1 (C(Ar)), 150.8 (C(Ar)), 152.9 (2×C(Ar)), 165.6 (CO) and 174.4 (CO); LC/MS (ES−) $t_r$=0.90 min m/z 386.24 ((M−1)−, 100%); MeOH/H$_2$O 95/5; HPLC $t_r$=1.55inin (99.0%). (CH$_3$CN/H$_2$O 90/10)

2-(3-Cyanobenzoyl)-6-hydroxy-7-methoxy-3,4-dihydro-2H-isoquinoline-1-one 144

White powder, 95 mg (59%), mp=197-198° C., $R_f$: 0.61 (Hexane/EtOAc 1:2), $^1$H NMR (270 MHz, CD$_3$COCCD$_3$) δ 3.14 (2H, t, J 6.2 Hz, CH$_2$), 3.85 (3H, s, CH$_3$O), 4.08 (2H, t, J 6.2 Hz, CH$_2$), 6.83 (1H, s, ArH), 7.42 (1H, s, ArH), 7.65 (1H, dd, J 8.2 and 7.6 Hz, ArH), 7.86-7.91 (2H, m, ArH), 8.00-8.06 (1H, m, ArH), 8.71 (1, br, OH), $^{13}$C NMR (67.5 MHz, CD$_3$COCCD$_3$) δ 27.4 (CH$_2$), 44.5 (CH$_2$), 55.5 (CH$_3$O), 111.2 (CH(Ar)), 112.0 (CN), 113.9 (CH(Ar)) 118.1 (C(Ar)), 119.4 (C(Ar)), 129.3 (CH(Ar)), 131.5 (CH(Ar)), 132.2 (CH(Ar)), 133.9 (CH(Ar)), 136.2 (C(Ar)), 139.0 (C(Ar)), 147.0 (C(Ar)), 152.1 (C(Ar)), 165.1 (CO) and 172.0 (CO); LC/MS (ES−) $t_r$=1.05 min m/z 321.47 (M−H)−; MeOH/H2O 95/5; HPLC $t_r$=1.23 min (98.61%). (CH3CN/H2O 90/10).

2-(4-Cyanobenzoyl)-6-hydroxy-7-methoxy-3,4-dihydro-2H-isoquinoline-1-one 145

White powder, 150 mg (94%), mp=198-199° C., $R_f$: 0.54 (Hexane/EtOAc 1:1), $^1$H NMR (270 MHz, CDCl$_3$) δ 3.08 (2H, t, J 6.2 Hz, CH$_2$), 3.87 (3H, s, CH$_3$O), 4.12 (2H, t, J 6.2 Hz, CH$_2$), 6.19 (1H, br, OH), 6.81 (1H, s, ArH), 7.49 (1H, s, ArH), 7.63 (2H, d, J 8.2 Hz, ArH), 7.69 (2H, d, J 8.2 Hz, ArH), $^{13}$C NMR (100 MHz, CDCl$_3$) δ 28.0 (CH$_2$), 44.3 (CH$_2$), 56.3 (CH$_3$O), 110.9 (CH(Ar)), 113.2 (CH(Ar)) 114.5 (CN), 118.3 (C(Ar)), 119.6 (C(Ar)), 128.2 (CH(Ar)), 132.1 (CH(Ar)), 135.6 (C(Ar)), 141.1 (C(Ar)), 146.2 (C(Ar)), 151.2 (C(Ar)), 165.5 (CO) and 172.6 (CO); LC/MS (AP−) $t_r$=1.00 min m/z 320.98 (M−H)−; MeOH/H$_2$O 95/5; HPLC $t_r$=1.49 min (99.2%). (CH$_3$CN/H$_2$O 90/10)

2-(Benzoyl)-6-O-sulfamoyl-3,4-dihydro-2H-isoquinolin-1-ones

General Method:

A solution of 2-benzoyl-6-hydroxy-3,4-dihydroisoquinoline-1-one (0.3 mmol) and sulfamoyl chloride (0.6 mmol) in DMA (1 mL) was stirred at rt under nitrogen for 24 hours. After addition of water (5 mL) the organics were extracted into ethyl acetate (2×50 mL), the organic layers washed with water and brine, then dried (MgSO$_4$) and evaporated. The crude product was purified by flash chromatography (hexane/ethyl acetate).

2-(3,5-Dimethoxybenzoyl)-6-O-sulfamoyl-3,4-dihydro-2H-isoquinoline-1-one 146

White powder, 85 mg (67%), mp=183-184° C., R$_f$: 0.58 (Hexane/EtOAc 1:2), $^1$H NMR (270 MHz, CD$_3$COCD$_3$) δ 3.30 (2H, t, J 6.4 Hz, CH$_2$), 3.78 (6H, s, CH$_3$O), 4.09 (2H, t, J 6.4 Hz, CH$_2$), 6.63 (1H, t, J 2.2 Hz, ArH), 6.76 (2H, d, J 2.2 Hz, ArH), 7.32 (1H, dd, J 8.8, 2.5 Hz, ArH), 7.38 (1H, d, J 2.5 Hz, ArH), 7.39 (2H, s, NH$_2$), 8.03 (1H, d, J 8.9 Hz, ArH), $^{13}$C NMR (67.5 MHz, CD$_3$COCD$_3$) δ 28.1 (CH$_2$), 44.3 (CH$_2$), 55.0 (2×CH$_3$O), 102.7 (CH(Ar)), 106.3 (2×CH(Ar)), 120.8 (CH(Ar)), 121.2 (CH(Ar)), 126.6 (C(Ar)), 131.1 (CH(Ar)), 138.9 (C(Ar)), 143.4 (C(Ar)), 154.2 (C(Ar)), 160.7 (2×C(Ar)), 164.4 (C(Ar)), and 173.7 (CO); LC/MS (ES−) t$_r$=0.99 min m/z 405.43 (M−H)$^−$; MeOH/H$_2$O 95/5; HPLC t$_r$=1.19 min (99.7%). (CH$_3$CN/H$_2$O 90/10.

2-(4-Methoxybenzoyl)-7-methoxy-6-O-sulfamoyl-3,4-dihydro-2H-isoquinolin-1-one 147

White powder, 85 mg (71%), mp 171-172° C., R$_f$: 0.66 (ethyl acetate/hexane 1:1), $^1$H NMR (270 MHz, CDCl$_3$/CD$_3$OD 5:1) δ 3.10 (2H, t, J 6.4 Hz, CH$_2$), 3.58 (2H, br, NH$_2$), 3.83 (3H, s, CH$_3$O), 3.85 (3H, s, CH$_3$O), 4.03 (2H, t, J 6.4 Hz, CH$_2$), 6.88 (2H, m, ArH), 7.31 (1H, s, ArH), 7.62 (2H, m, Ph), 7.67 (1H, s, ArH), $^{13}$C NMR (67.5 MHz, CDCl$_3$) δ 28.9 (CH$_2$), 46.5 (CH$_2$), 56.9 (CH$_3$O), 57.7 (CH$_3$O), 114.8 (CH(Ar)), 114.9 (CH(Ar)), 115.0 (2×CH(Ar)), 124.3 (CH(Ar)), 128.5 (C(Ar)), 129.2 (C(Ar)), 132.5 (2×CH(Ar)), 135.1 (C(Ar)), 144.5 (C(Ar)), 152.5 (C(Ar)), 164.4 (C(Ar)), 166.7 (CO), and 176.5 (CO); LC/MS (APCI+) t$_r$=0.96 min m/z 407.42 (M$^+$+H). (MeOH/H$_2$O 95/5); HPLC t$_r$=4.13 min (99.5%). (MeOH/H$_2$O 99/1); HRMS (ES) calcd. for C$_{18}$H$_{18}$N$_2$O$_7$S (MH$^+$), 407.0907 found. 407.0904

7-Methoxy-2-(2-methoxybenzoyl)-6-O-sulfamoyl-3,4-dihydro-2H-isoquinolin-1-one 148

White powder, 90 mg (75%), mp=165-166° C., R$_f$: 0.60 (Hexane/EtOAc 1:3), $^1$H NMR (400 MHz, DMSO-d$_6$) δ 3.05 (2H, t, J 6.2 Hz, CH$_2$), 3.60 (3H, s, CH$_3$O), 3.80 (3H, s, CH$_3$O), 4.11 (2H, t, J 6.2 Hz, CH$_2$), 6.96-7.03 (2H, m, ArH), 7.31 (1H, dd, J 7.7 and 1.7 Hz, ArH), 7.39 (1H, s, H8), 7.34-7.40 (1H, dt, J 8.4, 1.7 Hz, ArH), 7.53 (1H, s, H5), 8.18 (2H, br, NH$_2$), $^{13}$C NMR (100 MHz, DMSO-d$_6$) δ 27.4 (CH$_2$), 43.4 (CH$_2$), 56.0 (CH$_3$O), 56.1 (CH$_3$O), 111.4 (CH(Ar)), 112.4 (CH(Ar)), 120.3 (CH(Ar)), 122.0 (CH(Ar)), 126.3 (C(Ar)), 127.2 (C(Ar)), 128.1 (CH(Ar)), 131.2 (CH(Ar)), 133.8 (C(Ar)), 142.7 (C(Ar)), 150.6 (C(Ar)), 155.4 (C(Ar)), 163.7 (CO) and 169.9 (CO). LC/MS (ES−) t$_r$=1.00 min m/z 405.50 (M−H)−; MeOH/H$_2$O 95/5; HPLC t$_r$=1.21 min (98.7%). (CH$_3$CN/H$_2$O 90/10.

7-Methoxy-2-(3-methoxybenzoyl)-6-O-sulfamoyl-3,4-dihydro-2H-isoquinolin-1-one 149

White powder, 95 mg (77%), mp=173-174° C., R$_f$: 0.67 (Hexane/EtOAc 1:3), $^1$H NMR (400 MHz, DMSO-d$_6$) δ 3.15 (2H, t, J 5.9 Hz, CH$_2$), 3.77 (3H, s, CH$_3$O), 3.81 (3H, s, CH$_3$O), 4.01 (2H, t, J 5.9 Hz, CH$_2$), 7.08-7.18 (3H, m, ArH), 7.31-7.36 (1H, m, ArH), 7.41 (1H, s, H8), 7.57 (1H, s, ArH), 8.18 (2H, br, NH$_2$), $^{13}$C NMR (100 MHz, DMSO-d$_6$) δ 26.8 (CH$_2$), 44.4 (CH$_2$), 55.3 (CH$_3$O), 56.0 (CH$_3$O), 112.4 (CH(Ar)), 113.4 (CH(Ar)), 116.7 (CH(Ar)), 120.3 (CH(Ar)), 122.1 (CH(Ar)), 126.0 (C(Ar)), 127.2 (C(Ar)), 129.3 (CH(Ar)), 134.0 (C(Ar)), 137.8 (C(Ar)), 142.9 (C(Ar)), 150.6 (C(Ar)), 158.9 (C(Ar)), 164.3 (CO) and 173.7 (CO); LC/MS (ES−) t$_r$=1.01 min m/z 405.43 (M−H)$^−$; MeOH/H$_2$O 95/5; HPLC t$_r$=1.22 min (100%). (CH$_3$CN/H$_2$O 90/10.

2-(3,5-Dimethoxybenzoyl)-7-methoxy-6-O-sulfamoyl-3,4-dihydro-2H-isoquinolin-1-one 150

White solid, 105 mg (79%), mp 169-170° C., R$_f$: 0.26 (ethyl acetate/hexane 1:1), $^1$H NMR (270 MHz, CDCl$_3$/CD$_3$OD 10:1) δ 2.46 (2H, s, NH$_2$), 3.08 (2H, t, J 6.2 Hz, CH$_2$), 3.75 (6H, s, CH$_3$O), 3.82 (3H, s, CH$_3$O), 4.05 (2H, t, J 6.2 Hz, CH$_2$), 6.56 (1H, t, J 2.3 Hz, ArH), 6.68 (2H, d, J 2.3 Hz, ArH), 7.29 (1H, s, ArH), 7.65 (1H, s, ArH), $^{13}$C NMR (67.5 MHz, CDCl$_3$/CD$_3$OD 10:1) δ 27.6 (CH$_2$), 44.6 (CH$_2$), 55.5 (2×CH$_3$O), 56.4 (CH$_3$O), 103.7 (CH(Ar)), 105.9 (2×CH(Ar)), 113.1 (CH(Ar)), 122.9 (CH(Ar)), 127.0 (C(Ar)), 133.7 (C(Ar)), 138.1 (C(Ar)), 143.1 (C(Ar)), 150.9 (C(Ar)), 160.6 (2×C(Ar)), 165.0 (CO) and 174.4 (CO). LC/MS (APCI+) t$_r$=3.86 min m/z 437.39 (M$^+$+H). (gradient MeOH/H$_2$O from 50/50 to 95/5 in 5 min); HPLC t$_r$=2.41 min (100%). (CH$_3$CN/H$_2$O 90/10).

2-(3,4-Dimethoxybenzoyl)-7-methoxy-6-O-sulfamoyl-3,4-dihydro-2H-isoquinolin-1-one 151

White powder, 100 mg (77%), mp=180-181° C., R$_f$: 0.67 (Hexane/EtOAc 1:3), $^1$H NMR (270 MHz, CD$_3$COCD$_3$) δ 3.19 (2H, t, J 6.2 Hz, CH$_2$), 3.81 (3H, s, CH$_3$O), 3.87 (3H, s, CH$_3$O), 3.88 (3H, s, CH$_3$O), 4.03 (2H, t, J 6.2 Hz, CH$_2$), 6.96 (1H, d, J 8.9 Hz, ArH), 7.21 (2H, br, NH$_2$), 7.28 (1H, s, ArH), 7.30 (1H, d, J 8.9 Hz, ArH), 7.39 (1H, s, ArH), 7.62 (1H, s, ArH), $^{13}$C NMR (67.5 MHz, CD$_3$COCD$_3$) δ 37.4 (CH$_2$), 45.4 (CH$_2$), 56.2 (2×CH$_3$O), 56.6 (CH$_3$O), 111.2 (CH(Ar)), 112.2 (CH(Ar)), 112.9 (CH(Ar)), 122.6 (CH(Ar)), 122.4 (CH(Ar)), 126.8 (C(Ar)), 128.5 (C(Ar)), 134.3 (C(Ar)), 143.3 (C(Ar)), 148.7 (C(Ar)), 151.1 (C(Ar)), 152.6 (C(Ar)), 165.0 (CO) and 174.2 (CO). LC/MS (ES−) t$_r$=1.01 min m/z 435.44 (M−H)$^−$; MeOH/H$_2$O 95/5; HPLC t$_r$=1.18 min (99.6%). (CH$_3$CN/H$_2$O 90/10).

7-methoxy-6-O-sulfamoyl-2-(3,4,5-trimethoxybenzoyl)-3,4-dihydro-2H-isoquinolin-1-one 152

White powder, 115 mg (82%), mp 196-197° C., R$_f$: 0.29 (ethyl acetate), $^1$H NMR (270 MHz, DMSO) δ 3.16 (2H, t, J 5.7 Hz, CH$_2$), 3.72 (3H, s, CH$_3$O), 3.75 (6H, s, 2×CH$_3$O), 3.81 (3H, s, CH$_3$O), 3.98 (2H, t, J 5.7 Hz, CH$_2$), 6.90 (2H, s, ArH), 7.40 (1H, s, ArH), 7.57 (1H, s, ArH), 8.18 (2H, br, NH$_2$); $^{13}$C NMR (100 MHz, DMSO) δ 27.2 (CH$_2$), 45.2 (CH$_2$), 56.5 (CH$_3$O), 56.7 (2×CH$_3$O), 56.8 (CH$_3$O), 106.4 (2×CH(Ar)), 112.9 (CH(Ar)), 122.5 (CH(Ar)), 126.7 (C(Ar)), 132.3 (C(Ar)), 134.4 (C(Ar)), 140.9 (C(Ar)), 143.3 (C(Ar)), 151.1 (C(Ar)), 153.0 (2×C(Ar)), 164.7 (CO) and 174.1 (CO). LC/MS (ES−) t$_r$=0.94 min m/z 465.22 ((M−H)$^−$, 100%); MeOH/H$_2$O 95/5 HPLC t$_r$=1.50 min (100%). (CH$_3$CN/H$_2$O 90/10).

2-(3-Cyanobenzoyl)-7-methoxy-6-O-sulfamoyl-3,4-dihydro-2H-isoquinoline-1-one 153

White powder (85 mg, 70%), mp=171-172° C., R$_f$: 0.60 (Hexane/EtOAc 1:2), $^1$H NMR (270 MHz, CD$_3$COCCD$_3$) δ 3.23 (2H, t, J 6.2 Hz, CH$_2$), 3.88 (3H, s, CH$_3$O), 4.14 (2H, t, J 6.2 Hz, CH$_2$), 7.24 (2H, br, NH$_2$), 7.40 (1H, s, ArH), 7.58 (1H, s, ArH), 7.69 (1H, dt, J 7.9 and 0.8 Hz, ArH), 7.91-7.98 (2H, m, ArH), 8.06 (1H, dt, J 1.8 and 0.8 Hz, ArH), $^{13}$C NMR (67.5 MHz, CD$_3$COCCD$_3$) δ 27.0 (CH$_2$), 44.5 (CH$_2$), 55.7 (CH$_3$O), 112.1 (CN), 112.7 (CH(Ar)), 118.0 (C(Ar)), 123.0 (CH(Ar)), 126.8 (C(Ar)), 129.4 (CH(Ar)), 131.6 (CH(Ar)), 132.3 (CH(Ar)), 134.2 (CH(Ar)), 134.3 (C(Ar)), 138.5 (C(Ar)), 143.4 (C(Ar)), 151.4 (C(Ar)), 165.1 (CO) and 172.0 (CO); LC/MS (ES−) t$_r$=1.00 min m/z 400.53 (M−H)$^-$; MeOH/H$_2$O 95/5; HPLC t$_r$=1.18 min (99.3%). (CH$_3$CN/H$_2$O 90/10)

6-O-PG-2-(benzyl)-7-methoxy-3,4-dihydro-2H-isoquinolin-1-ones

General Method:

A solution of 7-methoxy-6-(triisopropylsilyloxy)-3,4-dihydro-2H-isoquinolin-1-one (524 mg, 1.5 mmol) or 6-benzyloxy-7-methoxy-3,4-dihydro-2H-isoquinolin-1-one (425 mg, 1.5 mmol) in dry DMF (5 mL) was cooled to 0° C. and NaH 60% (120 mg, 3 mmol) was added in a portion wise manner. The suspension was stirred at 0° C. for 30 minutes and methoxybenzylbromide/chloride (1.8 mmol) was added in a dropwise manner. The solution was stirred at room temperature for 6 hours then a saturated aqueous solution of NH$_4$Cl (10 mL) was added drop wise and the organics were extracted with ethyl acetate (80 mL). The organic layer was washed with water, brine, dried (MgSO$_4$), filtered and evaporated under educed pressure. The resulting oil was purified by flash chromatography (hexane/ethyl acetate 10:1 to 5:1).

7-Methoxy-2-(4-methoxybenzyl)-6-(triisopropylsilyloxy)-3,4-dihydro-2H-isoquinolin-1-one 154

Colorless oil, 385 mg (55%), R$_f$: 0.83 (EtOAc/Hexane 1:1), $^1$H NMR (270 MHz, CDCl$_3$) δ 1.07 (18H, d, J 6.9 Hz, (CH$_3$)$_2$CHSi), 1.22 (3H, hept, J 6.9 Hz, (CH$_3$)$_2$CHSi), 2.77 (2H, t, J 6.7 Hz, CH$_2$), 3.42 (2H, t, J 6.7 Hz, CH$_2$), 3.78 (3H, s, CH$_3$O), 3.84 (3H, s, CH$_3$O), 4.68 (2H, s, NCH$_2$), 6.60 (1H, s, ArH), 6.84 (2H, m, ArH), 7.24 (2H, m, ArH), 7.60 (1H, s, ArH). $^{13}$C NMR (67.5 MHz, CDCl$_3$) δ 13.0 ((CH$_3$)$_2$CHSi), 18.0 (CH$_3$)$_2$CHSi), 27.4 (CH$_2$), 45.6 (CH$_2$), 49.9 (NCH$_2$), 55.3 (CH$_3$O), 55.6 (CH$_3$O), 111.5 (CH(Ar)), 113.9 (2×CH(Ar)), 118.5 (CH(Ar)), 122.4 (C(Ar)), 129.5 (CH(Ar)), 129.9 (C(Ar)), 131.4 (C(Ar)), 148.8 (C(Ar)), 150.0 (C(Ar)), 158.9 (C(Ar)) and 164.8 (CO). LC/MS (APCI+) t$_r$=3.30 min m/z 470.57 (M$^+$+H); (gradient MeOH/H$_2$O from 50/50 to 95/5 in 5 min); HPLC t$_r$=8.87 min (99.8%). (CH$_3$CN/H$_2$O 90/10)

7-Methoxy-2-(3-methoxybenzyl)-6-(3-methoxybenzyloxy)-3,4-dihydro-2H-isoquinolin-1-one 155

White powder, 120 mg (18%), mp 85-86° C., R$_f$: 0.42 (EtOAc/Hexane 1:1), $^1$H NMR (270 MHz, CDCl$_3$) δ 2.77 (2H, t, J 6.6 Hz, CH$_2$), 3.41 (2H, t, J 6.6 Hz, CH$_2$), 3.75 (3H, s, CH$_3$O), 3.77 (3H, s, CH$_3$O), 3.92 (3H, s, CH$_3$O), 4.72 (2H, s, CH$_2$), 5.14 (2H, s, OCH$_2$), 6.61 (1H, s, ArH), 6.76-6.89 (m, 4H, ArH), 6.98 (m, 2H, Ph), 7.21 (2H, t, J 7.9 Hz, ArH), 7.25 (t, J 8.1 Hz, 1H, ArH), 7.66 (1H, s, ArH), $^{13}$C NMR (67.5 MHz, CDCl$_3$) δ 27.6 (CH$_2$), 45.6 (CH$_2$), 50.4 (CH$_2$), 55.2 (2×CH$_3$O), 56.2 (CH$_3$O), 70.8 (OCH$_2$), 111.2 (CH(Ar)), 111.5 (CH(Ar)), 112.6 (CH(Ar)), 112.8 (CH(Ar)), 113.6 (2×CH(Ar)), 118.5 (CH(Ar)), 119.4 (CH(Ar)), and 120.4 (CH(Ar)), 122.3 (C(Ar)), 129.7 (CH(Ar)), 129.8 (CH(Ar)), 131.6 (C(Ar)), 138.2 (CH(Ar)), 139.3 (CH(Ar)), 148.5 (C(Ar)), 151.0 (C(Ar)), 159.9 (2×C(Ar)) and 164.7 (CO). LC/MS (APCI+) t$_r$=1.29 min m/z 434.56 (M$^+$+H); MeOH/H$_2$O 95/5; HPLC t$_r$=2.25 min (99.9%). (CH$_3$CN/H$_2$O 96/4)

7-Methoxy-2-(2-methoxybenzyl)-6-(2-methoxybenzyloxy)-3,4-dihydro-2H-isoquinolin-1-one 156

White powder, 350 mg (90%), mp 133-134° C., R$_f$: 0.40 (EtOAc/Hexane 1:1), $^1$H NMR (270 MHz, CDCl$_3$) δ 2.81 (2H, t, J 6.7 Hz, CH$_2$), 3.50 (2H, t, J 6.7 Hz, CH$_2$), 3.83 (3H, s, CH$_3$O), 3.85 (3H, s, CH$_3$O), 3.93 (3H, s, CH$_3$O), 4.78 (2H, s, CH$_2$), 5.22 (2H, s, OCH$_2$), 6.64 (1H, s, ArH), 6.84-6.95 (m, 4H, ArH), 7.18-7.32 (m, 3H, ArH), 7.44 (dd, J 7.4 and 1.5 Hz, 1H, ArH), 7.65 (1H, s, ArH). $^{13}$C NMR (67.5 MHz, CDCl$_3$) δ 27.9 (CH$_2$), 45.4 (CH$_2$), 46.3 (NCH$_2$), 55.4 (2×CH$_3$O), 56.3 (CH$_3$O), 65.9 (OCH$_2$), 110.2 (CH(Ar)), 110.3 (CH(Ar)), 111.1 (CH(Ar)), 111.2 (CH(Ar)), 120.7 (CH(Ar)), 120.8(CH(Ar)), 122.3 (C(Ar)), 124.9 (C(Ar)), 125.6 (C(Ar)), 128.2(CH(Ar)), 128.4(CH(Ar)), 128.9 (CH(Ar)), 129.4 (CH(Ar)), 131.7 (C(Ar)), 148.4 (C(Ar)), 151.1 (C(Ar)), 156.5 (C(Ar)), 157.6 (C(Ar)) and 164.8 (CO). LC/MS (APCI+) t$_r$=1.40 min m/z 434.56 (M$^+$+H); MeOH/H$_2$O 95/5; HPLC t$_r$=2.38 min (99.8%). (CH$_3$CN/H$_2$O 96/4).

6-(Benzyloxy)-2-(3,5-dimethoxybenzyl)-7-methoxy-3,4-dihydro-2H-isoquinolin-1-one 157

White powder, 440 mg (68%), mp 82-83° C., R$_f$: 0.74 (EtOAc/Hexane 1:1), $^1$H NMR (270 MHz, CDCl$_3$) δ 2.79 (2H, t, J 6.7 Hz, CH$_2$), 3.43 (2H, t, J 6.7 Hz, CH$_2$), 3.75 (6H, s, 2×CH$_3$O), 3.93 (3H, s, CH$_3$O), 4.69 (2H, s, CH$_2$), 5.17 (2H, s, CH$_2$), 6.35 (1H, t, J 2.5 Hz, ArH), 6.45 (2H, d, J 2.5 Hz, ArH), 6.62 (1H, s, ArH), 7.27-7.45 (5H, s, Ph), 7.66 (1H, s, ArH); $^{13}$C NMR (100 MHz, CDCl$_3$) δ 27.8 (CH$_2$), 45.5 (CH$_2$), 50.5 (CH$_2$), 55.5 (2×CH$_3$O), 56.3 (CH$_3$O), 70.9 (CH$_2$), 99.3 (CH(Ar)), 106.0 (2×CH(Ar)), 111.2 (CH(Ar)), 111.5 (CH(Ar)) 122.3 (C(Ar)), 127.3 (2×CH(Ar)), 128.1 (CH(Ar)), 128.8 (2×CH(Ar)), 131.6 (C(Ar)), 136.6 (C(Ar)), 140.2 (C(Ar)), 148.6 (C(Ar)), 151.0 (C(Ar)), 161.1 (C(Ar)), 164.7 (CO); LC/MS (ES+) t$_r$=1.13 min m/z 456.03 ((M+Na)$^+$, 100%), 434.05 (M+H)$^+$; MeOH/H$_2$O 95/5; HPLC t$_r$=2.13 min (100%). (CH$_3$CN/H$_2$O 90/10).

6-(benzyloxy)-7-methoxy-2-(3,4,5-trimethoxybenzyl)-3,4-dihydro-2H-isoquinolin-1-one 158

White powder, 570 mg (82%), mp 136-137° C., R$_f$: 0.42 (EtOAc/Hexane 1:1), $^1$H NMR (270 MHz, CDCl$_3$) δ 2.80 (2H, t, J 6.8 Hz, CH$_2$), 3.43 (2H, t, J 6.8 Hz, CH$_2$), 3.82 (9H, s, 3×CH$_3$O), 3.93 (3H, s, CH$_3$O), 4.68 (2H, s, CH$_2$), 5.17 (2H, s, CH$_2$), 6.52 (2H, s, ArH), 6.63 (1H, s, ArH), 7.26-7.43 (5H, s, Ph), 7.66 (1H, s, ArH); $^{13}$C NMR (100 MHz, CDCl$_3$) δ 27.8 (CH$_2$), 45.5 (CH$_2$), 50.6 (CH$_2$), 56.3 (3×CH$_3$O), 61.0 (CH$_3$O), 70.9 (CH$_2$), 105.0 (2×CH(Ar)), 111.2 (CH(Ar)), 111.5 (CH(Ar)) 122.3 (C(Ar)), 127.2 (2×CH(Ar)), 128.1 (CH(Ar)), 128.8 (2×CH(Ar)), 131.5 (C(Ar)), 133.5 (C(Ar)), 136.5 (C(Ar)), 137.2 (C(Ar)), 148.6 (C(Ar)), 151.1 (C(Ar)), 153.5 (2×C(Ar)), 164.7 (CO); LC/MS (ES+) t$_r$=0.98 min m/z 486.26 ((M+Na)$^+$, 100%), 464.28 (M+H)$^+$; MeOH/H$_2$O 95/5; HPLC t$_r$=1.95 min (99.7%). (CH$_3$CN/H$_2$O 90/10)

2-(Benzyl)-6-hydroxy-7-methoxy-3,4-dihydro-2H-isoquinolin-1-ones

6-Hydroxy-7-methoxy-2-(4-methoxybenzyl)-3,4-dihydroisoquinolin-1(2H)-one 159

A solution of 6-(benzyloxy)-7-methoxy-2-(4-methoxybenzyl)-3,4-dihydro-2H-isoquinolin-1-one (0.24 g, 0.51 mmol) in THF (10 mL) was cooled to 0° C. before 0.61 mL of a 1M solution of TBAF in THF was added drop wise. The solution was stirred at rt o/n. After addition of water (5 mL), the organics was extracted with ethyl acetate and the organic layer was washed with water, brine, dried (MgSO4), filtered and the solvents evaporated under reduced pressure. The crude product was purified by flash chromatography (hexane/ethyl acetate 4:1 to 2:1) to give 110 mg (69%) of a white solid. mp 171-172° C., $R_f$: 0.27 (ethyl acetate/hexane 1:1), $^1$H NMR (270 MHz, CDCl$_3$) δ 2.78 (2H, t, J 6.7 Hz, CH$_2$), 3.41 (2H, t, J 6.7 Hz, CH$_2$), 3.77 (3H, s, CH$_3$O), 3.90 (3H, s, CH$_3$O), 4.69 (2H, s, CH$_2$), 6.33 (1H, br, OH), 6.66 (1H, s, ArH), 6.91 (2H, m, ArH), 7.24 (2H, m, ArH), 7.63 (1H, s, ArH), $^{13}$C NMR (67.5 MHz, CDCl$_3$) δ 27.5 (CH$_2$), 45.5 (CH$_2$), 49.9 (CH$_2$), 55.3 (CH$_3$O), 56.2 (CH$_3$O), 110.6 (CH(Ar)), 112.8 (CH(Ar)), 114.0 (2×CH(Ar)), 121.5 (C(Ar)), 129.4 (CH(Ar)), 129.7 (C(Ar)), 132.4 (C(Ar)), 145.8 (C(Ar)), 149.0 (C(Ar)), 159.0 (C(Ar)) and 164.8 (CO). LC/MS (APCI+) $t_r$=1.00 min m/z 314.42 (M$^+$+B); MeOH/H$_2$O 95/5; HPLC $t_r$=4.27 min (>99.99%). (MeOH/H$_2$O 99/1) HRMS (ES) calcd. for C$_{18}$H$_{19}$NO$_4$ (MH$^+$), 314.1387 found. 314.1381

6-Hydroxy-7-methoxy-2-(3-methoxy-benzyl)-3,4-dihydro-2H-isoquinolin-1-one 160

7-methoxy-2-(3-methoxybenzyl)-6-(3-methoxybenzyloxy)-3,4-dihydro-2H-isoquinolin-1-one (85 mg, 0.196 mmol) was stirred in THF (10 mL) and methanol (10 mL) with 10% Pd/C (20 mg) under hydrogen for 2 hours. After filtration and evaporation of the solvents under reduced pressure, a yellow solid (70 mg) was obtained which was purified by flash chromatography (hexane/ethyl acetate 1:1) to give 52 mg (76%) of a white solid. mp 181-182° C., $R_f$: 0.26 (EtOAc/Hexane 1:1), $^1$H NMR (270 MHz, CDCl$_3$) δ 2.82 (2H, t, J 6.7 Hz, CH$_2$), 3.44 (2H, t, J 6.7 Hz, CH$_2$), 3.77 (3H, s, CH$_3$O), 3.93 (3H, s, CH$_3$O), 4.74 (2H, s, CH$_2$), 6.03 (1H, s, OH), 6.68 (1H, s, ArH), 6.80 (1H, dd, J 7.4 and 1.7 Hz, ArH), 6.84 (1H, d, J 1.7 Hz, Ar), 6.90 (1H, d, J 7.7 Hz, ArH), 7.23 (t, J 7.9 Hz, 1H, ArH), 7.64 (1H, s, ArH), $^{13}$C NMR (67.5 MHz, CDCl$_3$) δ 27.6 (CH$_2$), 45.6 (CH$_2$), 50.4 (CH$_2$), 55.3 (CH$_3$O), 56.3 (CH$_3$O), 110.6 (CH(Ar)), 112.7(CH(Ar)), 112.9 (CH(Ar)), 113.6 (CH(Ar)), 120.4 (CH(Ar)), 121.7 (C(Ar)), 129.8 (CH(Ar)), 132.5 (C(Ar)), 139.4 (C(Ar)), 145.7 (C(Ar)), 148.9 (C(Ar)), 159.9 (C(Ar)) and 164.7 (CO). LC/MS (APCI+) $t_r$=4.18 min m/z 314.23 (M$^+$+H); (gradient MeOH/H$_2$O from 50/50 to 95/5 in 5 min); HPLC $t_r$=2.11 min (98.1%). (CH$_3$CN/H$_2$O 90/10).

6-Hydroxy-7-methoxy-2-(2-methoxybenzyl)-3,4-dihydro-2H-isoquinolin-1-one 161

A mixture of 7-methoxy-2-(2-methoxybenzyl)-6-(2-methoxybenzyloxy)-3,4-dihydro-2H-isoquinolin-1-one (290 mg, 0.67 mmol) and 10% Pd/C in THF (20 mL) and methanol (20 mL) was stirred under hydrogen at rt for 4 hours. After filtration over celite and evaporation under reduced pressure the residual solid was stirred in diethyl ether, filtered and dried under vacuum to give 195 mg (93%) of a white powder. mp 164-165° C., $R_f$: 0.28 (EtOAc/Hexane 1:1), $^1$H NMR (270 MHz, CDCl$_3$) δ 2.83 (2H, t, J 6.7 Hz, CH$_2$), 3.51 (2H, t, J 6.7 Hz, CH$_2$), 3.83 (3H, s, CH$_3$O), 3.92 (3H, s, CH$_3$O), 4.78 (2H, s, CH$_2$), 6.02 (1H, s, OH), 6.68 (1H, s, ArH), 6.87 (1H, d, J 7.4 Hz, ArH), 6.91 (1H, dd, J 7.4 and 1.0 Hz, ArH), 7.23 (1H, dt, J 7.4 & 1.5 Hz, ArH), 7.30 (1H, dd, J 7.9 and 1.5 Hz, ArH), 7.63 (1H, s, ArH). $^{13}$C NMR (67.5 MHz, CDCl$_3$) δ 27.7 (CH$_2$), 45.5 (CH$_2$), 46.3 (CH$_2$), 55.3 (CH$_3$O), 56.3 (CH$_3$O), 110.3 (CH(Ar)), 110.5 (CH(Ar)), 112.7 (CH(Ar)), 120.7 (CH(Ar)), 121.9 (C(Ar)), 125.7 (C(Ar)), 128.4 (CH(Ar)), 129.3 (CH(Ar)), 132.6 (C(Ar)), 139.4 (C(Ar)), 145.5 (C(Ar)), 148.9 (C(Ar)), 157.6 (C(Ar)) and 164.9 (CO). LC/MS (APCI+) $t_r$=4.29 min m/z 314.17 (M$^+$+H); (gradient MeOH/H$_2$O from 50/50 to 95/5 in 5 min); HPLC $t_r$=2.36 min (99.1%). (CH$_3$CN/H$_2$O 90/10).

2-(3,5-dimethoxybenzyl)-6-hydroxy-7-methoxy-3,4-dihydro-2H-isoquinolin-1-one 162

A mixture of 6-benzyloxy-2-(3,5-dimethoxybenzyl)-7-methoxy-3,4-dihydro-2H-isoquinolin-1-one (216 mg, 0.5 mmol) and 10% Pd/C in THF (20 mL) and methanol (20 mL) was stirred under hydrogen at rt for 4 hours. After filtration over celite and evaporation under reduced pressure the residual solid was purified by flash chromatography (hexane/ethyl acetate) and the resultant solid stirred in diethyl ether, filtered and dried under vacuum to give 155 mg (92%) of a white powder, mp 166-167° C., $R_f$: 0.76 (ethyl acetate), $^1$H NMR (270 MHz, CDCl$_3$) δ 2.82 (2H, t, J 6.7 Hz, CH$_2$), 3.44 (2H, t, J 6.7 Hz, CH$_2$), 3.75 (9H, s, 3×CH$_3$O), 3.93 (3H, s, CH$_3$O), 4.70 (2H, s CH$_2$), 6.04 (1H, s, OH), 6.35 (1H, t, J 2.5 Hz, ArH), 6.46 (2H, d, J 2.5 Hz, ArH), 6.68 (1H, s, ArH), 7.63 (1H, s, ArH); $^{13}$C NMR (100 MHz, CDCl$_3$) δ 27.6 (CH$_2$), 45.6 (CH$_2$), 50.5 (CH$_2$), 55.5 (2×CH$_3$O), 56.3 (CH$_3$O), 99.3 (CH(Ar)), 105.9 (CH(Ar)), 110.6 (CH(Ar)), 112.7 (CH(Ar)), 121.6 (C(Ar)), 132.6 (C(Ar)), 140.2 (C(Ar)), 145.7 (C(Ar)), 148.9 (C(Ar)), 161.1 (C(Ar)), 164.8 (CO). LC/MS (ES−) $t_r$=0.94 min m/z 342.09 ((M−H)$^-$, 100%); MeOH/H$_2$O 95/5; HPLC $t_r$=1.63 min (100%). (CH$_3$CN/H$_2$O 90/10)

6-hydroxy-7-methoxy-2-(3,4,5-trimethoxybenzyl)-3,4-dihydro-2H-isoquinolin-1-one 163

A mixture of 6-benzyloxy-7-methoxy-2-(3,4,5-trimethoxybenzyl)-3,4-dihydro-2H-isoquinolin-1-one (230 mg, 0.5 mmol) and 10% Pd/C in THF (20 mL) and methanol (20 mL) was stirred under hydrogen at RT for 4 hours. After filtration over celite and evaporation under reduced pressure the residual solid was purified by flash chromatography (hexane/ethyl acetate) and the resultant solid stirred in diethyl ether, filtered and dried under vacuum to give 160 mg (86%) of a white powder, mp 168-169° C., $R_f$: 0.63 (ethyl acetate), $^1$H NMR (270 MHz, CDCl$_3$) δ 2.82 (2H, t, J 6.7 Hz, CH$_2$), 3.44 (2H, t, J 6.7 Hz, CH$_2$), 3.82 (9H, s, 3×CH$_3$O), 3.92 (3H, s, CH$_3$O), 4.69 (2H, s, CH$_2$), 6.08 (1H, br, OH), 6.53 (2H, s, ArH), 6.69 (1H, s, ArH), 7.63 (1H, s, ArH); $^{13}$C NMR (100 MHz, CDCl$_3$) δ 27.7 (CH$_2$), 45.5 (CH$_2$), 50.6 (CH$_2$), 56.2 (3×CH$_3$O), 61.0 (CH$_3$O), 104.9 (2×CH(Ar)), 110.5 (CH(Ar)), 112.8 (CH(Ar)) 121.6 (C(Ar)), 132.5 (C(Ar)), 133.5 (C(Ar)), 137.2 (C(Ar)), 145.7 (C(Ar)), 149.0 (C(Ar)), 153.5 (2×C(Ar)), 164.8 (CO). LC/MS (ES−) $t_r$=0.89 min m/z 372.07 ((M−H)$^-$, 100%); MeOH/H$_2$O 95/5; HPLC $t_r$=1.56 min (100%). (CH$_3$CN/H$_2$O 90/10).

2-(Benzyl)-7-methoxy-6-O-sulfamoyl-3,4-dihydro-2H-isoquinolin-1-ones

General Method:
A solution of 2-benzyl-6-hydroxy-3,4-dihydro-2H-isoquinoline-1-one (0.3 mmol) and sulfamoyl chloride (0.6 mmol) in DMA (1 mL) was stirred at rt under nitrogen for 24 hours. After addition of water (5 mL) the organics were extracted into ethyl acetate (2×50 mL), the organic layers washed with water and brine, then dried (MgSO$_4$) and evaporated. The crude product was purified by flash chromatography (hexane/ethyl acetate) and the resulting solid stirred in diethyl ether, filtered and dried under vacuum.

7-Methoxy-2-(4-methoxybenzyl)-6-O-sulfamoyl-3,4-dihydro-2H-isoquinoline 164

White solid, 86 mg (73%), mp 159-160° C., $R_f$: 0.32 (Hexane/EtOAc 1:2), $^1$H NMR (270 MHz, CDCl$_3$/CD$_3$OD 10:1) δ 2.12 (2H, s, NH2), 2.81 (2H, t, J 6.7 Hz, CH$_2$), 3.42 (2H, t, J 6.7 Hz, CH$_2$), 3.76 (3H, s, CH$_3$O), 3.90 (3H, s, CH$_3$O), 4.67 (2H, s, CH$_2$), 6.82 (2H, m, ArH), 7.14 (1H, s, ArH), 7.21 (2H, m, ArH), 7.72 (1H, s, ArH), $^{13}$C NMR (67.5 MHz, CDCl$_3$/CD$_3$OD 10:1) δ 27.0 (CH$_2$), 45.3 (CH$_2$), 50.2 (CH$_2$), 55.3 (CH$_3$O), 56.4 (CH$_3$O), 112.8 (CH(Ar)), 114.1 (2×CH(Ar)), 122.7 (CH(Ar)), 128.6 (C(Ar)), 129.0 (C(Ar)),129.4 (2×CH (Ar)), 131.3 (C(Ar)), 141.3 (C(Ar)), 150.6 (C(Ar)), 159.1 (C(Ar)) and 163.8 (CO); LC/MS (APCI+) $t_r$=0.97 min m/z 393.38 (M$^+$+H). (MeOH/H$_2$O 95/5); HPLC $t_r$=1.90 min (100%). (CH$_3$CN/H$_2$O 90/10); HRMS (ES) calcd. for C$_{18}$H$_{20}$N$_2$O$_6$S (MH$^+$), 393.1115 found. 393.1117.

7-Methoxy-2-(2-methoxybenzyl)-6-O-sulfamoyl-3,4-dihydro-2H-isoquinoline 165

White solid, 90 mg (77%), mp 142-143° C., $R_f$: 0.16 (Hexane/EtOAc 1:1), $^1$H NMR (270 MHz, CDCl$_3$) δ 2.86 (2H, t, J 6.7 Hz, CH$_2$), 3.54 (2H, t, J 6.7 Hz, CH$_2$), 3.84 (3H, s, CH$_3$O), 3.93 (3H, s, CH$_3$O), 4.77 (2H, s, CH$_2$), 5.16 (2H, s, NH$_2$), 6.87 (1H, d, J 8.2 Hz, ArH), 6.91 (1H, dt, J 7.4 and 1.0 Hz, ArH), 7.14 (1H, s, ArH), 7.21-7.31 (2H, m, ArH), 7.77 (1H, s, ArH), $^{13}$C NMR (67.5 MHz, CDCl$_3$) δ 27.1 (CH$_2$), 45.8 (CH$_2$), 46.1 (CH$_2$), 55.4 (CH$_3$O), 56.7 (CH$_3$O), 110.4 (CH(Ar)), 113.0 (CH(Ar)), 120.8 (CH(Ar)), 122.8 (CH(Ar)), 125.1 (C(Ar)), 128.8 (CH(Ar)), 129.4 (C(Ar)), 129.6 (CH(Ar)), 131.7 (C(Ar)), 141.1 (C(Ar)), 150.4 (C(Ar)), 157.6 (C(Ar)) and 163.6 (CO). LC/MS (APCI+) $t_r$=3.99 min m/z 393.45 (M$^+$+H); (gradient MeOH/H$_2$O from 50/50 to 95/5 in 5 min); HPLC $t_r$=2.42 min (100%). (CH$_3$CN/H$_2$O 90/10).

7-Methoxy-2-(3-methoxybenzyl)-6-O-sulfamoyl-3,4-dihydro-2H-isoquinoline 166

White solid, 80 mg (68%), mp 139-140° C., $R_f$: 0.15 (Hexane/EtOAc 1:1), $^1$H NMR (270 MHz, CDCl$_3$) δ 2.86 (2H, t, J 6.7 Hz, CH$_2$), 3.47 (2H, t, J 6.7 Hz, CH$_2$), 3.78 (3H, s, CH$_3$O), 3.94 (3H, s, CH$_3$O), 4.73 (2H, s, CH$_2$), 5.19 (2H, s, NH$_2$), 6.79-6.89 (3H, m, ArH), 7.15 (1H, s, ArH), 7.24 (1H, dt, J 7.6 and 1.0 Hz, ArH), 7.78 (1H, s, ArH), $^{13}$C NMR (67.5 MHz, CDCl$_3$) δ 27.1 (CH$_2$), 45.8 (CH$_2$), 50.7 (CH$_2$), 55.3 (CH$_3$O), 56.6 (CH$_3$O), 113.0 (CH(Ar)), 113.1 (CH(Ar)), and 113.7 (CH(Ar)), 120.3 (CH(Ar)), 122.9 (CH(Ar)), 128.9 (C(Ar)) 129.8 (CH(Ar)), 131.5 (C(Ar)), 138.6 (C(Ar)), 141.2 (C(Ar)), 150.6 (C(Ar)), 159.9 (C(Ar)) and 163.6 (CO); LC/MS (APCI+) $t_r$=3.72 min m/z 393.64 (M$^+$+H); (gradient MeOH/H$_2$O from 50/50 to 95/5 in 5 min); HPLC $t_r$=2.27 min (100%). (CH$_3$CN/H$_2$O 90/10).

2-(3,5-Dimethoxybenzyl)-7-methoxy-6-O-sulfamoyl-3,4-dihydro-2H-isoquinolin-1-one 167

White powder, 98 mg (77%), mp 164-165° C., $R_f$: 0.67 (ethyl acetate), $^1$H NMR (270 MHz, CDCl$_3$) δ 2.89 (2H, t, J 6.3 Hz, CH$_2$), 3.47 (2H, t, J 6.3 Hz, CH$_2$), 3.71 (6H, s, 2×CH$_3$O), 3.84 (3H, s, CH$_3$O), 4.64 (2H, s, CH$_2$), 6.40-6.45 (3H, m, ArH), 7.26 (1H, s, ArH), 7.61 (1H, s, ArH), 8.07 (2H, br, NH$_2$); $^{13}$C NMR (67.5 MHz, CDCl$_3$) δ 27.0 (CH$_2$), 46.0 (CH$_2$), 50.4 (CH$_2$), 55.7 (CH$_3$O), 56.5 (2×CH$_3$O), 99.3 (CH (Ar)), 106.0 (2×CH(Ar)), 112.4 (CH(Ar)), 122.3 (2×CH(Ar)) 128.1 (C(Ar)), 131.7 (C(Ar)), 140.5 (C(Ar)), 141.8 (C(Ar)), 151.0 (C(Ar)), 161.2 (2×C(Ar)), 163.3 (CO); LC/MS (ES−) $t_r$=0.93 min m/z 421.13 ((M−H)$^−$, 100%); MeOH/H$_2$O 95/5; HPLC $t_r$=1.54 min (100%). (CH$_3$CN/H$_2$O 90/10)

7-methoxy-6-O-sulfamoyl-2-(3,4,5-trimethoxybenzyl)-3,4-dihydroisoquinolin-1 (2H)-one 168

White powder, 100 mg (74%), mp 201-203° C., $R_f$: 0.58 (ethyl acetate), $^1$H NMR (270 MHz, DMSO-d6) δ 2.90 (2H, t, J 6.6 Hz, CH$_2$), 3.49 (2H, t, J 6.6 Hz, CH$_2$), 3.63 (3H, s, CH$_3$O), 3.74 (6H, s, 2×CH$_3$O), 3.84 (3H, s, CH$_3$O), 4.64 (2H, s, CH$_2$), 6.61 (2H, s, ArH), 7.26 (1H, s, ArH), 7.61 (1H, s, ArH), 8.08 (2H, br, NH$_2$); $^{13}$C NMR (67.5 MHz, DMSO-d6) δ 27.0 (CH$_2$), 45.8 (CH$_2$), 50.4 (CH$_2$), 56.4 (2×CH$_3$O), 56.5 (CH$_3$O), 56.6 (CH$_3$O), 105.3 (2×CH(Ar)), 112.5 (CH(Ar)), 122.3 (CH(Ar)) 128.2 (C(Ar)), 131.8 (C(Ar)), 133.9 (C(Ar)), 137.1 (C(Ar)), 141.8 (C(Ar)), 151.0 (C(Ar)), 153.5 (2×C (Ar)), 163.9 (CO); LC/MS (ES−) $t_r$=0.89 min m/z 451.18 ((M−H)$^−$, 100%); MeOH/H$_2$O 95/5; HPLC $t_r$=2.27 min (99.7%). (CH$_3$CN/H$_2$O 70/30)

N-Sulfonyl Tetrahydroisoquinolines

6-Benzyloxy-7-methoxy-2-(3-methoxy-benzenesulfonyl)-1,2,3,4-tetrahydroisoquinoline 169

To a solution of the substituted tetrahydroisoquinoline (300 mg, 1.11 mmol) in DCM (10 ml) was added triethylamine (0.19 ml, 1.35 mmol) followed by 3-methoxy sulfonyl chloride (0.19 ml, 1.34 mmol). The reaction mixture was stirred at rt for 12 h. Saturated aqueous sodium hydrogen carbonate (30 ml) was added and DCM (30 ml). The layers were separated and the aqueous layer extracted with DCM (2×30 ml). The combined organic layers were washed with brine (30 ml), dried (MgSO$_4$) and concentrated in vacuo. Purification (flashmaster: 20 g, 100% Hex to 100% EtOAc) afforded the title compound (270 mg, 55%) as a colourless solid. mp 124-125° C. $^1$H NMR (270 MHz; CDCl$_3$) 2.76 (2H, t, J 5.8 Hz, CH$_2$), 3.32 (2H, t, J 5.8 Hz, CH$_2$), 3.81 (3H, s, OCH$_3$), 3.83 (3H, s, OCH$_3$), 4.18 (2H, s CH$_2$), 5.07 (2H, s, CH$_2$Ph), 6.52 (1H, s, CH), 6.56 (1H, s, CH), 7.09 (1H, dt, J 6.9, 2.7 Hz, CH), 7.28-7.45 (8H, m, phenyl CH and 3×CH). $^{13}$C NMR (67.5 MHz; CDCl$_3$) 28.38 (CH$_2$), 43.88 (CH$_2$), 47.34 (CH$_2$), 55.76 (OCH$_3$), 56.16 (OCH$_3$), 71.13 (CH$_2$Ph), 109.53 (CH), 112.66 (CH), 114.16 (CH), 118.98 (CH), 119.87 (CH), 124.03 (C), 125.00 (C), 127.33 (2×CH), 127.95 (CH), 128.63 (2×CH), 130.22 (CH), 137.02 (C), 137.62 (C), 147.09 (C), 148.47 (C), 159.97 (C). LC/MS (APCI+) $t_r$=5.0 min, m/z 440.54 (M$^+$+H). HPLC $t_r$=5.09 min, >99%.

6-Benzyloxy-7-methoxy-2-(3-trifluoromethoxy-benzenesulfonyl)-1,2,3,4-tetrahydroisoquinoline 170

471 mg, 86%, cream solid. Recrystallisation from EtOH afforded a pure sample as a colourless powder. mp 118-120° C. $^1$H NMR (270 MHz; CDCl$_3$) 2.76 (2H, t, J 5.9 Hz, CH$_2$), 3.35 (2H, t, J 5.9 Hz, CH$_2$), 3.82 (3H, s, OCH$_3$), 4.20 (2H, s CH$_2$), 5.07 (2H, s, CH$_2$Ph), 6.52 (1H, s, CH), 6.56 (1H, s, CH), 7.28-7.44 (6H, m, 6×CH), 7.56 (1H, t, J 7.9 Hz, CH), 7.67 (1H, brs, CH), 7.74 (1H, dt, J 7.7, 1.5 Hz, CH). $^{13}$C NMR (100 MHz; CDCl$_3$) 28.05 (CH$_2$), 43.70 (CH$_2$), 47.11 (CH$_2$), 56.02 (OCH$_3$), 70.98 (CH$_2$Ph), 109.33 (CH), 114.01 (CH), 120.15 (CH), 120.23 (q, J 257.7 Hz, CF$_3$), 123.48 (C), 124.66 (C), 125.06 (CH), 125.76 (CH), 127.19 (CH), 127.84 (CH), 128.51 (CH), 130.71 (CH), 136.84 (C), 138.72 (C), 147.07

(C), 148.44 (C), 149.29 (app. d, J 1.5 Hz, C). LC/MS (APCI+) t$_r$=5.31 min, m/z 494.97 (M$^+$+H). HPLC t$_r$=5.40 min (>99%). Anal. Calcd. for C$_{24}$H$_{22}$F$_3$NO$_5$S: C, 58.41; H, 4.49; N, 2.84. Found: C, 58.4, H, 4.50; N, 2.66%.

6-Benzyloxy-7-methoxy-2-(toluene-3-sulfonyl)-1,2,3,4-tetrahydroisoquinoline 171

211 mg, 45%, colourless solid. Recrystallisation from EtOH afforded a pure sample. mp 144-147° C. $^1$H NMR (270 MHz; CDCl$_3$) 2.41 (3H, s, CH$_3$), 2.77 (2H, t, J=5.9 Hz, CH$_2$), 3.309 (2H, t, J=5.9 Hz, CH$_2$), 3.81 (3H, s, OCH$_3$), 4.16 (2H, s CH$_2$), 5.07 (2H, s, CH$_2$Ph), 6.52 (1H, s, CH), 6.56 (1H, s, CH), 7.27-7.42 (7H, m, 7×CH), 7.59-7.62 (2H, m, 2×CH). $^{13}$C NMR (67.5 MHz; CDCl$_3$) 21.50 (CH$_3$), 28.40 (CH$_2$), 43.87 (CH$_2$), 47.35 (CH$_2$), 56.16 (OCH$_3$), 71.12 (CH$_2$Ph), 109.53 (CH), 114.12 (CH), 124.08 (C), 124.94 (CH), 125.02 (C), 127.33 (2×CH), 127.95 (CH), 128.08 (CH), 128.64 (2×CH), 128.99 (CH), 133.72 (CH), 136.18 (C), 137.02 (C), 139.35 (C), 147.05 (C), 148.44 (C). LC/MS (APCI+) t$_r$=5.12 min, m/z 424.46 (M$^+$+H). HPLC t$_r$=5.08 min (>99%). Anal. Calcd. for C$_{24}$H$_{25}$NO$_4$S: C, 68.06; H, 5.95; N, 3.31. Found: C, 67.8; H, 5.93; N, 3.25%.

6-Benzyloxy-7-methoxy-2-(3-trifluoromethyl-benzenesulfonyl)-1,2,3,4-tetrahydroisoquinoline 172

457 mg, 86%, cream foam. mp 136-138.5° C. $^1$H NMR (270 MHz; CDCl$_3$) 2.756 (2H, t, J=5.9 Hz, CH$_2$), 3.37 (2H, t, J=5.9 Hz, CH$_2$), 3.82 (3H, s, OCH$_3$), 4.220 (2H, s CH$_2$), 5.07 (2H, s, CH$_2$Ph), 6.53 (1H, s, CH), 6.55 (1H, s, CH), 7.28-7.41 (5H, m, 5×CH, phenyl), 7.65 (1H, t, J=7.8 Hz, CH), 7.82 (1H, d, J=7.4 Hz, CH), 8.00 (1H, d, J=7.9 Hz, CH), 8.06 (1H, s, CH). $^{13}$C NMR (100 MHz; CDCl$_3$) 29.95 (CH$_2$), 43.70 (CH$_2$), 47.13 (CH$_2$), 56.0 (OCH$_3$), 70.96 (CH$_2$Ph), 109.31 (CH), 114.00 (CH), 123.41 (C), 123.15 (q, J=271.3 Hz, CF$_3$), 124.47 (q, J 3.8 Hz, CH), 124.60 (C), 127.18 (2×CH), 127.83 (CH), 128.50 (2×CH), 129.38 (q, J=3.8 Hz, CH), 129.84 (CH), 130.69 (CH), 131.70 (q, J=33.5 Hz, C), 136.83 (C), 138.07 (C), 147.09 (C), 148.46 (C). $^{19}$F NMR (376 MHz; CDCl$_3$) −62.74 (CF$_3$). LC/MS (APCI+) t$_r$=5.22 min, m/z 478.42 (M$^+$+H). HPLC t$_r$=5.29 min (>99%). Anal. Calcd. for C$_{24}$H$_{22}$F$_3$NO$_4$S: C, 60.37; H, 4.64; N, 2.93. Found: C, 60.1; H, 4.65; N, 2.88%.

6-Benzyloxy-2-(3-chloro-benzenesulfonyl)-7-methoxy-1,2,3,4-tetrahydroisoquinoline 173

290 mg, 59%, cream solid. Recrystallisation from EtOH afforded a pure sample as a white powder. $^1$H NMR (270 MHz; CDCl$_3$) 2.77 (2H, t, J=5.98 Hz, CH$_2$), 3.34 (2H, t, J=5.9 Hz, CH$_2$), 3.82 (3H, s, OCH$_3$), 4.20 (2H, s CH$_2$), 5.08 (2H, s, CH$_2$Ph), 6.53 (1H, s, CH), 6.56 (1H, s, CH), 7.26-7.47 (6H, m, 6×CH), 7.52-7.56 (1H, m, CH), 7.69 (1H, dt, J=7.7,1.5 Hz, CH), 7.80 (1H, t, J=1.7 Hz, CH). $^{13}$C NMR (67.5 MHz; CDCl$_3$) 28.27 (CH$_2$), 43.87 (CH$_2$), 47.30 (CH$_2$), 55.16 (OCH$_3$), 71.11 (CH$_2$Ph), 109.47 (CH), 114.12 (CH), 123.69 (C), 124.83 (C), 125.76 (CH), 127.32 (CH), 127.73 (CH), 127.97 (CH), 128.65 (CH), 130.47 (CH), 133.02 (CH), 135.44 (C), 136.97 (C), 138.40 (C), 147.16 (C), 148.53 (C). LC/MS (APCI+) t$_r$=5.25 min, m/z 444.49 (M$^+$+H). HPLC t$_r$=5.26 min (>99%). Anal. Calcd. for C$_{23}$H$_{22}$ClNO$_4$S: C, 62.23; H, 4.99; N, 3.16. Found: C, 62.2; H, 5.01; N, 3.12%.

2-(3-Cyano-benzenesulfonyl)-6-triisopropylsilyloxy-7-methoxy-1,2,3,4-tetrahydroisoquinoline 174

To a solution of the substituted tetrahydroisoquinoline (300 mg, 0.9 mmol) in DCM (10 ml) was added triethylamine (0.14 ml, 0.99 mmol) followed by 3-cyanobenzene sulfonyl chloride (199 mg, 0.99 mmol). The reaction mixture was stirred at rt for 12 h. Saturated aqueous sodium hydrogen C(Ar)bonate (30 ml) was added and DCM (30 ml). The layers were separated and the aqueous layer extracted with DCM (2×30 ml). The combined organic layers were washed with brine (30 ml), dried (MgSO$_4$) and concentrated in vacuo. The crude material was purified (flashmaster: 20 g, 100% hex to 50% hex/50% EtOAc over 20 min then to 100% EtOAc over 5 min) to afford the title compound (308 mg, 76%) as a colourless solid. $^1$H NMR (270 MHz; CDCl$_3$) 1.04 (18H, d, J=6.7 Hz, 6×CH$_3$CH), 1.12-1.32 (3H, m, 3×CHCH$_3$), 2.76 (2H, t, J=5.7 Hz, CH$_2$), 3.39 (2H, t, J=5.9 Hz, CH$_2$), 3.73 (3H, s, OCH$_3$), 4.22 (2H, s CH$_2$), 6.46 (1H, s, CH), 6.54 (1H, s, CH), 7.64 (1H, td, J=7.9, 0.5 Hz, CH), 7.82-7.86 (1H, m, CH), 8.0-8.04 (1H, m, CH), 8.11 (1H, t, J=1.3 Hz, CH). $^{13}$C NMR (67.5 MHz; CDCl$_3$) 12.92 (CH), 17.98 (CH$_3$), 27.87 (CH$_2$), 43.95 (CH$_2$), 47.37 (CH$_2$), 55.59 (OCH$_3$), 109.47 (CH), 113.82 (C), 117.24 (C), 120.33 (CH), 123.24 (C), 124.58 (C), 130.23 (CH), 131.22 (CH), 131.48 (CH), 135.88 (CH), 138.84 (C), 144.61 (C), 149.85 (C). LC/MS (ES+) t$_r$=2.59 min, m/z 343.28 (M$^+$−H—SiOiPr$_3$).

2-(2-Cyano-benzenesulfonyl)-6-triisopropylsilyloxy-7-methoxy-1,2,3,4-tetrahydroisoquinoline 175

280 mg, 63%, colourless solid. $^1$H NMR (270 MHz; CDCl$_3$) 1.05 (18H, d, J=6.7 Hz, 6×CH$_3$CH), 1.12-1.26 (3H, m, 3×CHCH$_3$), 2.78 (2H, t, J=5.9 Hz, CH$_2$), 3.57 (2H, t, J=5.9 Hz, CH$_2$), 3.72 (3H, s, OCH$_3$), 4.39 (2H, s CH$_2$), 6.48 (1H, s, CH), 6.54 (1H, s, CH), 7.63-7.77 (2H, m, 2×CH), 7.83 (1H, dd, J=7.4, 1.7 Hz, CH), 8.09(1H, dd, J=7.8, 1.3 Hz, CH). $^{13}$C NMR. (67.5 MHz; CDCl$_3$) 12.92 (CH), 18.00 (CH$_3$), 27.85 (CH$_2$), 43.86 (CH$_2$), 47.17 (CH$_2$), 55.59 (OCH$_3$), 109.60 (CH), 110.96 (C), 116.46 (C), 120.34 (CH), 123.65 (C), 124.81 (C), 130.37 (CH), 131.71 (CH), 132.98 (CH), 135.67 (CH), 140.98 (C), 144.49 (C), 149.73 (C). LC/MS (ES+) t$_r$=2.45 min, m/z 343.41 (M$^+$−H—SiOiPr$_3$).

7-Methoxy-2-(2-methoxy-benzenesulfonyl)-6-triisopropylsilyloxy-1,2,3,4-tetrahydroisoquinoline 176

332 mg, 73%, cream solid. $^1$H NMR (270 MHz; CDCl$_3$) 1.05 (18H, d, J=6.7 Hz, 6×CH$_3$), 1.13-1.29 (3H, m, 3×CH), 2.57 (2H, t, J=5.6 Hz, CH$_2$), 3.54 (2H, t, J=5.6 Hz, CH$_2$), 3.69 (3H, s OCH$_3$), 3.72 (3H, s, OCH$_3$), 4.41 (2H, s, CH$_2$), 6.47 (1H, s, CH), 6.53 (1H, s, CH), 6.88-6.92 (1H, m, CH), 6.99-7.05 (1H, m, CH), 7.44-7.51 (1H, m, CH), 7.94-7.98 (1H, m, CH). LC/MS (ES+) t$_r$=2.26 min, m/z 504.68 (M$^+$−H).

7-Methoxy-2-(4-methoxy-benzenesulfonyl)-6-triisopropylsilyloxy-1,2,3,4-tetrahydroisoquinoline 177

292 mg, 65%, colourless solid. $^1$H NMR (270 MHz; CDCl$_3$) 1.04 (18Hm, d, J=6.8 Hz, 6×CH$_3$CH), 1.12-1.28 (3H, m, 3×CH), 2.76 (2H, t, J=5.8 Hz, CH$_2$), 3.28 (2H, t, J=5.8 Hz, CH$_2$), 3.71 (3H, s, OCH$_3$), 3.84 (3H, s, OCH$_3$), 4.13 (2H, s, CH$_2$), 6.44 (1H, s, CH), 6.54 (1H,s, CH), 6.93-6.98 (2H, m, 2×CH), 7.73-7.76 (2H, m, 2×CH). $^{13}$C NMR (67.5 MHz; CDCl$_3$) 12.91 (3×CH), 17.99 (6×CH$_3$), 28.11 (CH$_2$), 43.95 (CH$_2$), 47.50 (CH$_2$), 55.59 (OCH$_3$), 55.69 (OCH$_3$), 109.66 (CH), 114.27 (2×CH), 120.27 (CH), 124.07 (C), 124.97 (C), 127.96 (C), 129.91 (2×CH), 144.32 (C), 149.63 (C), 163.07 (C). LC/MS (ES+) t$_r$=4.35, m/z 528.67 (M$^+$+Na).

7-Methoxy-2-(2-(methoxycarbonyl)benzenesulfonyl)-6-benzyloxy-1,2,3,4-tetrahydroisoquinoline 177A (456 mg, 88%) was obtained as a pale yellow foam. $^1$H NMR (270 MHz; CDCl$_3$) 2.75 (2H, t, J 5.9 Hz, CH$_2$), 3.47 (2H, t, J 5.9 Hz, CH$_2$), 3.82 (3H, s, OCH$_3$), 3.91 (3H, s, OCH$_3$), 4.34 (2H, s, CH$_2$), 5.08 (2H, s, CH$_2$Ph), 6.56 (1H, s, CH), 6.57 (1H, s, CH), 7.26-7.62 (5H, m, 5×CH), 7.47-7.62 (3H, m, 3×CH), 7.84-7.87 (1H, m, CH). $^{13}$C NMR (67.5 MHz; CDCl$_3$) 28.37 (CH$_2$), 43.62 (CH$_2$), 46.98 (CH$_2$), 53.28 (OCH$_3$), 56.19 (OCH$_3$), 71.12 (CH$_2$), 109.53 (CH), 114.22 (CH), 124.29 (C), 125.14 (C), 127.34 (2×CH), 127.94 (CH), 128.48 (CH), 128.63 (2×CH), 129.08 (CH), 130.26 (CH), 132.53 (CH), 133.61 (C), 135.72 (C), 137.05 (C), 147.08 (C), 148.47 (C), 168.54 (C). LC/MS (APCI−) t$_r$=0.92 min, m/z 466.29 (M−H)$^-$. HPLC t$_r$=2.07 min (>98%).

6-Hydroxy-7-methoxy-2-(3-methoxy-benzenesulfonyl)-1,2,3,4-tetrahydroisoquinoline 178

Hydrogenolysis afforded the title compound (214 mg, 95%) as a colourless solid. mp 168-170° C. $^1$H NMR (270 MHz; CDCl$_3$) 2.79 (2H, t, J=5.9 Hz, CH$_2$), 3.33 (2H, t, J=5.9 Hz, CH$_2$), 3.81 (3H, s, OCH$_3$), 3.83 (3H, s, OCH$_3$), 4.18 (2H, s, CH$_2$), 5.49 (1H, s, OH), 6.47 (1H, s, CH), 6.61 (1H, s, CH), 7.09 (1H, dt, J=6.9, 2.5 Hz, CH), 7.31-7.42 (3H, m, 3×CH). $^{13}$C NMR (67 MHz; CDCl$_3$) 28.25 (CH$_2$), 43.93 (CH$_2$), 47.39 (CH$_2$), 55.76 (OCH$_3$), 56.07 (OCH$_3$), 108.35 (CH), 112.68 (CH), 114.33 (CH), 118.96 (CH), 119.87 (CH), 122.84 (C), 125.80 (C), 130.22 (CH), 137.64 (C), 144.56 (C), 145.41 (C), 159.96 (C). LC/MS (APCI+) t$_r$=3.87 min, m/z 350.53 (M$^+$+H). HPLC t$_r$=3.8 min (>98%).

6-Hydroxy-7-methoxy-2-(3-trifluoromethoxy-benzenesulfonyl)-1,2,3,4-tetrahydroisoquinoline 179

150 mg, 51%, colourless powder. mp 202-203° C. $^1$H NMR (270 MHz; CDCl$_3$) 2.50 (2H, t, J=5.9 Hz, CH), 3.06 (2H, t, J=5.9 Hz, CH$_2$), 3.53 (3H, s, OCH$_3$), 3.89 (2H, s, CH$_2$), 6.23 (1H, s, CH), 6.30 (1H, s, CH), 7.17-7.21 (1H, m, CH), 7.33-7.38 (2H, m, 2×CH), 7.49 (1H, d, J=8.2 Hz, CH), 7.83 (1H, s, OH). $^{13}$C NMR (100 MHz; CDCl$_3$) 27.22 (CH$_2$), 43.21 (CH$_2$), 46.58 (CH$_2$), 55.27 (OCH$_3$), 108.33 (CH), 114.44 (CH), 119.35 (CH), 120.87 (C), 124.32 (C), 124.54 (CH), 125.22 (CH), 130.35 (CH), 137.88 (C), 144.69 (C), 145.80 (C), 148.52 (C). $^{19}$F NMR (376 MHz; CDCl$_3$) -53.07 (OCF$_3$). LC/MS (APCI+) t$_r$=1.09 min, m/z 404.42 (M$^+$+H). HRMS (ES+) calcd. for C$_{17}$H$_{17}$F$_3$NO$_5$S (M$^+$+H) 404.0774, found 404.0770. HPLC t$_r$=4.05 min (>98%).

6-Hydroxy-7-methoxy-2-(toluene-3-sulfonyl)-1,2,3,4-tetrahydroisoquinoline 180

69 mg, 50%, colourless powder. mp 176-179° C. $^1$H NMR (270 MHz; CDCl$_3$) 2.41 (3H, s, CH$_3$), 2.79 (2H, t, J=5.9 Hz, CH), 3.31 (2H, t, J=5.9 Hz, CH$_2$), 3.81 (3H, s, OCH$_3$), 4.16 (2H, s, CH$_2$), 5.48 (1H, s, OH), 6.48 (1H, s, CH), 6.60 (1H, s, CH), 7.33-7.42 (2H, m, 2×CH), 7.60-7.62 (2H, m, 2×CH). $^{13}$C NMR (67.5 MHz; CDCl$_3$) 21.50 (CH$_3$), 28.25 (CH$_2$), 43.91 (CH$_2$), 47.40 (CH$_2$), 56.08 (OCH$_3$), 108.37 (CH), 114.31 (CH), 122.90 (C), 124.94 (CH), 125.84 (C), 128.07 (CH), 128.99 (CH), 133.71 (CH), 136.25 (C), 139.35 (C), 144.44 (C), 145.38 (C). LC/MS (APCI+) t$_r$=3.94 min, m/z 334.46 (M$^+$+H). HRMS (ES+) calcd. for C$_{17}$H$_{20}$NO$_4$S (M$^+$+H) 334.1108, found 334.1111. HPLC t$_r$=3.95 min (>95%).

6-Hydroxy-7-methoxy-2-(3-trifluoromethyl-benzenesulfonyl)-1,2,3,4-tetrahydroisoquinoline 181

300 mg, 93%, colourless powder. mp 178-180° C. $^1$H NMR (270 MHz; CDCl$_3$) 2.78 (2H, t, J=5.9 Hz, CH), 3.38 (2H, t, J=5.9 Hz, CH$_2$), 3.82 (3H, s, OCH$_3$), 4.23 (2H, s, CH$_2$), 5.50 (1H, s, OH), 6.49 (1H, s, CH), 6.59 (1H, s, CH), 7.66 (1H, t, J=7.8 Hz, CH), 7.82 (1H, d, J=7.9 Hz, CH), 8.00 (1H, d, J=7.7 Hz, CH), 8.06 (1H, s, CH). $^{13}$C NMR (100 MHz; CDCl$_3$) 26.95 (CH$_2$), 43.71 (CH$_2$), 46.99 (CH$_2$), 55.57 (OCH$_3$), 110.00 (CH), 115.086 (CH), 121.50 (C), 123.39 (q, J=271.4 Hz, CF$_3$), 123.73 (q, J=3.8 Hz, CH), 124.70 (C), 129.94 (q, J=3.8 Hz, CH), 130.01 (q, J=32.8 Hz, C—CF$_3$), 131.10 (CH), 131.44 (CH), 137.73 (C), 145.29 (C), 146.34 (C). $^{19}$F NMR (376 MHz; CDCl$_3$) −61.31 (CF$_3$). LC/MS (APCI+) t$_r$=4.28 min, m/z 388.44 (M$^+$+H). HPLC t$_r$=3.88 min (>99%). Anal. Calc. for C$_{17}$H$_{16}$F$_3$NO$_4$S: C, 52.71; H, 4.16; N, 3.62. Found: C, 52.4; H, 4.16; N, 3.47%.

2-(3-Chloro-benzenesulfonyl)-6-hydroxy-7-methoxy-1,2,3,4-tetrahydroisoquinoline 182

200 mg, 90%, off-white powder. mp 175-178° C. $^1$H NMR (270 MHz; CDCl$_3$) 2.79 (2H, t, J=5.7 Hz, CH), 3.35 (2H, t, J=6.0 Hz, CH$_2$), 3.82 (3H, s, OCH$_3$), 4.19 (2H, s, CH$_2$), 5.50 (1H, s, OH), 6.49 (1H, s, CH), 6.61 (1H, s, CH), 7.45 (1H, t, J=7.9 Hz, CH), 7.54 (1H, ddd, J=7.9, 2.0, 1.2 Hz, CH), 7.69 (1H, dt, J=7.7, 1.2 Hz, CH), 7.80 (1H, t, J=2.0 Hz, CH). $^{13}$C NMR (67.5 MHz; CDCl$_3$) 28.14 (CH$_2$), 43.91 (CH$_2$), 47.36 (CH$_2$), 56.09 (OCH$_3$), 108.32 (CH), 114.36 (CH), 122.53 (C), 125.67 (C), 125.75 (CH), 127.73 (CH), 130.46 (CH), 133.01 (CH), 135.42 (C), 138.47 (C), 144.57 (C), 145.47 (C). LC/MS (APCI+) t$_r$=4.24 min, m/z 354.44 (M$^+$+H). HRMS (ES+) calcd. for C$_{16}$H$_{17}$ClNO$_4$S (M$^+$+H) 354.0561, found 354.0562. HPLC t$_r$=3.89 min (>96%).

Desilylations

2-(2-Cyano-benzenesulfonyl)-6-hydroxy-7-methoxy-1,2,3,4-tetrahydroisoquinoline 183

Silyl deprotection as described above. 188 mg, 91%, cream solid. mp=164-167° C. $^1$H NMR (270 MHz; CDCl$_3$) 2.80 (2H, t, J=5.9 Hz, CH$_2$), 3.55 (2H, t, J=5.9 Hz, CH$_2$), 3.82 (3H, s, OCH$_3$), 4.41 (2H, s, CH$_2$), 5.52 (1H, s, OH), 6.52 (1H, s, CH), 6.60 (1H, s, CH), 7.63-7.77 (2H, m, 2×CH), 7.84 (1H, dd, J=7.4, 1.5 Hz, CH), 8.09 (1H, dd, J=7.7, 1.2 Hz, CH). $^{13}$C NMR (100 MHz; CDCl$_3$) 27.83 (CH$_2$), 43.62 (CH$_2$), 47.0 (CH$_2$), 55.98 (OCH$_3$), 108.28 (CH), 110.77 (C), 114.28 (CH), 116.27 (C), 122.52 (C), 125.56 (C), 130.23 (CH), 132.65 (CH), 132.88 (CH), 135.55 (CH), 140.95 (C), 144.47 (C), 145.36 (C). LC/MS (ES−) t$_r$=0.93 min, m/z 343 .28 (M$^+$−H). HPLC t$_r$=3.77 min (>99%). Anal. Calc. for C$_{17}$H$_{16}$N$_2$O$_4$S: C, 59.12; H, 4.96; N, 8.11. Found: C, 59.1; H, 4.69; N, 7.89%.

6-Hydroxy-7-methoxy-2-(2-methoxy-benzenesulfonyl)-1,2,3,4-tetrahydroisoquinoline 184

The corresponding silyl compound (332 mg, 0.66 mmol) was desilylated following the method described above to afford the title compound (103 mg, 45%) as a colourless foam. mp 140-142° C. $^1$H NMR (270 MHz; CDCl$_3$) 2.62 (2H, t, J=5.9 Hz, CH$_2$), 3.55 (2H, t, J=5.9 Hz, CH$_2$), 3.71 (3H, s, OCH$_3$), 3.82 (3H, s, OCH$_3$), 4.41 (2H, s, CH$_2$), 5.46 (1H, s, OH), 6.49 (1H, s, CH), 6.61 (1H, s, CH), 6.92 (1H, d, J=8.2 Hz, CH), 7.03 (1H, td, J=7.7, 1.0 Hz, CH), 746-7.51 (1H, m, CH), 7.96 (1H, dd, J=7.7, 1.7 Hz, CH). $^{13}$C NMR (100 MHz; CDCl$_3$) 28.05 (CH$_2$), 43.78 (CH$_2$), 46.79 (CH$_2$), 55.70 (OCH$_3$), 56.00 (OCH$_3$), 108.09 (CH), 111.10 (CH), 114.38 (CH), 120.28 (CH), 123.99 (C), 126.37 (C), 127.15 (C), 131.73 (CH), 134.42 (CH), 144.14 (C), 145.25 (C), 156.91 (C). LC/MS (ES−) t$_r$=1.02 min, m/z 348.27 (M−H)$^-$. HPLC t$_r$=1.35 min (>99%).

6-Hydroxy-7-methoxy-2-(4-methoxy-benzenesulfonyl)-1,2,3,4-tetrahydroisoquinoline 185

177 mg, 95%, colourless solid after recrystallisation from hexane/DCM. mp 147-149° C. $^1$H NMR (270 MHz; CDCl$_3$) 2.79 (2H, t, J=5.9 Hz, CH$_2$), 3.29 (2H, t, J=5.9 Hz, CH$_2$), 3.82 (3H, s, OCH$_3$), 3.85 (3H, s, OCH$_3$), 4.14 (2H, s, CH$_2$), 5.46 (1H, s, OH), 6.47 (1H, s, CH), 6.61 (1H, s, CH), 6.95-6.98 (2H, m, 2×CH), 7.73-7.76 (2H, m, 2×CH). $^{13}$C NMR (67.5 MHz; CDCl$_3$) 28.26 (CH$_2$), 43.88 (CH$_2$), 47.43 (CH$_2$), 55.72 (OCH$_3$), 56.07 (OCH$_3$), 108.41 (CH), 114.29 (2×CH), 122.94 (C), 125.83 (C), 127.97 (C), 129.90 (2×CH), 144.43 (C), 145.40 (C), 163.09 (C). LC/MS (ES−) t$_r$=1.03 min, m/z 348.48 (M−H)$^-$. HPLC t$_r$=1.32 min (>99%).

2-(3-Cyano-benzenesulfonyl)-6-hydroxy-7-methoxy-1,2,3,4-tetrahydroisoquinoline 186

99.5 mg, 75%, yellow solid. mp 204-206° C. $^1$H NMR (270 MHz; CDC$_3$) 2.78 (2H, t, J=5.9 Hz, CH$_2$), 3.39 (2H, t, 5.9 Hz, CH$_2$), 3.84 (3H, s, CH$_3$), 4.23 (2H, s, CH$_2$), 5.50 (1H, s, OH), 6.50 (1H, s, CH), 6.60 (1H,s, CH), 7.65 (1H, t, J=7.9 Hz, CH), 7.84 (1H, dt, J=7.9, 1.4 Hz, CH), 8.03 (1H, dt, J=7.9, 1.4 Hz, CH), 8.09 (1H, t, J=1.5 Hz, CH). $^{13}$C NMR (67.5 MHz; CDCl$_3$) 27.91 (CH$_2$), 43.90 (CH$_2$), 47.37 (CH$_2$), 56.09 (CH$_3$), 108.39 (CH), 113.75 (C), 114.57 (CH), 117.22 (C), 122.01 (C), 125.34 (C), 130.26 (CH), 131.19 (CH), 131.46 (CH), 135.92 (CH), 138.83 (C), 144.87 (C), 145.79 (C). LC/MS (ES−) t$_r$=1.01 min, m/z 343.15 (M$^+$−H). HPLC t$_r$=3.68 min (>99%). Anal. Calc. for C$_{17}$H$_{16}$N$_2$O$_4$S: C 59.29, H 4.68, N 8.13. Found: C 59.2, H 4.71, N 8.08%.

7-Methoxy-2-(2-(methoxycarbonyl)benzenesulfonyl)-6-hydroxy-1,2,3,4-tetrahydroisoquinoline 186A Purification (flashmaster: 20 g, gradient elution hex/EtOAc) afforded the title compound (267 mg, 77%). mp 134-138° C. $^1$H NMR (270 MHz; CDCl$_3$) 2.77 (2H, t, J 5.9 Hz, CH$_2$), 3.48 (2H, t, J 5.9 Hz, CH$_2$), 3.81 (3H, s, OCH$_3$), 3.92 (3H, s, OCH$_3$), 4.33 (2H, s, CH$_2$), 5.51 (1H, s, OH), 6.51 (1H, s, CH), 6.61 (1H, s, CH), 7.46-7.61 (3H, m, 3×CH), 7.84-7.87 (1H, m, CH). $^{13}$C NMR (67.5 MHz; CDCl$_3$) 28.24 (CH$_2$), 43.66 (CH$_2$), 47.01 (CH$_2$), 53.28 (OCH$_3$), 56.09 (OCH$_3$), 108.38 (CH), 114.39 (CH), 123.10 (C), 125.93 (C), 128.48 (CH), 129.06 (CH), 130.28 (CH), 132.53 (CH), 133.61 (C), 135.71 (C), 144.46 (C), 145.42 (C), 168.57 (C). LC/MS (APCI−) t$_r$=0.81 min, m/z 375.91 (M−H)$^-$. HPLC t$_r$=1.54 min (>99%).

Sulfamoylations

2-(3-Cyano-benzenesulfonyl)-7-methoxy-6-O-sulfamoyl-1,2,3,4-tetrahydroisoquinoline 187

50 mg, 58%, colourless solid. mp 183-185° C. $^1$H NMR (270 MHz; DMSO-d$_6$) 2.77 (2H, t, J=5.9 Hz, CH$_2$), 3.35 (2H, brs, under water peak, CH$_2$), 3.74 (3H, s, CH$_3$), 4.26 (2H, s, CH$_2$), 6.97 (1H, s, CH), 7.03 (1H,s, CH), 7.80-7.86 (3H, m, CH and NH$_2$), 8.13 (1H, dt, J=7.9, 1.5 Hz, CH), 8.18 (1H, dt, J=7.9, 1.5 Hz, CH), 8.29 (1H, t, J=3.1 Hz, CH). $^{13}$C NMR (100 MHz; DMSO-d$_6$) 27.05 (CH$_2$), 43.47 (CH$_2$), 47.02 (CH$_2$), 55.87 (CH$_3$), 111.15 (CH), 112.82 (C), 117.56 (C), 122.94 (CH), 124.75 (C), 130.35 (C), 130.92 (CH), 131.08 (CH), 131.76 (CH), 136.84 (C), 137.52 (CH), 137.55 (C), 150.03 (C). LC/MS (ES−) t$_r$=0.94 min, m/z 422.30 (M$^+$−H). HPLC t$_r$=3.37 min (>99%). Anal. Calc. for C$_{17}$H$_{17}$N$_3$O$_6$S$_2$ (H$_2$O): C 46.25, H 4.34, N 9.52. Found: C 46.7, H 4.01, N 9.76%.

7-Methoxy-2-(3-methoxy-benzenesulfonyl)-6-O-sulfamoyl-1,2,3,4-tetrahydroisoquinoline 188

174 mg, 84%, colourless solid. mp 153-156° C. $^1$H NMR (270 MHz; DMSO-d$_6$) 2.77 (2H, t, J=5.5 Hz, CH$_2$), 3.29 (2H, t, J=5.5 Hz, CH$_2$), 3.74 (3H, s, OCH$_3$), 3.83 (3H, s, OCH$_3$), 4.19 (2H, s, CH$_2$), 7.00 (1H, s, CH), 7.05 (1H, s, CH), 7.26-7.30 (2H, m, 2×CH), 7.39 (1H, d, J=7.7 Hz, CH), 7.57 (1H, t, J=7.7 Hz, CH), 7.89 (2H, s, NH$_2$). $^{13}$C NMR (67 MHz; DMSO-d$_6$) 27.80 (CH$_2$), 44.08 (CH$_2$), 47.67 (CH$_2$), 56.22 (OCH$_3$), 56.40 (OCH$_3$), 111.73 (CH), 112.81 (CH), 119.66 (CH), 119.95 (CH), 123.44 (CH), 123.36 (C), 131.01 (C), 131.30 (CH), 137.634 (C), 137.99 (C), 150.54 (C), 160.10 (C). LC/MS (APCI+) t$_r$=3.62 min, m/z 429.52 (M$^+$+H). HPLC t$_r$=3.34 min (>99%). Anal. Calc. for C$_{17}$H$_{20}$N$_2$O$_7$S$_2$: C 47.65, H 4.70, N 6.54. Found: C 47.0, H 4.65, N 6.48%.

7-Methoxy-6-O-sulfamoyl-2-(3-trifluoromethyl-benzenesulfonyl)-1,2,3,4-tetrahydroisoquinoline 189

176 mg, 69% colourless powder. mp 165-166.5° C. $^1$H NMR (270 MHz; DMSO-d$_6$) 2.76 (2H, t, J=5.9 Hz, CH), 3.39 (2H, t, J=5.9 Hz, CH$_2$), 3.74 (3H, s, OCH$_3$), 4.28 (2H, s, CH$_2$), 7.00 (1H, s, CH), 7.02 (1H, s, CH), 7.86-7.92 (2H, m, 2×CH), 7.89 (2H, s, NH$_2$), 8.04 (1H, s, CH), 8.09-8.17 (2H, m, 2×CH). $^{13}$C NMR (100 MHz; DMSO-d$_6$) 26.94 (CH$_2$), 43.44 (CH$_2$), 47.00 (CH$_2$), 55.85 (OCH$_3$), 111.16 (CH), 112.90 (CH), 123.35 (q, J=267.5 Hz, CF$_3$), 123.74 (q, J=3.8 Hz, CH), 124.69 (C), 130.06 (q, J=3.0 Hz, CH), 130.07 (q, J=32.7 Hz, C—CF$_3$), 130.32 (C), 131.20 (CH), 131.44 (CH), 137.53 (C), 137.72 (C), 150.03 (C). LC/MS (APCI−) t$_r$=1.08 min, m/z 465.36 (M$^+$−H). HPLC t$_r$=4.08 min (>99%). Anal. Calcd. for C$_{17}$H$_{17}$F$_3$N$_2$O$_6$S$_2$: C 43.77, H 3.67, N 6.01. Found: C 43.7, H 3.72, N 5.90%.

2-(3-Chloro-benzenesulfonyl)-7-methoxy-6-O-sulfamoyl-1,2,3,4-tetrahydroisoquinoline 190

119 mg, 65%, colourless powder.mp 154-155° C. $^1$H NMR (270 MHz; DMSO-d$_6$) 2.78 (2H, t, J=5.9 Hz, CH), 3.27-3.39 (2H, m, overlapping CH$_2$), 3.74 (3H, s, OCH$_3$), 4.23 (2H, s, CH$_2$), 7.00 (1H, s, CH), 7.04 (1H, s, CH), 7.64-7.70 (1H, m, CH), 7.78-7.83 (3H, m, 3×CH), 7.88 (2H, s, NH$_2$). $^{13}$C NMR (67.5 MHz; DMSO-d$_6$) 27.70 (CH$_2$), 44.02 (CH$_2$), 47.59 (CH$_2$), 56.40 (OCH$_3$), 111.72 (CH), 123.46 (CH), 125.29 (C), 126.63 (CH), 127.44 (CH), 130.90 (C), 132.10 (CH), 133.84 (CH), 134.72 (CH), 138.03 (C), 138.55 (C), 150.55 (C). LC/MS (ES−) t$_r$=4.03 min, m/z 431.17 (M−H)$^-$. HPLC t$_r$=4.90 min (>96%).

7-Methoxy-6-O-sulfamoyl-2-(toluene-3-sulfonyl)-1,2,3,4-tetrahydroisoquinoline 191

26 mg, 47%, colourless powder after recrystallisation from EtOH. mp 161-163° C. $^1$H NMR (270 MHz; DMSO-d$_6$) 2.40

(3H, s, CH$_3$), 2.77 (2H, t, J=5.9 Hz, CH), 3.27 (2H, t, J=5.9 Hz, CH$_2$), 3.74 (3H, s, OCH$_3$), 4.16 (2H, s, CH$_2$), 6.99 (1H, s, CH), 7.04 (1H, s, CH), 7.51-7.63 (4H, m, 4×CH), 7.88 (2H, s, NH$_2$). $^{13}$C NMR (67.5 MHz; DMSO-d$_6$) 21.40 (CH$_3$), 27.79 (CH$_2$), 44.07 (CH$_2$), 47.67 (CH$_2$), 56.41 (OCH$_3$), 111.73 (CH), 123.43 (CH), 125.13 (CH), 125.36 (C), 128.11 (CH), 129.86 (CH), 131.01 (C), 134.47 (CH), 136.30 (C), 137.99 (C), 139.85 (C), 150.53 (C). LC/MS (ES−) t$_r$=0.99 min, m/z 411.28 (M$^+$−H). HPLC t$_r$=3.60 min (>97%).

7-Methoxy-6-O-sulfamoyl-2-(3-trifluoromethoxy-benzenesulfonyl)-1,2,3,4-tetrahydroisoquinoline 192

130 mg, 79%, colourless powder. mp 165-167° C. $^1$H NMR (270 MHz; DMSO-d$_6$) 2.77 (2H, t, J=5.9 Hz, CH), 3.33-3.41 (2H, m, CH$_2$), 3.74 (3H, s, OCH$_3$), 4.25 (2H, s, CH$_2$), 6.99 (1H, s, CH), 7.04 (1H, s, CH), 7.76-7.83 (3H, m, 3×CH), 7.87 (1H, t, J=1.8 Hz, CH), 7.89 (2H, brs, NH$_2$). $^{13}$C NMR (100 MHz; DMSO-d$_6$) 27.05 (CH$_2$), 43.47 (CH$_2$), 47.00 (CH$_2$), 55.86 (OCH$_3$), 111.15 (CH), 119.94 (CH), 122.93 (CH), 124.72 (C), 125.97 (CH), 126.56 (CH), 130.30 (CH), 132.03 (CH), 137.53 (C), 138.35 (C), 148.44 (C), 150.04 (C), CF$_3$ too weak to be seen. $^{19}$F NMR (376 MHz; DMSO-d$_6$) −55.99 (CF$_3$). LC/MS (ES−) t$_r$=0.98 min, m/z 481.09 (M$^+$−H). HPLC t$_r$=3.89 min (>99%). Anal. Calc. for C$_{17}$H$_{17}$F$_3$N$_2$O$_7$S$_2$: C 42.32, H 3.55, N 5.81. Found: C 42.4, H 3.57, N 5.65.

2-(2-Cyano-benzenesulfonyl)-7-methoxy-6-O-sulfamoyl-1,2,3,4-tetrahydroisoquinoline 193

90 mg, 90%, colourless foam. mp 194-197° C. $^1$H NMR (270 MHz; DMSO-d$_6$) 2.80 (2H, t, J=5.9 Hz, CH$_2$), 3.53 (2H, t, J=5.9 Hz, CH$_2$), 3.74 (3H, s, OCH$_3$), 4.38 (2H, s, CH$_2$), 6.97 (1H, s, CH), 7.07 (1H, s, CH), 7.86-7.94 (3H, m, CH and NH$_2$), 7.98 (1H, dd, J=7.7, 1.5 Hz, CH), 8.11 (1H, dd, J=7.7, 1.0 Hz, CH), 8.16 (1H, dd, J=7.2, 1.7 Hz, CH). $^{13}$C NMR (100 MHz; DMSO-d$_6$) 27.08 (CH$_2$), 43.10 (CH$_2$), 46.64 (CH$_2$), 55.91 (OCH$_3$), 109.42 (C), 111.08 (CH), 116.36 (C), 123.11 (CH), 124.80 (C), 130.13 (CH), 130.39 (CH), 133.79 (CH), 134.10 (CH), 136.32 (CH), 137.54 (C), 139.42 (C), 150.11 (C). LC/MS (ES−) t$_r$=0.98 min, m/z 422.30 (M$^+$+H). Anal. Calc. for C$_{17}$H$_{17}$N$_3$O$_6$S$_2$: C 48.22, H 4.05, N 9.92. Found: C 48.3, H 4.02, N 9.96%.

7-Methoxy-2-(2-methoxy-benzenesulfonyl)-6-O-sulfamoyl-1,2,3,4-tetrahydroisoquinoline 194

74 mg, 69%), colourless powder. mp 160-163° C. $^1$H NMR (270 MHz; DMSO-d$_6$) 2.62 (2H, t, J=5.9 Hz, CH$_2$), 3.47 (2H, t, J=5.9 Hz, CH$_2$), 3.72 (3H, s, OCH$_3$), 3.74 (3H, s, OCH$_3$), 4.37 (2H, s, CH$_2$), 7.0 (1H, s, CH), 7.04 (1H, s, CH), 7.11 (1H, td, J=7.7, 1.0 Hz, CH), 7.18 (1H, d, J=7.9 Hz, CH), 7.59-7.66 (1H, m, CH), 7.82 (1H, dd, J=7.9, 1.7 Hz, CH), 7.85 (2H, brs, NH$_2$). $^{13}$C NMR (100 MHz; DMSO-d$_6$) 27.21 (CH$_2$), 43.04 (CH$_2$), 46.64 (CH$_2$), 55.83 (OCH$_3$), 55.90 (OCH$_3$), 108.98 (CH), 112.94 (CH), 120.21 (CH), 122.96 (CH), 125.26 (C), 126.43 (C), 130.68 (CH), 131.54 (C), 134.99 (CH), 137.30 (C), 149.99 (C), 156.63 (C). LC/MS (ES+) t$_r$=0.97 min, m/z 451.38 (M$^+$+H). HPLC t$_r$=1.27 min (>99%). Anal. Calcd. for C$_{17}$H$_{20}$N$_2$O$_7$S$_2$: C 47.65, H 4.70, N 6.54. Found: C 47.7, H 4.73, N 6.54%.

7-Methoxy-2-(4-methoxy-benzenesulfonyl)-6-O-sulfamoyl-1,2,3,4-tetrahydroisoquinoline 195

147 mg, 72%, colourless solid. mp 83-86° C. $^1$H NMR (270 MHz; DMSO-d$_6$) 2.78 (2H, t, J=5.8 Hz, 2H, t, J=5.8 Hz, CH$_2$), 3.74 (3H, s, OCH$_3$), 3.84 (3H, s, OCH$_3$), 4.12 (2H, s, CH$_2$), 6.98 (1H, s, CH), 7.05 (1H, s, CH), 7.13-7.18 (2H, m, 2×CH), 7.72-7.77 (2H, m, 2×CH), 7.88 (2H, brs, NH$_2$). $^{13}$C NMR (67.5 MHz; DMSO-d$_6$) 28.87 (CH$_2$), 44.04 (CH$_2$), 47.72 (CH$_2$), 56.30 (OCH$_3$), 56.41 (OCH$_3$), 111.74 (CH), 115.17 (2×CH), 123.44 (CH), 125.38 (C), 127.73 (C), 130.25 (2×CH), 131.04 (C), 138.0 (C), 150.55 (C), 163.35 (C). LC/MS (ES+) t$_r$=1.0 min, m/z 451.38 (M$^+$+Na). Anal. Calcd. for C$_{17}$H$_{20}$N$_2$O$_7$S$_2$: C 47.65, H 4.70, N 6.54. Found: C 47.7, H 4.78, N 6.31%. HPLC t$_r$=1.22 min (>99%).

7-Methoxy-2-(2-(methoxycarbonyl)benzenesulfonyl)-6-O-sulfamoyl-1,2,3,4-tetrahydroisoquinoline 195A Purification (flashmaster: 10 g, gradient elution hex/EtOAc) afforded the title compound (138 mg, 71%) as a colourless powder. mp 136-138° C. $^1$H NMR (270 MHz; DMSO-d$_6$) 2.76 (2H, t, J=5.6 Hz, CH$_2$), 3.46 (2H, t, J=5.8 Hz, CH$_2$), 3.76 (3H, s, OCH$_3$), 3.86 (3H, s, OCH$_3$), 4.37 (2H, s, CH$_2$), 6.97 (2H, s, CH), 7.06 (2H, s, CH), 7.62-7.79 (3H, m, 3×CH), 7.89 (2H, brs, NH$_2$), 7.91-7.95 (1H, m, CH). $^{13}$C NMR (67.5 MHz; DMSO-d$_6$) 27.81 (CH$_2$), 43.60 (CH$_2$), 47.24 (CH$_2$), 53.52 (OCH$_3$), 56.46 (OCH$_3$), 111.52 (CH), 123.63 (CH), 125.50 (C), 128.99 (CH), 129.39 (CH), 131.26 (C), 131.42 (CH), 133.36 (C), 133.75 (CH), 135.43 (C), 138.01 (C), 150.62 (C), 168.37 (C). LC/MS (APCI−) t$_r$=0.82 min, m/z 454.89 (M−H)$^−$. HPLC t$_r$=1.46 min (>99%). Anal. Calcd. for C$_{18}$H$_{20}$N$_2$O$_8$S$_2$: C 47.36, H 4.42, N 6.14. Found C 47.4, H 4.31, N 6.01%.

N-Sulfonyl tetrahydroisoquinolinones

6-Benzyloxy-7-methoxy-2-(3-methoxy-benzenesulfonyl)-3,4-dihydro-2H-isoquinolin-1-one 196

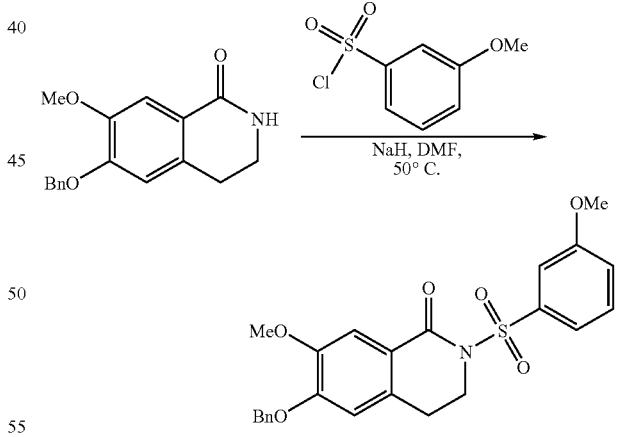

To a suspension of sodium hydride (60% dispersion in mineral oil, 46 mg, 1.9 mmol) in DMF (5 ml) was added the isoquinlone (300 mg, 1.0 mmol) and the reaction mixture was heated at 50° C. for 30 min. The reaction mixture was cooled to rt and 3-methoxybenzenesulfonyl chloride (0.15 ml, 1.0 mmol) was added dropwise. The reaction mixture was stirred for 3.5 h and turned from yellow to almost colourless after addition of the sulfonyl chloride. A further 0.5 eq (0.07 ml) of the sulfonyl chloride was added and the reaction mixture stirred for a further 2 h. The reaction mixture was poured into sat. aq. NaHCO$_3$ (100 ml) and extracted with chloroform (3×50 ml). The combined organic layers were washed with water (4×50 ml) and brine (50 ml), dried (MgSO$_4$) and concentrated in vacuo. Purification by column chromatography eluting with hex:EtOAc; 2:1 afforded the title compound (129 mg, 27%) as a colourless foam. mp 140-145° C. $^1$H NMR (270 MHz; CDCl$_3$) 2.99 (2H, t, J=6.2 Hz, CH$_2$), 3.84 (3H, s, OCH$_3$), 3.87 (3H, s, OCH$_3$), 4.18 (2H, t, J=6.2 Hz; CH$_2$), 5.18 (2H, s, CH$_2$Ph), 6.64 (1H, s, CH), 7.12 (1H, ddd, J=8.2, 2.7, 1.0 Hz, CH), 7.31-7.44 (6H, m, 6×CH), 7.47 (1H, s, CH), 7.58-7.63 (2H, m, 2×CH). $^{13}$C NMR (100 MHz; CDCl$_3$) 28.54 (CH$_2$), 45.07 (CH$_2$), 55.69 (OCH$_3$), 56.10 (OCH$_3$), 70.83 (CH$_2$), 111.02 (CH), 111.11 (CH), 113.16 (CH), 119.94 (CH), 120.30 (CH), 120.59 (C), 127.12 (2×CH), 128.20 (CH), 128.71 (2×CH), 129.77 (CH), 133.44 (C), 135.88 (C), 140.39 (C), 148.79 (C), 152.59 (C), 159.50 (C), 163.27 (C). LC/MS (ES+) t$_r$=1.19 min, m/z 476.50 (M$^+$+Na). HPLC t$_r$=4.34 min (>98%).

6-Benzyloxy-7-methoxy-2-(2-methoxy-benzenesulfonyl)-3,4-dihydro-2H-isoquinolin-1-one 197

314 mg, 65%, colourless solid. mp 202-203° C. $^1$H NMR (270 MHz; CDCl$_3$) 2.99 (2H, t, J=6.3 Hz, CH$_2$), 3.80 (3H, s, OCH$_3$), 3.88 (3H, s, OCH$_3$), 4.24 (2H, t, J=6.3 Hz, CH$_2$), 5.19 (2H, s, CH$_2$Ph), 6.66 (1H, s, CH), 6.96 (1H, d, J=8.2 Hz, CH), 7.14 (1H, td, J=7.6, 1.0 Hz, CH), 7.31-7.44 (6H, m, 6×CH), 7.52-7.58 (1H, m, CH), 8.20 (1H, dd, J=7.9, 1.7 Hz, CH). $^{13}$C NMR (67.5 MHz; CDCl$_3$) 28.53 (CH$_2$), 45.34 (CH$_2$), 56.17 (OCH$_3$), 56.28 (OCH$_3$), 111.07 (CH), 111.21 (CH), 112.06 (CH), 120.75 (CH), 120.92 (C), 127.25 (2×CH), 127.52 (C), 128.30 (CH), 128.84 (2×CH), 132.44 (CH), 133.65 (C), 135.44 (CH), 136.09 (C), 148.78 (C), 152.52 (C), 156.60 (C), 163.37 (C). LC/MS (ES+) t$_r$=1.08 min, m/z 454.46 (M$^+$+H). HPLC t$_r$=1.52 min (>99%). Anal. Calcd. for C$_{24}$H$_{23}$NO$_6$S: C 63.56, H 5.11, N 3.09. Found: C 63.5, H 5.11, N 3.20%.

6-Benzyloxy-7-methoxy-2-(4-methoxy-benzenesulfonyl)-3,4-dihydro-2H-isoquinolin-1-one 198

152 mg, 32%, colourless oil. $^1$H NMR (270 MHz; CDCl$_3$) 2.97 (2H, t, J=6.3 Hz, CH$_2$), 3.82 (3H, s, OCH$_3$), 3.87 (3H, s, OCH$_3$), 4.16 (2H, t, J=6.3 Hz, CH$_2$), 5.17 (2H, s, CH$_2$Ph), 6.63 (1H, s, CH), 6.95-6.99 (2H, m, 2×CH), 7.28-7.41 (5H, m, 5×CH, phenyl), 7.46 (1H, s, CH), 7.98-8.03 (2H, m, 2×CH). $^{13}$C NMR (67.5 MHz; CDCl$_3$) 28.66 (CH$_2$), 44.99 (CH$_2$), 55.74 (OCH$_3$), 56.20 (OCH$_3$), 70.95 (CH$_2$Ph), 111.12 (CH), 111.24 (CH), 114.00 (CH), 120.86 (C), 127.23 (CH), 128.29 (CH), 128.82 (CH), 130.78 (C), 130.93 (CH), 133.51 (C), 136.04 (C), 148.88 (C), 152.61 (C), 163.45 (C), 163.70 (C). LC/MS (ES+) t$_r$=1.16 min, m/z 454.60 (M$^+$+H). HPLC t$_r$=1.62 min (>92%).

6-Benzyloxy-2-(3-chloro-benzenesulfonyl)-7-methoxy-3,4-dihydro-2H-isoquinolin-1-one 199

259 mg, 54%, yellow foam. mp 155-158° C. $^1$H NMR (270 MHz; CDCl$_3$) 3.00 (2H, t, J=6.2 Hz, CH$_2$), 3.83 (3H, s, OCH$_3$), 4.18 (2H, t, J=6.2 Hz, CH$_2$), 5.18 (2H, s, CH$_2$Ph), 6.65 (1H, s, CH), 7.27-7.49 (7H, m, 7×CH), 7.57 (1H, ddd, J=7.9, 2.0, 1.2 Hz, CH), 7.96-8.01 (1H, m, CH). $^{13}$C NMR (67.5 MHz; CDCl$_3$) 28.65 (CH$_2$), 45.23 (CH$_2$), 56.23 (OCH$_3$), 70.96 (CH$_2$Ph), 111.05 (CH), 111.25 (CH), 120.41 (C), 126.94 (CH), 127.24 (CH), 128.34 (CH), 128.41 (CH), 128.85 (CH), 130.13 (CH), 133.62 (C), 133.84 (CH), 134.98 (C), 135.93 (C), 140.95 (C), 148.97 (C), 152.87 (C), 163.41 (C). LC/MS (ES+) t$_r$=5.66 min, m/z 458.52 (M$^+$+H). HPLC t$_r$=1.87 min, >97%.

6-Benzyloxy-7-methoxy-2-(3-carboxymethyl-benzenesulfonyl)-3,4-dihydro-2H-isoquinolin-1-one 199A (176 mg, 35%) was obtained as a colourless powder. Recrystallisation from DCM and hexane afforded a pure sample. $^1$H NMR (270 MHz; CDCl$_3$) 3.05 (2H, t, J 6.2 Hz, CH$_2$), 3.83 (3H, s, OCH$_3$), 3.92 (3H, s, OCH$_3$), 4.19 (2H, t, J 6.2 Hz, CH$_2$), 5.18 (2H, s, CH$_2$Ph), 6.65 (1H, s, CH), 7.28-7.41 (5H, m, 5×CH), 7.46 (1H, s, CH), 7.61-7.71 (3H, m, 3×CH), 8.55 (1H, dd, J 6.4, 2.0 Hz, CH). $^{13}$C NMR (67.5 MHz; CDCl$_3$) 28.33 (CH$_2$), 44.88 (CH$_2$), 53.19 (OCH$_3$), 56.19 (OCH$_3$), 70.94 (CH$_2$), 111.00 (CH), 111.26 (CH), 120.74 (C), 127.25 (2×CH), 128.28 (CH), 128.82 (2×CH), 129.07 (CH), 130.57 (CH), 132.30 (C), 133.36 (CH), 133.73 (CH), 133.95 (C), 136.07 (C), 137.87 (C), 148.79 (C), 152.66 (C), 163.52 (C), 167.24 (C). LC/MS (APCI–) t$_r$=0.95 min, m/z 482.29 (M–H)$^-$. HPLC t$_r$=2.0 min (>99%).

Debenzylations

6-Hydroxy-7-methoxy-2-(2-methoxy-benzenesulfonyl)-3,4-dihydro-2H-isoquinolin-1-one 200

145 mg, 57%, colourless powder. mp 222-224° C. $^1$H NMR (270 MHz; CDCl$_3$) 3.02 (2H, t, J=6.3 Hz, CH$_2$), 3.81 (3H, s, OCH$_3$), 3.88 (3H, s, OCH$_3$), 4.25 (2H, t, J=6.3 Hz, CH$_2$), 6.07 (1H, s, OH), 6.72 (1H, s, CH), 6.96 (1H, d, J=8.4 Hz, CH), 7.12 (1H, t, J=7.7 Hz, CH), 7.42 (1H, s, CH), 7.51-7.58 (1H, m, CH), 8.19 (1H, dd, J=7.9, 1.7 Hz, CH). $^{13}$C NMR (67.5 MHz; CDCl$_3$) 28.35 (CH$_2$), 45.32 (CH$_2$), 56.26 (CH$_3$), 56.27 (OCH$_3$), 110.66 (CH), 112.07 (CH), 112.89 (CH), 120.44 (C), 120.73 (CH), 132.44 (CH), 134.59 (C), 135.39 (CH), 145.94 (C), 150.51 (C), 156.62 (C), 163.38 (C). LC/MS (ES–) t$_r$=1.0 min, m/z 362.33 (M–H)$^-$. HPLC t$_r$=1.24 min (>99%). Anal. Calcd. for C$_{17}$H$_{17}$NO$_6$S: C 56.19, H 4.72, N 3.85. Found: C 55.7, H 4.68, N 3.85%.

6-Hydroxy-7-methoxy-2-(3-methoxy-benzenesulfonyl)-3,4-dihydro-2H-isoquinolin-1-one 201

48 mg, 50%, colourless solid. mp 195-197° C. $^1$H NMR (270 MHz; CDCl$_3$) 3.02 (2H, t, J=6.3 Hz, CH$_2$), 3.84 (3H, s, OCH$_3$), 3.86 (3H, s, OCH$_3$), 4.19 (2H, t, J=6.3 Hz; CH$_2$), 6.07 (1H, s, OH), 6.71 (1H, s, CH), 7.11 (1H, ddd, J=8.4, 2.6, 1.0 Hz, CH), 7.41 (1H, t, J=8.1 Hz, CH), 7.45 (1H, s, CH), 7.57-7.63 (2H, m, 2×CH). $^{13}$C NMR (100 MHz; CDCl$_3$) 28.42 (CH$_2$), 45.10 (CH$_2$), 55.70 (OCH$_3$), 56.21 (OCH$_3$), 110.63 (CH), 112.82 (CH), 113.13 (CH), 119.96 (CH), 120.15 (C), 120.34 (CH), 129.78 (CH), 134.43 (C), 140.51 (C), 145.93 (C), 150.60 (C), 159.54 (C), 163.31 (C). LC/MS (ES–) t$_r$=1.08 min, m/z 362.42 (M–H)$^-$. HPLC t$_r$=1.28 min (>99%). Anal. Calcd. for C$_{17}$H$_{17}$NO$_6$S: C 56.19, H 4.72, N 3.85. Found: C 56.0, H 4.80, N 3.67%.

6-Hydroxy-7-methoxy-2-(4-methoxy-benzenesulfonyl)-3,4-dihydro-2H-isoquinolin-1-one 202

74 mg, 62%, colourless powder. mp 202-204° C. $^1$H NMR (270 MHz; CDCl$_3$) 3.0 (2H, t, J=6.3 Hz, CH$_2$), 3.84 (3H, s, OCH$_3$), 3.85 (3H, s, OCH$_3$), 4.17 (2H, t, J=6.2 Hz, CH$_2$), 6.08 (1H, s, OH), 6.70 (1H, s, CH), 6.95-6.99 (2H, m, 2×CH), 7.45 (1H, s, CH), 7.99-8.03 (2H, m, 2×CH). $^{13}$C NMR (100 MHz; CDCl$_3$) 23.37 (CH$_2$), 44.89 (CH$_2$), 55.63 (OCH$_3$), 56.16 (OCH$_3$), 110.51 (CH), 112.77 (CH), 113.89 (2×CH), 120.21 (C), 130.68 (C), 130.80 (2×CH), 134.37 (C), 145.87 (C), 150.45 (C), 163.39 (C), 163.57. LC/MS (ES−) $t_r$=1.25 min, m/z 362.33 (M−H)⁻. HPLC $t_r$=1.25 min (>99%).

2-(3-Chloro-benzenesulfonyl)-6-hydroxy-7-methoxy-3,4-dihydro-2H-isoquinolin-1-one 203

158 mg, 82%, colourless solid. mp 178-181° C. ¹H NMR (270 MHz; CDCl₃) 3.03 (2H, t, J=6.2 Hz, CH₂), 3.85 (3H, s, OCH₃), 4.19 (2H, t, J=6.3 Hz; CH₂), 6.11 (1H, s, OH), 6.72 (2H, s, CH₂), 7.44 (1H, s, CH), 7.44-7.50 (1H, m, CH), 7.54-7.59 (1H, m, CH), 7.96-8.0 (1H, m, CH, 8.02 (1H, t, J=1.5 Hz, CH). ¹³C NMR (67.5 MHz; CDCl₃) 28.46 (CH₂), 45.25 (CH₂), 56.31 (OCH₃), 110.64 (CH), 113.02 (CH), 119.89 (C), 126.87 (CH), 128.45 (CH), 130.11 (CH), 133.80 (CH), 134.58 (C), 134.95 (C), 140.99 (C), 146.11 (C), 150.93 (C), 163.44 (C). LC/MS (ES−) $t_r$=1.12 min, m/z 366.46 (M−H)⁻. HPLC $t_r$=1.38 min (>99%). Anal. Calcd. for C₁₆H₁₄ClNO₅S: C 52.25, H 3.84, N 3.81. Found: C 52.0, H 4.02, N 3.66%.

6-Hydroxy-7-methoxy-2-(3-carboxymethyl-benzenesulfonyl)-3,4-dihydro-2H-isoquinolin-1-one 203A Purification (flashmaster: 20 g, gradient elution hex/EtOAc) afforded the title compound (99 mg, 76%) as a colourless solid. mp 236-239° C. ¹H NMR (270 MHz; CDCl₃) 3.08 (2H, t, J=6.2 Hz, CH₂), 3.83 (3H, s, OCH₃), 3.93 (3H, s, OCH₃), 4.19 (2H, t, J=6.2 Hz, CH₂), 6.08 (1H, s, OH), 6.71 (1H, s, CH), 7.44 (1H, s, CH), 7.60-7.70 (3H, m, 3×CH), 8.54 (1H, dd, J=6.2, 1.7 Hz, CH). ¹³C NMR (67.5 MHz; CDCl₃) 28.15 (CH₂), 44.88 (CH₂), 53.21 (OCH₃), 56.26 (OCH₃), 110.52 (CH), 112.92 (CH), 120.23 (C), 129.06 (CH), 130.53 (CH), 132.43 (C), 133.34 (CH), 133.70 (CH), 134.91 (C), 137.91 (C), 145.90 (C), 150.62 (C), 163.55 (C), 167.25 (C). LC/MS (APCI−) $t_r$=0.86 min, m/z 390.08 (M−H)⁻. HPLC $t_r$=1.56 min (>99%). Anal. Calcd. for C₁₈H₁₇NO₇S: C 55.24, H 4.38, N 3.58. Found: C 55.3, H 3.42, N 4.42%.

Sulfamoylations

7-Methoxy-2-(2-methoxy-benzenesulfonyl)-6-O-sulfamoyl-3,4-dihydro-2H-isoquinolin-1-one 204

115 mg, 75%, white powder. mp 195-197° C. ¹H NMR (270 MHz; DMSO-d₆) 3.09 (2H, t, J=6.2 Hz, CH₂), 3.78 (3H, s, OCH₃), 3.89 (3H, s, OCH₃), 4.18 (2H, t, J=6.2 Hz, CH₂), 7.18 (1H, t, J=7.7 Hz, CH), 7.24 (1H, d, J=8.4 Hz, CH), 7.37 (1H, s, CH), 7.44 (1H, s, CH), 7.68 (1H, td, J=8.4, 1.6 Hz, CH), 7.79 (1H, dd, J=7.8, 1.6 Hz, CH), 8.14 (2H, brs, NH₂). ¹³C NMR (67.5 MHz; DMSO-d₆) 27.71 (CH₂), 45.60 (CH₂), 56.60 (OCH₃), 57.04 (OCH₃), 112.62 (CH), 113.61 (CH), 120.81 (CH), 122.47 (CH), 126.45 (C), 127.27 (C), 131.84 (CH), 133.50 (C), 136.34 (CH), 143.36 (C), 151.28 (C), 156.96 (C), 162.42 (C). LC/MS (ES−) $t_r$=0.96 min, m/z 441.17 (M−H)⁻. HPLC $t_r$=1.24 min (>99%). Anal. Calcd. for C₁₇H₁₈N₂O₈S₂: C 46.15, H 4.10, N 6.33. Found: C 45.8, H 4.04, N 6.20%

7-Methoxy-2-(3-methoxy-benzenesulfonyl)-6-O-sulfamoyl-3,4-dihydro-2H-isoquinolin-1-one 205

18 mg, 49%, colourless powder. mp 164-166° C. ¹H NMR (270 MHz; DMSO-d₆) 3.12 (2H, t, J=6.1 Hz, CH₂), 3.78 (3H, s, OCH₃), 3.84 (3H, s, OCH₃), 4.21 (2H, t, J=6.1 Hz, CH₂), 7.30 (1H, dt, J=7.6, 2.1 Hz, CH), 7.36 (1H, s, CH), 7.47 (2H, brs, 2×CH), 7.52-7.61 (2H, m, 2×CH), 8.15 (2H, brs, NH₂). LC/MS (ES−) $t_r$=1.0 min, m/z 441.38 (M−H)⁻. HPLC $t_r$=1.27 min (>99%).

7-Methoxy-2-(4-methoxy-benzenesulfonyl)-6-O-sulfamoyl-3,4-dihydro-2H-isoquinolin-1-one 206

30 mg, 56%, colourless solid. mp 177-180° C. ¹H NMR (400 MHz; DMSO-d₆) 3.09 (2H, t, J=6.0 Hz, CH₂), 3.79 (3H, s, OCH₃), 3.86 (3H, s, OCH₃), 4.17 (2H, t, J=6.2 Hz, CH₂), 7.12-7.16 (2H, m, 2×CH), 7.34 (1H, s, CH), 7.46 (1H, s, CH), 7.94-7.97 (2H, m, 2×CH), 8.13 (2H, brs, NH₂). ¹³C NMR (100 MHz; DMSO-d₆) 27.21 (CH₂), 44.75 (CH₂), 55.84 (OCH₃), 56.05 (OCH₃), 111.99 (CH), 114.22 (2×CH), 121.85 (CH), 125.79 (C), 130.10 (C), 130.55 (2×CH), 132.94 (C), 142.85 (C), 150.69 (C), 162.06 (C), 163.36 (C). LC/MS (ES−) $t_r$=0.94 min, m/z 441.31 (M−H)⁻. HPLC $t_r$=1.28 min (>99%). Anal. Calcd. for C₁₇H₁₈N₂O₈S₂: C 46.15, H 4.10, N 6.33, Found : C 45.8, H 4.08, N 6.21%.

2-(3-Chloro-benzenesulfonyl)-7-methoxy-6-O-sulfamoyl-3,4-dihydro-2H-isoquinolin-1-one 207

132 mg, 90%, colourless solid. mp 170-173° C. ¹H NMR (270 MHz; DMSO-d₆) 3.14 (2H, t, J=6.2 Hz, CH₂), 3.79 (3H, s, OCH₃), 4.24 (2H, t, J=6.2 Hz; CH₂), 7.37 (1H, s, CH), 7.48 (1H, s, CH), 7.68 (1H, t, J=8.0 Hz, CH), 7.82-7.85 (1H, m, CH), 8.0 (1H, d, J=8.2 Hz, CH), 8.06 (1H, s, CH), 8.17 (2H, s, NH₂). ¹³C NMR (67.5 MHz; DMSO-d₆) 27.73 (CH₂), 45.51 (CH₂), 56.65 (OCH₃), 112.62 (CH), 122.46 (CH), 126.02 (C), 127.33 (CH), 128.22 (CH), 131.77 (CH), 133.68 (C), 134.14 (C), 134.58 (CH), 141.17 (C), 143.59 (C), 151.28 (C), 162.86 (C). LC/MS (ES−) $t_r$=1.02 min, m/z 445.30 (M−H)⁻. HPLC $t_r$=1.28 min (>97%). Anal. Calcd. for C₁₆H₁₅ClN₂O₇S₂: C 43.0, H 3.38, N 6.27. Found: C 42.9, H 3.43, N 6.20%.

6-O-Sulfamoyl-7-methoxy-2-(3-carboxymethyl-benzenesulfonyl)-3,4-dihydro-2H-isoquinolin-1-one 207A Purification (flashmaster: 10 g, gradient elution hex/EtOAc) afforded the title compound (49 mg, 60%) as a colourless powder. mp 181-186° C. ¹H NMR (270 MHz; DMSO-d₆) 3.14 (2H, t, J=5.8 Hz, CH₂), 3.80 (3H, s, OCH₃), 3.88 (3H, s, OCH₃), 4.13 (2H, t, J=5.8 Hz, CH₂), 7.37 (1H, s, CH), 7.49 (1H, s, CH), 7.72-7.87 (3H, m, 3×CH), 8.16 (2H, brs, NH₂), 8.32-8.35 (1H, m, CH). ¹³C NMR (67.5 MHz; DMSO-d₆) 27.49 (CH₂), 45.04 (CH₂), 53.78 (CH₃), 56.63 (CH₃), 112.62 (CH), 122.46 (CH), 126.17 (C), 129.67 (CH), 131.33 (CH), 132.66 (C), 132.97 (CH), 133.52 (C), 134.77 (CH), 136.98 (C), 143.49 (C), 151.30 (C), 162.62 (C), 167.47 (C). LC/MS (APCI−) $t_r$=0.86 min, m/z 390.02 (M−SO₂NH₂)⁻. HPLC $t_r$=1.48 min (>99%). Anal. Calcd. for C₁₈H₁₈N₂O₉S₂: C 45.95, H 3.86, N 5.95. Found C 46.0, H 3.93, N 5.87%.

Experimental for Substituted Tetrahydroisoquinolines

2-(Benzyloxy)-1-methoxy-4-((E)-2-nitroprop-1-enyl)benzene 208

3-Benzyloxy-4-methoxybenzaldehyde (8.0 g, 33.05 mmol), ammonium acetate (2.55 g, 33.05 mmol) and nitroethane (120 ml) were stirred under reflux for 22 h. The reaction mixture was cooled to rt and nitroethane was removed in vacuo. The solid residue was dissolved in ethyl acetate (200 ml), washed with water (40 ml) and brine (2×40 ml), dried (MgSO$_4$) and concentrated in vacuo. Recrystallisation from ethanol afforded the title compound (6.19 g, 63%) as yellow crystals. mp=102-104° C. $^1$H NMR (270 MHz; CDCl$_3$) 2.27 (3H, s, CH$_3$), 3.94 (3H, s, OCH$_3$), 5.19 (2H, s, CH$_2$Ph), 6.91 (1H, d, J=2.0 Hz, CH), 6.94 (1H, d, J=8.4 Hz, CH), 7.05 (1H, dd, J=8.4, 2.0 Hz, CH), 7.30-7.43 (4H, m, 4×CH), 7.97 (1H, s, CH). $^{13}$C NMR (67.5 MHz; CDCl$_3$) 14.03 (CH$_3$), 56.15 (OCH$_3$), 71.25 (CH$_2$Ph), 111.69 (CH), 115.77 (CH), 124.93 (C), 124.94 (CH), 127.16 (CH), 128.19 (CH), 128.83 (CH), 133.84 (CH), 136.65 (C), 145.92 (C), 148.00 (C), 151.51 (C). LC/MS (APCI−) t$_r$=1.07 min, m/z 297.93 (M−H)$^-$.

2-(Benzyloxy)-1-methoxy-4-(2-nitropropyl)benzene 209

To a suspension of sodium borohydride (1.52 g, 40 mmol) in ethanol (20 ml) at 0° C. was added a solution of 208 (6 g, 20 mmol) in THF (40 ml). The addition was over 20 min, the reaction mixture was stirred for 1 h at 0° C. and at rt for 30 min. 2M HCl (20 ml) was added (care—vigorous reaction!) and ethyl acetate (100 ml). The layers were separated and the aqueous layer was extracted with ethyl acetate (2×60 ml). The combined organic layers were washed with water (60 ml) and brine (60 ml), dried (MgSO$_4$) and concentrated in vacuo to afford the crude material as an orange oil. Purification by flash column chromatography eluting with hex:EtOAc; 4:1 afforded the title compound (3.35 g, 55%) as a pale green solid. $^1$H NMR (270 MHz; CDCl$_3$) 1.44 (3H, d, J=6.7 Hz, CH$_3$), 2.87 (1H, dd, J=14.1, 6.9 Hz, one of CH$_2$), 3.19 (1H, dd, J 14.1, 7.4 Hz, one of CH$_2$), 3.85 (3H, s, OCH$_3$), 4.65 (1H, sext, J=6.9 Hz, CH), 5.12 (2H, s, CH$_2$Ph), 6.65-6.71 (2H, m, 2×CH), 6.81 (1H, d, J=8.2 Hz, CH), 7.25-7.43 (5H, m, 5×CH). $^{13}$C NMR (67.5 MHz; CDCl$_3$) 18.71 (CH$_3$), 40.80 (CH$_2$), 56.08 (OCH$_3$), 71.17 (CH$_2$), 84.64 (CH), 112.0 (CH), 115.15 (CH), 121.93 (CH), 127.47 (CH), 127.87 (C), 128.0 (CH), 128.67 (CH), 136.99 (C), 148.14 (C), 149.13 (C), LC/MS (APCI−) t$_r$=1.1 min, m/z 300.01 (M−H)$^-$.

1-(3-(Benzyloxy)-4-methoxyphenyl)propan-2-amine 210

Raney nickel (50%, slurry in water, 2.0 g) was washed with MeOH (3×). To this was added MeOH (70 ml) and 209 (3.05 g, 10.1 mmol). The mixture was cooled (ice-bath) and hydrazine hydrate (2.53 g, 50.5 mmol) was added dropwise. The mixture was heated to 40° C. for 1 h, then further Raney nickel (50% slurry in water, 1.0 g) was added as a suspension in MeOH (10 ml). The reaction mixture was heated at 40° C. for a further 18 h. The resulting solution was cooled to rt and filtered through celite, washing through with MeOH (200 ml). The filtrate was concentrated in vacuo and purification (flashmaster: 50 g, EtOAc/MeOH) afforded the title compound (2.074 g, 76%) as a pale yellow oil. $^1$H NMR (270 MHz; CDCl$_3$) 1.04 (3H, d, J=6.4 Hz, CH$_3$), 2.36 (1H, dd, J=13.3, 8.2 Hz, CHH), 2.58 (1H, dd, J=13.3, 5.2 Hz, CHH), 2.98-3.1 (1H, m, CH), 3.86 (3H, s, OCH$_3$), 5.13 (2H, s, CH$_2$), 6.67-6.83 (3H, m, 3×CH), 7.25-7.43 (5H, m, 5×CH, phenyl). LC/MS (ES+) t$_r$=1.82 min, m/z 272.19 (M$^+$+H).

N-(1-(3-(Benzyloxy)-4-methoxyphenyl)propan-2-yl) acetamide 211

To a solution of 210 (2.07 g, 7.6 mmol) was added triethyl amine (1.6 ml, 11.4 mmol). The solution was cooled to 0° C. and acetic anhydride was added slowly dropwise. The reaction mixture was stirred at 0° C. for 1 h and then at rt for 23 h. Water (30 ml) and DCM (30 ml) were added, the layers separated and the aqueous layer extracted with DCM (3×30 ml). The combined organic phases were washed with brine (30 ml), dried (MgSO$_4$) and concentrated in vacuo to afford the title compound (2.268 g, 95%) as a white powder. mp=139.142° C. $^1$H NMR (270 MHz; CDCl$_3$) 0.99 (3H, d, J=6.7 Hz, CH$_3$CH), 1.91 (3H, s, CH$_3$CO), 2.57 (1H, dd, J=13.6, 7.2 Hz, CH), 2.70 (1H, dd, J=13.6, 5.7 Hz, CH), 3.85 (3H, s, OCH$_3$), 4.1-4.22 (1H, m, CH), 5.12 (2H, s, CH$_2$Ph), 5.17-5.23 (1H, m, NH), 6.68-6.71 (2H, m, 2×CH), 6.79-6.82 (1H, m, CH), 7.24-7.44 (5H, m, 5×CH, phenyl). $^{13}$C NMR (67.5 MHz; CDCl$_3$) 19.86 (CH$_3$), 23.62 (CH$_3$), 41.84 (CH$_2$), 46.07 (CH), 56.12 (OCH$_3$), 71.07 (CH$_2$), 111.83 (CH), 115.62 (CH), 122.21 (CH), 127.40 (CH), 127.90 (CH), 128.62 (CH), 130.36 (C), 137.23 (C), 147.91 (C), 148.45 (C), 169.31 (C). LC/MS (APCI−) t$_r$=0.89 min, m/z 312.29 (10%, M−H$^-$), 21 1.95 (82), 120.85 (100).

1-(6-(Benzyloxy)-3,4-dihydro-7-methoxy-3-methyl-isoquinolin-2(1H)-yl)ethanone 212

Paraformaldehyde (6.32 g) was added portionwise to a solution of 211 (2.21 g, 7.04 mmol) in toluene (55 ml) with pTSA (60 mg). The reaction mixture was heated under reflux for 2 h. Further paraformaldehyde (632 mg) was added and heating under reflux was continued overnight. Additional pTSA (60 mg) and paraformaldehyde (1.9 g) was added to the reaction mixture portionwise over 2 h. The solution was cooled to rt, water (50 ml) and ethyl acetate (60 ml) were added. The layers were separated and the organic layer was washed with water (2×50 ml) and brine (50 ml), dried (MgSO$_4$) and concentrated in vacuo to afford the title compound (2.15 g, 94%) as a colourless oil. $^1$H NMR indicated a mixture of conformers, signals for both conformers are listed 1.04, 1.12 (3H, d, J=6.7 Hz, CH$_3$CH), 2.14, 2.17 (3H, s, CH$_3$CO), 2.38-2.51 (1H, m, CHH for both conformers), 2.89-3.06 (1H, m, CHH for both conformers), 3.84, 3.85 (3H, s, OCH$_3$), 4.06-4.6 (2H, m, CH$_2$ for both conformers), 5.01-5.02 (3H, m, CHCH$_3$ and CH$_2$Ph for both conformers), 6.6-6.64 (2H, m, 2×CH for both conformers), 7.28-7.44 (5H, m, 5×CH, phenyl for both conformers). LC/MS (ES+) t$_r$=1.02 min, m/z 348.19 (M$^+$+Na).

6-(Benzyloxy)-1,2,3,4-tetrahydro-7-methoxy-3-methylisoquinoline 213

A solution of 212 (2.1 g, 6.5 mmol) in EtOH (60 ml) with 10% NaOH (15 ml) was heated under reflux for 20 h. A further 15 ml of 10% NaOH was added and heating continued for another 24 h. The reaction mixture was cooled to rt and concentrated to remove the EtOH. Chloroform (30 ml) was added, the layers separated and the aqueous layers extracted with chloroform (3×). The combined organic layers were dried (MgSO$_4$) and concentrated in vacuo to afford an orange oil. Purification by flash column chromatography eluting with EtOAc to 20% MeOH/80% EtOAc/0.5% TEA afforded the title compound (858 mg, 47%) as an orange powder. $^1$H NMR (270 MHz; CDCl$_3$) 1.20 (3H, d, J=6.4 Hz, CH$_3$CH), 1.46 (1H, brs, NH), 2.35 (1H, dd, J=15.8, 10.6 Hz, CHH), 2.61 (1H, dd, J=15.8, 3.7 Hz, CHH), 2.88-3.0 (1H, m, CH$_3$CH), 3.83 (3H, s, OCH$_3$), 3.93 (1H, d, J=15.6 Hz, one of ArCH$_2$N), 4.04 (1H, d, J=15.6 Hz, one of ArCH$_2$N), 5.09 (2H, s, CH$_2$Ph), 6.54 (1H, s, CH), 6.57 (1H, s, CH), 7.25-7.43 (5H, m, 5×CH, phenyl). $^{13}$C NMR (67.5 MHz; CDCl$_3$) 22.60 (CH$_3$), 36.76 (CH$_2$), 48.43 (CH$_2$), 49.37 (CH), 56.16 (OCH$_3$), 71.23 (CH$_2$), 109.51 (CH), 114.75 (CH), 126.82 (C), 127.37

(CH), 127.82 (CH), 128.09 (C), 128.59 (CH), 137.41 (C), 146.62 (C), 148.0 (C). LC/MS (ES+) $t_r$=1.21 min, m/z 284.13 (M$^+$+H). HPLC $t_r$=2.49 min (>99%).

2-(3-Methoxybenzyl)-6-(benzyloxy)-1,2,3,4-tetrahydro-7-methoxy-3-methylisoquinoline 214

General Method:
A solution of 213 (300 mg, 1.1 mmol), TEA (0.3 ml, 2.1 mmol) and 3-methoxybenzyl chloride (0.18 ml, 1.3 mmol) in EtOH (3 ml) was heated in the microwave at 130° C. for 1.5 h. The reaction mixture was concentrated in vacuo and the crude residue was dissolved in EtOAc (30 ml) and washed with brine (30 ml). The organic layer was dried (MgSO$_4$) and concentrated in vacuo. Purification (flashmaster: 20 g, 100% hex to 100% EtOAc over 25 min) afforded the title compound (357 mg, 84%) as a colourless oil. $^1$H NMR (270 MHz; CDCl$_3$) 1.12 (3H, d, J=6.4 Hz, CH$_3$CH), 2.47 (1H, dd, J=16.1, 5.7 Hz, CHH), 2.86 (1H, dd, J=$\overline{16}$.1, 4.9 Hz, CHH), 3.0-3.11 (1H, m, $\overline{CH}_3$CH), 3.55 (2H, t, J=13.4 Hz, CH$_2$), 3.76-3.81 (2H, m, CH$_2$), 3.80 (6H, s, 2×OCH$_3$), 5.10 (2H, s, CH$_2$Ph), 6.47 (1H, s, CH), 6.60 (1H, s, CH), 6.79 (1H, ddd, J=8.2, 2.5, 1.0 Hz, CH), 6.94-6.97 (2H, m, 2×CH), 7.15-7.45 (6H, m, 5×CH, phenyl and CH). $^{13}$C (67.5 MHz; CDCl$_3$) 15.31 (CH$_3$), 35.03 (CH$_2$), 51.51 (CH$_2$), 52.27 (CH), 55.32 (CH$_3$), 56.11 (CH$_3$), 57.24 (CH$_2$), 71.21 (CH$_2$), 109.95 (CH), 112.48 (CH), 114.36 (CH), 114.56 (CH), 121.32 (CH),125.83 (C), 126.95 (C), 127.37 (CH), 127.82 (CH), 128.59 (CH), 129.30 (CH), 137.47 (C), 141.35 (C), 146.73 (C), 147.91 (C), 159.77 (C). LC/MS (ES+) $t_r$=1.52 min, m/z 404.25 (M$^+$+H).

2-(3,5-Dimethoxybenzyl)-6-(benzyloxy)-1,2,3,4-tetrahydro-7-methoxy-3-methylisoquinoline 215

Method as for 214 afforded the title compound (222 mg, 46%) as a colourless oil. $^1$H NMR (270 MHz; CDCl$_3$) 1.10 (3H, d, J=6.4 Hz, CH$_3$CH), 2.45 (1H, dd, J=15.9, 5.8 Hz, CHH), 2.86 (1H, dd, J=15.9, 4.7 Hz, CHH), 3.02-3.11 (1H, m, $\overline{CH}_3$CH), 3.45-3.71 (4H, m, 2×CH$_2$), 3.77 (6H, s, 2×CH$_3$), 3.79 (3H, s, OCH$_3$), 5.09 (2H, s, CH$_2$Ph), 6.35 (1H, t, J=2.2 Hz, CH), 6.48 (1H, s, CH), 6.54 (1H, d, J=2.2 Hz, CH), 6.60 (1H, s, CH), 7.28-7.44 (5H, m, 5×CH, phenyl). $^{13}$C (67.5 MHz; CDCl$_3$) 15.22 (CH$_3$), 34.94 (CH$_2$), 51.48 (CH$_2$), 52.15 (CH), 55.43 (CH$_3$), 56.11 (CH$_3$), 57.40 (CH$_2$), 71.21 (CH$_2$), 99.03 (CH), 106.72 (CH), 109.96 (CH), 114.53 (CH), 125.79 (C), 126.93 (C), 127.37 (CH), 127.82 (CH), 128.58 (CH), 137.46 (C), 142.16 (C), 146.73 (C), 147.91 (C), 160.81 (C). LC/MS (ES+) $t_r$=1.43 min, m/z 434.36 (M$^+$+H). HRMS (ES+) calcd. for C$_{27}$H$_{32}$NO$_4$ 434.2326, found 434.2330. HPLC $t_r$=3.74 min (>94%).

2-(3,4,5-Trimethoxybenzyl)-6-(benzyloxy)-1,2,3,4-tetrahydro-7-methoxy-3-methylisoquinoline 216

Method as for 214 afforded the title compound as a colourless oil (190 mg, 34%). $^1$H NMR (270 MHz; CDCl$_3$) 1.11 (3H, d, J=6.4 Hz, CH$_3$CH), 2.46 (1H, dd, J=16.1, 5.7 Hz, CHH), 2.87 (1H, dd, J 16.1, 4.8 Hz, CHH), 3.04-3.11 (1H, m, CH), 3.46-3.75 (4H, m, 2×CH$_2$), 3.80 (3H, s, OCH$_3$), 3.84 (3H, s, OCH$_3$), 3.84 (6H, s, 2×OCH$_3$), 5.10 (2H, s, CH$_2$Ph), 6.50 (1H, s, CH), 6.60 (2H, s, 2×CH), 6.61 (1H, s, CH), 7.26-7.44 (5H, m, 5×CH). $^{13}$C NMR (67.5 MHz; CDCl$_3$) 15.09 (CH$_3$), 34.76 (CH$_2$), 51.37 (CH$_2$), 52.02 (CH), 56.13 (OCH$_3$), 56.20 (OCH$_3$), 57.37 (CH$_2$), 60.98 (OCH$_3$), 71.16 (CH$_2$), 105.44 (CH), 109.91 (CH), 114.44 (CH), 125.75 (C), 126.81 (C), 127.37 (CH), 127.84 (CH), 128.61 (CH), 135.37 (C), 136.71 (C), 146.65 (C), 146.75 (C), 147.90 (C), 153.20 (C). LC/MS (ES+) $t_r$=0.64 min, m/z 464.22 (M$^+$+H). HRMS (ES+) calcd. for C$_{28}$H$_{34}$NO$_5$ (M$^+$+H) 464.2431, found 464.2436. HPLC $t_r$=3.46 min (>94%).

2-(3-Methoxybenzyl)-1,2,3,4-tetrahydro-7-methoxy-3-methylisoquinolin-6-ol 217

A solution of 214 (330 mg, 0.82 mmol) in THF (6 mL) and EtOH (6 mL) was treated with 10% Pd/C (33 mg) and stirred under an atmosphere of hydrogen. The reaction was monitored by TLC. Upon completion, the resultant suspension was filtered through celite, washed with ethyl acetate and then evaporated under reduced pressure. Purification (personal flashmaster: 20 g, hex:EtOAc; 2:1) afforded the title compound (118 mg, 46%) as a pale yellow solid. mp=100-105° C. $^1$H NMR (270 MHz; CDCl$_3$) 1.12 (3H, d, J=6.7 Hz, CH$_3$CH), 2.49 (1H, dd, J=16.1, 5.8 Hz, CHH), 2.89 (1H, dd, J=$\overline{16}$.1, 4.8 Hz, CHH), 3.01-3.12 (1H, m, $\overline{CH}$CH$_3$), 3.48-3.74 (4H, m, 2×CH$_2$), 3.78 (3H, s, OCH$_3$), 3.79 (3H, s, OCH$_3$), 5.42 (1H, s, OH), 6.42 (1H, s, CH), 6.63 (1H, s, CH), 6.77-6.81 (1H, m, CH), 6.93-6.96 (2H, m, 2×CH), 7.21 (1H, d, J=8.2 Hz, CH). $^{13}$C NMR (67.5 MHz; CDCl$_3$) 15.39 (CH$_3$), 34.68 (CH$_2$), 51.43 (CH$_2$), 52.30 (CH), 55.31 (OCH$_3$), 55.99 (OCH$_3$), 57.07 (CH$_2$), 108.73 (CH), 112.54 (CH), 114.35 (CH), 114.54 (CH), 121.36 (CH), 125.48 (C), 126.56 (C), 129.29 (CH), 141.20 (C), 144.04 (C), 144.92 (C), 159.75 (C). LC/MS (ES+) $t_r$=2.43 min, m/z 314.18 (M$^+$+H). HRMS (ES+) calcd. for C$_{19}$H$_{24}$NO$_3$ 314.1751, found 314.1748.

2-(3,5-Dimethoxybenzyl)-1,2,3,4-tetrahydro-7-methoxy-3-methylisoquinolin-6-ol 218

Method as for 217 to afford the title compound (81 mg, 69%) as a pale yellow powder. mp=155-158° C. $^1$H NMR (270 MHz; CDCl$_3$) 1.12 (3H, d, J=6.4 Hz, CH$_3$CH), 2.48 (1H, dd, J=16.1, 5.8 Hz, CHH), 2.88 (1H, dd, J=16.1, 4.7 Hz, CHH), 3.0-3.12 (1H, m, CH$_3$CH), 3.47-3.78 (4H, m, 2×CH$_2$), 3.78 (6H, m, 2×CH$_3$), 3.79 (3H, s, OCH$_3$), 5.52 (1H, brs, OH), 6.35 (1H, t, J=2.3 Hz, CH), 6.43 (1H, s, CH), 6.55 (2H, d, J=2.3 Hz, CH), 6.62 (1H, s, CH). LC/MS (ES+) $t_r$=1.01 min, m/z 344.16 (M$^+$+H). HRMS (ES+) calcd. for C$_{20}$H$_{26}$NO$_4$ 344.1856, found 344.1857. HPLC $t_r$=2.33 min (>90%).

2-(3,4,5-Trimethoxybenzyl)-1,2,3,4-tetrahydro-7-methoxy-3-methylisoquinolin-6-ol 219

Method as for 217 to afford the title compound (80 mg, 66%) as a yellow solid. mp=127-132° C. $^1$H NMR (270 MHz; CDCl$_3$) 1.13 (3H, d, J=6.2 Hz, CH$_3$CH), 2.49 (1H, dd, J=16.0, 5.8 Hz, CHH), 2.90 (1H, dd, J=$\overline{16}$.0, 4.9 Hz, CHH), 3.08-3.11 (1H, m, $\overline{CH}$CH$_3$), 3.47-3.80 (4H, m, 2×CH$_2$), 3.80 (3H, s, OCH$_3$), 3.83 (3H, s, OCH$_3$), 3.84 (6H, s, 2×OCH$_3$), 5.52 (1H, brs, OH), 6.45 (1H, s, CH), 6.61 (2H, s, 2×CH), 6.64 (1H, s, CH). $^{13}$C NMR (67.5 MHz; CDCl$_3$) 15.19 (CH$_3$), 34.58 (CH$_2$), 51.39 (CH$_2$), 52.12 (CH), 56.03 (OCH$_3$), 56.21 (OCH$_3$), 57.31 (CH$_2$), 60.94 (OCH$_3$), 105.56 (CH), 108.76 (CH), 114.58 (CH), 125.59 (C), 126.61 (C), 135.39 (C), 144.08 (C), 144.96 (C), 155.23 (C). LC/MS (ES–) $t_r$=0.94 min, m/z 372.32 (M$^+$–H). HRMS (ES+) calcd. for C$_{21}$H$_{28}$NO$_5$ 374.1962, found 374.1964. HPLC $t_r$=2.23 min (>81%).

2-(3-Methoxybenzyl)-1,2,3,4-tetrahydro-7-methoxy-3-methylisoquinolin-6-O-sulfamate 220

A solution of sulfamoyl chloride in toluene (0.6M, 2.33 ml, 1.4 mmol) was concentrated in vacuo and cooled in an ice bath until the sulfamoyl chloride solidified. DMA (1 ml) was added and the resulting solution was added directly to 217 (88 mg, 0.28 mmol) at 0° C. The reaction was stirred at rt for 16 h. Water (10 ml) was added and solid sodium hydrogen carbonate to neutralise and the aqueous layer was extracted with ethyl acetate (3×20 ml). The combined organic layers were washed with water (4×20 ml), dried (MgSO$_4$) and concentrated in vacuo. Purification (flashmaster: 20 g, gradient elution 100% hex-100% EtOAc over 20 min) afforded the title compound (56 mg, 51%) as a pale yellow solid. mp=154-156° C. $^1$H NMR (270 MHz; DMSO-d$_6$) 1.06 (3H, d, J=6.5 Hz, CH$_3$CH), 2.44-2.51 (1H, m, CHH), 2.89 (1H, dd, J=16.0, 4.6 Hz, CH$_3$CH), 3.01-3.07 (1H, m, CHCH$_3$), 3.46-3.60 (4H, m, 2×CH$_2$), 3.70 (3H, s, OCH$_3$), 3.73 (3H, s, OCH$_3$), 6.79 (1H, s, CH), 6.82 (1H, dd, J=7.2, 2.02 Hz, CH), 6.89-6.94 (2H, m, 2×CH), 7.02 (1H, s, CH), 7.24 (1H, t, J=8.0 Hz, CH), 7.85 (2H, brs, NH$_2$). $^{13}$C NMR (67.5 MHz; DMSO-d$_6$) 14.99 (CH$_3$), 39.752 (CH$_2$), 52.05 (CH), 55.48 (OCH$_3$), 56.29 (OCH$_3$), 57.34 (CH$_2$), 111.47 (CH), 112.74 (CH), 114.44 (CH), 121.21 (CH), 123.64 (CH), 125.88 (C), 129.84 (CH), 133.61 (C), 141.66 (C), 150.13 (C), 159.86 (C). LC/MS (ES+) t$_r$=0.63 min, m/z 393.10 (M$^+$+H). HPLC t$_r$=1.91 min (>98%).

2-(3,5-dimethoxy-benzyl)-7-methoxy-3-methyl-1,2,3,4-tetrahydro-isoquinolin-6-O-sulfamate 221

Sulfamoylation following the method of 220 afforded the title compound (80 mg, 64%) as a pale yellow solid. mp=146-149° C. $^1$H NMR (270 MHz; DMSO-d$_6$) 1.05 (3H, d, J=6.2 Hz, CH$_3$CH), 2.43-2.51 (1H, m, CHH), 2.88 (1H, dd, J=16.0, 4.7 Hz, CH$_3$CH), 3.0-3.07 (1H, m, CHCH$_3$), 3.66-3.99 (4H, m, 2×CH$_2$), 3.70 (3H, s, OCH$_3$), 3.71 (6H, s, 2×OCH$_3$), 6.37 (1H, t, J=2.2 Hz, CH), 6.51 (1H, d, J=2.2 Hz, CH), 6.80 (1H, s, CH), 7.02 (1H, s, CH), 7.85 (2H, brs, NH$_2$). $^{13}$C NMR (67.5 MHz; DMSO-d$_6$) 14.96 (CH$_3$), 39.42 (CH$_2$), 51.20 (CH$_2$), 52.0 (CH), 55.63 (OCH$_3$), 56.3 (OCH$_3$), 57.49 (CH$_2$), 99.10 (CH), 106.73 (CH), 111.50 (CH), 123.64 (CH), 125.88 (C), 133.63 (C), 137.60 (C), 142.51 (C), 150.14 (C), 160.97 (C). LC/MS (ES+) t$_r$=0.62 min, m/z 423.09 (M$^+$+H). HRMS (ES+) calcd. for C$_{20}$H$_{27}$N$_2$O$_6$S 423.1584, found 423.1580. HPLC t$_r$=1.85 min (>95%).

2-(3,4,5-Trimethoxybenzyl)-1,2,3,4-tetrahydro-7-methoxy-3-methylisoquinolin-6-O-sulfamate 222

Sulfamoylation following the method of 220 afforded the title compound (55 mg, 70%) as a yellow powder. mp=137-143° C. $^1$H NMR (270 MHz; DMSO-d$_6$) 1.06 (3H, d, J=6.4 Hz, CH$_3$CH), 2.44-2.51 (1H, m, CHH), 2.90 (1H, dd, J=16.5, 5.1 Hz, CHH), 3.03-3.09 (1H, m, CHCH$_3$), 3.49-3.66 (4H, m, 2×CH$_2$), 3.64 (3H, s, OCH$_3$), 3.71 (3H, s, OCH$_3$), 3.75 (6H, s, 2×OCH$_3$), 6.65 (2H, s, 2×CH), 6.82 (1H, s, CH), 7.03 (1H, s, CH), 7.82 (2H, s, NH$_2$). $^{13}$C NMR (67.5 MHz; DMSO-d$_6$) 14.84 (CH$_3$), 39.47 (CH$_2$), 51.10 (CH$_2$), 51.86 (CH), 56.36 (OCH$_3$), 57.52 (CH$_2$), 60.52 (CH$_3$), 105.88 (CH), 111.59 (CH), 123.62 (CH), 125.91 (C), 133.60 (C), 135.58 (C), 136.78 (C), 137.70 (C), 150.16 (C), 153.38 (C). LC/MS (ES+) t$_r$=0.95 min, m/z 453.38 (M$^+$+H). HRMS (ES+) calcd. for C$_{21}$H$_{29}$N$_2$O$_7$S (M$^+$+H) 453.1690, found 453.1688. HPLC t$_r$=1.63 min (>97%).

3,4-Dihydro-7-methoxy-3,3-dimethylisoquinolin-6-ol 223

To a flask (ice cooled) containing acetic acid (7.2 ml) was added potassium cyanide (1.29 mg, 36.7 mmol) in small portions (CARE: HCN may be evolved). To this was added a mixture of acetic acid (3.6 ml) and sulfuric acid (7.3 g) slowly with stirring. The ice bath was removed and a solution of 5-(2-hydroxy-2-methylpropyl)-2-methoxyphenol (6.0 mg, 30.6 mmol) in acetic acid (4 ml) was added dropwise by syringe over 15 min. The reaction mixture was stirred at rt for 24 h. The reaction mixture was poured onto ice-water and the aqueous solution neutralised with sodium Carbonate, then extracted with diethyl ether (2×) and ethyl acetate (2×) after saturation with sodium chloride. Purification by column chromatography eluting with DCM:EtOAc; 1:1 then EtOAc:MeOH; 4:1 afforded the title compound (1.72 g, 30%) as a colourless solid. mp=152-157° C. $^1$H NMR (270 MHz; CDCl$_3$) 1.21 (6H, s, 2×CH$_3$), 2.62 (2H, s, CH$_2$), 3.91 (3H, s, OCH$_3$), 5.69 (1H, brs, OH), 6.60 (1H, s, CH), 6.85 (1H, s, CH), 8.07 (1H, s, CH). $^{13}$C NMR (67.5 MHz; CDCl$_3$) 28.07 (CH$_3$), 37.96 (CH$_2$), 54.74 (C(CH$_3$)$_2$), 56.04 (CH$_3$), 110.63 (CH), 113.83 (CH), 120.88 (C), 128.02 (C), 144.86 (C), 149.47 (C), 157.19 (C). LC/MS (ES+) t$_r$=0.97 min, m/z 205.9 (M$^+$+H). HRMS (ES+) calcd. for C$_{12}$H$_{15}$NO$_2$ (M$^+$+H) 206.1176, found 206.1169.

1,2,3,4-Tetrahydro-7-methoxy-3,3-dimethylisoquinolin-6-ol 224

To a solution of 223 (1.67 mg, 8.2 mmol) in ethanol (30 ml) at 0° C. was added sodium borohydride (618 mg, 16.3 mmol). The reaction mixture was stirred at rt for 3 h. Water (50 ml) was added and the aqueous layer neutralised (2M HCl) and extracted with ethyl acetate (3×60 ml). The combined organic layers were washed with brine (30 ml), dried (MgSO$_4$) and concentrated in vacuo to afford the title compound (1.34 mg, 80%) as a white solid. mp=170-173° C. $^1$H NMR (270 MHz; DMSO-d$_6$) 1.04 (6H, s, 2×CH$_3$), 2.42 (2H, s, CH$_2$), 3.70 (3H, s, OCH$_3$), 3.72 (2H, s, CH$_2$), 6.43 (1H, s, CH), 6.54 (1H, s, CH), 8.60 (1H, brs, NH). LC/MS (ES+) t$_r$=1.19 min, m/z 208.23 (M$^+$+H). HRMS (ES+) calcd. for C$_{12}$H$_{17}$NO$_2$ (M$^+$+H) 208.1332, found 208.1322.

7-Methoxy-3,3-dimethyl-6-triisopropylsilanyloxy-1,2,3,4-tetrahydro-isoquinoline 225

To a solution of 224 (1.25 g, 6 mmol) in DCM (50 ml) was added imidazole (1.73 g, 25.4 mmol) and triisopropylsilyl chloride (2.71 ml, 12.7 mmol). The reaction mixture was stirred at rt for 22 h. Water (30 ml) and Chloroform (30 ml) were added. The layers separated and the aqueous layer extracted with chloroform (3×30 ml). The combined organic layers were washed with brine (30 ml), dried (MgSO$_4$) and concentrated in vacuo. Purification by column chromatography eluting with EtOAc:MeOH:TEA; 10:1:01 afforded the title compound (1.78 g, 81%) as colourless oil. $^1$H NMR (270 MHz; CDCl$_3$) 1.06 (18H, d, J=6.7 Hz, 6×CH$_3$CH), 1.14 (6H, s, 2×CH$_3$), 1.14-1.28 (3H, m, 3×CH), 2.51 (2H, s, CH$_2$), 3.74 (3H, s, OCH$_3$), 3.89 (2H, s, CH$_2$), 6.46 (1H, s, CH), 6.51 (1H, s, CH). $^{13}$C NMR (67.5 MHz; CDCl$_3$) 12.95 (CH$_3$), 18.03 (CH$_3$), 27.76 (CH), 41.17 (CH$_2$), 43.97 (CH$_2$), 48.78 (C(CH$_3$)$_2$), 55.56 (OCH$_3$), 112.96 (CH), 117.39 (CH), 126.24 (C), 126.92 (C), 143.58 (C), 149.34 (C). LC/MS (ES+) t$_r$=2.65 min, m/z 364.36 (M$^+$+H).

7-Methoxy-2-(3-methoxy-benzyl)-3,3-dimethyl-6-triisopropylsilanyloxy-1,2,3,4-tetrahydro-isoquinoline 226

A mixture of 225 (300 mg, 0.83 mmol), 3-methoxybenzyl chloride (0.13 ml, 0.91 mmol) and TEA (0.3 ml, 1.65 mmol)

in EtOH (3 ml) was heated in the microwave at 130° C. for 1.5 h. The reaction mixture was concentrated in vacuo. The crude residue was dissolved in EtOAc (30 ml), washed with brine (20 ml), dried (MgSO$_4$) and concentrated in vacuo. Purification (flashmaster: 20 g, 100% hex to 50% hex/50% EtOAc and then to 100% EtOAc) afforded the title compound (246 mg, 62%) as colourless oil. $^1$H NMR (270 MHz; CDCl$_3$) 1.04 (18H, d, J=6.7 Hz, CH$_3$CH), 1.12-1.22 (3H, m, 3×SiCHCH$_3$), 1.17 (6H, s, 2×CH$_3$), 2.65 (2H, s, CH$_2$), 3.47 (2H, s, CH$_2$), 3.64 (2H, s, CH$_2$), 3.74 (3H, s, OCH$_3$), 3.79 (3H, s, OCH$_3$), 6.41 (1H, s, CH), 6.48 (1H, s, CH), 6.77 (1H, ddd, J=8.2, 2.2, 1.2 Hz, CH), 6.95-6.98 (2H, m, 2×CH), 7.22 (1H, t, J=8.2 Hz, CH). $^{13}$C NMR (67.5 MHz; CDCl$_3$) 12.38 (CH), 17.49 (CH$_3$), 23.26 (CH$_3$), 42.28 (CH$_2$), 49.64 (CH$_2$), 52.11 (C), 53.22 (CH$_2$), 54.72 (OCH$_3$), 55.04 (OCH$_3$), 111.42 (CH), 111.69 (CH), 113.77 (CH), 117.21 (CH), 120.56 (CH), 125.68 (C), 126.34 (C), 128.69 (CH), 142.09 (C), 142.89 (C), 148.66 (C), 159.15 (C). LC/MS (ES+) t$_r$=4.54 min, m/z 484.83 (M$^+$+H). HRMS (ES+) calcd. for C$_{29}$H$_{46}$NO$_3$Si (M$^+$+H) 484.3241, found 484.3242.

7-Methoxy-3,3-dimethyl-6-triisopropylsilanyloxy-2-(3,4,5-trimethoxy-benzyl)-1,2,3,4-tetrahydro-isoquinoline 227

Following the method of 226, the title compound (127 mg, 28%) was obtained as a colourless oil. $^1$H NMR (270 MHz; CDCl$_3$) 1.04 (18H, d, J=6.7 Hz, 6×CH$_3$CH), 1.12-1.27 (3H, m, 3×CH), 1.17 (3H, s, CH$_3$), 2.65 (2H, s, CH$_2$), 3.49 (2H, s, CH$_2$), 3.60 (2H, s, CH$_2$), 3.74 (3H, s, OCH$_3$), 3.83 (3H, s, OCH$_3$), 3.84 (6H, s, 2×OCH$_3$), 6.44 (1H, s, CH), 6.50 (1H, s, CH), 6.61 (2H, s, 2×CH). LC/MS (ES+) t$_r$=3.13 min, m/z 544.46 (M$^+$+H).

2-(3-Methoxybenzyl)-1,2,3,4-tetrahydro-7-methoxy-3,3-dimethylisoquinolin-6-ol 228

To a solution of 226 (237 mg, 0.45 mmol) in THF (10 ml) at 0° C. (ice-bath) was added TBAF (1.0 M in THF, 0.53 ml, 0.53 mmol). The reaction mixture was stirred at 0° C. for 18 h. water (10 ml) was added and the aqueous layer was extracted with EtOAc (3×). The combined organic layer were washed with brine (10 ml), dried (MgSO$_4$) and concentrated in vacuo. Purification (flashmaster: 20 g, 100% hex to 100% EtOAc over 25 min) afforded the title compound (70 mg, 43%) as a colourless oil. $^1$H NMR (270 MHz; CDCl$_3$) 1.18 (6H, s, 2×CH$_3$), 2.66 (2H, s, CH$_2$), 3.50 (2H, s, CH$_2$), 3.65 (2H, s, CH$_2$), 3.79 (3H, s, OCH$_3$), 3.83 (3H, s, OCH$_3$), 6.47 (1H, s, CH), 6.52 (1H, s, CH), 6.75-6.79 (1H, m, CH), 6.95-6.97 (2H, m, 2×CH), 7.21 (1H, t, J=8.0 Hz, CH). $^{13}$C NMR (100 MHz; CDCl$_3$) 23.72 (CH$_3$), 45.54 (CH$_2$), 49.97 (CH$_2$), 52.49 (C), 53.45 (CH$_2$), 55.13 (OCH$_3$), 55.86 (OCH$_3$), 110.69 (CH), 111.73 (CH), 111.90 (CH), 114.09 (CH), 120.88 (CH), 125.60 (C), 126.86 (C), 129.11 (C), 142.41 (C), 143.49 (C), 144.99 (C), 159.59 (C). LC/MS (ES−) t$_r$=1.85 min, m/z 326.27 (M−H)$^-$. HRMS (ES+) calcd. for C$_{20}$H$_{26}$NO$_3$ (M$^+$+H) 328.1907, found 328.1904.

7-Methoxy-3,3-dimethyl-2-(3,4,5-trimethoxy-benzyl)-1,2,3,4-tetrahydro-isoquinolin-6-ol 229

TBAF deprotection of 227 (in analogy to the synthesis of 228) afforded the title compound (95 mg, 71%) as a yellow oil that crystallised on trituration with DCM/hexane to afford a yellow powder. mp=143-147° C. $^1$H NMR (270 MHz; CDCl$_3$) 1.17 (6H, s, 2×CH$_3$), 2.66 (2H, s, CH$_2$), 3.52 (2H, s, CH$_2$), 3.60 (2H, s, CH$_2$), 3.82 (3H, s, OCH$_3$), 3.83 (6H, s, 2×OCH$_3$), 3.84 (3H, s, OCH$_3$), 5.44 (1H, brs, OH), 6.50 (1H, s, CH), 6.53 (1H, s, CH), 6.60 (2H, s, 2×CH). $^{13}$C NMR (100 MHz; CDCl$_3$) 23.82 (CH$_3$), 42.41 (CH$_2$), 50.02 (CH$_2$), 52.53 (C), 53.78 (CH$_2$), 55.88 (OCH$_3$), 56.05 (OCH$_3$), 60.84 (OCH$_3$), 105.02 (CH), 110.68 (CH), 111.73 (CH), 125.62 (C), 126.85 (C), 136.44 (C), 143.54 (C), 145.02 (C), 153.08 (C). LC/MS (ES−) t$_r$=1.17 min, m/z 386.26 (M−H)$^-$. HRMS (ES+) calcd. for C$_{22}$H$_{30}$NO$_5$ (M$^+$+H) 388.2118, found 388.2111. HPLC t$_r$=2.73 min (>82%).

2-(3-Methoxybenzyl)-1,2,3,4-tetrahydro-7-methoxy-3,3-dimethylisoquinolin-6-yl sulfamate 230

Sulfamoylation of 226 with H$_2$NSO$_2$Cl and DMA as described above afforded the title compound (86 mg, 89%) as a colourless foam. $^1$H NMR (400 MHz; DMSO-d$_6$) 1.14 (6H, s, 2×CH$_3$), 2.69 (2H, s, CH$_2$), 3.43 (2H, s, CH$_2$), 3.62 (2H, s, CH$_2$), 3.73 (3H, s, OCH$_3$), 3.75 (3H, s, OCH$_3$), 6.80 (1H, dd, J=8.0, 2.0 Hz, CH), 6.83 (1H, s, CH), 6.89-6.94 (3H, m, 3×CH), 7.23 (1H, t, J=8.0 Hz, CH), 7.79 (2H, s, NH$_2$). $^{13}$C NMR (100 MHz; DMSO-d$_6$) 42.80 (CH$_2$), 49.42 (CH$_2$), 52.05 (C), 53.0 (CH$_2$), 54.94 (OCH$_3$), 55.79 (OCH$_3$), 111.83 (CH), 112.97 (CH), 114.10 (CH), 120.30 (CH), 120.61 (CH), 125.77 (C), 129.25 (CH), 133.04 (C), 136.80 (C), 142.19 (C), 149.88 (C), 159.28 (C). LC/MS (ES+) t$_r$=1.14 min, m/z 407.28 (M$^+$+H). HRMS (ES+) cald. for C$_{20}$H$_{27}$N$_2$O$_5$S (M$^+$+H) 407.1635, found 407.1636. HPLC t$_r$=2.10 min (>98%).

2-(3,4,5-Trimethoxybenzyl)-1,2,3,4-tetrahydro-7-methoxy-3,3-dimethylisoquinolin-6-yl sulfamate 231

Sulfamoylation of 299 with H$_2$NSO$_2$Cl and DMA as described above afforded the title compound (58 mg, 73%) as a colourless solid. Purification by prep HPLC eluting with 80% MeOH/20% H$_2$O afforded a pure sample as a colourless solid. $^1$H NMR (400 MHz; DMSO-d$_6$) 1.14 (6H, s, 2×CH$_3$), 2.69 (2H, s, CH$_2$), 3.46 (2H, s, CH$_2$), 3.58 (2H, s, CH$_2$), 3.63 (3H, s, OCH$_3$), 3.74 (6H, s, 2×OCH$_3$), 3.75 (3H, s, OCH$_3$), 6.64 (2H, s, 2×CH), 6.83 (1H, s, CH), 6.92 (1H, s, CH), 7.80 (2H, s, NH$_2$). LC/MS (ES+) t$_r$=1.31 min, m/z 467.18 (M$^+$+H). HRMS (ES+) calcd. for C$_{22}$H$_{31}$N$_2$O$_7$S (M$^+$+H) 467.1847, found 467.1848. HPLC t$_r$=2.0 min (>95%).

(7-Methoxy-3,3-dimethyl-6-triisopropylsilanyloxy-3,4-dihydro-1H-isoquinolin-2-yl)-(3,4,5-trimethoxy-phenyl)-methanone 232

To a solution of 225 (300 mg, 0.83 mmol) in DCM (5 ml) was added TEA (0.23 ml, 1.65 mmol) and 3,4,5-trimethoxybenzoyl chloride (228 ml, 0.99 mmol). The reaction mixture was stirred at rt for 12 h. Water (10 ml) was added and the aqueous layer was extracted with DCM (3×30 ml). The combined organic phases were washed with sat. aq. NaHCO$_3$ (10 ml) and brine (10 ml), dried (MgSO$_4$) and concentrated in vacuo. Purification (flashmaster: 20 g, gradient elution 100% hex to 100% EtOAc over 25 min) afforded the title compound (240 mg, 52%) as a colourless oil. $^1$H NMR (270 MHz; CDCl$_3$) 1.04 (18H, d, J=6.7 Hz, 6×CH$_3$CH), 1.14-1.24 (3H, m, 3×CH), 1.55 (6H, s, 2×CH$_3$), 2.74 (2H, s, CH$_2$), 3.80 (3H, s, OCH$_3$), 3.85 (6H, s, 2×OCH$_3$), 3.86 (3H, s, OCH$_3$), 4.19 (2H, s, CH$_2$), 6.53 (1H, s, CH), 6.56 (2H, s, 2×CH), 6.71 (1H, s, CH). LC/MS (ES+) t$_r$=0.2.23 min, m/z 580.24 (M$^+$+Na). HRMS (ES+) calcd for C$_{31}$H$_{47}$NO$_6$Si (M$^+$+H) 558.3245, found 558.3237.

(3,5-Dimethoxy-phenyl)-(7-methoxy-3,3-dimethyl-6-triisopropylsilanyloxy-3,4-dihydro-1H-isoquinolin-2-yl)-methanone 233

Following the method of 232, the title compound (331 mg, 57%) was obtained as a colourless oil. $^1$H NMR (400 MHz;

CDCl₃) 1.05 (18H, d, J=7.6 Hz, 6×CH₃), 1.08-1.25 (3H, m, 3×CH), 1.55 (6H, s, 2×CH₃), 2.73 (2H, s, CH₂), 3.79 (6H, s, 2×OCH₃), 3.79 (3H, s, OCH₃), 4.17 (2H, s, CH₂), 6.48 (3H, s, 3×CH), 6.52 (1H, s, CH), 6.71 (1H, s, CH). $^{13}$C NMR (100 MHz; CDCl₃) 12.82 (CH), 17.86 (CH₃), 25.77 (CH₃), 45.24 (CH₂), 48.95 (CH₂), 55.47 (OCH₃), 55.53 (OCH₃), 57.18 (C), 101.39 (CH), 104.29 (CH), 111.72 (CH), 117.61 (CH), 127.11 (C), 129.40 (C), 140.69 (C), 143.81 (C), 150.33 (C), 160.85 (C), 170.56 (C). LC/MS (ES+) $t_r$=2.56 min, m/z 550.69 (M⁺+Na) and 528.65 (M⁺+H). HRMS (ES+) calcd. for C₃₀H₄₆NO₅Si (M⁺+H) 528.3140, found 528.3125.

(6-Hydroxy-7-methoxy-3,3-dimethyl-3,4-dihydro-1H-isoquinolin-2-yl)-(3,4,5-trimethoxy-phenyl)-methanone 234

TBAF deprotection of 232 afforded the title compound (151 mg, quant.) as a colourless solid. mp=159-162° C. $^1$H NMR (270 MHz; CDCl₃) 1.57 (6H, s, 2×CH₃), 2.75 (2H, s, CH₂), 3.85 (6H, s, 2×OCH₃), 3.86 (3H, s, OCH₃), 3.90 (3H, s, OCH₃), 4.21 (2H, s, CH₂), 5.55 (1H, s, OH), 6.56 (2H, s, 2×CH), 6.61 (1H, s, CH), 6.75 (1H, s, CH). $^{13}$C NMR (67.5 MHz; CDCl₃) 25.93 (CH₃), 45.29 (CH₂), 49.12 (CH₂), 56.21 (OCH₃), 56.29 (OCH₃), 57.27 (C(Me)₂), 61.02 (OCH₃), 103.79 (CH), 110.58 (CH), 111.63 (CH), 128.17 (C), 134.25 (C), 138.78 (C), 144.23 (C), 146.06 (C), 153.37 (C), 170.81 (C). LC/MS (ES−) $t_r$=0.94 min, m/z 400.12 (M−H)⁻. HPLC $t_r$=1.60 min (>99%). Anal. Calcd. for C₂₂H₂₇NO₆: C 65,82, H 6.78, N 3.49. Found: C 62.8, H 6.52, N 3.23%.

(3,4-Dihydro-6-hydroxy-7-methoxy-3,3-dimethyl-isoquinolin-2(1H)-yl)(3,5-dimethoxyphenyl)methanone 235

TBAF deprotection of 233 afforded the title compound (112 mg, 56%) as a colourless powder. mp=163-166° C. $^1$H NMR (270 MHz; CDCl₃) 1.56 (6H, s, 2×CH₃), 2.73 (2H, s, CH₂), 3.79 (6H, s, 2×OCH₃), 3.89 (3H, s, OCH₃), 4.18 (2H, s, CH₂), 5.56 (1H, s, OH), 6.47 (3H, brs, 3×CH), 6.58 (1H, s, CH), 6.73 (1H, s, CH). $^{13}$C NMR (67.5 MHz; CDCl₃) 25.92 (CH₃), 45.29 (CH₂), 49.09 (CH₂), 55.60 (OCH₃), 56.22 (OCH₃), 57.29 (C), 101.66 (CH), 104.24 (CH), 110.48 (CH), 111.79 (CH), 128.03 (C), 128.18 (C), 140.71 (C), 144.19 (C), 146.03 (C), 160.96 (C), 170.71 (C). LC/MS (ES−) $t_r$=1.44 min, m/z 370.24 (M−H)⁻. HRMS (ES+) calcd. for C₂₁H₂₆NO₅ (M⁺+H) 372.1805, found 372.1803. HPLC $t_r$=2.81 min (>99%).

Sulfamic acid 7-methoxy-3,3-dimethyl-2-(3,4,5-trimethoxy-benzoyl)-1,2,3,4-tetrahydro-isoquinolin-6-yl ester 236

Sulfamoylation of 234 afforded the title compound (151 mg, 76%) as a colourless solid. mp=172-176° C. $^1$H NMR (270 MHz; DMSO-d₆) 1.50 (6H, s, 2×CH₃), 2.88 (2H, s, CH₂), 3.71 (3H, s, OCH₃), 3.80 (6H, s, 2×OCH₃), 3.81 (3H, s, OCH₃), 4.29 (2H, s, OCH₃), 6.62 (2H, s, 2×CH), 7.08 (1H, s, CH), 7.12 (1H, s, CH), 7.84 (2H, brs, NH₂). $^{13}$C NMR (67.5 MHz; DMSO-d₆) 26.17 (CH₃), 44.63 (CH₂), 48.89 (CH₂), 56.56 (OCH₃), 56.99 (C(Me)₂), 60.62 (OCH₃), 104.38 (CH), 113.28 (CH), 120.61 (CH), 127.69 (C), 134.55 (C), 136.31 (C), 137.40 (C), 138.51 (C), 151.62 (C), 153.38 (C), 170.01 (C). LC/MS (ES−) $t_r$=0.83 min, m/z 479.33 (M−H)⁻. HPLC $t_r$=1.49 min (>99%). Anal. Calcd. for C₂₂H₂₈N₂O₈S: C 54.99, H 5.87, N 5.83. Found: C 54.7, H 5.85, N 5.76%.

Sulfamic acid 2-(3,5-dimethoxy-benzoyl)-7-methoxy-3,3-dimethyl-1,2,3,4-tetrahydro-isoquinolin-6-yl ester 237

Sulfamoylation of 235 afforded the title compound (89 mg, 90%) as a colourless powder. mp=>180° C. dec. $^1$H NMR (270 MHz; DMSO-d₆) 1.49 (6H, s, 2×CH₃), 2.86 (2H, s, CH₂), 3.77 (6H, s, 2×OCH₃), 3.80 (3H, s, OCH₃), 4.23 (2H, s, CH₂), 6.45 (2H, d, J=2.2 Hz, 2×CH), 6.56 (1H, t, J=2.2 Hz, CH), 7.01 (1H, s, CH), 7.12 (1H, s, CH), 7.84 (2H, s, NH₂). $^{13}$C NMR (67.5 MHz; DMSO-d₆) 26.11 (CH₃), 44.56 (CH₂), 48.84 (CH₂), 55.97 (OCH₃), 56.56 (OCH₃), 57.03 (C), 101.69 (CH), 104.57 (CH), 113.28 (CH), 120.57 (CH), 127.49 (C), 136.31 (C), 137.37 (C), 141.15 (C), 151.67 (C), 161.01 (C), 169.88 (C). LC/MS (ES+) $t_r$=1.29 min, m/z 473.28 (M⁺+Na). HRMS (ES+) calcd. for C₂₁H₂₇₂O₇S (M⁺+H) 451.1533, found 451.1519. HPLC $t_r$=1.55 min (>99%).

3,4-Dihydro-7-methoxy-1,3,3-trimethylisoquinolin-6-ol 238

To a flask (ice cooled) containing acetic acid (1.2 ml) was added 5-(2-hydroxy-2-methylpropyl)-2-methoxyphenol (500 mg, 2.5 mmol) and acetonitrile (0.27 ml, 5.1 mmol). To this was added sulfuric acid (1.2 ml) slowly with stirring. The reaction mixture was allowed to warm to rt and stirred for 4 h. The reaction mixture was poured onto ice-water and the aqueous solution neutralised with sodium C(Ar)bonate, then extracted with diethyl ether (2×) and ethyl acetate (2×) after saturation with sodium chloride. Purification (flashmaster: 20 g, 100% DCM to 100% EtOAc, then 30% MeOH/70% EtOAc) afforded the title compound (324 mg, 56%) as a pale brown solid. mp=160° C. dec. $^1$H NMR (270 MHz; CDCl₃) 1.18 (6H, s, 2×CH₃), 2.28 (3H, s, CH₃), 2.59 (2H, s, CH₂), 3.91 (3H, s, OCH₃), 6.60 (1H, s, CH), 7.07 (1H, s, CH). $^{13}$C NMR (67.5 MHz; CDCl₃) 23.21 (CH₃), 28.02 (2×CH₃), 38.81 (CH₂), 53.78 (C(CH₃)₂), 55.98 (CH₃), 110.47 (CH), 112.35 (CH)<121.96 (C), 128.86 (C), 144.35 (C), 148.88 (C), 161.39 (C N). LC/MS (ES+) $t_r$=1.2 min, m/z 219.95 (M⁺+H).

1,2,3,4-Tetrahydro-7-methoxy-1,3,3-trimethylisoquinolin-6-ol 239

Following the method for 224, the title compound (228 mg, 78%) was obtained as a beige solid. mp=80-185° C. $^1$H NMR (270 MHz; DMSO-d₆) 0.97 (3H, s, CH₃), 1.15 (3H, s, CH₃), 1.26 (3H, d, J=6.7 Hz, CH₃CH), 2.35 (1H, brd, J=15.3 Hz, CHH), 2.55 (1H, d, J=15.3 Hz, CHH), 3.70 (3H, s, OCH₃), 3.87 (1H, q, J=6.7 Hz, CHCH₃), 6.53 (1H, s, CH), 6.59 (1H, s, CH). LC/MS (ES+) $t_r$=1.21 min, m/z 222.09 (M⁺+H). HRMS (ES+) calcd. for C₁₃H₂₀NO₂ (M⁺+H) 222.1489, found 222.1486.

7-Methoxy-1,3,3-trimethyl-6-triisopropylsilanyloxy-1,2,3,4-tetrahydro-isoquinoline 240

239 (183 mg, 0.83 mmol), TIPS-Cl (237 mg, 3.5 mmol) and imidazole (237 mg, 3.5 mmol) in DCM (10 ml) were stirred at rt for 24 h. The reaction mixture was quenched with water (5 ml) and extracted with DCM (3×10 ml). The combined organic extracts were washed with brine (10 ml), dried (MgSO₄) and concentrated in vacuo. Purification (personal flashmaster: 20 g, EtOAc:MeOH:TEA; 100:10:1) afforded the title compound (332 mg) as a yellow oily solid. $^1$H NMR (270 MHz; CDCl₃) 1.07 (18H, d, J=6.4 Hz, 6×CH₃CH), 1.08 (3H, s, CH₃), 1.15-1.28 (3H, m, 3×CHCH₃), 1.25 (3H, s, CH₃), 1.21 (3H, d, J=6.4 Hz, CH₃CH), 2.44 (1H, d, J=15.8

Hz, CHH), 2.65 (1H, d, J=15.8 Hz, CHH), 3.74 (3H, s, OCH₃), 4.0 (1H, q, J=6.4 Hz, CHCH₃), 6.46 (1H, s, CH), 6.67 (1H, s, CH). LC/MS (ES+) t$_r$=1.8 min, m/z 378.24 (M⁺+H).

7-Methoxy-2-(3-methoxy-benzyl)-1,3,3-trimethyl-6-triisopropylsilanyloxy-1,2,3,4-tetrahydro-isoquinoline 241

To a solution of 240 (170 mg, 0.45 mmol) in acetone (1.5 ml) was added cesium C(Ar)bonate (162 mg, 0.5 mmol) followed by 3-methoxy benzyl bromide (0.063 ml, 0.54 mmol). The reaction mixture was stirred at rt for 23 h. The resulting solution was diluted with water and extracted with ethyl acetate (3×). The combined organic phases were washed with brine, dried (MgSO₄) and concentrated in vacuo. Purification (Flashmaster; 10 g, 100% hex to 95% hex:5% EtOAc over 25 min) afforded the title compound (79 mg, 35%) as a colourless oil. ¹H NMR (270 MHz; CDCl₃) 0.94 (3H, s, CH₃), 1.07 (18H, d, J=6.7 Hz, 6×SiCHCH₃), 1.09 (3H, s, CH₃), 1.15-1.29 (3H, m, 3×CH), 1.20 (3H, d, J=6.2 Hz, C H₃CH), 2.37 (1H, d, J=15.3 Hz, one of CH₂), 2.94 (1H, d, J=15.3 Hz, one of CH₂), 3.50 (1H, d, J=17.3 Hz, one of CH₂), 3.71 (1H, q, J=6.2 Hz, CHCH₃), 3.76 (3H, s, OCH₃), 3.79 (3H, s, OCH₃), 4.09 (1H, d, J=17.3 Hz, one of CH₂), 6.48 (1H, s, CH), 6.59 (1H, s, CH), 6.71 (1H, dd, J=7.7, 2.2 Hz, CH), 7.0 (1H, d, J=7.7 Hz, CH), 7.09 (1H, brs, CH), 7.19 (1H, t, J=7.9 Hz, CH). ¹³C NMR (100 MHz; CDCl₃) 12.85 (CH₃), 17.92 (CH₃), 18.69 (CH₃), 24.35 (CH₃), 30.03 (CH₃), 44.29 (CH₂), 53.29 (CH₂), 53.72 (C), 55.08 (OCH), 55.47 (OCH₃), 57.40 (OCH₃), 111.06 (CH), 111.84 (CH), 112.92 (CH), 118.13 (CH), 119.34 (CH), 126.70 (C), 128.81 (CH), 132.34 (C), 143.23 (C), 146.35 (C), 148.81 (C), 159.46 (C). LC/MS (ES+) t$_r$=7.09 min, m/z 498.42 (M⁺+H). HPLC t$_r$=7.03 min (>98%).

2-(3-Methoxybenzyl)-1,2,3,4-tetrahydro-7-methoxy-1,3,3-trimethylisoquinolin-6-ol 242

TBAF deprotection of 241 afforded the title compound (28 mg, 54%) as a colourless oil that turned orange on standing. ¹H NMR (270 MHz; CDCl₃) 0.97 (3H, s, CH₃), 1.12 (3H, s, CH₃), 1.24 (3H, d, J=6.4 Hz, CH₃CH), 2.39 (1H, d, J=15.2 Hz, one of CH₂), 2.95 (1H, d, J=15.2 Hz, one of CH₂), 3.52 (1H, d, J=17.0 Hz, one of CH₂), 3.75 (1H, q, J=6.4 Hz, CH), 3.79 (3H, s, OCH₃), 3.86 (3H, s, OCH₃), 4.1 (1H, d, J=17.0 Hz, of CH₂), 5.45 (1H, s, OH), 6.52 (1H, s, CH), 6.67 (1H, s, CH), 6.72 (1H, dd, J=8.0, 2.4 Hz, CH), 7.0 (1H, d, J=7.7 Hz, CH), 7.09 (1H, s, CH), 7.20 (1H, t, J=7.9 Hz, CH). LC/MS (ES+) t$_r$=1.27 min, m/z 342.21 (M⁺+H). HPLC t$_r$=2.92 min (>96%).

6-(Benzyloxy)-3,4-dihydro-7-methoxy-1,3,3-trimethylisoquinoline 243

To a solution of 239 (970 mg, 4.4 mmol) in acetone (10 ml) was added potassium C(Ar)bonate (3.06 g, 22.0 mmol), benzyl bromide (1.05 ml, 8.8 mmol) and tetrabutyl ammonium iodide (163 mg, 0.44 mmol). The reaction mixture was heated at 55° C. for 60 h. The reaction mixture was cooled to rt, water (20 ml) was added and the aqueous layer was extracted with ethyl acetate (3×30 ml). The combined organic phases were dried (MgSO₄) and concentrated in vacuo. Purification by flash column chromatography eluting with EtOAc then EtOAc:MeOH:TEA; 10:1:0.1 afforded the title compound (882 mg, 64%) as a pale orange solid. mp=87.9-90° C. ¹H NMR (270 MHz; CDCl₃) 1.16 (6H, s, 2×CH₃), 2.22 (3H, s, CH₃), 2.59 (2H, s, CH₂), 3.90 (3H, s, OCH₃), 5.13 (2H, s, CH₂Ph), 6.63 (1H, s, CH), 7.0 (1H, s, CH), 7.27-7.46 (5H, m, 5×CH, phenyl). ¹³C NMR (67.5 MHz; CDCl₃) 23.54 (CH₃), 28.15 (2×CH₃), 38.70 (CH₂), 53.65 (C(CH₃)), 56.07 (OCH₃), 71.87 (CH₂Ph), 111.40 (CH), 112.57 (CH), 121.49 (C), 127.58 (CH), 128.08 (CH), 128.68 (CH), 130.78 (C), 137.15 (C), 146.33 (C), 151.79 (C), 160.65 (C). LC/MS (ES+) t$_r$=2.5 min, m/z 310.05 (M⁺+H). HRMS (ES+) calcd. for C₂₀H₂₄NO₂ (M⁺+H) 310.1802, found 310.1801.

6-(Benzyloxy)-1,2,3,4-tetrahydro-7-methoxy-1,3,3-trimethylisoquinoline 244

Sodium borohydride reduction following the method described for the synthesis of 224 afforded the title compound (494 mg, 91%) as a pale yellow solid. mp ¹H NMR (270 MHz; CDCl₃) 1.06 (3H, s, CH₃), 1.22 (3H, s, CH₃), 1.32 (3H, d, J=6.4 Hz, CH₃CH), 2.46 (1H, d, J=15.8 Hz, one of CH₂), 2.63 (1H, d, J=15.8 Hz, one of CH₂), 3.84 (3H, s, OCH₃), 3.98 (1H, q, J=6.4 Hz, CHCH₃), 5.10 (2H, s, CH₂Ph), 6.53 (1H, s, CH), 6.68 (1H, s, CH), 7.25-7.45 (5H, m, 5×CH, phenyl). ¹³C NMR (67.5 MHz; CDCl₃) 22.72 (CH₃), 24.21 (CH₃), 31.80 (CH₃), 42.03 (CH₂), 47.68 (CH), 49.02 (C), 55.90 (OCH₃), 71.40 (CH₂Ph), 111.72 (CH), 112.39 (CH), 127.27 (C), 127.37 (CH), 127.73 (CH), 128.45 (CH), 130.98 (C), 137.37 (C), 146.26 (C), 148.07 (C). LC/MS (ES+) t$_r$=1.06 min, m/z 312.10 (M⁺+H). HRMS (ES+) calcd. for C₂₀H₂₆NO₂ (M⁺+H) 312.1958, found 312.1959.

(6-(Benzyloxy)-3,4-dihydro-7-methoxy-1,3,3-trimethylisoquinolin-2(1H)-yl)-(3,4,5-trimethoxyphenyl) methanone 245

To a solution of 244 (467 mg, 1.5 mmol) in DCM (10 ml) was added triethyl amine (0.42 ml) and 3,4,5-trimethoxybenzoyl chloride (520 mg, 2.3 mmol). The reaction mixture was stirred at rt for 21 h. TLC analysis indicated the presence of starting material so the reaction mixture was heated in the microwave for 5 min at 60° C. and for 15 min at 80° C. A further 0.5 eq of benzoyl chloride was added and the reaction mixture was heated in the microwave at 80° C. for 15 min. Water (20 ml) was added, the layers separated and the aqueous layer extracted with DCM (3×60 ml). The combined organic phases were washed with sat. aq. sodium hydrogen C(Ar)bonate (60 ml) and brine (60 ml), dried (MgSO₄) and concentrated in vacuo. Purification (flashmaster: 20 g, EtOAc/hex then Hex/DCM) afforded the title compound (440 mg, 58%) as a colourless foam. mp 175-177° C. ¹H NMR (270 MHz; CDCl₃) 1.32 (3H, d, J=6.9 Hz, CH₃CH), 1.39 (3H, s, CH₃), 1.87 (3H, s, CH₃), 2.53 (1H, d, J=15.3 Hz, one of CH₂), 3.27 (1H, d, J=15.3 Hz, one of CH₂), 3.82 (6H, s, 2×OCH₃), 3.86 (3H, s, OCH₃), 3.88 (3H, s, OCH₃), 4.69 (1H, q, J=6.9 Hz, CHCH₃), 5.04 (2H, ABq, J=12.1 Hz, CH₂Ph), 6.47 (3H, s, 3×CH), 6.75 (1H, s, CH), 7.25-7.41 (5H, m, 5×CH, phenyl). ¹³C NMR (100 MHz; CDCl₃) 23.43 (CH₃), 25.28 (CH₃), 29.40 (CH₃), 44.18 (CH₂), 56.18 (4×OCH₃), 57.68 (C), 60.92 (CH), 71.38 (CH₂), 102.51 (CH), 111.45 (CH), 112.36 (CH), 127.09 (C), 127.28 (CH), 127.87 (CH), 128.49 (CH), 130.61 (C), 135.07 (C), 136.09 (C), 137.89 (C), 146.88 (C), 149.06 (C), 153.41 (C), 170.97 (C). LC/MS (ES+) t$_r$=1.03 min, m/z 528.27 (M⁺+Na). HPLC t$_r$=2.38 min (>99%). Anal. Calcd. for C₃₀H₃₅NO₆: C 71.27, H 6.98, N 2.77. Found: C 71.1, H 6.99, N 2.70%.

(3,4-Dihydro-6-hydroxy-7-methoxy-1,3,3-trimethylisoquinolin-2(1H)-yl)(3,4,5-trimethoxyphenyl) methanone 246

Method as for 217 afforded the title compound (252 mg, 74%) as a colourless solid. mp=198-200° C. ¹H NMR (270

MHz: CDCl$_3$) 1.34 (3H, d, J=6.9 Hz, CH$_3$CH),1.39 (3H, s, CH$_3$), 1.86 (3H, s, CH$_3$), 2.53 (1H, d, J=1.53 Hz, one of CH$_2$), 3.27 (1H, d, J=15.3 Hz, one of CH$_2$), 3.84 (6H, s, 2×OCH$_3$), 3.86 (3H, s, OCH$_3$), 3.88 (3H, s, OCH$_3$), 4.74 (1H, q, J=6.9 Hz, CHCH$_3$), 5.56 (1H, d, J=0.6 Hz, OH), 6.48 (2H, s, 2×CH), 6.50 (1H, s, CH), 6.70 (1H, s, CH). $^{13}$C NMR (100 MHz; CDCl$_3$) 23.28 (CH$_3$), 25.22 (CH$_3$), 29.37 (CH$_3$), 44.18 (CH$_2$), 56.07 (OCH$_3$), 56.11 (OCH$_3$), 56.17 (OCH$_3$), 57.68 (C), 60.90 (CH), 102.56 (CH), 110.98 (CH), 111.36 (CH), 125.67 (C), 131.38 (C), 134.94 (C), 137.97 (C), 144.22 (C), 145.71 (C), 153.40 (C), 171.03 (C). LC/MS (ES−) t$_r$=0.91 min, m/z 414.27 (M$^+$+H). HPLC t$_r$=2.70 min (>99%).

Sulfamic acid 7-methoxy-1,3,3-trimethyl-2-(3,4,5-trimethoxy-benzoyl)-1,2,3,4-tetrahydro-isoquinolin-6-yl ester 247

Sulfamoylation as for 220 afforded the title compound (59 mg, 62%) as colourless solid. mp=170-173° C. $^1$H NMR (400 MHz; DMSO-d$_6$) 1.32 (3H, s, CH$_3$), 1.33 (3H, d, J=7.2 Hz, CH$_3$CH), 1.80 (3H, s, CH$_3$), 2.75 (1H, d, J=15.4 Hz, one of CH$_2$), 3.30 (1H, d, J=15.4 Hz, one of CH$_2$), 3.70 (3H, s, OCH$_3$), 3.78 (6H, s, OCH$_3$), 3.80 (3H, s, OCH$_3$), 4.73 (1H, q, J=7.2 Hz, CHCH$_3$), 6.51 (2H, s, 2×CH), 6.98 (1H, s, CH), 7.09 (1H, s, CH), 7.84 (2H, s, NH$_2$). $^{13}$C NMR (100 MHz; DMSO-d$_6$) 22.97 (CH$_3$), 25.17 (CH$_3$), 28.89 (CH$_3$), 43.18 (CH$_2$), 55.10 (OCH$_3$), 55.05 (OCH$_3$), 56.08 (OCH$_3$), 56.88 (C), 60.13 (CH), 102.67 (CH), 113.36 (CH)<120.07 (CH), 130.51 (C), 133.35 (C), 134.84 (C), 136.97 (C), 137.27 (C), 150.97 (C), 153.04 (C), 169.79 (C). LC/MS (ES−) t$_r$=1.27 min, m/z 493.25 (M−H$^-$). HPLC t$_r$=2.44 min (>99%). Anal. Calcd. for C$_{23}$H$_{30}$N$_2$O$_8$S: C 55.86, H 6.11, N 5.66. Found C 56.1, H 6.31, N 5.50%.

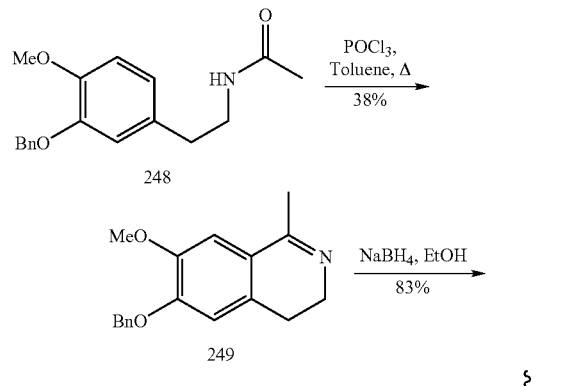

6-(Benzyloxy)-3,4-dihydro-7-methoxy-1-methylisoquinoline 249

A mixture of 248 (2.68 mg, 8.9 mmol) and phosphorus oxychloride (8.23 ml, 53.7 mmol) in toluene (50 ml) was heated under reflux for 3 h. The reaction mixture was cooled to rt, iced water (50 ml) was added and chloroform. The layers were separated and the aqueous layer was basified to pH 9 and extracted with chloroform (2×). The combined organic layers were washed with water, dried (MgSO$_4$) and concentrated in vacuo to afford the title compound (949 mg, 38%) a yellow oil. $^1$H NMR (270 MHz; CDCl$_3$) 2.51 (3H, s, CH$_3$), 2.68 (2H, t, J=7.7 Hz, CH$_2$), 3.66 (2H, td, J=7.7, 1.2 Hz, CH$_2$), 3.90 (3H, s, OCH$_3$), 5.19 (2H, s, CH$_2$), 6.72 (1H, s, CH), 7.04 (1H, s, CH), 7.28-7.44 (5H, m, 5×CH, phenyl). LC/MS (ES+) t$_r$=0.57 min, m/z 282.06 (M$^+$+H).

6-(Benzyloxy)-1,2,3,4-tetrahydro-7-methoxy-1-methylisoquinoline 250

To a solution of 249 (949 mg, 3.4 mmol) in EtOH (15 ml) at 0° C. was added sodium borohydride (256 mg, 6.8 mmol) portionwise. The reaction mixture was stirred at rt for 1.5 h. Water (100 ml) was added and the aqueous layer was neutralised. The aqueous layer was saturated with sodium chloride and extracted with EtOAc (3×100 ml). The combined organic layers were washed with sat. aq. sodium hydrogen C(Ar) bonate (100 ml), dried (MgSO$_4$) and concentrated in vacuo to afford the title compound (600 mg, 63%) a yellow oil. $^1$H NMR (400 MHz; DMSO-d$_6$) 1.58 (3H, d, J=6.4 Hz, CH$_3$CH), 2.50 (2H, s, CH$_2$), 2.82-2.95 (2H, m, CH$_2$), 3.76 (3H, s, OCH$_3$), 4.42 (1H, q, J=6.4 Hz, CH$_3$CH), 5.06 (2H, s, CH$_2$Ph), 6.86 (1H, s, CH), 6.88 (1H, s, CH), 7.31-7.44 (5H, m, 5×CH, phenyl), 9.40 (1H, brs, NH). LC/MS (ES+) t$_r$=0.73 min, m/z 284.13 (M$^+$+H).

2-(3,4,5-Trimethoxybenzyl)-6-(benzyloxy)-1,2,3,4-tetrahydro-7-methoxy-1-methylisoquinoline 251

A solution of 250 (170 mg, 0.6 mmol), 3,4,5-trimethoxybenzyl chloride (156 mg, 0.72 mmol) and triethyl amine (0.17 ml, 1.2 mmol) in EtOH (3 ml) was heated in the microwave at 130° C. for 1.5 h, then at 170° C. for 30 min. The reaction mixture was concentrated in vacuo. Purification (flashmaster: 20 g, gradient elution 100% hex to 50% hex:50% EtOAc over 25 min) afforded The title compound (58 mg, 21%) as a colourless oil. $^1$H NMR (270 MHz; CDCl$_3$) 1.36 (3H, d, J=6.7 Hz, CH$_3$CH), 2.47-2.55 (1H, m, one of CH$_2$), 2.67-2.84 (2H, m, 2×CH, CH$_2$), 2.98-3.07 (1H, m, one of CH$_2$), 3.59-3.73 (2H, m, CH$_2$), 3.83 (9H, s, 3×OCH$_3$), 3.88 (3H, s, OCH$_3$), 5.09 (2H, s, CH$_2$), 6.56-6.62 (4H, m, 4×CH), 7.27-7.44 (5H, m, 5×CH, phenyl). LC/MS (ES+) t$_r$=1.26 min, m/z 464.34 (M$^+$+H).

2-(3-Methoxybenzyl)-6-(benzyloxy)-1,2,3,4-tetrahydro-7-methoxy-1-methylisoquinoline 252

Following the method of 251, the title compound (254 mg, 62%) was obtained as a colourless oil. $^1$H NMR (400 MHz; CDCl$_3$) 1.18 (3H, d, J=6.8 Hz, CH$_3$CH), 2.49-2.55 (1H, m, one of CH$_2$), 2.66-2.82 (2H, m, CH$_2$), 3.0-3.07 (1H, m, one of CH$_2$), 3.72-3.81 (2H, m, CH$_2$), 3.80 (3H, s, OCH$_3$), 3.81-3.86 (1H, m, overlapping signals, CHCH$_3$), 3.84 (3H, s, OCH$_3$), 5.11 (2H, s, CH$_2$Ph), 6.56 (1H, s, CH), 6.61 (1H, s, CH), 6.80 (1H, dd, J=8.2, 1.8 Hz, CH), 6.95-6.98 (2H, m, 2×CH), 7.23 (1H, t, J=8.0 Hz, CH), 7.25-7.45 (5H, m, 5×CH). $^{13}$C NMR (100 MHz; CDC$_3$) 19.79 (CH$_3$), 26.64 (CH$_2$), 43.75 (CH$_2$), 55.18 (OCH$_3$), 55.77 (CH), 56.12 (OCH$_3$), 57.99 (CH$_2$), 70.96 (CH$_2$), 110.96 (CH), 112.39 (CH), 113.92 (CH), 113.93 (CH), 121.0 (CH), 126.14 (C), 127.26 (CH), 127.71 (CH), 128.47 (CH), 129.12 (CH), 132.77 (C), 137.31 (C), 141.35 (C), 146.51 (C), 147.76 (C), 159.64 (C). LC/MS (ES+) t$_r$=1.37 min, m/z 404.06 (M$^+$+H). HRMS (ES+) calcd. for C$_{26}$H$_{30}$NO$_3$ (M$^+$+H) 404.2220, found 404.2224.

2-(3-Methoxybenzyl)-1,2,3,4-tetrahydro-7-methoxy-1-methylisoquinolin-6-ol 253

Hydrogenation of 252 the title compound (150 mg, 70%) was obtained a yellow foam. mp=97-99° C. $^1$H NMR (270 MHz; CDCl$_3$) 1.36 (3H, d, J=6.6 Hz, CH$_3$CH), 2.40-2.58 (1H, m, one of CH$_2$), 2.67-2.87 (2H, m, two of CH$_2$), 3.02-3.11 (1H, m, one of CH$_2$), 3.72 (2H, ABq, J=13.5 Hz, CH$_2$), 2.78-3.83 (1H, m, overlapping signals, CHCH$_3$), 3.80 (3H, s, OCH$_3$), 3.83 (3H, s, OCH$_3$), 6.51 (1H, s, CH), 6.63 (1H, s, CH), 6.80 (1H, dd, J=8.2, 2.7 Hz, CH), 6.95-6.99 (2H, m, 2×CH), 7.23 (1H, t, J=7.7 Hz, CH). $^{13}$C NMR (67.5 MHz; CDCl$_3$) 20.24 (CH$_3$), 26.40 (CH$_2$), 43.83 (CH$_2$), 55.32 (OCH$_3$), 55.86 (CH), 56.06 (OCH$_3$), 58.07 (CH$_2$), 109.68 (CH), 112.58 (CH), 114.04 (CH), 114.35 (CH), 126.94 (C), 129.25 (CH), 131.64 (C), 141.42 (C), 143.84 (C), 144.99 (C), 159.76 (C). LC/MS (ES+) t$_r$=1.06 min, m/z 314.18 (M$^+$+H). HRMS (ES+) calcd. for C$_{19}$H$_{24}$O$_3$ (M$^+$+H) 314.1751, found 314.1742. HPLC t$_r$=2.65 min (>97%).

2-(3,4,5-Trimethoxybenzyl)-1,2,3,4-tetrahydro-7-methoxy-1-methylisoquinolin-6-ol 254

Hydrogenation of 251 gave the title compound (72 mg, 65%) as a pale yellow foam. $^1$H NMR (270 MHz; CDCl$_3$) 1.35 (3H, d, J=6.6 Hz, CH$_3$CH), 2.50-2.57 (1H, m, one of CH$_2$), 2.69-2.85 (2H, m, CH$_2$), 3.02-3.11 (1H, m, one of CH$_2$), 3.67 (2H, ABq, J=13.9 Hz, CH$_2$), 3.77-3.84 (1H, m, overlapping signals, CHCH$_3$), 3.84 (12H, s, 4×OCH$_3$), 6.51 (1H, s, CH), 6.62 (2H, s, 2×CH), 6.64 (1H, s, CH). LC/MS (ES+) t$_r$=0.95 min, m/z 374.21 (M$^+$+H). HRMS (ES+) calcd. for C$_{21}$H$_{28}$NO$_5$ (M$^+$+H) 374.1962, found 374.1959. HPLC t$_r$=2.48 min (>98%).

2-(3-Methoxybenzyl)-1,2,3,4-tetrahydro-7-methoxy-1-methylisoquinolin-6-yl sulfamate 255

Sulfamoylation of 253 (carried out as described above) afforded the title compound (127 mg, 77%) as a pale yellow foam. $^1$H NMR (400 MHz; DMSO-d$_6$) 1.31 (3H, d, J=6.4 Hz, CH$_3$CH), 2.50-2.54 (1H, m, one of CH$_2$), 2.63-2.66 (1H, m, one of CH$_2$), 2.73-2.81 (1H, m, one of CH$_2$), 2.93-2.98 (1H, m, one of CH$_2$), 3.69 (2H, ABq, J=14.0 Hz, CH$_2$), 3.73 (3H, s, OCH$_3$), 3.74 (3H, s, OCH$_3$), 3.80 (1H, q, J=6.5 Hz, CHCH$_3$), 6.81 (1H, dd, J=7.8, 2.2 Hz, CH), 6.86 (1H, s, CH), 6.92-6.93 (2H, m, 2×CH), 7.01 (1H, s, CH), 7.24 (1H, t, J=8.0 Hz, CH), 7.86 (2H, s, NH$_2$). $^{13}$C NMR (100 MHz; DMSO-d$_6$) 19.17 (CH$_3$), 25.88 (CH$_2$), 42.99 (CH$_2$), 54.95 (OCH$_3$), 55.19 (CH), 55.86 (OCH$_3$), 57.21 (CH$_2$), 112.10 (CH), 112.30 (CH), 113.70 (CH), 120.56 (CH), 122.86 (CH), 125.75 (C), 129.30 (CH), 136.92 (C), 139.07 (C), 141.14 (C), 146.69 (C), 159.37 (C). LC/MS (ES+) t$_r$=1.70 min, m/z 393.17 (M$^+$+H). HRMS calcd. for C$_{19}$H$_{25}$N$_2$O$_5$S (M$^+$+H) 393.1479, found 393.1476. HPLC t$_r$=2.05 min (>94%).

2-(3,4,5-Trimethoxybenzyl)-1,2,3,4-tetrahydro-7-methoxy-1-methylisoquinolin-6-yl sulfamate 256

Sulfamoylation of 254 (carried out as described above) afforded the title compound (75 mg, 95%) as a yellow foam. $^1$H NMR (400 MHz; DMSO-d$_6$) 1.33 (3H, d, J=6.8 Hz, CH$_3$CH), 2.50-2.55 (1H, m, one of CH$_2$), 2.61-2.82 (2H, m, two of CH$_2$), 2.91-3.11 (1H, m, one of CH$_2$), 3.64 (3H, s, OCH$_3$), 3.65 (2H, q, J=6.8 Hz, CHCH$_3$), 3.74 (9H, s, 3×OCH$_3$), 3.82 (1H, q, J=6.8 Hz, CHCH$_3$), 6.67 (2H, s, 2×CH), 6.88 (1H, s, CH), 7.02 (1H, s, CH), 7.87 (2H, s, NH$_2$). $^{13}$C NMR (100 MHz; DMSO-d$_6$) 19.39 (CH$_3$), 25.73 (CH$_2$), 42.81 (CH$_2$), 55.19 (CH), 55.76 (OCH$_3$), 55.87 (OCH$_3$), 57.36 (CH$_2$), 59.97 (OCH$_3$), 104.99 (CH), 112.17 (CH), 122.85 (CH), 125.75 (C), 135.20 (C), 136.10 (C), 136.94 (C), 139.04 (C), 149.69 (C), 152.85 (C). LC/MS (ES+) t$_r$=0.89 min, m/z 453.15 (M$^+$+H). HRMS (ES+) calcd. for C$_{21}$H$_{29}$N$_2$O$_7$S (M$^+$+H) 453.1690, found 453.1695. HPLC t$_r$=1.85 min (>94%).

2-Benzyloxy-1-methoxy-4-(2-nitro-but-1-enyl)-benzene 257

3-Benzyloxy-4-methoxybenzaldehyde (24.23 g, 100 mmol) and ammonium acetate (7.73 g, 100 mmol) were covered with 1-nitropropane (90 mL, 1008 mmol) and heated to 160° C. for 22 h. The reaction mixture was then cooled to room temperature and the excess of 1-nitropropane was removed in vacuo. The residue was dissolved in ethyl acetate (300 mL), washed with water (100 mL), brine (50 mL), dried (MgSO$_4$), filtered and concentrated in vacuo. The residue was boiled up in ethanol (100 mL). After cooling to room temperature the yellow precipitate was collected on a sinter funnel and washed with ethanol (4×30 mL). The solid was dried in vacuo to give the title compound as yellow powder (14.07 g, 44%). $^1$H NMR (270 MHz, CDCl$_3$) δ 1.14 (3H, t, J 7.3, CH$_2$CH$_3$), 2.71 (2H, q, J 7.4, CH$_2$CH$_3$), 3.93 (3H, s, OCH$_3$), 5.19 (2H, s, OCH$_2$Ph), 6.91 (1H, d, J 1.9, CH), 6.94 (1H, d, J 8.5, CH), 7.05 (1H, dd, J 8.4, CH), 7.25-7.48 (5H, m, OCH$_2$C$_6$H$_5$), 7.91 (1H, s, HC=CNO$_2$).

2-Benzyloxy-1-methoxy-4-(2-nitro-butyl)-benzene 258

Finely powdered sodium borohydride (3.38 g, 89.3 mmol) was covered with THF (40 mL) and ethanol (40 mL) and cooled to 0° C. 257 (13.95 g, 44.5 mmol) was dissolved in THF (120 mL) and added slowly over 2 h via dropping funnel. The reaction mixture was stirred for 4 h at 0° C. and then for 60 h at room temperature. Hydrochloric acid (2M, 45 mL) was added very carefully. The two layers were separated and the organic layer was concentrated in vacuo. The crude product was purified by flash column chromatography (SiO$_2$: 100 g, hexane/ethyl acetate 90:10) to give the title compound (8.83 g, 62%) as yellow solid. $^1$H NMR (270 MHz, CDCl$_3$) δ 0.91 (3H, t, J 7.4, CH$_2$CH$_3$), 1.62-1.79 (1H, m, one of CHCH$_2$CH$_3$), 1.81-2.00 (1H, m, one of CHCH$_2$CH$_3$), 2.88 (1H, dd, J 14.3, 6.0, one of ArCH$_2$CH), 3.12 (1H, dd, J 14.3, 8.3, one of ArCH$_2$CH), 3.84 (3H, s, OCH$_3$), 4.42-4.55 (1H, m, CHNO$_2$), 5.11 (2H, OCH$_2$Ph), 6.65 (1H, d, J 1.9, CH), 6.69 (1H, dd, J 8.2, 1.9, CH), 6.80 (1H, d, J 8.0, CH), 7.25-7.45 (5H, m, OCH$_2$C$_6$H$_5$).

N-[1-(3-Benzyloxy-4-methoxy-benzyl)-propyl]-acetamide 259

Raney-Nickel (3.82 g, 50% in water, ~32.5 mmol) and a large heavy oval stirring bar were placed in a 500 mL RBF. The water was removed via pipette and the Raney-Nickel was washed with methanol (2×10 mL). Then methanol (100 mL) and 258 (7.88 g, 25.0 mmol) were added and the mixture was cooled to 0° C. Hydrazine hydrate (6.30 g, 126 mmol) was added dropwise via syringe. The reaction mixture was stirred for 30 min at 0° C., then for 7 h at 50° C. The mixture was passed through a sinter funnel with celite to remove the Raney-Nickel. The sinter was washed with methanol (4×20 mL). The combined filtrates were concentrated in vacuo to receive the crude amine as brownish green oil (7.72 g) which was used without further purification. The crude amine (7.41 g, max. 24.0 mmol) was dissolved in dichloromethane (80 mL) and cooled to 0° C. Triethylamine (3.68 g, 36.4 mmol) was added, then acetic anhydride (2.96 g, 29.0 mmol) added dropwise via syringe. The reaction mixture was stirred for 4 h. Water (40 mL) and hydrochloric acid (5M, 10 mL) were added and the layers separated. The aqueous layer was extracted with dichloromethane (2×100 mL). The combined organic layers were washed with brine (80 mL), dried (MgSO$_4$), filtered and concentrated in vacuo to give the title compound (8.73 g, >99%) as beige solid. $^1$H NMR (270 MHz, CDCl$_3$) δ 0.83 (3H, t, J 7.4, CH$_2$CH$_3$), 1.09-1.27 (1H, m, one of CH$_2$CH$_3$), 1.32-1.50 (1H, m, one of CH$_2$CH$_3$), 1.87 (3H, s, NCOCH$_3$), 2.64 (2H, d, J 6.3, ArCH$_2$CH), 3.85 (3H, s, OCH$_3$), 3.89-4.07 (1H, m, ArCH$_2$CH), 5.08 (1H, d, br, J 8.8, NH), 5.13 (2H, s, OCH$_2$Ph), 6.63-6.72 (2H, m, 2×CH), 6.77-6.82 (1H, m, CH), 7.24-7.44 (5H, m, OCH$_2$C$_6$H$_5$).

2-Acyl-3-ethyl-6-benzyloxy-7-methoxytetrahydroisoquinoline 260

N-[1-(3-Benzyloxy-4-methoxy-benzyl)-propyl]acetamide 259 (8.70 g, max. 23.0 mmol), para-toluenesulfonic acid monohydrate (2.12 g, mmol) and para-formaldehyde (220 mg, mmol) were covered with toluene (140 mL) and heated to 140° C. for 22 h. The solvent was removed in vacuo to obtain the crude product (8.0 g) which appeared to be a mixture of product (~60%) and starting material (~40%). The crude product was dry-loaded onto SiO$_2$ (30 g) and purified by flash column chromatography (SiO$_2$: 120 g, ethyl acetate 100%) to give a mixture of the title compound and starting material. The whole mixture was treated again with para-toluenelsulfonic acid monohydrate (218 mg, mmol) and para-formaldehyde (2.10 g, mmol) in toluene (140 mL) at 120° C. for 16 h. The mixture was concentrated in vacuo, water (100 mL) added and extracted with ethyl acetate (3×100 mL). The combined organic layers were washed with water (50 mL) and brine (2×20 mL), dried (MgSO$_4$), filtered and concentrated in vacuo to give the title compound (6.33 g, 81%) as viscous orange oil. $^1$H NMR (270 MHz, CDCl$_3$) δ 0.86 (3H, t, J 7.5, CH$_2$CH$_3$), 1.23-1.64 (2H, m, CH$_2$CH$_3$), 2.16 (3H, s, NCOCH$_3$), 2.44-2.61 (1H, m, one of ArCH$_2$CH), 2.80-3.06 (1H, m, one of ArCH$_2$CH), 3.82 (3H, s, OCH$_3$), 3.92-4.03 (1H, m, CHN), 4.33 (1H, d, J 16.2, one of ArCH$_2$N), 4.55 (1H, d, J 16.2, one of ArCH$_2$N), 5.08 (2H, s, OCH$_2$Ph), 6.53-6.64 (2H, m, 2×CH), 7.18-7.44 (5H, m, OCH$_2$C$_6$H$_5$).

3-Ethyl-6-benzyloxy-7-methoxytetrahydroisoquinoline 261

A solution of 260 (6.281 g, 18.5 mmol) in ethanol (69 mL) was treated with potassium hydroxide (10.14 g, 181 mmol) in water (23 mL) and heated at 120° C. for 88 h. A further aliquot of potassium hydroxide (10.12 g) was then added as a solution in water (23 mL) and heating continued at 140° C. for another 80 h. The reaction mixture was cooled to room temperature and concentrated in vacuo. The formed precipitate was treated with water (100 mL) and collected on a sinter funnel. The solid was dissolved in dichloromethane (100 mL) and washed with water (50 mL) and brine (50 mL), dried (MgSO$_4$), filtered and concentrated in vacuo. The crude product (5.01 g) was dry-loaded onto SiO$_2$ (15 g) and purified by flash column chromatography (SiO$_2$: 80 g, ethyl acetate 100% and 0.5% triethylamine to ethyl acetate/methanol 80:20 and 0.5% triethylamine) to obtain the title compound (4.23 g, 76%) as beige solid. $^1$H NMR (270 MHz, CDCl$_3$) δ 0.98 (3H, t, J 7.4, CH$_2$CH$_3$), 1.39-1.63 (2H, m, CH$_2$CH$_3$), 1.72 (1H, s, br, NH), 2.34 (1H, dd, J 16.0, 10.2, one of ArCH$_2$CH), 2.63 (1H, dd, J 15.8, 3.8, one of ArCH$_2$CH), 2.65-2.78 (1H, m, ArCH$_2$CH), 3.82 (3H, s, OCH$_3$), 3.93 (1H, d, J 15.7, one of ArCH$_2$NH), 4.01 (1H, d, J 15.7, one of ArCH$_2$NH), 5.09 (2H, s, OCH$_2$Ph), 6.53 (1H, s, CH), 6.58 (1H, s, CH), 7.23-7.45 (5H, m, OCH$_2$C$_6$H$_5$). $^{13}$C NMR (67.5 MHz, CDCl$_3$) δ 10.4, 29.5, 34.4, 48.3, 55.2, 56.0, 71.0, 109.3, 114.6, 126.6, 127.2, 127.7, 128.1, 128.4, 137.2, 146.5, 147.8.

3-Ethyl-6-benzyloxy-7-methoxy-2-(3,4,5-trimethoxybenzyl)tetrahydroisoquinoline 262

A solution of 261 (297 mg, 1.0 mmol) in anhydrous DMF (3.0 mL), DIPEA (264 mg, 2.0 mmol) and 3,4,5-trimethoxybenzyl chloride (238 mg, 1.1 mmol) was heated to 80° C. for 12 h, cooled to room temperature and poured into water (50 mL) and ammonium chloride (saturated, 2 mL). The mixture was extracted with ethyl acetate (2×30 mL). The combined organic layers were dried (MgSO$_4$), filtered and concentrated in vacuo. The residue was purified by flash column chromatography using Flashmaster (SiO$_2$: 20 g, hexane 100% to hexane/ethyl acetate 50:50). The title compound was obtained as pale yellow oil (350 mg, 73%). $^1$H NMR (270 MHz, CDCl$_3$) δ 0.97 (3H, t, J 7.0, CH$_2$CH$_3$), 1.43 (1H, sept, J 7.0, one of CH$_2$CH$_3$), 1.67 (1H, sept, J 7.0, one of CH$_2$CH$_3$), 2.42-2.58 (1H, m, one of ArCH$_2$CH), 2.72-2.95 (2H, m, one of ArCH$_2$CH, CHN), 3.51-3.74 (4H, m, 2×ArCH$_2$N), 3.80 (3H, s, OCH$_3$), 3.83 (6H, s, 2×OCH$_3$), 3.88 (3H, s, OCH$_3$), 5.10 (2H, s, OCH$_2$Ph), 6.45-6.56 (1H, m, CH), 6.56-6.70 (3H, m, 3×CH), 7.24-7.52 (5H, m, OCH$_2$C$_6$H$_5$).

3-Ethyl-6-benzyloxy-7-methoxy-2-(3-methoxybenzyl)-tetrahydroisoquinoline 263

A solution of 261 (297 mg, 1.0 mmol) in anhydrous DMF (3.0 mL), DIPEA (263 mg, 2.0 mmol) and 3-methoxybenzyl bromide (222 mg, 1.1 mmol) was heated to 80° C. for 12 h, cooled to room temperature and poured into water (50 mL) and ammonium chloride (saturated, 2 mL). The mixture was extracted with ethyl acetate (2×30 mL). The combined organic layers were dried (MgSO$_4$), filtered and concentrated in vacuo. The residue was purified by flash column chromatography using Flashmaster (SiO$_2$: 20 g, hexane 100% to hexane/ethyl acetate 70:30). The title compound was obtained as pale yellow oil (323 mg, 77%). $^1$H NMR (270 MHz, CDCl$_3$) δ 1.02 (3H, t, J 7.4, CH$_2$CH$_3$), 1.46 (1H, sept, J 7.2, one of CH$_2$CH$_3$), 1.73 (1H, sept, J 6.8, one of CH$_2$CH$_3$), 2.55 (1H, dd, J 16.2, 6.1, one of ArCH$_2$CH), 2.82 (1H, dd, J 16.2, 5.0, one of ArCH$_2$CH), 2.85-2.98 (1H, m, CHN), 3.61-3.77 (4H, m, 2×ArCH$_2$N), 3.84 (6H, s, 2×OCH$_3$), 5.16 (2H, s, OCH$_2$Ph), 6.52 (1H, s, CH), 6.67 (1H, s, CH), 6.81-6.87 (1H, m, CH), 6.95-7.02 (2H, m, 2×CH), 7.23-7.52 (5H, m, OCH$_2$C$_6$H$_5$), 7.27 (1H, t, J 6.9, CH).

3-Ethyl-6-hydroxy-7-methoxy-2-(3,4,5-trimethoxybenzyl)tetrahydroisoquinoline 264

Pd/C (10%, 30.7 mg) was covered with THF (2.0 mL) and ethanol (2.0 mL) and stirred under an atmosphere of hydrogen (balloon pressure) for 15 min at room temperature. Then 262 (334 mg, 0.7 mmol) was added as a solution in THF (4.0 mL). The reaction mixture was stirred for 18 h at room temperature, then filtered through celite. The celite was washed with ethyl acetate (4×5 mL) and the combined filtrates were concentrated in vacuo. The residue was recrystallised from ether/dichloromethane to obtain the title compound as yellow solid (253 mg, 93%). $^1$H NMR (400 MHz, CDCl$_3$) δ 0.98 (3H, t, J 7.4, CH$_2$CH$_3$), 1.41 (1H, sept, J 7.0, one of CH$_2$CH$_3$), 1.68 (1H, sept, J 6.9, one of CH$_2$CH$_3$), 2.51 (1H, dd, J 16.4, 5.9, one of ArCH$_2$CH), 2.75-2.84 (2H, m, one of ArCH$_2$CH, CHN), 3.51-3.75 (4H, m, 2×ArCH$_2$N), 3.80 (3H, s, OCH$_3$), 3.83 (9H, s, 3×OCH$_3$), 6.44 (1H, s, CH), 6.60 (2H, s, 2×CH), 6.65 (1H, s, CH). $^{13}$C NMR (100 MHz, CDCl$_3$) δ 11.1, 23.0, 29.4, 50.8, 55.2, 55.9, 56.0, 58.3, 60.9, 105.3, 108.8, 114.6, 125.4, 126.7, 135.6, 136.5, 143.9, 144.9, 153.1. LC/MS (ES$^+$) t$_r$ 1.03 min; m/z 388.13 ((M+H)$^+$, 100%); MeOH/H$_2$O 95:5 (1.0 mL/min), HPLC tr 2.58 min (>97%); CH$_3$CN/H$_2$O 90:10 (1.0 mL/min).

3-Ethyl-6-hydroxy-7-methoxy-2-(3-methoxybenzyl)-tetrahydroisoquinoline 265

Pd/C (10%, 30.3 mg), THF (2.0 mL) and ethanol (2.0 mL) were reacted with 263 (292, 0.7 mmol) in THF (4.0 mL) as described for the synthesis of 264. The residue was purified by flash column chromatography using Flashmaster (SiO$_2$: 5 g, hexane 100% to hexane/ethyl acetate 60:40). The title compound was obtained as yellow oil (211 mg, 92%). $^1$H NMR (400 MHz, CDCl$_3$) δ 0.98 (3H, t, J 7.2, CH$_2$CH$_3$), 1.42 (1H, sept, J 7.1, one of CH$_2$CH$_3$), 1.69 (1H, sept, J 6.8, one of CH$_2$CH$_3$), 2.52 (1H, dd, J 16.4, 6.3, one of ArCH$_2$CH), 2.80 (1H, dd, J 16.4, 5.1, one of ArCH$_2$CH), 2.86-2.90 (1H, m, CHN), 3.58-3.73 (4H, m, 2×ArCH$_2$N), 3.80 (6H, s, 2×OCH$_3$), 6.42 (1H, s, CH), 6.64 (1H, s, CH), 6.79 (1H, dd, J 8.0, 2.2, CH), 6.92-6.98 (2H, m, 2×CH), 7.22 (1H, t, J 7.8, CH). $^{13}$C NMR (100 MHz, CDCl$_3$) δ 11.1, 23.0, 29.5, 50.9, 55.0, 55.1, 55.9, 58.5, 108.8, 112.3, 114.1, 114.6, 121.1, 125.3, 126.7, 129.1, 141.5, 143.9, 144.9, 159.6. LC/MS (ES$^+$) t$_r$ 1.13 min; m/z 328.10 ((M+H)$^+$, 100%); MeOH/H$_2$O 95:5 (1.0 mL/min), HPLC tr 2.86 min (>99%); CH$_3$CN/H$_2$O 90:10 (1.0 mL/min).

3-Ethyl-6-O-sulfamoyl-7-methoxy-2-(3-methoxybenzyl)tetrahydroisoquinoline 266

A solution of 265 (164 mg, 0.5 mmol) in anhydrous DMA (1.0 mL) was cooled to 0° C. then treated with sulfamoyl chloride (1.5 mmol) in anhydrous DMA (2.0 mL). The reaction mixture was stirred for 2 h at 0° C., then diluted with ethyl acetate (30 mL). The mixture was washed with Na$_2$CO$_3$ (half-saturated, 50 mL), dried (MgSO$_4$) and concentrated in vacuo. The residue was purified by flash column chromatography using Flashmaster (SiO$_2$: 20 g, hexane 100% to hexane/ethyl acetate 50:50). The residue was dissolved in dichloromethane (5 mL) and ether (25 mL) and concentrated in vacuo very quickly to obtain the title compound as yellow solid (106 mg, 52%). $^1$H NMR (400 MHz, DMSO-d$_6$) δ 0.93 (3H, t, J 7.2, CH$_2$CH$_3$, 1.34 (1H, sept, J 7.0, one of CH$_2$CH$_3$), 1.63 (1H, sept, J 6.8, one of CH$_2$CH$_3$), 2.47-2.58 (1H, m, one of ArCH$_2$CH), 2.74-2.88 (2H, m, one of ArCH$_2$CH, CHN), 3.51-3.68 (4H, m, 2×ArCH$_2$N), 3.70 (3H, s, OCH$_3$), 3.72 (3H, s, OCH$_3$), 6.78 (1H, s, CH), 6.78-6.83 (1H, m, CH), 6.87-6.93 (2H, m, 2×CH), 7.03 (1H, s, CH), 7.23 (1H, t, J 8.0, CH), 7.85 (2H, s, NH$_2$). $^{13}$C NMR (100 MHz, DMSO-d$_6$) δ 11.1, 22.3, 29.2, 50.6, 55.1, 55.1, 56.0, 57.9, 111.4, 112.4, 114.0, 120.8, 123.5, 125.7, 129.5, 133.1, 137.2, 141.5, 149.9, 159.5. LC/MS (ES$^-$) t$_r$ 1.19 min; m/z 405.01 ((M+H)$^-$, 100%); MeOH/H$_2$O 95:5 (1.0 mL/min), HPLC tr 2.09 min 97.4%); CH$_3$CN/H$_2$O 90:10 (1.0 mL/min).

3-Ethyl-6-O-sulfamoyl-7-methoxy-2-(3,4,5-tri-methoxybenzyl)tetrahydroisoquinoline 267

A solution of 263 (194 mg, 0.5 mmol) in anhydrous DMA (1.0 mL) was cooled to 0° C. and treated with sulfamoyl chloride (1.5 mmol) in anhydrous DMA (2.0 mL) as described for the synthesis of 266. The residue was purified by flash column chromatography using Flashmaster (SiO$_2$: 20 g, hexane 100% to hexane/ethyl acetate 20:80). The residue was dissolved in dichloromethane (30 mL) and concentrated in vacuo very quickly to obtain the title compound as fluffy yellow solid (172 mg, 73%). $^1$H NMR (400 MHz, DMSO-d$_6$) δ 0.94 (3H, t, J 7.4, CH$_2$CH$_3$), 1.33 (1H, sept, J 7.0, one of CH$_2$CH$_3$), 1.62 (1H, sept, J 6.8, one of CH$_2$CH$_3$), 2.46-2.54 (1H, m, one of ArCH$_2$CH), 2.76-2.87 (2H, m, one of ArCH$_2$CH, CHN), 3.51-3.66 (4H, m, 2×ArCH$_2$N), 3.63 (3H, s, OCH$_3$), 3.70 (3H, s, OCH$_3$), 3.73 (6H, s, 2×OCH$_3$), 6.64 (2H, s, CH), 6.81 (1H, s, CH), 7.03 (1H, s, CH), 7.85 (2H, s, NH$_2$). $^{13}$C NMR (100 MHz, DMSO-d$_6$) δ 11.2, 22.3, 29.0, 50.5, 55.3, 55.9, 56.0, 57.6, 60.2, 105.3, 111.4, 123.3, 125.7, 133.2, 135.5, 136.3, 137.3, 149.9, 153.0. LC/MS (ES$^+$) t$_r$ 1.13 min; m/z 467.11 ((M+H)$^+$, 100%); MeOH/H$_2$O 95:5 (1.0 mL/min), HPLC tr 1.86 min (97.6%); CH$_3$CN/H$_2$O 90:10 (1.0 mL/min).

N-Acyl-3-methoxyphenethylamine 268

To a 0° C. solution of 3-methoxyphenethylamine (10 g, 66 mmol) and triethylamine (11.03 mL, 79.4 mmol) in dichloromethane (100 mL) was added acetic anhydride in a dropwise manner. The reaction mixture was then allowed to come to room temperature overnight and then washed with water (3×100 mL), brine (100 mL), dried and evaporated to give the desired product as a pale yellow oil (10.97 g, 93.7%) which showed $^1$H NMR δ 1.90 (3H, s, Ac), 2.77 (2H, t, J 6.9, ArCH$_2$), 3.48 (2H, m, NCH$_2$), 3.77 (3H, s, OMe), 5.62 (1H, br, NH), 6.68-6.82 (3H, m) and 7.21 (1H, t, J 8.0); $^{13}$C δ 22.3, 33.6, 40.5, 55.1, 111.7, 114.4, 121.0, 140.4, 159.7, 170.0; HRMS [ES+ve] C$_{11}$H$_{15}$NO$_2$ found 194.1172 calculated 194.1176 [M$^+$+H].

6-Methoxy-2-acyl-tetrahydroisoquinoline 269

A mixture of N-acyl-3-methoxyphenethylamine (10.9 g, 61.5 mmol), paraformaldehyde (5 g) and tosic acid (0.5 g) in toluene (200 mL) was refluxed for three days with extra aliquots of paraformaldehyde (2 g) being added after 24 and 48 h. The reaction was then cooled to rt, the organic layers washed with water, brine, dried and evaporated to give the desired tetrahydroisoquinoline as a pale yellow oil (9.4 g, 74.5%) which appears to exist as two conformers by NMR $^1$H NMR δ 2.14 & 2.15 (3H, 2×s), 2.80 & 2.86 (2H, 2×t, J 6.0), 3.63 & 3.80 (2H, 2×t, J 6.0), 3.77 (3H, 2×s), 4.5 &4.63 (2H, 2×s) and 6.64-7.08 (3H, m); HRMS [ES+ve] C$_{12}$H$_{15}$NO$_2$ found 206.1175 calculated 206.1176 [M$^+$+H].

7-Acyl-6-methoxy-2-acyl-tetrahydroisoquinoline 270

To an ice cold suspension of aluminium trichloride (3.20 g, 2.4 mmol) in dichloromethane (20 mL) was added acetyl chloride (1.59 mL, 22.5 mmol) and then, after 0.5 h stirring at rt, 6-methoxy-2-acyl-tetrahydroisoquinoline (1.91 g, 9.3 mmol). The reaction turned red on addition of the isoquinolone and turned an intense red/brown colour on further stirring. After 2.5 h the reaction was quenched by pouring onto ice water (50 mL), the mixture was then treated with dichloromethane (50 mL) and the organic layer separated, washed with water, then brine, dried and evaporated to give an orange oil. Chromatography (eluant 0-10% methanol in ethyl acetate afforded the desired product as a beige solid (1.7 g, 73.9%) which was contaminated by ca 10% of the corresponding 6-hydroxy compound and showed $^1$H NMR δ 2.14

(3H, s), 2.57 & 2.59 (3H, 2×s), 2.84 & 2.89 (2H, 2×t, J 5.8), 3.65 & 3.79 (2H, 2×t, J 5.8), 3.87 & 3.88 (3H, 2×s, OMe), 6.70 & 6.72 (1H, 2×s) and 7.51 (1H, s).

7-Acyl-6-hydroxy-2-acyl-tetrahydroisoquinoline 271

To an ice cold suspension of aluminium trichloride (9.17 g, 68.7 mmol) in dichloromethane (33 mL) was added trimethylamine hydrochloride (3.28 g, 34.3 mmol), the mixture was then stirred for 1 h during which time most of the $AlCl_3$ dissolved. A solution of the methyl ether (1.70 g, 6.87 mmol) in DCM (14 mL) was then introduced in a dropwise manner and then the reaction was heated to reflux for 2 h. The reaction was then cooled to rt and then cautiously poured onto ice (100 g, strong exotherm), before adding an aliquot of DCM (20 ml). The organic layer was separated, washed with water (2×20 mL), 2M HCl (20 mL), water (20 mL) then brine, dried and evaporated to give a pale brown oil which solidifies to give a beige solid on standing. As with previous compounds in the series the $^1$H NMR shows two conformers δ 2.13,& 2.15 (3H, 2×s), 2.56 & 2.57 (3H, 2×s), 2.79 & 2.86 (2H, 2×t, J 6.0), 3.62 & 3.74 (2H, 2×t, J 6.0), 4.54 & 4.63 (2H, 2×s), 6.72 & 6.73 (1H, 2×s), 7.44 & 7.46 (1H, 2×s) and 12.1 (1H, 2×s).

7-Acyl-6-benzyloxy-2-acyl tetrahydroisoquinoline 272

A solution of the 7-acyl-6-hydroxy-2-acyl-tetrahydroisoquinoline (4.5 g, 19.3 mmol) in DMF (75 mL) was treated with potassium C(Ar)bonate (6.67 g, 48.3 mmol) and benzyl bromide (2.41 mL, 20.3 mmol) then heated to 90° C. for 1 h. The reaction was cooled and treated with water (100 mL) and ethyl acetate (100 mL), the organic layer separated, washed with water (5×100 mL), brine (100 mL), dried and evaporate to give a brown oil. Column chromatography (0-10% methanol in ethyl acetate) gave a beige solid which showed $^1$H NMR δ 2.14 (3H, s), 2.54 & 2.56 (3H, 2×s), 2.78-2.90 (2H, m), 3.62 & 3.77 (2H, 2×t, J 5.8), 4.54 & 4.65 (2H, 2×s), 5.11 & 5.12 (2H, 2×s), 6.77 & 6.79 (1H, 2×s), 7.28-7.44 (5H, m) and 7.52 (1H, s).

7-O-Acyl-6-benzyloxy-2-acyl tetrahydroisoquinoline 273

A solution of 7-acyl-6-benzyloxy-2-acyl tetrahydroisoquinoline (4.4 g, 13.6 mmol) in dichloromethane (140 mL) was treated with mCPBA (4 eq) and then stirred at room temperature overnight. The solvent was then removed by evaporation and the residues dissolved in ethyl acetate (150 mL) and stirred with aqueous potassium C(Ar)bonate (50 mL, 10%) for 0.25 h. The organic layer was then separated, washed with aqueous potassium C(Ar)bonate (100 mL, 10%), water (150 mL), brine (100 ml), dried and evaporated. Column chromatography (ethyl acetate) gave the desired acetate as a pale yellow oil (2.3 g, 49.8%) which showed $^1$H NMR δ 2.14 (3H, s), 2.25 & 2.26 (3H, 2×s), 2.76 & 2.81 (2H, 2×t, J 6.0), 3.62 & 3.77 (2H, 2×t, J 6.0), 4.51 & 4.62 (2H, 2×s), 5.04 & 5.05 (2H, 2×s), 6.73-6.83 (2H, m) and 7.28-7.43 (5H, m).

7-Hydroxy-6-benzyloxy-2-acyl tetrahydroisoquinoline 274

A solution of 7-O-acyl-6-benzyloxy-2-acyl tetrahydroisoquinoline (2.0 g, 5.9 mmol) in acetone (60 mL) was treated with sodium hydroxide (15 mL, 30 mmol). After 0.75 h HCl (2M) was added to neutralise the solution, acetone was removed by evaporation and the residues taken up in ethyl acetate, washed with water, brine, dried and evaporated to give the desired phenol which was used without further purification.

7-Ethoxy-6-benzyloxy-2-acyl tetrahydroisoquinoline 275

7-Hydroxy-6-benzyloxy-2-acyl tetrahydroisoquinoline (5.9 mmol), potassium C(Ar)bonate (2.76 g, 20 mmol), tetrabutyl ammonium iodide (50 mg) and ethyl iodide (0.97 mL, 12 mmol) were treated with DMF (30 mL) and stirred overnight. Water and ethyl acetate (100 mL each) were then introduced and the resultant organic layer was separated, washed with water (3×), brine, dried and evaporated to give the desired ethoxy compound as an amber oil which was used without further purification.

7-Ethoxy-6-benzyloxytetrahydroisoquinoline acetate 276

7-Ethoxy-6-benzyloxy-2-acyl tetrahydroisoquinoline (1.5 g) was refluxed overnight with ethanol (60 mL) and sodium hydroxide (15 mL, 10%). The solution was neutralised by adding acetic acid, the solvent removed by evaporation and the residue taken up in chloroform. The organic extract was washed with water, brine, dried and evaporated to give the desired tetrahydroisoquinoline as its acetate salt which showed $^1$H NMR δ 1.39 (3H, t, J 7.0), 1.88 (3H, s), 2.63 (2H, t, J 7.0), 3.07 (2H, t, J 6.0), 3.43 (2H, app d, J 0.5), 3.90 (2H, s), 4.04 (2H, q, J 7.0), 5.08 (2H, s), 6.52 (1H, s), 6.61 (1H, s) and 7.26-7.47 (5H, m).

7-Ethoxy-6-benzyloxy-2-(3,4,5-trimethoxybenzyl)-tetrahydroisoquinoline 277

A solution of 7-ethoxy-6-benzyloxytetrahydroisoquinoline acetate (293 mg, 0.86 mmol), Hunig's base (0.325 mL, 1.96 mmol) and 3,4,5-trimethoxybenzyl chloride (247 mg, 1.14 mmol) in DMF (8 mL) were heated to 80° C. overnight. Water and ethyl acetate (50 mL each) were then added to the cooled solution, the organic layer separated and washed with water (5×), brine, dried and evaporated. The desired product was isolated by column chromatography (3:2 hexane/ethyl acetate) to give the product as a clear colourless oil (340 mg, 85%) which showed $^1$H NMR δ 1.41 (3H, t, J 7.0), 2.63-2.80 (4H, m), 3.54 (2H, s), 3.58 (2H, s), 3.84 (3H, s), 3.84 (6H, s), 4.03 (2H, q, J 7.0), 5.09 (2H, s), 6.54 (1H, s), 6.61 (2H, s), 6.65 (1H, s) and 7.26-7.44 (5H, m). m/z HRMS [ES+] found 464.2413, $C_{28}H_{34}NO_5$ ($M_+$+H) requires 464.2437.

7-Ethoxy-6-hydroxy-2-(3,4,5-trimethoxybenzyl)-tetrahydroisoquinoline 278

7-Ethoxy-6-benzyloxy-2-(3,4,5-trimethoxybenzyl)-tetrahydroisoquinoline acetate (307 mg, 0.66 mmol) was dissolved in ethanol and ethyl acetate (5 mL each), degassed, treated with 10% Pd/C (50 mg) then placed under an atmosphere of hydrogen. After 0.5 h no starting material was evident by TLC and the reaction was filtered through celite and evaporated. The resultant oil was precipitated from ethyl acetate/hexane to give a yellow powder (240 mg, 97%). $^1$H NMR δ 1.39 (3H, t, J 7.0), 2.68 (2H, t, J 5.7), 2.75 (2H, t, J 5.7), 3.52 (2H, s), 3.58 (2H, s), 3.83 (3H, s), 3.84 (6H, s), 4.01 (2H, q, J 7.0), 5.50 (1H, br), 6.46 (1H, s), 6.61 (2H, s) and 6.67 (1H, s).

7-Ethoxy-6-O-sulfamoyl-2-(3,4,5-trimethoxybenzyl)-tetrahydroisoquinoline 279

7-Ethoxy-6-hydroxy-2-(3,4,5-trimethoxybenzyl)-tetrahydroisoquinoline (140 mg, 0.375 mmol) was reacted with a solution of sulfamoyl chloride (1.5 mmol) in dimethyl acetamide (1.5 mL). After stirring overnight ethyl acetate (50 mL) and water (25 mL) were added, the aqueous basified by addition of sodium biC(Ar)bonate, the organic layer separated, washed with water (5×), brine, dried and evaporated. The desired sulfamate was purified by column chromatography (3:2 chloroform/acetone) to give a pale yellow oil (118 mg, 70%). Precipitation from ether/hexane then gave a yellow powder 74 mg. $^1$H NMR δ 1.40 (3H, t, J 6.9), 2.71 (2H, t, J 5.5), 2.82 (2H, t, J 5.5), 3.55 (2H, s), 3.59 (2H, s), 3.83 (3H, s), 3.84 (6H, s), 4.04 (2H, q, J 6.9), 5.02 (2H, br), 6.60 (1H, s), 6.60 (2H, s) and 7.06 (1H, s); m/z [ES−] 450.99 (100%, M$^+$−H); HRMS [ES+] found 453.1690, $C_{21}H_{29}H_2O_7S$ (M$^+$+H) requires 452.1696.

7-Ethyl-6-hydroxy-2-acyl-tetrahydroisoquinoline 280

A stirred solution of 7-acyl-6-hydroxy-2-acyl-tetrahydroisoquinoline (8.2 g, 35.2 mmol) in trifluoroacetic acid (27.1 mL, 352 mmol) was treated with triethylsilane (12.36 mL, 77.4 mmol) in a dropwise manner at rt. After 14 h the solvent was evaporated, methanol was added and then mixture re-evaporated to remove any residual TFA and the residue loaded onto silica gel. Column chromatography (2:1 chloroform/ethyl acetate) gave the desired product as a brown oil (5.4 g, 70%) which showed $^1$H NMR δ 1.19 & 1.20 (3H, 2×t, J 7.4), 2.22 & 2.24 (3H, 2×s), 2.58 & 2.60 (2H, 2×q, J 7.4), 2.73 & 2.77 (2H, 2×t, J 6.1), 3.64 & 3.78 (2H, 2×t, J 6.1), 4.54 & 4.65 (2H, 2×s), 6.60 (1H, 2×s), 6.85 & 6.86 (1H, 2×s) and 9.00-10.50 (1H, br).

7-Ethyl-6-O-benzyl-2-acyl-tetrahydroisoquinoline 281

A solution of 7-ethyl-6-hydroxy-2-acyl-tetrahydroisoquinoline (3.1 g, 14.1 mmol) in DMF (70 mL) was treated with sodium hydride (800 mg, 20 mmol) and then, after 15 minutes, benzyl bromide (2.38 mL, 20 mmol). After 72 h the reaction was quenched by adding water (100 mL) followed by ethyl acetate (100 mL). The organic layer was separated and washed repeatedly with water, then brine, dried and evaporated. The crude product was purified by column chromatography (ethyl acetate with 4 drops Et$_3$N per 100 mL to basify) to give the desired benzylated product as a pale yellow oil (2.2 g, 51%) which showed $^1$H NMR δ 1.20 & 1.21 (3H, 2×t, J 7.4), 2.16 & 2.17 (3H, 2×s), 2.66 & 2.67 (2H, 2×q, J 7.4), 2.78 & 2.83 (2H, 2×t, J 5.9), 3.64 & 3.79 (2H, 2×t, J 5.9), 4.54 & 4.65 (2H, 2×s), 5.06 & 5.09 (2H, 2×s), 6.65 & 6.68 (1H, 2×s), 6.90 & 6.94 (1H, 2×s) and 7.29-7.45 (5H, m).

7-Ethyl-6-O-benzyl tetrahydroisoquinoline 282

7-Ethyl-6-O-benzyl-2-acyl-tetrahydroisoquinoline (2.2 g, 7.1 mmol) was refluxed with ethanol (60 mL) and sodium hydroxide (2M, 15 mL) overnight. The solvent was then removed by evaporation and the residue extracted into chloroform (100 mL), the extract washed with water (2×50 mL), brine (50 mL), dried and evaporated to give a pale yellow oil (1.9 g, quant.) which was used without purification. $^1$H NMR δ 1.19 (3H, t, J 7.4), 1.74 (1H, br), 2.64 (2H, q, J 7.4), 2.73 (2H, t, J 5.8), 3.10 (2H, t, J 5.8), 3.94 (2H, s), 5.04 (2H, s), 6.61 (1H, s), 6.81 (1H, s) and 7.28-7.47 (5H, m).

7-Ethyl-6-O-benzyl-2-(3-methoxybenzyl)tetrahydroisoquinoline 283

A solution of 7-ethyl-6-O-benzyl tetrahydroisoquinoline (358 mg, 1.34 mmol), dimethylformamide (8 mL), Hunig's base (443 μL, 2.67 mmol) and 3-methoxybenzyl chloride (214 μL, 1.47 mmol) were stirred overnight at 80° C. Ethyl acetate (40 mL) was added to the cooled reaction mixture and the organic layer was washed with water (4×40 mL), brine, dried and evaporated to give a brown oil. Column chromatography (3:1 hexane/ethyl acetate with 4 drops Et$_3$N per 100 mL to basify) gave the desired product as a pale yellow oil (300 mg, 58%) which showed $^1$H NMR δ 1.18 (3H, t, J 7.4), 2.63 (2H, q, J 7.4), 2.71 (2H, t, J 5.8), 2.84 (2H, t, J 5.8), 3.56 (2H, s), 3.65 (2H, s), 3.81 (3H, s), 5.04 (2H, s), 6.64 (1H, s), 6.78-6.84 (2H, m), 6.94-7.01 (2H, m) and 7.20-7.47 (6H, m).

7-Ethyl-6-hydroxy-2-(3-methoxybenzyl)tetrahydroisoquinoline 284

A solution of 7-ethyl-6-O-benzyl-2-(3-methoxybenzyl)tetrahydroisoquinoline (260 mg, 0.67 mmol) in ethanol (5 mL) and ethyl acetate (5 mL) was degassed by boiling, treated with 5% Pd/C (50 mg) and then placed under an atmosphere of hydrogen at room temperature for 5 h. The mixture was then filtered through celite and the solvent evaporated. Column chromatography (3:2 Hexane/ethyl acetate with 4 drops Et$_3$N per 100 mL to basify) delivered then desired product (140 mg, 70%) as an off white solid which showed $^1$H NMR δ 1.16 (3H, t, J 7.4), 2.53 (2H, q, J 7.4), 2.68-2.78 (4H, m), 3.53 (2H, s), 3.64 (2H, s), 3.78 (3H, s), 5.10-5.30 (2H, br), 6.37 (1H, s), 6.73 (1H, s), 6.81 (1H, m), 6.95-6.98 (2H, m) and 7.23 (1H, dd, J 7.9 & 7.9)

7-Ethyl-6-O-sulfamoyl-2-(3-methoxybenzyl)tetrahydroisoquinoline 285

7-Ethyl-6-hydroxy-2-(3-methoxybenzyl)tetrahydroisoquinoline (98 mg, 0.33 mmol) was treated with a solution of sulfamoyl chloride (1 mmol) in DMA (1.5 mL). After overnight stirring the reaction was worked up by diluting with ethyl acetate (30 mL) and saturated sodium biC(Ar)bonate solution (15 mL), the organic layer was separated and washed with water (5×), then brine, dried and evaporated to give the desired sulfamate (90 mg, 72%) as a pale yellow oil which showed $^1$H NMR δ 1.14 (3H, t, J 7.4), 2.63 (2H, q, J 7.4), 2.74 (2H, t, J 5.8), 2.85 (2H, t, J 5.8), 3.60 (2H, s), 3.68 (2H, s), 3.79 (3H, s), 4.70-5.20 (2H, br), 6.78-6.84 (1H, m), 6.87 (1H, s), 6.94-6.98 (2H, m) 7.09 (1H, s) and 7.20-7.26 (1H, m).

Synthesis of 1-(benzyl)-6-benzyloxy-7-methoxy-3,4-dihydro-1H-quinolin-2-ones General Method:

NaH (120 mg, 3 mmol) was added portion wise under nitrogen to a stirred solution of 6-(benzyloxy)-7-methoxy-3,4-dihydroquinolin-2(1H)-one (425 mg, 1.5 mmol) in DMF (5 mL). The mixture was stirred for 30 minutes before the appropriate benzyl bromide or benzyl chloride (1.65 mmol) was added and the mixture stirred for 6 hours at rt. After addition of water, the organics were extracted with ethyl acetate (2×50 mL). The organic layer was washed with water, brine, dried (MgSO$_4$), filtered and the solvent evaporated under vacuum. The residual solid was purified by flash chromatography.

6-(Benzyloxy)-7-methoxy-1-(2-methoxybenzyl)-3,4-dihydro-1H-quinolin-2-one 286

Colorless oil, 430 mg (71%), R$_f$: 0.66 (hexane/ethyl acetate 1:1), $^1$H NMR (270 MHz, CDCl$_3$) δ 2.68-2.86 (4H, m, 2×CH$_2$), 3.65 (3H, s, CH$_3$O), 3.88 (3H, s, CH$_3$O), 5.06 (2H, s, CH$_2$), 5.17 (2H, s, CH$_2$), 6.50 (1H, s, ArH), 6.69 (1H, s, ArH), 6.81-6.89 (2H, m, ArH), 7.01 (1H, dd, J 7.4 and 1.4 Hz, ArH), 7.16-7.43 (6H, m, ArH); $^{13}$C NMR (67.5 MHz, CDCl$_3$) δ 25.0 (CH$_2$), 32.2 (CH$_2$), 40.6 (CH$_2$), 55.5 (CH$_3$O), 56.2 (CH$_3$O), 71.7 (CH$_2$), 101.9 (CH), 110.3 (CH), 114.5 (CH), 118.0 (C), 121.0 (CH), 125.0 (C), 127.4 (2×CH), 128.0 (CH), 128.2 (CH), 128.6 (2×CH), 133.9 (C), 137.3 (C), 143.6 (C), 148.7 (C), 156.6 (C), 170.5 (CO).

6-(Benzyloxy)-7-methoxy-1-(3-methoxybenzyl)-3,4-dihydro-1H-quinolin-2-one 287

Yellow oil, 350 mg (58%), R$_f$: 0.63 (hexane/ethyl acetate 1:1), $^1$H NMR (270 MHz, CDCl$_3$) δ 2.67-2.88 (4H, m, 2×CH$_2$), 3.64 (3H, s, CH$_3$O), 3.74 (3H, s, CH$_3$O), 5.06 (2H, s, CH$_2$), 5.11 (2H, s, CH$_2$), 6.50 (1H, s, ArH), 6.69 (1H, s, ArH), 6.71-6.84 (3H, m, ArH), 7.18-7.42 (6H, m, ArH). HPLC t$_r$=5.12 min (71.3%) and 6.10 (28.7%). (CH$_3$CN/H$_2$O 70/30); LC/MS (ES+) t$_r$=2.52 min m/z 426.17 ((M+Na)$^+$, 100%), 404.19 (M+H)$^+$ and tr=3.21 min m/z 438.2 ((M+Na)$^+$, 100%), 416.22 (M+H)$^+$; MeOH/H$_2$O 80/20

6-(Benzyloxy)-7-methoxy-1-(4-methoxybenzyl)-3,4-dihydro-1H-quinolin-2-one 288

White solid, 390 mg (64%), R$_f$: 0.71 (hexane/ethyl acetate 3:1), $^1$H NMR (270 MHz, CDCl$_3$) δ 2.66-2.84 (4H, m, 2×CH$_2$), 3.66 (3H, s, CH$_3$O), 3.78 (3H, s, CH$_3$O), 5.06 (2H, s, CH$_2$), 5.07 (2H, s, CH$_2$), 6.52 (1H, s, ArH), 6.67 (1H, s, ArH), 6.82 (2H, d, J 8.8 Hz, ArH), 7.15 (2H, d, J 8.8 Hz, ArH), 7.26-7.44 (5H, m, ArH); HPLC t$_r$=4.97 min (84.5%). (CH$_3$CN/H$_2$O 90:10); LC/MS (ES+) t$_r$=6.38 min m/z 426.24 (M+Na)$^+$, 404.19 (M+H)$^+$; MeOH/H$_2$O 70/30

6-(Benzyloxy)-7-methoxy-1-(3,4,5-trimethoxybenzyl)-3,4-dihydro-1H-quinolin-2-one 289

White solid, 300 mg (43%), mp 129-130° C., R$_f$: 0.28 (hexane/ethyl acetate 1:1), $^1$H NMR (270 MHz, CDCl$_3$) δ 2.67-2.74 (2H, m, CH$_2$), 2.79-2.85 (2H, m, CH$_2$), 3.68 (3H, s, CH$_3$O), 3.78 (6H, s, 2×CH$_3$O), 3.80 (3H, s, CH$_3$O), 5.05 (2H, s, CH$_2$), 5.07 (2H, s, CH$_2$), 6.45 (2H, s, ArH), 6.54 (1H, s, ArH), 6.70 (1H, s, ArH), 7.26-7.42 (5H, m, Ph); $^{13}$C NMR (100 MHz, CDCl$_3$) δ 25.0 (CH$_2$), 32.2 (CH$_2$), 46.7 (CH$_2$), 56.1 (2×CH$_3$O), 56.3 (CH$_3$O), 60.8 (CH$_3$O), 71.6 (CH$_2$), 101.9 (CH), 103.5 (2×CH), 114.4 (CH), 118.1 (C), 127.3 (2×CH), 127.9 (CH), 128.5 (2×CH), 128.6 (2×CH), 133.2 (C), 133.9 (C), 137.0 (C), 143.7 (C), 148.7 (C), 153.5 (C), 170.4 (CO). LC/MS (ES+) t$_r$=0.99 min m/z 486.13 (M+Na)$^+$, 464.15 (M+H)$^+$; MeOH/H$_2$O 95/5 HPLC t$_r$=3.91 min (98.8%). (CH$_3$CN/H$_2$O 70:30).

Synthesis of 1-(benzyl)-6-hydroxy-7-methoxy-3,4-dihydro-1H-quinolin-2-ones

General Method:
A solution of 1-benzyl-6-(benzyloxy)-3,4-dihydro-1H-quinolin-2-one (1 mmol) in THF (20 mL) and methanol (20 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The crude mixture was purified by flash chromatography (hexane/ethyl acetate) and the resulting solid stirred in diethyl ether.

6-Hydroxy-7-methoxy-1-(3-methoxybenzyl)-3,4-dihydro-1H-quinolin-2-one 290

White powder, 240 mg (77%), mp 177-178° C., R$_f$: 0.34 (hexane/ethyl acetate 1:1), $^1$H NMR (270 MHz, CDCl$_3$) δ 2.68-2.75 (2H, m, CH$_2$), 2.82-2.88 (2H, m, CH$_2$), 3.64 (3H, s, CH$_3$O), 3.88 (3H, s, CH$_3$O), 5.14 (2H, s, CH$_2$), 5.35 (1H, s, OH), 6.44 (1H, s, ArH), 6.70 (1H, s, ArH), 6.81-6.88 (2H, m, ArH), 6.98-7.02 (1H, m, ArH), 7.15-7.22 (1H, m, ArH); $^{13}$C NMR (100 MHz, CDCl$_3$) δ 24.9 (CH$_2$), 32.2 (CH$_2$), 40.5 (CH$_2$), 55.4 (CH$_3$O), 55.9 (CH$_3$O) 100.3 (CH), 110.1 (CH), 113.8 (CH), 118.9 (C), 120.9 (CH), 125.0 (C), 127.3 (CH), 128.1 (CH), 132.6 (C), 140.8 (C), 145.2 (C), 156.5 (C), 170.5 (CO). LC/MS (ES−) t$_r$=0.92 min m/z 312.17 (M−H)$^-$; MeOH/H$_2$O 95/5; HPLC t$_r$=2.39 min (100.0%). (acetonitrile/water 70/30)

6-Hydroxy-7-methoxy-1-(3-methoxybenzyl)-3,4-dihydro-1H-quinolin-2-one 291

White powder, 80 mg (25%), mp 137-138° C., R$_f$: 0.32 (hexane/ethyl acetate 1:1), $^1$H NMR (270 MHz, CDCl$_3$) δ 2.68-2.75 (2H, m, CH$_2$), 2.81-2.88 (2H, m, CH$_2$), 3.63 (3H, s, CH$_3$O), 3.74 (3H, s, CH$_3$O), 5.10 (2H, s, CH$_2$), 5.39 (1H, s, OH), 6.43 (1H, s, ArH), 6.70 (1H, s, ArH), 6.74-6.76 (2H, m, ArH), 6.81 (1H, d, J 7.7 Hz, ArH); $^{13}$C NMR (67.5 MHz, CDCl$_3$) δ 25.0 (CH$_2$), 32.3 (CH$_2$), 46.5 (CH$_2$), 55.2 (CH$_3$O), 56.0 (CH$_3$O) 100.6 (CH), 112.4 (2×CH), 114.0 (CH), 118.9 (CH), 119.1 (C), 129.9 (CH), 132.7 (C), 139.2 (C), 141.1 (C), 145.3 (C), 160.1 (C), 170.5 (CO). LC/MS (ES−) t$_r$=0.93 min m/z 312.10 (M−H)$^-$; MeOH/H$_2$O 95/5 HPLC t$_r$=2.31 min (100.0%). (acetonitrile/water 70/30)

6-Hydroxy-7-methoxy-1-(4-methoxybenzyl)-3,4-dihydro-1H-quinolin-2-one 292

White powder, 125 mg (40%), mp 168-169° C., R$_f$: 0.30 (hexane/ethyl acetate 1:1), $^1$H NMR (270 MHz, CDCl$_3$) δ 2.68-2.74 (2H, m, CH$_2$), 2.80-2.86 (2H, m, CH$_2$), 3.66 (3H, s, CH$_3$O), 3.76 (3H, s, CH$_3$O), 5.07 (2H, s, CH$_2$), 5.34 (1H, br, OH), 6.46 (1H, s, ArH), 6.70 (1H, s, ArH), 6.83 (2H, d, J 8.5 Hz, ArH), 7.15 (2H, d, J 8.5 Hz, ArH); $^{13}$C NMR (67.5 MHz, CDCl$_3$) δ 25.0 (CH$_2$), 32.3 (CH$_2$), 45.9 (CH$_2$), 55.4 (CH$_3$O), 56.0 (CH$_3$O) 100.5 (CH), 114.0 (CH), 114.3 (2×CH), 119.2 (C), 127.9 (2×CH), 129.5 (C), 132.8 (C), 141.0 (C), 145.2 (C), 158.7 (C), 170.5 (CO). LC/MS (ES−) t$_r$=0.90 min m/z 312.10 (M−H)$^-$; MeOH/H$_2$O 95/5 HPLC t$_r$=2.28 min (99.0%). (acetonitrile/water 70/30)

6-Hydroxy-7-methoxy-1-(3,4,5-trimethoxybenzyl)-3,4-dihydro-1H-quinolin-2-one 293

White powder, 300 mg (80%), mp 157-158° C., R$_f$: 0.53 (ethyl acetate), $^1$H NMR (270 MHz, CDCl$_3$) δ 2.68-2.75 (2H, m, CH$_2$), 2.81-2.87 (2H, m, CH$_2$), 3.67 (3H, s, CH$_3$O), 3.78 (6H, s, 2×CH$_3$O), 3.79 (3H, s, CH$_3$O), 5.05 (2H, s, CH$_2$), 5.36 (1H, s, OH), 6.44 (1H, s, ArH), 6.48 (2H, s, ArH), 6.72 (1H, s, ArH); $^{13}$C NMR (100 MHz, CDCl$_3$) δ 25.0 (CH$_2$), 32.2 (CH$_2$), 46.8 (CH$_2$), 56.0 (CH$_3$O), 56.1 (2×CH$_3$O), 60.8

(CH₃O) 100.4 (CH), 103.4 (2×CH), 113.9 (CH), 119.1 (C), 132.8 (C), 133.3 (C), 137.0 (C), 141.1 (C), 145.2 (C), 153.6 (C), 170.4 (CO). LC/MS (ES−) t$_r$=0.86 min m/z 372.13 (M−H)⁻; MeOH/H₂O 95/5 HPLC t$_r$=1.57 min (99.7%). (acetonitrile/water 90/10)

Synthesis of 1-benzyl-7-methoxy-6-O-sulfamoyl-3,4-dihydro-1H-quinolin-2-ones

General Method:

A solution of 1-(benzyl)-6-hydroxy-7-methoxy-3,4-dihydro-1H-quinolin-2-ones (0.2 mmol) and sulfamoyl chloride (0.4 mmol) in DMA (1 mL) was stirred at rt under nitrogen for 24 hours. After addition of water (5 mL) the organics were extracted into ethyl acetate (2×50 mL), the organic layers washed with water and brine, then dried (MgSO₄) and evaporated. The crude product was purified by flash chromatography (hexane/ethyl acetate or DCM/ethyl acetate) and the resulting solid stirred in diethyl ether, filtered and dried under vacuum.

7-methoxy-1-(2-methoxybenzyl)-6-O-sulfamoyl-3,4-dihydro-1H-quinolin-2-one 294

White powder, 60 mg (76%), mp 175-176° C., R$_f$: 0.68 (DCM/EtOAc 1:1), ¹H NMR (270 MHz, DMSO-d6) δ 2.62-2.670 (2H, m, CH₂), 2.84-2.90 (2H, m, CH₂), 3.59 (3H, s, CH₃O), 3.87 (3H, s, CH₃O), 5.09 (2H, s, CH₂), 6.58 (1H, s, ArH), 6.85 (1H, t, J 7.4 Hz, ArH), 6.96 (1H, dd, J 7.4 and 1.4 Hz, ArH), 7.03 (1H, d, J 8.4 Hz, ArH), 7.15 (1H, s, ArH), 7.24 (1H, dt, J 8.4 and 1.4 Hz, ArH), 7.86 (2H, br, NH₂); ¹³C NMR (67.5 MHz, DMSO-d6) δ 23.8 (CH₂), 31.4 (CH₂), 39.9 (CH₂), 55.5 (CH₃O), 55.9 (CH₃O) 101.5 (CH), 110.8 (CH), 117.9 (C), 120.6 (CH), 122.6 (CH), 124.4 (C), 127.0 (CH), 128.4 (CH), 133.4 (C), 138.1 (C), 150.6 (C), 156.5 (C), 169.7 (CO). LC/MS (ES−) t$_r$=0.87 min m/z 390.96 (M−H)⁻; MeOH/H₂O 95/5; HPLC t$_r$=2.29 min (100.0%). (acetonitrile/water 70/30)

7-methoxy-1-(3-methoxybenzyl)-6-O-sulfamoyl-3,4-dihydro-1H-quinolin-2-one 295

White powder, 48 mg (62%), mp 108-110° C., R$_f$: 0.70 (DCM/EtOAc 1:1), ¹H NMR (270 MHz, CDCl₃) δ 2.71-2.79 (2H, m, CH₂), 2.85-2.93 (2H, m, CH₂), 3.63 (3H, s, CH₃O), 3.75 (3H, s, CH₃O), 4.99 (2H, s, CH₂), 5.11 (2H, s, NH₂), 6.53 (1H, s, ArH), 6.74-6.81 (3H, m, ArH), 7.11 (1H, s, ArH), 7.23 (1H, t, J 8.0 Hz, ArH); ¹³C NMR (67.5 MHz, CDCl₃) δ 24.5 (CH₂), 31.7 (CH₂), 46.5 (CH₂), 55.2 (CH₃O), 56.3 (CH₃O) 101.9 (CH), 112.3 (CH), 112.4 (CH), 118.7 (CH), 119.0 (C), 123.4 (CH), 130.0 (CH), 133.6 (C), 138.5 (C), 139.5 (C), 150.3 (C), 160.1 (C), 170.4 (CO). LC/MS (ES−) t$_r$=0.87 min m/z 390.96 (M−H)⁻; MeOH/H₂O 95/5; HPLC t$_r$=2.29 min (100.0%). (acetonitrile/water 70/30)

7-methoxy-1-(4-methoxybenzyl)-6-O-sulfamoyl-3,4-dihydro-1H-quinolin-2-one 296

White powder, 61 mg (78%), mp 179-180° C., R$_f$: 0.68 (DCM/EtOAc 1:1), ¹H NMR (270 MHz, DMSO-d6) δ 2.61-2.68 (2H, m, CH₂), 2.80-2.86 (2H, m, CH₂), 3.65 (3H, s, CH₃O), 3.70 (3H, s, CH₃O), 5.13 (2H, s, CH₂), 6.75 (1H, s, ArH), 6.87 (2H, d, J 8.8 Hz, ArH), 7.12 (1H, s, ArH), 7.23 (2H, d, J 8.8 Hz, ArH), 7.85 (2H, br, NH₂); ¹³C NMR (67.5 MHz, DMSO-d6) δ 23.8 (CH₂), 31.4 (CH₂), 43.6 (CH₂), 55.0 (CH₃O), 56.1 (CH₃O) 102.2 (CH), 114.0 (2×CH), 118.1 (CH), 122.5 (CH), 128.3 (2×CH), 129.3 (C), 133.4 (C), 137.9 (C), 150.5 (C), 158.3 (C), 169.7 (CO). LC/MS (ES−) t$_r$=0.85 min m/z 391.15 (M−H)⁻; MeOH/H₂O 95/5; HPLC t$_r$=1.83 min (99.5%). (acetonitrile/water 70/30)

7-methoxy-6-O-sulfamoyl-1-(3,4,5-trimethoxybenzyl)-3,4-dihydro-1H-quinolin-2-one 297

White powder, 66 mg (73%), mp 154-155° C., R$_f$: 0.37 (ethyl acetate), ¹H NMR (270 MHz, DMSO-d6) δ 2.65-2.70 (2H, m, CH₂), 2.82-2.88 (2H, m, CH₂), 3.60 (3H, s, CH₃O), 3.69 (3H, s, CH₃O), 3.71 (6H, s, 2×CH₃O), 5.12 (2H, s, CH₂), 6.65 (2H, s, ArH), 6.82 (1H, s, ArH), 7.13 (1H, s, ArH), 7.85 (2H, br, NH₂); ¹³C NMR (67.5 MHz, DMSO-d6) δ 24.3 (CH₂), 31.9 (CH₂), 45.0 (CH₂), 56.3 (2×CH₃O), 56.6 (CH₃O), 60.5 (CH₃O) 102.7 (CH), 104.9 (2×CH), 118.7 (CH), 123.1 (C), 133.9 (C), 134.0 (C), 136.9 (C), 138.6 (C), 151.1 (C), 153. (2×C), 170.4 (CO). LC/MS (ES−) t$_r$=0.93 min m/z 451.24 (M−H)⁻; MeOH/H₂O 95/5; HPLC t$_r$=1.78 min (100%). (acetonitrile/water 90/10)

9-Benzyloxy-10-methoxy-6,7-dihydro-5H-benzo[e]tetrazolo[1,5-a]azepine 298, 7-benzyloxy-8-methoxy-2,3,4,5-tetrahydro-1H-benzo[c]azepin-1-one 299 and 7-benzyloxy-8-methoxy-4,5-dihydro-1H-benzo[b]azepin-2(3H)-one 300

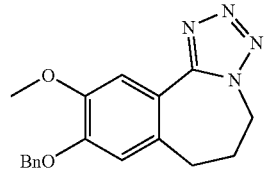

298

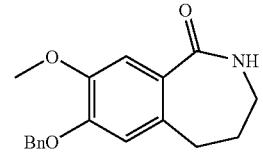

299

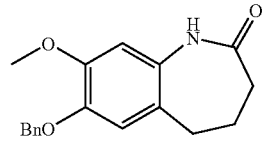

300

A solution of 6-O-benzyl-7-methoxytetralone (4.6 g, 16.2 mmol) in DCM (150 mL) was stirred at 0° C. and methanesulfonic acid (8.1 mL, 125 mmol) added dropwise followed by NaN₃ (2.11 g, 32.5 mmol). The mixture was stirred at 0° C. for 6 hours then O/N at rt. After addition of water, the organic layer was washed with biC(Ar)bonate, water, dried (MgSO₄), filtered and concentrated to give 5 g of crude brown solid. Column chromatography (hexane/ethyl acetate/MeOH 3:1 to 0:20:1) afforded successively of 9-benzyloxy-10-methoxy-6,7-dihydro-5H-benzo[c]tetrazolo[1,5-a]azepine 298 (350 mg (7%)), 7-benzyloxy-8-methoxy-4,5-dihydro-1H-benzo[b]azepin-2(3H)-one 299 (1.1 g, 22%) and 7-benzyloxy-8-methoxy-2,3,4,5-tetrahydro-1H-benzo[c]azepin-1-one 300 (1.85 g (39%)).

9-Benzyloxy-10-methoxy-6,7-dihydro-5H-benzo[c]tetrazolo azepine 298

White powder, mp 168-170° C., R$_f$: 0.50 (hexane/ethyl acetate), ¹H NMR (270 MHz, DMSO-d6) δ 2.18-2.27 (2H, m), 2.97-3.02 (2H, m), 3.83 (3H, s), 4.62-4.67 (2H, m), 5.16 (2H, s), 7.13 (1H, s), 7.33-7.50 (5H, m), 7.78 (1H, s); $^{13}$C NMR (67.5 MHz, CDCl$_3$) δ 24.8 (CH$_2$), 32.5 (CH$_2$), 49.5 (CH$_2$), 55.7 (CH$_3$O), 69.9 (CH$_2$), 112.2 (CH), 114.5 (C), 115.0 (CH), 128.0 (2×CH), 128.1 (CH), 128.5 (2×CH), 134.3 (C), 136.6 (C), 147.5 (C), 148.4 (C), 150.0 (CH), 153.6 (C). LC/MS (ES+) t$_r$=0.94 min m/z 345.11 ((M+Na)$^+$, 100%), 323.13 (M+1)$^+$; MeOH/H$_2$O 95/5; HPLC t$_r$=2.68 min (89.7%), 3.34 (10.3%) (CH$_3$CN/H$_2$O 70/30)

7-Benzyloxy-8-methoxy-4,5-dihydro-1H-benzo[b]azepin-2(3H)-one 299

White powder, mp 178-180° C., R$_f$: 0.33 (hexane/ethyl acetate), $^1$H NMR (270 MHz, DMSO-d6) δ 1.85 (2H, m), 2.67 (2H, t, J 6.9 Hz), 2.91 (2H, m), 3.76 (3H, s), 5.11 (2H, s), 6.99 (1H, s), 7.07 (1H, s), 7.31-7.49 (5H, m), 7.92 (1H, t, J 5.5 Hz); $^{13}$C NMR (100 MHz, DMSO-d6) δ 28.3 (CH$_2$), 29.2 (CH$_2$), 32.9 (CH$_2$), 55.7 (CH$_3$O), 70.3 (CH$_2$O) 106.7 (CH), 115.1 (CH), 125.5 (C), 127.9 (CH), 128.0 (2×CH), 128.4 (2×CH), 131.9 (C), 137.2 (C), 144.7 (C), 147.8 (C), 173.3 (CO). LC/MS (ES+) t$_r$=1.18 min m/z 320.10 ((M+Na)$^+$, 100%), 298.12 (M+H)$^+$; MeOH/H$_2$O 95/5; HPLC t$_r$=1.93 min (99.4%). (CH$_3$CN/H$_2$O 90/10)

7-Benzyloxy-8-methoxy-2,3,4,5-tetrahydro-1H-benzo[c]azepin-1-one 300

White powder, mp 192-193° C., R$_f$: 0.10 (ethyl acetate), $^1$H NMR (270 MHz, DMSO-d6) δ 1.85 (2H, m), 2.67 (2H, t, J 6.9 Hz), 2.91 (2H, m), 3.76 (3H, s), 5.11 (2H, s), 6.99 (1H, s), 7.07 (1H, s), 7.31-7.49 (5H, m), 7.92 (1H, t, J 5.5 Hz), $^{13}$C NMR (100 MHz, DMSO-d6) δ 29.4 (CH$_2$), 30.3 (CH$_2$), 38.7 (CH$_2$), 55.6 (CH$_3$O), 69.9 (CH$_2$O) 102.7 (CH), 111.8 (CH), 113.5 (CH), 128.0 (CH), 128.1 (CH), 128.5 (2×CH), 131.2 (C), 136.8 (C), 147.4 (C), 149.4 (C), 172.0 (CO). LC/MS (ES+) t$_r$=1.18 min m/z 320.10 ((M+Na)$^+$, 100%), 298.12 (M+H)$^+$; MeOH/H$_2$O 95/5; HPLC t$_r$=2.52 min (100%). (CH$_3$CN/H$_2$O 70/30)

7-(benzyloxy)-8-methoxy-2,3,4,5-tetrahydro-1H-benzo[c]azepine 301

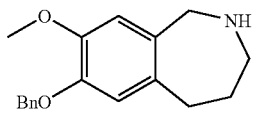

A solution of 7-(benzyloxy)-8-methoxy-2,3,4,5-tetrahydro-1H-benzo[c]azepin-1-one 300 (1.2 g, 4 mmol) in THF (50 mL) was cooled to 0° C. and LAH (380 mg, 10 mmol) added portion wise. The mixture was refluxed for 8 hours, cooled to rt, cautiously quenched with ice and 6 ml 2M aqueous 2M NaOH then filtered through celite. The filtrate was extracted with EtOAc and the organic layer was washed with water, brine, dried, filtered and concentrated giving 0.95 g (84%) of yellow oil slowly solidifying which upon purification by flash chromatography (EtOAc/MeOH/TEA 1/0/0 to 20/1/0.5) gave 088 g (78%) of a white powder, mp=79-80° C., R$_f$: 0.24 (ethyl acetate/MeOH/TEA 10:1:0.5), $^1$H NMR (270 MHz, CDCl$_3$) δ 1.41 (1H, br), 1.62-1.71 (2H, m), 2.78-2.82 (2H, m), 3.14-3.18 (2H, m), 3.85 (5H, s, MeO and CH$_2$N), 5.11 (2H, s), 6.66 (1H, s), 6.72 (1H, s), 7.26-7.44 (5H, m), $^{13}$C NMR (100 MHz, CDCl$_3$) δ 31.1 (CH$_2$), 35.7 (CH$_2$), 53.6 (CH$_2$), 54.9 (CH$_2$), 56.2 (CH$_2$), 71.3 (CH$_2$O), 113.0 (CH), 116.2 (CH), 127.3 (CH), 127.7 (CH), 128.4 (CH), 135.1 (C), 136.0 (C), 137.3 (C), 146.4 (C), 147.1 (C). LC/MS (ES+) t$_r$=min m/z ((M+Na)$^+$, 100%), (M+1)$^+$; MeOH/H$_2$O 95/5; HPLC t$_r$=3.03 min (97.5%) (CH$_3$CN/H$_2$O 70/30); HRMS (ES) calcd. for C$_{18}$H$_{22}$NO$_2$ (MH), 284.1651 found. 284.1645

Synthesis of 2-benzyl-7-benzyloxy-8-methoxy-2,3,4,5-tetrahydro-1H-benzo[c]azepines General Method:

A solution of 7-(benzyloxy)-8-methoxy-2,3,4,5-tetrahydro-1H-benzo[c]azepine (440 mg, 1.5 mmol) and the appropriate benzyl bromide (1.65 mmol) in TEA (0.5 mL, 3.6 mmol) and ethanol (2.5 mL) was heated at 130 C. for 90 minutes under microwave energy. After addition of water (20 mL) and ethyl acetate (80 mL), the organic layer was separated and washed with water, brine, dried (MgSO$_4$) and concentrated under reduced pressure. The resulting yellow solid was purified by flash chromatography (hexane/ethyl acetate or DCM/ethyl acetate) to give the desired compound.

7-Benzyloxy-8-methoxy-2-(2-methoxybenzyl)-2,3,4,5-tetrahydro-1H-benzo[c]azepine 302

Cream color powder, 370 mg (61%), mp 105-106° C., R$_f$: 0.36 (ethyl acetate), $^1$H NMR (270 MHz, CDCl$_3$) δ 1.72-1.77 (2H, m, CH$_2$), 2.75-2.80 (2H, m, CH$_2$), 3.05-3.09 (2H, m, CH$_2$), 3.55 (2H, s, CH$_2$), 3.80 (3H, s, CH$_3$O), 3.82 (3H, s, CH$_3$O), 3.83 (2H, s, CH$_2$), 5.12 (2H, s, CH$_2$), 6.61 (1H, s, ArH), 6.72 (1H, s, ArH), 6.88 (1H, dd, J 8.3 and 1.0 Hz, ArH), 6.91 (1H, dt, J 7.4 and 1.0 Hz), 7.21 (1H, dd, J 8.2 and 1.7 Hz, ArH), 7.26-7.46 (6H, s,ArH). $^{13}$C NMR (67.5 MHz, CDCl$_3$) δ 26.0 (CH$_2$), 35.8 (CH$_2$), 51.6 (CH$_2$), 55.5 (CH$_2$), 56.3 (CH$_2$), 58.8 (CH$_3$O), 59.6 (CH$_3$O), 71.4 (CH$_2$O), 110.5 (CH), 114.7 (CH), 115.7 (CH), 127.4 (2×CH), 127.6 (C), 127.8 (CH), 128.0 (CH), 128.6 (2×CH), 130.6 (CH), 132.7 (C), 135.6 (C), 137.5 (C), 146.6 (C), 147.2 (C), 159.9 (C). LC/MS (ES+) t$_r$=1.45 min m/z 404.19 ((MH)$^+$, 100%); MeOH/H$_2$O 95/5; HPLC t$_r$=6.74 min (99.5%) (CH$_3$CN/H$_2$O 90/10)

7-Benzyloxy-8-methoxy-2-(3-methoxybenzyl)-2,3,4,5-tetrahydro-1H-benzoazepine 303

White powder, 410 mg (68%), mp 92-93° C., R$_f$: 0.5 (ethyl acetate), $^1$H NMR (270 MHz, CDCl$_3$) δ 1.68-1.74 (2H, m, CH$_2$), 2.77-2.81 (2H, m, CH$_2$), 3.10-3.14 (2H, m, CH$_2$), 3.51 (2H, s, CH$_2$), 3.79 (3H, s, CH$_3$O), 3.80 (5H, s, CH$_2$ and CH$_3$O), 5.13 (2H, s, CH$_2$), 6.48 (1H, s, ArH), 6.73 (1H, s, ArH), 6.77-6.88 (3H, m, ArH), 7.21 (1H, t, J 8.2 Hz, ArH), 7.27-7.46 (5H, s, Ph). $^{13}$C NMR (67.5 MHz, CDCl$_3$) δ 25.4 (CH$_2$), 35.8 (CH$_2$), 55.3 (CH$_2$), 56.2 (CH$_2$), 57.6 (CH$_2$), 58.7 (CH$_2$O), 59.2 (CH$_3$O), 71.4 (CH$_3$O), 112.7 (CH), 114.4 (CH), 114.7 (CH), 115.6 (CH), 121.5 (CH), 127.5 (2×CH), 127.9 (CH), 128.6 (2×CH), 129.1 (CH), 132.2 (C), 135.4 (C), 137.5 (C), 141.1 (C), 146.6 (C), 147.1 (C), 159.8 (C). LC/MS (ES+) t$_r$=1.38 min m/z 404.25 ((MH)$^+$, 100%); MeOH/H$_2$O 95/5; HPLC t$_r$=4.08 min (98.4%) (CH$_3$CN/H$_2$O 90/10)

7-Benzyloxy-8-methoxy-2-(4-methoxybenzyl)-2,3,4,5-tetrahydro-1H-benzo[c]azepine 304

Light yellow powder, 350 mg (58%), mp 87-88° C., R$_f$: 0.31 (ethyl acetate), $^1$H NMR (270 MHz, CDCl$_3$) δ 1.66-1.74 (2H, m, CH$_2$), 2.77-2.81 (2H, m, CH$_2$), 3.08-3.12 (2H, m, CH$_2$), 3.48 (2H, s, CH$_2$), 3.78 (2H, s, CH$_2$), 3.80 (6H, s, 2×CH$_3$O), 5.13 (2H, s, CH$_2$), 6.48 (1H, s, ArH), 6.73 (1H, s, ArH), 6.85 (2H, d, J 8.5 Hz, ArH), 7.21 (2H, d, J 8.5 Hz, ArH), 7.27-7.47 (5H, s, Ph). $^{13}$C NMR (67.5 MHz, CDCl$_3$) δ 25.4 (CH$_2$), 35.8 (CH$_2$), 55.4 (CH$_2$), 56.2 (CH$_3$O), 56.9 (CH$_2$), 58.6 (CH$_2$), 59.0 (CH$_3$O), 71.3 (CH$_2$), 113.6 (2×CH), 114.7 (CH), 115.6 (CH), 127.5 (2×CH), 127.9 (CH), 128.6 (2×CH), 130.4 (2×CH), 131.3 (C), 132.1 (C), 135.5 (C), 137.5 (C), 146.6 (C), 147.1 (C), 158.7 (C). LC/MS (ES+) t$_r$=1.40 min m/z 404.13 ((MH)$^+$, 100%); MeOH/H$_2$O 95/5; HPLC t$_r$=5.13 min (97.8%) (CH$_3$CN/H$_2$O 90/10).

7-Benzyloxy-8-methoxy-2-(3,4,5-trimethoxybenzyl)-2,3,4,5-tetrahydro-1H-benzo[c]azepine 305

White solid, 420 mg (58%) mp 44-46° C., R$_f$: 0.26 (ethyl acetate), $^1$H NMR (270 MHz, CDCl$_3$) δ 1.67-1.75 (2H, m), 2.77-2.81 (2H, m, CH$_2$), 3.10-3.13 (2H, m, CH$_2$), 3.47 (2H, s, CH$_2$), 3.76 (3H, s, CH$_3$O), 3.79 (2H, s, CH$_2$), 3.82 (6H, s, 2×CH$_3$O), 3.84 (3H, s, CH$_3$O), 5.12 (2H, s, CH$_2$), 6.45 (1H, s, ArH), 6.53 (2H, s, ArH), 6.73 (1H, m, ArH), 7.26-7.46 (5H, s, Ph); $^{13}$C NMR (67.5 MHz, CDCl$_3$) δ 25.4 (CH$_2$), 35.8 (CH$_2$), 56.2 (CH$_3$), 56.3 (2×CH$_3$), 55.8 (CH$_2$), 58.5 (CH$_2$), 59.2 (CH$_3$O), 61.0 (CH$_2$), 71.3 (CH$_2$), 105.5 (2×CH), 114.7 (CH), 115.6 (CH), 127.5 (2×CH), 127.9 (CH), 128.6 (2×CH), 132.2 (C), 135.2 (C), 135.5 (C), 136.7 (C), 137.5 (C), 146.7 (C), 147.1 (C), 153.2 (2×C). LC/MS (ES+) t$_r$=2.05 min m/z 464.28 ((MH)$^+$, 100%); MeOH/H$_2$O 95/5; HPLC t$_r$=1.99 min (94.8%) and 2.36 (5%), idem? (CH$_3$CN/H$_2$O 90/10).

Synthesis of 2-benzyl-7-hydroxy-8-methoxy-2,3,4,5-tetrahydro-1H-benzo[e]azepines General Method:

A solution of 2-benzyl-7-(benzyloxy)-8-methoxy-2,3,4,5-tetrahydro-1H-benzo[c]azepines (1 mmol) in THF (20 mL) and methanol (20 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The crude mixture was purified by flash chromatography (hexane/ethyl acetate) and the resulting solid stirred in diethyl ether, filtered and dried under vacuum.

7-Hydroxy-8-methoxy-2-(2-methoxybenzyl)-2,3,4,5-tetrahydro-1H-benzo[c]azepine 306

White powder, 240 mg (77%), mp 136-137° C., R$_f$: 0.25 (ethyl acetate), $^1$H NMR (270 MHz, CDCl$_3$) δ 1.72-1.78 (2H, m, CH$_2$), 2.78-2.82 (2H, m, CH$_2$), 3.05-3.09 (2H, m, CH$_2$), 3.54 (2H, s, CH$_2$), 3.79 (3H, s, CH$_3$O), 3.82 (3H, s, CH$_3$O), 3.84 (2H, s, CH$_2$), 5.48 (1H, br, OH), 6.56 (1H, s, ArH), 6.73 (1H, m, ArH), 6.85 (1H, d, J 8.5 Hz, ArH), 6.90 (1H, t, J 7.4 Hz, ArH), 7.18-7.22 (1H, m, ArH), 7.32 (1H, d, J 7.4 Hz); $^{13}$C NMR (67.5 MHz, CDCl$_3$) δ 25.6 (CH$_2$), 35.5 (CH$_2$), 51.3 (CH$_2$), 55.4 (CH$_3$), 58.1 (CH$_3$), 58.5 (CH$_2$), 59.6 (CH$_2$), 110.3 (CH), 113.1 (CH), 115.5 (CH), 120.1 (CH), 127.5 (C), 127.9 (CH), 130.5 (CH), 131.3 (C), 136.3 (C), 143.9 (C), 157.8 (C). LC/MS (ES+) t$_r$=1.12 min m/z 314.06 ((MH)$^+$, 100%); MeOH/H$_2$O 95/5; HPLC t$_r$=4.45 min (99.6%) (CH$_3$CN/H$_2$O 90/10)

7-Hydroxy-8-methoxy-2-(3-methoxybenzyl)-2,3,4,5-tetrahydro-1H-benzo[e]azepine 307

White powder, 225 mg (72%), mp 114-115° C., R$_f$: 0.36 (ethyl acetate), $^1$H NMR (270 MHz, CDCl$_3$) δ 1.65-1.74 (2H, m, CH$_2$), 2.77-2.82 (2H, m, CH$_2$), 3.08-3.13 (2H, m, CH$_2$), 3.50 (2H, s, CH$_2$), 3.78 (5H, s, CH$_2$ and CH$_3$O), 3.79 (3H, s, CH$_3$O), 5.48 (1H, br, OH), 6.41 (1H, s, ArH), 6.73 (1H, m, ArH), 6.77-6.87 (3H, m, ArH), 7.21 (1H, t, J 7.5 Hz); $^{13}$C NMR (67.5 MHz, CDCl$_3$) δ 25.2 (CH$_2$), 35.4 (CH$_2$), 55.2 (CH$_2$), 56.0 (CH$_3$), 57.2 (CH$_3$), 58.6 (CH$_2$), 59.0 (CH$_2$), 112.5 (CH), 113.2 (CH), 114.3 (CH), 115.5 (CH), 121.4 (CH), 129.0 (CH), 130.8 (C), 136.1 (C), 141.0 (C), 143.8 (C), 143.9 (C), 159.6 (C). LC/MS (ES+) t$_r$=1.05 min m/z 313.99 ((MH)$^+$, 100%); MeOH/H$_2$O 95/5; HPLC t$_r$=2.67 min (100%) (CH$_3$CN/H$_2$O 90/10)

7-Hydroxy-8-methoxy-2-(4-methoxybenzyl)-2,3,4,5-tetrahydro-1H-benzo[c]azepine 308

White powder, 140 mg (45%), mp 105-107° C., R$_f$: 0.28 (ethyl acetate), $^1$H NMR (270 MHz, CDCl$_3$) δ 1.68-1.74 (2H, m, CH$_2$), 2.76-2.81 (2H, m, CH$_2$), 3.07-3.11 (2H, m, CH$_2$), 3.47 (2H, s, CH$_2$), 3.78 (3H, s, CH$_3$O), 3.80 (5H, s, CH$_2$ and CH$_3$O), 5.49 (1H, br, OH), 6.43 (1H, s, ArH), 6.72 (1H, m, ArH), 6.84 (2H, d, J 8.5 Hz, ArH), 7.19 (2H, d, J 8.5 Hz, ArH); $^{13}$C NMR (67.5 MHz, CDCl$_3$) δ 25.2 (CH$_2$), 35.5 (CH$_2$), 55.4 (CH$_2$), 56.1 (CH$_3$), 56.6 (CH$_3$), 58.5 (CH$_2$), 58.6 (CH$_2$), 113.4 (CH), 113.6 (2×CH), 115.7 (CH), 130.4 (2×CH), 131.0 (C), 136.2 (C), 144.0 (C), 144.2 (C), 158.7 (C). LC/MS (ES+) t$_r$=1.13 min m/z 314.18 ((MH)$^+$, 100%); MeOH/H$_2$O 95/5; HPLC t$_r$=2.96 min (99.4%) (CH$_3$CN/H$_2$O 90/10)

7-Hydroxy-8-methoxy-2-(3,4,5-trimethoxybenzyl)-2,3,4,5-tetrahydro-1H-benzo[c]azepine 309

Light yellow powder, 280 mg (75%), mp 46-48° C., R$_f$: 0.15 (ethyl acetate), $^1$H NMR (270 MHz, CDCl$_3$) δ 1.68-1.75 (2H, m, CH$_2$), 2.78-2.82 (2H, m, CH$_2$), 3.09-3.13 (2H, m, CH$_2$), 3.46 (2H, s, CH$_2$), 3.75 (3H, s, CH$_3$O), 3.79 (2H, s, CH$_3$O), 3.82 (6H, s, 2CH$_3$O), 3.83 (3H, s, CH$_3$O), 5.52 (1H, br, OH), 6.38 (1H, s, ArH), 6.52 (2H, s, ArH), 6.73 (1H, m, ArH), $^{13}$C NMR (67.5 MHz, CDCl$_3$) δ 25.2 (CH$_2$), 35.5 (CH$_2$), 56.2 (2×CH$_3$), 57.5 (CH$_3$), 58.6 (CH$_2$), 59.0 (CH$_3$O), 61.0 (CH$_2$), 105.5 (2×CH), 113.3 (CH), 115.6 (CH), 130.8 (C), 135.2 (C), 136.2 (C), 136.6 (C), 143.9 (C), 144.0 (C), 153.1 (2×C). LC/MS (ES+) t$_r$=1.09 min m/z 374.08 ((MH)$^+$, 100%); MeOH/H$_2$O 95/5; HPLC t$_r$=3.04 min (98.3%) (CH$_3$CN/H$_2$O 90/10)

Synthesis of 2-benzyl-8-methoxy-7-O-sulfamoyl-2,3,4,5-tetrahydro-1H-benzo[c]azepines General Method:

A solution of 2-benzyl-7-hydroxy-8-methoxy-2,3,4,5-tetrahydro-1H-benzo[c]azepines (0.5 mmol) and sulfamoyl chloride (1 mmol) in DMA (1 mL) was stirred at rt under nitrogen for 24 hours. After addition of water (5 mL) and sodium hydrogenoC(Ar)bonate (170 mg, 2 mmol) the organics were extracted into ethyl acetate (2×50 mL), the organic layers washed with water and brine, then dried (MgSO$_4$) and evaporated. The crude product was purified by flash chromatography (hexane/ethyl acetate) and the resulting solid stirred in diethyl ether, filtered and dried under vacuum.

8-Methoxy-2-(2-methoxybenzyl)-7-O-sulfamoyl-2,3,4,5-tetrahydro-1H-benzo[c]azepin-7-yl sulfamate 310

White powder, 76 mg (39%), mp=79-80° C., R$_f$: 0.21 (ethyl acetate), $^1$H NMR (270 MHz, CDCl$_3$) δ 1.74-1.78 (2H, m, CH$_2$), 2.79-2.83 (2H, m, CH$_2$), 3.03-3.06 (2H, m, CH$_2$), 3.58 (2H, s, CH$_2$), 3.79 (3H, s, CH$_3$O), 3.81 (3H, s, CH$_3$O), 3.85

(2H, s, CH$_2$), 4.96 (2H, br, NH$_2$), 6.69 (1H, s, ArH), 6.84-6.94 (2H, m), 7.11 (1H, s, ArH), 7.20-7.32 (2H, m); LC/MS (ES+) t$_r$=1.00 min m/z 393.10 ((M+H)$^+$, 100%); MeOH/H$_2$O 95/5

8-Methoxy-2-(3-methoxybenzyl)-7-O-sulfamoyl-2,3,4,5-tetrahydro-1H-benzo[c]azepin-7-yl sulfamate 311

White powder, 165 mg (84%), mp=62-64° C., R$_f$: 0.41 (ethyl acetate), $^1$H NMR (270 MHz, CDCl$_3$) δ 1.70-1.75 (2H, m, CH$_2$), 2.80-2.83 (2H, m, CH$_2$), 3.07-3.10 (2H, m, CH$_2$), 3.52 (2H, s, CH$_2$), 3.77 (3H, s, CH$_3$O), 3.78 (3H, s, CH$_3$O), 3.79 (2H, s, CH$_2$), 5.11 (2H, br, NH$_2$), 6.55 (1H, s, ArH), 6.77-6.85 (3H, m), 7.10 (1H, s, ArH), 7.21 (1H, t, J 7.7 Hz); LC/MS (ES+) t$_r$=0.91 min m/z 393.10 ((M+H)$^+$, 100%); MeOH/H$_2$O 95/5

8-Methoxy-2-(4-methoxybenzyl)-7-O-sulfamoyl-2,3,4,5-tetrahydro-1H-benzo[e]azepin-7-yl sulfamate 312

White powder, 150 mg (77%), mp=64-65° C., R$_f$: 0.27 (ethyl acetate), $^1$H NMR (270 MHz, CDCl$_3$) δ 1.68-1.75 (2H, m, CH$_2$), 2.79-2.83 (2H, m, CH$_2$), 3.04-3.08 (2H, m, CH$_2$), 3.50 (2H, s, CH$_2$), 3.78 (3H, s, CH$_3$O), 3.79 (5H, s, CH$_2$ and CH$_3$O), 5.28 (2H, s, NH$_2$), 6.57 (1H, s, ArH), 6.83 (2H, d, J 8.5 Hz), 7.10 (1H, s, ArH), 7.19 (1H, d, J 8.5 Hz); Hz); LC/MS (ES+) t$_r$=0.94 min m/z 393.04 ((M+H)$^+$, 100%); MeOH/H$_2$O 95/5

8-Methoxy-7-O-sulfamoyl-2-(3,4,5-trimethoxybenzyl)-2,3,4,5-tetrahydro-1H-benzo[c]azepin-7-yl sulfamate 313

White powder, 170 mg (76%), mp=78-80° C., R$_f$: 0.11 (ethyl acetate), $^1$H NMR (270 MHz, CDCl$_3$) δ 1.70-1.77 (2H, m, CH$_2$), 2.81-2.86 (2H, m, CH$_2$), 3.08-3.12 (2H, m, CH$_2$), 3.48 (2H, s, CH$_2$), 3.76 (3H, s, CH$_3$O), 3.78 (2H, s, CH$_2$), 3.81 (6H, s, 2×CH$_3$O), 3.82 (3H, s, CH$_3$O), 5,01 (2H, br, NH$_2$), 6.50 (3H, s, ArH), 7.11 (1H, s, ArH); $^{13}$C NMR (67.5 MHz, CDCl$_3$) δ 25.1 (CH$_2$), 35.1 (CH$_2$), 56.2 (2×CH$_3$), 56.3 (CH$_2$), 58.1 (CH$_2$), 58.8 (2×CH$_3$O), 61.0 (CH$_2$), 105.5 (2×CH), 115.1 (CH), 124.7 (CH), 134.6 (C), 136.4 (C), 136.8 (C), 137.2 (C), 139.6 (C), 148.8 (C), 153.2 (2×C). LC/MS (ES−) t$_r$=0.92 min m/z 451.11 ((M−H)$^-$, 100%); MeOH/H$_2$O 95/5; HPLC t$_r$=1.86 min (100%) (CH$_3$CN/H$_2$O 90/10)

Synthesis of 2-benzyl-7-benzyloxy-8-methoxy-2,3,4,5-tetrahydro-1H-benzo[c]azepin-1-ones A solution of 7-(benzyloxy)-8-methoxy-2,3,4,5-tetrahydro-1H-benzo[c]azepin-1-one (297 mg, 1.0 mmol) and NaH (80 mg, 2 mmol) was stirred in DMF (5 mL) for 10 minutes at rt and the appropriate benzyl bromide or benzyl chloride (1.1 mmol) added. The mixture was stirred o/n at rt. After addition of water the organics extracted with ethyl acetate, washed with water, brine, dried (MgSO$_4$), filtered and concentrated. The crude yellow oil was purified by flash chromatography (hexane/EtOAc 1:0 to 1:1) and the resultant solid was stirred in Et$_2$O, filtered and dried under vacuum.

7-Benzyloxy-8-methoxy-2-(3,4,5-trimethoxybenzyl)-2,3,4,5-tetrahydro-1H-benzo[c]azepin-1-one 314

White powder, 270 mg (57%), mp 134-135° C., R$_f$: 0.17 (hexane/ethyl acetate 1:1) $^1$H NMR (270 MHz, CDCl$_3$) δ 1.69-1.79 (2H, m, CH$_2$), 2.61 (2H, t, J 7.2 Hz, CH$_2$), 3.20 (2H, t, J 6.3 Hz, CH$_2$), 3.83 (3H, s, CH$_3$O), 3.84 (6H, s), 3.90 (3H, s, CH$_3$O), 4.68 (2H, s, CH$_2$), 5.15 (2H, s, CH$_2$), 6.59 (2H, s, ArH), 6.63 (1H, s, ArH), 7.25-7.44 (6H, s, ArH); $^{13}$C NMR (67.5 MHz, CDCl$_3$) δ 29.9 (CH$_2$), 30.1 (CH$_2$), 46.2 (CH$_2$), 50.9 (CH$_2$), 56.2 (3×CH$_3$), 61.0 (CH$_3$), 71.0 (CH$_2$), 105.3 (2×CH), 112.3 (CH), 113.8 (CH), 127.4 (2×CH), 128.1 (CH), 128.3 (C), 128.7 (2×CH), 130.8 (C), 134.2 (C), 136.7 (C), 137.4 (C), 148.4 (C), 150.0 (C), 153.4 (2×C), 171.4 (CO). LC/MS (ES+) t$_r$=1.60 min m/z 500.24 ((M+Na)$^+$, 100%), 478.26 (M+H)$^+$; MeOH/H$_2$O 95/5; HPLC t$_r$=3.72 min (99.3%), (CH$_3$CN/H$_2$O 90/10)

Synthesis of 2-benzyl-7-hydroxy-8-methoxy-2,3,4,5-tetrahydro-1H-benzo[c]azepin-1-ones General Method:
A solution of 2-benzyl-7-benzyloxy-8-methoxy-2,3,4,5-tetrahydro-1H-benzo[c]azepin-1-one (1 mmol) in THF (20 mL) and methanol (20 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The resulting solid was stirred in diethyl ether, filtered and dried under vacuum or purified by flash chromatography (hexane/ethyl acetate) and the resultant solid stirred in diethyl ether, filtered and dried under vacuum.

7-Hydroxy-8-methoxy-2-(3,4,5-trimethoxybenzyl)-2,3,4,5-tetrahydro-1H-benzo[c]azepin-1-one 316

White powder, 305 mg (79%) mp 172 173-° C., R$_f$: 0.11 (hexane/ethyl acetate 1:1), 0.34 (EtOAc), $^1$H NMR (270 MHz, CDCl$_3$) δ 1.70-1.82 (2H, m, CH$_2$), 2.64 (2H, t, J 7.2 Hz, CH$_2$), 3.21 (2H, t, J 6.5 Hz, CH$_2$), 3.83 (3H, s, CH$_3$O), 3.84 (6H, s, 2×CH$_3$O), 3.90 (3H, s, CH$_3$O), 4.68 (2H, s, CH$_2$), 5.86 (1H, s, OH), 6.59 (2H, s, ArH), 6.67 (1H, s, ArH), 7.25 (1H, s, ArH); $^{13}$C NMR (67.5 MHz, CDCl$_3$) δ 29.8 (CH$_2$), 29.9 (CH$_2$), 46.2 (CH$_2$), 51.0 (CH$_2$), 56.2 (3×$_3$), 61.0 (CH$_3$), 105.3 (2×CH), 111.5 (CH), 114.6 (CH), 127.5 (C), 131.8 (C), 134.2 (C), 137.3 (C), 145.4 (C), 147.7 (C), 153.4 (2×C), 171.5 (CO). LC/MS (ES−) t$_r$=0.91 min m/z 386.05 ((M−H)$^-$, 100%); MeOH/H$_2$O 95/5; HPLC t$_r$=1.70 min (100%), (CH$_3$CN/H$_2$O 90/10)

Synthesis of 2-benzyl-8-methoxy-7-O-sulfamoyl-2,3,4,5-tetrahydro-1H-benzo[e]azepin-1-ones A solution of 2-benzyl-7-hydroxy-8-methoxy-2,3,4,5-tetrahydro-1H-benzo[c]azepine-1-one (0.5 mmol) and sulfamoyl chloride (1 mmol) in DMA (1 mL) was stirred at rt under nitrogen for 24 hours. After addition of water (5 mL) the organics were extracted into ethyl acetate, the organic layers washed with water and brine, then dried (MgSO$_4$) and evaporated. The crude product was purified by flash chromatography (hexane/ethyl acetate) and the resulting solid stirred in diethyl ether, filtered and dried under vacuum.

8-methoxy-7-O-sulfamoyl-2-(3,4,5-trimethoxybenzyl)-2,3,4,5-tetrahydro-1H-benzo[e]azepin-1-one 317

White powder, 185 mg (79%), mp 211-213° C., R$_f$: 0.37 (EtOAc), $^1$H NMR (270 MHz, DMSO-d6) δ 1.72-1.77 (2H, m, CH$_2$), 2.63 (2H, t, J 6.6 Hz, CH$_2$), 3.18 (2H, t, J 7.1 Hz, CH$_2$), 3.65 (3H, s, CH$_3$O), 3.77 (6H, s, 2×CH$_3$O), 3.83 (3H, s, CH$_3$O), 4.63 (2H, s, CH$_2$), 6.70 (2H, s, ArH), 7.18 (1H, s, ArH), 7.29 (1H, s, ArH), 8.01 (2H, s, NH$_2$); $^{13}$C NMR (100 MHz, DMSO-d$_6$) δ 28.7 (CH$_2$), 28.9 (CH$_2$), 45.3 (CH$_2$), 49.6 (CH$_2$), 55.9 (2×CH$_3$), 56.1 (CH$_3$), 60.1 (CH$_3$), 105.3 (2×CH), 113.2 (CH), 123.1 (CH), 129.7 (C), 134.2 (C), 134.6 (C), 136.7 (C), 140.0 (C), 150.3 (C), 152.9 (2×C), 169.2 (CO). HPLC t$_r$=1.63 min (100%), (CH$_3$CN/H$_2$O 90/10)

Synthesis of 1-benzyl-7-benzyloxy-8-methoxy-4,5-dihydro-1H-benzo[b]azepin-2(3H)-one General Method:

A solution of 7-benzyloxy-8-methoxy-4,5-dihydro-1H-benzo[b]azepin-2(3H)-one (297 mg, 1.0 mmol) and NaH (80 mg, 2 mmol) was stirred in DMF (5 mL) for 10 minute at rt and the appropriate benzyl bromide or benzyl chloride (1.1 mmol) added. The mixture was stirred o/n at rt. After addition of water the organics extracted with ethyl acetate, washed with water, brine, dried (MgSO$_4$), filtered and concentrated. The crude yellow oil was purified by flash chromatography (hexane/EtOAc 1:0 to 1:1) and the resultant solid stirred in Et$_2$O, filtered and dried under vacuum.

7-benzyloxy-8-methoxy-1-(3,4,5-trimethoxybenzyl)-4,5-dihydro-1H-benzo[b]azepin-2(3H)-one 318

White powder, 225 mg (47%), mp 129-130° C., R$_f$: 0.21 (hexane/ethyl acetate 1:1), $^1$H NMR (270 MHz, CDCl$_3$) δ 2.05-2.40 (6H, m, 3×CH$_2$), 3.72 (6H, s, 2×CH$_3$O), 3.78 (3H, s, CH$_3$O), 3.82 (3H, s, CH$_3$O), 4.86 (2H, br, CH$_2$), 5.10 (2H, s, CH$_2$), 6.44 (2H, s, ArH), 6.65 (1H, s, ArH), 6.69 (1H, s, ArH), 7.27-7.43 (5H, s, Ph), $^{13}$C NMR (67.5 MHz, CDCl$_3$) δ 29.3 (CH$_2$), 29.5 (CH$_2$), 33.3 (CH$_2$), 51.4 (CH$_2$), 56.1 (2×CH$_3$), 56.3 (CH$_3$), 60.9 (CH$_2$), 71.3 (CH$_2$), 105.3 (2×CH), 107.8 (CH), 114.5 (CH), 127.4 (2×CH), 128.1 (CH), 128.3 (C), 128.7 (2×CH), 133.9 (C), 135.3 (C), 136.9 (C), 137.2 (C), 146.4 (C), 148.7 (C), 153.2 (2×C), 173.6 (CO). LC/MS (ES+) t$_r$=1.75 min m/z 500.30 ((M+Na)$^+$, 100%), 478.26 (M+H)$^+$; MeOH/H$_2$O 95/5 HPLC t$_r$=1.99 min (98.2%), (CH$_3$CN/H$_2$O 90/10)

Synthesis of 1-benzyl-7-hydroxy-8-methoxy-4,5-dihydro-1H-benzo[b]azepin-2(3H)-one General Method:

A solution of 2-benzyl-7-(benzyloxy)-8-methoxy-2,3,4,5-tetrahydro-1H-benzo[c]azepin-1-one (1 mmol) in THF (20 mL) and methanol (20 mL) was treated with 10% Pd/C (40 mg) and stirred under an atmosphere of hydrogen. The reaction was monitored by TLC. Upon completion, the resultant suspension was filtered through celite, washed with ethyl acetate and then evaporated under reduced pressure. The resulting solid was stirred in diethyl ether, filtered and dried under vacuum or purified by flash chromatography (hexane/ethyl acetate) then stirred in diethyl ether, filtered and dried under vacuum.

7-Hydroxy-8-methoxy-1-(3,4,5-trimethoxybenzyl)-4,5-dihydro-1H-benzo[b]azepin-2(3H)-one 319

White powder, 305 mg (79%), mp 170-171° C., R$_f$: 0.61 (ethyl acetate), $^1$H NMR (270 MHz, CDCl$_3$) δ 2.00-2.16 (2H, m, CH$_2$), 2.26-2.32 (2H, m, CH$_2$), 2.39-2.46 (2H, m, CH$_2$), 3.75 (6H, s, 2×CH$_3$O), 3.76 (3H, s, CH$_3$O), 3.79 (3H, s, CH$_3$O), 4.86 (2H, br, CH$_2$), 5.57 (1H, s, OH), 6.45 (2H, s, ArH), 6.62 (1H, s, ArH), 6.69 (1H, s, ArH); $^{13}$C NMR (67.5 MHz, CDCl$_3$) δ 29.2 (CH$_2$), 29.3 (CH$_2$), 33.2 (CH$_2$), 51.6 (CH$_2$), 56.2 (3×CH$_3$), 61.0 (CH$_2$), 105.3 (2×CH), 106.5 (CH), 114.8 (CH), 129.1 (C), 134.0 (C), 134.3 (C), 137.1 (C), 143.9 (C), 145.5 (C), 153.2 (2×C), 173.8 (CO). LC/MS (ES−) t$_r$=0.90 min m/z 386.18((M−H)$^-$, 100%); MeOH/H$_2$O 95/5; HPLC t$_r$=1.61 min (100%), (CH$_3$CN/H$_2$O 90/10)

Synthesis of 1-benzyl-8-methoxy-7-O-sulfamoyl-4,5-dihydro-1H-benzo[b]azepin-2(3H)-one A solution of 1-benzyl-7-hydroxy-8-methoxy-4,5-dihydro-1H-benzo[b]azepin-2(3H)-one (0.5 mmol) and sulfamoyl chloride (1 mmol) in DMA (1 mL) was stirred at rt under nitrogen for 24 hours. After addition of water (5 mL) the organics were extracted into ethyl acetate, the organic layers washed with water and brine, then dried (MgSO$_4$) and evaporated. The crude yellow solid was stirred in diethyl ether, filtered and dried under vacuum.

8-methoxy-7-O-sulfamoyl-1-(3,4,5-trimethoxybenzyl)-4,5-dihydro-1H-benzo[b]azepin-2(3H)-one 320

White powder, 225 mg (96%), mp 172-173° C., R$_f$: 0.48 (ethyl acetate), $^1$H NMR (270 MHz, DMSO-d6) δ 2.00-2.16 (2H, m, CH$_2$), 2.01-2.25 (4H, m, 2×CH$_2$), 2.45-2.50 (2H, m, CH$_2$), 3.58 (3H, s, CH$_3$O), 3.66 (3H, s, 2×CH$_3$O), 3.78 (3H, s, CH$_3$O), 4.99 (2H, br, CH$_2$), 6.51 (2H, s, ArH), 7.13 (1H, s, ArH), 7.17 (1H, s, ArH), 7.94 (2H, s, NH$_2$); $^{13}$C NMR (100 MHz, DMSO-d$_6$) δ 28.6 (2×CH$_2$), 32.9 (CH$_2$), 49.3 (CH$_2$), 55.7 (2×CH$_3$), 56.2 (CH$_3$), 60.0 (CH$_3$), 105.2 (2×CH), 108.6 (CH), 123.3 (CH), 127.4 (C), 133.8 (C), 136.2 (C), 136.4 (C), 140.1 (C), 150.7 (C), 152.7 (2×C), 172.1 (CO). LC/MS (ES−) t$_r$=0.85 min m/z 465.10 ((M−H)$^-$, 100%); MeOH/H$_2$O 95/5 HPLC t$_r$=1.43 min (99.8%), (CH$_3$CN/H$_2$O 90/10)

6-Benzyloxy-7-methoxy-2-(2,4,6-trimethoxybenzoyl)-1,2,3,4-tetrahydroisoquinoline F1

A solution of 6-benzyloxy-7-methoxy-1,2,3,4-tetrahydroisoquinoline (539 mg, 2 mmol) and 2,4,6-trimethoxybenzoic acid in dry DCM (25 mL) was stirred at 0° C. under nitrogen before EDCI (767 mg, 4 mmol) was added portion wise. The mixture was stirred for 1 hour at 0° C. then 1 hour at rt. After addition of DCM (25 mL), the organic layer was washed with water, 10% citric acid, water, brine, dried (MgSO$_4$), filtered and concentrated. Column chromatography (hexane/EtOAc 5/1 to 0/1) afforded 0.73 g of a white powder (79%), m.p. 70-72° C., 2-rotamers present by $^1$H NMR: set 1: $^1$H NMR (270 MHz, CDCl$_3$) δ 2.62 (2H, t, J=5.5 Hz), 3.44 (2H, t, J=5.5 Hz), 3.75 (6H, s), 3.82 (3H, s), 3.86 (3H, s), 4.85 (2H, s), 5.10 (2H, s), 6.11 (2H, s), 6.60 (1H, s), 6.68 (1H, s), 7.28-7.44 (5H, m); set 2: $^1$H NMR (270 MHz, CDCl$_3$) δ 2.78 (2H, t, J=5.8 Hz), 3.66 (6H, s), 3.78 (3H, s), 3.82 (3H, s), 3.96 (2H, t, J=5.8 Hz), 4.32 (2H, s), 5.11 (2H, s), 6.10 (2H, s), 6.41 (1H, s), 6.67 (1H, s), 7.28-7.44 (5H, m). HRMS (ES) calcd. for C$_{27}$H$_{30}$NO$_6$ (M$^+$+H), 464.2068 found 464.2070 HPLC: tr=2.40 (99.6%) CH$_3$CN/H$_2$O 90/10

6-Benzyloxy-7-methoxy-2-(2,4,6-trimethoxybenzyl)-1,2,3,4-tetrahydroisoquinoline F2

A solution of F1 (720 mg, 1.55 mmol) in THF (20 mL) was cooled to 0° C. before LiAlH$_4$ (76 mg, 2.0 mmol) was added portion wise. The mixture was refluxed for 2 hours, cooled to 0° C. and 15% aqueous NaOH (1 mL) was added drop wise. The mixture was stirred for 30 minutes, MgSO$_4$ added and the mixture stirred another 30 minutes, filtered and concentrated. The crude product (700 mg) was purified by flash chromatography (hexane/EtOAc 10/1 to 0/1) yielding 500 mg of a white powder (72%). m.p.: 129-131° C., $^1$H NMR (270 MHz, CDCl$_3$) δ 2.67-2.78 (4H, m), 3.59 (2H, s), 3.69 (2H, s), 3.80 (6H, s), 3.81 (6H, s), 5.07 (2H, s), 6.14 (2H, s), 6.50 (1H, s), 6.56 (1H, s), 7.24-7.41 (5H, m); $^{13}$C NMR (100 MHz, CDCl$_3$) δ 28.6 (CH$_2$), 48.8 (CH$_2$), 50.5 (CH$_2$), 55.2 (CH$_2$), 55.4 (CH$_3$), 55.9 (2×CH$_3$), 56.2 (CH$_3$), 56.6 (CH$_3$), 71.2 (CH$_2$), 90.6 (2×CH), 107.2 (C), 110.4 (CH), 114.4 (CH), 126.6 (C), 127.4 (2×CH), 127.7 (CH), 128.5 (2×CH), 137.5 (C), 146.5 (C), 147.8 (C), 160.2 (2×C) and 160.6 (C). HRMS (ES) calcd. for C$_{27}$H$_{32}$NO$_5$ (MH$^+$), 450.2275 found 450.2263 see Method 1 of the "Synthesis of 6-hydroxy-2-benzyl-1,2,3,4-tetrahydroisoquinolines"

7-Methoxy-2-(2,4,6-trimethoxybenzyl)-1,2,3,4-tetrahydroisoquinolin-6-ol F3

260 mg, (71%), light yellow powder, m.p. 150-151° C., $^1$H NMR (270 MHz, CDCl$_3$) δ 2.70-2.77 (4H, m), 3.58 (2H, s), 3.69 (2H, s), 3.80 (9H, s), 3.81 (3H, s), 5.56 (1H, br), 6.13 (2H, s), 6.44 (1H, s), 6.56 (1H, s); $^{13}$C NMR (100 MHz, CDCl$_3$) δ27.1 (CH$_2$), 48.0 (CH$_2$), 49.7 (CH$_2$), 55.3 (CH$_2$), 55.4 (CH$_3$), 55.8 (2×CH$_3$), 56.2 (CH$_3$), 56.6 (CH$_3$), 90.5 (2×CH), 103.8 (C), 108.9 (C), 114.2 (C), 125.9 (C), 126.1 (C), 144.2 (C), 145.1 (C), 160.2 (2×C) and 160.6 (C). HRMS (ES) calcd. for C$_{20}$H$_{26}$NO$_5$ (MH$^+$), 360.1805 found 360.1790. HPLC: tr=1.01 (99.5%) CH$_3$CN/H$_2$O 90/10 see "Synthesis of 6-O-sulfamoyl-2-benzyl-1,2,3,4-tetrahydroisoquinolines"

7-Methoxy-6-O-sulfamoyl-2-(2,4,6-trimethoxybenzyl)-1,2,3,4-tetrahydroisoquinoline F4

165 mg, (76%), yellow powder, m. p. 151-153° C., $^1$H NMR (270 MHz, CDCl$_3$/CD$_3$OD 10:1) δ 2.72-2.76 (4H, m), 3.24 (2H, br), 2.58 (2H, s), 3.72 (2H, s), 3.75 (9H, s), 3.76 (3H, s), 6.09 (2H, s), 6.53 (1H, s), 7.00 (1H, s); $^{13}$C NMR (100 MHz, CDCl$_3$) δ 27.3 (CH$_2$), 48.4 (CH$_2$), 49.7 (CH$_2$), 54.6 (CH$_2$), 55.2 (CH$_3$), 55.5 (2×CH$_3$), 56.0 (CH$_3$), 56.6 (CH$_3$), 90.2 (2×CH), 103.8 (C), 110.8 (CH), 123.4 (CH), 126.5 (C), 133.8 (C), 137.3 (C), 149.4 (C), 160.2 (2×C) and 160.9 (C). HRMS (Electrospray) calcd. for C$_{20}$H$_{27}$N$_2$O$_7$S (MH$^+$), 439.1533 found 439.1521. HPLC: tr=0.99 (98.0%) CH$_3$CN/H$_2$O 90/10 see Method 1 for the "Synthesis of 6-(benzyloxy)-2-benzyl-1,2,3,4-tetrahydroisoquinolines"

6-Benzyloxy-2-(3,5-difluorobenzyl)-7-methoxy-1,2,3,4-tetrahydroisoquinoline F5

475 mg, (80%), white powder, m.p. 116-117° C., $^1$H NMR (270 MHz, CDCl$_3$) δ 2.67-2.79 (4H, m), 3.53 (2H, s), 3.62 (2H, s), 3.82 (3H, s), 5.10 (2H, s), 6.50 (1H, s), 6.63 (1H, s), 6.69 (1H, tt, J=9.0 and 2.5 Hz), 6.90-6.94 (2H, m), 7.28-7.44 (5H, m); $^{13}$C NMR (10 MHz, CDCl$_3$) δ 28.6 (CH$_2$), 50.8 (CH$_2$), 55.6 (CH$_2$), 56.1 (CH$_3$), 61.9 (CH$_2$), 71.1 (CH), 102.4 (CH, t, J=25.3 Hz), 110.1 (CH), 111.3 (2×CH), dd, J$_{CF}$=18.4 and 6.9 Hz), 114.4 (CH), 126.0 (C), 127.0 (C), 127.2 (2×CH), 127.7 (CH), 128.5 (2×CH), 137.3 (CH), 143.0 (C, t, J$_{CF}$=9.2 Hz), 146.8 (C), 148.0 (C), 163.1 (2×C, dd, J$_{CF}$=248.4 and 13.0 Hz). HRMS (Electrospray) calcd. for C$_{24}$H$_{24}$F$_2$NO$_2$ (MH$^+$), 396.1770 found 396.1755. HPLC t$_r$=4.29 min (99.7%), (CH$_3$CN/H$_2$O 90/10)

Method 1 of the "Synthesis of 6-hydroxy-2-benzyl-1,2,3,4-tetrahydroisoquinolines"

2-(3,5-Difluorobenzyl)-7-methoxy-1,2,3,4-tetrahydroisoquinolin-6-ol F6

220 mg (72%), light yellow powder, m.p. 110-111° C., $^1$H NMR (270 MHz, CDCl$_3$) δ 2.68-2.72 (2H, m), 2.77-2.81 (2H, m), 3.52 (2H, s), 3.62 (2H, s), 3.81 (3H, s), 5.51 (1H, br), 6.45 (1H, s), 6.66 (1H, s), 6.70 (1H, dt, J=8.9 and 2.5 Hz), 6.90-6.95 (2H, m); $^{13}$C NMR (100 MHz, CDCl$_3$) δ 28.4 (CH$_2$), 50.9 (CH$_2$), 55.6 (CH$_2$), 56.0 (CH$_3$), 61.8 (CH$_2$), 102.4 (CH, t, J=25.3 Hz), 108.7 (CH), 111.4 (2×CH), dd, J$_{CF}$=18.4 and 6.9 Hz), 114.2 (CH), 125.7 (C), 126.8 (C), 143.0 (C, t, J$_{CF}$=9.2 Hz), 144.1 (C), 144.9 (C), 163.1 (2×C, dd, J$_{CF}$=248.4 and 13.0 Hz). HRMS (ES) calcd. for C$_{17}$H$_{18}$F$_2$NO$_2$ (MH$^+$), 306.1300 found 306.1292. HPLC t$_r$=2.37 min (100%), (CH$_3$CN/H$_2$O 90/10)

see "Synthesis of 6-O-sulfamoyl-2-benzyl-1,2,3,4-tetrahydroisoquinolines"

2-(3,5-Difluorobenzyl)-7-methoxy-1,2,3,4-tetrahydroisoquinoline 6-O-sulfamate F7

120 mg (79%), m.p. 142-143° C., $^1$H NMR (270 MHz, CDCl$_3$) δ 2.72 (2H, t, J=5.6 Hz), 2.83 (2H, t, J=5.6 Hz), 3.56 (2H, s), 3.63 (2H, s), 3.82 (3H, s), 5.01 (2H, br), 6.60 (1H, s), 6.70 (1H, tt, J=9.0 and 2.2 Hz), 6.91 (2H, d, J=6.3 Hz), 7.08 (1H, s); $^{13}$C NMR (100 MHz, CDCl$_3$) δ 28.2 (CH$_2$), 50.6 (CH$_2$), 55.7 (CH$_2$), 56.4 (CH$_3$), 61.8 (CH$_2$), 102.7 (CH, t, J=25.3 Hz), 111.3 (CH), 111.5 (2×CH), dd, J$_{CF}$=18.4 and 7.0 Hz), 124.2 (CH), 127.5 (C), 134.5 (C), 137.4 (C), 143.0 (C, t, J$_{CF}$=9.2 Hz), 149.4 (C), 163.2 (2×, dd, J$_{CF}$=247.0 and 13.9 Hz). HRMS (ES) calcd. for C$_{17}$H$_{19}$F$_2$N$_2$O$_4$S (MH$^+$), 385.1028 found 385.1013. HPLC t$_r$=1.20 min (98.8%), (CH$_3$CN/H$_2$O 90/10)

Synthesis of 4-functionalised 1,2,3,4-tetrahydroisoquinoline derivatives

N-(2,2-Diethoxyethyl)-4-benzyloxy-3-methoxybenzylamine F8

4-Benzyloxy-3-methoxybenzaldehyde (50 g, 206 mmol) and amino acetaldehyde diethyl acetal (31.6 mL, 217 mmol) were heated up to 65° C. for 6 hours then cooled to rt. The resulting yellow oil was stirred in ethanol (250 mL), cooled to 0° C. and NaBH$_4$ (8.3 g, 220 mmol) was added portion wise. The mixture was refluxed for 4 hours then cooled to 0° C. and water added. The solution was stirred for 30 minutes, extracted with ethyl acetate and the organic layer was washed with water, brine, dried and concentrated to yield 72 g (97%) of a yellow oil, $^1$H NMR (270 MHz, CDCl$_3$) δ 1.19 (6H, t, J=7.2 Hz), 1.51 (1H, br s), 2.72 (2H, d, J=5.5 Hz), 3.51 (2H, dq, J=7.2 and 1.9 Hz), 3.67 (2H, dq, J=7.2 and 1.9 Hz), 3.72 (2H, s), 3.88 (3H, s), 4.60 (1H, t, J=5.5 Hz), 5.13 (2H, s), 6.75 (1H,dd, J=8.3 and 1.4 Hz), 6.81 (1H, d, J=8.3 Hz), 6.89 (1H, d, J=1.4 Hz), 7.27-7.44 (5H, m). HRMS (ES) calcd. for C$_{21}$H$_{30}$NO$_4$ (MH$^+$), 360.2169 found 360.2161; HPLC: tr=3.92 (99.2%) CH$_3$CN/H$_2$O 90/10.

6-Benzyloxy-7-methoxy-1,2,3,4-tetrahydro-isoquinolin-4-ol F9

A suspension of F8 (30 g, 83.5 mmol) in dioxane (40 mL) and 6M HCl (500 mL) was stirred at 40° C.: The initial suspension dissolved and a precipitate appeared after approximately 30 minutes. The mixture was stirred for an additional 30 minutes: and the reaction mixture was cooled to 0° C. The white precipitate was collected by filtration, washed with water, diethyl ether, resuspended in water (300 mL) and the mixture made alkaline with 5M aqueous sodium hydroxide. The white suspension was collected by filtration, washed with water, diethyl ether and dried under vacuum (17 g, 71%). m.p. 148-149° C., $^1$H NMR (270 MHz, CDCl$_3$) δ 2.33 (2H, br), 2.94 (1H, dd, J=13.0 and 2.8 Hz), 2.94 (1H, dd, J=13.0 and 2.8 Hz), 3.79 (1H, d, J=2.2 Hz), 3.84 (3H, s), 4.39 (1H, t, J=2.8 Hz), 5.12 (2H, s), 6.4 (1H, s), 6.89 (1H, s), 7.27-7.44 (5H, m). HRMS (ES) calcd. for C$_{17}$H$_{20}$NO$_3$ (MH$^+$), 286.1438 found 286.1425. HPLC: tr=4.70 (99.7%) CH$_3$CN/H$_2$O 90/10.

2-tert-Butoxycarbonyl-6-benzyloxy-7-methoxy-3,4-dihydro-1H-isoquinoline-4-ol F10

A solution of F9 (14.2 g, 49.8 mmol) Boc$_2$O (13.1 g, 60 mmol) in THF (150 mL) was refluxed for 6 hours. The suspension was then cooled to 0° C. filtered, washed with ice cold THF and dried under vacuum, affording 18.3 g (95%) of a white solid. m.p. 196-197° C., $^1$H NMR (270 MHz, CDCl$_3$) δ 1.48 (9H, s), 3.48 (1H, dd, J=13.5 and 3.3 Hz), 3.86 (3H, s), 3.92 (1H, dd, J=13.5 and 4.4 Hz), 4.30 (1H, d, J=16.8 Hz), 4.59 (1H, br), 4.69 (1H, d, J=16.8 Hz), 5.09 (1H, d, J=12.1 Hz), 5.16 (1H, d, J=12.1 Hz), 6.60 (1H, s), 6.96 (1H, s), 7.28-7.44 (5H, m). HRMS (ES) calcd. for C$_{22}$H$_{27}$NO$_5$Na (M+Na$^+$), 408.1781 found 408.1782; HPLC: tr=1.95 (100%) CH$_3$CN/H$_2$O 90/10.

2-tert-Butoxycarbonyl-6-benzyloxy-4,7-dimethoxy-3,4-dihydro-1H-isoquinolin-4-ol F11

A suspension of F10 (5.8 g, 15 mmol) in dry THF (50 mL) and DMF (10 mL) was cooled to 0° C. and treated with 60% NaH (0.8 g, 20 mmol in a portion wise manner. The mixture was stirred for 30 minutes at 0° C. before methyl iodide (1.25 mL, 20 mmol) was added and the mixture stirred at rt for 16 hours. After careful addition of water, the mixture was extracted with ethyl acetate, the combined organic layers washed with water, brine, dried and evaporated. The resulting yellow oil (6.5 g) was purified by flash chromatography (hexane/EtOAc 20/1 to 3/1) to afford a white solid (5.7 g, 95%), m.p. 86-88° C. $^1$H NMR (270 MHz, CDCl$_3$) δ 1.48 (9H, s), 3.38 (3H, s), 3.33-3.52(1H, m), 3.85 (3H, s), 3.94-4.18 (2H, m), 4.28-4.40 (1H, m), 4.58-4.76 (1H, m), 5.10 (1H, d, J=12.1 Hz), 5.15 (1H, d, J=12.1 Hz), 6.61 (1H, s), 6.86 and 690 (1H, s), 7.28-7.45 (5H, m). HRMS (ES) calcd. for C$_{23}$H$_{29}$NO$_5$Na (M+Na$^+$), 422.1938 found 422.1927. HPLC: tr=2.40 (100%) CH$_3$CN/H$_2$O 90/10.

6-Benzyloxy-4,7-dimethoxy-1,2,3,4-tetrahydroisoquinoline F12

F11 (5.4 g, 13.5 mmol) was stirred in THF (80 mL) and methanol (10 mL) and cooled to 0° C. before acetyl chloride (5.8 mL, 80 mmol) was added drop wise. The solution was stirred at rt o/n, After addition of DCM (100 mL), the organic layer was successively washed with saturated aqueous NaHCO$_3$, water and brine, dried (MgSO$_4$), filtered and concentrated to afford 4.2 g of a crude dark yellow solid. Column chromatography (petroleum ether/ethyl acetate 9/1 to 0/1 then ethyl acetate/methanol 1/0 to 10/1) afforded 1.8 g (45%) of 6-Benzyloxy-4,7-dimethoxy-1,2,3,4-tetrahydroisoquinoline F12 and 6-benzyloxy-7-methoxyisoquinoline F13 (400 mg, 11%);

F12 white powder, m.p. 108-109° C., $^1$H NMR (270 MHz, CDCl$_3$) δ 1.95 (1H, br), 2.90 (1H, dd, J=13.8 and 2.8 Hz), 3.33 (3H, s), 3.35 (1H, dd, J=13.8 and 5.9 Hz), 3.84 (3H, s), 3.87-3.96 (3H, m), 5.13 (2H, s), 6.54 (1H, s), 6.80 (1H, s), 7.28-7.45 (5H, m). HRMS (ES) calcd. for C$_{18}$H$_{22}$NO$_3$ (MH$^+$), 300.1594 found 300.1584. HPLC: tr=4.32 (97.2%) CH$_3$CN/H$_2$O 90/10

F13 cream colour powder, m.p. 138-139° C., $^1$H NMR (270 MHz, CDCl$_3$) δ 4.02 (3H, s), 5.29 (2H, s), 7.09 (1H, s), 7.21 (1H, s), 7.29-7.50 (6H, m), 8.35 (1H, d, J=5.8 Hz), 9.03 (1H, s); HRMS (ES) calcd. for C$_{17}$H$_{16}$NO$_2$ (MH$^+$), 266.1176 found 266.1165. HPLC: tr=2.70 (99.2%) CH$_3$CN/H$_2$O 90/10

2-tert-Butoxycarbonyl-4-ethoxy-6-benzyloxy-7-methoxy-3,4-dihydro-1H-isoquinoline F14

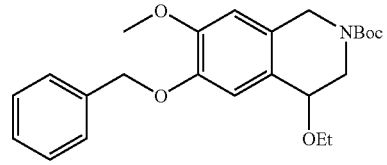 [SMILES: CCOC1CN(C(=O)OC(C)(C)C)Cc2cc(OC)c(OCc3ccccc3)cc21]

A suspension of F10 (5.8 g, 15 mmol) in dry THF (50 mL) and dry DMF (10 mL) was cooled to 0° C. and treated with 60% NaH (0.8 g, 20 mmol) in a portion wise manner. The reaction mixture was stirred for 30 minutes at 0° C. before ethyl iodide (1.6 mL, 20 mmol) was added and the mixture stirred at rt for 16 hours. After careful addition of water, the mixture was extracted with ethyl acetate, the organic layers separated, washed with water, brine, dried (MgSO$_4$), filtered and concentrated. The resulting yellow oil (6.5 g) was purified by flash chromatography (hexane/EtOAc 20/1 to 3/1) to afford F14 as a white solid (4.7 g, 76%), m.p. 85-86° C., $^1$H NMR (270 MHz, CDCl$_3$) δ 1.19 (3H, t, J=6.9 Hz), 1.47 (9H, s), 3.37-3.71(3H, m), 3.85 (3H, s), 3.88-4.00 (1H, m), 4.22-4.42 (2H, m), 4.55-4.73 (1H, m), 5.13 (2H, s), 6.60 (1H, s), 6.85 and 690 (1H, s), 7.27-7.45 (5H, m). HRMS (ES) calcd. for C$_{24}$H$_{31}$NNaO$_5$ (M+Na$^+$), 436.2094 found 436.2095. HPLC: tr=2.74 (99.3%) CH$_3$CN/H$_2$O 90/10.

6-Benzyloxy-4-ethoxy-7-methoxy-1,2,3,4-tetrahydroisoquinoline F15

6-Benzyloxy-4-ethoxy-7-methoxy-3,4-dihydro-1H-isoquinoline-2-carboxylic acid tert-butyl ester (4.7 g, 11.4 mmol) was stirred in THF (50 mL) and methanol (5 mL) and cooled to 0° C. before acetyl chloride (2 mL, 28 mmol) was added drop wise. The solution was stirred at rt for an o/n. After addition of DCM (100 mL) the organic layer was washed with a solution of saturated aqueous NaHCO$_3$, water, brine, dried (MgSO$_4$), filtered and concentrated to afford 3.6 g of crude product. Column chromatography (petroleum ether/ethyl acetate 9/1 to 0/1 then ethyl acetate/methanol 1/0 to 10/1) afford 1.5 g (42%) of 6-Benzyloxy-4-ethoxy-7-methoxy-1,2,3,4-tetrahydroisoquinoline F15 and 6-benzyloxy-7-methoxyisoquinoline F16 (0.7 g, 23%). F15 white powder, m.p. 55-56° C., $^1$H NMR (270 MHz, CDCl$_3$) δ 1.16 (3H, t, J=6.9 Hz), 2.10 (1H, br), 2.91 (1H, dd, J=13.8 and 2.8 Hz), 3.29 (1H, dd, J=13.8 and 2.5 Hz), 3.37-3.61 (2H, m), 3.84 (3H, s), 3.87-3.95 (2H, m), 4.00-4.06 (1H, m), 5.14 (2H, s), 6.53 (1H, s), 6.78 (1H, s), 7.26-7.44 (5H, m). HRMS (ES) calcd. for C$_{19}$H$_{24}$NO$_3$ (MH$^+$), 314.1751 found 314.1744. HPLC: tr=4.16 (95.8%) CH$_3$CN/H$_2$O 90/10.

For N-benzylations see Method 1 for the "Synthesis of 6-(benzyloxy)-2-benzyl-1,2,3,4-tetrahydroisoquinolines"

6-Benzyloxy-7-methoxy-2-(3-methoxybenzyl)-1,2,3,4-tetrahydroisoquinolin-4-ol F17

480 mg (79%), white powder, m.p. 115-116° C., $^1$H NMR (270 MHz, CDCl$_3$) δ 2.60 (1H, dd, J=11.6 and 2.9 Hz), 2.66 (1H, br), 3.04 (1H, dd, J=11.6 and 2.8 Hz), 3.28 (1H, d, J=14.9 Hz), 3.62-3.75 (3H, m), 3.80 (3H, s), 3.81 (3H, s), 4.47 (1H, br), 5.08 (H, d, J=12.1 Hz), 5.16 (H, d, J=12.1 Hz), 6.50 (1H, s), 6.80-6.84 (1H, m), 6.93-6.96 (3H, m), 7.25 (1H, t, J=7.7 Hz), 7.29-7.44 (5H, m); $^{13}$C NMR (100 MHz, CDCl$_3$) δ 55.2 (CH$_3$), 55.4 (CH$_2$), 56.0 (CH$_3$), 58.4 (CH$_2$), 62.6 (CH$_2$), 67.1 (C), 70.9 (CH$_2$), 109.1 (CH), 112.7 (CH), 114.1 (CH), 114.5 (CH), 121.3 (CH), 127.3 (2×CH), 127.7 (C), 127.8 (CH), 128.5 (2×CH), 128.7 (C), 129.4 (CH), 137.0 (C), 139.5 (C), 147.1 (C), 149.3 (C) and 159.7 (C). HRMS (ES) calcd. for C$_{25}$H$_{28}$NO$_4$ (MH$^+$), 406.2013 found 406.1997. HPLC: tr=2.13 (99.5%) CH$_3$CN/H$_2$O 90/10.

6-Benzyloxy-7-methoxy-2-(3,4,5-trimethoxybenzyl)-1,2,3,4-tetrahydroisoquino-lin-4-ol F18

450 mg, (64%), white powder, m.p.: 126-127° C., $^1$H NMR (270 MHz, CDCl$_3$) δ 2.53 (1H, dd, J=11.9 and 2.8 Hz), 3.04 (1H, d, J=10.7 Hz), 3.03 (1H, dd, J=11.9 and 2.8 Hz), 3.31 (1H, d, J=14.9 Hz), 3.63 (2H, s), 3.74 (1H, d, J=14.9 Hz), 3.83 (3H, s), 3.84 (9H, s), 4.48 (1H, dt, 10.7 and 2.8 Hz), 5.09 (1H, d, J=12.2 Hz), 5.16 (1H, d, J=12.2 Hz), 6.53 (1H, s), 6.59 (2H, s), 6.94 (1H, s), 7.28-7.45 (5H, m); $^{13}$C NMR (100 MHz, CDCl$_3$) δ 55.7 (CH$_2$), 56.0 (CH$_3$), 56.1 (2×CH$_3$), 58.2 (CH$_2$), 60.9 (CH$_3$), 62.8 (CH$_2$), 67.1 (CH), 71.0 (CH$_2$), 105.5 (2×CH), 109.2 (CH), 114.0 (CH), 127.3 (2×CH), 127.7 (C), 127.8 (CH), 128.5 (2×CH), 128.7 (C), 133.7 (C), 137.0 (C), 147.1 (C), 149.4 (C) and 153.2 (2×C). HRMS (ES) calcd. for C$_{27}$H$_{32}$NO$_6$ (MH$^+$), 466.2224 found 466.2210. HPLC: tr=1.92 (98%) CH$_3$CN/H$_2$O 90/10.

6-Benzyloxy-4,7-dimethoxy-2-(2-methoxybenzyl)-1,2,3,4-tetrahydroisoquinoline F19

465 mg, (74%), light yellow powder, m.p.: 101-102° C., $^1$H NMR (270 MHz, CDCl$_3$) δ 2.78 (1H, dd, J=11.8 and 4.1 Hz), 2.91 (1H, dd, J=11.8 and 5.1 Hz), 3.34 (3H, s), 3.49 (1H, d, J=14.6 Hz), 3.68 (1H, d, J=14.6 Hz), 3.75 (2H, s), 3.82 (3H, s), 3.84 (3H, s), 4.31 (1H, dd, J=5.1 and 4.1 Hz), 5.08 (1H, d, J=12.1 Hz), 5.14 (1H, d, J=12.1 Hz), 6.53 (1H, s), 6.88 (1H, d, J=8.2 Hz), 6.91-6.97 (2H, m), 7.20-7.49 (7H, m); $^{13}$C NMR (100 MHz, CDCl$_3$) δ 54.1 (CH$_2$), 55.4 (CH$_3$), 55.5 (CH$_2$), 55.7 (CH$_2$), 56.0 (2×CH$_3$), 71.0 (CH$_2$), 75.2 (CH), 109.2 (CH), 110.3 (CH), 114.0 (CH), 120.4 (CH), 126.0 (C), 126.4 (C), 127.4 (2×CH), 127.7 (CH), 128.0 (CH), 128.5 (2×CH), 129.0 (C), 130.3 (CH), 137.2 (C), 146.8 (C), 149.2 (C) and 157.7 (C). HRMS (ES) calcd. for C$_{26}$H$_{30}$NO$_4$ (MH$^+$), 420.2169 found 420.2166. HPLC: tr=3.24 (94.0%) CH$_3$CN/H$_2$O 90/10

6-Benzyloxy-4,7-dimethoxy-2-(3-methoxybenzyl)-1,2,3,4-tetrahydroisoquinoline F20

490 mg (77%), light yellow powder, m.p.: 96-97° C., $^1$H NMR (270 MHz, CDCl$_3$) δ 2.70 (1H, dd, J=11.8 and 4.1 Hz), 2.89 (1H, dd, J=11.8 and 4.7 Hz), 3.31 (3H, s), 3.44 (1H, d, J=14.6 Hz), 3.59 (1H, d, J=13.2 Hz), 3.66 (1H, d, J=14.6 Hz), 3.76 (1H, d, J=13.2 Hz), 3.80 (3H, s), 3.81 (3H, s), 4.30 (1H, dd, J=4.7 and 4.1 Hz), 5.09 (1H, d, 12.4 Hz), 5.15 (1H, d, J=12.4 Hz), 6.53 (1H, s), 6.80-6.84 (1H, m), 6.94 (1H, s), 6.96-6.99 (2H, m), 7.24 (1H, t, J=8.3 Hz), 7.26-7.45 (5H, m); $^{13}$C NMR (100 MHz, CDCl$_3$) δ 53.9 (CH$_2$), 55.2 (CH$_3$), 55.7 (CH$_2$), 56.0 (CH$_3$), 62.5 (CH$_2$), 71.0 (CH$_2$), 75.1 (CH), 109.2 (CH), 112.9 (CH), 114.1 (CH), 114.2 (CH), 121.3 (CH), 126.3 (C), 127.4 (2×CH), 127.7 (CH), 128.4 (2×CH), 128.7 (C), 129.2 (CH), 137.2 (C), 139.7 (C), 146.9 (C), 149.3 (C) and 159.7 (C). HRMS (ES) calcd. for C$_{26}$H$_{30}$NO$_4$ (MH$^+$), 420.2169 found 420.2152. HPLC: tr=2.60 (100%) CH$_3$CN/H$_2$O 90/10.

6-Benzyloxy)-4,7-dimethoxy-2-(4-methoxybenzyl)-1,2,3,4-tetrahydroisoquinoline F21

500 mg (80%), light yellow powder, $^1$H NMR (400 MHz, CDCl$_3$) δ 2.71 (2H, dd, J=11.7 and 3.9 Hz), 2.87 (2H, dd, J=11.7 and 5.1 Hz), 3.31 (3H, s), 3.42 (1H, d, J=14.5 Hz), 3.47 (1H, d, J=12.9 Hz), 3.64 (1H, d, J=14.5 Hz), 3.72 (1H, d, J=12.9 Hz), 3.80 (3H, s), 3.81 (3H, s), 4.29 (1H, dd, J=5.1 and 3.9 Hz), 5.10 (1H, d, J=12.2 Hz), 5.15 (1H, d, J=12.2 Hz), 6.53 (1H, s), 6.86-6.89 (2H, m), 6.94 (1H, s), 7.26-7.38 (5H, m), 7.42-7.45 (2H, m); $^{13}$C NMR (100 MHz, CDCl$_3$) δ 53.7 (CH$_2$), 55.1 (CH$_3$), 55.6 (CH$_2$), 55.9 (2×CH$_3$), 61.9 (CH$_2$), 71.0 (CH$_2$), 75.1 (CH), 109.2 (CH), 113.6 (2×CH), 114.1 (CH), 126.3 (C), 127.4 (2×CH), 127.7 (CH), 128.4 (2×CH), 128.7 (C), 130.2 (2×CH), 137.1 (C), 146.8 (C), 149.3 (C) and 158.7 (C). HRMS (ES) calcd. for C$_{26}$H$_{30}$NO$_4$ (MH$^+$), 420.2169 found 420.2157. HPLC: tr=3.11 (95.2%) CH$_3$CN/H$_2$O 90/10.

6-Benzyloxy-4,7-dimethoxy-2-(3,4,5-trimethoxybenzyl)-1,2,3,4-tetrahydroisoquinoline F22

490 mg (68%), white powder, m.p. 89-90° C., $^1$H NMR (400 MHz, CDCl$_3$) δ 2.64 (1H, dd, J=11.8 and 3.9 Hz), 2.91 (1H, dd, J=11.8 and 4.3 Hz), 3.32 (3H, s), 3.45 (1H, d, J=14.5 Hz), 3.51 (1H, d, J=13.3 Hz), 3.70 (1H, d, J=14.5 Hz), 3.76 (1H, d, J=13.3 Hz), 3.83 (3H, s), 3.84 (3H, s), 3.85 (6H, s), 4.27 (1H, dd, J=4.3 and 3.9 Hz), 5.10 (1H, d, J=12.0 Hz), 5.14 (1H, d, J=12.0 Hz), 6.55 (1H, s), 6.55 (2H, s), 6.93 (1H, s), 7.27-7.30 (1H, m), 7.33-7.37 (2H, m), 7.43 (2H, d, J=7.0 Hz); $^{13}$C NMR (100 MHz, CDCl$_3$) δ 53.5 (CH$_2$), 56.0 (CH$_2$), 56.0 (CH$_3$), 56.1 (2×CH$_3$), 60.9 (CH$_3$), 60.9 (CH$_3$), 62.7 (CH$_2$), 71.1 (CH$_2$), 75.2 (CH), 105.5 (2×CH), 109.3 (CH), 114.2 (CH), 126.3 (C), 127.4 (2×CH), 127.7 (CH), 128.4 (2×CH), 128.6 (C), 134.0 (C), 136.9 (C), 137.1 (C), 147.0 (C), 149.4 (C) and 153.2 (2×C). HRMS (Electrospray) calcd. for C$_{28}$H$_{34}$NO$_6$ (MH$^+$), 480.2381 found 480.2363. HPLC: tr=2.74 (95.3%) CH$_3$CN/H$_2$O 90/10.

6-Benzyloxy-4-ethoxy-7-methoxy-2-(2-methoxybenzyl)-1,2,3,4-tetrahydroisoquinoline F23

395 mg (61%), yellow oil, $^1$H NMR (270 MHz, CDCl$_3$) δ 1.19 (3H, t, J=6.9 Hz), 2.83 (1H, d, J=4.9 Hz), 3.48-3.58 (3H, m), 3.66 (1H, d, J=14.3 Hz), 3.74 (2H, s), 3.81 (3H, s), 3.82 (3H, s), 4.41 (1H, t, J=4.9 Hz), 5.13 (2H, s), 6.52 (1H, s), 6.86-6.97 (3H, m), 7.20-7.51 (7H, m), $^{13}$C NMR (100 MHz, CDCl$_3$) δ 15.6 (CH$_3$), 54.8 (CH$_2$), 55.2 (CH$_3$), 55.4 (CH$_2$), 55.7 (CH$_2$), 55.9 (CH$_3$), 63.7 (CH$_2$), 71.0 (CH$_2$), 73.8 (CH), 109.1 (CH), 110.2 (CH), 113.9 (CH), 120.2 (CH), 126.1 (C), 127.0 (C), 127.2 (2×CH), 127.6 (CH), 127.8 (CH), 128.3 (2×CH), 128.8 (C), 130.0 (CH), 137.2 (C), 146.8 (C), 149.1 (C) and 157.6 (C). HRMS (ES) calcd. for C$_{27}$H$_{32}$NO$_4$ (MH$^+$), 434.2326 found 434.2335. HPLC: tr=3.64 (95.2%) CH$_3$CN/H$_2$O 90/10.

6-Benzyloxy-4-ethoxy-7-methoxy-2-(3-methoxybenzyl)-1,2,3,4-tetrahydroisoquinoline F24

405 mg (62%), yellow oil, $^1$H NMR (270 MHz, CDCl$_3$) δ 1.16 (3H, t, J=6.9 Hz), 2.78 (2H, d, J=5.0 Hz), 3.44-3.63 (5H, m), 3.74 (1H, d, J=13.2 Hz), 3.80 (3H, s), 3.82 (3H, s), 4.40 (1H, t, J=5.0 Hz), 5.14 (2H, s), 6.51 (1H, s), 6.81 (1H, dd, J=8.0 and 2.5 Hz), 6.94 (1H, s), 6.96-6.99 (2H, m), 7.21-7.46 (6H, m); $^{13}$C NMR (100 MHz, CDCl$_3$) δ 15.7 (CH$_3$), 54.7 (CH$_2$), 55.2 (CH$_3$), 55.8 (CH$_2$), 56.0 (CH$_3$), 62.5 (CH$_2$), 63.8 (CH$_2$), 71.1 (CH$_2$), 73.8 (CH), 109.1 (CH), 112.7 (CH), 113.9 (CH), 114.2 (CH), 121.3 (CH), 127.0 (C), 127.3 (2×CH), 127.7 (CH), 128.4 (2×CH), 128.5 (C), 129.2 (CH), 137.3 (C), 139.8 (C), 146.9 (C), 149.2 (C) and 159.7 (C). HRMS (ES) calcd. for C$_{27}$H$_{32}$NO$_4$ (MH$^+$), 434.2326 found 434.2331. HPLC: tr=3.11 (94.8%) CH$_3$CN/H$_2$O 90/10.

6-Benzyloxy-4-ethoxy-7-methoxy-2-(4-methoxybenzyl)-1,2,3,4-tetrahydroisoquinoline F25

435 mg (67%), yellow powder, m.p. 84-85° C., $^1$H NMR (270 MHz, CDCl$_3$) δ 1.15 (3H, t, J=7.2 Hz), 2.68-2.80 (2H, m), 3.40-3.59 (5H, m), 3.69 (1H, d, J=12.9 Hz), 3.80 (3H, s), 3.81 (3H, s), 4.38 (1H, dd, J=5.2 and 4.7 Hz), 5.12 (2H, s), 6.49 (1H, s), 6.6.85 (2H, d, =8.5 Hz), 6.92 (1H, s), 7.26-7.39 (5H, m), 7.42 (2H, d, J=8.5 Hz); $^{13}$C NMR (100 MHz, CDCl$_3$) δ 15.7 (CH$_3$), 54.6 (CH$_2$), 55.2 (CH$_3$), 55.7 (CH$_2$), 56.0 (CH$_3$), 61.9 (CH$_2$), 63.8 (CH$_2$), 71.1 (CH$_2$), 73.8 (CH), 109.1 (CH), 109.2 (CH), 113.6 (2×CH), 114.0 (CH), 127.1 (C), 127.3 (2×CH), 127.7 (CH), 128.4 (2×CH), 128.6 (C), 130.1 (2×CH), 137.3 (C), 146.9 (C), 149.2 (C) and 158.7 (C). HRMS (ES) calcd. for C$_{27}$H$_{32}$NO$_4$ (MH$^+$), 434.2326 found 434.2314. HPLC: tr=3.64 (97.8%) CH$_3$CN/H$_2$O 90/10.

6-Benzyloxy-4-ethoxy-7-methoxy-2-(3,4,5-trimethoxybenzyl)-1,2,3,4-tetrahydro-isoquinoline F26

385 mg (52%), light yellow powder, m.p. 132-133° C., $^1$H NMR (270 MHz, CDCl$_3$) δ 1.14 (3H, t, J=6.9 Hz), 2.71 (1H, dd, J=11.6 and 4.4 Hz), 2.79 (1H, dd, J=11.6 and 5.2 Hz), 3.41-3.74 (6H, m), 3.83 (3H, s), 3.84 (9H, s), 4.38 (1H, dd, J=5.2 and 4.4 Hz), 5.13 (2H, s), 6.53 (1H, s), 6.63 (2H, s), 6.92 (1H, s), 7.27-7.44 (5H, m), $^{13}$C NMR (100 MHz, CDCl$_3$) δ 15.7 (CH$_3$), 54.6 (CH$_2$), 55.9 (CH$_2$), 56.0 (CH$_3$), 56.1 (2×CH$_3$), 60.9 (CH$_3$), 62.8 (CH$_2$), 63.9 (CH$_2$), 71.1 (CH$_2$), 73.8 (CH), 105.5 (2×CH), 109.2 (CH), 114.0 (CH), 126.9 (C), 127.3 (2×CH), 127.7 (CH), 128.5 (2×CH), 134.0 (C), 137.3 (C), 147.0 (C), 149.3 (C) and 153.2 (2×C). HRMS (ES) calcd. for C$_{29}$H$_{36}$NO$_6$ (MH$^+$), 494.2537 found 494.2523. HPLC: tr=2.54 (99.0%) CH$_3$CN/H$_2$O 90/10.

4-O-Acetyl-6-benzyloxy-7-methoxy-2-(3-methoxybenzyl)-1,2,3,4-tetrahydroisoquinoline F27

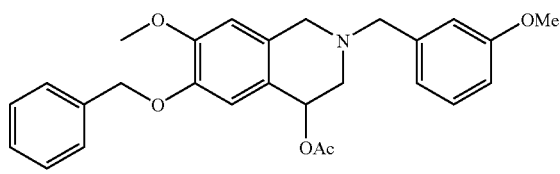 [SMILES: COc1cccc(CN2Cc3cc(OC)c(OCc4ccccc4)cc3C(OC(C)=O)C2)c1]

A solution of F17 (330 mg, 0.81 mmol) in DCM (20 mL) and TEA (0.14 mL, 0.9 mmol) was cooled to 0° C. before Ac$_2$O (0.085 mL, 0.9 mL) was added dropwise. The mixture was stirred at rt o/n. After addition of water (50 mL), the organics were extracted with DCM and the organic layer washed with aq. NaHCO$_3$ water, brine, dried (MgSO$_4$), filtered and concentrated. The crude oil (0.5 g) was purified by flash chromatography to give a yellow powder (340 mg, 94%), m.p.: 96-97° C., $^1$H NMR (270 MHz, CDCl$_3$) δ 2.01 (3H, s), 2.65 (1H, dd, J=12.7 and 3.6 Hz), 2.97 (1H, dd, J=12.7 and 3.3 Hz), 3.39 (1H, d, J=14.6 Hz), 3.59 (1H, d, J=13.2 Hz), 3.75-3.83 (8H, m), 5.07 (H, d, J=12.4 Hz), 5.14 (H, d, J=12.4 Hz), 5.85 (1H, dd, J=3.6 and 3.3 Hz), 6.54 (1H, s), 6.79 (1H, d, J=2.2 Hz), 6.82 (1H, s), 6.94-6.97 (2H, m), 7.20-7.42 (6H, m); $^{13}$C NMR (100 MHz, CDCl$_3$) δ 21.3 (CH$_3$), 54.8 (CH$_2$), 55.1 (CH$_3$), 55.3 (CH$_2$), 55.9 (CH$_3$), 62.0 (CH$_2$), 68.5 (CH), 70.8 (CH$_2$), 109.2 (CH), 112.5 (CH), 114.3 (CH), 114.5 (CH), 121.3 (CH), 123.9 (C), 127.3 (2×CH), 127.7 (CH), 128.4 (2×CH), 129.1 (C), 129.2 (CH), 136.9 (C), 139.2 (C), 146.8 (C), 149.8 (C), 159.6 (C) and 171.0 (CO). HRMS (ES) calcd. for C$_{27}$H$_{30}$NO$_5$ (MH$^+$), 448.2118 found 448.2104. HPLC: tr=2.41 (97.7%) CH$_3$CN/H$_2$O 90/10.

Deprotections of the O-benzyl group: see Method 1 of the "Synthesis of 6-hydroxy-2-benzyl-1,2,3,4-tetrahydroisoquinolines"

7-Methoxy-2-(3-methoxybenzyl)-1,2,3,4-tetrahydroisoquinoline-4,6-diol F28

240 mg (75%), yellow powder, m.p. 137-138° C., $^1$H NMR (400 MHz, CDCl$_3$) δ 2.63 (1H, dd, J=11.5 and 2.3 Hz), 3.07 (1H, dd, J=11.5 and 2.0 Hz), 3.29 (1H, d, J=14.5 Hz), 3.66 (1H, d, 14.5 Hz), 3.70 (1H, d, 13.3 Hz), 3.73 (1H, d, 13.3 Hz), 3.81 (3H, s), 3.82 (3H, s), 4.51 (1H, dd, J=2.4 and 2.0 Hz), 6.47 (1H, s), 6.81-6.85 (1H, m), 6.94-6.97 (3H, m), 7.25 (1H, t, J=7.8 Hz); $^{13}$C NMR (100 MHz, CDCl$_3$) δ 55.2 (CH$_3$), 55.5 (CH$_2$), 55.9 (CH$_3$), 58.5 (CH$_2$), 62.6 (CH$_2$), 66.9 (CH), 108.1 (CH), 112.8 (CH), 114.5 (CH), 114.7 (CH), 121.4 (CH), 126.4 (C), 129.4 (CH), 129.6 (C), 144.5 (C), 146.4 (C) and 159.7 (C). HRMS (ES) calcd. for C$_{18}$H$_{22}$NO$_4$ (MH$^+$), 316.1543 found 316.1534. HPLC: tr=1.62 (99.2%) CH$_3$CN/H$_2$O 90/10.

7-Methoxy-2-(3,4,5-trimethoxybenzyl)-1,2,3,4-tetrahydroisoquinoline-4,6-diol F29

325 mg (87%), yellow powder, m.p. 62-63° C., $^1$H NMR (270 MHz, CDCl$_3$) δ 2.59 (1H, dd, J=11.8 and 2.8 Hz), 2.65 (1H, br), 3.05 (1H, dd, J=11.8 and 2.8 Hz), 3.29 (1H, d, J=14.3 Hz), 3.63 (2H, s), 3.73 (1H, d, J=14.3 Hz), 3.83 (3H, s), 3.84 (9H, s), 4.52 (1H, br s), 5.59 (1H, br s), 6.48 (1H, s), 6.59 (2H, s), 6.95 (1H, s); $^{13}$C NMR (100 MHz, CDCl$_3$) δ 55.7 (CH$_2$), 55.9 (CH$_3$), 56.1 (2×CH$_3$), 58.3 (CH$_2$), 60.9 (CH$_3$), 62.8 (CH$_2$), 66.9 (CH), 105.6 (2×CH), 108.1 (CH), 114.7 (CH), 126.5 (C), 129.5 (C), 133.7 (C), 137.0 (C), 144.5 (C), 146.4 (C) and 153.2 (2×C). HRMS (ES) calcd. for C$_{20}$H$_{26}$NO$_6$ (MH$^+$), 376.1755 found 376.1745. HPLC: tr=1.92 (98%) CH$_3$CN/H$_2$O 90/10.

4,7-Dimethoxy-2-(2-methoxybenzyl)-1,2,3,4-tetrahydro-isoquinolin-6-ol F30

285 mg (86%), yellow powder, m.p. 45-47° C., $^1$H NMR (270 MHz, CDCl$_3$) δ 2.76 (1H, dd, J=11.8 and 3.8 Hz), 2.93 (1H, dd, J=11.8 and 4.9 Hz), 3.41 (3H, s), 3.48 (1H, d, J=14.4 Hz), 3.68 (1H, d, J=14.4 Hz), 3.76 (2H, s), 3.82 (3H, s), 3.84 (3H, s), 4.31 (1H, dd, J=4.9 and 3.8 Hz), 5.50 (1H, br), 6.48 (1H, s), 6.88 (1H, d, J=8.3 Hz), 6.93 (1H, t, J=7.4 Hz), 6.94 (1H, s), 7.24 (1H, dd, J=7.4 and 1.4 Hz), 7.48 (1H, dd, J=7.4 and 1.4 Hz); $^{13}$C NMR (100 MHz, CDCl$_3$) δ 54.2 (CH$_2$), 55.4

($CH_3$), 55.5 ($CH_2$), 55.7 ($CH_2$), 55.9 ($CH_3$), 56.3 ($CH_3$), 75.2 ($CH_2$), 108.1 (CH), 110.3 (CH), 114.3 (CH), 120.4 (CH), 126.0 (C), 127.3 (C), 127.6 (C), 128.0 (CH), 130.4 (CH), 144.2 (C), 146.2 (C) and 157.8 (C). HRMS (ES) calcd. for $C_{19}H_{24}NO_4$ (MH$^+$), 330.1700 found 330.1684. HPLC: tr=2.20 (98.7%) $CH_3CN/H_2O$ 90/10.

4,7-Dimethoxy-2-(3-methoxybenzyl)-1,2,3,4-tetrahydro-isoquinolin-6-ol F31

220 mg (67%), yellow powder, m.p. 133-134° C., $^1$H NMR (400 MHz, CDCl$_3$) δ 2.72 (1H, dd, J=11.8 and 4.0 Hz), 2.90 (1H, dd, J=11.8 and 4.7 Hz), 3.38 (3H, s), 3.44 (1H, d, J=14.6 Hz), 3.61 (1H, d, J=13.5 Hz), 3.65 (1H, d, J=14.6 Hz), 3.77 (1H, d, J=13.5 Hz), 3.81 (3H, s), 3.82 (3H, s), 4.30 (1H, app. t, J=4.3 Hz), 5.50 (1H, br), 6.48 (1H, s), 6.81 (1H, dd, J=7.8 and 2.4 Hz), 6.95 (1H, s), 6.96-7.00 (2H, m), 7.24 (1H, t, J=7.8 Hz); $^{13}$C NMR (100 MHz, CDCl$_3$) δ 54.0 (CH$_2$), 55.2 (CH$_3$), 55.7 (CH$_2$), 55.9 (CH$_3$), 56.3 (CH$_2$), 62.5 (CH$_2$), 75.1 (CH), 108.3 (CH), 112.9 (CH), 114.2 (CH), 114.4 (CH), 121.4 (CH), 127.2 (C), 129.2 (CH), 137.2 (C), 139.7 (C), 144.3 (C), 146.3 (C) and 159.7 (C). HRMS (ES) calcd. for $C_{19}H_{24}NO_4$ (MH$^+$), 330.1700 found 330.1694. HPLC: tr=1.07 (99.2%) $CH_3CN/H_2O$ 90/10.

4,7-Dimethoxy-2-(4-methoxybenzyl)-1,2,3,4-tetrahydro-isoquinolin-6-ol F32

200 mg (62%), yellow powder, m.p. 84-85° C., $^1$H NMR (400 MHz, CDCl$_3$) δ 2.69 (1H, dd, J=11.8 and 4.1 Hz), 2.87 (1H, dd, J=11.8 and 4.9 Hz), 3.36 (3H, s), 3.40 (1H, d, J=14.6 Hz), 3.57 (1H, d, J=13.0 Hz), 3.62 (1H, d, J=14.6 Hz), 3.71 (1H, d, J=13.0 Hz), 3.79 (3H, s), 3.80 (3H, s), 4.28 (1H, app. t, J=4.4 Hz), 5.52 (1H, br), 6.46 (1H, s), 6.86 (2H, d, J=8.5 Hz), 6.93 (1H, s), 7.30 (2H, d, J=8.5 Hz); $^{13}$C NMR (100 MHz, CDCl$_3$) δ 54.0 (CH$_2$), 55.3 (CH$_3$), 55.7 (CH$_2$), 56.0 (CH$_3$), 56.4 (CH$_3$), 62.0 (CH$_2$), 75.2 (CH), 108.2 (CH), 113.7 (2×CH), 114.5 (CH), 127.3 (C), 127.4 (C), 130.0 (C), 130.4 (2×CH), 144.3 (C), 146.4 (C) and 158.9 (C). HRMS (ES) calcd. for $C_{19}H_{24}NO_4$ (MH$^+$), 330.1700 found 330.1686. HPLC: tr=1.04 (99.2%) $CH_3CN/H_2O$ 90/10.

4,7-Dimethoxy-2-(3,4,5-trimethoxybenzyl)-1,2,3,4-tetrahydro-isoquinolin-6-ol F33

310 mg (80%), light yellow powder, m.p. 51-54° C., $^1$H NMR (400 MHz, CDCl$_3$) δ 2.61 (1H, dd, J=11.8 and 3.6 Hz), 2.93 (1H, dd, J=11.8 and 4.4 Hz), 3.39 (3H, s), 3.44 (1H, d, J=14.3 Hz), 3.50 (1H, d, J=13.2 Hz), 3.69 (1H, d, J=14.3 Hz), 3.75 (1H, d, J=13.2 Hz), 3.83 (3H, s), 3.84 (3H, s), 3.85 (6H, s), 4.27 (1H, app. t, J=4.1 Hz), 5.50 (1H, br), 6.50 (1H, s), 6.65 (2H, s), 6.94 (1H, s); $^{13}$C NMR (100 MHz, CDCl$_3$) δ 53.8 (CH$_2$), 56.0 (CH$_2$), 56.1 (2×CH$_3$), 56.6 (CH$_3$), 61.0 (CH$_3$), 62.8 (CH$_2$), 75.3 (CH), 105.6 (2×CH), 108.2 (CH), 114.6 (CH), 127.1 (C), 127.4 (C), 127.4 (C), 128.5 (C), 134.1 (C), 144.4 (C), 146.5 (C) and 153.3 (2×C). HRMS (ES) calcd. for $C_{21}H_{28}NO_6$ (MH$^+$), 390.1911 found 390.1893. HPLC: tr=1.04 (98.3%) $CH_3CN/H_2O$ 90/10.

4-Ethoxy-7-methoxy-2-(2-methoxybenzyl)-1,2,3,4-tetrahydroisoquinolin-6-ol F34

260 mg (75%), yellow powder, m.p. 101-102° C., $^1$H NMR (270 MHz, CDCl$_3$) δ 1.23 (3H, t, J=7.2 Hz), 2.83 (2H, d, J=5.0 Hz), 3.52 (1H, d, J=14.6 Hz), 3.56-3.66 (3H, m), 3.74 (2H, s), 3.81 (3H, s), 3.83 (3H, s), 4.42 (1H, t, J=5.0 Hz), 5.42 (1H, br), 6.47 (1H, s), 6.87 (1H, d, J=8.3 Hz), 6.92 (1H, d, J.=8.3 Hz), 7.20-7.26 (1H, m), 7.50 (1H, dd, J=7.4 and 1.6 Hz); $^{13}$C NMR (100 MHz, CDCl$_3$) δ 15.8 (CH$_3$), 54.9 (CH$_2$), 55.5 (CH$_2$), 55.6 (CH$_3$), 55.9 (CH$_2$), 56.0 (CH$_3$), 64.4 (CH$_2$), 74.0 (CH), 108.1 (CH), 110.4 (CH), 114.2 (CH), 120.5 (CH), 126.3 (C), 127.6 (C), 128.0 (C), 128.1 (CH), 130.3 (CH), 144.3 (C), 146.2 (C) and 157.8 (C). HRMS (ES) calcd. for $C_{20}H_{26}NO_4$ (MH$^+$), 344.1856 found 344.1844. HPLC: tr=1.05 (97.5%) $CH_3CN/H_2O$ 90/10.

4-Ethoxy-7-methoxy-2-(3-methoxy-benzyl)-1,2,3,4-tetrahydroisoquinolin-6-ol F35

250 mg (73%), yellow powder, m.p. 134-135° C., $^1$H NMR (270 MHz, CDCl$_3$) δ 1.22 (3H, t, J=6.9 Hz), 2.76 (1H, dd, J=12.2 and 5.2 Hz), 2.81 (1H, dd, J=12.2 and 4.9 Hz), 3.46 (1H, d, J=14.3 Hz), −3.53-3.62 (4H, m), 3.75 (1H, d, J=13.2 Hz), 3.80 (3H, s), 3.81 (3H, s), 4.41 (1H, dd, J=5.2 and 4.9 Hz), 5.49 (1H, br), 6.46 (1H, s), 6.80 (1H, dd, J=8.0 and 2.5 Hz), 6.96-6.99 (3H, m), 7.23 (1H, t, J=8.0 Hz); $^{13}$C NMR (100 MHz, CDCl$_3$) δ 15.7 (CH$_3$), 54.7 (CH$_2$), 55.2 (CH$_3$), 55.7 (CH$_2$), 55.9 (CH$_3$), 62.4 (CH$_2$), 64.3 (CH$_2$), 73.7 (CH), 108.0 (CH), 112.9 (CH), 114.1 (CH), 114.2 (CH), 121.4 (CH), 127.8 (C), 129.2 (CH), 144.3 (C), 146.2 (C), and 159.7 (C). HRMS (ES) calcd. for $C_{20}H_{26}NO_4$ (MH$^+$), 344.1856 found 344.1841. HPLC: tr=1.79 (100%) $CH_3CN/H_2O$ 90/10.

4-Ethoxy-7-methoxy-2-(4-methoxybenzyl)-1,2,3,4-tetrahydroisoquinolin-6-ol F36

260 mg (75%), light yellow powder, m.p. 154-157° C., $^1$H NMR (400 MHz, CDCl$_3$) δ 1.21 (3H, t, J=7.2 Hz), 2.75-2.80 (2H, m), 3.45 (1H, d, J=14.9 Hz), 3.54-3.59 (4H, m), 3.71 (1H, d, J=12.9 Hz), 3.80 (3H, s), 3.81 (3H, s), 4.41 (1H, t, J=4.8 Hz), 5.48 (1H, br), 6.45 (1H, s), 6.86 (2H, d, =8.4 Hz), 6.96 (1H, s), 7.30 (2H, d, J=8.4 Hz); $^{13}$C NMR (100 MHz, CDCl$_3$) δ 15.7 (CH$_3$), 54.6 (CH$_2$), 55.2 (CH$_3$), 55.7 (CH$_2$), 55.9 (CH$_3$), 61.8 (CH$_2$), 64.2 (CH$_2$), 73.8 (CH), 108.0 (CH), 113.6 (2×CH), 114.1 (CH), 127.2 (C), 128.0 (C), 129.9 (C), 130.2 (2×CH), 144.3 (C), 146.1 (C) and 158.8 (C). HRMS (ES) calcd. for $C_{20}H_{26}NO_4$ (MH$^+$), 344.1856 found 344.1840. HPLC: tr=1.00 (99.4%) $CH_3CN/H_2O$ 90/10.

4-Ethoxy-7-methoxy-2-(3,4,5-trimethoxybenzyl)-1,2,3,4-tetrahydroisoquinolin-6-ol F37

125 mg (31%), yellow powder, m.p. 94-96° C., $^1$H NMR (270 MHz, CDCl$_3$) δ 1.21 (3H, t, J=6.9 Hz), 2.74 (1H, dd, J=11.8 and 4.4 Hz), 2.80 (1H, dd, J=11.8 and 5.2 Hz), 3.46 (1H, d, J=15.1 Hz), 3.54-3.71 (4H, m), 3.73 (1H, d, J=13.2 Hz), 3.82 (3H, s), 3.84 (9H, s), 4.40 (1H, dd, J=5.2 and 4.4 Hz), 5.49 (1H, br), 6.48 (1H, s), 6.64 (2H, s), 6.96 (1H, s); $^{13}$C NMR (100 MHz, CDCl$_3$) δ 15.8 (CH$_3$), 54.8 (CH$_2$), 56.0 (CH$_3$), 56.1 (CH$_2$), 56.2 (2×CH$_3$), 61.0 (CH$_3$), 62.9 (CH$_2$), 64.4 (CH$_2$), 73.9 (CH), 105.6 (2×CH), 108.1 (CH), 114.2 (CH), 127.2 (C), 127.8 (C), 134.2 (C), 136.9 (C), 144.4 (C), 146.3 (C) and 153.2 (2×C). HRMS (ES) calcd. for $C_{22}H_{30}NO_6$ (MH$^+$), 404.2068 found 404.2054. HPLC: tr=2.03 (97.3%) $CH_3CN/H_2O$ 90/10.

4-O-Acetyl-6-hydroxy-7-methoxy-2-(3-methoxy-benzyl)-1,2,3,4-tetrahydroisoquinoline F38

295 mg (82%), yellow powder, m.p. 44-46° C., $^1$H NMR (270 MHz, CDCl$_3$) δ 2.08 (3H, s), 2.69 (1H, dd, J=12.4 and 3.6 Hz), 2.96 (1H, dd, J=12.4 and 3.3 Hz), 3.40 (1H, d, J=14.6 Hz), 3.59 (1H, d, J=13.5 Hz), 3.74 (1H, d, J=14.6 Hz), 3.77 (1H, d, J=13.5 Hz), 3.79 (3H, s), 3.83 (3H, s), 5.55 (1H, br), 5.86 (1H, t, J=3.6 Hz), 6.51 (1H, s), 6.81 (1H, dd, J=8.0 and 2.5 Hz), 6.85 (1H, s), 6.94-6.97 (2H, m), 7.23 (1H, t, J=8.0 Hz); $^{13}$C NMR (100 MHz, CDCl$_3$) δ 21.3 (CH$_3$), 54.9 (CH$_2$), 55.2 (CH$_3$), 55.3 (CH$_2$), 55.9 (CH$_3$), 61.9 (CH$_2$), 68.5 (CH), 108.2 (CH), 112.6 (CH), 114.5 (CH), 114.6 (CH), 121.3 (CH), 124.8 (C), 127.9 (C), 129.2 (CH), 139.2 (C), 144.4 (C), 146.8 (C), 159.7 (C), and 171.0 (CO). HRMS (ES) calcd. for C$_{20}$H$_{24}$NO$_5$ (MH$^+$), 358.1649 found 358.1634. HPLC: tr=1.76 (99.1%) CH$_3$CN/H$_2$O 90/10.

see "Synthesis of 6-O-sulfamoyl-2-benzyl-1,2,3,4-tetrahydroisoquinolines"

4,7-Dimethoxy-6-O-sulfamoyl-2-(2-methoxybenzyl)-1,2,3,4-tetrahydroisoquinoline F39

175 mg (86%), yellow powder, m.p. 139-141° C., $^1$H NMR (270 MHz, CDCl$_3$) δ 2.74-2.82 (1H, m), 2.92 (1H, dd, J=11.8 and 4.9 Hz), 3.39 (3H, s), 3.52 (1H, d, J=15.1 Hz), 3.72 (1H, d, J=15.1 Hz), 3.76 (2H, s), 3.80 (3H, d, J=3.3 Hz), 3.84 (3H, s), 4.31 (1H, m), 5.18 (2H, br), 6.62 (1H, s), 6.89 (1H, d, J=8.3 Hz), 6.95 (1H, d, J=7.4 Hz), 6.94 (1H, s), 7.22-7.28 (1H, m), 7.35 (1H, d, J=3.3 Hz), 7.43 (1H, d, J=7.4 Hz); $^{13}$C NMR (100 MHz, CDCl$_3$) δ 53.8 (CH$_2$), 55.5 (CH$_3$), 55.6 (CH$_2$), 55.7 (CH$_2$), 56.3 (CH$_3$), 56.6 (CH$_3$), 74.9 (CH), 110.5 (CH), 110.6 (CH), 120.6 (CH), 124.4 (CH), 125.6 (C), 127.8 (C), 127.6 (C), 128.4 (CH), 130.6 (CH), 136.0 (C), 137.7 (C), 150.9 (C) and 157.9 (C). HRMS (ES) calcd. for C$_{19}$H$_{25}$N$_2$O$_6$S (MH$^+$), 409.1428 found 409.1412. HPLC: tr=1.80 (97.6%) CH$_3$CN/H$_2$O 90/10.

4,7-Dimethoxy-2-(3-methoxybenzyl)-6-O-sulfamoyl-1,2,3,4-tetrahydroisoquinoline F40

130 mg (64%), yellow powder, m.p. 142-144° C., $^1$H NMR (270 MHz, CDCl$_3$) δ 2.75 (1H, dd, J=11.8 and 4.1 Hz), 2.88 (1H, dd, J=11.8 and 4.9 Hz), 3.38 (3H, s), 3.48 (1H, d, J=15.1 Hz), 3.61 (1H, d, J=13.2 Hz), 3.68 (1H, d, J=15.1 Hz), 3.77 (1H, d, J=13.2 Hz), 3.80 (3H, s), 3.82 (3H, s), 4.32 (1H, dd, J=4.9 and 4.1 Hz), 5.08 (2H, br), 6.62 (1H, s), 6.81 (1H, dd, J=8.0 and 2.5 Hz), 6.94-6.97 (2H, m), 7.24 (1H, t, J=8.0 Hz), 7.37 (1H, s); $^{13}$C NMR (100 MHz, CDCl$_3$) δ 53.4 (CH$_2$), 55.3 (CH$_3$), 55.5 (CH$_2$), 56.3 (CH$_3$), 56.6 (CH$_3$), 62.2 (CH$_2$), 74.6 (CH), 110.5 (CH), 113.2 (CH), 114.4 (CH), 121.4 (CH), 122.9 (C), 124.3 (CH), 127.6 (C), 129.4 (CH), 132.2 (C), 137.7 (C), 151.0 (C) and 159.8 (C). HRMS (ES) calcd. for C$_{19}$H$_{25}$N$_2$O$_6$S (MH$^+$), 409.1428 found 409.1412. HPLC: tr=1.17 (99.7%) CH$_3$CN/H$_2$O 90/10

4,7-Dimethoxy-2-(4-methoxybenzyl)-6-O-sulfamoyl-1,2,3,4-tetrahydroisoquinoline F41

125 mg (61%), yellow powder, m.p.: 95-96° C., $^1$H NMR (270 MHz, CDCl$_3$) δ 2.73 (1H, dd, J=11.8 and 4.1 Hz), 2.88 (1H, dd, J=11.8 and 4.8 Hz), 3.35 (3H, s), 3.46 (1H, d, J=15.1 Hz), 3.59 (1H, d, J=12.9 Hz), 3.67 (1H, d, J=15.1 Hz), 3.76 (1H, d, J=12.9 Hz), 3.79 (3H, s), 3.80 (3H, s), 4.27-4.31 (1H, m), 5.30 (2H, br), 6.60 (1H, s), 6.86 (2H, d, J=8.5 Hz), 7.27 (2H, d, J=8.5 Hz), 7.34 (1H, s); $^{13}$C NMR (100 MHz, CDCl$_3$) δ 53.3 (CH$_2$), 55.4 (CH$_3$), 55.5 (CH$_3$), 56.3 (CH$_3$), 56.6 (CH$_3$), 61.8 (CH$_2$), 74.7 (CH), 110.5 (CH), 113.8 (2×CH), 124.4 (CH), 127.6 (C), 129.2 (CH), 130.4 2×CH), 135.4 (C), 137.7 (C), 151.0 (C) and 159.0 (C). HRMS (ES) calcd. for C$_{19}$H$_{25}$N$_2$O$_6$S (MH$^+$), 409.1428 found 409.1418. HPLC: tr=1.11 (98.7%) CH$_3$CN/H$_2$O 90/10.

4,7-Dimethoxy-6-O-sulfamoyl-2-(3.4.5-trimethoxybenzyl)-1,2,3,4-tetrahydroisoquinoline F42

110 mg (47%), yellow powder, m.p. 125-126° C., $^1$H NMR (400 MHz, CDCl$_3$) δ 2.64 (1H, dd, J=11.8 and 3.6 Hz), 2.92 (1H, dd, J=11.8 and 4.5 Hz), 3.35 (3H, s), 3.47 (1H, d, J=14.9 Hz), 3.51 (1H, d, J=13.2 Hz), 3.73 (1H, d, J=14.9 Hz), 3.76 (3H, s), 3.83 (3H, s), 3.81-3.83 (10H, m), 4.27 (1H, dd, J=4.4 and 3.6 Hz), 5.50 (2H, br), 6.61 (1H, s), 6.63 (2H, s), 7.31 (1H, s); $^{13}$C NMR (100 MHz, CDCl$_3$) δ 53.1 (CH$_2$), 55.9 (CH$_2$), 56.2 (2×CH$_3$), 56.3 (CH$_2$), 56.7 (CH$_3$), 60.9 (CH$_3$), 62.5 (CH$_2$), 74.9 (CH), 105.7 (2×CH), 110.5 (CH), 124.3 (CH), 127.3 (C), 133.4 (C), 135.4 (C), 137.1 (C), 137.7 (C), 151.1 (C), and 153.3 (2×C). HRMS (ES) calcd. for C$_{21}$H$_{29}$N$_2$O$_8$S (MH$^+$), 469.1639 found 469.1625. HPLC: tr=1.04 (98.3%) CH$_3$CN/H$_2$O 90/10.

4-Ethoxy-7-methoxy-2-(2-methoxybenzyl)-6-O-sulfamoyl-1,2,3,4-tetrahydroisoquinoline F42

150 mg (71%), yellow powder, m.p. 68-70° C., $^1$H NMR (270 MHz, CDCl$_3$) δ 1.21 (3H, t, J=7.3 Hz), 2.77-2.91 (2H, m), 3.53-3.63 (3H, m), 3.71 (1H, d, J=15.1 Hz), 3.76 (2H, s), 3.78 (3H, s), 3.83 (3H, s), 4.41 (1H, t, J=4.7 Hz), 5.22 (2H, br), 6.60 (1H, s), 6.88 (1H, d, J=8.3 Hz), 6.94 (1H, d, J=7.4 Hz), 7.21-7.28 (1H, m), 7.34 (1H, s), 7.43 (1H, dd, J=7.4 and 1.2 Hz); $^{13}$C NMR (100 MHz, CDCl$_3$) δ 15.6 (CH$_3$), 54.3 (CH$_2$), 55.4 (CH$_2$), 55.6 (CH$_2$), 56.2 (CH$_3$), 56.3 (CH$_3$), 64.5 (CH$_2$), 73.44 (CH), 110.3 (CH), 110.4 (CH), 120.4 (CH), 124.1 (CH), 125.4 (C), 128.1 (C), 128.3 (CH), 130.4 (CH), 135.5 (C), 137.7 (C), 150.7 (C) and 157.8 (C). HRMS (ES) calcd. for C$_{20}$H$_{27}$N$_2$O$_6$S (MH$^+$), 423.1584 found 423.1564. HPLC: tr=1.07 (95.5%) CH$_3$CN/H$_2$O 90/10.

4-Ethoxy-7-methoxy-2-(3-methoxybenzyl)-6-O-sulfamoyl-1,2,3,4-tetrahydroisoquinoline F43

150 mg (72%), yellow powder, m.p. 47-48° C., $^1$H NMR (270 MHz, CDCl$_3$) δ 1.21 (3H, t, J=6.9 Hz), 2.80 (1H, d, J=4.8 Hz), 3.47-3.76 (6H, m), 3.79 (6H, s), 4.42 (1H, t, J=4.8 Hz), 5.24 (2H, br), 6.60 (1H, s), 6.81 (1H, dd, J=8.0 and 2.5 Hz), 6.95-6.97 (2H, m), 7.24 (1H, t, J=8.0 Hz), 7.36 (1H, s); $^{13}$C NMR (100 MHz, CDCl$_3$) δ 15.6 (CH$_3$), 54.2 (CH$_2$), 55.2 (CH$_3$), 55.7 (CH$_2$), 56.2 (CH$_3$), 62.3 (CH$_2$), 64.5 (CH$_2$), 73.3 (CH), 110.3 (CH), 114.3 (CH), 121.3 (CH), 124.1 (CH), 128.2 (C), 129.3 (CH), 135.4 (C), 137.6 (C), 139.2 (C), 150.7 (C), and 159.7 (C). HRMS (ES) calcd. for C$_{20}$H$_{27}$N$_2$O$_4$S (MH$^+$), 423.1584 found 423.1576; HPLC: tr=1.74 (98.2%) CH$_3$CN/H$_2$O 90/10.

4-Ethoxy-7-methoxy-2-(4-methoxybenzyl)-6-O-sulfamoyl-1,2,3,4-tetrahydroiso-quinoline F44

160 mg (77%), yellow powder, m.p. 128-130° C., $^1$H NMR (270 MHz, CDCl$_3$) δ 1.21 (3H, t, J=7.2 Hz), 2.80 (2H, d, J=4.8 Hz), 3.47-3.76 (6H, m), 3.79 (6H, s), 3.80 (3H, s), 3.81 (3H, s), 4.41 (1H, t, J=4.8 Hz), 5.40 (2H, br), 6.60 (1H, s), 6.86 (2H, d, =8.0 Hz), 7.24 (2H, d, J=8.0 Hz), 7.36 (1H, s); HRMS (ES) calcd. for C$_{20}$H$_{27}$N$_2$O$_4$S (MH$^+$), 423.1584 found 423.1579. HPLC: tr=1.34 (100%) CH$_3$CN/H$_2$O 90/10.

4-Ethoxy-7-methoxy-2-(3,4,5-trimethoxybenzyl)-6-O-sulfamoyl-1,2,3,4-tetrahydroisoquinoline F45

180 mg (75%), yellow powder, m.p. 77-79° C., $^1$H NMR (270 MHz, CDCl$_3$/CD$_3$OD 5:1) δ 1.10 (3H, t, J=7.1 Hz), 2.68 (1H, d, J=4.7 Hz), 3.34-3.65 (8H, m), 3.69 (3H, s), 3.70 (3H, s), 3.72 (3H, s), 4.32 (1H, t, J=4.7 Hz), 6.51 (2H, s), 6.53 (1H, s), 7.25 (1H, s); $^{13}$C NMR (100 MHz, CDCl$_3$/CD$_3$OD 5:1) δ 15.1 (CH$_3$), 53.9 (CH$_2$), 55.5 (CH$_2$), 55.8 (3×CH$_3$), 60.6 (CH$_3$), 62.3 (CH$_2$), 64.5 (CH$_2$), 73.3 (CH), 105.5 (2×CH), 109.9 (CH), 123.5 (CH), 126.9 (C), 133.2 (C), 134.7 (C), 136.6 (C), 137.6 (C), 151.1 (C) and 152.9 (2×C). HRMS (ES) calcd. for $C_{22}H_{31}N_2O_8S$ (MH$^+$), 483.1796 found 483.1793. HPLC: tr=1.59 (100%) $CH_3CN/H_2O$ 90/10.

4-O-Acetyl-7-methoxy-2-(3-methoxy-benzyl)-6-sulfamoyloxy-1,2,3,4-tetrahydroisoquinoline F46

170 mg (79%), yellow powder, m.p. 65-66° C., $^1$H NMR (270 MHz, CDCl$_3$) δ 2.08 (3H, s), 2.73 (1H, dd, J=12.4 and 3.9 Hz), 2.95 (1H, dd, J=12.4 and 3.9 Hz), 3.45 (1H, d, J=15.4 Hz), 3.60 (1H, d, J=13.2 Hz), 3.75-3.83 (8H, m), 5.15 (2H, br), 5.86 (1H, t, J=3.9 Hz), 6.66 (1H, s), 6.81 (1H, dd, J=8.2 and 2.5 Hz), 6.93-6.95 (2H, m), 7.23 (1H, t, J=8.2 Hz), 7.29 (1H, s); $^{13}$C NMR (100 MHz, CDCl$_3$) δ 21.3 (CH$_3$), 54.7 (CH$_2$), 55.2 (CH$_3$), 55.3 (CH$_2$), 56.3 (CH$_3$), 61.9 (CH$_2$), 68.0 (CH), 110.6 (CH), 112.6 (CH), 114.6 (CH), 121.2 (CH), 124.7 (CH), 125.3 (C), 129.3 (CH), 136.4 (C), 137.7 (C), 139.0 (C), 151.3 (C), 159.7 (C), and 171.0 (CO). HRMS (ES) calcd. for $C_{20}H_{25}N_2O_7S$ (MH$^+$), 437.1377 found 437.1364. HPLC: tr=1.60 (100%) $CH_3CN/H_2O$ 90/10.

4,6-Diacetoxy-7-methoxy-2-(3-methoxy-benzyl)-1,2,3,4-tetrahydro-isoquinolin-4-yl ester F47

A solution of 7-Methoxy-2-(3-methoxy-benzyl)-1,2,3,4-tetrahydroisoquinoline-4,6-diol (158 mg, 0.5 mmol) in DCM (20 mL) and TEA (0.42 mL, 3 mmol) was cooled to 0° C. before Ac$_2$O (0.19 mL, 2 mmol) was added dropwise. The mixture was stirred at 0° C. for 2 hours then rt for 1 hour. After addition of water (50 mL), the organics were extracted with DCM and the organic layer washed with a solution of. NaHCO$_3$, water, brine, dried (MgSO$_4$), filtered and concentrated. The crude solid (0.22 g) was purified by flash chromatography to give 135 mg of a white powder (68%), m.p. 112-114° C., $^1$H NMR (270 MHz, CDCl$_3$) δ 2.07 (3H, s), 2.28 (3H, s), 2.71 (1H, dd, J=12.4 and 3.6 Hz), 2.97 (1H, dd, J=12.4 and 3.6 Hz), 3.44 (1H, d, J=14.9 Hz), 3.60 (1H, d, J=13.2 Hz), 3.76-3.83 (8H, m), 5.88 (1H, t, J=3.6 Hz), 6.61 (1H, s), 6.80 (1H, dd, J=8.3 and 2.5 Hz), 6.94-6.96 (2H, m), 7.01 (1H, s), 7.23(1H, t, J=8.0 Hz); $^{13}$C NMR (100 MHz, CDCl$_3$) δ 20.6 (CH$_3$), 21.3 (CH$_3$), 54.7 (CH$_2$), 55.2 (CH$_3$), 55.5 (CH$_2$), 55.9 (CH$_3$), 61.9 (CH$_2$), 68.5 (CH), 109.8 (CH), 112.7 (CH), 114.5 (CH), 121.2 (CH), 123.4 (CH), 124.6 (C), 129.3 (CH), 135.0 (C), 138.5 (C), 139.2 (C), 151.0 (C), 159.7 (C), 169.0 (CO), and 171.0 (CO). HRMS (ES) calcd. for $C_{22}H_{26}NO_6$ (MH$^+$), 400.1755 found 400.1756. HPLC: tr=1.91 (100%) $CH_3CN/H_2O$ 90/10.

3-Ethyl-benzoic acid W1

Magnesium turnings (829 mg, 34.1 mmol) were placed in an oven-dried 50 mL RBF and heated three times under high vacuum, then filled with nitrogen. The flask was sealed with a rubber septum and a pressure release system. Anhydrous THF (6.0 mL) and 1-bromo-3-ethylbenzene (297 mg, 1.6 mmol) were added. The reaction mixture was heated to 50-60° C. for 5 min. 1-Bromo-3-ethylbenzene (5.812 g, 31.4 mmol) was dissolved in anhydrous THF (12.0 mL) and added drop-wise via syringe maintaining 50-60° C. The reaction mixture was stirred for 2 h cooling to room temperature. The septum was replaced by a balloon with carbon dioxide and stirred for 16 h at room temperature. The reaction was quenched with a few grams of dry ice, acidified with hydrochloric acid (2M, 50 mL) and extracted with diethylether (2×100 mL). The combined organic layers were washed with a solution of sodium hydroxide (1M, 100 mL). The organic layer was disposed. The aqueous layer was acidified with hydrochloric acid (2M, 100 mL) and extracted with diethylether (2×100 mL). The combined organic of this extraction were dried (MgSO$_4$), filtered and concentrated in vacuo. The title compound was obtained as pale pink crystalline solid (2.698 g, 54%).

$^1$H NMR (270 MHz, CDCl$_3$): δ 1.26 (3H, t, J 7.7, CH$_2$CH$_3$), 2.71 (2H, q, J 7.6, CH$_2$CH$_3$), 7.37 (1H, t, J 7.3, CH), 7.43 (1H, t, J 7.7, CH), 7.89-7.97 (1H, m, CH). $^{13}$C NMR (67.5 MHz, CDCl$_3$): δ 15.5, 28.6, 127.6, 128.5, 129.3, 129.6, 133.5, 144.6, 172.7.

2-(3-Ethylbenzoyl)-3-methyl-6-benzyloxy-7-methoxy-1,2,3,4-tetrahydroisoquinoline W2

3-Methyl-6-benzyloxy-7-methoxy-1,2,3,4-tetrahyoisoquinoline (425 mg, 1.5 mmol) and W1 (339 mg, 2.25 mmol) were placed in an oven-dried tube and dissolved in anhydrous DCM (4.5 mL) and anhydrous THF (1.5 mL). EDCI (578 mg, 3.0 mmol) was added and the reaction mixture was stirred for 20 h at room temperature. The reaction mixture was diluted with hydrochloric acid (1M, 50 mL) and extracted with DCM/ethyl acetate (~9:1, 2×50 mL). The combined organic layers were filtered (MgSO$_4$) and concentrated in vacuo. The residue was purified by flash column chromatography using Flashmaster (SiO$_2$ (20 g, hexane to hexane/EtOAc 70/30). W2 was obtained as colourless sticky foam (534 mg, 85%).
$^1$H NMR (270 MHz, CDCl$_3$) δ 1.14 (3H, s, br, CHCH$_3$), 1.24 (3H, t, J 7.6, ArCH$_2$CH$_3$), 2.28-2.56 (1H, m, br, one of ArCH$_2$CH), 2.67 (2H, q, J 7.5, ArCH$_2$CH$_3$), 3.06 (1H, d, br, J 11.6, one of ArCH$_2$CH), 3.85 (3H, s, OCH$_3$), 4.17-4.54 (2H, m, br, CHCH$_3$, one of ArCH$_2$N), 5.06-5.44 (1H, m, br, one of ArCH$_2$N), 5.11 (2H, s, OCH$_2$Ph), 6.44 (0.30×1H, s, br, CH), 6.63 (1H, s, br, CH), 6.68 (0.70×1H, s, br, CH), 7.16-7.47 (9H, m, OCH$_2$C$_6$H$_5$, 4×CH).

2-(3-Ethylbenzyl)-7-methoxy-3-methyl-6-benzyloxy-1,2,3,4-tetrahydroisoquinoline W3

Lithium aluminium hydride (114 mg, 3.0 mmol) was placed in an oven-dried tube and covered with anhydrous THF (1.0 mL). W2 (250 mg, 0.6 mmol) was dissolved in anhydrous THF (3.0 mL) and added drop-wise via syringe at room temperature. The reaction mixture was stirred for 30 min at room temperature. EtOAc (5 mL) was added carefully. The mixture was then diluted with EtOAc (100 mL) and standing for about 30 min in a beaker. After the salts settled the mixture was poured through a sinter funnel containing a pad of celite. The sinter was washed with EtOAc (4×10 mL) and the filtrate was concentrated in vacuo. W3 was obtained as colourless oil (240 mg, 99%). $^1$H NMR (270 MHz, CDCl$_3$) δ 1.13 (3H, d, J 6.6, CHCH$_3$), 1.23 (3H, t, J 7.6, ArCH$_2$CH$_3$), 2.48 (1H, dd, J 16.1, 5.9, one of ArCH$_2$CH), 2.64 (2H, q, J 7.6, ArCH$_2$CH$_3$), 2.86 (1H, dd, J 16.0, 4.7, one of ArCH$_2$CH), 3.06 (1H, sext, J 6.1, CHCH$_3$), 3.44-3.71 (3H, m, three of 2×ArCH$_2$N), 3.73-3.88 (1H, m, one of ArCH$_2$N), 3.79 (3H, s, OCH$_3$), 5.10 (2H, s, OCH$_2$Ph), 6.47 (1H, s, CH), 6.60 (1H, s, CH), 7.06-7.51 (9H, m, OCH$_2$C$_6$H$_5$, 4×CH). $^{13}$C NMR (67.5 MHz, CDCl$_3$): δ 15.2, 15.6, 28.8, 34.8, 51.4, 52.1, 56.0, 57.1, 71.1, 109.8, 114.4, 125.7, 126.2, 126.4, 126.8, 127.2, 127.7, 128.4, 128.5, 137.3, 139.3, 144.2, 146.6, 147.8.

2-(3-Ethyl-benzyl)-3-methyl-6-hydroxy-7-methoxy-1,2,3,4-tetrahydroisoquinoline W4

Palladium on charcoal (10%, 30.9 mg) was covered with THF (8.0 mL) and ethanol (8.0 mL). W3 (240 mg, 0.6 mmol) was added as solution in THF (16.0 mL). The mixture was heated twice to reflux using a heat gun and stirred under an atmosphere of hydrogen (balloon pressure) for 1 h at room temperature. The reaction mixture was filtered through celite. The celite was washed with methanol (4×5 mL) and the combined filtrates were concentrated in vacuo. The residue was purified by flash column chromatography using Flashmaster (SiO$_2$: 20 g, hexane 100% to hexane/ethyl acetate/methanol 49:50:1). W4 was obtained as pale yellow solid (112 mg, 60%). $^1$H NMR (270 MHz, CDCl$_3$) δ 1.16 (3H, d, J 6.6, CHCH$_3$), 1.24 (3H, t, J 7.6, ArCH$_2$CH$_3$), 2.51 (1H, dd, J 16.1, 6.2, one of ArCH$_2$CH), 2.64 (2H, q, J 7.5, ArCH$_2$CH$_3$), 2.90 (1H, dd, J 16.2, 5.0, one of ArCH$_2$CH), 3.09 (1H, sext, J 6.1, CHCH$_3$), 3.49-3.67 (3H, m, three of 2×ArCH$_2$N), 3.75-3.83 (1H, m, one of ArCH$_2$N), 3.79 (3H, s, OCH$_3$), 6.43 (1H, s, CH), 6.63 (1H, s, br, CH), 7.07-7.14 (1H, m, CH), 7.15-7.29 (3H, m, 3×CH). $^{13}$C NMR (67.5 MHz, CDCl$_3$): δ 15.3, 15.6, 28.8, 34.5, 51.3, 52.2, 55.9, 56.9, 108.6, 114.4, 125.3, 126.3, 126.4, 128.2, 128.5, 139.1, 143.9, 144.3, 144.8. LC/MS (ES$^+$) t$_r$ 2.31 min; m/z 312.4 ((M+H)$^+$, 100%); MeOH/H$_2$O 90:10 (1.0 mL/min), HPLC tr 3.45 min (99.3%); CH$_3$CN/H$_2$O 90:10 (1.0 mL/min).

2-(3-Ethyl-benzyl)-3-methyl-6-O-sulfamoyl-7-methoxy-1,2,3,4-tetrahydroisoquinoline W5

W4 (93.5 mg, 0.3 mmol) was placed in an oven-dried 50 mL RBF and dissolved in anhydrous DMA (0.5 mL). Sulfamoyl chloride (0.45M in toluene, 2.0 mL, 0.9 mmol) was concentrated in vacuo and re-dissolved in anhydrous DMA (1.5 mL). This solution was added drop-wise via syringe at 0° C. The reaction mixture was stirred for 18 h at room temperature. DCM (100 mL) was added and the mixture was washed with Na$_2$CO$_3$ (half-saturated, 100 mL). The organic layer was dried (MgSO$_4$), filtered and concentrated in vacuo. The residue was purified by flash column chromatography using Flashmaster (SiO$_2$: 20 g, hexane 100% to hexane/ethyl acetate 50/50). W5 was obtained as pale yellow solid (66 mg, 56%) after re-crystallisation from diethyl ether. $^1$H NMR (270 MHz, CDCl$_3$) δ 1.07 (3H, d, J 6.6, CHCH$_3$), 1.16 (3H, t, J 7.7, ArCH$_2$CH$_3$), 2.46 (1H, dd, J 16.2, 5.8, one of ArCH$_2$CH), 2.57 (2H, q, J 7.6, ArCH$_2$CH$_3$), 2.86 (1H, dd, J 16.2, 5.0, one of ArCH$_2$CH), 3.01 (1H, sext, J 5.9, CHCH$_3$), 3.41-3.62 (3H, m, three of 2×ArCH$_2$N), 3.66-3.77 (1H, m, one of ArCH$_2$N), 3.71 (3H, s, OCH$_3$), 6.21 (2H, s, br, NH$_2$), 6.49 (1H, s, CH), 7.00 (1H, s, br, CH), 7.00-7.25 (4H, m, 4×CH).
$^{13}$C NMR (67.5 MHz, CDCl$_3$): δ 14.9, 15.5, 27.5, 28.6, 51.1, 51.9, 55.9, 57.0, 110.6, 124.0, 126.0, 126.3, 126.4, 128.1, 128.2, 133.5, 137.3, 144.2, 149.5.
LC/MS (ES$^+$) t$_r$ 1.96 min; m/z 391.4 ((M+H)$^+$, 100%); MeOH/H$_2$O 90:10 (1.0 mL/min), HPLC tr 2.31 min (97.6%); CH$_3$CN/H$_2$O 90:10 (1.0 mL/min).

2-(2-Fluoro-5-methoxy-benzyl)-3-methyl-6-benzyloxy-7-methoxy-1,2,3,4-tetrahydroisoquinoline W6

3-Methyl-6-benzyloxy-7-methoxy-1,2,3,4-tetrahydroisoquinoline (339 mg, 1.2 mmol) was dissolved in anhydrous DMF (3.6 mL), DIPEA (314 mg, 2.4 mmol) and 2-fluoro-5-methoxybenzyl bromide (401 mg, 74 wt %, 1.35 mmol) were added. The mixture was heated to 80° C. for 20 h, cooled to room temperature and poured into water (50 mL) and ammonium chloride (saturated, 2 mL) The mixture was extracted with ethyl acetate (2×50 mL). The combined organic layers were dried (MgSO$_4$), filtered and concentrated in vacuo. The residue was purified by flash column chromatography using Flashmaster (SiO$_2$: 20 g, hexane 100% to hexane/ethyl acetate 60/40). W6 compound was obtained as orange oil (363 mg, 71%). $^1$H NMR (270 MHz, CDCl$_3$) δ 1.14 (3H, d, J 6.3, CHCH$_3$), 2.47 (1H, dd, J 16.2, 6.1, one of ArCH$_2$CH), 2.86 (1H, dd, J 16.2, 5.0, one of ArCH$_2$CH), 3.09 (1H, sext, J 6.1, CHCH$_3$), 3.54-3.68 (3H, m, three of 2×ArCH$_2$N), 3.69-3.81 (1H, m, one of ArCH$_2$N), 3.75 (3H, s, OCH$_3$), 3.80 (3H, s, OCH$_3$), 5.09 (2H, s, OCH$_2$Ph), 6.49 (1H, s, CH), 6.59 (1H, s, CH), 6.72 (1H, dt, J 9.1, 3.7, CH), 6.94 (1H, t, J 9.1, CH), 7.01 (1H, dd, J 5.9, 3.2, CH), 7.23-7.45 (5H, m, OCH$_2$C$_6$H$_5$).
$^{13}$C NMR (67.5 MHz, CDCl$_3$): δ 15.2, 34.8, 49.5 (d, J 1.5), 51.3, 52.4, 55.7, 56.0, 71.0, 109.8, 113.4 (d, J 8.2), 114.4, 115.6 (dd, J 14.2, 9.5), 125.6, 126.5, 126.7, 127.0, 127.2, 127.7, 128.4, 137.3, 146.6, 147.8, 154.0, 155.6 (d, J 2.1).
LC/MS (ES$^+$) t$_r$ 3.67 min; m/z 422.3 ((M+H)$^+$, 100%); MeOH/H$_2$O 90:10 (1.0 mL/min).

2-(2-Chloro-5-methoxy-benzyl)-3-methyl-6-benzyloxy-7-methoxy-1,2,3,4-tetrahydroisoquinoline W7

3-Methyl-6-benzyloxy-7-methoxy-1,2,3,4-tetrahydroisoquinoline (339 mg, 1.2 mmol) was dissolved in anhydrous DMF (3.6 mL), DIPEA (315 mg, 2.4 mmol) and 2-chloro-5-methoxybenzyl bromide (414 mg, 76 wt %, 1.34 mmol) were added. The mixture was heated to 80° C. for 20 h, cooled to room temperature and poured into water (50 mL) and ammonium chloride (saturated, 2 mL). The mixture was extracted with ethyl acetate (2×50 mL). The combined organic layers were dried (MgSO$_4$), filtered and concentrated in vacuo. The residue was purified by flash column chromatography using Flashmaster (SiO$_2$: 20 g, hexane 100% to hexane/ethyl acetate 70/30). W7 was obtained as orange oil (407 mg, 77%). $^1$H NMR (270 MHz, CDCl$_3$) δ 1.13 (3H, d, J 6.6, CHCH$_3$), 2.48 (1H, dd, J 16.0, 5.8, one of ArCH$_2$CH), 2.90 (1H, dd, J 16.0, 5.0, one of ArCH$_2$CH), 3.13 (1H, sext, J 6.0, CHCH$_3$), 3.58-3.84 (4H, m, 2×ArCH$_2$N), 3.77 (3H, s, OCH$_3$), 3.81 (3H, s, OCH$_3$), 5.11 (2H, s, OCH$_2$Ph), 6.50 (1H, s, CH), 6.61 (1H, s, CH), 6.72 (1H, dd, J 8.7, 3.2, CH), 7.14 (1H, d, J 3.0, CH), 7.23 (1H, d, J 8.8, CH), 7.24-7.47 (5H, m, OCH$_2$C$_6$H$_5$).
$^{13}$C NMR (67.5 MHz, CDCl$_3$): δ 15.2, 34.7, 51.2, 52.5, 53.8, 55.5, 56.0, 71.1, 109.8, 113.5, 114.4, 115.7, 125.3, 125.6, 126.7, 127.3, 127.7, 128.5, 129.9, 137.3, 138.1, 146.7, 147.8, 158.3. LC/MS (ES$^+$) t$_r$ 5.29 min; m/z 438.4 ((M+H)$^+$, 100%); MeOH/H$_2$O 90:10 (1.0 mL/min).

2-(2,5-Dimethoxy-benzyl)-3-methyl-6-benzyloxy-7-methoxy-1,2,3,4-tetrahydroisoquinoline W8

3-Methyl-6-benzyloxy-7-methoxy-1,2,3,4-tetrahydroisoquinoline (338 mg, 1.2 mmol) was dissolved in anhydrous DMF (3.6 mL), DIPEA (314 mg, 2.4 mmol) and 2,5-dimethoxybenzyl chloride (279 mg, 1.5 mmol) were added. The mixture was heated to 80° C. for 20 h, cooled to room temperature and poured into water (50 mL) and ammonium chloride (saturated, 2 mL). The mixture was extracted with ethyl acetate (2×50 mL). The combined organic layers were dried (MgSO$_4$), filtered and concentrated in vacuo. The residue was purified by flash column chromatography using Flashmaster (SiO$_2$: 20 g, hexane 100% to hexane/ethyl acetate 50/50). W8 was obtained as sticky orange oil (395 mg, 76%). $^1$H NMR (270 MHz, CDCl$_3$) δ 1.14 (3H, d, J 6.3, CHCH$_3$), 2.48 (1H, dd, J 16.3, 6.0, one of ArCH$_2$CH), 2.86 (1H, dd, J 16.1, 4.8, one of ArCH$_2$CH), 3.11 (1H, sext, J 6.1, CHCH$_3$), 3.58-3.77 (4H, m, 2×ArCH$_2$N), 3.76 (3H, s, OCH$_3$), 3.77 (3H, s, OCH$_3$), 3.81 (3H, s, OCH$_3$), 5.11 (2H, s, OCH$_2$Ph), 6.50 (1H, s, CH), 6.61 (1H, s, CH), 6.74 (1H, dd, J 8.8, 3.0, CH), 6.80 (1H, d, J 8.8, CH), 7.07 (1H, d, J 2.8, CH), 7.24-7.47 (5H, m, OCH$_2$C$_6$H$_5$). $^{13}$C NMR (67.5 MHz, CDCl₃): δ 15.5, 34.5, 50.0, 51.4, 52.4, 55.7, 56.0, 56.0, 71.0, 109.9, 111.3, 111.9, 114.4, 116.0, 125.8, 127.0, 127.2, 127.7, 128.4, 128.9, 137.3, 146.5, 147.7, 151.9, 153.6.

2-(2-Fluoro-5-methoxy-benzyl)-3-methyl-6-hydroxy-7-methoxy-1,2,3,4-tetrahydroisoquinoline W9

Palladium on charcoal (10%, 30.4 mg) was covered with THF (8.0 mL) and ethanol (8.0 mL). W6 (337 mg, 0.8 mmol) was added as solution in THF (16.0 mL). The mixture was heated twice to reflux using a heat gun and stirred under an atmosphere of hydrogen (balloon pressure) for 2 h at room temperature. The reaction mixture was filtered through celite. The celite was washed with ethyl acetate (5×20 mL) and methanol (5×20 mL) and the combined filtrates were concentrated in vacuo. The residue was purified by flash column chromatography (SiO₂: 20 g, chloroform/acetone 95:5 to 90:10). W9 was obtained as pale yellow solid (221 mg, 83%). A small sample (22 mg) was further purified by preparative HPLC (RP18, acetonitrile/water 90:10). ¹H NMR (270 MHz, CDCl₃) δ 1.13 (3H, d, J 6.3, CHCH₃), 2.49 (1H, dd, J 16.1, 5.9, one of ArCH₂CH), 2.88 (1H, dd, J 16.1, 4.8, one of ArCH₂CH), 3.09 (1H, sext, J 6.1, CHCH₃), 3.52-3.66 (3H, m, three of 2×ArCH₂N), 3.67-3.81 (1H, m, one of ArCH₂N), 3.75 (3H, s, OCH₃), 3.79 (3H, s, OCH₃), 6.44 (1H, s, CH), 6.62 (1H, s, CH), 6.72 (1H, dt, J 8.8, 3.6, CH), 6.93 (1H, t, J 9.1, CH), 7.01 (1H, dd, J 5.6, 3.3, CH). LC/MS (ES⁺) t, 2.00 min; m/z 332.4 ((M+H)⁺, 100%); MeOH/H₂O 90:10 (1.0 mL/min).

2-(2-Chloro-5-methoxy-benzyl)-3-methyl-6-hydroxy-7-methoxy-1,2,3,4-tetrahydroisoquinoline W10

Palladium on charcoal (10%, 30.6 mg) was covered with THF (8.0 mL) and ethanol (8.0 mL). W7 (350 mg, 0.8 mmol) was added as solution in THF (16.0 mL). The mixture was heated twice to reflux using a heat gun and stirred under an atmosphere of hydrogen (balloon pressure) for 2 h at room temperature. The reaction mixture was filtered through celite. The celite was washed with ethyl acetate (5×20 mL) and methanol (5×20 mL) and the combined filtrates were concentrated in vacuo. The residue was purified by flash column chromatography using Flashmaster (SiO₂: 20 g, hexane 100% to hexane/ethyl acetate/methanol 69:30:1). W10 was obtained as pale yellow solid (150 mg, 54%). ¹H NMR (270 MHz, CDCl₃) δ 1.14 (3H, d, J 6.3, CHCH₃), 2.50 (1H, dd, J 16.0, 5.8, one of ArCH₂CH), 2.92 (1H, dd, J 16.2, 5.0, one of ArCH₂CH), 3.14 (1H, sext, J 6.1, CHCH₃), 3.57-3.84 (4H, m, 2×ArCH₂N), 3.77 (3H, s, OCH₃), 3.80 (3H, s, OCH₃), 5.11 (1H, s, br, OH), 6.45 (1H, s, CH), 6.64 (1H, s, CH), 6.73 (1H, dd, J 8.8, 3.0, CH), 7.16 (1H, d, J 3.1, CH), 7.23 (1H, d, J 8.5, CH).
¹³C NMR (67.5 MHz, CDCl₃): δ 15.2, 34.5, 51.3, 52.6, 53.7, 55.5, 55.9, 108.6, 113.5, 114.5, 115.6, 125.3, 125.4, 126.4, 129.8, 138.1, 143.9, 144.8, 158.3. LC/MS (ES⁺) t, 2.41 min; m/z 348.4 ((M+H)⁺, 100%); MeOH/H₂O 90:10 (1.0 mL/min), HPLC tr 2.76 min (99.2%); CH₃CN/H₂O 90:10 (1.0 mL/min).

2-(2,5-Dimethoxy-benzyl)-3-methyl-6-hydroxy-7-methoxy-1,2,3,4-tetrahydroisoquinoline W11

Palladium on charcoal (10%, 30.9 mg) was covered with THF (8.0 mL) and ethanol (8.0 mL). W8 (346 mg, 0.8 mmol) was added as solution in THF (16.0 mL). The mixture was heated twice to reflux using a heat gun and stirred under an atmosphere of hydrogen (balloon pressure) for 2 h at room temperature. The reaction mixture was filtered through celite. The celite was washed with ethyl acetate (5×20 mL) and methanol (5×20 mL) and the combined filtrates were concentrated in vacuo. The residue was purified by flash column chromatography using Flashmaster (SiO₂: 20 g, ethyl acetate/methanol 99:1). W11 was obtained as pale yellow solid (230 mg, 83%). A small sample (24 mg) was further purified by preparative HPLC (RP18, acetonitrile/water 90:10). ¹H NMR (270 MHz, CDCl₃) δ 1.14 (3H, d, J 6.3, CHCH₃), 2.49 (1H, dd, J 16.1, 6.2, one of ArCH₂CH), 2.87 (1H, dd, J 16.1, 4.8, one of ArCH₂CH), 3.11 (1H, sext, J 6.2, CHCH₃), 3.56-3.71 (4H, m, 2×ArCH₂N), 3.74 (3H, s, OCH₃), 3.76 (3H, s, OCH₃), 3.78 (3H, s, OCH₃), 5.56 (1H, s, br, OH), 6.44 (1H, s, CH), 6.61 (1H, s, CH), 6.73 (1H, dd, J 8.8, 2.7, CH), 6.79 (1H, d, J 8.8, CH), 7.07 (1H, d, J 2.8, CH). ¹³C NMR (67.5 MHz, CDCl₃): δ 15.5, 34.3, 50.0, 51.5, 52.5, 55.7, 55.9, 56.0, 108.7, 111.4, 112.0, 114.5, 116.0, 125.6, 126.6, 128.9, 143.8, 144.8, 152.0, 153.6. LC/MS (ES⁺) t, 1.72 min; m/z 344.5 ((M+H)⁺, 100%); MeOH/H₂O 90:10 (1.0 mL/min).

2-(2-Fluoro-5-methoxy-benzyl)-3-methyl-6-O-sulfamoyl-7-methoxy-1,2,3,4-tetrahydroisoquinoline W12

W9 (199 mg, 0.6 mmol) was placed in an oven-dried 50 mL RBF and dissolved in anhydrous DMA (2.0 mL). Sulfamoyl chloride (0.45M in toluene, 6.7 mL, 3.0 mmol) was concentrated in vacuo and re-dissolved in anhydrous DMA (3.0 mL). This solution was added drop-wise via syringe at 0° C. The reaction mixture was stirred for 2 h at room temperature. DCM (100 mL) was added and the mixture was washed with Na₂CO₃ (half-saturated, 100 mL). The organic layer was dried (MgSO₄), filtered and concentrated in vacuo. The residue was purified by flash column chromatography using Flashmaster (SiO₂: 20 g, hexane 100% to hexane/ethyl acetate 50/50). W12 compound was obtained as white solid (43 mg, 17%) after re-crystallisation from diethyl ether. ¹H NMR (270 MHz, CDCl₃) δ 1.16 (3H, d, J 6.3, CHCH₃), 2.54 (1H, dd, J 16.1, 5.4, one of ArCH₂CH), 2.94 (1H, dd, J 16.2, 4.4, one of ArCH₂CH), 3.12 (1H, sext, J 5.9, CHCH₃), 3.56-3.83 (4H, m, 2×ArCH₂N), 3.77 (3H, s, OCH₃), 3.80 (3H, s, OCH₃), 6.49 (2H, s, br, NH₂), 6.60 (1H, s, CH), 6.74 (1H, dt, J 8.8, 3.7, CH), 6.95 (1H, t, J 9.4, CH), 6.96-7.04 (1H, m, CH), 7.08 (1H, s, CH). LC/MS (ES⁺) t, 1.72 min; m/z 411.4 ((M+H)⁺, 100%); MeOH/H₂O 90:10 (1.0 mL/min), HPLC tr 1.79 min (97.1%); CH₃CN/H₂O 90:10 (1.0 mL/min).

2-(2-Chloro-5-methoxy-benzyl)-3-methyl-6-O-sulfamoyl-7-methoxy-1,2,3,4-tetrahydroisoquinoline W13

W10 (105 mg, 0.3 mmol) was placed in an oven-dried 50 mL RBF and dissolved in anhydrous DMA (0.5 mL). Sulfamoyl chloride (0.45M in toluene, 3.3 mL, 1.5 mmol) was concentrated in vacuo and re-dissolved in anhydrous DMA (1.5 mL). This solution was added drop-wise via syringe at 0° C. The reaction mixture was stirred for 18 h at room temperature. DCM (100 mL) was added and the mixture was washed with Na₂CO₃ (half-saturated, 100 mL). The organic layer was dried (MgSO₄), filtered and concentrated in vacuo. The residue was purified by flash column chromatography using (SiO₂: 20 g, chloroform/acetone 95:5 to 90:10). W13 was obtained as yellow glass (61 mg, 47%). ¹H NMR (270 MHz, CDCl₃) δ 1.15 (3H, d, J 6.6, CHCH₃), 2.55 (1H, dd, J 16.3, 5.5, one of ArCH₂CH), 2.97 (1H, dd, J 16.1, 4.8, one of ArCH₂CH), 3.16 (1H, sext, J 6.0, CHCH₃), 3.60-3.74 (3H, m, three of 2×ArCH$_2$N), 3.75-3.85 (1H, m, one of 2×ArCH$_2$N), 3.79 (3H, s, OCH$_3$), 3.81 (3H, s, OCH$_3$), 6.15 (1H, s, br, NH$_2$), 6.60 (1H, s, CH), 6.74 (1H, dd, J 8.7, 3.2, CH), 7.09 (1H, s, CH), 7.12 (1H, d, J 3.4, CH), 7.25 (1H, d, J 8.8, CH). $^{13}$C NMR (67.5 MHz, CDCl$_3$): δ 15.0, 34.3, 51.1, 52.3, 53.9, 55.4, 56.0, 87.5, 110.7, 113.4, 115.8, 124.2, 126.5, 129.9, 133.7, 137.4, 137.7, 149.5, 158.3.

2-(2,5-Dimethoxy-benzyl)-3-methyl-6-O-sulfamoyl-7-methoxy-1,2,3,4-tetrahydroisoquinoline W14

W11 (206 mg, 0.6 mmol) was placed in an oven-dried 50 mL RBF and dissolved in anhydrous DMA (1.0 mL). Sulfamoyl chloride (0.45M in toluene, 6.7 mL, 2.5 mmol) was concentrated in vacuo and re-dissolved in anhydrous DMA (2.0 mL). This solution was added drop-wise via syringe at 0° C. The reaction mixture was stirred for 18 h at room temperature. DCM (100 mL) was added and the mixture was washed with Na$_2$CO$_3$ (half-saturated, 100 mL). The organic layer was dried (MgSO$_4$), filtered and concentrated in vacuo. The residue was purified by flash column chromatography using Flashmaster (SiO$_2$: 20 g, hexane 100% to hexane/ethyl acetate 30/70 and flash column chromatography (SiO$_2$: 20 g, chloroform/acetone 80:20 to 75:25). The product was recrystallised from diisopropylether and washed with diethylether (~20×1 mL). W14 was obtained as white solid (33 mg, 12%) containing still diisopropylether (5.1 wt % by $^1$H NMR). $^1$H NMR (270 MHz, CDCl$_3$) δ 1.12 (3H, d, J 6.3, CHCH$_3$), 2.51 (1H, dd, J 16.0, 6.1, one of ArCH$_2$CH), 2.90 (1H, dd, J 16.2, 4.7, one of ArCH$_2$CH), 3.11 (1H, sext, J 6.0, CHCH$_3$), 3.54-3.71 (4H, m, 2×ArCH$_2$N), 3.73 (3H, s, OCH$_3$), 3.75 (3H, s, OCH$_3$), 3.77 (3H, s, OCH$_3$), 5.82 (2H, s, br, NH$_2$), 6.56 (1H, s, CH), 6.71 (1H, dd, J 8.8, 3.0, CH), 6.77 (1H, d, J 8.8, CH), 7.01 (1H, d, J 2.8, CH), 7.04 (1H, s, CH). $^{13}$C NMR (67.5 MHz, CDCl$_3$): δ 15.0, 33.9, 49.8, 51.1, 52.0, 55.3, 55.7, 110.4, 111.2, 111.5, 115.7, 123.8, 126.2, 128.4, 133.6, 137.1, 149.4, 151.6, 153.3. LC/MS (ES$^+$) t$_r$ 1.96 min; m/z 423.3 ((M+H)$^+$, 100%); MeOH/H$_2$O 90:10 (1.0 mL/min), HPLC tr 2.46 min (99.3%); CH$_3$CN/H$_2$O 90:10 (1.0 mL/min).

4-Ethoxy-3,5-dimethoxy-benzoic acid ethyl ester W15

Syringic acid (3.962 g, 20.0 mmol) and potassium carbonate (11.058 g, 80.0 mmol) were placed in a 500 mL RBF and covered with anhydrous DMF (30 mL). Iodoethane (6.898 g, 44.2 mmol) was added drop-wise and the reaction mixture stirred at room temperature for 18 h. The reaction mixture was diluted with water (400 mL) and extracted with DCM/ethyl acetate (~9:1; 2×200 mL). The combined organics were dried (MgSO$_4$), filtered and concentrated in vacuo to give W15 as brown oil which solidified upon standing overnight (3.185 g; 62%). $^1$H NMR (270 MHz, CDCl$_3$): δ 1.34 (3H, t, J 7.2, OCH$_2$CH$_3$), 1.37 (3H, t, J 7.0, OCH$_2$CH$_3$), 3.87 (6H, s, 2×OCH$_3$), 4.09 (2H, q, J 7.1, OCH$_2$CH$_3$), 4.35 (2H, q, J 7.1, OCH$_2$CH$_3$), 7.27 (2H, s, 2×CH). $^{13}$C NMR (67.5 MHz, CDCl$_3$): δ 14.4, 15.5, 56.2, 61.1, 69.0, 106.6, 125.3, 140.9, 153.2, 166.3.

4-Ethoxy-3,5-dimethoxy-benzoic acid W16

W15 (3.177 g, 12.5 mmol) was dissolved in methanol (37.5 mL) and sodium hydroxide (2.021 g, 50.5 mmol) was added as solution in water (12.5 mL). The reaction mixture was heated for 2 h at 60° C. The reaction mixture was concentrated in vacuo, diluted with hydrochloric acid (2M, 100 mL) and extracted with ethyl acetate (2×100 mL). The combined organics were dried (MgSO$_4$), filtered and concentrated in vacuo to give W16 as beige solid (2.744 g; 97%). $^1$H NMR (270 MHz, CDCl$_3$): δ 1.31 (3H, dt, J 7.0, 1.4, OCH$_2$CH$_3$), 3.84 (6H, d, J 1.4, 2×OCH$_3$), 4.07 (2H, dq, J 7.0, OCH$_2$CH$_3$), 7.29 (2H, d, J 1.6, 2×CH), 10.04 (1H, s, br, CO$_2$H). $^{13}$C NMR (67.5 MHz, CDCl$_3$): δ 15.4, 56.1, 68.9, 106.8, 125.2, 140.9, 153.1, 169.1.

2-(4-Ethoxy-3,5-dimethoxybenzoyl)-3-ethyl-6-benzyloxy-7-methoxy-1,2,3,4-tetrahydroisoquinoline W17

3-Methyl-6-benzyloxy-7-methoxy-1,2,3,4-tetrahydroisoquinoline (356 mg, 1.2 mmol) and W16 (406 mg, 1.8 mmol) were placed in an oven-dried tube and dissolved in anhydrous DCM (4.5 mL) and anhydrous THF (1.5 mL). EDCI (460 mg, 2.4 mmol) was added and the reaction mixture was stirred for 22 h at room temperature. The reaction mixture was diluted with DCM (50 mL), washed with hydrochloric acid (1M, 20 mL) and brine (20 mL). The combined organics were filtered (MgSO$_4$) and concentrated in vacuo. The residue was purified by flash column chromatography using Flashmaster (SiO$_2$ (20 g), hexane to hexane/ethyl acetate 60/40). W17 was obtained as colourless glass (534 mg, 88%). $^1$H NMR (270 MHz, CDCl$_3$): δ 0.80 (0.67×3H, t, J 10.7, CHCH$_2$CH$_3$), 1.01 (0.33×3H, s, br, CHCH$_2$CH$_3$), 1.34 (3H, t, J 7.0, OCH$_2$CH$_3$), 1.44-1.78 (2H, m, CHCH$_2$CH$_3$), 2.36-2.62 (1H, m, one of ArCH$_2$CH), 3.04 (1H, dd, 15.4, 4.4, one of ArCH$_2$CH), 3.77 (0.40×3H, s, br, OCH$_3$), 3.82 (6H, s, 2×OCH$_3$), 3.85 (0.60× 3H, s, br, OCH$_3$), 3.97-4.11 (1H, m, CHCH$_2$CH$_3$), 4.05 (2H, q, J 10.5, OCH$_2$CH$_3$), 4.15 (0.35×1H, s, br, one of ArCH$_2$N), 4.39 (0.60×1H, dd, J 57.8, 15.1, one of ArCH$_2$N), 4.97 (0.40× 1H, s, br, one of ArCH$_2$N), 5.09 (2H, s, OCH$_2$Ph), 5.29 (0.65×1H, d, J 17.3, one of ArCH$_2$N), 6.41 (0.30×1H, s, br, CH), 6.60 (3H, s, 3×CH), 6.66 (0.70×1H, s, CH), 7.23-7.45 (5H, m, OCH$_2$C$_6$H$_5$).

2-(4-Ethoxy-3,5-dimethoxy-benzyl)-3-ethyl-6-benzyloxy-7-methoxy-1,2,3,4-tetrahydroisoquinoline W18

Lithium aluminium hydride (113 mg, 3.0 mmol) was placed in an oven-dried tube and covered with anhydrous THF (2.0 mL). W17 (505 mg, 1.0 mmol) was dissolved in anhydrous THF (6.0 mL) and added dropwise via syringe at room temperature. The reaction mixture was stirred for 4 h at room temperature. Ethyl acetate (5 mL) was added carefully. The mixture was then diluted with ethyl acetate (100 mL) and standing for about 30 min in a beaker. After the salts settled the mixture was poured through a sinter funnel containing a pad of celite. The sinter was washed with ethyl acetate (4×10 mL) and the filtrate was concentrated in vacuo. W18 was obtained as colourless sticky oil (463 mg, 94%). $^1$H NMR (270 MHz, CDCl$_3$): δ 0.97 (3H, t, J 7.3, CH$_2$CH$_3$), 1.34 (3H, t, J 7.0, CH$_2$CH$_3$), 1.38-1.54 (1H, m, one of CHCH$_2$CH$_3$), 1.66 (1H, sext, J 6.7, one of CHCH$_2$CH$_3$), 2.48 (1H, dd, J 16.2, 6.1, one of ArCH$_2$CH), 2.78 (1H, dd, J 16.4, 4.8, one of ArCH$_2$CH), 2.82-2.94 (1H, m, ArCH$_2$CH), 3.52-3.74 (4H, m, 2×ArCH$_2$N), 3.80 (3H, s, OCH$_3$), 3.81 (6H, s, 2×OCH$_3$), 4.03 (2H, q, J 7.0, OCH$_2$CH$_3$), 5.10 (2H, s, OCH$_2$Ph), 6.49 (1H, s, CH), 6.58 (2H, s, 2×CH), 6.62 (1H, s, CH), 7.22-7.46 (5H, m, OCH$_2$C$_6$H$_5$).

2-(4-Ethoxy-3,5-dimethoxy-benzyl)-3-ethyl-6-hydroxy-7-methoxy-1,2,3,4-tetrahydroisoquinoline W19

Palladium on charcoal (29.3 mg) was placed in a 50 mL RBF and covered with THF (2.0 mL) and ethanol (2.0 mL).

The flask was closed with a balloon containing hydrogen. The mixture was stirred for 30 min. Then W18 (443 mg, 0.9 mmol) was dissolved in THF (6.0 mL) and added drop-wise via syringe. The reaction mixture was stirred for 6 h at room temperature, filtered through a sinter funnel containing a pad of celite. The sinter was washed with ethyl acetate (4×5 mL) and methanol (4×5 mL). The residue was purified by flash column chromatography using Flashmaster (SiO$_2$: 20 g, hexane to hexane/ethyl acetate/methanol 49/50/1). W19 was obtained as pale yellow solid (236 mg, 65%). $^1$H NMR (270 MHz, CDCl$_3$): δ 0.97 (3H, t, J 7.3, CH$_2$CH$_3$), 1.34 (3H, t, J 7.0, CH$_2$CH$_3$), 1.35-1.50 (1H, m, one of CHCH$_2$CH$_3$), 1.57-1.76 (1H, m, one of CHCH$_2$CH$_3$), 2.50 (1H, dd, J 16.1, 5.9, one of ArCH$_2$CH), 2.79 (1H, dd, J 16.4, 5.1, one of ArCH$_2$CH), 2.83-2.94 (1H, m, ArCH$_2$CH), 3.51-3.72 (4H, m, 2×ArCH$_2$N), 3.79 (3H, s, OCH$_3$), 3.80 (6H, s, 2×OCH$_3$), 4.02 (2H, q, J 7.1, OCH$_2$CH$_3$), 6.44 (1H, s, CH), 6.58 (2H, s, 2×CH), 6.64 (1H, s, CH).

2-(4-Ethoxy-3,5-dimethoxy-benzyl)-3-ethyl-6-O-sulfamoyl-7-methoxy-1,2,3,4-tetrahydroisoquinoline W20

W19 (200 mg, 0.5 mmol) was placed in an oven-dried 50 mL RBF and dissolved in anhydrous DMA (0.5 mL). Sulfamoyl chloride (0.65M in toluene, 3.8 mL, 2.5 mmol) was concentrated in vacuo and re-dissolved in anhydrous DMA (1.5 mL). This solution was added dropwise via syringe at 0° C. The reaction mixture was stirred for 18 h at room temperature. DCM (50 mL) was added and the mixture was washed with Na$_2$CO$_3$ (half-saturated, 50 mL). The residue was purified by flash column chromatography using Flashmaster (SiO$_2$: 20 g, hexane to hexane/ethyl acetate 70/30). W20 was obtained as pale yellow fluffy solid (177 mg, 73%) after re-dissolving in diethyl ether/DCM (~9:1, ~10 mL) and removing the solvent in vacuo very quickly. $^1$H NMR (400 MHz, CDCl$_3$): δ 0.98 (3H, t, J 7.4, CH$_2$CH$_3$), 1.34 (3H, t, J 7.0, CH$_2$CH$_3$), 1.40 (1H, sext, J 6.8, one of CHCH$_2$CH$_3$), 1.66 (1H, sext, J 6.7, one of CHCH$_2$CH$_3$), 2.54 (1H, dd, J 16.0, 5.5, one of ArCH$_2$CH), 2.83 (1H, dd, J 15.3, 5.1, one of ArCH$_2$CH), 2.83-2.92 (1H, m, ArCH$_2$CH), 3.54-3.74 (4H, m, 2×ArCH$_2$N), 3.78 (3H, s, OCH$_3$), 3.81 (6H, s, 2×OCH$_3$), 4.02 (2H, q, J 7.0, OCH$_2$CH$_3$), 6.57 (1H, s, CH), 6.58 (2H, s, 2×CH), 7.05 (1H, s, CH). $^{13}$C NMR (100 MHz, CDCl$_3$): δ 11.0, 15.5, 22.9, 29.1, 50.9, 55.4, 56.0, 56.1, 58.0, 68.8, 105.2, 111.0, 124.4, 127.2, 134.3, 135.0, 135.5, 137.2, 149.3, 153.3. LC/MS (ES$^+$) $t_r$ 1.83 min; m/z 481.7 ((M+H)$^+$, 100%); MeOH/H$_2$O 90:10 (1.0 mL/min), HPLC tr 2.02 min (98.2%); CH$_3$CN/H$_2$O 90:10 (1.0 mL/min).

B1 1,2,3,4-tetrahydroisoquinolin-6-ol hydrobromide

6-Methoxy-1,2,3,4-tetrahydroisoquinoline hydrochloride (300 mg, 1.5 mmol), was dissolved in 48% HBr in water (6 mL) and heated at 120° C. for 18 hours. The mixture was cooled and concentrated in vacuo prior to re-evaporation from ethanol (5 mL). Crystallisation from hot ethanol afforded B1 as a tan solid (256 mg, 74%). $^1$H NMR (270 MHz, CDCl$_3$) δ 2.91 (2H, t, J=6.3), 3.33 (2H, t, J=6.3), 4.14 (2H, s), 6.60 (1H, s), 6.69 (1H, d, J=), 7.01 (1H, d, J=8.3), 8.97 (2H, br s), 9.47 (1H, br s); LC/MS (ES+) $t_r$=1.34 min , m/z 150.2 (M$^+$+H); HPLC $t_r$=2.586 min (>99%)

B2 2-Piperonyl-1,2,3,4-tetrahydroisoquinolin-6-ol

An ice cold solution of amine B1 (345 mg, 1.5 mmol) and piperonylic acid (374 mg, 2.25 mmol) in DCM (10 mL) was treated with EDCI (575 mg, 3 mmol) then triethylamine (251 μL, 1.8 mmol) and the solution stirred for 30 minutes prior to warming to room temperature and stirring for 18 hours. The resultant solution was diluted with DCM and washed with water (10 mL), 1M HCl (10 mL), NaHCO$_3$ (sat.) and brine, dried over MgSO$_4$ filtered and solvent evaporated under reduced pressure. Purification by column chromatography afforded both the amide B2 in 37% (164 mg) and the product with the additional phenolic ester B3 52 mg.

B2 2-Piperonyl-1,2,3,4-tetrahydroisoquinolin-6-ol

Gummy foam; m.p. 63-87° C.; $^1$H NMR (270 MHz, CDCl$_3$) δ 2.92 (2H, br s), 3.78 (2H, br s), 4.77 (2H, br s), 6.00 (2H, s), 6.07 (2H, s), 6.81-7.05 (7H, m), 7.58 (1H, d, J=1.4), 7.80 (1H, dd, J=1.6, 8.3); HRMS (ESI+) calcd. for C$_{17}$H$_{16}$NO$_3$ (M$^+$+H) 298.1060, found 298.1065; LC/MS (APCI) $t_r$=1.54 min, m/z 298.4 (M$^+$+H); HPLC $t_r$=1.452 min (>97%).

B3 2-Piperonyl-1,2,3,4-tetrahydroisoquinolin-6-O-piperonyl ester

Mixture of rotamers; m.p. 63-78° C.; $^1$H NMR (270 MHz, CDCl$_3$) δ 2.92 (2H, br s), 3.78 (2H, br s), 4.77 (2H, br s), 6.00 (2H, s), 6.07 (2H, s), 6.82-7.01 (7H, m), 7.58 (1H, d, J=1.4), 7.79 (1H, dd, J=1.6, 8.3); HRMS (ESI+) calcd. for C$_{25}$H$_{20}$NO$_7$ (M$^+$+H) 446.1234, found 446.1235; LC/MS (APCI) $t_r$=2.48 min, m/z 446.1 (M$^+$+H); HPLC $t_r$=1.803 min (>95%).

B4 2-(3-Ethoxybenzoyl)-1,2,3,4-tetrahydroisoquinolin-6-ol

B1 (345 mg, 1.5 mmol) and 3-ethoxybenzoic acid (274 mg, 1.65 mmol) were reacted as described for the synthesis of B2. 83% (372 mg). m.p. 150-151° C.; R$_f$: 0.25 (petrol 40-60° C.:ethylacetate; 1:1); $^1$H NMR (270 MHz, CDCl$_3$) δ 1.38 (3H, t, J=6.9), 2.72 and 2.82 (2H, m), 3.58 and 3.92 (2H, m), 3.94-4.03 (2H, m), 4.48 and 4.78 (2H, br s), 6.58 (1H, s), 6.62 and 6.98 (1H, m), 6.67-6.71 (1H, m), 6.90-6.96 (3H, m), 7.25-7.33 (1H, m), 7.76 (1H, br s); HRMS (ESI+) calcd. for C$_{18}$H$_{20}$NO$_3$ (M$^+$+H) 298.1438, found 298.1440; LC/MS (APCI) $t_r$=1.58 min (>?%), m/z 298.4 (M$^+$+H); HPLC $t_r$=1.561 min (>99%).

B5 2-(3,4,5-Trimethoxyphenylacetyl)-1,2,3,4-tetrahydroisoquinolin-6-ol

B1 (345 mg, 1.5 mmol) and 3,4,5-trimethoxyphenylacetic acid (373 mg, 1.65 mmol) were reacted as described for the synthesis of B2. 88% (470 mg). Gummy foam m.p. 37-53° C.; $^1$H NMR (270 MHz, CDCl$_3$) δ 2.66 and 2.78 (2H, t, J=6.2), 3.64 and 3.81 (2H, t, J=6.2), 3.70-3.82 (9H, m), 4.55 and 4.67 (2H, s), 5.50 (1H, br s), 6.39 and 6.46 (2H, s), 6.56-6.68 (2H, m), 6.83 and 6.97 (1H, d, J=8.1), 7.25 (1H, s); HRMS (ESI+) calcd. for C$_{20}$H$_{24}$NO$_5$ (M$^+$+H) 358.1649, found 358.1643; Anal. calcd. for CHNO: C, H, N. found: C, H, N%; LC/MS (APCI) $t_r$=1.30 min, m/z 358.3 (M$^+$+H); HPLC $t_r$=1.447 min (>99%)

B6 2-(3,4-Diethoxybenzoyl)-1,2,3,4-tetrahydroisoquinolin-6-ol

B1 (345 mg, 1.5 mmol) and 3,4-diethoxybenzoic acid (347 mg, 1.65 mmol) were reacted as described for the synthesis of B2. Purification by column chromatography afforded B6 (39 mg, 8%) together with 242 mg of material contaminated with 8% of the ester/amide. B6 shows m.p. 149-160° C.; $^1$H NMR (270 MHz, CDCl$_3$) δ 1.38-1.49 (6H, m), 2.81 (2H, br s), 3.68 and 3.89 (2H, br s), 4.02-4.16 (4H, m), 4.61 and 4.73 (2H, br s), 6.60 (1H, d, J=4.1), 6.68 (1H, br s), 6.68 (1H, br s), 6.84-6.89 (1H, m), 6.96-7.05 (2H, m), 7.16 (1H, br s); HRMS (ESI+) calcd. for C$_{20}$H$_{24}$NO$_4$ (M$^+$+H) 342.1700, found 342.1693; LC/MS (APCI) t$_r$=1.57 min, m/z 342.3 (M$^+$+H). HPLC t$_r$=1.525 min (>97%).

B7 2-(2,5-Dimethoxybenzoyl)-1,2,3,4-tetrahydroisoquinolin-6-ol

B1 (345 mg, 1.5 mmol) and 2,5-dimethoxybenzoic acid (301 mg, 1.65 mmol) were reacted as described for the synthesis of B2. Foam. m.p. 61-86° C.; $^1$H NMR (270 MHz, CDCl$_3$) δ 2.63-2.71 (1H, m), 2.79 (1H, t, J=6.1), 3.43 and 3.69 (2H, m), 3.64-3.73 (6H, m), 3.80 and 4.01 (1H, m), 4.34 (1H, app q, J=15.7), 4.80 (1H, s)<6.54-6.68 (2H, m), 6.79-6.92 (4H, m), 7.72 and 7.81 (1H, br s); HRMS (ES+) calcd. for C$_{18}$H$_{20}$NO$_4$ (M$^+$+H) 314.1387, found 314.1376; LC/MS (APCI) t$_r$=1.86 min, m/z 314.3 (M$^+$+H); HPLC t$_r$=2.097 min (>99%)

B8 2-(2,4-Dimethoxybenzoyl)-1,2,3,4-tetrahydroisoquinolin-6-ol

The amine hydrobromide salt (345 mg, 1.5 mmol) and 2,4-dimethoxybenzoic acid were reacted as described for the synthesis of B2. Purification by column chromatography afforded B8 (265 mg, 56%). m.p. 62-87° C.; R$_f$: 0.25 (1:2, petrol:ethyl acetate); $^1$H NMR (270 MHz, CDCl$_3$) δ 2.72 and 2.86 (2H, m), 3.46 (1H, m), 3.68 and 3.78 (3H, s), 3.82 (3H, s), 4.09 and 4.32 (1H, m), 4.81 (1H, s), 5.27 and 5.35 (1H, s), 6.45-6.76 (4H, m), 7.16-7.21 (2H, m); HRMS (ES+) calcd. for C$_{18}$H$_{20}$NO$_4$ (M$^+$+H) 314.1387, found 314.1384; LC/MS (APCI) t$_r$=1.75 min, m/z 314.1 (M$^+$+H); HPLC t$_r$=1.450 min (>97%)

B9 2-(2,3-Dimethoxybenzoyl)-1,2,3,4-tetrahydroisoquinolin-6-ol

B1 (345 mg, 1.5 mmol) and 2,3-dimethoxybenzoic acid (301 mg, 1.65 mmol) were reacted as described for the synthesis of B2. Purification by column chromatography afforded the B9 (262 mg, 56%). m.p. 167-172° C.; R$_f$: 0.32 (1:2, petrol:ethyl acetate); $^1$H NMR (270 MHz, CDCl$_3$) δ 2.65-2.88 (2H, m), 3.40-3.48 (1H, m), 3.79-3.88 (1H, m), 3.79 and 3.83 (3H, s), 3.88 (3H, s), 4.09-4.40 (1H, m), 4.84 (1H, s), 5.43 and 5.46 (1H, s), 6.56-6.60 (1H, m), 6.67-6.73 (1H, m), 6.79-6.86 (1H, m), 6.92-7.13 (3H, m); HRMS (ES+) calcd. for C$_{18}$H$_{19}$NO$_4$ (M$^+$+H) 314.1387, found 314.1390; LC/MS (APCI) t$_r$=1.69 min, m/z 314.2 (M$^+$+H); HPLC t$_r$=1.466 min (>98%).

B10 2-(3,4-Dimethoxybenzoyl)-1,2,3,4-tetrahydroisoquinolin-6-ol

B1 (345 mg, 1.5 mmol) and 3,4-dimethoxybenzoic acid (301 mg, 1.65 mmol) were reacted as described for the synthesis of B2. Purification by column chromatography afforded B10 (345 mg, 73%). m.p. 58-77° C.; R$_f$: 0.16 (1:2, petrol:ethyl acetate); $^1$H NMR (270 MHz, CDCl$_3$) δ 2.85 (2H, br s), 3.75-3.95 (2H, br m), 3.87 (3H, s), 3.91 (3H, s), 4.72 (2H, br s), 5.15 (1H, s), 6.63-6.69 (2H, m), 6.86 (1H, d, J=8.5), 7.01-7.04 (2H, m); HRMS (ESI+) calcd. for C$_{18}$H$_{20}$NO$_4$ (M$^+$+H) 314.1387, found 314.1395; LC/MS (ES+) t$_r$=1.40 min, m/z 314.4 (M$^+$+H); HPLC t$_r$=1.587 min (>98%).

B11 2-(2,4,5-Trimethoxybenzoyl)-1,2,3,4-tetrahydroisoquinolin-6-ol

B1 (345 mg, 1.5 mmol) and 2,4,5-trimethoxybenzoic acid (350 mg, 1.65 mmol) were reacted as described for the synthesis of B2. Purification by column chromatography afforded B11 (222 mg, 45%). m.p. 180-188° C.; $^1$H NMR (270 MHz, CDCl$_3$) δ 2.62-2.76 (1H, m), 2.77-2.86 (2H, m), 3.43-3.51 (1H, m), 3.68 and 3.74 (3H, s), 3.77 and 3.78 (3H, s), 3.89 (3H, s), 4.03-4.14 (1H, m), 4.25-4.45 (1H, m), 4.79 (1H, s), 6.49 (1H, d, J=3.9), 6.55-6.62 (1H, m), 6.60 and 6.93 (1H, d, J=8.3), 6.65-6.67 (1H, m), 6.80 (1H, d, J=7.2), 7.35 (1H, s); HRMS (ESI+) calcd. for C$_{19}$H$_{22}$NO$_5$ (M$^+$+H) 344.1492, found 344.1477; LC/MS (ES+) t$_r$=1.70 min (>?%), m/z 344.3 (M$^+$+H); HPLC t$_r$=1.412 min (>99.5%).

B12 2-(3,5-Dimethoxybenzoyl)-1,2,3,4-tetrahydroisoquinolin-6-ol

B1 (345 mg, 1.5 mmol) and 3,5-dimethoxybenzoyl chloride (331 mg, 1.65 mmol) were dissolved in DCM (10 mL) and cooled to 0° C. Triethylamine (627 μL, 4.5 mmol) and the solution stirred for 30 minutes prior to warming to room temperature and stirring for 18 hours. The resultant solution was diluted with DCM and washed with NaHCO$_3$ (sat.) and brine, dried over MgSO$_4$ filtered and solvent evaporated under reduced pressure. Purification by column chromatography afforded B12 (146 mg, 31%). $^1$H NMR (270 MHz, CDCl$_3$) δ 2.74-2.85 (2H, m), 3.58 and 3.91 (2H, m), 3.77 (3H, s), 4.48 and 4.77 (2H, s), 6.49-6.71 (5H, m), 6.72 and 6.98 (1H, d, J=7.7); HRMS (ESI+) calcd. for C$_{18}$H$_{20}$NO$_4$ (M$^+$+H) 314.1387, found 314.1378; LC/MS (ES+) t$_r$=2.09 min (>?%), m/z 314.3 (M$^+$+H); HPLC t$_r$=1.476 min (>99%).

B13 2-(2,4,6-Trimethoxybenzoyl)-1,2,3,4-tetrahydroisoquinolin-6-ol

B1 (345 mg, 1.5 mmol) and 2,4,6-trimethoxybenzoic acid (350 mg, 1.65 mmol) were reacted as described for the synthesis of B2. Purification by column chromatography afforded B13 (308 mg, 62%). $^1$H NMR (270 MHz, MeOD-d$_4$) δ 2.71 and 2.85 (2H, t, J=5.2), 3.45 and 3.87 (2H, t, J=6.1), 3.67 (3H, d, J=1.3), 3.78 (3H, d, J=1.3), 3.84 (3H, t, J=1.3), 4.30 and 4.73 (2H, s), 6.26 (2H, dd, J=8.0, 1.3), 6.54-6.67 (2H, m), 6.73 and 7.01 (1H, d, J=8.3); HRMS (ESI+) calcd. for C$_{19}$H$_{22}$NO$_5$ (M$^+$+H) 344.1492, found 311.1479; LC/MS (ES+) t$_r$=1.95 min (>?%), m/z 344.3 (M$^+$+H); HPLC t$_r$=1.423 min (>99%)

B14 2-(3,4,5-Triethoxybenzoyl)-1,2,3,4-tetrahydroisoquinolin-6-ol

B1 (690 mg, 3 mmol) and 3,4,5-triethoxybenzoic acid (1.14 g, 4.5 mmol) were reacted as described for the synthesis of B2. Purification by column chromatography afforded B14 2-(3,4,5-Triethoxybenzoyl)-1,2,3,4-tetrahydroisoquinolin-6-ol in 63% (731 mg) m.p. 158° C.; $^1$H NMR (270 MHz, CDCl$_3$) δ 1.32-1.42 (9H, m), 2.80 (2H, br s), 3.62 and 3.92 (2H, br s), 3.98-4.11 (6H, m), 4.51 and 4.75 (2H, br s), 5.97 (1H, br s), 6.62-6.66 (4H, m), 6.67 and 7.00 (1H, br s); HRMS (ESI+) calcd. for C$_{22}$H$_{28}$NO$_5$ (M$^+$+H) 386.1962, found 386.1960; LC/MS (APCI) t$_r$=1.69 min, m/z 386.5 (M$^+$+H); HPLC t$_r$=1.663 min (>97%).

In addition phenolic ester B14 2-(3,4,5-Triethoxybenzoyl)-6-O-(3,4,5-triethoxybenzoyl)-1,2,3,4-tetrahydroisoquinoline 94 mg was also isolated and showed $^1$H NMR (270 MHz, CDCl$_3$) δ 1.32-1.48 (18H, m), 2.92 (2H, br s), 3.68 and 4.05 (2H, br s), 4.01-4.19 (12 H, m), 4.64 and 4.83 (2H, br s), 6.62 (2H, s), 6.95 and 7.21 (1H, m), 7.00 (2H, app s), 7.38 (2H, s); HRMS (ESI+) calcd. for $C_{35}H_{44}NO_9$ (M$^+$+H) 622.3011, found 622.3004; LC/MS (APCI) $t_r$=3.69 min, m/z 622.1 (M$^+$+H); HPLC $t_r$=3.555 min (>85%)

B15 Benzylation of 6-methoxytetrahydroisoquinoline hydrochloride

A microwave tube (10 mL) was charged with 6-methoxytetrahydroisoquinoline hydrochloride (300 mg, 1.5 mmol), 3,4,5-trimethoxybenzylchloride (325 mg, 1.5 mmol), triethylamine (0.5 mL, 3.6 mmol) dissolved in ethanol (5 mL) and sealed. The Vial was heated to 120° C. with 150 W for 60 minutes. After cooling to room temperature the solution was dissolved in ethyl acetate and washed with water (2×10 mL), brine (10 mL), dried over MgSO$_4$ and evaporated to dryness in vacuo. Purification by flash column chromatography on a flashmaster system (1:0-1:1 petrol 40-60:ethylacetate) afforded the desired compound in 16% yield (81 mg) and >97% purity as a soft solid. m.p. 102-103° C.; $^1$H NMR (270 MHz, CDCl$_3$) δ 2.69 (2H, d, J=7.8), 2.87 (2H, t, J=7.8), 3.58 (2H, s), 3.59 (2H, s), 3.77 (3H, s), 3.84 (3H, s), 3.85 (6H, s), 6.62-6.71 (4H, m), 6.92 (1H, d, J=8.2); HRMS (ESI+) calcd. for $C_{20}H_{26}NO_4$ (M$^+$+H) 344.1856, found 344.1842; LC/MS (ES+) $t_r$=2.165 min, m/z 344.4 (M$^+$+H); HPLC $t_r$=2.47 min (>97%).

B16 2-(2-Methoxybenzyl)-1,2,3,4-tetrahydroisoquinolin-6-ol

A solution of B1 (345 mg, 1.5 mmol), and 2-methoxybenzyl chloride (230 µL, 1.65 mmol) in DMF (10 mL) was treated with Huning's base (1.82 mL, 10.5 mmol) and heated to 80° C. for 60 h. After cooling to room temperature, water (5 mL) was added and the product extracted with ethyl acetate (4×10 mL). The combined organics were washed with water, brine and dried over MgSO$_4$, prior to evaporation and purification by flash column chromatography. B16 was isolated as a white solid in 85% yield (345 mg). m.p. 148-155° C.; R$_f$: 0.23 (1:1 Petrol:ethyl acetate) $^1$H NMR (270 MHz, CDCl$_3$) δ 2.66-2.70 (2H, m), 2.73-2.76 (2H, m), 3.59 (2H, br s), 3.74 (2H, br s), 3.75 (3H, s), 6.20 (1H, d, J=2.43), 6.39 (1H, dd, J=2.7, 9.2), 6.73 (1H, d, J=9.2) 6.83-6.92 (2H, m), 7.24 (1H, dt, J=1.6, 8.1), 7.36 (1H, dd, J=1.4, 8.1); HRMS (ES+) calcd. for $C_{17}H_{20}NO_2$ (M$^+$+H) 270.1489, found 270.1478; LC/MS (ES+) $t_r$=1.92 min, m/z 270.4 (M$^+$+H); HPLC $t_r$=2.917 min (>98%).

B17 2-(4-methoxybenzyl)-1,2,3,4-tetrahydroisoquinolin-6-ol

B1 (345 mg, 1.5 mmol) and 4-methoxybenzyl bromide (238 µL, 1.65 mmol) were reacted as described for the synthesis of B16. Purification by flash column chromatography gave B17 as a tan solid in 61% yield (246 mg). m.p. 158-160° C.; $^1$H NMR (270 MHz, CDCl$_3$) δ 3.65-3.75 (4H, m), 3.52 (2H, s), 3.63 (2H, m), 3.78 (5H, app s), 6.21 (1H, d, J=2.2), 6.43 (1H, dd, J=8.3, 2.2), 6.72 (1H, d, J=8.3), 6.85 (2H, d, J=8.5), 7.29 (2H, d, J=8.5); HRMS (ESI+) calcd. for $C_{17}H_{20}NO_2$ (M$^+$+H) 270.1489, found 270.1477; LC/MS (APCI) $t_r$=1.77 min (>?%), m/z 270.3 (M$^+$+H); HPLC $t_r$=2.952 min (>97%)

B18 2-(3-Ethoxybenzyl)-1,2,3,4-tetrahydroisoquinolin-6-ol

The amide B4 (200 mg, 0.67 mmol) was dissolved in THF (2 mL) and added dropwise to a stirred suspension of lithium aluminium hydride (127 mg, 3.4 mmol) in THF (5 mL) cooled in an ice bath. The resultant mixture was stirred for 30 mins at 0° C. and then allowed to warm to room temperature overnight. The solution was then cooled in an ice bath and quenched with by the slow addition of ethyl acetate (10 mL) and left to stand for 30 mins. Solids were removed by filtration through a Celite® plug and solvent removed in vacuo. The crude product was purified by flash column chromatography to afford B18 as a white solid (75 mg, 38%). m.p. 120-121° C.; $^1$H NMR (400 MHz, CDCl$_3$) δ 1.38 (3H, t, J=7.2), 2.73 (4H, app s), 3.56 (2H, s), 3.67 (2H, s), 3.98 (2H, q, J=7.2), 6.32 (1H, d, J=2.4), 6.49 (1H, dd, J=8.4, 2.4), 6.77 (1H, d, J=8.0), 6.82 (1H, dd, J=8.0, 2.4), 6.94-6.98 (2H, m), 7.23 (1H, t, J=8.0); $^{13}$C NMR (100 MHz, CDCl$_3$) δ 14.81 (CH$_3$), 28.60 (CH$_2$), 50.51 (CH$_2$), 55.30 (CH$_2$), 62.74 (CH$_2$), 63.28 (CH$_2$), 113.60 (CH), 113.67 (CH), 115.11 (CH), 115.18 (CH), 121.73 (CH), 125.65 (C), 127.54 (CH), 129.22 (CH), 135.12 (C), 138.77(C), 154.56 (C), 158.98 (C); HRMS (ESI+) calcd. for $C_{18}H_{22}NO_2$ (M$^+$+H) 284.1645, found 284.1632; HPLC $t_r$=2.234 min (>97%)

B19 2-(2,5-Dimethoxybenzyl)-1,2,3,4-tetrahydroisoquinolin-6-ol

B1 (345 mg, 1.5 mmol) and 2-methoxybenzyl chloride (308 mg, 1.65 mmol) were reacted as described for the synthesis of B16. Purification by crystallisation from ethanol gave B19 as an off white solid in 73% yield (327 mg). m.p. 178-192° C. $^1$H NMR (270 MHz, CDCl$_3$) δ 2.77-2.83 (4H, m), 3.59 (2H, s), 3.71 (2H, s), 3.75 (3H, s), 3.79 (3H, s), 6.52-6.56 (2H, m), 6.81-6.98 (4H, m); HRMS (ES+) calcd. for $C_{18}H_{22}NO_3$ (M$^+$+H) 300.1594, found 300.1580; LC/MS (APCI) $t_r$=0.83 min, m/z 300.4 (M$^+$+H); HPLC $t_r$=1.303 min (>99.9%)

B20 2-(3,5-Dimethoxybenzyl)-1,2,3,4-tetrahydroisoquinolin-6-ol

B1 (345 mg, 1.5 mmol) and 3,5-methoxybenzyl chloride (308 mg, 1.65 mmol) were reacted as described for the synthesis of B16. Purification by crystallisation from ethanol gave B20 as an off white solid in 19% yield (85 mg). m.p. 189-195° C. $^1$H NMR (270 MHz, MeOD-d$_4$) δ 2.68-2.73 (2H, m), 2.21-2.86 (2H, m), 3.52 (2H, s), 3.60 (2H, s), 3.76 (3H, s), 3.77 (3H, s), 3.39 (1H, m), 6.53-6.57 (4H, m), 6.82 (1H, d, J=8.0); HRMS (ES+) calcd. for $C_{18}H_{22}NO_3$ (M$^+$+X) 300.1594, found 300.1582; LC/MS (APCI) $t_r$=0.78 min, m/z 300.2 (M$^+$+H); HPLC $t_r$=1.098 min (>99.9%).

B21 2-(2,3-Dimethoxybenzyl)-1,2,3,4-tetrahydroisoquinolin-6-ol

The amide B9 (163 mg, 0.52 mmol) in THF (5 mL), was added slowly to a cooled stirred suspension of LiAlH$_4$ (99 mg, 2.6 mmol) in THF (3 mL). After warming to room temperature the suspension was stirred for 18 hours before being cooled to 0° C. Water (99 µL) was added slowly followed by 15% NaOH (99 µL) then water (297 µL). The solution was allowed to warm to room temperature and stirred for 15 minutes. The thick suspension was diluted with ethyl acetate and MgSO$_4$ added. The resulting mixture was stirred for a further 15 minutes then filtered to remove the salts, evaporated to dryness and purified by flash column chromatography to afford the desired product as a colourless solid, (136 mg, 87%). m.p. 111-115° C.; $^1$H NMR (270 MHz, CDCl$_3$) δ 2.70-2.74 (4H, m), 3.58 (2H, s), 3.76 (2H, s), 3.82 (3H, s), 3.86 (3H, s), 6.27 (1H, d, J=2.2), 6.45 (1H, dd, J=2.2, 8.3), 6.74 (1H, d, J=8.3), 6.83 (1H, dd, J=1.7, 7.7), 6.97-7.06 (2H, m); $^{13}$C NMR (100 MHz, CDCl$_3$) δ 8.7(CH$_2$), 50.4(CH$_2$), 55.0(CH$_2$), 55.6(CH$_2$), 55.7(CH$_3$), 60.8(CH$_3$), 111.3(CH), 113.5(CH), 115.1(CH), 122.9(CH), 123.8(CH), 125.8(C), 127.4(CH), 130.9(C), 135.1(C), 147.8(C), 152.6(C), 154.5 (C); HRMS (ESI+) calcd. for C$_{18}$H$_{22}$NO$_3$ (M$^+$+H) 300.1594, found 300.1581; LC/MS (ES+) t$_r$=2.15 min, m/z 300.3 (M$^+$+H); HPLC t$_r$=2.346 min (>97%)

B22 2-(3,4-Diethoxybenzyl)-1,2,3,4-tetrahydroisoquinolin-6-ol

The amide B6 (240 mg, 0.7 mmol) in THF (5 mL), was added slowly to a cooled stirred suspension of LiAlH$_4$ (133 mg, 3.5 mmol) in THF (3 mL). After warming to room temperature the suspension was stirred for 18 hours before being cooled to 0° C. Water (133 μL) was added slowly followed by 15% NaOH (133 μL) then water (399 μL). The solution was allowed to warm to room temperature and stirred for 15 minutes. The thick suspension was diluted with ethyl acetate and MgSO$_4$ added. The resulting mixture was stirred for a further 15 minutes then filtered to remove the salts, evaporated to dryness and purified by flash column chromatography to afford the desired product as a colourless solid, (103 mg, 45%). m.p. 150-154° C.; $^1$H NMR (270 MHz, CDCl$_3$) δ 1.35 (3H, t, J=6.9), 1.42 (3H, t, J=6.9), 2.67 (4H, s), 3.50 (2H, s), 3.59 (2H, s), 3.95 (2H, q, J=6.9), 4.04 (2H, q, J=6.9), 6.21 (1H, d, J=1.7), 6.43 (1H, dd, J=2.5, 8.3), 6.73 (1H, d, J=8.3), 6.77-6.85 (2H, m); HRMS (ESI+) calcd. for C$_{20}$H$_{26}$NO$_3$ (M$^+$+H) 328.1907, found 328.1892; LC/MS (ES+) t$_r$=2.22 min, m/z 328.3 (M$^+$+H); HPLC t$_r$=2.519 min (>99%).

B23 2-(3,4-Dimethoxybenzyl)-1,2,3,4-tetrahydroisoquinolin-6-ol

The amide B10 (210 mg, 0.67 mmol) in THF (5 mL), was added slowly to a cooled stirred suspension of LiAlH$_4$ (127 mg, 3.35 mmol) in THF (3 mL). Reaction and work up as B22, flash column chromatography gave B23 as a colourless solid, (127 mg, 64%). m.p. 119-122° C.; $^1$H NMR (270 MHz, CDCl$_3$) δ 2.67-2.70 (4H, m), 3.50 (2H, s), 3.60 (2H, s), 3.74 (3H, s), 3.85 (3H, s), 6.19 (1H, d, J=2.2), 6.42 (1H, dd, J=2.2, 8.3), 6.71-6.87 (3H, m), 6.99 (1H, d, J=1.4); $^{13}$C NMR (100 MHz, CDCl$_3$) δ 28.5(CH$_2$), 50.4(CH$_2$), 55.3(CH$_2$), 55.7(CH$_3$), 55.8(CH$_3$), 62.5(CH$_2$), 110.6(CH), 112.5(CH), 113.6(CH), 115.1(CH), 121.7(CH), 125.5(C), 127.5(CH), 129.8(C), 135.1(C), 148.2(C), 148.9(C), 154.7(C); HRMS (ESI+) calcd. for C$_{18}$H$_{22}$NO$_3$ (M$^+$+H) 300.1594, found 300.1582; LC/MS (ES+) t$_r$=1.89 min, m/z 300.3 (M$^+$+H); HPLC t$_r$=2.157 min (>97%)

B24 2-(Benzo[d][1,3]dioxol-5-ylmethyl)-1,2,3,4-tetrahydroisoquinolin-6-ol

The amide B2 (160 mg, 0.54 mmol) in THF (5 mL), was added slowly to a cooled stirred suspension of LiAlH$_4$ (102 mg, 2.69 mmol) in THF (3 mL). After warming to room temperature the suspension was stirred for 18 hours before being cooled to 0° C. Water (102 μL) was added slowly followed by 15% NaOH (102 μL) then water (306 μL). The solution was allowed to warm to room temperature and stirred for 15 minutes. The thick suspension was diluted with ethyl acetate and MgSO$_4$ added. The resulting mixture was stirred for a further 15 minutes then filtered to remove the salts, evaporated to dryness and purified by flash column chromatography to afford B24 as a colourless solid (89 mg, 59%). m.p. 169-172° C.; $^1$H NMR (270 MHz, MeOD-d$_4$) δ 2.69 (2H, app t, J=6.0), 2.81 (2H, app t, J=6.0), 3.50 (2H, s), 3.58 (2H, s), 5.92 (2H, s), 6.53-6.57 (2H, m), 6.78-6.83 (3H, m), 6.90 (1H, s); $^{13}$C NMR (100 MHz, CDCl$_3$) δ 29.6 (CH$_2$), 51.4 (CH$_2$), 56.5 (CH$_2$), 63.4 (CH$_2$), 102.3 (CH$_2$), 108.8 (CH), 110.9 (CH), 114.4 (CH), 115.6 (CH), 124.2 (CH), 126.3 (C), 128.5 (CH), 132.1 (C), 136.2 (C), 148.5 (C), 149.2 (C), 156.9 (C); HRMS (ESI+) calcd. for C$_{17}$H$_{18}$NO$_3$ (M$^+$+H) 284.1281, found 284.1275; LC/MS (ES+) t$_r$=2.15 min, m/z 284.2 (M$^+$+H); HPLC t$_r$=2.066 min (>96.6%).

B25 2-(2,4-Dimethoxybenzyl)-1,2,3,4-tetrahydroisoquinolin-6-ol

The amide B8 (200 mg, 0.64 mmol) in THF (5 mL), was added slowly to a cooled stirred suspension of LiAlH$_4$ (121 mg, 3.2 mmol) in THF (3 mL). After warming to room temperature the suspension was stirred for 18 hours before being cooled to 0° C. Water (121 μL) was added slowly followed by 15% NaOH (121 μL) then water (363 μL). The solution was allowed to warm to room temperature and stirred for 15 minutes. The thick suspension was diluted with ethyl acetate and MgSO$_4$ added. The resulting mixture was stirred for a further 15 minutes then filtered to remove the salts, evaporated to dryness and purified by recrystallisation from hot methanol to afford the B25 as a colourless solid, (92 mg, 48%). m.p. 149-152° C.; $^1$H NMR (270 MHz, MeOD-d$_4$) δ 2.72-2.75 (2H, m), 2.80-2.83 (2H, m), 3.55 (2H, s), 3.66 (2H, s), 3.80 (3H, s), 3.82 (3H, s), 6.49-6.56 (4H, m), 6.82 (1H, d, J=8.4), 7.22 (1H, d, J=8.4); $^{13}$C NMR (100 MHz, MeOD-d$_4$) δ 29.6 (CH$_2$), 49.2 (CH$_3$), 51.4 (CH$_2$), 55.8 (CH$_3$), 56.2 (CH$_2$), 56.3 (CH$_2$), 99.2 (CH), 105.4 (CH), 114.3 (CH), 115.6 (CH), 118.0, 126.5, 128.5 (CH), 133.4 (CH), 136.2, 156.2, 156.8, 160.6, 162.2; HRMS (ESI+) calcd. for C$_{18}$H$_{22}$NO$_3$ (M$^+$+H) 300.1594, found 300.1984; LC/MS (ES+) t$_r$=0.77 min, m/z 300.2 (M$^+$+H); HPLC t$_r$=1.047 min (>99.15%)

B26 2-(2,4,5-Trimethoxybenzyl)-1,2,3,4-tetrahydroisoquinolin-6-ol

The amide B11 (55 mg, 0.16 mmol) in THF (5 mL), was added slowly to a cooled stirred suspension of LiAlH$_4$ (86 mg, 2.6 mmol) in THF (3 mL). After warming to room temperature the suspension was stirred for 18 hours before being cooled to 0° C. Water (86 μL) was added slowly followed by 15% NaOH (86 μL) then water (258 μL). The solution was allowed to warm to room temperature and stirred for 15 minutes. The thick suspension was diluted with ethyl acetate and MgSO$_4$ added. The resulting mixture was stirred for a further 15 minutes then filtered to remove the salts, evaporated to dryness and purified by flash column chromatography and recrystallisation from hot methanol to afford B26 as a colourless solid, (29 mg, 56%). m.p. 188-191° C.; $^1$H NMR (270 MHz, CDCl$_3$) δ 2.68-2.78 (4H, m), 3.58 (2H, s), 3.64 (2H, s), 3.80 (6H, s), 3.88 (3H, s), 6.44-6.45 (1H, m), 6.52-6.55 (2H, m), 6.83 (1H, d, J=8.0), 6.99 (1H, s); HRMS (ESI+) calcd. for C$_{19}$H$_{24}$NO$_4$ (M$^+$+H) 330.1700, found 330.1688; LC/MS (ES+) t$_r$=0.76 min, m/z 330.3 (M$^+$+H); HPLC t$_r$=1.025 min (>99.21%).

B27 2-(3,4,5-triethoxybenzyl)-1,2,3,4-tetrahydroisoquinolin-6-ol

The amide B14 (258 mg, 0.67 mmol) was dissolved in THF (2 mL) and added dropwise to a stirred suspension of lithium aluminium hydride (127 mg, 3.4 mmol) in THF (5 mL) cooled in an ice bath. The resultant mixture was stirred for 30 mins at 0° C. and then allowed to warm to room temperature overnight. After which time the solution was cooled in an ice bath and quenched with by the slow addition of ethylacetate (10 mL) and left to stand for 30 mins. Solids were removed by filtration through a Celite plug and solvent removed in vacuo. The crude product was purified by flash column chromatography to afford B27 as a white solid (75 mg, 38%). m.p. 140-142° C.; $^1$H NMR (400 MHz, CDCl$_3$) δ 1.34 (3H, t, J=7.2), 1.35 (3H, t, J=6.8), 2.68 (4H, s), 3.52 (2H, s), 3.57 (2H, s), 3.97 (2H, q, J=6.8), 4.04 (2H, q, J=7.2), 6.27 (1H, d, J=2.4), 6.45 (1H, dd, J=8.4, 2.4), 6.59 (2H, s), 6.75 (1H, d, J=8.4); $^{13}$C NMR (100 MHz, CDCl$_3$) δ 14.91 (CH$_3$), 15.57 (CH$_3$), 28.57 (CH$_2$), 50.46 (CH$_2$), 55.40 (CH$_2$), 63.01 (CH$_2$), 64.48 (CH$_2$), 68.81 (CH$_2$), 107.74 (CH), 113.58 (CH), 115.05 (CH), 127.52 (CH), 132.60 (C), 135.09 (C), 136.79 (C), 152.70 (C), 154.70 (C); HRMS (ESI+) calcd. for C$_{22}$H$_{30}$NO$_4$ (M$^+$+H) 372.2169, found 372.2156; HPLC t$_r$=2.501 min (>98%)

B28 2-(2-Hydroxy-4,6-dimethoxybenzyl)-1,2,3,4-tetrahydroisoquinolin-6-ol

Lithium aluminium hydride was added to a suspension of amide B13 in anhydrous dioxane under an atmosphere of nitrogen and stirred overnight. TLC showed little conversion so the reaction solution was heated to 110° C. for 4 hours. Upon cooling to 0° C. the solution was quenched with water (395 µL), 15% sodium hydroxide solution (395 µL) and water (1.19 mL). the solution was allowed to warm to room temperature and stirred for 20 minutes, diluted with ethyl acetate and dried with MgSO$_4$. After stirring for an additional 20 minutes salts were removed my filtration and the product crystallised from dichloromethane to afford B28, 130 mg of a white solid (20% yield). m.p. 109-112° C.; $^1$H NMR (400 MHz, MeOD-d$_4$) δ 2.79-2.83 (4H, m), 3.62 (2H, s), 3.73 (3H, s), 3.75 (3H, s), 3.84 (2H, s), 5.98 (1H, d, J=2.0), 6.06 (1H, d, J=2.4), 6.54 (1H, d, J=2.0), 6.56 (1H, d, J=2.4), 6.58 (1H, d, J=2.0), 6.83 (1H, d, J=8.4); $^{13}$C NMR (100 MHz, CDCl$_3$) δ 29.7 (CH$_2$), 51.1 (CH$_2$), 53.7 (CH$_2$), 55.57 and 55.61 (CH$_3$), 55.8 (CH$_2$), 55.93 and 55.96 (CH$_3$), 90.9 (CH), 94.9 (CH), 102.8 (C), 114.5 (CH), 115.7 (CH), 125.8 (C), 128.6 (CH), 135.8 (C), 157.0 (C), 160.3 (C), 160.9 (C), 162.3 (C); HRMS (ESI+) calcd. for C$_{18}$H$_{22}$NO$_4$ (M$^+$+H) 316.1543, found 316.1532; LC/MS (ES+) t$_r$=0.78 min, m/z 316.4 (M$^+$+H); HPLC t$_r$=1.027 min (>99.4%).

B29 2-(3,4,5-Trimethoxyphenethyl)-1,2,3,4-tetrahydroisoquinolin-6-ol

The amide B5 (200 mg, 0.56 mmol) in THF (5 mL), was added slowly to a cooled stirred suspension of LiAlH$_4$ (106 mg, 2.79 mmol) in THF (3 mL). After warming to room temperature the suspension was stirred for 18 hours before being cooled to 0° C. Water (106 µL) was added slowly followed by 15% NaOH (106 µL) then water (318 µL). The solution was allowed to warm to room temperature and stirred for 15 minutes. The thick suspension was diluted with ethyl acetate and MgSO$_4$ added. The resulting mixture was stirred for a further 15 minutes then filtered to remove the salts, evaporated to dryness and purified by flash column chromatography to afford B29 as a colourless solid, (120 mg, 63%). m.p. 180-186° C.; $^1$H NMR (270 MHz, CDCl$_3$) δ 2.72-2.87 (4H, m), 3.64 (2H, s), 3.82 (3H, s), 3.84 (6H, s), 6.44 (2H, s), 6.54 (1H, d, J=2.5), 6.59 (1H, dd, J=2.5, 8.3), 6.89 (1H, d, J=8.3), 7.25 (1H, s); $^{13}$C NMR (100 MHz, CDCl$_3$) δ 28.7 (CH$_2$), 34.0 (CH$_2$), 51.0 (CH$_2$), 55.4 (CH$_2$), 56.1 (CH$_3$), 60.2 (CH$_2$), 60.8(CH$_3$), 105.6 (CH), 113.8 (CH), 115.2 (CH), 125.4 (C), 127.6 (CH), 135.1 (C), 135.8 (C), 136.3 (C), 153.1 (C), 154.9 (C); HRMS (ESI+) calcd. for C$_{20}$H$_{26}$NO$_4$ (M$^+$+H) 344.1856, found 344.1840; LC/MS (ES+) t$_r$=1.95 min, m/z 344.3 (M$^+$+H); HPLC t$_r$=2.358 min (>98%).

C1

N-benzyl-4-(benzyloxy)-3-methoxybenzylamine

To a stirred solution of benzylamine (13.1 mL, 0.12 mol) and 4-benzyloxy-3-methoxybenzaldehyde (24.2 g, 0.1 mol) in 1,2-dichloroethane (50 mL) and chloroform (250 mL) was added sodium triacetoxyborohydride (31.79 g, 0.15 mol). The mixture was stirred at room temperature for 18 hrs, saturated NaHCO$_3$ was added. The organic phase was separated and aqueous phase extracted with chloroform. The combined extracts were washed with brine, dried over MgSO$_4$ and evaporated to afford the crude product. Purification by flash column chromatography afforded the title compound as a pale yellow oil in 76% yield (25.2 g). R$_f$: 0.17 (petrol:ethyl acetate; 1:1). $^1$H NMR (270 MHz, CDCl$_3$) δ 3.73 (2H, s), 3.79 (2H, s), 3.89 (3H, s), 5.13 (2H, s), 6.75-6.84 (2H, m), 6.91 (1H, d, J=1.4), 7.23-7.44 (10H, m); HRMS (ESI+) calcd. for C$_{22}$H$_{24}$NO$_2$ (M$^+$+H) 334.1802, found 334.1787; LC/MS (ES+) t$_r$=1.19 min, m/z 334.5 (M$^+$+H);

C3 N-Benzyl-3,4-dimethoxybenzylamine

To a stirred solution of benzylamine (3.94 mL, 36 mmol) and 4,3-dimethoxybenzaldehyde (5.0 g, 30 mmol) in chloroform (120 mL), was added sodium triacetoxyborohydride (9.53 g, 45 mmol). The mixture was stirred at rt for 18 hrs prior to addition of saturated NaHCO$_3$. The organic phase was separated and the aqueous phase extracted with chloroform. The combined extracts were washed with brine, dried over MgSO$_4$ and evaporated to afford the crude product. Purification by flash column chromatography afforded the title compound as a pale yellow oil (5.47 g, 71%). $^1$H NMR (270 MHz, CDCl$_3$) δ 3.74 (2H, s), 3.80 (2H, s), 3.86 (3H, s), 3.88 (3H, s), 6.80-6.89 (3H, m), 7.22-7.34 (5H, m); HRMS (ESI+) calcd. for C$_{16}$H$_{20}$NO$_2$ (M$^+$+H) 258.1489, found 258.1478; LC/MS (ES+) t$_r$=0.79 min, m/z 258.2 (M$^+$+H).

C5

N-Benzyl-2-chloromethyl-4,5-dimethoxybenzylamine hydrochloride

Concentrated hydrochloric acid (22 mL) was added to a cooled solution of benzylamine C3 (2.72 g, 10.6 mmol) and paraformaldehyde (952 mg, 32 mmol). The mixture was then heated to 50° C. for 16 hours after which the solvent was removed under reduced pressure. Acetone 10 mL was added to the residue and left to stand overnight. Crystals were removed by filtration and dried to afford 3.05 g (84%). $^1$H NMR (270 MHz, CDCl$_3$) δ 3.72 (3H, s), 3.78-3.89 (4H, m), 3.93 (3H, s), 4.35 (2H, s), 6.69 (1H, s), 7.33-7.40 (4H, m), 7.46-7.50 (2H, m), 10.20 (2H, br s).

C7 2-Benzyl-5,6-dimethoxyisoindoline

The amine salt C5 (1.67 g, 4.88 mmol) was added to a suspension of K$_2$CO$_3$ (1.71 g, 12.4 mmol) in toluene (30 mL) and stirred at room temperature overnight. TLC showed little reaction had occurred so chloroform (30 mL) was added and the solution heated at 50° C. for 16 hours. The solution was filtered, solvent removed in vaccuo and purified by flash column chromatography to afford 667 mg (51% yield) of the desired product. $^1$H NMR (270 MHz, CDCl$_3$) δ 3.83 (6H, s), 3.88 (4H, s), 3.89 (2H, s), 6.71 (2H, s), 7.26-7.42 (5H, m); LC/MS (ES+) $t_r$=0.81 min, m/z 270.2 (M$^+$+H).

C8 2-Benzyl-5,6-dimethoxyisoindoline

A CEM microwave tube was charged with a mixture of the HCl salt C5 (150 mg, 0.44 mmol), triethylamine (305 µL, 2.2 mmol), in ethanol and heated at 120° C. (150 W) for 10 minutes. TLC showed little conversion and the reaction reheated at 120° C. for 60 mins. The solution was diluted with water and the product extracted into ethylacetate (×3) and the combined organics dried with brine and MgSO$_4$. purification of the crude product by flash column chromatography afford the desired compound in 74% yield as a white solid which darkens over time. R$_f$: 0.41 (1:1 petrol:ethylacetate);

$^1$H NMR (270 MHz, CDCl$_3$) δ 3.83 (6H, s), 3.88 (4H, s), 3.89 (2H, s), 6.71 (2H, s), 7.26-7.42 (5H, m); HRMS (ESI+) calcd. for C$_{17}$H$_{20}$NO$_2$, (M$^+$+H) 270.1489, found 270.1479; LC/MS (ES+) $t_r$=0.81 min, m/z 270.2 (M$^+$+H).

Biological Data

The following biological data were obtained using the Protocols described herein.

Antiproliferative assays. DU145 cells were seeded into 96 well microtiter plates (5000 cells/well) and treated with 10$^9$ to 10$^4$ M of compounds or with vehicle control. At 96 hours post-treatment, live cell counts were determined by WST-1 cell proliferation assay (Roche, Penzberg, Germany), as per manufacturer's instructions. Viability results were expressed as a percentage of mean control values resulting in the calculation of the 50% growth inhibition (GI50). All experiments were performed in triplicate.

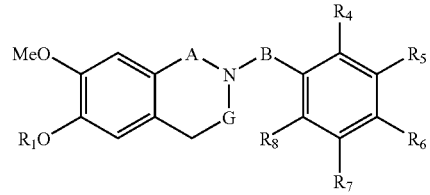

| Cmp No. | R$_1$ | A | G | B | R$_4$ | R$_5$ | R$_6$ | R$_7$ | R$_8$ | DU-145 GI$_{50}$ µM |
|---|---|---|---|---|---|---|---|---|---|---|
| 2 | Bn | CH$_2$ | CH$_2$ | CH$_2$ | H | H | H | H | H | 50 to 100 |
| 3 | Bn | CH$_2$ | CH$_2$ | CH$_2$ | H | H | OMe | H | H | 50 to 100 |
| 4 | Bn | CH$_2$ | CH$_2$ | CH$_2$ | H | OMe | H | H | H | 50 to 100 |
| 5 | Bn | CH$_2$ | CH$_2$ | CH$_2$ | OMe | H | H | H | H | 10 to 50 |
| 6 | Bn | CH$_2$ | CH$_2$ | CH$_2$ | H | OMe | H | OMe | H | >100 |
| 7 | Bn | CH$_2$ | CH$_2$ | CH$_2$ | H | Me | H | H | H | >100 |
| 8 | Bn | CH$_2$ | CH$_2$ | CH$_2$ | H | OPh | H | H | H | >100 |
| 16 | Bn | CH$_2$ | CH$_2$ | CH$_2$ | OMe | OMe | OMe | H | H | NT |
| 17 | Bn | CH$_2$ | CH$_2$ | CH$_2$ | OMe | H | OMe | OMe | H | 10 to 50 |
| 19 | Bn | CH$_2$ | CH$_2$ | CH$_2$ | H | OMe | OMe | H | H | 10 to 50 |
| 20 | Bn | CH$_2$ | CH$_2$ | CH$_2$ | OMe | OMe | H | H | H | 10 to 50 |
| 21 | Bn | CH$_2$ | CH$_2$ | CH$_2$ | OMe | H | H | OMe | H | 10 to 50 |
| 22 | Bn | CH$_2$ | CH$_2$ | CH$_2$ | H | F | H | H | H | >100 |
| 30 | Bn | CH$_2$ | CH$_2$ | CH$_2$ | H | OH | H | H | H | NA |
| 34 | Bn | CH$_2$ | CH$_2$ | CH$_2$ | H | NH$_2$ | H | H | H | >100 |
| 38 | H | CH$_2$ | CH$_2$ | CH$_2$ | H | H | H | H | H | >100 |
| 39 | H | CH$_2$ | CH$_2$ | CH$_2$ | H | H | OMe | H | H | >100 |
| 40 | H | CH$_2$ | CH$_2$ | CH$_2$ | H | OMe | H | H | H | >100 |
| 41 | H | CH$_2$ | CH$_2$ | CH$_2$ | OMe | H | H | H | H | >100 |
| 42 | H | CH$_2$ | CH$_2$ | CH$_2$ | H | OMe | H | OMe | H | 50 to 100 |
| 43 | H | CH$_2$ | CH$_2$ | CH$_2$ | H | OPh | H | H | H | 10 to 50 |
| 44 | H | CH$_2$ | CH$_2$ | CH$_2$ | H | Me | H | H | H | >100 |
| 50 | H | CH$_2$ | CH$_2$ | CH$_2$ | H | NHAc | H | H | H | >100 |
| 51 | H | CH$_2$ | CH$_2$ | CH$_2$ | H | OAc | H | H | H | NT |
| 54 | H | CH$_2$ | CH$_2$ | CH$_2$ | H | OMe | OMe | OMe | H | <10 |
| 55 | H | CH$_2$ | CH$_2$ | CH$_2$ | OMe | H | H | OMe | H | 50 to 100 |
| 56 | H | CH$_2$ | CH$_2$ | CH$_2$ | OMe | OMe | H | H | H | >100 |
| 57 | H | CH$_2$ | CH$_2$ | CH$_2$ | H | OMe | OMe | H | H | >100 |
| 58 | H | CH$_2$ | CH$_2$ | CH$_2$ | OMe | OMe | OMe | H | H | >100 |
| 59 | H | CH$_2$ | CH$_2$ | CH$_2$ | OMe | H | OMe | OMe | H | <10 |
| 60 | H | CH$_2$ | CH$_2$ | CH$_2$ | H | F | H | H | H | >100 |
| 61 | H | CH$_2$ | CH$_2$ | CH$_2$ | H | O-i-Pr | H | H | H | >100 |
| 63 | H | CH$_2$ | CH$_2$ | CH$_2$ | H | OEt | H | H | H | >100 |
| 64 | H | CH$_2$ | CH$_2$ | CH$_2$ | H | CN | H | H | H | >100 |
| 65 | H | CH$_2$ | CH$_2$ | CH$_2$ | H | H | CN | H | H | >100 |
| 66 | H | CH$_2$ | CH$_2$ | CH$_2$ | H | NO$_2$ | H | H | H | >100 |
| 67 | H | CH$_2$ | CH$_2$ | CH$_2$ | H | Cl | H | H | H | 50 to 100 |
| 68 | H | CH$_2$ | CH$_2$ | CH$_2$ | H | OCF$_3$ | H | H | H | 50 to 100 |
| 69 | H | CH$_2$ | CH$_2$ | CH$_2$ | OH | H | H | H | H | >100 |
| 70 | H | CH$_2$ | CH$_2$ | CH$_2$ | H | OH | H | H | H | >100 |
| 72 | SO$_2$NH$_2$ | CH$_2$ | CH$_2$ | CH$_2$ | H | OMe | H | H | H | <10 |
| 73 | SO$_2$NH$_2$ | CH$_2$ | CH$_2$ | CH$_2$ | H | H | OMe | H | H | 50 to 100 |
| 74 | SO$_2$NH$_2$ | CH$_2$ | CH$_2$ | CH$_2$ | H | H | H | H | H | 50 to 100 |
| 75 | SO$_2$NH$_2$ | CH$_2$ | CH$_2$ | CH$_2$ | OMe | H | H | H | H | <10 |
| 76 | SO$_2$NH$_2$ | CH$_2$ | CH$_2$ | CH$_2$ | H | OMe | H | OMe | H | <10 |

-continued

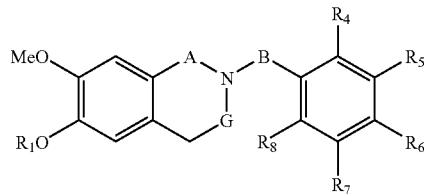

| Cmp No. | $R_1$ | A | G | B | $R_4$ | $R_5$ | $R_6$ | $R_7$ | $R_8$ | DU-145 $GI_{50}\,\mu M$ |
|---|---|---|---|---|---|---|---|---|---|---|
| 77 | $SO_2NH_2$ | $CH_2$ | $CH_2$ | $CH_2$ | H | Me | H | H | H | 10 to 50 |
| 78 | $SO_2NH_2$ | $CH_2$ | $CH_2$ | $CH_2$ | H | OPh | H | H | H | 10 to 50 |
| 79 | $SO_2NH_2$ | $CH_2$ | $CH_2$ | $CH_2$ | H | $OSO_2NH_2$ | H | H | H | 10 to 50 |
| 80 | $SO_2NH_2$ | $CH_2$ | $CH_2$ | $CH_2$ | H | OEt | H | H | H | <10 |
| 82 | $SO_2NH_2$ | $CH_2$ | $CH_2$ | $CH_2$ | H | Ac | H | H | H | <10 |
| 85 | $SO_2NH_2$ | $CH_2$ | $CH_2$ | $CH_2$ | H | NHAc | H | H | H | >100 |
| 87 | $SO_2NH_2$ | $CH_2$ | $CH_2$ | $CH_2$ | H | OAc | H | H | H | 50 to 100 |
| 90 | $SO_2NH_2$ | $CH_2$ | $CH_2$ | $CH_2$ | H | OMe | OMe | OMe | H | <10 |
| 91 | $SO_2NH_2$ | $CH_2$ | $CH_2$ | $CH_2$ | OMe | OMe | H | H | H | <10 |
| 92 | $SO_2NH_2$ | $CH_2$ | $CH_2$ | $CH_2$ | H | OMe | OMe | H | H | <10 |
| 93 | $SO_2NH_2$ | $CH_2$ | $CH_2$ | $CH_2$ | OMe | OMe | OMe | H | H | 10 to 50 |
| 94 | $SO_2NH_2$ | $CH_2$ | $CH_2$ | $CH_2$ | OMe | H | H | OMe | H | <10 |
| 95 | $SO_2NH_2$ | $CH_2$ | $CH_2$ | $CH_2$ | OMe | H | OMe | OMe | H | <10 |
| 97 | $SO_2NH_2$ | $CH_2$ | $CH_2$ | $CH_2$ | H | OH | H | H | H | 50 to 100 |
| 98 | $SO_2NH_2$ | $CH_2$ | $CH_2$ | $CH_2$ | H | ON | H | H | H | NA |
| 99 | $SO_2NH_2$ | $CH_2$ | $CH_2$ | $CH_2$ | H | H | CN | H | H | 50 to 100 |
| 100 | $SO_2NH_2$ | $CH_2$ | $CH_2$ | $CH_2$ | H | $NO_2$ | H | H | H | <10 |
| 101 | $SO_2NH_2$ | $CH_2$ | $CH_2$ | $CH_2$ | H | Cl | H | H | H | <10 |
| 102 | $SO_2NH_2$ | $CH_2$ | $CH_2$ | $CH_2$ | H | $OCF_3$ | H | H | H | <10 |
| 104 | $SO_2NH_2$ | $CH_2$ | $CH_2$ | $CH_2$ | H | O-i-Pr | H | H | H | <10 |
| 108 | Bn | $CH_2$ | $CH_2$ | CO | H | H | OMe | H | H | 10 to 50 |
| 109 | Bn | $CH_2$ | $CH_2$ | CO | H | OMe | OMe | H | H | 10 to 50 |
| 110 | Bn | $CH_2$ | $CH_2$ | CO | H | OMe | H | OMe | H | 10 to 50 |
| 115 | H | $CH_2$ | $CH_2$ | CO | OMe | H | H | H | H | 50 to 100 |
| 116 | H | $CH_2$ | $CH_2$ | CO | H | OMe | H | H | H | 10 to 50 |
| 117 | H | $CH_2$ | $CH_2$ | CO | H | H | OMe | H | H | >100 |
| 118 | H | $CH_2$ | $CH_2$ | CO | H | OMe | OMe | H | H | >100 |
| 119 | H | $CH_2$ | $CH_2$ | CO | H | OMe | H | OMe | H | <10 |
| 120 | H | $CH_2$ | $CH_2$ | CO | H | OMe | OMe | OMe | H | <10 |
| 122 | $SO_2NH_2$ | $CH_2$ | $CH_2$ | CO | OMe | H | H | H | H | 10 to 50 |
| 123 | $SO_2NH_2$ | $CH_2$ | $CH_2$ | CO | H | OMe | H | H | H | <10 |
| 124 | $SO_2NH_2$ | $CH_2$ | $CH_2$ | CO | H | H | OMe | H | H | <10 |
| 125 | $SO_2NH_2$ | $CH_2$ | $CH_2$ | CO | H | OMe | OMe | H | H | >100 |
| 125 | $SO_2NH_2$ | $CH_2$ | $CH_2$ | CO | H | OMe | H | OMe | H | <10 |
| 127 | $SO_2NH_2$ | $CH_2$ | $CH_2$ | CO | H | OMe | OMe | OMe | H | <10 |
| 128 | Bn | CO | $CH_2$ | CO | H | H | OMe | H | H | >100 |
| 129 | Bn | CO | $CH_2$ | CO | H | OMe | H | OMe | H | >100 |
| 130 | Bn | CO | $CH_2$ | CO | OMe | H | H | H | H | >100 |
| 131 | Bn | CO | $CH_2$ | CO | H | OMe | H | H | H | NA |
| 133 | Bn | CO | $CH_2$ | CO | H | OMe | OMe | H | H | >100 |
| 134 | Bn | CO | $CH_2$ | CO | H | OMe | OMe | OMe | H | >100 |
| 135 | Bn | CO | $CH_2$ | CO | H | CN | H | H | H | >100 |
| 136 | Bn | CO | $CH_2$ | CO | H | H | CN | H | H | >100 |
| 138 | H | CO | $CH_2$ | CO | OMe | H | H | H | H | <10 |
| 139 | H | CO | $CH_2$ | CO | H | OMe | H | H | H | <10 |
| 140 | H | CO | $CH_2$ | CO | H | H | OMe | H | H | >100 |
| 141 | H | CO | $CH_2$ | CO | H | OMe | H | OMe | H | <10 |
| 142 | H | CO | $CH_2$ | CO | H | OMe | OMe | H | H | <10 |
| 143 | H | CO | $CH_2$ | CO | H | OMe | OMe | OMe | H | <10 |
| 144 | H | CO | $CH_2$ | CO | H | CN | H | H | H | 50 to 100 |
| 145 | H | CO | $CH_2$ | CO | H | H | CN | H | H | >100 |
| 147 | $SO_2NH_2$ | CO | $CH_2$ | CO | H | H | OMe | H | H | >100 |
| 148 | $SO_2NH_2$ | CO | $CH_2$ | CO | OMe | H | H | H | H | <10 |
| 149 | $SO_2NH_2$ | CO | $CH_2$ | CO | H | OMe | H | H | H | <10 |
| 150 | $SO_2NH_2$ | CO | $CH_2$ | CO | H | OMe | H | OMe | H | <10 |
| 151 | $SO_2NH_2$ | CO | $CH_2$ | CO | H | OMe | OMe | H | H | <10 |
| 152 | $SO_2NH_2$ | CO | $CH_2$ | CO | H | OMe | OMe | OMe | H | <10 |
| 153 | $SO_2NH_2$ | CO | $CH_2$ | CO | H | CN | H | H | H | 10 to 50 |
| 154 | TIPS | CO | $CH_2$ | $CH_2$ | H | H | OMe | H | H | >100 |
| 155 | 3-MeOBn | CO | $CH_2$ | $CH_2$ | H | OMe | H | H | H | >100 |
| 156 | 2-MeOBn | CO | $CH_2$ | $CH_2$ | OMe | H | H | H | H | >100 |
| 157 | Bn | CO | $CH_2$ | $CH_2$ | H | OMe | H | OMe | H | >100 |
| 158 | Bn | CO | $CH_2$ | $CH_2$ | H | OMe | OMe | OMe | H | >100 |
| 159 | H | CO | $CH_2$ | $CH_2$ | H | H | OMe | H | H | >100 |
| 160 | H | CO | $CH_2$ | $CH_2$ | H | OMe | H | H | H | >100 |

-continued

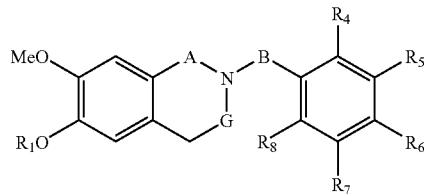

| Cmp No. | $R_1$ | A | G | B | $R_4$ | $R_5$ | $R_6$ | $R_7$ | $R_8$ | DU-145 $GI_{50}$ μM |
|---|---|---|---|---|---|---|---|---|---|---|
| 161 | H | CO | $CH_2$ | $CH_2$ | OMe | H | H | H | H | >100 |
| 162 | H | CO | $CH_2$ | $CH_2$ | H | OMe | H | OMe | H | >100 |
| 163 | H | CO | $CH_2$ | $CH_2$ | H | OMe | OMe | OMe | H | >100 |
| 164 | $SO_2NH_2$ | CO | $CH_2$ | $CH_2$ | H | H | OMe | H | H | >100 |
| 165 | $SO_2NH_2$ | CO | $CH_2$ | $CH_2$ | OMe | H | H | H | H | >100 |
| 166 | $SO_2NH_2$ | CO | $CH_2$ | $CH_2$ | H | OMe | H | H | H | >100 |
| 167 | $SO_2NH_2$ | CO | $CH_2$ | $CH_2$ | H | OMe | H | OMe | H | >100 |
| 168 | $SO_2NH_2$ | CO | $CH_2$ | $CH_2$ | H | OMe | OMe | OMe | H | >100 |
| 169 | Bn | $CH_2$ | $CH_2$ | $SO_2$ | H | OMe | H | H | H | >100 |
| 170 | Bn | $CH_2$ | $CH_2$ | $SO_2$ | H | $OCF_3$ | H | H | H | >100 |
| 171 | Bn | $CH_2$ | $CH_2$ | $SO_2$ | H | Me | H | H | H | >100 |
| 172 | Bn | $CH_2$ | $CH_2$ | $SO_2$ | H | $CF_3$ | H | H | H | >100 |
| 173 | Bn | $CH_2$ | $CH_2$ | $SO_2$ | H | Cl | H | H | H | >100 |
| 174 | Bn | $CH_2$ | $CH_2$ | $SO_2$ | H | CN | H | H | H | >100 |
| 178 | H | $CH_2$ | $CH_2$ | $SO_2$ | H | OMe | H | H | H | >100 |
| 179 | H | $CH_2$ | $CH_2$ | $SO_2$ | H | $OCF_3$ | H | H | H | >100 |
| 180 | H | $CH_2$ | $CH_2$ | $SO_2$ | H | Me | H | H | H | >100 |
| 181 | H | $CH_2$ | $CH_2$ | $SO_2$ | H | $CF_3$ | H | H | H | >100 |
| 182 | H | $CH_2$ | $CH_2$ | $SO_2$ | H | Cl | H | H | H | >100 |
| 183 | H | $CH_2$ | $CH_2$ | $SO_2$ | CN | H | H | H | H | >100 |
| 184 | H | $CH_2$ | $CH_2$ | $SO_2$ | OMe | H | H | H | H | >100 |
| 185 | H | $CH_2$ | $CH_2$ | $SO_2$ | H | H | OMe | H | H | >100 |
| 186 | H | $CH_2$ | $CH_2$ | $SO_2$ | H | CN | H | H | H | >100 |
| 187 | $SO_2NH_2$ | $CH_2$ | $CH_2$ | $SO_2$ | H | CN | H | H | H | >100 |
| 188 | $SO_2NH_2$ | $CH_2$ | $CH_2$ | $SO_2$ | H | OMe | H | H | H | 50 to 100 |
| 189 | $SO_2NH_2$ | $CH_2$ | $CH_2$ | $SO_2$ | H | $CF_3$ | H | H | H | 10 to 50 |
| 190 | $SO_2NH_2$ | $CH_2$ | $CH_2$ | $SO_2$ | H | Cl | H | H | H | 10 to 50 |
| 191 | $SO_2NH_2$ | $CH_2$ | $CH_2$ | $SO_2$ | H | Me | H | H | H | 10 to 50 |
| 192 | $SO_2NH_2$ | $CH_2$ | $CH_2$ | $SO_2$ | H | $OCF_3$ | H | H | H | 50 to 100 |
| 193 | $SO_2NH_2$ | $CH_2$ | $CH_2$ | $SO_2$ | CN | H | H | H | H | <10 |
| 194 | $SO_2NH_2$ | $CH_2$ | $CH_2$ | $SO_2$ | OMe | H | H | H | H | >100 |
| 195 | $SO_2NH_2$ | $CH_2$ | $CH_2$ | $SO_2$ | H | H | OMe | H | H | >100 |
| 195 | Bn | CO | $CH_2$ | $SO_2$ | H | OMe | H | H | H | >100 |
| 197 | Bn | CO | $CH_2$ | $SO_2$ | OMe | H | H | H | H | >100 |
| 199 | Bn | CO | $CH_2$ | $SO_2$ | H | Cl | H | H | H | >100 |
| 200 | H | CO | $CH_2$ | $SO_2$ | OMe | H | H | H | H | >100 |
| 201 | H | CO | $CH_2$ | $SO_2$ | H | OMe | H | H | H | >100 |
| 202 | H | CO | $CH_2$ | $SO_2$ | H | H | OMe | H | H | >100 |
| 203 | H | CO | $CH_2$ | $SO_2$ | H | Cl | H | H | H | >100 |
| 204 | $SO_2NH_2$ | CO | $CH_2$ | $SO_2$ | OMe | H | H | H | H | >100 |
| 205 | $SO_2NH_2$ | CO | $CH_2$ | $SO_2$ | H | OMe | H | H | H | >100 |
| 206 | $SO_2NH_2$ | CO | $CH_2$ | $SO_2$ | H | H | OMe | H | H | >100 |
| 207 | $SO_2NH_2$ | CO | $CH_2$ | $SO_2$ | H | Cl | H | H | H | >100 |
| 217 | H | $CH_2$ | CHMe | $CH_2$ | H | OMe | H | H | H | <10 |
| 218 | H | $CH_2$ | CHMe | $CH_2$ | H | OMe | H | OMe | H | 10 to 50 |
| 219 | H | $CH_2$ | CHMe | $CH_2$ | H | OMe | OMe | OMe | H | NA |
| 220 | $SO_2NH_2$ | $CH_2$ | CHMe | $CH_2$ | H | OMe | H | H | H | <10 |
| 221 | $SO_2NH_2$ | $CH_2$ | CHMe | $CH_2$ | H | OMe | H | OMe | H | <10 |
| 222 | $SO_2NH_2$ | $CH_2$ | CHMe | $CH_2$ | H | OMe | OMe | OMe | H | <10 |
| 228 | H | $CH_2$ | $CMe_2$ | $CH_2$ | H | OMe | H | H | H | NA |
| 229 | H | $CH_2$ | $CMe_2$ | $CH_2$ | H | OMe | OMe | OMe | H | NA |
| 230 | $SO_2NH_2$ | $CH_2$ | $CMe_2$ | $CH_2$ | H | OMe | H | H | H | >100 |
| 231 | $SO_2NH_2$ | $CH_2$ | $CMe_2$ | $CH_2$ | H | OMe | OMe | OMe | H | >100 |
| 234 | H | $CH_2$ | $CMe_2$ | CO | H | OMe | OMe | OMe | H | >100 |
| 236 | H | $CH_2$ | $CMe_2$ | CO | H | OMe | H | OMe | H | >100 |
| 236 | $SO_2NH_2$ | $CH_2$ | $CMe_2$ | CO | H | OMe | OMe | OMe | H | >100 |
| 237 | $SO_2NH_2$ | $CH_2$ | $CMe_2$ | CO | H | OMe | H | OMe | H | >100 |
|  | $SO_2Me$ | $CH_2$ | $CH_2$ | $CH_2$ | H | OMe | OMe | OMe | H | <10 |
|  | Ac | $CH_2$ | $CH_2$ | $CH_2$ | H | OMe | OMe | OMe | H | <10 |
|  | Bn | $CH_2$ | $CH_2$ | $CH_2$ | H | OAc | H | H | H | 10 to 50 |
|  | $SO_2NH_2$ | $CH_2$ | $CH_2$ | $CH_2$ | H | F | H | H | H | 50 to 100 |
|  | Bn | $CH_2$ | $CH_2$ | $CH_2$ | H | $NHSO_2NH_2$ | H | H | H | 50 to 100 |
|  | Me | $CH_2$ | $CH_2$ | $CH_2$ | H | OMe | OMe | OMe | H | >100 |
|  | Bn | $CH_2$ | $CH_2$ | $CH_2$ | H | H | CN | H | H | >100 |
|  | H | $CH_2$ | $CH_2$ | $CH_2$ | H | $NHSO_2NH_2$ | H | H | H | >100 |

-continued

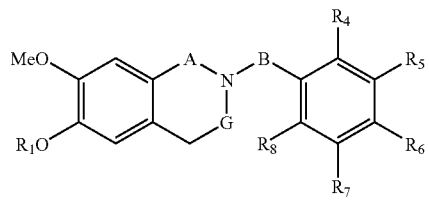

| Cmp No. | $R_1$ | A | G | B | $R_4$ | $R_5$ | $R_6$ | $R_7$ | $R_8$ | DU-145 $GI_{50}\,\mu M$ |
|---|---|---|---|---|---|---|---|---|---|---|
| | $SO_2NH_2$ | $CH_2$ | $CH_2$ | $CH_2$ | H | $NHSO_2NH_2$ | H | H | H | >100 |
| | Bn | $CH_2$ | $CH_2$ | $CH_2$ | H | OMe | OMe | OMe | H | >100 |
| | $SO_2NH_2$ | $CH_2$ | $CH_2$ | $SO_2$ | $CO_2Me$ | H | H | H | H | 10 to 50 |
| | Bn | $CH_2$ | $CH_2$ | $SO_2$ | $CO_2Me$ | H | H | H | H | >100 |
| | H | $CH_2$ | $CH_2$ | $SO_2$ | $CO_2Me$ | H | H | H | H | >100 |
| | $SO_2NH_2$ | CO | $CH_2$ | CO | H | H | CN | H | H | NA |
| | H | CO | $CH_2$ | $SO_2$ | $CO_2Me$ | H | H | H | H | >100 |
| | $SO_2NH_2$ | CO | $CH_2$ | $SO_2$ | $CO_2Me$ | H | H | H | H | >100 |

All publications and patents mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:
1. A compound of Formula I or Formula II

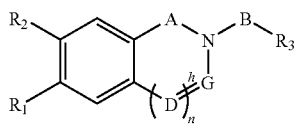

Formula I

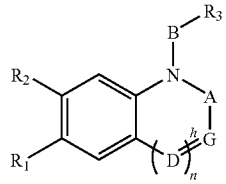

Formula II wherein
A is $CR_{10}R_{11}$, —S(=O)$_2$—, —$NR_{12}$—, or C=O, wherein $R_{10}$ and $R_{11}$ independently represent H, —OH, hydrocarbyl, —CN, —$NO_2$, or halogen, $R_{12}$ is H or hydrocarbyl;

B is $(CR_{13}R_{14})_{1-3}$, C=O, $CR_{15}R_{16}$C=O, —S(=O)$_2$—, —$NR_{17}$— or —$NR_{18}$—C(=O)—,
wherein each of $R_{13}$, $R_{14}$, $R_{15}$ and $R_{16}$ independently represents H, —OH, hydrocarbyl, —CN, —$NO_2$, or halogen, $R_{17}$ and $R_{18}$ independently represents H or hydrocarbyl;

$R_1$ is —$OSO_2NR_{19}R_{20}$,
wherein each of $R_{19}$ and $R_{20}$ independently represents H or hydrocarbyl, wherein at least one of $R_{19}$ and $R_{20}$ is H;

$R_2$ is H, —O-hydrocarbyl, —S-hydrocarbyl, hydrocarbyl, —CN, —$NO_2$, or halogen, $R_3$ is

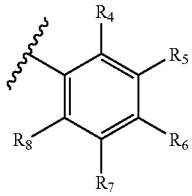

Formula A

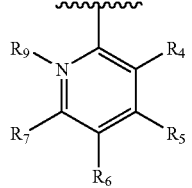

Formula B

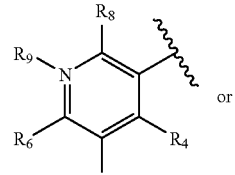

Formula C or

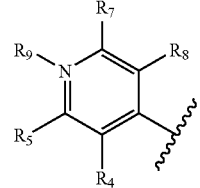

Formula D wherein each of $R_4$, $R_5$, $R_6$, $R_7$ and $R_8$ independently represents H, —OH, hydrocarbyl, —O-hydrocarbyl, —COOH, an ester of —COOH, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen, $R_9$ is H or hydrocarbyl, and each $R_{29}$ to $R_{33}$ independently represents H or hydrocarbyl; and wherein two or more of $R_4$, $R_5$, $R_6$, $R_7$, $R_8$ and $R_9$ may together form a ring;

wherein when $R_1$ is OH and $R_3$ is of Formula D, (i) at least one of $R_4$, $R_5$, $R_6$, $R_7$ and $R_8$ independently represent halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, and halogen, or (ii) two or more of $R_4$, $R_5$, $R_6$, $R_7$ and $R_8$ together form a ring, or (iii) at least three of $R_4$, $R_5$, $R_6$, $R_7$ and $R_8$ independently represent —OH, hydrocarbyl, —O-hydrocarbyl, halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen wherein h is an optional bond, wherein G is $CR_{24}R_{25}$, wherein $R_{24}$ and $R_{25}$ independently represent H, —OH, hydrocarbyl, —CN, —$NO_2$, or halogen, or wherein when h is present G is $CR_{24}$, wherein $R_{24}$ is H, —OH, hydrocarbyl, —CN, —$NO_2$, or halogen;

n is 0, 1 or 2, each D independently represents O, $NR_{26}$ or $CR_{27}R_{28}$, wherein each $R_{26}$ independently represents H or hydrocarbyl; and each $R_{27}$ and $R_{28}$ independently represents —H, —OH, hydrocarbyl, —CN, —$NO_2$, or halogen;

or salts of the compound.

2. The compound of claim 1, wherein the compound is of Formula I.

3. The compound of claim 1, wherein A is $CR_{10}R_{11}$ or C=O, wherein $R_{10}$ and $R_{11}$ independently represent H, —OH, hydrocarbyl, —CN, —$NO_2$, or halogen.

4. The compound of claim 1, wherein A is $CR_{10}R_{11}$ or C=O, wherein $R_{10}$ and $R_{11}$ independently represent H, —OH, hydrocarbyl or halogen.

5. The compound of claim 1, wherein A is $CH_2$ or C=O.

6. The compound of claim 1, wherein B is $(CR_{13}R_{14})_{1-3}$, C=O, or —S(=O)$_2$—, wherein each of $R_{13}$ and $R_{14}$, independently represents H, —OH, hydrocarbyl, —CN, —$NO_2$, or halogen.

7. The compound of claim 1, wherein B is $CR_{13}R_{14}$, C=O, or —S(=O)$_2$—, wherein each of $R_{13}$ and $R_{14}$, independently represents H, —OH, hydrocarbyl, —CN, —$NO_2$, or halogen.

8. The compound of claim 1, wherein B is $(CH_2)_{1-3}$, C=O, or —S(=O)$_2$—.

9. The compound of claim 1, wherein B is $CH_2$, C=O, or —S(=O)$_2$—.

10. The compound of claim 1, wherein $R_{19}$ and $R_{20}$ are H.

11. The compound of claim 1, wherein $R_2$ is an —O-hydrocarbyl group.

12. The compound of claim 11, wherein $R_2$ is a $C_{1-6}$ alkoxy group.

13. The compound of claim 11, wherein $R_2$ is methoxy.

14. The compound of claim 1, wherein $R_3$ is a group of Formula A

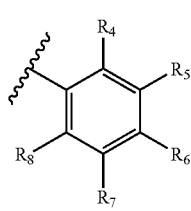

Formula A wherein each of $R_4$, $R_5$, $R_6$, $R_7$ and $R_8$ independently represents H, —OH, hydrocarbyl, —O-hydrocarbyl, —COOH, an ester of —COOH, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen, wherein each $R_{29}$ to $R_{33}$ independently represents H or hydrocarbyl; and wherein two or more of $R_4$, $R_5$, $R_6$, $R_7$, $R_8$ and $R_9$ may together form a ring.

15. The compound of claim 1, wherein $R_3$ is a group of Formula B

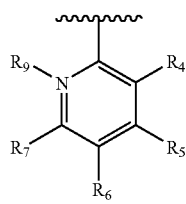

Formula B wherein each of $R_4$, $R_5$, $R_6$, and $R_7$ independently represents H, —OH, hydrocarbyl, —O-hydrocarbyl, —COOH, an ester of —COOH, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen, $R_9$ is H or hydrocarbyl, and each $R_{29}$ to $R_{33}$ independently represents-H or hydrocarbyl; and wherein two or more of $R_4$, $R_5$, $R_6$, $R_7$, and $R_9$ may together form a ring.

16. The compound of claim 1, wherein $R_3$ is a group of Formula C

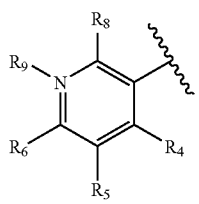

Formula C wherein each of $R_4$, $R_5$, $R_6$, and $R_8$ independently represents H, —OH, hydrocarbyl, —O—hydrocarbyl, —COOH, an ester of —COOH, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen, $R_9$ is H or hydrocarbyl, and each $R_{29}$ to $R_{33}$ independently represents H or hydrocarbyl; and wherein two or more of $R_4$, $R_5$, $R_6$, $R_8$, and $R_9$ may together form a ring.

17. The compound of claim 1, wherein $R_3$ is a group of Formula D

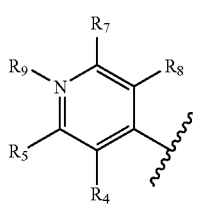

Formula D wherein each of $R_4$, $R_5$, $R_7$, and $R_8$ independently represents H, —OH, hydrocarbyl, —O-hydrocarbyl, —COOH, an ester of —COOH, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen, $R_9$ is H or hydrocarbyl, and each $R_{29}$ to $R_{33}$ independently represents H or hydrocarbyl; and wherein two or more of $R_4$, $R_5$, $R_7$, $R_8$, and $R_9$ may together form a ring.

18. The compound of claim 1, wherein each of $R_4$, $R_5$, $R_6$, $R_7$ and $R_8$ independently represents H, —OH, $C_{1-6}$ alkyl, $C_{1-6}$ aryl, —O—$C_{1-6}$ alkyl, —O—$C_{1-6}$ aryl, —COOH, $C_{1-6}$ alkyl ester of —COOH, $C_{1-6}$ halocarbyl, —O—$C_{1-6}$ halocarbyl, —O-acetyl, —$NR_{29}$-acetyl, —O—$SO_2NR_{19}R_{20}$, —$NR_{30}R_{31}$, —$NR_{32}SO_2R_{33}$, —CN, —$NO_2$, or halogen, wherein each $R_{29}$ to $R_{33}$ independently represents H or $C_{1-6}$ alkyl.

19. The compound of claim 1, wherein each of $R_4$, $R_5$, $R_6$, $R_7$ and $R_8$ independently represents H, —OH, $C_{1-6}$ alkyl, $C_{1-6}$ aryl, —O—$C_{1-6}$ alkyl, —O—$C_{1-6}$ aryl, —COOH, $C_{1-6}$ alkyl ester of —COOH, $C_{1-6}$ halocarbyl, —O—$C_{1-6}$ halocarbyl, —O-acetyl, —NH-acetyl, —O—$SO_2NH_2$, —$NH_2$, —NH—$SO_2$—$NH_2$, —CN, —$NO_2$, or halogen.

20. The compound of claim 1, wherein each of $R_4$, $R_5$, $R_6$, $R_7$ and $R_8$ independently represents H, —OH, Me, Et, —OMe, —OEt, —OPh, —O-iPr —COOMe, —$CF_3$, —$OCF_3$, F, Cl, —O-acetyl, —NH-acetyl, —O—$SO_2NH_2$, —$NH_2$, —NH—$SO_2$—$NH_2$, —CN, or —$NO_2$.

21. The compound of claim 1, wherein $R_4$ is H, —OH, —O-hydrocarbyl, —COOH, a salt of —COOH, or —CN.

22. The compound of claim 1, wherein $R_4$ is H, —OH, —OMe, —COOH or —CN.

23. The compound of claim 1, wherein $R_5$ is H, —OH, hydrocarbyl, —O-hydrocarbyl, halocarbyl, —O-halocarbyl, acyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen.

24. The compound of claim 1, wherein $R_5$ is H, —OH, Me, Et, —OMe, —OEt, —OPh, —O-iPr , —$CF_3$, —$OCF_3$, F, Cl, —O-acetyl, —NH-acetyl, —O—$SO_2NH_2$, —$NH_2$, —NH—$SO_2$—$NH_2$, —CN, or —$NO_2$.

25. The compound of claim 1, wherein $R_6$ is H, —O-hydrocarbyl or —CN.

26. The compound of claim 1, wherein $R_6$ is H, —OMe, or —CN.

27. The compound of claim 1, wherein $R_7$ is H, or —O-hydrocarbyl.

28. The compound of claim 1, wherein $R_7$ is H or —OMe.

29. The compound of claim 1, wherein $R_9$ is H.

30. The compound of claim 1, wherein $R_9$ is H or $C_{1-6}$ alkyl.

31. The compound of claim 1, wherein each $R_{29}$ to $R_{33}$ independently represents H or $C_{1-6}$ alkyl.

32. The compound of claim 1, wherein at least one of $R_4$, $R_5$, $R_6$, $R_7$ and $R_8$ independently represents halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, or halogen.

33. The compound of claim 1, wherein two or more of $R_4$, $R_5$, $R_6$, $R_7$ and $R_8$ together form a ring.

34. The compound of claim 1, wherein at least three of $R_4$, $R_5$, $R_6$, $R_7$ and $R_8$ independently represent —OH, hydrocarbyl, —O-hydrocarbyl, halocarbyl, —O-halocarbyl, —O-acyl, —$NR_{29}$-acyl, —O—$SO_2NR_{19}R_{20}$, —$NR_{30}R_{31}$, —$NR_{32}SO_2R_{33}$, —CN, —$NO_2$, or halogen.

35. The compound of claim 1, wherein h is not present.

36. The compound of claim 1, wherein when h is not present G is $CR_{24}R_{25}$, wherein $R_{24}$ and $R_{25}$ independently represent H or hydrocarbyl, and when h is present G is $CR_{24}$, wherein $R_{24}$ is H or hydrocarbyl.

37. The compound of claim 1, wherein when h is not present G is $CR_{24}R_{25}$, wherein $R_{24}$ and $R_{25}$ independently represent H or $C_{1-6}$ alkyl, and when h is present G is $CR_{24}$, wherein $R_{24}$ is H or $C_{1-6}$ alkyl.

38. The compound of claim 1, wherein when h is not present G is $CR_{24}R_{25}$, wherein $R_{24}$ and $R_{25}$ independently represent H, Et or Me, and when h is present G is $CR_{24}$, wherein $R_{24}$ is H or Me.

39. The compound of claim 1, wherein when h is not present G is —$CH_2$—, —CHEt—, —CHMe— or —$CMe_2$—, and when h is present G is —CH— or —CMe—.

40. The compound of claim 1, wherein n is 1.

41. The compound of claim 1, wherein each D independently represents $CR_{27}R_{28}$, wherein each $R_{27}$ and $R_{28}$ independently represents H, —OH, hydrocarbyl, —CN, —$NO_2$, or halogen.

42. The compound of claim 1, wherein each D independently represents $CR_{27}R_{28}$, wherein each $R_{27}$ and $R_{28}$ independently represents H, OH, $C_{1-6}$ alkoxy or $C_{1-6}$ alkyl.

43. The compound of claim 1, wherein each D independently represents CHOH, CHOMe, CHOEt, or $CH_2$.

44. The compound of claim 1, wherein —$SO_2$-hydrocarbyl is a —$SO_2$—$C_{1-6}$ alkyl group.

45. The compound of claim 1, wherein —$SO_2$-hydrocarbyl is —$SO_2$-Me.

46. A pharmaceutical composition comprising the compound of claim 1, and a pharmaceutically acceptable carrier, diluent, excipient or adjuvant.

47. The compound of claim 1, wherein the compound is:
7-Methoxy-2-(3-methoxybenzyl)-6-O-sulfamoyl-1,2,3,4-tetrahydroisoquinoline;
7-Methoxy-2-(4-methoxybenzyl)-6-O-sulfamoyl-1,2,3,4-tetrahydroisoquinoline;
2-Benzyl-7-methoxy-6-O-sulfamoyl-1,2,3,4-tetrahydroisoquinoline;
7-Methoxy-2-(2-methoxybenzyl)-6-O-sulfamoyl-1,2,3,4-tetrahydroisoquinoline;
2-(3,5-Dimethoxybenzyl)-7-methoxy-6-O-sulfamoyl-1,2,3,4-tetrahydroisoquinoline;
7-Methoxy-2-(3-methylbenzyl)-6-O-sulfamoyl-1,2,3,4-tetrahydroisoquinoline;
7-Methoxy-2-(3-phenoxybenzyl)-6-O-sulfamoyl-1,2,3,4-tetrahydroisoquinoline;
7-Methoxy-2-(3-(O-sulfamoy)benzyl)-6-O-sulfamoyl-1,2,3,4-tetrahydroisoquinoline;
2-(3-Ethoxybenzyl)-7-methoxy-6-O-sulfamoyl-1,2,3,4-tetrahydroisoquinoline;
2-(3-Acetylbenzyl)-7-methoxy-6-O-sulfamoyl-1,2,3,4-tetrahydroisoquinoline;
2-(3-Acetamidobenzyl)-7-methoxy-6-O-sulfamoyl-1,2,3,4-tetrahydroisoquinoline;
2-(3-Acetoxybenzyl)-7-metoxy-6-O-sulfamoyl-1,2,3,4-tetrahydroisoquinoline;
7-Methoxy-2-(3,4,5-trimethoxybenzyl)-6-O-sulfamoyl-1,2,3,4-tetrahydroisoquinoline;
7-Methoxy-2-(2,3-dimethoxybenzyl)-6-O-sulfamoyl-1,2,3,4-tetrahydroisoquinoline;
7-Methoxy-2-(3,4-dimethoxybenzyl)-6-O-sulfamoyl-1,2,3,4-tetrahydroisoquinoline;
7-Methoxy-2-(2,3,4-trimethoxybenzyl)-6-O-sulfamoyl-1,2,3,4-tetrahydroisoquinoline;
7-Methoxy-2-(2,5-dimethoxybenzyl)-6-O-sulfamoyl-1,2,3,4-tetrahydroisoquinoline;
7-Methoxy-2-(2,4,5-trimethoxybenzyl)-6-O-sulfamoyl-1,2,3,4-tetrahydroisoquinoline;

2-(3-Hydroxybenzyl)-7-methoxy-6-O-sulfamoyl-1,2,3,4-tetrahydroisoquinoline;
2-(3-Cyanobenzyl)-7-methoxy-6-O-sulfamoyl-1,2,3,4-tetrahydroisoquinoline;
2-(4-Cyanobenzyl)-7-methoxy-6-O-sulfamoyl-1,2,3,4-tetrahydroisoquinoline;
7-Methoxy-2-(3-nitrobenzyl)-6-O-sulfamoyl-1,2,3,4-tetrahydroisoquinoline;
2-(3-Chlorobenzyl)-7-methoxy-6-O-sulfamoyl-1,2,3,4-tetrahydroisoquinoline;
7-Methoxy-2-(3-trifluoromethoxybenzyl)-6-O-sulfamoyl-1,2,3,4-tetrahydroisoquinoline;
2-(3-Isopropoxybenzyl)-7-methoxy-6-O-sulfamoyl-1,2,3,4-tetrahydroisoquinoline;
7-Methoxy-2-(2-methoxybenzoyl)-6-O-sulfamoyl-1,2,3,4-tetrahydroisoquinoline;
7-Methoxy-2-(3-methoxybenzoyl)-6-O-sulfamoyl-1,2,3,4-tetrahydroisoquinoline;
7-Methoxy-2-(4-methoxybenzoyl)-6-O-sulfamoyl-1,2,3,4-tetrahydroisoquinoline;
2-(3,4-Dimethoxybenzoyl)-7-methoxy-6-O-sulfamate-1,2,3,4-tetrahydroisoquinoline;
2-(3,5-Dimethoxybenzoyl)-7-methoxy-6-O-sulfamoyl-1,2,3,4-tetrahydroisoquinoline;
7-methoxy-6-O-sulfamoyl-2-(3,4,5-trimethoxybenzoyl)-1,2,3,4-tetrahydroisoquinoline;
2-(4-Methoxybenzoyl)-7-methoxy-6-O-sulfamoyl-3,4-dihydro-2H-isoquinolin-1-one;
7-Methoxy-2-(2-methoxybenzoyl)-6-O-sulfamoyl-3,4-dihydro-2H-isoquinolin-1-one;
7-Methoxy-2-(3-methoxybenzoyl)-6-O-sulfarnoyl-3,4-dihydro-2H-isoquinolin-1-one;
2-(3,5-Dimethoxybenzoyl)-7-methoxy-6-O-sulfamoyl-3,4-dihydro-2H-isoquinolin-1-one;
2-(3,4-Dimethoxybenzoyl)-7-methoxy-6-O-sulfamoyl-3,4-dihydro-2H-isoquinolin-1-one;
7-methoxy-6-O-sulfamoyl-2-(3,4,5-trimethoxybenzoyl)-3,4-dihydro-2H-isoquinolin-1-one;
2-(3-Cyanobenzoyl)-7-methoxy-6-O-sulfamoyl-3,4-dihydro-2H-isoquinoline-1-one;
7-Methoxy-2-(4-methoxybenzyl)-6-O-sulfamoyl-3,4-dihydro-2H-isoquinoline;
7-Methoxy-2-(2-methoxybenzyl)-6-O-sulfamoyl-3,4-dihydro-2H-isoquinoline;
7-Methoxy-2-(3-methoxybenzyl)-6-O-sulfamoyl-3,4-dihydro-2H-isoquinoline;
2-(3,5-Dimethoxybenzyl)-7-methoxy-6-O-sulfamoyl-3,4-dihydro-2H-isoquinolin-1-one;
7-methoxy-6-O-sulfamoyl-2-(3,4,5-trimethoxybenzyl)-3,4-dihydroisoquinolin-1(2H)-one;
2-(3-Cyano-benzenesulfonyl)-7-methoxy-6-O-sulfamoyl-1,2,3,4-tetrahydroisoquinoline;
7-Methoxy-2-(3-methoxy-benzenesulfonyl)-6-O-sulfamoyl-1,2,3,4-tetrahydroisoquinoline;
7-Methoxy-6-O-sulfamoyl-2-(3-trifluoromethyl-benzenesulfonyl)-1,2,3,4-tetrahydroisoquinoline;
2-(3-Chloro-benzenesulfonyl)-7-methoxy-6-O-sulfamoyl-1,2,3,4-tetrahydroisoquinoline;
7-Methoxy-6-O-sulfamoyl-2-(toluene-3-sulfonyl)-1,2,3,4-tetrahydroisoquinoline;
7-Methoxy-6-O-sulfamoyl-2-(3-trifluoromethoxy-benzenesulfonyl)-1,2,3,4-tetrahydroisoquinoline;
2-(2-Cyano-benzenesulfonyl)-7-methoxy-6-O-sulfamoyl-1,2,3,4-tetrahydroisoquinoline;
7-Methoxy-2-(2-methoxy-benzenesulfonyl)-6-O-sulfamoyl-1,2,3,4-tetrahydroisoquinoline;
7-Methoxy-2-(4-methoxy-benzenesulfonyl)-6-O-sulfamoyl-1,2,3,4-tetrahydroisoquinoline;
7-Methoxy-2-(2-methoxy-benzenesulfonyl)-6-O-sulfamoyl-3,4-dihydro-2H-isoquinolin-1-one;
7-Methoxy-2-(3-methoxy-benzenesulfonyl)-6-O-sulfamoyl-3,4-dihydro-2H-isoquinolin-1-one;
7-Methoxy-2-(4-methoxy-benzenesulfonyl)-6-O-sulfamoyl-3,4-dihydro-2H-isoquinolin-1-one;
2-(3-Chloro-benzenesulfonyl)-7-methoxy-6-O-sulfamoyl-3,4-dihydro-2H-1-isoquinolin-1-one;
2-(3-Methoxybenzyl)-1,2,3,4-tetrahydro-7-methoxy-3-methylisoquinolin-6-O-sulfamate;
2-(3,5-dimethoxy-benzyl)-7-methoxy-3-methyl-1,2,3,4-tetrahydro-isoquinolin-6-O-sulfmate;
2-(3,4,5-Trimethoxybenzyl)-1,2,3,4-tetrahydro-7-methoxy-3-methylisoquinolin-6-O-sulfamate;
2-(3-Methoxybenzyl)-1,2,3,4-tetrahydro-7-methoxy-3,3-dimethylisoquinolin-6-yl sulfamate;
2-(3,4,5-Trimethoxybenzyl)-1,2,3,4-tetrahydro-7-methoxy-3,3-dimethylisoquinolin-6-yl sulfamate;
Sulfamic acid 7-methoxy-3,3-dimethyl-2-(3,4,5-trimethoxy-benzoyl)-1,2,3,4-tetrahydro-isoquinolin-6-yl ester; or
Sulfamic acid 2-(3,5-dimethoxy-benzoyl)-7-methoxy-3,3-dimethyl-1,2,3,4-tetrahydro-isoquinolin-6-yl ester.

48. A pharmaceutically active composition comprising the compound of claim 47.

* * * * *

UNITED STATES PATENT AND TRADEMARK OFFICE
CERTIFICATE OF CORRECTION

PATENT NO. : 8,394,825 B2  
APPLICATION NO. : 12/593560  
DATED : March 12, 2013  
INVENTOR(S) : Leese et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 563 days.

Signed and Sealed this

First Day of September, 2015

Michelle K. Lee  
*Director of the United States Patent and Trademark Office*